US009962419B2

(12) United States Patent
Alves Mendes et al.

(10) Patent No.: US 9,962,419 B2
(45) Date of Patent: May 8, 2018

(54) COMPOSITIONS COMPRISING COCKTAILS OF ANTIBACTERIAL PHAGES AND USES THEREOF FOR THE TREATMENT OF BACTERIAL INFECTIONS

(71) Applicants: TECNIFAR—INDUSTRIA TECNICA FARMACEUTICA, S.A., Lisbon (PT); TECHNOPHAGE, INVESTIGAÇ ÃO E DESENVOLVIMENTO EM BIOTECNOLOGIA, SA, Lisbon (PT)

(72) Inventors: João João Duarte Alves Mendes, Paço de Arcos (PT); Clara Isabel Rodrigues Leandro, Parede (PT); Sofia Volker Côrte-Real, Cruz Quebrada (PT)

(73) Assignee: Tecnifar—Industria Tecnica Farmaceutica, S.A. Technophage, Investigação E Desenvolvimento Em Biotecnologia, SA, Lisboa (PT)

( * ) Notice: Subject to any disclaimer, the term of this patent is extended or adjusted under 35 U.S.C. 154(b) by 13 days.

(21) Appl. No.: 14/385,828

(22) PCT Filed: Mar. 19, 2013

(86) PCT No.: PCT/PT2013/000016
§ 371 (c)(1),
(2) Date: Sep. 17, 2014

(87) PCT Pub. No.: WO2013/141730
PCT Pub. Date: Sep. 26, 2013

(65) Prior Publication Data
US 2015/0150919 A1 Jun. 4, 2015

Related U.S. Application Data

(60) Provisional application No. 61/612,531, filed on Mar. 19, 2012.

(51) Int. Cl.

| | |
|---|---|
| ***A61K 35/76*** | (2015.01) |
| ***A61K 45/06*** | (2006.01) |
| ***C12N 7/00*** | (2006.01) |
| ***C12N 9/50*** | (2006.01) |
| ***A61B 17/3205*** | (2006.01) |
| ***A61K 9/00*** | (2006.01) |
| ***A61M 1/00*** | (2006.01) |
| *A61K 38/18* | (2006.01) |
| *A61B 17/32* | (2006.01) |

(52) U.S. Cl.
CPC .......... *A61K 35/76* (2013.01); *A61B 17/3205* (2013.01); *A61K 9/0014* (2013.01); *A61K 45/06* (2013.01); *A61M 1/008* (2013.01); *C12N 9/503* (2013.01); *A61B 2017/320008* (2013.01); *A61K 38/18* (2013.01)

(58) Field of Classification Search
CPC ........ A61K 35/76; A61K 45/06; A61K 38/47; A61K 38/48; A61K 38/18; A61K 9/0014; C12N 2795/00022; C12N 2795/00031; C12N 2795/00032; C12N 7/00; C12N 9/2462; C12N 9/503
See application file for complete search history.

(56) References Cited

U.S. PATENT DOCUMENTS 9,222,077 B2 * 12/2015 Da Costa Garcia ... A61K 35/76
9,399,049 B2 * 7/2016 Da Costa Garcia ... A61K 35/76

FOREIGN PATENT DOCUMENTS

WO WO 2003/080823 10/2003
WO WO 2010/090542 8/2010
WO WO 2012/036580 3/2012

OTHER PUBLICATIONS

Seffernick et al. (J. Bacteriol. 183(8): 2405-2410, 2001).*
Benjamin et al., "Diagnosis and Treatment of Diabetic Foot Infections," Clinical Infectious Diseases, vol. 39, No. 7, pp. 885-910, Oct. 2004.
Hanlon et al., "Bacteriophages: an Appraisal of Their Role in the Treatment of Bacterial Infections," International Journal of Antimicrobial Agents, vol. 30, No. 2, pp. 118-128, Jun. 2007.
Hermosa et al., "Taking Aim on Bacterial Pathogens: from Phage Therapy to Enzybiotics," Current Opinion in Microbiology, Current Biology, vol. 10, No. 5, pp. 461-472, Oct. 2007.
Richard et al., "Growth Factors and Treatment of Diabetic Foot Ulcers," STV, John Libbey Eurotext, vol. 14, No. 3, pp. 158-171, Jan. 2002.
Sulakvelidze et al., "Bacteriophage Therapy," Antimicrobial Agents and Chemotherapy, vol. 45, No. 3, pp. 649-659, Mar. 2001.
Synnott, et al., "Isolation from Sewage Influent and Characterization of Novel *Staphylococcus aureus* Bacteriophages with Wide Host Ranges and Potent Lytic Capabilities," Applied and Environmental Microbiology, 75(13) pp. 4483-4490, 2009.
Notification of Reasons for Refusal for Japanese Patent Application No. 2015-501614, dated Jan. 5, 2017, 11 pages, with English translation.

* cited by examiner

*Primary Examiner* — Padmavathi Baskar
(74) *Attorney, Agent, or Firm* — Margaret B. Brivanlou; Nicole Fortune; King & Spalding LLP

(57) ABSTRACT

The present invention is directed to the field of phage therapy for the treatment and control of bacterial infections, in particular diabetic foot infections. More specifically, the present invention is directed to novel cocktails of bacteriophage strains F44/10, F1 25/10, F770/05, F510/08, F1 245/05, and/or variants thereof; and methods of using same in the treatment and prevention of bacterial infections, including cutaneous ulcers associated with diabetic foot infections, caused by, e.g., *Staphylococcus aureus, Pseudomonas aeruginosa*, and/or *Acinetobacter baumannii*. The cocktails are used as pharmaceutical compositions either alone or in further combination with other therapies, e.g., antibiotics, growth factors, or other standard, as well as non-standard, therapies for diabetic foot infections.

13 Claims, 14 Drawing Sheets

[1] wound assessment: diabetic foot ulcer PEDIS classification system including techniques to assess surface area ( high resolution digital photography, and computerized planimetry software), type of exudate, and wound healing, infection and exudate continuums

COMPOSITIONS COMPRISING COCKTAILS OF ANTIBACTERIAL PHAGES AND USES THEREOF FOR THE TREATMENT OF BACTERIAL INFECTIONS

1. SEQUENCE LISTING

The instant application contains a Sequence Listing which has been submitted in ASCII format via EFS-Web and is hereby incorporated by reference in its entirety. Said ASCII copy, created on Mar. 14, 2012, is named 16395105.txt and is 574,104 bytes in size.

2. FIELD OF THE INVENTION

The present invention is directed to the field of phage therapy for the treatment and control of bacterial infections, in particular chronic ulcers such as diabetic foot infections. More specifically, the present invention is directed to novel cocktails of bacteriophage strains F44/10, F125/10, F770/05, F510/08, F1245/05, other phage, and/or variants thereof; and methods of using same in the treatment and prevention of bacterial infections, including cutaneous ulcers associated with diabetic foot infections, caused by, e.g., *Staphylococcus aureus, Pseudomonas aeruginosa*, and/or *Acinetobacter baumannii*. The cocktails are used as pharmaceutical compositions either alone or in further combination with other therapies, e.g., antibiotics, growth factors, or other standard and non-standard therapies for chronic ulcers.

3. BACKGROUND

Diabetic foot infections (DFIs) are a frequent and serious complication of diabetes mellitus (DM) and are the world leading cause of non-traumatic lower limb amputation (Jeffcoate W J, et al. 2003. Lancet 361:1545-1551). In current clinical practice, the treatment of DFIs includes debridement and systemic antibiotics (see, e.g., Lipsky B A, et al. 2004. Clin Infect Dis. 39:885-910). Nonetheless, because of deficient vascularization and the local microenvironment, antibiotic concentrations are many times sub-therapeutical (Lipsky B A, et al. 2009. Clin Infect Dis. 49:1541-1549). Moreover, the increasing incidence of multidrug resistant organisms, such as methicillin-resistant *Staphylococcus aureus*, as well as pan-drug-resistant non-fermenting negative bacilli, is threatening the outcome in increasing numbers of community and hospitalized patients (Mendes J J, et al. 2012. Diabetes Res Clin Pract. 95(1):153-161; Tascini C, et al. 2011. Diabetes Res Clin Pract 94 (1):133-139). Accordingly, there remains a need to identify new strategies for the treatment, control, and management of DFIs.

Topical treatment provides the advantages of avoiding systemic adverse effects, providing increased target site concentration, and allowing the use of agents not available for systemic therapy. Mechanical debridement improves topical treatment because it reduces the bio-burden of bacteria present and also opens a time-dependent therapeutic window for topical antimicrobial therapy (TAT) (Wolcott R D, et al. 2010. J Wound Care 19:320-328). Nevertheless, to date, no TAT agent has been proven to be effective for treating DFI (Nelson E A, et al. 2006. Diabet Med 23:348-359).

Bacteriophage (phage) are viruses that specifically infect and lyse bacteria. Phage therapy, a method of using whole phage viruses for the treatment of bacterial infectious diseases, was introduced in the 1920s by Felix d'Herelle. With the development of antibiotics in the 1940s, however, interest in phage-based therapeutics declined in the Western world. One of the most important factors that contributed to this decline was the lack of standardized testing protocols and methods of production. The failure to develop industry wide standards for the testing of phage therapies interfered with the documentation of study results, leading to a perceived lack of efficacy, as well as problems of credibility, regarding the value of phage therapy. Another problem in phage production related to the purity grade of commercial preparations of phage, with preparations containing undesired bacterial components, e.g., endotoxins. Accordingly, adverse events were often associated with the preparations, particularly in patients receiving them intravenously.

Nevertheless, in Eastern Europe and the former Soviet Union, where access to antibiotics was limited, the development and use of phage therapy continued jointly with, or in place of, antibiotics. Further, with the rise of antibiotic resistant strains of many bacteria, interest in phage-based therapeutics has returned in the Western world. That is, even though novel classes of antibiotics may be developed, the prospect that bacteria will eventually develop resistance to the new drugs has intensified the search for non-chemotherapeutic means for controlling, preventing, and treating bacterial infections.

Lytic bacteriophage, especially when complemented by adequate mechanical debridement, offer a solution to treating DFIs, e.g., for use as novel TAT agents. Lytic bacteria can offer the advantages of specificity and efficiency in lysing pathogenic bacteria, even those associated with multidrug resistance (Rossney A S, et al. 1994. J Hosp Infect 26:219-234.) Further advantages can include absence of pathogenicity to man and animals (Burrowes B, et al. 2011. Expert Rev Anti Infect Ther 9:775-785), antibacterial activity against bacteria in biofilms, and activity in microaerophilic environments, even with high bacterial load (Azeredo J, et al. 2008. Curr Pharm Biotechnol 9:261-266), as well as the generally accepted safety of bacteriophage therapy in some parts of the world (Sulakvelidze A, et al., 2001, Antimicrob Agents Chemother. 45(3): 649-659). Recent animal trials of bacteriophage therapy have demonstrated its potential to heal or improve skin bacterial diseases, both in internal (McVay C S, et al. 2007. Antimicrob Agents Chemother 51:1934-1938) and external applications (Soothill J S. 1994. Burns 20:209-211; Wills Q F, et al. 2005. Antimicrob Agents Chemother 49:1220-1221). However, there is little published evidence supporting the use of bacteriophage to cure infections established for longer than a few hours (Ryan E M, et al. 2011 J Pharm Pharmacol 63:1253-1264).

In particular, phage cocktails may provide advantages to the use of phages individually, e.g., to increase the lytic activity against a particular bacterial strain, and to decrease the possibility of emergence of bacteria resistant to an individual bacteriophage. That is, different bacteriophage can be mixed as cocktails to broaden their properties, preferably resulting in a collectively greater antibacterial spectrum of activity e.g., an expanded host range, to which development of resistance is less likely. Nonetheless, to date, few phage cocktails exist with antimicrobial activity against different bacteria, possibly because of the difficulty in combining different specificities of bacteriophage while maintaining storage stability.

There is therefore a need to develop novel phage products as therapeutic and/or prophylactic agents for use in vivo against pathogenic bacteria. There also is a need for better treatments, particularly topical treatments, for DFIs. In particular, there is a need for bacteriophage cocktails capable of lysing bacteria responsible for DFIs, including *Staphylococcus aureus, Pseudomonas aeruginosa*, and/or *Acinetobacter baumannii*. This application addresses this and other needs.

4. SUMMARY OF THE INVENTION

In one aspect, the present invention is directed to compositions comprising phage cocktails. In some embodiments, the invention provides compositions comprising at least two different isolated strains of bacteriophage, each having a genome that comprises a nucleic acid sequence selected from the group of consisting of SEQ ID NO:1 (F44/10), SEQ ID NO:2 (F125/10), SEQ ID NO:3 (F770/05), SEQ ID NO:4 (F510/08), and SEQ ID NO:5 (F1245/05), or a variant thereof, the variant having at least 95% sequence identity to the corresponding nucleic acid sequence and showing antibacterial activity against at least one of *Staphylococcus aureus, Pseudomonas aeruginosa*, and/or *Acinetobacter baumannii*. In some embodiments, one of the at least two bacteriophage strains is the strain having a genome that comprises the nucleic acid sequence of SEQ ID NO:1 or SEQ ID NO:2, or the variant thereof. In some embodiments, the at least two bacteriophage strains are the strains having genomes that comprise the nucleic acid sequences of SEQ ID NO:1 and SEQ ID NO:2, or variants thereof. In some embodiments, the composition further comprises at least a third bacteriophage strain, the third strain having a genome that comprises a nucleic acid sequence selected from the group consisting of SEQ ID NO:3, SEQ ID NO:4, and SEQ ID NO:5, or the variant thereof. In some embodiments, the composition further comprises at least a third and a fourth bacteriophage strain, the third and fourth strains each having a genome that comprises a nucleic acid sequence selected from the group consisting of SEQ ID NO:3, SEQ ID NO:4, and SEQ ID NO:5, or the variant thereof. In some embodiments, one of the at least two bacteriophage strains is the strain having a genome that comprises the nucleic acid sequence of SEQ ID NO:3 or SEQ ID NO:4, or the variant thereof. In some embodiments, the at least two bacteriophage strains are the strains having genomes that comprise the nucleic acid sequences of SEQ ID NO:3 and SEQ ID NO:4 or the variant thereof. In some embodiments, the composition further comprises at least a third bacteriophage strain, the third strain having a genome that comprises a nucleic acid sequence selected from the group consisting of SEQ ID NO:1, SEQ ID NO:2, and SEQ ID NO:5, or the variant thereof. In some embodiments, the composition further comprises at least third and fourth bacteriophage strains, the third and fourth strains each having a genome that comprises a nucleic acid sequence selected from the group consisting of SEQ ID NO:1, SEQ ID NO:2, and SEQ ID NO:5, or the variant thereof. In some embodiments, one of the at least two bacteriophage strains is the strain having a genome that comprises the nucleic acid sequence of SEQ ID NO:5, or the variant thereof. In some embodiments, the composition further comprises at least a third bacteriophage strain, the third strain having a genome that comprises a nucleic acid sequence selected from the group consisting of SEQ ID NO:1, SEQ ID NO:2, SEQ ID NO:3, and SEQ ID NO:4, or the variant thereof. In some embodiments, the composition further comprises at least third and fourth bacteriophage strains, the third and fourth strains each having a genome that comprises a nucleic acid sequence selected from the group consisting of SEQ ID NO:1, SEQ ID NO:2, SEQ ID NO:3, and SEQ ID NO:4, or the variant thereof.

In some preferred embodiments, the invention is directed to a composition comprising at least five isolated bacteriophage strains, the strains having genomes that comprise nucleic acid sequences of SEQ ID NO:1, SEQ ID NO:2, SEQ ID NO:3, SEQ ID NO:4, and SEQ ID NO:5, or a variant thereof, where the variant has at least 95% sequence identity to the corresponding nucleic acid sequence and shows antibacterial activity against at least one of *Staphylococcus aureus, Pseudomonas aeruginosa*, and/or *Acinetobacter baumannii*. In some embodiments, the bacteriophage strains having genomes that comprise the nucleic acid sequences of SEQ ID NOs:1, 2, 4, and 5, or the variants thereof, are each present in the composition in an amount corresponding to about 10 times that of the bacteriophage strain having a genome that comprises the nucleic acid sequence of SEQ ID NO:3, or the variant thereof. In some embodiments, the composition comprises bacteriophage strains having genomes that comprise nucleic acid sequences of SEQ ID NO:1, SEQ ID NO:2, SEQ ID NO:3, SEQ ID NO:4, and SEQ ID NO:5.

In another aspect, the instant invention is directed to pharmaceutical compositions comprising phage cocktails, specifically, pharmaceutical compositions comprising any of the compositions described above and a pharmaceutically acceptable carrier. In some embodiments, the pharmaceutical composition is formulated for topical application. In some embodiments, the pharmaceutical composition comprises a sterile buffer, e.g., a buffer comprising about 0.05 M Tris-HCl, about 0.1M NaCl, and about 10 mM $MgSO_4.7H_2O$. In some embodiments, the pharmaceutical composition is contained in an ampoule.

In some embodiments, the pharmaceutical composition further comprises an additional agent, e.g., an agent selected from the group consisting of an antibiotic agent, an anti-inflammatory agent, an antiviral agent, a local anesthetic agent, a growth factor, and a corticosteroid. In some embodiments, the additional agent is an antibiotic agent, e.g., an antibiotic agent having antibacterial activity against *Acinetobacter baumannii, Pseudomonas aeruginosa*, and/or *Staphylococcus aureus*; or an antibiotic agent having antibacterial activity against bacteria other than *Acinetobacter baumannii, Pseudomonas aeruginosa*, and *Staphylococcus aureus*. More specifically, in some embodiments, the additional agent is an antibiotic agent having antibacterial activity against *Staphylococcus aureus* or an antibiotic agent having antibacterial activity against bacteria other than *Staphylococcus aureus*. In some embodiments, the additional agent is an antibiotic agent having antibacterial activity against *Pseudomonas aeruginosa* or an antibiotic agent having antibacterial activity against bacteria other than *Pseudomonas aeruginosa*. In some embodiments, the additional agent is an antibiotic agent having antibacterial activity against *Acinetobacter baumannii* or an antibiotic agent having antibacterial activity against bacteria other than *Acinetobacter baumannii*. In some embodiments, administration of the antibiotic agent comprises systemic administration.

In some embodiments, the composition is for use in treating a bacterial infection associated with an area of non-intact skin, and each of the phage strains is present in the composition in an amount corresponding to $10^3$ to $10^{13}$ phage particles/$cm^2$ of the area. In some embodiments, each of the phage strains is present in the composition in an amount corresponding to $10^7$ to $10^9$ phage particles/$cm^2$ of the area.

Another aspect of the instant invention is directed to methods of treating or preventing a bacterial infection in a subject in need thereof comprising administering to the subject a therapeutically effective amount of the pharmaceutical composition according to the invention. In some embodiments, the bacterial infection is an infection by one or more of *Acinetobacter baumannii, Pseudomonas aeruginosa*, and *Staphylococcus aureus*. In some embodiments, the pharmaceutical composition is administered topically. In some embodiments, the subject is a mammal, e.g., a human. In some embodiments, the bacterial infection is diabetic foot infection. In some embodiments, the diabetic foot infection comprises a cutaneous ulcer. In some embodiments, the bacterial infection is associated with an area of non-intact skin selected from a sore associated with cellulitis, an erysipelas lesion, a burn wound, a chronic ulcer, a decubitus ulcer, and a pressure sore. In some embodiments, the treatment comprises topically administering the pharmaceutical composition to a cutaneous ulcer associated with diabetic foot infection. In some preferred embodiments, administration follows mechanical debridement of the ulcer. In some embodiments, administration comprises use of at least one of a dressing, an instillation device, and a negative pressure wound therapy device.

In some embodiments, the pharmaceutical composition is administered every 4 hours or every 6 hours for an initial 24 hours. In some embodiments, following the initial 24 hours, the pharmaceutical composition is administered every 12 hours or every 24 hours for at least 3 additional days. In some embodiments, the pharmaceutical composition is administered every 12 hours or every 24 hours for at least 4 additional days.

In some embodiments, the method is used in combination with a standard therapy for diabetic foot infection, e.g., a standard therapy selected from the group consisting of extracellular matrix replacement therapy, moist wound therapy, negative pressure wound therapy, arterial re-vascularization therapy, hyperbaric oxygen therapy, administration of an antibiotic agent, and administration of a growth factor. In some embodiments, the moist wound therapy comprises use of an adhesive-backing film, a silicone-coated foam, a hydrogel, and/or a hydrocolloid. In some embodiments, the extracellular matrix replacement therapy comprises use of bio-engineered tissue. In some embodiments, administration of the antibiotic agent comprises systemic administration. In some embodiments, the growth factor is at least one selected from the group consisting of platelet-derived growth factor, granulocyte colony-stimulating factor, epidermal growth factor, fibroblast growth factor, nerve growth factor, and vascular endothelial growth factor. In some embodiments, administration of the growth factor comprises topical administration. In some embodiments, the method is used in combination with a non-standard therapy for diabetic foot infection, e.g., where diabetic foot infection is refractory to a standard therapy.

4.1 DEFINITIONS

As used herein, the term "isolated" in the context of nucleic acid molecules refers to a first nucleic acid molecule which is separated from other nucleic acid molecules which are present in the natural source of the first nucleic acid molecule. Moreover, an "isolated" nucleic acid molecule, such as a cDNA molecule, is substantially free of other cellular material, or culture medium when produced by recombinant techniques, or substantially free of chemical precursors or other chemicals when chemically synthesized and may be free of other cDNA or other genomic DNA molecules, e.g., where it has been isolated from other clones in a nucleic acid library. Further, "isolated" genomic DNA is substantially free of other viral cellular material, or culture medium when produced by recombinant techniques, or substantially free of chemical precursors or other chemicals when chemically synthesized, and may be free of other cDNA or other genomic DNA molecules, e.g., where it has been isolated from preparations containing more than bacteriophage and/or bacterial strain.

The term "purified" with respect to a bacteriophage means that the phage has been measurably increased in concentration by any purification process, including but not limited to, isolation from the environment or culture, e.g., isolation from culture following propagation and/or amplification, centrifugation, etc., thereby partially, substantially, nearly completely, or completely removing impurities, such as host cells and host cell components. One of skill in the art will appreciate the amount of purification necessary for a given use. For example, an isolated phage meant for use in therapeutic compositions intended for administration to humans ordinarily must be of high purity in accordance with regulatory standards and good manufacturing processes.

The term "purified" means that the peptide, polypeptide, fusion protein, or nucleic acid molecule has been measurably increased in concentration by any purification process, including but not limited to, column chromatography, HPLC, precipitation, electrophoresis, etc., thereby partially, substantially, nearly completely, or completely removing impurities, such as precursors or other chemicals involved in preparing the peptide, polypeptide, fusion protein, or nucleic acid molecule. One of skill in the art will appreciate the amount of purification necessary for a given use. For example, isolated genomic DNA meant for use in therapeutic compositions intended for administration to humans ordinarily must be of high purity in accordance with regulatory standards and good manufacturing processes.

As used herein, the term "variant" in the context of nucleic acid sequences refers to a nucleic acid sequence that comprises or consists of a nucleic acid sequence having a sequence identity of at least 80%, 85%, 90%, 93%, 94%, 95%, 96%, 97%, 98%, or at least 99% with a reference nucleic acid sequence. A variant may be selected that maintains one or more function of the reference nucleic acid sequence. For example, a variant bacteriophage may exhibit at least one biological activity, e.g., antimicrobial or antibacterial activity (e.g., lytic killing activity), of the bacteriophage from which it is derived.

As used herein, the term "host cell" refers to the particular subject cell transfected with a nucleic acid molecule and the progeny or potential progeny of such a cell that contain the nucleic acid molecule or chromosomally integrated version thereof. Progeny of such a cell may not be identical to the parent cell transfected with the nucleic acid molecule due to mutations or environmental influences that may occur in succeeding generations or integration of the nucleic acid molecule into the host cell genome. For the generation of bacteriophage, the host cell may or may not be of the same species or strain from which the bacteriophage was isolated or cultured.

As used herein, the term "in combination" or "in further combination" or "further in combination" refers to the use of an additional prophylactic and/or therapeutic agent as well as a phage cocktail of the invention. The use of the term "in combination" does not restrict the order in which prophylactic and/or therapeutic agents are administered to a subject. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject.

As used herein, the terms "prophylactic agent" and "prophylactic agents" refer to an agent, such as a bacteriophage cocktail of the invention, which can be used in the prevention, management, or control of one or more symptoms of a disease or disorder, in particular, a disease or disorder associated with a bacterial infection, such as diabetic foot infection.

As used herein, the terms "therapeutic agent" and "therapeutic agents" refer to an agent, such as a bacteriophage cocktail of the invention, that can be used in the treatment, management, or control of one or more symptoms of a disease or disorder, in particular, a disease or disorder associated with a bacterial infection, such as diabetic foot infection.

As used herein, the terms "treat", "treatment" and "treating" refer to obtaining a therapeutic benefit in a subject receiving a pharmaceutical composition. With respect to achieving a therapeutic benefit, the object is to eliminate, lessen, decrease the severity of, ameliorate, or slow the progression of the symptoms or underlying cause (e.g., bacterial infection) associated with the pathological condition or disorder. A "therapeutically effective amount" refers to that amount of a therapeutic agent, such as a phage cocktail pharmaceutical composition of the invention, sufficient to achieve at least one therapeutic benefit in a subject receiving the pharmaceutical composition.

As used herein, the terms "prevent", "prevention" and "preventing" refer to obtaining a prophylactic benefit in a subject receiving a pharmaceutical composition. With respect to achieving a prophylactic benefit, the object is to delay or prevent the symptoms or underlying cause (e.g., bacterial infection) associated with the pathological condition or disorder. A "prophylactically effective amount" refers to that amount of a prophylactic agent, such as a phage cocktail pharmaceutical composition of the invention, sufficient to achieve at least one prophylactic benefit in a subject receiving the pharmaceutical composition.

As used herein, the terms "antibacterial activity" and "antimicrobial activity", with reference to a bacteriophage (or variant or fragment thereof) or bacteriophage product, are used interchangeably to refer to the ability to kill and/or inhibit the growth or reproduction of a microorganism, in particular, the bacteria of the species or strain that the bacteriophage infects. In certain embodiments, antibacterial or antimicrobial activity is assessed by culturing bacteria, e.g., Gram-positive bacteria (e.g., *S. aureus*), Gram-negative bacteria (e.g., *A. baumannii, E. coli*, and/or *P. aeruginosa*) or bacteria not classified as either Gram-positive or Gram-negative, according to standard techniques (e.g., in liquid culture or on agar plates), contacting the culture with a bacteriophage or variant thereof of the invention and monitoring cell growth after said contacting. For example, in a liquid culture, the bacteria may be grown to an optical density ("OD") representative of a mid-point in exponential growth of the culture; the culture is exposed to one or more concentrations of one or more bacteriophage of the invention, or variants thereof, and the OD is monitored relative to a control culture. Decreased OD relative to a control culture is representative of a bacteriophage exhibiting antibacterial activity (e.g., exhibits lytic killing activity). Similarly, bacterial colonies can be allowed to form on an agar plate, the plate exposed to one or more bacteriophage of the invention, or variants thereof, and subsequent growth of the colonies evaluated related to control plates. Decreased size of colonies, or decreased total numbers of colonies, indicate a bacteriophage with antibacterial activity.

5. BRIEF DESCRIPTION OF THE FIGURES

5.1 DETAILED DESCRIPTION

Figure 1:
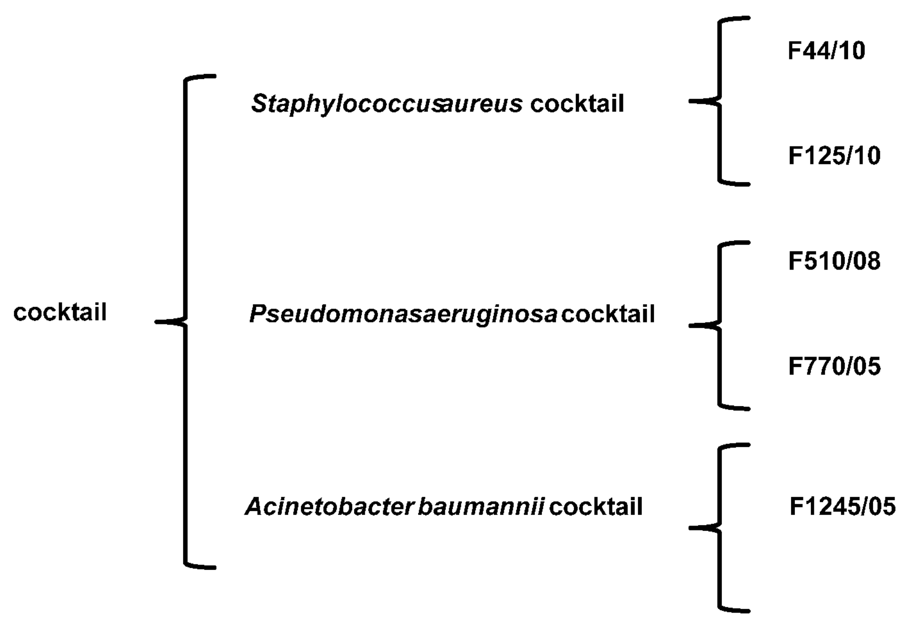
FIG. 1 illustrates the preparation of an exemplary phage cocktail composition in accordance with the instant invention.

The present invention is directed to phage therapy for the treatment and control of bacterial infections, in particular, diabetic foot infections. In one aspect, the invention relates to novel cocktail compositions of different bacteriophage strains. The "cocktail" may comprise at least two different isolated strains of bacteriophage, for example, two, three, four, five, six, seven, eight, nine, ten, or more different isolated bacteriophage strains. The cocktail may be used alone or in further combination with other therapies, e.g., antibiotic agents and/or growth factors.

Phage cocktails provide advantages to the use of phages individually, e.g., to increase the lytic activity against a particular bacterial strain and/or to decrease the possibility of emergence of bacteria resistant to an individual bacteriophage. Different bacteriophage can be mixed as cocktails to broaden their properties, preferably resulting in a collectively greater antibacterial spectrum of activity. However, few phage cocktails exist with antimicrobial activity against different bacteria, probably because of the difficulty in combining different specificities of bacteriophage strains, while maintaining infecting ability and/or lytic activity of the individual bacteriophage in the presence of distinct bacteriophage strains.

In some particularly preferred embodiments, the instant invention provides a cocktail composition comprising the five isolated bacteriophage strains F44/10, F125/10, F770/05, F510/08, and F1245/05, where the cocktail composition is formulated as a topical formulation and finds use in the treatment and/or prevention of diabetic foot infections.

The instant invention, in some embodiments, provides cocktail compositions comprising at least two different isolated bacteriophage strains, with antibacterial activity against the same or different bacterial species or strains. In preferred embodiments, the therapeutic components of the cocktail target two or more species or strains of bacteria. In some embodiments, the phage cocktail comprises at least 2 phage strains, at least 3 phage strains, at least 4 phage strains, at least 5 phage strains, at least 6 phage strains, at least 7 phage strains, at least 8 phage stains, at least 9 phage strains, at least 10 phage strains, or more. In some embodiments, the phage cocktail comprises 2-20 phage strains, 2-15 phage strains, 2-10 phage strains, 3-8 phage strains, or 4-6 phage strains. In more preferred embodiments, the combination does not impair or reduce (or does not substantially or significantly impair or reduce) infecting ability and/or lytic activity of the individual bacteriophage in the presence of distinct bacteriophage strains In some embodiments, at least one phage strain of the cocktail is a strain with antibacterial activity against at least one Gram-negative bacterium, including but not limited to *Acinetobacter baumannii* and *Pseudomonas aeruginosa*; and/or against at least one Gram-positive bacteria including but not limited to *Staphylococcus aureus*. In some embodiments, the cocktail composition comprises at least two different isolated bacteriophage strains where the strains show antibacterial activity against at least one of *S. aureus, P. aeruginosa*, and/or *A. baumannii*. In some preferred embodiments, the cocktail composition shows antibacterial activity against at least two of *S. aureus, P. aeruginosa*, and/or *A. baumannii*. In some even more preferred embodiments, the cocktail composition shows antibacterial activity against each of *S. aureus, P. aeruginosa*, and *A. baumannii*.

In some embodiments, the cocktail composition comprises at least one phage strain showing antibacterial activity against *Staphylococcus aureus*. *S. aureus* is a Gram-positive spherical facultative anaerobe, which grows as grape-like clusters with a characteristic golden color, and the most common cause of staph infections. It is frequently part of the flora of human skin and responsible for a range of infections, including pimples, carbuncles, scalded skin syndrome, pneumonia, gastroenteritis, meningitis, osteomyelitis, endocarditis, toxic shock syndrome, bacteremia, and sepsis. It also is frequently involved in diabetic foot infections, including but not limited to cutaneous ulcers. Such cutaneous ulcers also are referred to herein as "diabetic foot ulcers."

Of particular concern are the methicillin-resistant *Staphylococcus aureus* strains (MRSA). MRSA remained an uncommon occurrence in hospital setting until the 1990's, when there was an explosion in MRSA prevalence in hospitals. MRSA now is considered endemic to hospitals, especially in the UK (Johnson A P et al. 2001 J. Antimicrobial Chemotherapy 48(1): 143-144). Moreover, MRSA presents a new threat in diabetic foot infections (Retrieved Jan. 17, 2009, from CDC: Centers for Disease Control and Prevention Web site). The ulcers and open sores that can occur in diabetic feet put patients at risk for contracting MRSA, and recent studies show evidence of MRSA impairing healing when present in the diabetic wound (Bowling F L, et al. 2009 Curr Diab Rep 9(6):440-444). See also, Kosinski, M A, et al. 2010. Expert Rev AntiInfect Ther. 8(11):1293-1305.

In some embodiments, the invention provides a cocktail composition comprising a bacteriophage having a genome comprising or consisting of the nucleic acid sequence of SEQ ID NO:1. A specific example in accordance with this embodiment is the isolated bacteriophage F44/10, which targets a number of strains of *Staphylococcus* species, including *S. aureus*. Strain F44/10 was deposited on Sep. 16, 2011, under the terms of the Budapest Treaty at NCIMB Limited (Ferguson Building, Craibstone Estate, Bucksburn, Aberdeen, AB21 9YA, Scotland UK) and bears accession number 41867. In some embodiments, the invention provides a cocktail composition comprising a bacteriophage having a genome comprising or consisting of the nucleic acid sequence of SEQ ID NO:2. A specific example in accordance with this embodiment is the isolated bacteriophage F125/10, which also targets a number of strains of *Staphylococcus* species, including *S. aureus*. Strain F125/10 was deposited on Sep. 16, 2011, under the terms of the Budapest Treaty at NCIMB Limited (Ferguson Building, Craibstone Estate, Bucksburn, Aberdeen, AB21 9YA, Scotland UK) and bears accession number 41866. In some embodiments, the cocktail composition includes at least both F44/10 and F125/10 phage strains. In certain embodiments, the phage cocktail comprises at least one phage strain exhibiting antibacterial activity against one or more strains of *S. aureus*. (e.g., F44/10 and/or F125/10) and at least one phage strain exhibiting antibacterial activity against a different bacteria. For example, in some embodiments, the phage cocktail comprises a phage strain having a genome comprising or consisting of SEQ ID NOs:1 or 2, or a variant thereof, in combination with at least one other phage strain having a genome comprising or consisting of SEQ ID NOs:3, 4, or 5, or a variant thereof.

In some embodiments, the cocktail composition comprises at least one phage strain showing antibacterial activity against *Pseudomonas aeruginosa*. *P. aeruginosa* is a common Gram-negative rod-shaped bacterium found in soil, water, skin flora and most man-made environments. It thrives not only in normal atmospheres, but also with little oxygen as a facultative anaerobe, and can infect damaged tissues or immunocompromised individuals, including diabetic patients. Indeed, *P. aeruginosa* frequently causes severe tissue damage in diabetic foot ulcers and a major problem with *P. aeruginosa* infection is that this pathogen exhibits a high degree of resistance to a broad spectrum of antibiotics (Murugan, S. et al. 2010 Intl J of Microbiol Res 1(3):123-128). For example, in the Murugan et al. study, 100% of *P. aeruginosa* isolates from diabetic foot ulcers were found to be resistant to meropenem and over 71% were found to be resistant to imipenem.

In some embodiments, the invention provides a cocktail composition comprising a bacteriophage having a genome comprising or consisting of the nucleic acid sequence of SEQ ID NO:3. A specific example in accordance with this embodiment is the isolated bacteriophage F770/05, which targets a number of strains of *Pseudomonas* species, including *P. aeruginosa*. See also, International Application Publication WO 2010/090542, disclosing said bacteriophage strain. Strain F770/05 was deposited on Sep. 16, 2011, under the terms of the Budapest Treaty at NCIMB Limited (Ferguson Building, Craibstone Estate, Bucksburn, Aberdeen, AB21 9YA, Scotland UK) and bears accession number 41864. In some embodiments, the invention provides a cocktail composition comprising a bacteriophage having a genome comprising or consisting of the nucleic acid sequence of SEQ ID NO:4. A specific example in accordance with this embodiment is the isolated bacteriophage F510/08, which also targets a number of strains of *Pseudomonas* species, including *P. aeruginosa*. Strain F510/08 was deposited on Sep. 16, 2011, under the terms of the Budapest Treaty at NCIMB Limited (Ferguson Building, Craibstone Estate, Bucksburn, Aberdeen, AB21 9YA, Scotland UK) and bears accession number 41868. In some embodiments, the cocktail composition includes at least both F770/05 and F510/08 phage strains. In certain embodiments, the phage cocktail comprises at least one phage strain exhibiting antibacterial activity against one or more strains of *P. aeruginosa* (e.g., F770/05 and/or F510/08) and at least one phage strain exhibiting antibacterial activity against different bacteria. For example, in some embodiments, the phage cocktail comprises a phage strain having a genome comprising or consisting of SEQ ID NOs:3 or 4, or a variant thereof, in combination with at least one other phage strain having a genome comprising or consisting of SEQ ID NOs:1, 2, or 5, or a variant thereof.

In some embodiments, the cocktail composition comprises at least one phage strain showing antibacterial activity against *Acinetobacter baumannii*. *A. baumannii* is a species of bacteria that causes a number of severe clinical infections, particularly in individuals with compromised immune systems, including diabetic patients. For example, *A. baumannii* has been isolated from diabetic patients with lower extremity infection (Colayco, C A S, et al 2002 Phil J Microbiol Infect Dis 31(4):151-106). *A. baumannii* is a pleomorphic aerobic gram-negative bacillus that often enters the body through open wounds, such as diabetic foot ulcers. It also is known to be resistant to multiple antibiotics and the number of nosocomial infections caused by *A. baumannii* has increased in recent years. See also Browne A C, et al. 2001 Ostomy Wound Management 47(10):44-49 (discussing the occurrence of *S. aureus, P. aeruginosa*, and *Acinetobacter* species in diabetic foot ulcers). *Acinetobacter baumannii* is a colonizer that generally appears later in the process of wound infection. Accordingly, in certain embodiments, it is important that the phage cocktail composition comprise bacteriophage that infect *Acinetobacter baumannii.*

In some embodiments, the invention provides a cocktail composition comprising a bacteriophage having a genome comprising or consisting of the nucleic acid sequence of SEQ ID NO:5. A specific example in accordance with this embodiment is the isolated bacteriophage F1245/05, which targets a number of strains of *Acinetobacter* species, including *A. baumannii*. See also, International Application Publication WO 2010/090542, disclosing said bacteriophage strain. Strain F1245/05 was deposited on Sep. 16, 2011, under the terms of the Budapest Treaty at NCIMB Limited (Ferguson Building, Craibstone Estate, Bucksburn, Aberdeen, AB21 9YA, Scotland UK) and bears accession number 41865. In certain embodiments, the phage cocktail comprises at least one phage strain exhibiting antibacterial activity against one or more strains of *A. baumannii* (e.g., F1245/05) and at least one phage strain exhibiting antibacterial activity against different bacteria. For example, in some embodiments, the phage cocktail comprises a phage strain having a genome comprising or consisting of SEQ ID NO:5, or a variant thereof, in combination with at least one other phage strain having a genome comprising or consisting of SEQ ID NOs:1, 2, 3, or 4, or a variant thereof.

In certain embodiments, the cocktail of the invention comprises a bacteriophage that is a variant of any of the nucleic acid sequences SEQ ID NO:1, SEQ ID NO:2, SEQ ID NO:3, SEQ ID NO:4, and SEQ ID NO:5, which variant bacteriophage exhibits at least one biological activity, e.g., antimicrobial or antibacterial activity (e.g., lytic killing activity), of one or more of bacteriophage strains F44/10, F125/10, F770/05, F510/08, and F1245/05. In some preferred embodiments, a variant of bacteriophage strains F44/10 or F125/10 maintains antimicrobial or antibacterial activity (e.g., lytic killing activity) against one or more of strains of *Staphylococcus* species, more preferably including *S. aureus*. In some preferred embodiments, the cocktail comprises a variant of bacteriophage strains F770/05 or F510/08 that maintains antimicrobial or antibacterial activity (e.g., lytic killing activity) against one or more of strains of *Pseudomonas* species, more preferably including *P. aeruginosa*. In some preferred embodiments, the cocktail comprises a variant of bacteriophage strain P1245/05 that maintains antimicrobial or antibacterial activity (e.g., lytic killing activity) against one or more of strains of *Acinetobacter* species, more preferably including *A. baumannii.*

A variant bacteriophage strain may comprise or consist of a genome having a sequence identity of at least 80%, 85%, 90%, 93%, 94%, 95%, 96%, 97%, 98%, or at least 99% with the nucleic acid sequence of SEQ ID NO: 1, SEQ ID NO: 2, SEQ ID NO: 3, SEQ ID NO: 4, and/or SEQ ID NO: 5, which bacteriophage exhibits at least one biological activity, e.g., antimicrobial or antibacterial activity (e.g., lytic killing activity), of bacteriophage F44/10, F125/10, F770/05, F510/08, and F1245/05, respectively. In some preferred embodiments, a variant of bacteriophage strain F44/10 comprises or consists of a genome having a sequence identity of at least 80%, 85%, 90%, 93%, 94%, 95%, 96%, 97%, 98%, or at least 99% with the nucleic acid sequence of SEQ ID NO:1 and maintains antimicrobial or antibacterial activity (e.g., lytic killing activity) against one or more of strains of *Staphylococcus* species, more preferably including *S. aureus*. In some preferred embodiments, a variant of bacteriophage strain F125/10 comprises or consists of a genome having a sequence identity of at least 80%, 85%, 90%, 93%, 94%, 95%, 96%, 97%, 98%, or at least 99% with the nucleic acid sequence of SEQ ID NO:2 and maintains antimicrobial or antibacterial activity (e.g., lytic killing activity) against one or more of strains of *Staphylococcus* species, more preferably including *S. aureus*. In some preferred embodiments, a variant of bacteriophage strain F770/05 comprises or consists of a genome having a sequence identity of at least 80%, 85%, 90%, 93%, 94%, 95%, 96%, 97%, 98%, or at least 99% with the nucleic acid sequence of SEQ ID NO:3 and maintains antimicrobial or antibacterial activity (e.g., lytic killing activity) against one or more of strains of *Pseudomonas* species, more preferably including *P. aeruginosa*. In some preferred embodiments, a variant of bacteriophage strain F510/08 comprises or consists of a genome having a sequence identity of at least 80%, 85%, 90%, 93%, 94%, 95%, 96%, 97%, 98%, or at least 99% with the nucleic acid sequence of SEQ ID NO:4 and maintains antimicrobial or antibacterial activity (e.g., lytic killing activity) against one or more of strains of *Pseudomonas* species, more preferably including *P. aeruginosa*. In some preferred embodiments, a variant of bacteriophage strain P1245/05 comprises or consists of a genome having a sequence identity of at least 80%, 85%, 90%, 93%, 94%, 95%, 96%, 97%, 98%, or at least 99% with the nucleic acid sequence of SEQ ID NO:5 and maintains antimicrobial or antibacterial activity (e.g., lytic killing activity) against one or more of strains of *Acinetobacter* species, more preferably including *A. baumannii*.

Alternatively, or in addition, the cocktail of the invention comprises a variant that has a genome comprising a functional fragment of the nucleic acid sequence of SEQ ID NO:1, SEQ ID NO:2, SEQ ID NO:3, SEQ ID NO:4, and/or SEQ ID NO: 5, which variant bacteriophage exhibits at least one biological activity, e.g., antimicrobial or antibacterial activity (e.g., lytic killing activity), of bacteriophage F44/10, F125/10, F770/05, F510/08, and F1245/05, respectively, preferably as described above.

In some embodiments, the invention provides a cocktail composition comprising at least two different isolated strains of bacteriophage, each strain having a genome that comprises a nucleic acid sequence selected from the group of consisting of SEQ ID NO:1 (F44/10), SEQ ID NO:2 (F125/10), SEQ ID NO:3 (F770/05), SEQ ID NO:4 (F510/08), and SEQ ID NO:5 (F1245/05), or a variant thereof, as described above. In some preferred embodiments, the cocktail composition comprises at least one of the bacteriophage strains having a genome that comprises the nucleic acid sequence of SEQ ID NO:1 or SEQ ID NO:2, or a variant thereof. In some more preferred embodiments, the cocktail composition comprises at least both bacteriophage strains having genomes that comprise the nucleic acid sequences of SEQ ID NO:1 and SEQ ID NO:2, or variants thereof. In some still more preferred embodiments, the cocktail composition comprises at least a third bacteriophage strain, said third strain having a genome that comprises a nucleic acid sequence selected from the group consisting of SEQ ID NO:3, SEQ ID NO:4, and SEQ ID NO:5, or a variant thereof. In some even more preferred embodiments, the cocktail composition comprises at least a third and a fourth bacteriophage strain, said third and fourth strains each having a genome that comprises a nucleic acid sequence selected from the group consisting of SEQ ID NO:3, SEQ ID NO:4, and SEQ ID NO:5, or a variant thereof.

In some preferred embodiments, the cocktail composition comprises at least one of the bacteriophage strains having a genome that comprises the nucleic acid sequence of SEQ ID NO:3 or SEQ ID NO:4, or a variant thereof. In some more preferred embodiments, the cocktail composition comprises at least both bacteriophage strains having genomes that comprise the nucleic acid sequences of SEQ ID NO:3 and SEQ ID NO:4, or variant(s) thereof. In some still more preferred embodiments, the cocktail composition comprises at least a third bacteriophage strain, said third strain having a genome that comprises a nucleic acid sequence selected from the group consisting of SEQ ID NO:1, SEQ ID NO:2, and SEQ ID NO:5, or variant(s) thereof. In some even more preferred embodiments, the cocktail composition comprises at least a third and a fourth bacteriophage strain, said third and fourth strains each having a genome that comprises a nucleic acid sequence selected from the group consisting of SEQ ID NO:1, SEQ ID NO:2, and SEQ ID NO:5, or variant(s) thereof.

In some preferred embodiments, the cocktail composition includes the bacteriophage strain having a genome that comprises the nucleic acid sequence of SEQ ID NO:5, or a variant thereof. In some more preferred embodiments, the cocktail composition comprises the bacteriophage strain having a genome that comprises the nucleic acid sequence of SEQ ID NO:5, or a variant thereof, along with one, two, or three additional bacteriophage strains, each having a genome that comprises a nucleic acid sequence selected from the group consisting of SEQ ID NO:1, SEQ ID NO:2, SEQ ID NO:3, and SEQ ID NO:4, or a variant thereof.

In a particularly preferred embodiment, the invention provides a cocktail composition comprising at least five isolated bacteriophage strains, said strains having genomes that comprise nucleic acid sequences of SEQ ID NO:1, SEQ ID NO:2, SEQ ID NO:3, SEQ ID NO:4, and SEQ ID NO:5, or a variant thereof. In some such embodiments, the variant selected for any one of SEQ ID NO:1, SEQ ID NO:2, SEQ ID NO:3, SEQ ID NO:4, or SEQ ID NO:5 has at least 93%, 94%, 95%, 96%, 97%, 98%, or 99% sequence identity to the corresponding nucleic acid sequence, and shows antibacterial activity against at least one of *S. aureus, P. aeruginosa*, and *A. baumannii*. Particularly preferred embodiments combine antibacterial activities against all three bacterial strains. In some embodiments, the cocktail composition further comprises one or more additional phage strains, said additional phage strain having antibacterial activity against at least one of *S. aureus, P. aeruginosa*, and *A. baumannii*, and/or against other bacteria.

In a particularly preferred embodiment, the invention provides a cocktail composition comprising five isolated bacteriophage strains, said strains having genomes that comprise nucleic acid sequences of SEQ ID NO:1, SEQ ID NO:2, SEQ ID NO:3, SEQ ID NO:4, and SEQ ID NO:5, or a variant thereof, further in combination with at least one additional phage strain. In some preferred embodiments, the additional phage strain is selected from the group consisting of bacteriophage strain F168/08 having antibiotic activity against one or more strains of *E. faecalis* and/or *E. faecium* (as disclosed in WO 2011/065854 and US Patent Application Publication No. 2012/0052048), bacteriophage strain F170/08 having antibiotic activity against one or more strains of *E. faecalis* and/or *E. faecium* (as disclosed in WO 2011/065854 and US Patent Application Publication No. 2012/0052048), bacteriophage strain F197/08 having antibacterial activity against one or more strains of *Staphylococcus aureus* (as disclosed in US Patent Application Publication No. 2012/0052048), bacteriophage strain F86/06 having antibacterial activity against one or more strains of *Staphylococcus aureus* (as disclosed in US Patent Application Publication No. 2012/0052048), bacteriophage strain F87s/06 having antibacterial activity against one or more strains of *Staphylococcus aureus* (as disclosed in US Patent Application Publication No. 2012/0052048), bacteriophage strain F91a/06 having antibacterial activity against one or more strains of *Staphylococcus aureus* (as disclosed in US Patent Application Publication No. 2012/0052048), bacteriophage strain F391/08 having antibacterial activity against one or more strains of *Klebsiella pneumoniae* (as disclosed in U.S. Provisional Application No. 61/384,015), bacteriophage strain F394/08 having antibacterial activity against one or more strains of *Acinetobacter baumannii* (as disclosed in U.S. Provisional Application No. 61/384,01), bacteriophage strain F488/08 having antibacterial activity against one or more strains of *Escherichia coli* (as disclosed in U.S. Provisional Application No. 61/384,01), and bacteriophage strain F387/08 having antibacterial activity against one or more strains of *Klebsiella pneumoniae* (as disclosed in U.S. Provisional Application No. 61/384,015) (the contents of each are hereby incorporated by reference in their entireties). The contents of U.S. Provisional Application No. 61/384,015, filed on Sep. 17, 2010, and International Application PCT/PT2011/000031, filed on Sep. 19, 2011, also are hereby incorporated by reference in their entireties In some embodiments, the invention provides a composition comprising at least five isolated bacteriophage strains, said strains having genomes that comprise nucleic acid sequences of SEQ ID NO:1, SEQ ID NO:2, SEQ ID NO:3, SEQ ID NO:4, and SEQ ID NO:5, or a variant thereof, where the bacteriophage strains having genomes that comprise the nucleic acid sequences of SEQ ID NOs:1, 2, 4, and 5, or said variants thereof, are each present in said composition in higher amounts compared to that of said bacteriophage strain having a genome that comprises the nucleic acid sequence of SEQ ID NO:3, or said variant thereof. In some preferred embodiments, the bacteriophage strains having genomes that comprise the nucleic acid sequences of SEQ ID NOs:1, 2, 4, and 5, or variants thereof, are each present in a cocktail composition in an amount corresponding to about 2 times, about 5 times, about 8 times, about 9, times, about 10 times, about 11 times, about 12 times, about 15 times, or about 20 times, that of the bacteriophage strain having a genome that comprises the nucleic acid sequence of SEQ ID NO:3, or a variant thereof.

In some embodiments, the phage cocktail composition may or may not involve phage selected for increased in vivo half-life, e.g., as disclosed in U.S. Pat. No. 5,688,501, the contents of which are incorporated herein by reference. In some embodiments, the cocktail is administered in the absence of an isolated polypeptide, such as in the absence of a lyase.

The invention also provides for isolated bacteria infected with one or more of the bacteriophage of the invention. In certain embodiments, the invention provides isolated *S. aureus* infected with a bacteriophage having a genome comprising or consisting of the nucleic acid sequence of SEQ ID NO:1 and/or 2, or a variant thereof. In certain embodiments, the invention provides isolated *P. aeruginosa* infected with a bacteriophage having a genome comprising or consisting of the nucleic acid sequence of SEQ ID NO:3 and/or 4, or a variant thereof. In certain embodiments, the invention provides isolated *A. baumannii* infected with a bacteriophage having a genome comprising or consisting of the nucleic acid sequence of SEQ ID NO:5, or a variant thereof.

The bacteriophage for use in the phage cocktails of the invention can be produced and/or isolated by any methods known in the art and/or disclosed herein. For example, the skilled artisan can use one or more methods to produce and/or isolate a bacteriophage having a genome comprising or consisting of the nucleic acid sequence of SEQ ID NO:1, SEQ ID NO:2, SEQ ID NO:3, SEQ ID NO:4, or SEQ ID NO:5, as well of variants thereof. A method of producing and/or isolating a bacteriophage having a genome that comprises or consists of the nucleic acid sequence of SEQ ID NO: 1 and/or SEQ ID NO: 2, and/or a variant of either, may comprise (i) obtaining a culture of *S. aureus*; (ii) infecting it with the bacteriophage having a genome comprising or consisting of the nucleic acid sequence of SEQ ID NO:1 and/or SEQ ID NO:2, and/or a variant of either; (iii) culturing until significant lysis of the culture is observed; and (iv) isolating from the culture the bacteriophage. The host used may be any bacterial strain, for example, any *S. aureus* strain, susceptible to infection by the bacteriophage and that can be used to replicate same. In some embodiments, the host cell used is *S. aureus* strain 743/06, deposited on Sep. 16, 2011, under the terms of the Budapest Treaty at NCIMB Limited (Ferguson Building, Craibstone Estate, Bucksburn, Aberdeen, AB21 9YA, Scotland UK) with accession number NCIMB 41862. A method of producing and/or isolating a bacteriophage having a genome that comprises or consists of the nucleic acid sequence of SEQ ID NO:3 and/or SEQ ID NO:4, and/or a variant of either, may comprise (i) obtaining a culture of *P. aeruginosa*, (ii) infecting it with the bacteriophage having a genome comprising or consisting of the nucleic acid sequence of SEQ ID NO:3 and/or SEQ ID NO:4, and/or a variant of either; (iii) culturing until significant lysis of the culture is observed; and (iv) isolating from the culture the bacteriophage. The host cell used may be any bacterial strain, for example, any *P. aeruginosa* strain, susceptible to infection by the bacteriophage and that can be used to replicate same. In some embodiments, the host cell used may be, for example, *P. aeruginosa* strain 433/07, deposited on Sep. 16, 2011, under the terms of the Budapest Treaty at NCIMB Limited (Ferguson Building, Craibstone Estate, Bucksburn, Aberdeen, AB21 9YA, Scotland UK) with accession number NCIMB 41861. A method of producing and/or isolating a bacteriophage having a genome that comprises or consists of the nucleic acid sequence of SEQ ID NO:5 and/or a variant thereof, may comprise (i) obtaining a culture of *A. baumannii*; (ii) infecting it with the bacteriophage having a genome comprising or consisting of the nucleic acid sequence of SEQ ID NO:5 and/or a variant thereof; (iii) culturing until significant lysis of the culture is observed; and (iv) isolating from the culture the bacteriophage. The host cell used may be any bacterial strain, for example, any *A. baumannii* strain, susceptible to infection by the bacteriophage and that can be used to replicate same. In some embodiments, the host cell used may be, for example, *A. baumannii* strain 1305/05, deposited on Sep. 16, 2011, under the terms of the Budapest Treaty at NCIMB Limited (Ferguson Building, Craibstone Estate, Bucksburn, Aberdeen, AB21 9YA, Scotland UK) with accession number NCIMB 41863.

Bacteriophage may be isolated from a bacterial sample using any method described herein or known in the art (see, e.g., Carlson, "Working with bacteriophage: common techniques and methodological approaches," In, Kutter and Sulakvelidze (Eds) Bacteriophage: Biology and Applications, $5^{th}$ ed. CRC Press (2005); incorporated herein by reference in its entirety). Specific bacterial strains that may be used include, e.g. *Staphylococcus aureus* 743/06 strain (e.g., for isolating phage F44/10 and F125/10), *Pseudomonas aeruginosa* 433/07 strain (e.g., for isolating phage F770/05 and F510/08), and *Acinetobacter baumannii* strain 1305/05 (e.g., for isolating phage F1245/05). *Staphylococcus aureus* 743/06, *Pseudomonas aeruginosa* 433/07, and *Acinetobacter baumannii* 1305/05 strains were deposited on Sep. 16, 2011, under the terms of the Budapest Treaty at NCIMB Limited (Ferguson Building, Craibstone Estate, Bucksburn, Aberdeen, AB21 9YA, Scotland UK) and bear accession numbers NCIMB 41862, NCIMB 41861, and NCIMB 41863, respectively. Bacteriophage also may be isolated from any other bacterial strain susceptible to infection by one or more of the bacteriophage, and in which the bacteriophage replicate.

5.2 ANTIBIOTIC COMPOSITIONS

The phage cocktails of the present invention are incorporated into a pharmaceutical composition for the use in treatment and/or prevention of bacterial infections (e.g., diabetic foot infections) caused by bacteria including, but not limited to, *A. baumannii, P. aeruginosa*, and/or *S. aureus*. A cocktail of different phage strains, e.g., as disclosed herein, may be combined with a pharmaceutically acceptable carrier, such as an excipient or stabilizer. Examples of pharmaceutically acceptable carriers, excipients, and stabilizers include, but are not limited to, buffers such as phosphate, citrate, and other organic acids; antioxidants including ascorbic acid; low molecular weight polypeptides; proteins, such as serum albumin and gelatin; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™. The pharmaceutical compositions of the present invention (e.g., antibacterial compositions) can also include a lubricant, a wetting agent, a sweetener, a flavoring agent, an emulsifier, a suspending agent, and a preservative, e.g., in addition to the above ingredients.

The bacteriophage cocktail compositions of the present invention may also be combined with one or more non-phage therapeutic and/or prophylactic agents, useful for the treatment and/or prevention of bacterial infections, as described herein and/or known in the art (e.g. one or more antibiotic agents). Other therapeutic and/or prophylactic agents that may be used in combination with the phage cocktails of the invention include, but are not limited to, antibiotic agents, anti-inflammatory agents, antiviral agents, local anesthetic agents, growth factors, and corticosteroids. In some preferred embodiments, the pharmaceutical composition is formulated for treatment and/or prevention of diabetic foot infections and comprises one or more additional therapeutic and/or prophylactic agents selected from antibiotic agents, local anesthetic agents, and growth factors. In some embodiments, the phage cocktail is administered in the absence of an antibiotic agent.

Standard antibiotics that may be used with pharmaceutical compositions comprising a phage cocktail of the invention include, but are not limited to, amikacin, gentamicin, kanamycin, neomycin, netilmicin, paromomycin, rhodostreptomycin, streptomycin, tobramycin, apramycin, rifamycin, naphthomycin, mupirocin, geldanamycin, ansamitocin, carbacephems, imipenem, meropenem, ertapenem, faropenem, doripenem, panipenem/betamipron, biapenem, PZ-601, cephalosporins, cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, cefcapene, cefdaloxime, cefdinir, cefditoren, cefetamet, cefixime, cefmenoxime, cefteram, ceftibuten, ceftiofur, ceftiolene, ceftizoxime, ceftriaxone, cefoperazone, ceftazidime latamoxef, cefclidine, cefepime, cefluprenam, cefoselis, cefozopran, cefpirome, cefquinome, flomoxef. ceftobiprole, azithromycin, clarithromycin, dirithromycin, erythromycin, roxithromycin, aztreonam, pencillin and penicillin derivatives, actinomycin, bacitracin, colistin, polymyxin B, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, garenoxacin, gemifloxacin, stifloxacin, trovalfloxacin, prulifloxacin, acetazolamide, benzolamide, bumetanide, celecoxib, chlorthalidone, clopamide, dichlorphenamide, dorzolamide, ethoxyzolamide, furosemide, hydrochlorothiazide, indapamide, mafendide, mefruside, metolazone, probenecid, sulfacetamide, sulfadimethoxine, sulfadoxine, sulfanilamides, sulfamethoxazole, sulfasalazine, sultiame, sumatriptan, xipamide, tetracycline, chlortetracycline, oxytetracycline, doxycycline, lymecycline, meclocycline, methacycline, minocycline, rolitetracycline, methicillin, nafcillin, oxacilin, cloxacillin, vancomycin, teicoplanin, clindamycin, co-trimoxazole, flucloxacillin, dicloxacillin, ampicillin, amoxicillin and any combination thereof in amounts that are effective to additively or synergistically enhance the therapeutic and/or prophylactic effect of a phage cocktail of the invention for a given infection.

In some preferred embodiments, the pharmaceutical composition of the invention comprises an antibiotic agent having antibacterial activity against one or more of *A. baumannii, P. aeruginosa*, and/or *S. aureus*. In some more preferred embodiments, the pharmaceutical composition of the invention comprises an antibiotic agent having antibacterial activity against *A. baumannii, P. aeruginosa*, and *S. aureus*. In some other embodiments, the pharmaceutical composition of the invention comprises an antibiotic agent having antibacterial activity against bacteria other than *A. baumannii, P. aeruginosa*, and/or *S. aureus*.

In some embodiments, the pharmaceutical composition of the invention is formulated for use in treating and/or preventing bacterial infections caused by *Staphylococcus* species, such as *S. aureus*. In some such embodiments, the pharmaceutical composition comprises a cocktail composition comprising a bacteriophage having a genome comprising or consisting of the nucleic acid sequence of SEQ ID NO:1, such as the isolated bacteriophage F44/10, which targets a number of strains of *Staphylococcus* species, including *S. aureus*. In some embodiments, the pharmaceutical composition comprises a cocktail comprising a bacteriophage having a genome comprising or consisting of the nucleic acid sequence of SEQ ID NO:2, such as isolated bacteriophage F125/10, which targets a number of strains of *Staphylococcus* species, including *S. aureus*. In some embodiments, the pharmaceutical composition comprises a cocktail including at least both F44/10 and F125/10 phage strains. In certain embodiments, the pharmaceutical composition comprises a cocktail including at least one phage strain exhibiting antibacterial activity against one or more strains of *S. aureus*. (e.g., F44/10 and/or F125/10) and at least one phage strain exhibiting antibacterial activity against a different bacteria. For example, in some embodiments, the pharmaceutical composition comprises a cocktail including a phage strain having a genome comprising or consisting of SEQ ID NOs:1 or 2, or a variant thereof, in combination with at least one other phage strain having a genome comprising or consisting of SEQ ID NOs:3, 4, or 5, or a variant thereof. In some embodiments, the pharmaceutical composition may further comprise an additional agent, e.g., an antibiotic agent having antibacterial activity against *S. aureus*; and/or an antibiotic agent having antibacterial activity against bacteria other than *S. aureus*.

In some embodiments, the pharmaceutical composition of the invention is formulated for use in treating and/or preventing bacterial infections caused by *Pseudomonas* species, such as *P. aeruginosa*. In some such embodiments, the pharmaceutical composition comprises a cocktail composition comprising a bacteriophage having a genome comprising or consisting of the nucleic acid sequence of SEQ ID NO:3, such as the isolated bacteriophage F770/05, which targets a number of strains of *Pseudomonas* species, including *P. aeruginosa*. In some embodiments, the pharmaceutical composition comprises a cocktail composition comprising a bacteriophage having a genome comprising or consisting of the nucleic acid sequence of SEQ ID NO:4, such as the isolated bacteriophage F510/08, which also targets a number of strains of *Pseudomonas* species, including *P. aeruginosa*. In some embodiments, the pharmaceutical composition comprises a cocktail including at least both F770/05 and F510/08 phage strains. In certain embodiments, the pharmaceutical composition comprises a cocktail including at least one phage strain exhibiting antibacterial activity against one or more strains of *P. aeruginosa* (e.g., F770/05 and/or F510/08) and at least one phage strain exhibiting antibacterial activity against different bacteria. For example, in some embodiments, the pharmaceutical composition comprises a cocktail including a phage strain having a genome comprising or consisting of SEQ ID NOs:3 or 4, or a variant thereof, in combination with at least one other phage strain having a genome comprising or consisting of SEQ ID NOs:1, 2, or 5, or a variant thereof. In some embodiments, the pharmaceutical composition may further comprise an additional agent, e.g., an antibiotic agent having antibacterial activity against *P. aeruginosa*; and/or an antibiotic agent having antibacterial activity against bacteria other than *P. aeruginosa*.

In some embodiments, the pharmaceutical composition of the invention is formulated for use in treating and/or preventing bacterial infections caused by *Acinetobacter* species, such as *A. baumannii*. In some such embodiments, the pharmaceutical composition comprises a cocktail composition comprising a bacteriophage having a genome comprising or consisting of the nucleic acid sequence of SEQ ID NO:5, such as the isolated bacteriophage F1245/05, which targets a number of strains of *Acinetobacter* species, including *A. baumannii*. In certain embodiments, the pharmaceutical composition comprises a cocktail including at least one phage strain exhibiting antibacterial activity against one or more strains of *A. baumannii* (e.g., F1245/05) and at least one phage strain exhibiting antibacterial activity against different bacteria. For example, in some embodiments, the pharmaceutical composition comprises a cocktail including a phage strain having a genome comprising or consisting of SEQ ID NO:5, or a variant thereof, in combination with at least one other phage strain having a genome comprising or consisting of SEQ ID NOs:1, 2, 3, or 4, or a variant thereof. In some embodiments, the pharmaceutical composition may further comprise an additional agent, e.g., an antibiotic agent having antibacterial activity against *A. baumannii*; and/or an antibiotic agent having antibacterial activity against bacteria other than *A. baumannii*.

Local anesthetics that may be formulated for use with pharmaceutical compositions of the invention include, but are not limited to, tetracaine, tetracaine hydrochloride, lidocaine hydrochloride, dimethisoquin hydrochloride, dibucaine, dibucaine hydrochloride, butambenpicrate, and pramoxine hydrochloride. An exemplary concentration of local anesthetic is about 0.025% to about 5% by weight of the total composition. In some preferred embodiments, the anesthetic agent is formulated with a cocktail of the invention in a pharmaceutical composition that is a topical formulation.

Corticosteroids that may be used with pharmaceutical compositions of the invention include, but are not limited to, betamethasone, dipropionate, fluocinolone, actinide, betamethasone valerate, triamcinolone actinide, clobetasol propionate, desoximetasone, diflorasone diacetate, amcinonide, flurandrenolide, hydrocortisone valerate, hydrocortisone butyrate, and desonide. An exemplary concentration of corticosteroid is about 0.01% to about 1% by weight of the total composition.

Growth factors that may be used with pharmaceutical compositions of the invention include, but are not limited to, platelet-derived growth factor, granulocyte colony-stimulating factor, epidermal growth factor, fibroblast growth factor, nerve growth factor, and vascular endothelial growth factor.

In some preferred embodiments, growth factors used in the treatment and control of diabetic foot ulcers can be used also in combination with a phage cocktail pharmaceutical composition of the invention. For example, platelet-derived growth factor (PDGF) and granulocyte colony-stimulating factor (GCSF) are important growth factors in the treatment and control of diabetic foot ulcers (Papanas et al. 2007. Lower Extremity Wounds 6(1):37-53). PDGF is believed to aid macrophage migration to the ulcer, as well as stimulate collagen synthesis, thus improving healing (see, e.g., Meyer-Ingold W et al. 1995 Cell Biol Int 19:389-398). PDGF is available commercially. Commercially available forms include Procurn (Curative Technologies In., New York), which comprises a solution of all platelet-associated growth factors suspended in a collagen base; and becaplermin (Regranex gel, Ortho-McNeil Pharmaceutical, Inc., Titusville, N.J.), which comprises a recombinant homodimeric PDGF. GCSF is believed to enhance bactericidal and phagocytic activity of neutrophils, activities that may be impaired in the diabetic patient (Roilides E et al 1991 J Infect Dis 163:579-583). PDGF also is available commercially. Commercially available forms include filgrastim (nonglycosylated GCSF; Neupogen, Amgen Inc., Thousand Oaks, Calif.) and lenograstim (glycosylated GCSF; Granocyte, Sanofi Aventis Inc., Paris France).

Additional growth factors used in the treatment and control of diabetic foot ulcers include, but are not limited to, epidermal growth factor (EGF), fibroblast growth factor (FGF), nerve growth factor (NGF), and vascular endothelial growth factor (VEGF). EGF is believed to promote collagen synthesis, epithelialization, and angiogenesis (Brown G L et al 1986 J Exp Med 163:1319-1342; and Brown G L et al 1991 Plast Reconstr Surg 88:189-194). FGF also is believed to promote collagen synthesis, epithelialization, and angiogenesis, as well as aiding fibroblast proliferation (Sasaki T 1992 J Dermatol 19:664-666; and Auirinia A et al 1998 Scand J Plast Reconstr Hand Surg 32:9-18). NGF is believed to promote healing by stimulating keratinocyte growth and new vessel formation (Generini S et al 2004 Exp Clin Endocrinol Diabetes 112:542-544). VEGF also has been shown to accelerate cutaneous healing and is believed to mobilize vascular progenitors and endothelial cells from bone marrow (Galiano R D et al. 2004 Am J Pathol 164:1935-1947). One or more of the growth factors disclosed herein and/or known in the art may be used in combination with a pharmaceutical composition comprising a phage cocktail of the invention.

Pharmaceutical compositions comprising a phage cocktail of the present invention can be formulated in a unit dose or multi-dose formulation. Preferred formulations are formulations that can be topically applied, e.g., formulations selected from ointments, solutions, and sprays. Other suitable formulations include suspensions, emulsions, extracts, powders, or granules; and additionally may include a dispersing agent or a stabilizing agent.

The pharmaceutical compositions of the invention preferably are administered topically (e.g., in the form of a lotion, solution, cream, ointment, or dusting powder), or epi- or transdermally (e.g., by use of a skin patch). In addition or alternatively, the pharmaceutical compositions of the invention can be administered by inhalation, in the form of a suppository or pessary, orally (e.g., as a tablet, which may contain excipients such as starch or lactose, as a capsule, ovule, elixir, solution, or suspension, each optionally containing flavoring, coloring agents, and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration, the compositions may be administered in the form of tablets or lozenges, which can be formulated in a conventional manner. In a preferred embodiment, a phage cocktail of the present invention is formulated for topical administration, either as a single agent, or in combination with other therapeutic and/or prophylactic agents, as described herein or known in the art.

In particularly preferred embodiments, the pharmaceutical compositions of the instant invention are formulated for topical administration, e.g., to an area of non-intact skin. Non-intact skin can include, but is not limited to, skin lesions, vesicles, chronic ulcers, cysts, blisters, bullae, open sores such as decubitus ulcers (bed sores) and other pressure sores, cellulitis sores, erysipelas lesions, wounds, burn wounds, carbuncles, cutaneous ulcers, e.g., cutaneous ulcers associated with diabetic foot infections, or other conditions where the skin is damaged, broken, cracked, breached and/or otherwise compromised. Topical formulations generally include a sterile buffer, such as a sterile PBS, water, or saline buffer, or a sterile SM buffer. One particular SM buffer suitable for use in certain embodiments of the instant invention comprises Tris-HCl, NaCl, and/or $MgSO_4.7H_2O$, e.g., about 0.05 M Tris-HCl (pH 7.4-7.5), about 0.1 M NaCl, and/or about 10 mM $MgSO_4.7H_2O$. In other embodiments, the formulation further comprises an SM buffer and 10 mM $MgCl_2$. In still other embodiments, the formulation further comprises an SM buffer and about 20% to about 30% ethanol.

For topical application to the skin, the pharmaceutical compositions of the present invention may be combined with one or a combination of carriers for topical formulations, which can include, but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof.

Carriers for topical formulations may comprise semi-solid and/or gel-like vehicles, which may include a polymer thickener, water, preservatives, active surfactants, emulsifiers, and/or a solvent or mixed solvent system. U.S. Pat. No. 5,863,560 discloses a number of different carrier combinations that can aid in the exposure of skin to a medicament, and its contents are incorporated herein by reference. The carrier may or may not involve a controlled-release formulation, e.g., as disclosed in US 2008/0260697, the contents of which are incorporated herein by reference. The carrier may or may not involve phage adsorbed on a matrix, e.g., as described in any one of US 2008/0038322, US 2008/0138311, US 2009/0130196, EP 1 812 025, EP 1 817 043, and EP 1 833 497, the contents of which are incorporated herein by reference. In some embodiments, the carrier may or may not involve a viscous formulation, e.g., a gel, e.g., as disclosed in US 2009/0191254, the contents of which are incorporated herein by reference.

In some particularly preferred embodiments, topical pharmaceutical compositions of the invention are provided in a hermetically sealed container. The container may a vial, tube, bottle, ampoule, or the like; and may comprise or consist of glass, plastic, or other suitable material. Ampoules, for example, generally are produced industrially from short lengths of glass tubing, shaped by heating with gas torches and gravity. Computer vision techniques often are employed, e.g., for quality control. The filling and sealing of ampoules may be done by automated machinery. Blank ampoules can be purchased from scientific glass supply houses and sealed, e.g., with a small gas torch, preferably under inert atmospheres. In some embodiments, the container also may be filled with an inert gas, in addition to the pharmaceutical composition. In some embodiments, the phage cocktail composition is provided in an ampoule, or other suitable container, and transferred for use to a vehicle suitable for direct contact with non-intact skin, e.g., a patch, wipe, bandage, dressing, as described below.

The topical mode of delivery may include a smear, a spray, a bandage, a time-release patch, a liquid-absorbed wipe, and combinations thereof. In some particularly preferred embodiments, the phage cocktail composition of the invention is provided, either directly or in a carrier(s), in a patch, wipe, bandage, dressing, or other vehicle suitable for direct contact with the skin, in particular, non-intact skin.

In some embodiments, topical administration of a pharmaceutical composition of the invention comprises use of a dressing. The pharmaceutical composition comprising a phage cocktail of the invention may be incorporated into a dressing and/or applied separately along with the use of a dressing. A dressing promotes healing by keeping a wound moist, creating a barrier against infection, and/or keeping the surrounding skin dry.

In some embodiments, the dressing comprises a moist wound dressing. Moist wound therapy, comprising use of moist wound dressings, represents a standard therapy in the treatment and control of non-healing wounds, including diabetic foot ulcers, for example. In moist wound therapy, wounds are dressed with materials that offer protection from outside contaminants, prevent wound desiccation, and provide an environment conducive to wound closure. The degree of moisture in a wound is to be considered when treating a diabetic ulcer. High levels of exudate warrant the choice of a moisture-absorbing material, including but not limited to alginates, foams, collagen-alginate combinations, carboxymethylcellulose materials, or gauze. Low exudate and desiccated wounds generally respond well to hydrogels. Hydrogel sheets often comprise three-dimensional networks of cross-linked hydrophilic polymers. Amorphous hydrogels are similar in composition to hydrogel sheets but lack the cross-linking. The gel also may comprise additional ingredients, such as collagens, alginate, or complex carbohydrates.

Standard dressing care for the treatment of diabetic foot ulcers in the US is still the use of wet-to-dry or wet-to-moist saline gauze dressings. Alginate dressings often comprise calcium or calcium-sodium salts of natural polysaccharides derived from brown seaweed. When the alginate material comes into contact with sodium-rich wound exudates, an ion exchange takes place, producing a hydrophilic gel.

Additional dressing choices include but are not limited to films including adhesive-backing films, gels, and foams including silicone-coated foams, hydrocolloids, collagen-based dressings, absorbent polymers, and the like. Hydrocolloid dressings often comprise adhesive, absorbent, and elastomeric components. Carboxymethylcellulose, for example, is a common absorptive ingredient. Hydrofiber dressing also often comprise carboxymethylcellulose, for example, sodium carboxymethylcellulose. Foam dressings often comprise a polymer, often polyurethane, with small, open cells that are able to hold fluids. Some varieties of foam dressings have a waterproof film covering the top surface and may have an adhesive coating on the wound contact side or on the wound border. Film dressings often comprise a single thin transparent sheet of polyurethane coated on one side with an adhesive. The sheet is permeable to gases and water vapor but impermeable to wound fluids. Hydrofiber dressings often comprise sodium carboxymethylcellulose fibers. Collagen-based dressings often comprise purified collagen derived from bovine, porcine, equine, or avian sources. Collagen-based dressings are believed to aid wound healing e.g., by stimulating fibroblast production.

In some embodiments, topical administration of a pharmaceutical composition of the invention comprises instillation. The pharmaceutical composition comprising a phage cocktail of the invention may be incorporated into an instillation and/or applied separately along with the use of an instillation. Instillation refers to administration by introduction of the fluid pharmaceutical composition gradually, e.g., drop by drop of the fluid. Typical instillation therapy instills fluid into a wound under a low positive pressure. Devices for use in instillation include, e.g., Kritter-type instillation catheters (see, e.g., Brent H. et al. 2005. Wounds 17(2):37-48). Techniques known in the art to improve instillation and distribution of the fluid include, but are not limited to, filling a wound with instillation fluid, applying porous wound fillers, and/or combining with negative pressure wound therapy.

In some embodiments, topical administration of a pharmaceutical composition of the invention comprises negative pressure wound therapy. Negative pressure wound therapy (NPWT) refers to use of reduced pressure in proximity to a wound, or other area of non-intact skin, to augment and/or accelerates the growth of new tissue. The therapy involves controlled application of sub-atmospheric pressure to the area, using a sealed wound dressing connected to a vacuum pump. "Negative pressure wound therapy" may also be referred to as "reduced pressure therapy" or "vacuum therapy". Typically, reduced pressure is applied to the area of non-intact skin through a porous pad. The porous will contain pores capable of distributing the reduced pressure to the area and/or channeling fluids drawn out.

A number of devices can be used in NPWT. NPWT devices often comprise a vacuum pump, drainage tubing, and/or a dressing set. The pump may be stationary or portable, rely on A C or battery power, and/or allow for regulation of the suction strength. The dressing sets may comprise foam or gauze dressing, e.g., to be placed on the wound, and an adhesive film drape for sealing the area. The drainage tubes may come in a variety of configurations depending on the dressings used or wound to be treated. Once the dressing is sealed, the vacuum pump can be set to deliver continuous or intermittent pressures, with levels of generally varying between −125 and −75 mmHg NPWT may be used for administration of a pharmaceutical composition of the invention, e.g., where the NPWT device used allows for delivery of fluids, such as a fluid pharmaceutical composition. (See, e.g., Gerry R, et al. 2007. Ann Plast Surg 59(1):58-62).

Modes of administration described herein and/or known in the art may be used to deliver desired dosages of the phage cocktails of the invention and in accordance with suitable dosage regimens. Dosages and dosage regimens may vary depending on the particular formulation, route of administration, condition being treated, and other factors. Animal experiments can provide reliable guidance for the determination of effective doses in human therapy, e.g., as within the skill of the ordinary physician. Interspecies scaling of effective doses can be performed by one of ordinary skill in the art following the principles described, e.g., by Mordenti, J. et al. "The use of interspecies scaling in toxicokinetics" in Toxicokinetics and New Drug Development, Yacobi et al., Eds., Pergamon Press, New York 1989, pp 42-96.

The pharmaceutical compositions of the invention can be administered according to a dosage regimen. In the treatment of chronic ulcers and diabetic foot infections, e.g., including but limited to the treatment of cutaneous ulcers associated therewith, a first dosage regimen may be followed initially, e.g., during an induction phase, and a second dosage regimen may be followed after, e.g., during a maintenance phase. In some embodiments, an induction phase dosage regimen is followed over an initial about 12 hours of treatment, or over an initial about 18 hours, about 24 hours, about 36 hours, or about 48 hours. In some preferred embodiments, the induction phase dosage regimen comprises administration of a pharmaceutical composition of the invention about every hour, about every 2 hours, 4 hours, 6 hours, 8 hours, 10 hours, or 12 hours. In more preferred embodiments, the induction phase dosage regimen comprises administration of a pharmaceutical composition of the invention about every 4 hours or about every 6 hours, e.g., over an initial 24 hours. In even more preferred embodiments, the pharmaceutical composition is administered topically in accordance with an induction phase dosage regimen.

In some embodiments, the induction phase is followed by a maintenance phase, e.g., where a different dosage regimen may be followed. The maintenance phase may continue for a number of days, weeks, months, or longer, following initial treatment. In some embodiments, the maintenance phase continues for about 1, 2, 3, 4, 5, 6, or 7 days following the induction phase. In some embodiments, the pharmaceutical composition is administered for 2, 3, or 4 weeks; 2, 4, 6, 8, 10, or 12 months; or 2, 3, 4, 5 or more years. In still some embodiments, the pharmaceutical composition according to the invention is administered chronically, e.g. for several years or over the life of the patient.

In some embodiments, the maintenance phase dosage regimen comprises administration of a pharmaceutical composition of the invention at a lower frequency of doses compared to the induction phase dosage regimen. For example, in some preferred embodiments, the pharmaceutical composition is administered about every 6 hours, 8 hours, 10 hours, 12 hours, 16 hours, 20 hours, 24 hours, 30 hours, 36 hours, 42 hours, or 48 hours. In more preferred embodiments, the maintenance phase dosage regimen comprises administration of a pharmaceutical composition of the invention about every 12 hours or about every 24 hours, e.g., for at least about 3 or 4 additional following the induction phase. In even more preferred embodiments, the pharmaceutical composition is administered topically in accordance with a maintenance phase dosage regimen.

5.3 THERAPEUTIC USE

Another aspect of the instant invention relates to the use of phage cocktail compositions in preventing and/or treating bacterial infections. In specific embodiments, the subject receiving a pharmaceutical composition of the invention is a mammal (e.g., bovine, ovine, caprine, equid, primate (e.g., human), rodent, lagomorph or avian (e.g., chicken, duck, goose)). In preferred embodiments, the subject receiving a pharmaceutical composition of the invention is a human, and particularly a diabetic patient that suffers from or is at risk of suffering from chronic ulcers, including diabetic foot infections. In the context of the present invention, "treatment" refers to obtaining a therapeutic benefit in a subject receiving the pharmaceutical composition. With respect to achieving a therapeutic benefit, the object is to eliminate, lessen, manage, decrease the severity of, prevent worsening, ameliorate, or slow the progression of the symptoms or underlying cause (e.g., bacterial infection) associated with the pathological condition or disorder. It is also contemplated that phage cocktails of the invention, in certain embodiments, may act as a prophylactic or preventative measure, preventing the onset of infection caused by one or more bacteria. "Prevention" refers to obtaining a prophylactic benefit in a subject receiving the pharmaceutical composition. With respect to achieving a prophylactic benefit, the object is to delay or prevent the symptoms or underlying cause (e.g., bacterial infection) associated with the pathological condition or disorder.

The phage cocktails of the present invention have activity against a plurality of bacterial strains. In some preferred embodiments, the phage cocktails have activity against a plurality of strains of *A. baumannii, P. aeruginosa*, and/or *S. aureus*. Accordingly, another aspect of the invention provides methods of treating and/or preventing infections associated with *A. baumannii, P. aeruginosa*, and/or *S. aureus* in both humans and animals using a phage cocktail composition. In other aspects, the invention provides methods of treating and/or preventing infections associated with related species or strains of these bacteria. In some particularly preferred embodiments, the bacterial infection is an infection associated with diabetic lower extremity infections, such as diabetic foot infections.

*A. baumannii, P. aeruginosa*, and *S. aureus* are responsible for many severe opportunistic infections, particularly in individuals with compromised immune systems, including diabetic patients. The pharmaceutical compositions of the present invention are contemplated for treating and/or preventing any infection associated with *A. baumannii, P. aeruginosa*, and/or *S. aureus*, or associated with other species or strains of bacteria, including, but not limited to, infections of the skin, infections in and around wounds, chronic ulcers, ulcers associated with burn wounds, post-operative infections, infections associated with catheters and surgical drains, and infections of the blood. In preferred embodiments, the pharmaceutical compositions of the invention find use in treating and/or preventing bacterial infections associated with areas of non-intact skin Infections associated with areas of non-intact skin include, but are not limited to, infections associated with cutaneous ulcers, such as diabetic foot ulcers, skin lesions, vesicles, cysts, blisters, bullae, open sores such as decubitus ulcers (bed sores) and other pressure sores, chronic ulcers, cellulitis and sores associated therewith, erysipelas and lesions associated therewith, wounds, burns and wounds associated therewith, carbuncles, or other conditions where the skin is damaged, cracked, broken, breached, and/or otherwise compromised.

In particularly preferred embodiments, the phage cocktail compositions of the instant invention find use in treating chronic ulcers. Chronic ulcers may arise from wounds caused by a variety of factors, especially in patients with impaired blood circulation, for example, caused by cardiovascular issues or external pressure from a bed or a wheelchair. More than 8 million patients are diagnosed with chronic skin ulcers each year in the United States alone (Harsha, A. et al., 2008, Journal of Molecular Medicine, 86(8): 961-969), which costs more than 10 billion dollars per year (Margolis, D J, et al., 2002, Journal of the American Academy of Dermatology 46(3): 381-386). Chronic ulcers may develop in the mouth, throat, stomach, and skin. Chronic skin ulcers include diabetic ulcers, venous ulcers, radiation ulcers, and pressure ulcers, the three major categories of chronic skin ulcers being diabetic ulcers, venous stasis ulcers, and pressure ulcers. Chronic ulcers can cause the loss of the integrity of large portions of the skin, even leading to morbidity and mortality.

In even more particularly preferred embodiments, the phage cocktail compositions of the instant invention find use in treating diabetic lower extremity infections, such as diabetic foot infections. Diabetic foot infection is one of the major complications of diabetes mellitus, occurring in about 15% of all diabetic patients and resulting in about 85% of all lower leg amputations. (Brem, et al., J. Clinical Invest., 2007, 117(5):1219-1222). Diabetes mellitus impedes the normal steps of the wound healing process, such that diabetic foot infections can become associated with non-healing, chronic cutaneous ulcers.

A chronic wound represents a failure of the normal processes of acute wound healing. Wound healing has traditionally been divided into three distinct phases: inflammation, proliferation and remodeling. The inflammatory phase of wound healing begins at the time of injury by forming a clot via a platelet plug, thereby initiating a response from neutrophils and macrophages. Neutrophils initially clear the wound of bacteria and debris by releasing a variety of proteases and reactive oxygen free radicals. Macrophages are then attracted to the wound site by chemoattractants and subsequently release their own chemoattractants to stimulate fibroblasts and more macrophages. During the proliferation phase, fibroblasts initiate epithelialization, angiogenesis, and collagenation. Epithelialization generally occurs from the basement membrane if it remains intact and from the wound margins if not intact. Fibroblasts synthesize type III collagen during this phase and transform into myofibroblasts, which help to stimulate wound contraction. During the remodeling phase, type III collagen begins to be replaced by type I collagen. Collagen is woven into an organized, cross-linked network whose strength approaches 80% of the original uninjured tissue.

There are many factors that can stall the three-phase healing process and convert an acute wound into a chronic wound. These may include a low proliferative capacity of the fibroblasts, downregulation of receptors, reduced growth factors, or the absence of a suitable protein matrix in the dermis. Further, poor perfusion and/or nutrition can cause a wound to halt in the inflammatory phase and lead to excessive build-up of exudate in the wound. A chronic ulcer can be considered to be a non-healing area of non-intact skin, such as an area of non-intact skin that fails to follow the normal processes of wound healing, e.g., as described above, and/or that fails to respond, or fails to respond appropriately, to initial treatment. A chronic ulcer on the skin may be characterized as a wound lesion lasting more than four weeks, without remarkable healing tendency or as a frequently recurrent wound (Fonder, M. et al., 2012, Journal of the American Academy of Dermatology 58(2): 185-206). A chronic wounds may appear with red granulation and yellow pus, a dim purple skin around granular tissues, or gray-white and swelling granulation. Standard care procedures for chronic skin ulcer include, e.g., the following: removal of necrotic or infected tissue; establishment of adequate blood circulation; maintenance of a moist wound environment; management of wound infection; wound cleansing; and nutritional support, including blood glucose control for subjects with diabetic ulcers. For example, in the diabetic patient, poor control of blood glucose levels allows bacteria to grow more rapidly in a wound; further still, neural degeneration in diabetes means the condition may not be painful and thus go undetected, at least initially. Chronic ulcers, including diabetic foot ulcers, often become further infected with opportunistic bacteria, leading to exacerbation of the condition. *A. baumannii, P. aeruginosa*, and *S. aureus* are associated with such infections.

*A. baumannii, P. aeruginosa*, and *S. aureus* also are associated with infections that involve organ systems that have a high fluid content, and it is contemplated that the phage cocktails of the invention have therapeutic and/or prophylactic use with respect to such infections. For example, the pharmaceutical compositions of the invention may be used for the prevention or treatment of infections of the respiratory tract, of the cerebrospinal fluid, of peritoneal fluid, and of the urinary tract. The compositions of the invention may also be used to prevent and/or treat nosocomial pneumonia, infections associated with continuous ambulatory peritoneal dialysis (CAPD), catheter-associated bacterimia, and nosocomial meningitis. In some embodiments, a phage cocktail composition of the invention is used prophylactically, e.g., in a hospital setting. For example, a phage cocktail composition of the instant invention may find use in preventing infections associated with wounds or damaged skin, e.g., due to catheterization and any other medical procedures or devices.

In some preferred embodiments, the pharmaceutical composition of the invention is formulated for use in methods of treating and/or preventing bacterial infections caused by *A. baumannii, P. aeruginosa*, and/or *S. aureus*. In some more preferred embodiments, the pharmaceutical composition of the invention is formulated for use in methods of treating and/or preventing bacterial infections caused by *A. baumannii, P. aeruginosa*, and *S. aureus*. In some other embodiments, the pharmaceutical composition of the invention is formulated for use in methods of treating and/or preventing bacterial infections caused by bacteria other than *A. baumannii, P. aeruginosa*, and/or *S. aureus*.

In some preferred embodiments, the pharmaceutical composition of the invention is formulated for use in methods of treating and/or preventing bacterial infections caused by *Staphylococcus* species, such as *S. aureus; Pseudomonas* species, such has *P. aeruginosa*; and *Acinetobacter* species, such as *A. baumannii*. In some such embodiments, the pharmaceutical composition comprises a cocktail composition comprising a bacteriophage having a genome comprising or consisting of the nucleic acid sequence of SEQ ID NOs:1, 2, 3, 4, and 5, or a variant thereof, such as the isolated bacteriophage strains F44/10, F125/10, F770/05, F510/08, and F1245/05, or variants thereof. In some particularly preferred embodiments, the pharmaceutical cocktail composition is used in the treatment, prevention, control, and/or management of chronic ulcers, such as diabetic foot infections and cutaneous ulcers associated therewith.

In some embodiments, the invention provides methods of treating and/or preventing chronic ulcers, comprising administering to a subject in need thereof a therapeutically or prophylactically effective amount of a pharmaceutical composition of the instant invention. In preferred embodiments, administration comprises topical administration to the area of non-intact skin associated with the chronic ulcer. In more preferred embodiments, topical administration follows debridement of the area to be treated In some embodiments, the invention provides methods of treating and/or preventing diabetic foot infections, comprising administering to a subject in need thereof a therapeutically or prophylactically effective amount of a pharmaceutical composition of the instant invention. In preferred embodiments, administration comprises topical administration to the area of non-intact skin associated with the diabetic foot infection, e.g., a cutaneous ulcer. In more preferred embodiments, topical administration follows debridement of the area to be treated.

Debridement can be accomplished by a number of approaches. Surgical debridement involves cutting away dead tissues of the wound or other area of non-intact skin. Mechanical debridement uses various methods to loosen and remove wound debris, such as a pressurized irrigation device, a whirlpool water bath, or specialized dressings. Autolytic debridement enhances the body's natural process of recruiting enzymes to break down dead tissue, for example, using an appropriate dressing that keeps the wound moist and clean. Enzymatic debridement uses chemical enzymes and appropriate dressings to further aid in the break down dead tissues at the site of a wound or other area of non-intact skin.

Debridement improves topical treatment because it reduces the bio-burden of bacteria present and also opens a time-dependent therapeutic window for topical antimicrobial therapy (TAT) (Wolcott R D, et al. 2010. J Wound Care 19:320-328). Regarding the timing for debridement, early or immediate debridement is preferred to delayed debridement once this treatment option is chosen in the management of a wound. Further, multiple debridements during wound management may be indicated (Wolcott R D, et al. 2009. J Wound Care 18(2):54-6). For example, in some embodiments, debridement precedes topical application of a phage cocktail composition of the instant invention, and is repeated before every administration of the cocktail composition. In some embodiments, debridement is performed only before every other administration of the cocktail composition, or only before every $3^{rd}$, $4^{th}$, $5^{th}$, or $6^{th}$ administration of the cocktail composition. In some embodiments, whether or not wound debridement is performed before topical administration of a cocktail composition of the instant invention is within the clinical judgment of a health care practitioner treating the wound, e.g., the physician, physician's assistant, or emergency medical personnel.

Phage cocktail compositions of the present invention can find use in the treatment, management, control, and/or prevention of infections associated with chronic ulcers, including diabetic foot infections and cutaneous ulcers associated therewith. In other embodiments, phage cocktail compositions of the present invention find use in the treatment, management, control, and/or prevention of bacterial infections associated with other areas of non-intact skin, such as a cellulites sore, an erysipelas lesion, a decubitus ulcer, a burn wound, and a pressure sore. In some such embodiments, the composition used may be a topical composition, formulated for topical administration, e.g., for direct application to an area of non-intact skin, such as described above.

Phage cocktail compositions of the present invention also find use in the treatment, management, control, and/or prevention of decubitus ulcers. Decubitus ulcers, also called pressure sores or pressure ulcers, are injuries to the skin and underlying tissues resulting from prolonged pressure on the area. For example, bedsores most often develop on skin that covers bony areas of the body, such as the heel, ankles, hips or buttocks.

Bedsores fall into one of four stages based on their severity. Stage I is the beginning stage of a pressure sore while the skin still is intact. The skin may appear red, ashen, bluish or purple, and fails to blanch when touched. Stage II often involves an open wound of non-intact skin. At this stage, the outer layer of skin (epidermis) and part of the underlying layer of skin (dermis) has been damaged or lost. The ulcer may appear as a shallow, pinkish-red, basin-shaped wound. In stage III, the ulcer is a deep wound, where the loss of skin may expose some amount of fat, and the ulcer has a crater-like appearance. The bottom of the wound also may have some yellowish dead tissue (slough). A Stage IV ulcer exhibits large-scale loss of tissue, where the wound may expose muscle, bone and tendons. The bottom of the wound will likely contain slough or dark, crusty, dead tissue (eschar).

As in the treatment of diabetic foot ulcers, debridement may be used to remove damaged, dead, or infected tissue from the wound, facilitating proper healing, e.g., as described herein and/or otherwise known in the art. In some embodiments, administration of a pharmaceutical composition of the invention follows debridement. For example, a pharmaceutical composition comprising a phage cocktail disclosed herein may be topically administered to a decubitus ulcer following surgical, mechanical, autolytic, or enzymatic debridement thereof.

Phage cocktail compositions of the present invention also find use in the treatment, management, control, and/or prevention of cellulitis and/or erysipelas, including but not limited to sores and lesions associated with cellulitis and erysipelas. Cellulitis and erysipelas are skin infections that develop as a result of bacterial entry via breaches in the protective barrier of the skin. For example, cracks in the skin, cuts, blisters, burns, insect bites, spider bites, tattoos, surgical wounds, intravenous drug injection, or sites of intravenous catheter insertion may provide a means of entry for bacteria. Group A *Streptococcus* and *Staphylococcus* are the most common bacteria involved in cellulitis. Cellulitis is observed most frequently among middle-aged and elderly individuals, while erysipelas occurs in young children and the elderly (Ellis Simonsen S M et al. 2006. Epidemiol Infect. 134(2):293; and Eriksson B. et al. 1996 Clin Infect Dis 23:1091). Also, people with immune deficiency, diabetes, alcoholism, fungal infections, and impaired lymphatic drainage are at increased risk. Diabetics are especially prone to cellulitis in the feet, because the disease causes impairment of blood circulation in the legs. The lower extremities are the most common site of infection for both erysipelas and cellulitis (Ellis Simonsen S M et al. 2006. Epidemiol Infect. 134(2):293; Chartier C et al 1996 Int J Dermatol 35:779).

Cellulitis and erysipelas often coexist and generally manifest as areas of skin erythema, edema, and warmth. They differ in that erysipelas involves the upper dermis and superficial lymphatics, whereas cellulitis involves the deeper dermis and subcutaneous fat. Accordingly, erysipelas has more distinctive anatomic features than cellulitis—erysipelas lesions may be raised above the level of surrounding skin with a clear line of demarcation between involved and uninvolved tissue (Bisno A L et al. 1996 N Engl J Med 334:240). The lesion may appear red, swollen, warm, hardened, and/or as a rash similar in consistency to an orange peel. Erysipelas may appear on the face, for example, in a "butterfly" pattern. More severe infections can result in vesicles, bullae, and petechiae, with possible skin necrosis. In addition, patients with erysipelas tend to have acute onset of symptoms with systemic manifestations, including fever and chills.

Patients with cellulitis tend to have a more gradual course of development, with symptoms appearing over a few days' time. Various forms of cellulitis include periorbital cellulitis, abdominal wall cellulitis (in morbidly obese individuals), buccal cellulitis (due to *Streptococcus pneumoniae*), Ludwig's angina (cellulitis within the submandibular space), and perianal cellulitis (due to group A beta-hemolytic *streptococcus*) (Barzilai A, et al, 1998 Pediatr Infect Dis J. 17(4):358; Thorsteinsdottir B, et al. 2005 Scand J Infect Dis. 37(8):605). Cellulitis also can result in influenza-like symptoms, with high temperatures and shaking.

In some embodiments, treatment of cellulitis or erysipelas further comprises administration of an antibiotic agent. For example, a pharmaceutical composition according to the invention may be topically administered to an erysipelas lesion, in combination with an antibiotic agent selected from the group consisting of penicillin, clindamycin, and erythromycin. As another example, a pharmaceutical composition according to the invention may be topically administered to a sore associated with cellulitis, in combination with an antibiotic agent selected from the group consisting of flucloxacillin, dicloxacillin, penicillins, ampicillin, and amoxicillin. The antibiotic may be administered orally, intravenously, or topically, e.g., along with topical administration of a cocktail of the instant invention.

Phage cocktail compositions of the present invention also find use in the treatment, management, control, and/or prevention of infections associated with burn wounds. A burn wound is any area of non-intact skin caused, directly or indirectly, from a burn. A burn is a type of injury to the skin that can be caused by heat, as well as electricity, chemicals, light, radiation or friction. Burns may affect only the skin (epidermal tissue), but in some cases also injure deeper tissues, such as muscle, bone, and blood vessels. Burns can be classified by mechanism of injury, depth, extent and associated injuries, and comorbidities. Burns conventionally are described based on the depth of injury to the dermis, being loosely classified as first, second, third, and fourth degree burns. Walls et al., 2009, Rosen's Emergency Medicine: Expert Consult Premium Edition (Rosen's Emergency Medicine: Concepts & Clinical Practice (2v) Important characteristics of a burn wound include its cause (thermal, chemical, electrical), anatomic location, depth (full or partial thickness), duration, and extent (percent total body surface area). Patient characteristics that affect burn wound healing include age, nutritional status, underlying medical conditions, and concomitant injury (e.g., head trauma, inhalation injury, bone fractures).

Infections among burn patients are a major problem, with the reported incidence of nosocomial infections varying at 63-240 per 100 patients and 53-93 per 1000 patient days, mainly depending on the definitions used (Chim H, et al, 2007, Burns 33:1008-1014; and Wibbenmeyer L, et al., 2006, J Burn Care Res 27:152-60). Moreover, bacterial infection of burn wounds are associated with adverse outcomes and mortality. In a series of 175 patients with severe burns, for example, infections preceded multiorgan dysfunction in 83% of patients and were considered the direct cause of death in 36% of patients who did not survive (Fitzwater J, et al., 2003, J Trauma 54:959-66). Burn wounds may become infected from multiple sources. Burn wounds may become initially infected with Gram positive bacteria, mainly staphylococci, that are normal deep inhabitants of the sweat glands and hair follicles exposed by the burn (Sharma B R., 2007, Infect Dis Clin North Am 21:745-59; ix). The moist, vascular burn eschar further may foster microbial growth. Gram negative bacterial infections may result from translocation from the colon, for example, due to reduced mesenteric blood flow at the time of burn and subsequent insults (Herndon D N, et al., 2000, Crit Care Med 28:1682-3). Furthermore, burns patients may develop immune deficits, including impaired cytotoxic T lymphocyte response, myeloid maturation arrest causing neutropenia, impaired neutrophil function, and decreased macrophage production (Sharma B R., 2007, Infect Dis Clin North Am 21:745-59, ix; Gamelli R L, et al., 2000, J Burn Care Rehabil 21:64-9; Hunt J P, et al., 1998, J Surg Res 80:243-51; and Shoup M, et al., 1998, Ann Surg 228:112-22). Finally, burns patients are susceptible to hospital acquired infections, common to other patients in intensive care units, including intravascular catheter related infections and ventilator associated pneumonia, with an overall incidence of infection higher than that of other patients in intensive care units (Chim H, et al., 2007, Burns 33:1008-14; and Wibbenmeyer L, et al., 2006, J Burn Care Res 27:152-60). Indeed, most episodes of bloodstream infection in burn patients after the first week are caused by hospital-type multidrug resistant bacteria (Wibbenmeyer L, et al., 2006, J Burn Care Res 27:152-60; and Ressner R A, et al., 2008, J Am Coll Surg 206:439-44).

Convention treatment of burns includes debridement and excision, applying dressings the wound, wound closure, skin grafting, fluid resuscitation, management of wound infection such as administering antibiotics, pain control, nutritional support, and/or measures to inhibit excessive scar formation. A burn may be covered with a clean and dry sheet or dressing (such as cling film). Early cooling with cool water, within 30 minutes of the burn, reduces burn depth and pain. Debridement, cleaning, and dressings are important aspects of burn wound care.

In some embodiments, treatment of a burn wound further comprises administration of an antibiotic agent. It has been shown that antibiotic prophylaxis may reduce mortality, bacteraemia, and ventilator associated pneumonia among patients in intensive care units (Silvestri L, et al, 2007, J Hosp Infect 65:187-203; and De Smet A M, et al., 2009, N Engl J Med 360:20-31). In burns patients, the skin is an additional source of infection (Avni T, et al., 2010, BMJ 340: c241). In some embodiments, treatment of a burn wound further comprises administration of an agent for managing pain. A pharmaceutical composition according to the invention may be topically administered to an burn wound, in combination with an agent for pain management selected from the group consisting of a simple analgesic, ibuprofen, acetaminophen, and a narcotic. The antibiotic agent and/or agent for managing pain may be administered orally, intravenously, or topically, e.g., along with topical administration of a cocktail of the instant invention. One or more other aspects of conventional treatment of burns also may be used in combination with a phage cocktail composition of the instant invention.

In some embodiments, the agent for pain management for use in combination with a phage cocktail composition of the invention includes one or more agents selected from the group consisting of: paracetamol (acetaminophen), a non steroidal anti-inflammatory drug, ibuprofen, ketoprofen, piroxicam, hydrocodone, morphine, hydromorphine, oxymorphone, fentanyl, oxycodone, diamorphine, methadone, buprenorphine, meperidine, pentazocine, dextromoramide, dipipanone, amitriptyline, dilaudid, tapentadol, and methadone. The agent for pain management may include any other agent for pain described herein and/or known in the art.

In some preferred embodiments, the agent for pain management is one that can be applied topically, such as a topical anesthetic agent. A topical anesthetic agent is a local anesthetic agent that is used to numb the surface of a body part, such as any area of the skin, the front of the eyeball, the inside of the nose, ear or throat, the anus, or the genital area. In some embodiments, the agent for pain management for use in combination with a phage cocktail composition of the invention includes one or more topical anesthetic agents selected from the group consisting of benzocaine, butamben, dibucaine, lidocaine, oxybuprocaine, pramoxine, prilocaine, proparacaine, proxymetacaine, and tetracaine (amethocaine). Topical anesthetic agents are available in creams, ointments, aerosols, sprays, lotions, and jellies. In further embodiments, the topical anesthetic agent may be used with one or more additional agents for pain management, such as another topical anesthetic agent, or a different agent for pain management, such as any other agent(s) for pain management described herein and/or known in the art.

Phage cocktail compositions of the invention will comprise a therapeutically and/or prophylactically effective amount of one of more phage strains, as described herein. A therapeutically and/or prophylactically effective amount refers to an amount required to bring about a therapeutic and/or prophylactic benefit, respectively, in a subject receiving said amount. A therapeutically and/or prophylactically effective amount will depend on the particular formulation, route of administration, condition being treated, whether other agents or therapies are used in combination with methods of the invention, and other factors.

In some specific embodiments, the phage cocktail compositions of the instant invention are formulated as pharmaceutical compositions for use in treating and/or preventing bacterial infections associated with areas of non-intact skin. The therapeutically and/or prophylactically effective amount will depend on the area of non-intact skin and the pharmaceutical compositions can be formulated to reflect same. For example, in some preferred embodiments, the pharmaceutical composition comprises phage strains where each is present in an amount corresponding to about $10^3$ to about $10^{13}$ phage particles/cm$^2$ of said area. In some more preferred embodiments, the therapeutic and/or prophylactic amount may correspond to at least about $10^4$, at least about $10^5$, at least about $10^6$, at least about $10^7$, at least about $10^8$, or at least about $10^9$, phage particles/cm$^2$ of the area of non-intact skin to be treated. In some more preferred embodiments, the therapeutic and/or prophylactic amount may correspond to less than about $10^{13}$, less than about $10^{12}$, less than about $10^{11}$, less than about $10^{10}$, less than about $10^9$, or less than about $10^8$ phage particles/cm$^2$ of the area of non-intact skin to be treated. In still more preferred embodiments, each phage strain is present in the pharmaceutical composition in an amount corresponding to $10^7$ to $10^9$ phage particles/cm$^2$ of the non-intact skin area.

In some embodiments, administration of a therapeutically effective amount of a phage cocktail composition, in accordance with the instant invention, results in improved wound closure, such as a reduction in the area of non-intact skin (wound area) compared to the area before initiation of treatment. Wound area can be expressed as a percentage of the initial wound area, at one or more time points after initiation of treatment. For example, in some preferred embodiments, wound area decreases by at least about 20%, at least about 30%, at least about 40%, at least about 50%, at least about 60%, at least about 70%, at least about 80%; or at least about 90% over a course of treatment with a phage cocktail composition of the invention. In some specific embodiments, the decrease in wound area occurs at least by day 1 after treatment initiation (t1), day 2 after treatment initiation (t2), day 3 after treatment initiation (t3), day 4 after treatment initiation (t4), day 5 after treatment initiation (t5), day 6 after treatment initiation (t6), day 7 after treatment initiation (t7), day 8 after treatment initiation (t8), day 9 after treatment initiation (t9), day 10 after treatment initiation (t10), day 12 after treatment initiation (t12), day 15 after treatment initiation (t15), day 20 after treatment initiation (t20), day 25 after treatment initiation (t25), or day 30 after treatment initiation (t30). In a particularly preferred embodiment, wound area is reduced by about 30% to about 40%, by at least day 9 after treatment initiation (t9). In a further particularly preferred embodiment, wound area is reduced by about 40% to about 50%, by at least day 9 after treatment initiation (t9). In still a further particularly preferred embodiment, wound area is reduced by about 50% to about 60%, by at least day 9 after treatment initiation (t9). In an even more particularly preferred embodiment, wound area is reduced by about 60% to about 70%, by at least day 9 after treatment initiation (t9).

In some embodiments, administration of a therapeutically effective amount of a phage cocktail composition, in accordance with the instant invention, results in improved wound healing, such as an improvement in ulcer grade based on the PEDIS classification compared to the ulcer grade before initiation of treatment. PEDIS is a routinely used, validated classification system for infections associated with wounds that has been developed by the International Working Group on the Diabetic Foot (IWGDF). IWGDF specifically developed a system for classifying wounds associated with diabetic foot infections that uses the acronym PEDIS, which stands for perfusion, extent (size), depth (tissue loss), infection, sensation (neuropathy). The classification originally was developed as a research tool (Schaper N C., 2004, Diabetes Metab Res Rev 20(Suppl 1):S90-5), and offers a semi-quantitative gradation for the severity of each of the categories. Specifically, PEDIS Grade 1 corresponds to no symptoms or signs of infection; Grade 2 corresponds to a local infection involving only the skin and subcutaneous tissue (without involvement of deeper tissues and without systemic signs), while any erythema involved must be between 0.5 cm and 2 cm; Grade 3 corresponds to a local infection, as described for Grade 2, but involving an erythema of greater than 2 cm or involving structures deeper than skin and subcutaneous tissues (e.g., abscess, osteomyelitis, septic arthritis, fasciitis), but without any systemic inflammatory response signs; and Grade 4 corresponds to a local infection, as described for Grades 2 and 3, but with the signs of systemic inflammatory response syndrome, as manifested by more than two of the following: a temperature >38° C. or <36° C.; a heart rate >90 beats/min; a respiratory rate >20 breaths/min or partial pressure of arterial carbon dioxide <32 mm Hg; and a white blood cell count >12000 or <4000 cells/μL or >10% immature (band) forms (see, e.g., Lipsky, B A, et al., 2012, CID 54:e132-e173). Another classification system has been developed by the IDSA (the Infectious Diseases Society of America), which rates the infection severity of infected wounds, in particular, diabetic foot infections. Specifically, the IDSA rates PEDIS Grades 1-4 as "uninfected", "mild", "moderate", and "severe", respectively (see, again, Lipsky, B A, et al., 2012, CID 54:e132-e173).

In some preferred embodiments, the PEDIS grade decreases from Grade 4 to Grade 3, Grade 2, or Grade 1, over a course of treatment with a phage cocktail composition of the invention. In other preferred embodiments, the PEDIS grade decreases from Grade 3 to grade 2 or Grade 1, over a course of treatment with a phage cocktail composition of the invention. In still other preferred embodiments, the PEDIS grade decreases from Grade 2 to Grade 1 over a course of treatment with a phage cocktail composition of the invention. In some specific embodiments, the decrease in ulcer grade occurs by at least day 1 after treatment initiation (t1), day 2 after treatment initiation (t2), day 3 after treatment initiation (t3), day 4 after treatment initiation (t4), day 5 after treatment initiation (t5), day 6 after treatment initiation (t6), day 7 after treatment initiation (t7), day 8 after treatment initiation (t8), day 9 after treatment initiation (t9), day 10 after treatment initiation (t10), day 12 after treatment initiation (t12), day 15 after treatment initiation (t15), day 20 after treatment initiation (t20), day 25 after treatment initiation (t25), or day 30 after treatment initiation (t30).

In certain embodiments, a phage cocktail composition of the invention is used as a single agent for treating or preventing infections caused by *A. baumannii, P. aeruginosa*, and/or *S. aureus*, such as diabetic foot infections. In other embodiments, a phage cocktail the invention is used in further combination with other agents, including other bacteriophage (for example, that target a different species or strain of bacteria involved in diabetic foot infections), or with antibiotics that target the same or different kinds of bacteria, including bacteria selected from any gram-positive bacteria, any gram-negative bacteria, and any other groups of bacteria that is not classified as gram-positive or gram-negative. The compositions of the invention may also be used in combination with any other means of treating bacterial infection known to one of skill in the art, in particular, any other means of treating diabetic foot ulcers.

In some embodiments, the cocktail composition according to the invention is used in combination with at least one additional phage strain against the same or a different bacteria species. In some preferred embodiments, the cocktail composition according to the invention is used in combination with at least one additional phage strain selected from the group consisting of bacteriophage strain F168/08 having antibiotic activity against one or more strains of *E. faecalis* and/or *E. faecium* (as disclosed in WO 2011/065854 and US Patent Application Publication No. 2012/0052048), bacteriophage strain F170/08 having antibiotic activity against one or more strains of *E. faecalis* and/or *E. faecium* (as disclosed in WO 2011/065854 and US Patent Application Publication No. 2012/0052048), bacteriophage strain F197/08 having antibacterial activity against one or more strains of *Staphylococcus aureus* (as disclosed in US Patent Application Publication No. 2012/0052048), bacteriophage strain F86/06 having antibacterial activity against one or more strains of *Staphylococcus aureus* (as disclosed in US Patent Application Publication No. 2012/0052048), bacteriophage strain F87s/06 having antibacterial activity against one or more strains of *Staphylococcus aureus* (as disclosed in US Patent Application Publication No. 2012/0052048), bacteriophage strain F91a/06 having antibacterial activity against one or more strains of *Staphylococcus aureus* (as disclosed in US Patent Application Publication No. 2012/0052048), bacteriophage strain F391/08 having antibacterial activity against one or more strains of *Klebsiella pneumoniae* (as disclosed in U.S. Provisional Application No. 61/384,015), bacteriophage strain F394/08 having antibacterial activity against one or more strains of *Acinetobacter baumannii* (as disclosed in U.S. Provisional Application No. 61/384,01), bacteriophage strain F488/08 having antibacterial activity against one or more strains of *Escherichia coli* (as disclosed in U.S. Provisional Application No. 61/384,01), and bacteriophage strain F387/08 having antibacterial activity against one or more strains of *Klebsiella pneumoniae* (as disclosed in U.S. Provisional Application No. 61/384,015) (the contents of each are hereby incorporated by reference in their entireties). The contents of U.S. Provisional Application No. 61/384,015, filed on Sep. 17, 2010, and International Application PCT/PT2011/000031, filed on Sep. 19, 2011, also are hereby incorporated by reference in their entireties.

As used herein, the term "in combination" or "in further combination" or "further in combination" refers to the use of an additional prophylactic and/or therapeutic agent as well as a phage cocktail of the invention. The use of the term "in combination" does not restrict the order in which prophylactic and/or therapeutic agents are administered to a subject. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (different from the first prophylactic or therapeutic agent) to a subject.

In some embodiments, the invention provides methods of treating and/or preventing diabetic foot infections comprising administering a phage cocktail of the invention in combination with a standard and/or non-standard therapy for diabetic foot infections. Standard therapies for diabetic foot infections, including but not limited to cutaneous ulcers associated therewith, includes extracellular matrix replacement therapy, moist wound therapy, negative pressure wound therapy, arterial re-vascularization therapy, hyperbaric oxygen therapy, administration of an antibiotic agent, and administration of a growth factor (Blume et al. 2008 Diabetes Care 31: 631-636).

In some embodiments, the phage cocktail composition of the invention is administered topically, e.g., to the site of a diabetic foot ulcer, while an additional agent is administered systemically. For example, in some preferred embodiments, a phage cocktail composition of the invention is administered topically, e.g., to the site of a diabetic foot ulcer, while an antibiotic agent is administered systemically. In still more preferred embodiments involving the treatment of diabetic foot ulcers, the systemically administered antibiotic agent has antibacterial activity against *A. baumannii, P. aeruginosa*, and/or *S. aureus*. In some embodiments, the phage cocktail composition of the invention is administered topically, e.g., to the site of a diabetic foot ulcer, along with an additional agent, also being administered topically. For example, in some preferred embodiments, the phage cocktail pharmaceutical composition of the invention is administered topically along with a growth factor, e.g., to the site of a diabetic foot ulcer.

Extracellular matrix therapy is used in the treatment, management, control, and/or prevention of non-healing areas of non-intact skin, and is a standard therapy for diabetic foot ulcers. The synthesis of the extracellular matrix (ECM) is a key feature in wound healing, especially when there has been a significant loss of tissue. Extracellular matrix therapy is designed to reduce protease levels in wound fluids by providing a competitive substrate (collagen) for the proteases, thereby reducing proteolytic destruction of essential extracellular matrix (ECM) components and promotes healing. For example, ECM therapy may comprise administration of agents that reduce proteolytic destruction of fibronectin and/or platelet-derived growth factors (PDGFs); as well as reduce the synthesis of matrix metalloproteinases (MMPs), such as a mixture of metal cations. ECM therapy also may comprise administration of amelogenin, an ECM protein with biological activity in the regeneration and repair of skin (Romanelli M. 2010 Wounds—Clinical Review 6(2):47-52).

ECM therapy also may comprise use of bio-engineered tissue, e.g., to replace the lost ECM. Bio-engineered tissues, also called "skin-replacement products" or "skin substitutes", often comprise biologic matrices, either with or without living cells (Brian D L et al. 2011. Expert Rev Dermatol. 6(3):255-262). Most bio-engineered tissues can be divided into living tissue substitutes versus bioactive adjuncts. The bio-engineered tissue may look like a thin, circular piece of real skin and can be placed directly on an area of non-intact skin. While the precise mechanism of healing is not completely understood, it is believed that bioengineered tissues improve healing by filling the wound with extracellular matrix proteins, and possibly also expressing additional growth factors and cytokines that facilitate healing. Particular examples of bioengineered tissues used in the treatment of diabetic foot ulcers include Apligraf and Dermagraft, which are commercially available.

Arterial revascularization therapy (ART) also is used in the treatment, management, control, and/or prevention of non-healing areas of non-intact skin, and also is a standard therapy for diabetic foot ulcers. A preferred approach in treating diabetic foot infections includes the percutaneous method of ART, which involves percutaneous balloon angioplasty, possibly with stenting. Other revascularization approaches include aortoiliac reconstruction with aortofemoral bypass and femoral-popliteal-tibial bypass using the saphenous vein.

Hyperbaric oxygen therapy (HBOT) also is used in the treatment, management, control, and/or prevention of non-healing areas of non-intact skin, and also is a standard therapy for diabetic foot ulcers. HBOT refers to intermittent treatment of the entire body at greater than normal atmospheric pressures, often with increased oxygen content compared to that of normal air. For example, using a hyperbaric oxygen chamber, pressure may be increased up to two times normal atmospheric pressure. Also, the patient may be exposed to oxygen at a concentration of up to 100%. The increased pressure, combined with the increase in oxygen content, dissolves oxygen in the blood plasma, body cells, tissues, and fluids, which in turn aids the wound-healing process. It is believed that HBOT can stimulate the growth of new blood vessels to locations with reduced circulation, improving blood flow to areas with arterial blockage.

In some other embodiments, the invention provides methods of treating and/or preventing diabetic foot infections comprising administering a phage cocktail composition of the invention in combination with a non-standard therapy for diabetic foot infections. Non-standard therapies generally are used where the diabetic foot ulcer is refractory to one or more standard therapies.

6. EXAMPLES

It is understood that the following examples and embodiments described herein are for illustrative purposes only and that various modifications or changes in light thereof will be suggested to persons skilled in the art and are to be included within the spirit and purview of this application and the scope of the appended claims.

Unless otherwise indicated, specific bacteriophage disclosed herein were isolated, processed and analyzed according to the following methods. Further, the study described below was approved locally by the Animal Ethics Committee of the Instituto de Medicina Molecular and approved nationally by the Portuguese General Directorate of Veterinary Services (Direcção Geral de Veterinária), in accordance with Portuguese law. All animals in the study were maintained in accordance with European Directive 86/609/EC (Council of the European Communities. Council Directive 86/609/EEC of 24 Nov. 1986 on the approximation of laws, regulations and administrative provisions of the Member States regarding the protection of animals used for experimental and other scientific purposes. Off J Eur Communities L358:1-28), Portuguese law (Portaria 1005/92) (Portuguese Agricultural Ministry. Portaria no. 1005/92 of 23 October on the protection of animals used for experimental and other scientific purposes. Diário da República I—Série B245: 4930-4942), and the Guide for the Care and Use of Laboratory Animals (NRC 2011) (Institute for Laboratory Animal Research. 2011. Guide for the care and use of laboratory animals. Washington (DC): National Academies Press.).

One aim of this study was to investigate the antimicrobial activity and wound-healing capability of topically delivered bacteriophage solutions against wounds with chronic *S. aureus, P. aeruginosa*, and *A. baumannii* infections in two animal models of DM (rat and porcine).

6.1.1 PREPARATION OF BACTERIAL STRAINS

*Staphylococcus aureus* 743/06, *Pseudomonas aeruginosa* 433/07 and *Acinetobacter baumannii* 1305/05 strains were isolated from human clinical skin wound samples collected from patients and identified in hospitals from the Lisbon area. The *Staphylococcus aureus* 743/06, *Pseudomonas aeruginosa* 433/07 and *Acinetobacter baumannii* 1305/05 strains were deposited on Sep. 16, 2011, under the terms of the Budapest Treaty at NCIMB Limited (Ferguson Building, Craibstone Estate, Bucksburn, Aberdeen, AB21 9YA, Scotland UK) and bear accession numbers NCIMB 41862, NCIMB 41861, and NCIMB 41863, respectively. Each isolate was streaked onto tryptone soy agar media plates (TSA, Biokar Diagnostics, PantinCedex, France) and incubated at 37° C. for 18 h. All host strains were stored in tryptone soy broth (TSB, Biokar Diagnostics, Pantin Cedex, France) with 15% glycerol (w/v) at −70° C. until needed.

Cryopreserved strains at −70° C. were grown overnight on TSA at 37° C.

For in vitro experiments, single colonies were grown overnight in TSB at 37° C. with agitation. Another bacterial suspension (a dilution of the overnight culture) was prepared, incubated at 37° C. with agitation, and harvested when it reached the exponential growth phase (optical density at 600 nm 0.3-0.5). An inoculum of approximately $2.0\times10^7$ cfu/ml was used for the growth curves.

For in vivo experiments, single colonies were grown overnight on tryptone soy agar (TSA, Biokar Diagnostics) at 37° C. After 24-h incubation, a bacterial suspension was prepared in saline (NaCl 0.9%, Applichem, Darmstadt, Germany) and compared with a McFarland Standard, that is, adjusted to McFarland's scale (bioMérieux, Craponne, France), with a subsequent 1:10 dilution, producing a final solution concentration of $2.0\times10^7$ cfu/mL. A single dose of $2.0\times10^6$ cfu of the clinical strains was used to inoculate the wounds.

6.1.2 PREPARATION OF BACTERIOPHAGE STRAINS

*Staphylococcus aureus* F44/10 and F125/10, *Pseudomonas aeruginosa* F770/05 and F510/08 and *Acinetobacter baumannii* F1245/05 lytic bacteriophage were isolated from sewage water from the Lisbon area and amplified in *Staphylococcus aureus* 743/06, *Pseudomonas aeruginosa* 433/07, and *Acinetobacter baumannii* 1305/05 clinical strains, respectively. Standard methods (Adams M. Bacteriophages. New York: Interscience Publishers, Inc., 1959) for bacteriophage isolation and amplification were employed using the host strains described above. To produce bacteriophage stocks in sufficient quantities for experiments, a previously described protocol of amplification, concentration by high-speed centrifugation, and purification on a cesium chloride gradient was used. (Miller H., 1987, Methods Enzymol. 152: 145-70). Final concentrations were determined with double agar overlay plaque assays (Kropinski et al., 2009, In: Clokie M, Kropinski A, editors. Bacteriophages Methods and Protocols, volume 1: isolation, characterization, and interactions. New York: Humana Press, Springer Science+Business Media, 69-76). The phage strains F44/10, F125/10, F770/05, F510/08, and F1245/05 were deposited on Sep. 16, 2011, under the terms of the Budapest Treaty at NCIMB Limited (Ferguson Building, Craibstone Estate, Bucksburn, Aberdeen, AB21 9YA, Scotland UK) and bear accession numbers NCIMB 41867, NCIMB 41866, NCIMB 41864, NCIMB 41868, and NCIMB 41865, respectively.

To isolate lytic bacteriophage against *Staphylococcus aureus, Pseudomonas aeruginosa* and *Acinetobacter baumannii*, three clinical strains were used (indicator strains). Sewage water from different origins of the Lisbon urban area was concentrated by high speed centrifugation, before being used in the double agar overlay plaque assay to determine the presence of bacteriophage.

Water samples, 50 ml, were centrifuged at 8000×g for 10 minutes at 4° C. Supernatants were filtered with 0.45 μm Millex filters (Millipore, Mass., USA) and centrifuged at 17000 rpm (Beckman J2-21M/E, rotor JA-20) for 3 hours at 4° C. The pellet was eluted in 5 ml of SM buffer (0.05 M Tris-HCl pH 7.5, 0.1 M NaCl, 10 mM $MgSO_4.7H_2O$, 0.03% gelatin) and allowed to elute overnight at 4° C. The re-suspended pellet was stored at 4° C. until needed.

Water samples were also enriched to increase the chance of bacteriophage isolation (Van Twest and Kropinski 2009). One single colony of *Staphylococcus aureus* 743/06 indicator strain was inoculated in 5 ml tryptone soy broth supplemented with 0.5% yeast extract (TSBY, Biokar Diagnostics, PantinCedex, France) and incubated overnight at 37° C. with agitation. A culture with 5 ml of TSBY, 50 μl of the overnight bacterial culture, 100 μl of the concentrated water, and 5 mM of $CaCl_2$ and $MgCl_2$ was prepared and incubated overnight at 37° C. with agitation. Before centrifuging the culture at 8000×g for 10 minutes at 4° C., chloroform was added and incubated for 5 to 10 minutes at room temperature to lyse the cells and free the intracellular bacteriophage in the medium. The supernatant was filtered with 0.45 μm Millex filters (Millipore, Mass., USA) and stored at 4° C. until needed.

After concentration and/or enrichment, the sewage water samples were tested for the presence of bacteriophage with the ability to infect *Staphylococcus aureus* 743/06, *Pseudomonas aeruginosa* 433/07 and *Acinetobacter baumannii* 1305/05 clinical strains by the double agar overlay plaque assay. Briefly, bacterial indicator strains were grown overnight in TSB or TSBY (for the isolation of *Staphylococcus aureus* bacteriophage) at 37° C. with agitation. Another bacterial suspension (a dilution of the overnight culture: 1:200 for *Staphylococcus aureus* indicator strain, 1:50 for *Pseudomonas aeruginosa* and *Acinetobacter baumannii* indicator strains) was prepared, incubated at 37° C. with agitation, and harvested when it reached the exponential growth phase (optical density at 600 nm 0.3-0.5). Each culture was supplemented with $CaCl_2$ and/or $MgCl_2$ (*Staphylococcus aureus* strain with 5 mM $CaCl_2$ and $MgCl_2$, *Pseudomonas aeruginosa* and *Acinetobacter baumannii* strains with 10 mM $MgCl_2$) and placed in glass tubes (200 μl for *Staphylococcus aureus,* 400 μl for *Pseudomonas aeruginosa* and 150 μl for *Acinetobacter baumannii* strains) with the concentrated and/or enriched water samples (100 □μl for the isolation of *Staphylococcus aureus* bacteriophage and 50 □μl for the isolation of *Pseudomonas aeruginosa* and *Acinetobacter baumannii* bacteriophage). The mixture was incubated at 37° C. for 30 minutes, after which 3 ml of soft agar was added (0.35% for the isolation of *Staphylococcus aureus* bacteriophage and 0.7% for the isolation of *Pseudomonas aeruginosa* and *Acinetobacter baumannii* bacteriophage) pre-equilibrated at 50° C. After a brief vortex, the agar-water-bacterial suspension was overlaid onto tryptone soy agar supplemented with 0.5% yeast extract (TSAY, Biokar Diagnostics, Pantin Cedex, France) for the isolation of *Staphylococcus aureus* bacteriophage or TSA plates 1.5% (for the isolation of *Pseudomonas aeruginosa* and *Acinetobacter baumannii* bacteriophage), allowed to solidify at room temperature and incubated at 37° C. After 18 to 24 hours, the plates were checked for bacteriophage (clearing zones) within the bacterial lawn, indicating the presence of bacteriophage. Bacteriophage plaques were picked using sterile pipette tips, transferred to 100 μl of SM buffer and stored at 4° C.

6.1.3 PHAGE PROPAGATION AND CHARACTERIZATION

The isolated bacteriophage were subject to a process of propagation, amplification, and purification (3 consecutive elutions) in the indicator strains, before evaluation of its host range. Sensibility of 30 bacterial isolates against a particular bacteriophage was performed using the small drop plaque assay system (Mazzocco A, et al. 2009. Bacteriophages, methods and protocols vol. 1 chapter 9 Humana Press.). Briefly, bacterial indicator strains were grown overnight in TSB at 37° C. with agitation. A new bacterial suspension (a dilution of the overnight culture: 1:200 for *Staphylococcus aureus* indicator strains, 1:50 for *Pseudomonas aeruginosa* and *Acinetobacter baumannii* indicator strains) was prepared, incubated at 37° C. with agitation, and harvested when it reached the exponential growth phase (optical density at 600 nm 0.3-0.5). Each culture was supplemented with $CaCl_2$ and/or $MgCl_2$ (*Staphylococcus aureus* strains with 5 mM $CaCl_2$ and $MgCl_2$, *Pseudomonas aeruginosa* and *Acinetobacter baumannii* strains with 10 mM $MgCl_2$) and placed in glass tubes (200 μl for *Staphylococcus aureus,* 400 μl for *Pseudomonas aeruginosa* and 150 μl for *Acinetobacter baumannii* strains) to which was added 3 ml of soft agar (0.35% for the isolation of *Staphylococcus aureus* bacteriophage and 0.7% for the isolation of *Pseudomonas aeruginosa* and *Acinetobacter baumannii* bacteriophage) pre-equilibrated at 50° C. After a brief vortex, the agar-bacterial suspension was overlaid onto TSA plates 1.5% and allowed to solidify at room temperature. A small volume (5 μl) of each of the newly-isolated bacteriophage was dropped onto the freshly prepared bacterial lawns and plates were allowed to dry at room temperature before incubation overnight at 37° C. The sensibility of 30 bacterial isolates against a particular bacteriophage was determined by observing the appearance of a lytic zone in the spot area.

The bacteriophage with the best percentage of infection in the host range were selected and passed to a new process of amplification, concentration by high speed centrifugation, purification in Cesium chloride (CsCl) gradient, extraction of bacteriophage genomic DNA, and restriction. The process was repeated on a host range with 100 bacterial isolates, until final selection of bacteriophage was made, and their genomes sequenced.

6.1.4 PHAGE COCKTAILS IN VITRO EFFICACY

In vitro assays were performed to study the lytic activity of *Staphylococcus aureus* F44/10 and F125/10, *Pseudomonas aeruginosa* F770/05 and F510/08, and *Acinetobacter baumannii* F1245/05 bacteriophage, each individually or combined in liquid cultures, against *Staphylococcus aureus* 743/06, *Pseudomonas aeruginosa* 433/07 and *Acinetobacter baumannii* 1305/05 indicator strains.

Bacterial indicator strains were grown overnight in TSB at 37° C. with agitation. A fresh bacterial suspension (a dilution of the overnight culture: 1:200 for *Staphylococcus aureus* indicator strains, 1:50 for *Pseudomonas aeruginosa* and *Acinetobacter baumannii* indicator strains) was prepared, incubated at 37° C. with agitation, and harvested when it reached the exponential growth phase (optical density at 600 nm 0.3-0.5). Each culture was supplemented with $CaCl_2$ and/or $MgCl_2$ (*Staphylococcus aureus* strains with 5 mM $CaCl_2$ and $MgCl_2$, *Pseudomonas aeruginosa* and *Acinetobacter baumannii* strains with 10 mM $MgCl_2$).

For each bacterium, three liquid cultures of 10 ml TSB were prepared and tested simultaneously. A control culture of bacteria was inoculated with medium and $2.0\times10^7$ cfu/ml of the respective indicator strain (*Staphylococcus aureus* 743/06, *Pseudomonas aeruginosa* 433/07, and *Acinetobacter baumannii* 1305/05) in the exponential growth phase. A control culture of bacteriophage was inoculated with medium and the bacteriophage to be tested against the indicator strain, at a predetermined multiplicity of infection (F44/10 MOI=10, F125/10 MOI=10, F770/05 MOI=1, F510/08 MOI=10, and F1245/05 MOI=10). A test culture was inoculated with medium, the bacteriophage to be tested (F44/10 MOI=10, F125/10 MOI=10, F770/05 MOI=1, F510/08 MOI=10 and F1245/05 MOI=10) and $2.0\times10^7$ cfus/ml of the respective indicator strain (*Staphylococcus aureus* 743/06, *Pseudomonas aeruginosa* 433/07, and *Acinetobacter baumannii* 1305/05) in the exponential growth phase. All cultures were supplemented with $CaCl_2$ and/or $MgCl_2$ (*Staphylococcus aureus* strains with 5 mM $CaCl_2$ and $MgCl_2$, *Pseudomonas aeruginosa* and *Acinetobacter baumannii* strains with 10 mM $MgCl_2$). Cultures were incubated at 37° C. with low agitation. Samples of 100 μl aliquots were taken from each culture at 1 hour intervals for a 24 hour-incubation period and used for serial dilutions.

Viable bacteria counts were quantified by the 10-fold serial dilution method (Murray P R, et al. 2003. Manual of clinical microbiology. Washington, D.C.: ASM Press.). For the control cultures of bacteria and test cultures, 100 μl of each dilution was inoculated onto the respective selective media plates: Chapman mannitol salt agar (Biokar diagnostics, PantinCedex, France) for *Staphylococcus aureus*, cetrimide agar (Merck Chemical, Darmstadt, Germany) for *Pseudomonas aeruginosa*, and CHROmagar *Acinetobacter* (CHROmagar, Paris, France) for *Acinetobacter baumannii*. The plates were incubated under aerobic conditions at 37° C. for 24 hours, after which colony counts were performed. The isolates grown on Chapman mannitol salt agar were presumptively identified as *Staphylococcus aureus*, based on colony morphology and mannitol salt agar fermentation (Chapman G H. 1946. J Bacteriol 51:409-410). The isolates grown on cetrimide agar were presumptively identified as *Pseudomonas aeruginosa*, based on colony morphology (Brown V I, et al. 1965. J Clin Pathol 18:752-756). The isolates grown on CHROmagar *Acinetobacter* were presumptively identified as *Acinetobacter baumannii*, based on colony red color (Wareham D W, et al. 2011. J Clin Pathol 64:164-167).

For the control cultures of bacteriophage, 100 μl aliquots were taken at time point (t0) and immediately diluted to determine the initial titre of each bacteriophage by the double agar overlay plaque assay. Briefly, bacterial indicator strains were grown overnight in TSB at 37° C. with agitation. A fresh bacterial suspension (a dilution of the overnight culture: 1:200 for *Staphylococcus aureus* indicator strain, 1:50 for *Pseudomonas aeruginosa* and *Acinetobacter baumannii* indicator strains) was prepared, incubated at 37° C. with agitation, and harvested when it reached the exponential growth phase (optical density at 600 nm 0.3-0.5). Each culture was supplemented with $CaCl_2$ and/or $MgCl_2$ (*Staphylococcus aureus* strain with 5 mM $CaCl_2$ and $MgCl_2$, *Pseudomonas aeruginosa* and *Acinetobacter baumannii* strains with 10 mM $MgCl_2$) and placed in glass tubes (200 μl for *Staphylococcus aureus,* 400 μl for *Pseudomonas aeruginosa*, and 150 μl for *Acinetobacter baumannii* strains) with 100 μl of the bacteriophage culture dilution. The mixture was incubated at 37° C. during 30 minutes, after which 3 ml of soft agar was added (0.35% for *Staphylococcus aureus* and 0.7% for *Pseudomonas aeruginosa* and *Acinetobacter baumannii* cultures) pre-equilibrated at 50° C. After a brief vortex, the agar-bacteriophage-bacterial suspension was overlaid onto TSA plates 1.5%, allowed to solidify at room temperature, and incubated at 37° C. After 18 to 24 hours, the bacteriophage titer was determined by enumeration of the plaque forming units (pfus).

6.1.5 PHAGE COCKTAIL PREPARATION

FIG. 1 illustrates the preparation of an exemplary phage cocktail composition in accordance with the instant invention. After the in vitro assays of F44/10, F125/10, F770/05, F510/08, and F1245/05 bacteriophage, individually and combined, the lytic activity of the five bacteriophage was tested together in a single bacteriophage cocktail. Three primary cocktails (an *S. aureus* cocktail, a *P. aeruginosa* cocktail, and an *A. baumannii* cocktail) and one final cocktail were prepared using different concentrations and relative proportions of purified bacteriophages. The bacteriophage cocktail was prepared in saline with each bacteriophage present at predetermined MOIs (F44/10 MOI=10, $10^{10}$ pfu/mL; F125/10 MOI=10, $10^{10}$ pfu/mL; F770/05 MOI=1, $10^9$ pfu/mL; F510/08 MOI=10, $10^{10}$ pfu/mL; and F1245/05 MOI=10, $10^{10}$ pfu/mL).

Each culture was performed as previously described for individual bacteriophage testing. Control cultures of bacteria, control culture of the bacteriophage cocktail, and test cultures were prepared for *Staphylococcus aureus* 743/06, *Pseudomonas aeruginosa* 433/07, and *Acinetobacter baumannii* 1305/05 indicator strains. Cultures were incubated at 37° C. with low agitation and 100 μl aliquots were taken at 1 hour intervals for 24 hours and used for serial dilutions.

Viable bacteria counts were quantified by the 10-fold serial dilution method (Murray P R, et al. 2003. Manual of clinical microbiology. Washington, D.C.: ASM Press.). For the control cultures of bacteria and test cultures, 100 μl of each dilution was inoculated onto the respective selective media plates: Chapman mannitol salt agar for *Staphylococcus aureus*, cetrimide agar for *Pseudomonas aeruginosa*, and CHROmagar *Acinetobacter* for *Acinetobacter baumannii*. The plates were incubated at 37° C. for 24 hours, after which colony counts were performed. The isolates grown on Chapman mannitol salt agar were presumptively identified as *Staphylococcus aureus*, based on colony morphology and mannitol salt agar fermentation (Chapman G H. 1946. J Bacteriol 51:409-410). The isolates grown on cetrimide agar were presumptively identified as *Pseudomonas aeruginosa*, based on colony morphology (Brown V I, et al. 1965. J Clin Pathol 18:752-756). The isolates grown on CHROmagar *Acinetobacter* were presumptively identified as *Acinetobacter baumannii*, based on colony red color (Wareham D W, et al. 2011. J Clin Pathol 64:164-167).

The initial bacteriophage titre was determined by the double agar overlay plaque assay. Samples of 100 μl aliquots were taken at time point (t0) and immediately diluted. Bacterial indicator strains were grown overnight in TSB at 37° C. with agitation. A fresh bacterial suspension (a dilution of the overnight culture: 1:200 for *Staphylococcus aureus* indicator strain, 1:50 for *Pseudomonas aeruginosa* and *Acinetobacter baumannii* indicator strains) was prepared, incubated at 37° C. with agitation, and harvested when it reached the exponential growth phase (optical density at 600 nm 0.3-0.5). Each culture was supplemented with $CaCl_2$ and/or $MgCl_2$ (*Staphylococcus aureus* strain with 5 mM $CaCl_2$ and $MgCl_2$, *Pseudomonas aeruginosa* and *Acinetobacter baumannii* strains with 10 mM $MgCl_2$) and placed in glass tubes (200 µl for *Staphylococcus aureus,* 400 µl for *Pseudomonas aeruginosa*, and 150 µl for *Acinetobacter baumannii* strains) with 100 □µl of the bacteriophage cocktail culture dilution. The mixture was incubated at 37° C. for 30 minutes, after which 3 ml of soft agar was added (0.35% for *Staphylococcus aureus* and 0.7% for *Pseudomonas aeruginosa* and *Acinetobacter baumannii* cultures) pre-equilibrated at 50° C. After a brief vortex, the agar-bacteriophage-bacterial suspension was overlaid onto TSA plates 1.5%, allowed to solidify at room temperature, and incubated at 37° C. After 18 to 24 hours, the bacteriophage titer was determined by pfu (plaque-forming unit) enumeration.

6.1.6 PHAGE COCKTAIL IN VIVO EFFICACY IN A RAT MODEL

Figure 2:
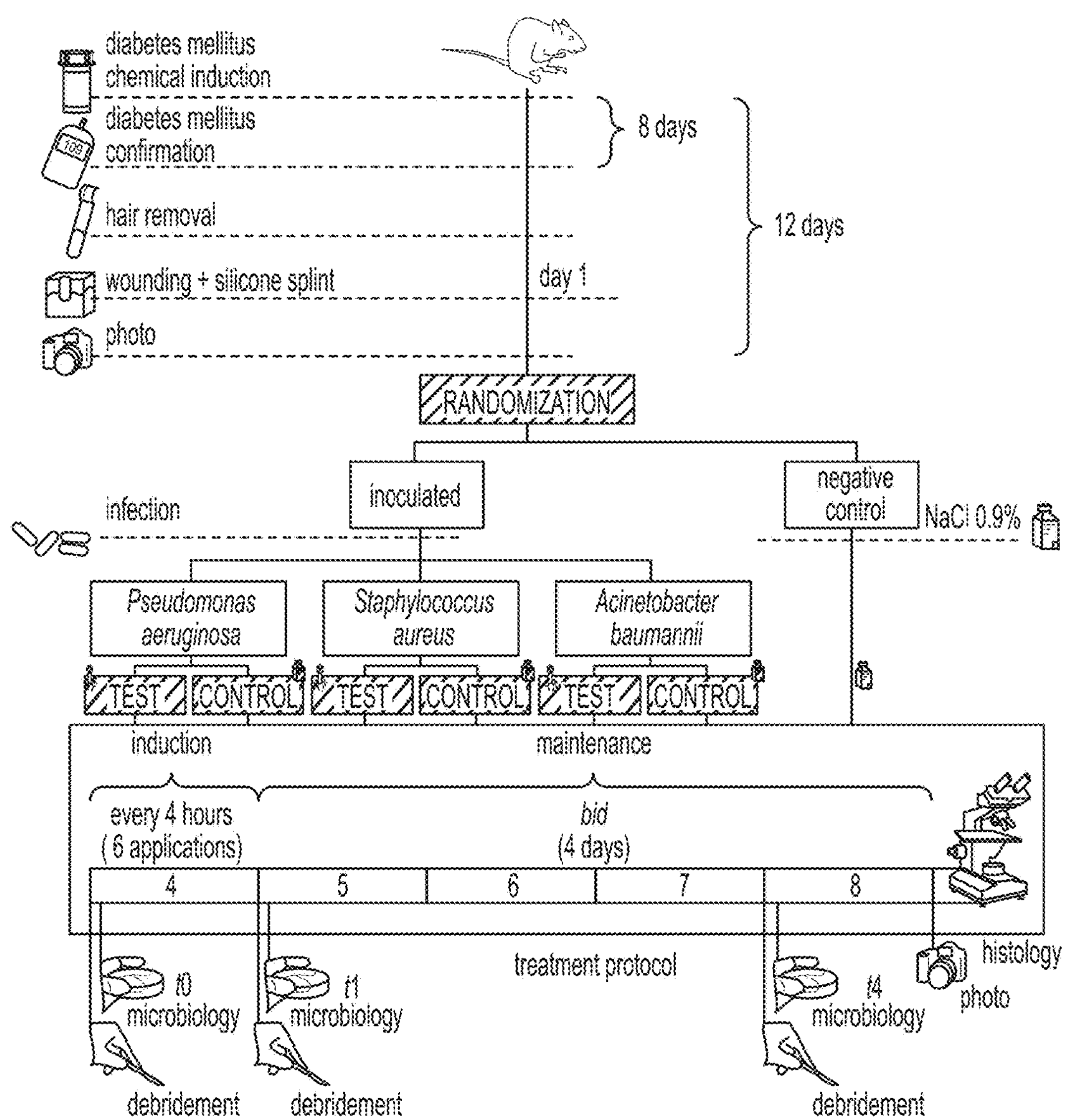
FIG. 2 illustrates the study protocol used for demonstrating in vivo efficacy in a rat model of an exemplary phage cocktail composition in accordance with the instant invention.

FIG. 2 illustrates the study protocol used for demonstrating in vivo efficacy in a rat model of an exemplary phage cocktail composition, in accordance with the instant invention. A previously optimized rodent wound infection model in chemically-induced diabetic Wistar mice was used (Mendes J J, et al. 2012. Comp Med 62:1-12).

Animals

Specific pathogen-free male Wistar rats [Crl:WI(Han)], weighing 250-350 g (8 to 10 weeks old) were obtained from Charles River Laboratories (L'Arbresle, Cedex, France). The animals were hosted in an approved animal care center under the following conditions: housing in microisolators in a room with controlled humidity (50-70%) and temperature (20-22° C.), a 14-hour light and 10-hour dark cycle, and free access to pelleted rodent chow and filter-sterilized water. The animals were initially housed in groups of two. After hair removal and subsequent procedures, they were housed individually to preserve skin and, later, dressing integrity. All surgical procedures were performed in a sanitized surgery room using autoclave-sterilized instruments.

Induction of DM

DM was chemically induced as described by Wu et al. (Wu K, et al. 2008. Curr Protoc Pharmacol 40:5.47.1-5.47.14). After a 12 hour fast, animals were given a single intraperitoneal (i.p.) injection of streptozotocin (65 mg/kg; Merck Chemical, Darmstadt, Germany) freshly prepared in 0.1 M citrate buffer (pH 4.5). A blood glucose measurement was performed on tail-vein blood using a glucometer 8 days later. Rats showing fasting blood glucose levels higher than 250 mg/dL were considered diabetic.

Hair Removal

After DM confirmation (eight days later), 42 diabetic rats were anesthetized by i.p. injection of xylazine hydrochloride (10 mg/kg) and ketamine hydrochloride (25 mg/kg), and their dorsal surface hair was trimmed with an electric clipper while the remaining hair was waxed thoroughly using cold wax strips (Veet cold wax strips, Reckitt Benckiser, West Ryde, Australia). The dorsum of the animals was then rinsed with a 10% povidone-iodine solution and, after drying and cleansing, a liquid film-forming acrylate (Cavilon Skin Cleanser, 3M Health Care, Saint Paul, Minn.) was applied evenly to cover the hair removal area.

Wounding, Splinting, First Photograph, and Dressing

Four days after hair removal, the animals were again anesthetized with the same protocol, and the dorsum skin was thoroughly washed with sterile saline followed by disinfection with 10% povidone-iodine and washing with 70% isopropyl alcohol after 10 minutes of povidone-iodine contact time. A round wound was created by making one full-thickness incision extending through the panniculus carnosus muscle in the interscapular region of the upper back of each rat using a punch biopsy instrument (diameter, 6 mm; Accu-Punch, Acuderm, Fort Lauderdale, Fla., USA), and the skin flap was excised using Iris scissors. An oval-shaped silicone splint was adapted from a self-adhesive corn cushion (Comforsil, Toledo, Spain). An immediately bonding cyanoacrylate glue in a disposable single-dose package (Loctite, Henkel Corporation, Westlake, Ohio) was used to fix the splint to the skin, followed by interrupted 3-0 nylon sutures to ensure its position. Before dressing, wounds were photographed from a standard height (a 1.5-cm distance) using a mounted digital microscope (SuperEyes 200× USB Digital Microscope, Shenzhen Tak and Assistive Technology, Shenzhen, China). Liquid film-forming acrylate was then applied to the epilated area, and the wound and the surrounding area were covered with a previously tailored, semi-occlusive, non-woven polyester dressing (Fixomull Stretch, BSN Medical, Hamburg, Germany). The splint and dressing were maintained in place throughout the entire course of the experiment using a jacket made from adhesive tape (Leukoplast surgical tape, BSN Medical, Hamburg, Germany).

Group Randomization

After applying the dressing, and with the animals still anesthetized, the animals were randomly divided into 7 groups: negative control (n=6), *Staphylococcus aureus*-inoculated control (n=6) and test (n=6), *Pseudomonas aeruginosa*-inoculated control (n=6) and test (n=6), and *Acinetobacter baumannii*-inoculated control (n=6) and test (n=6).

Wound Infection

The wounds of the animals in the negative control group were injected with 100 µL of sterile saline, whereas the wounds of the inoculated groups (test and control) were respectively inoculated with 100 µL of the cultured *Staphylococcus aureus, Pseudomonas aeruginosa*, or *Acinetobacter baumannii* (approximately $2.0\times10^6$ cfu) re-suspended in sterile saline by inserting a 27 G/19-mm needle attached to a 1-mL disposable syringe through the silicon splint at a 45° angle.

Debridement

On days 4, 5, and 8 post-wounding, the semi-occlusive dressing was cut off and the wound debrided, in all animals. Debridement consisted of the simple mechanical removal of the scab, defined as a crust of dried blood, serum, and exudate, using strict aseptic technique.

Bacteriophage Treatment Protocol

The bacteriophage treatment protocol was divided into an induction phase and a maintenance phase and performed in all test groups. The induction phase was carried out after the first debridement (post-wounding day 4) and consisted of six (every four hours) 100 µL primary bacteriophage solution administrations. The maintenance phase was carried out from day 5 to day 8 and consisted of twice daily (every 12 hours) 100 µL primary bacteriophage solution administrations. If debridement was performed, the bacteriophage administration followed. The control groups received 100 µL sterile saline with the same frequency.

Microbiological Analysis

On days 4, 5, and 8 post-wounding and after debridement, a liquid Amies elution swab (eSwab Collection and Preservation System, Copan, Corona, Calif.) was used to collect and transport swab cultures. Bacteria collection was performed using the one-point method described by Sullivan et al. (Sullivan P K et al. 2004 Wounds 16:115-123). Briefly, using the sterile swab, the center surface of each wound was scrubbed by rotating the swab 3 times clockwise with enough manual pressure to produce a small amount of exudate. The swab was then inserted into the tube and transported to the laboratory for immediate processing. The swab collection tube was vortexed (with the swab inside) for 5 seconds, and a 100-μL aliquot of the resulting suspension was used for serial dilutions.

Quantification was performed using the 10-fold serial dilution method (Murray P R et al. 2003. Manual of clinical microbiology. Washington, D.C.: ASM Press). In the infected/innoculated groups, 100 μL of each dilution was plated onto the respective selective media plates: Chapman mannitol salt agar (Biokar diagnostics, Pantin Cedex, France) for *Staphylococcus aureus*, cetrimide agar (Merck Chemical, Darmstadt, Germany) for *Pseudomonas aeruginosa*, and CHROmagar *Acinetobacter* (CHROmagar, Paris, France) for *Acinetobacter baumannii*. In *Acinetobacter baumannii*-infected groups, 100 μL of each dilution was simultaneously inoculated onto tryptone soy agar media plates (TSA, Biokar Diagnostics, Pantin Cedex, France). In the negative control group, 100 μL of each dilution was inoculated onto tryptone soy agar media plates. The plates were incubated under aerobic conditions at 37° C. for 24 hours, after which colony counts were performed. The isolates grown on Chapman mannitol salt agar were presumptively identified as *Staphylococcus aureus*, based on colony morphology and mannitol salt agar fermentation (Chapman G H. 1946. J Bacteriol 51:409-410). The isolates grown on cetrimide agar were presumptively identified as *Pseudomonas aeruginosa*, based on colony morphology (Brown V I, et al. 1965. J Clin Pathol 18:752-756). The isolates grown on CHROmagar *Acinetobacter* were presumptively identified as *Acinetobacter baumannii*, based on colony red color (Wareham D W, et al. 2011. J Clin Pathol 64:164-167).

Wound Closure Kinetics (Planimetry)

On post-wounding day 9, before sacrifice, wounds were photographed from a 1.5 cm standard height using a mounted digital microscope as previously described. Wound kinetics was quantified using image-processing software (ImageJ, US National Institutes of Health, Bethesda, Md.) to measure the wound area by planimetry; wound area was expressed as a percentage of the initial wound area.

Histological Analysis

All animals were sacrificed by i.p. injection of pentobarbital (200 mg) on day 9 post-wounding and each ulcer, including a 0.5-cm skin border, was entirely harvested using sterile surgical scissors and placed in a tube. The sample was fixed in 10% buffered formalin solution and, after overnight fixation, the tissue was trimmed and cut through at the widest margin, embedded in paraffin, and sectioned in 3-μm increments. Sections were made perpendicular to the anterior-posterior axis and perpendicular to the surface of the wound.

For each wound, two serial sections were placed on a slide and stained with hematoxylin and eosin. Under light microscopy, the sections were photographed using a motorized inverted bright-field microscope (Zeiss Axiovert 200M, Göttingen, Germany) equipped with a color camera (Leica DM2500, Leica Microsystems GmbH, Wetzlar, Germany) at 50× magnification. Panoramic cross-sectional digital images of each wound were prepared using microscopy automation software (MetaMorph, MDS Analytical Technologies, Sunnyvale, Calif.) and processed using an image-processing software (ImageJ, US National Institutes of Health, Bethesda, Md.). The images were analyzed for epithelial gap (EG) and dermal gap (DG) using the same image-processing software.

EG was defined as the distance between the advancing edges of clear, multiple-layer neoepidermis (Galiano R D, et al. 2004. Wound Repair Regen 12:485-492; Scherer S S, et al. 2008. Wounds 20:18-28), and its size was measured in mm, with an EG of zero representing a completely re-epithelialized wound. DG was defined as the distance between uninjured dermis on both sides of the wound (Galiano R D, et al. 2004. Wound Repair Regen 12:485-492; Scherer S S, et al. 2008. Wounds 20:18-28) and was measured in mm. All wound kinetics and histological measurements were performed with the investigator blinded as to sample origin (test or control).

6.1.7 PHAGE COCKTAIL IN VIVO EFFICACY IN A PIG MODEL

Figure 3:
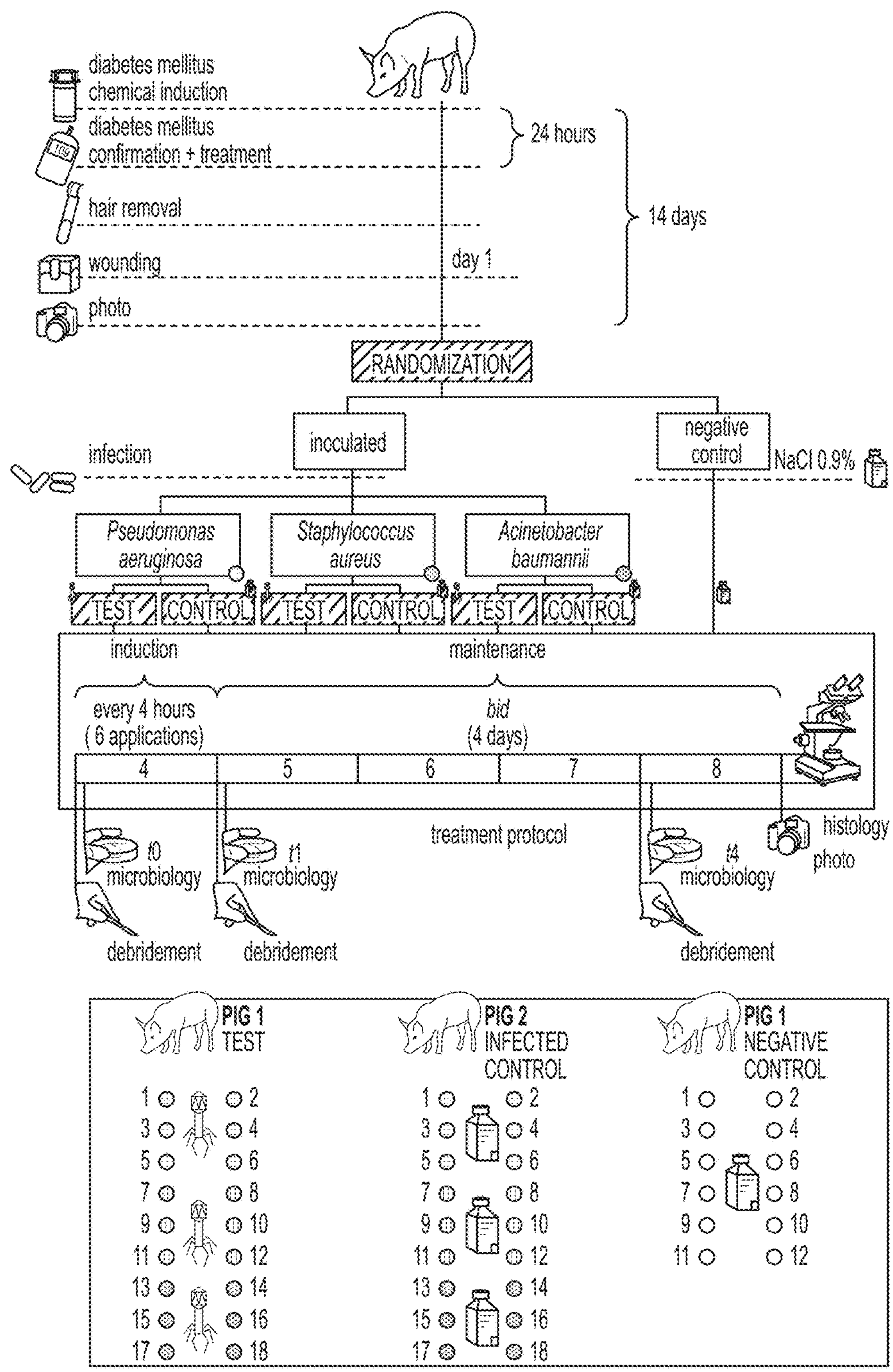
FIG. 3 illustrates the study protocol used for demonstrating in vivo efficacy in a pig model of an exemplary phage cocktail composition in accordance with the instant invention.

FIG. 3 illustrates the study protocol used for demonstrating in vivo efficacy in a pig model of an exemplary phage cocktail composition in accordance with the instant invention. A previously optimized pig wound infection model in animal with chemically induced DM, as described by Hirsch et al. (Hirsch T, et al. 2008. BMC Surg 8:5), was modified to fit the needs of the instant study. Three animals (negative control, inoculated-control, and inoculated-test) with a total of 48 excisional wounds (12 negative control wounds, 12 *Pseudomonas aeruginosa*-inoculated wounds, 12 *Staphylococcus aureus*-inoculated wounds, and 12 *Acinetobacter baumannii*-inoculated wounds) were used in this study.

Animals

Three female Yorkshire pigs (Farm) weighting ±60 kg at arrival were allowed to acclimatize for 1 week prior to initiation of the experiment. Animals were housed singly in a cage, had free access to water, and were fed twice daily with a standard diet. During procedures, pigs were kept in a containment device.

Induction and Control of DM

Pigs were fasted for 12 hours before DM induction. On the day of the procedure, the animals were weighed and given induction intramuscular anesthesia with xylazine hydrochloride and ketamine hydrochloride. While the animals were under anesthesia, a 21-Gauge intravenous (i.v.) catheter was inserted into an ear vein. Streptozotocin was prepared at a dose of 150 mg/kg body weight diluted in 10 mL/g sterile saline, sterilized by filtration, and administered through the catheter over 1 minute. After recovering from anesthesia, post-procedural anti-emetic therapy with metoclopramide was given. Pigs were continuously observed for the first 3 hours and then food was offered ad libitum, in order to avoid hypoglycemia. Blood glucose was measured on a daily basis during the experiment. To keep the blood glucose concentration between 250 and 400 mg/dL, pigs received daily injections of 16 IU of pre-mixed neutral suspension of neutral (30%) and isophane insulin (70%) (Mixtard 30, Novo Nordisk, Bagsværd, Denmark) subcutaneously.

Hair Removal, Wounding, First Photograph, and Infection

Fourteen days after induction of DM, pigs received induction anesthesia as previously described. After induction, they underwent endotracheal intubation and were mechanically ventilated with a volume-limited, time-cycled BIRD ventilator (Mark 9; Bird Corporation, Palm Springs, Calif.) on a mixture of room air and titrated isoflurane (0.5% to 1.5%). The tidal volume was set at 12 mL/kg and ventilator rate at 12 breaths per minute. Prior to surgery, the dorsal surface hair was trimmed with an electric clipper and the remaining hair was waxed thoroughly using cold wax strips, the paraspinal area was thoroughly disinfected using 10% povidone iodine paint, and then washed with 70% isopropanol after 15 minutes of contact time.

For the inoculated-control and inoculated-test pigs, nine full-thickness excisional wounds (measuring 6 mm in diameter and with a depth of 6 mm) were created in each side of the paraspinal area (eighteen in total) using a 6 mm diameter biopsy punch. For the negative control pig, only 6 excisional wounds were created in each side of the paraspinal area (twelve in total). Subsequently, sterile forceps and a surgical blade were used to remove the full-thickness skin flap, and sterile gauze was utilized to cleanse the wounds of any coagulated blood and to control bleeding. Before covering with the adhesive chamber, wounds were photographed from a standard height using a mounted digital microscope. A modified adhesive chamber, made of a colostomy bag (Two Piece 35-mm Ostomy, Hollister Incorporated, Libertyville, Ill.) covered by a semi-occlusive non-woven polyester dressing, was placed over each wound and secured in place with surgical staples (Manipler A Z, B. Braun, Tuttlingen, Germany) and adhesive bandages.

In the inoculated-control and inoculated-test animals, wounds were divided into three subgroups: *Staphylococcus aureus* (2×6 ulcers); *Pseudomonas aeruginosa* (2×6 ulcers); and *Acinetobacter baumannii* (2×6 ulcers). To immerse the enclosed surface, wounds were respectively inoculated with $2\times10^6$ *Staphylococcus aureus* cfu in 100 μL total solution (sterile 0.9% saline), $2\times10^6$ *Pseudomonas aeruginosa* cfu in 100 μL total solution (sterile 0.9% saline), and $2\times10^6$ *Acinetobacter baumannii* cfu in 100 μL total solution (sterile 0.9% saline). In the negative control group (12 ulcers), wounds were injected with 100 μL of sterile saline. After recovering from anesthesia, post-procedural anesthesia (buprenorphine 0.005 mg/kg) and anti-emetic therapy was given every 12 hours for 48 hours.

Debridement

On days 4, 5, and 8 post-wounding, the semi-occlusive dressing was cut off and the wound debrided. Debridement consisted of the simple mechanical removal of the scab, defined as a crust of dried blood, serum, and exudate, using strict aseptic technique, as described for the rodent model.

Bacteriophage Treatment Protocol

A bacteriophage treatment protocol divided into an induction phase and a maintenance phase, similar to the rodent model, was used. The induction phase was carried out after the first debridement (post-wounding day 4) and consisted of six (every four hours for 24 hours) 100 μL bacteriophage solution administrations, using the final bacteriophage cocktail. The maintenance phase was carried from day 5 to day 8 and consisted of twice daily (every 12 hours) 100 μL bacteriophage solution administrations, using the final bacteriophage cocktail. If debridement was performed, the bacteriophage administration followed. The control group received 100 μL sterile saline with the same frequency.

Microbiological Analysis

A microbiological analysis protocol similar to the rodent study was used. On days 4, 5, and 8 post-wounding, and after debridement, a liquid Amies elution swab was used to collect and transport swab cultures. Bacteria collection was performed using the one-point method described by Sullivan et al. (Sullivan P K, et al. 2004. Wounds 16:115-123), as previously described. The swab was then inserted into the tube and transported to the laboratory for immediate processing. Quantification was performed using the 10-fold serial dilution method (Murray P R, et al. 2003. Manual of clinical microbiology. Washington, D.C.: ASM Press).

In the infected/innoculated groups, 100 μL of each dilution was plated onto the respective selective media plates: Chapman mannitol salt agar, cetrimide agar, and CHROmagar *Acinetobacter*. In the negative control group, 100 μL of each dilution was inoculated onto tryptone soy agar media plates. The plates were incubated under aerobic conditions at 37° C. for 24 hours, after which colony counts were performed. The isolates were presumptively identified as previously described. In the negative control group, ulcers with more than $10^3$ cfu/swab on any given day were considered to be critically colonized, and excluded from further analysis.

Wound Closure Kinetics (Planimetry)

On post-wounding day 9, after sacrifice, wounds were photographed from a standard height using a mounted digital microscope as previously described. Wound kinetics were quantified using image-processing software, as for the rodent study. Wound area was expressed as a percentage of the initial wound area.

Histological Analysis

All animals were sacrificed by i.v. injection of pentobarbital on day 9 post-wounding and each ulcer, including a 0.5-cm skin border, was entirely harvested using sterile surgical scissors and placed in a tube. The samples were processed and photographed as described for the rodent study. The images were analyzed for epithelial gap (EG) using the same methods as in the rodent study.

Statistical Analysis

All quantitative microbiological results are presented as the mean with the respective standard deviation and expressed as logarithm-transformed values [log(cfu/swab) for swab samples and log(cfu/ulcer) for tissue samples]. The data were compared using a logarithmic scale owing to the wide variations in cfu/swab among cultures. Comparisons between groups were performed using two-tailed Student t-tests, and a p value $<0.05$ was considered significant. All planimetric results are expressed as the mean with the respective standard deviation of the percentage in area of the original wound size. Comparisons between groups were performed using two-tailed Student t-tests, and a p value $<0.05$ was considered significant. Histological measures results are presented as the mean values with the respective standard deviation. Comparisons between groups were performed using two-tailed Student t-tests, and a p value $<0.05$ was considered significant. All data was entered into a spreadsheet program (Excel, Microsoft, Redmond, Wash.) for statistical analysis. Analytical statistics were performed by Analyse-it version 2.21 Excel 12+ (Analyse-it Software, Leeds, UK), a statistical add-in program for the spreadsheet program.

6.1.8 RESULTS

Preclinical Studies—Pharmacology/Proof of Concept

Figure 4:
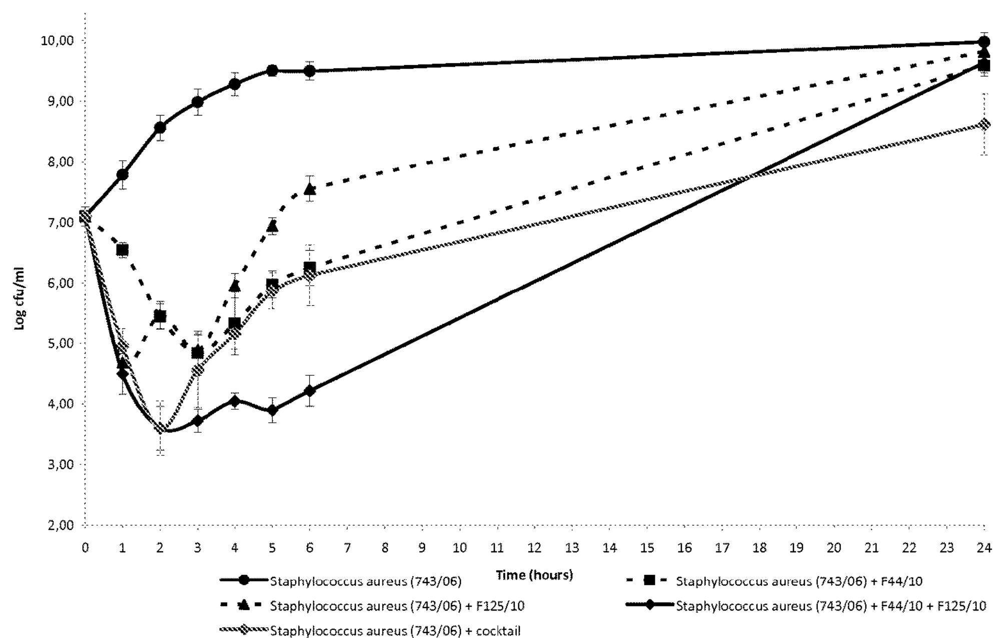
FIG. 4 illustrates results of lytic studies evaluated against *Staphylococcus aureus* 743/06, demonstrating in vitro efficacy of an exemplary phage cocktail composition in accordance with the instant invention.
Figure 5:
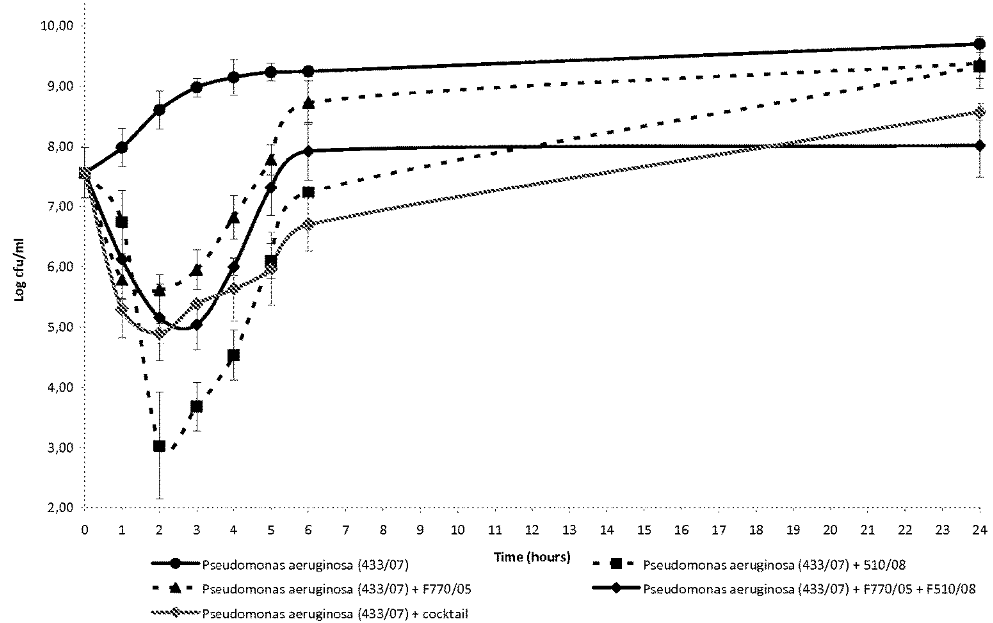
FIG. 5 illustrates results of lytic studies evaluated against *Pseudomonas aeruginosa* 433/07, demonstrating in vitro efficacy of an exemplary phage cocktail composition in accordance with the instant invention.
Figure 6:
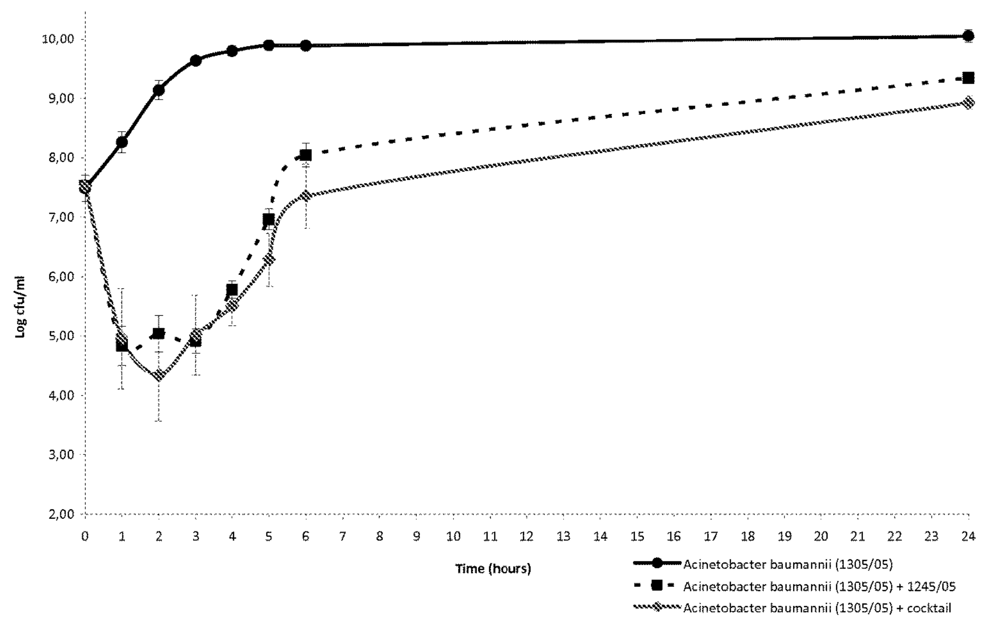
FIG. 6 illustrates results of lytic studies evaluated against *Acinetobacter baumannii* 1305/05, demonstrating in vitro efficacy of an exemplary phage cocktail composition in accordance with the instant invention.

To overcome the problem of the emergence of resistance to an individual bacteriophage strain being used, the instant inventors have developed bacteriophage cocktail compositions using more that one distinct bacteriophage strains, each having high lytic activity, despite previous difficulties in combining different specificities of bacteriophage, such as storage instability. The instant cocktails surprisingly demonstrate superior combined efficacy than when the phage are used individually, as illustrated in FIGS. 4, 5, and 6 kill curves for the in vitro assays. The decrease observed, for example, using cultures of F770/05 and F510/08 combined, in comparison with the use of cultures of the individual bacteriophage strains, demonstrates the advantage of using more than one bacteriophage strain (i.e., using bacteriophage cocktails in accordance with the instant invention) to increase the lytic activity against *Pseudomonas aeruginosa* strains while decreasing the emergence of bacteria resistant to the bacteriophage strains. Here, the inventors measured the capacity of infection of each of the selected bacteriophage in 100 different strains of bacteria—F510/08 has a host range of 80%, F770/05 has a host range of 55%, F44/10 and F125/10 both have a host range of 100%, and F1245/05 has a host range of 75%.

Development of Phage Cocktail

The lytic activities of the newly isolated and characterized *Staphylococcus aureus* bacteriophage strains F44/10 and F125/10, *Pseudomonas aeruginosa* bacteriophage strain F770/05 and F510/08, and *Acinetobacter baumannii* bacteriophage strain F1245/05 were evaluated against *Staphylococcus aureus* 743/06, *Pseudomonas aeruginosa* 433/07, and *Acinetobacter baumannii* 1305/05 strains, respectively, in order to develop a bacteriophage cocktail for application in wound infections. In vitro use of the bacteriophage cocktail (red line) lead to a significant reduction in *Staphylococcus aureus, Pseudomonas aeruginosa*, and *Acinetobacter baumannii* bacterial counts, as demonstrated in FIGS. 4, 5, and 6. The results of the in vitro use of the bacteriophage cocktail showed no inhibition of the bacteriophage strain's infecting ability due to the presence of different bacteriophage strains of distinct bacteria and further demonstrate that the cocktail actually enhances the lysis of bacteria in some cases (e.g, in the case of *Pseudomonas aeruginosa* and *Acinetobacter baumannii* bacteria).

Conventional growth curves were performed under controlled conditions using a previously determined bacterial inoculum. A preliminary study was conducted to determine the mass load of bacteria in a four day infection with *Staphylococcus aureus* 743/06, *Pseudomonas aeruginosa* 433/07, or *Acinetobacter baumannii* 1305/05 strains in the rat model. The cfu determination indicated a bacteria load of approximately $2.0\times10^7$ cfu/wound. This was the inoculum used in the in vitro assays.

Before evaluating a bacteriophage cocktail composition, each bacteriophage was tested individually and in combination, with different MOIs (data not shown) to screen their efficacy for potential therapeutic and experimental use in the animal models. Viable bacteria counts were monitored at 1-hour intervals for 24 hours.

FIG. 4 illustrates results of lytic studies evaluated against *Staphylococcus aureus* 743/06, demonstrating in vitro efficacy of an exemplary phage cocktail composition in accordance with the instant invention. Bacteriophage F44/10 was tested individually at MOI equal to 10 to infect *Staphylococcus aureus* 743/06. Within the first 3 hours viable bacteria counts were reduced by approximately 4 log units compared with the control culture of bacteria. Afterwards, bacteria began to increase and 6 hours post-infection of the culture, viable bacteria were at $2.1\times10^6$ cfu/ml. Although there was a reduction of 97% when compared to the control culture of bacteria (at 24-hour incubation, viable counts were at $9.9\times10^9$ cfu/ml), bacteriophage F44/10 failed to eliminate completely the host cells. Similar results were observed for the 5 bacteriophage when assayed individually and probably were the result of the appearance of less susceptible bacteria to the bacteriophage infection.

Bacteriophage F125/10 was used at MOI equal to 10 to infect *Staphylococcus aureus* 743/06 (as illustrated in FIG. 4) and, within one hour, reduced the viable counts of bacteria by approximately 3 log units when compared with the control culture of bacteria 743/06. At 6-hour incubation, viable bacteria were at $3.6\times10^7$ cfu/ml (lower than the values of F44/10 culture) and at the end of the incubation period (24-hours), viable bacteria were at $6.6\times10^9$ cfu/ml. The distinct behavior, seen in the variations during the three initial hours of incubation of bacteriophage F44/10 and F125/10 activities, reflects the differences in their adsorption rates, latent periods, and burst sizes (data not shown).

It was expected that the combination of the two bacteriophage strains (F44/10 and F125/10) to *Staphylococcus aureus* 743/06 would reduce further the bacterial growth compared to that observed individually. Bacteriophage F44/10 and F125/10 early lysed the bacteria reaching a 5 log unit reduction (viable bacteria at $1.9\times10^4$ cfu/ml) when compared with the control culture of bacteria. A low level of viable bacteria counts was maintained for four hours, however, despite the decrease when compared with the control culture of bacteria. At 24-hours incubation, viable bacteria counts had reached $4.3\times10^9$ cfu/ml (a 56.6% reduction of the bacterial counts).

FIG. 5 illustrates results of lytic studies evaluated against *Pseudomonas aeruginosa* 433/07, demonstrating in vitro efficacy of an exemplary phage cocktail composition in accordance with the instant invention. A similar trend as seen with *Staphylococcus aureus* 743/06 was observed for bacteriophage F770/05 and F510/08 infecting *Pseudomonas aeruginosa* 433/07.

Bacteriophage F770/05 was tested individually at MOI equal to 1 against *Pseudomonas aeruginosa* 433/07, as illustrated in FIG. 5. Within the first 2 hours of incubation, viable bacteria counts were reduced approximately 3 log units compared with the control culture of bacteria 433/07, reaching $4.6\times10^5$ cfu/ml. Within 3 hours of incubation, bacteria started to grow exponentially, and at 6 hours of incubation, viable bacteria were at $7.3\times10^7$ cfu/ml. At the end of the culture incubation period (24 hours), bacteria counts were $2.8\times10^9$ cfu/ml, a 41.6% reduction when compared with the control culture of bacteria with $4.8\times10^9$ cfu/ml.

Bacteriophage F510/08 was also tested individually at MOI equal to 10 against *Pseudomonas aeruginosa* 433/07, as illustrated in FIG. 5, before its use when combined with F770/05 was tested. Within 2 hours of incubation, bacteriophage F510/08 had lysed the bacteria reaching approximately a 5 log unit reduction in bacteria counts when compared with the control culture of bacteria. At 6 hours of incubation, viable bacteria were at $1.7\times10^7$ cfu/ml, reaching the initial inoculum of approximately $2.0\times10^7$ cfu/ml. After 24 hours, the culture of F510/08 presented bacterial counts similar to those of the control culture of bacteria, with $2.8\times10^9$ cfu/ml, equivalent to a 41.6% reduction.

The previous assays with bacteriophage F770/05 and F510/08 with different MOIs demonstrated a suitable multiplicity of infection for use in a combination of the two bacteriophage: use of F770/05 with MOI equal to 1 and F510/08 with MOI equal to 10 was more effective in infecting *Pseudomonas aeruginosa* 433/07.

Bacteriophage F770/05 and F510/08 with MOI equal to 1 and 10, respectively, were tested against *Pseudomonas aeruginosa* 433/07, also as illustrated in FIG. 5. Within 3 hours of incubation, the bacteria counts presented a 4 log unit reduction when compared with the control culture of bacteria, and a 1 log unit reduction when compared with the culture of F770/05 alone. At this time point, F510/08 appeared to be more effective alone. At 6 hours of incubation, that is, 6 hours post-infection of the culture, the viable bacteria counts were at $1.4\times10^8$ cfu/ml; while at the end of the incubation period (24 hours), viable bacteria were at $1.7\times10^8$ cfu/ml. This represents a 96.5% reduction when compared with the control culture of bacteria. This decrease observed using both F770/05 with F510/08, compared to the use of the individual cultures of each bacteriophage, demonstrates the advantage to using more than one bacteriophage (as in bacteriophage "cocktails"), e.g., as discussed herein.

FIG. 6 illustrates results of lytic studies evaluated against *Acinetobacter baumannii* 1305/05, demonstrating in vitro efficacy of an exemplary phage cocktail composition in accordance with the instant invention. Bacteriophage F1245/05 also was selected to be included in the exemplary bacteriophage cocktail composition illustrated here, and was tested individually at MOI equal to 10 against *Acinetobacter baumannii* 1305/05, as illustrated in FIG. 6. At this MOI, bacteriophage F1245/05 caused a rapid decrease in viable bacteria, such that in only 1 hour, counts were reduced from $2.0\times10^7$ cfu/ml to $6.8\times10^4$ cfu/ml. Low cfu values were maintained for approximately 3 hours, when compared with the control culture of bacteria. After 6 hours of incubation, viable bacteria counts were at $1.1\times10^8$ cfu/ml, and at the end of the incubation period (24 hours), cells had grown to $2.2\times10^9$ cfu/ml. Bacteriophage F1245/05 individually thus showed high lytic activity against *Acinetobacter baumannii* 1305/05, achieving at 24 hours of incubation, a 76.3% reduction of the bacterial counts when compared with the control culture.

The results indicate that use of individual bacteriophage strains eventually may lead to the emergence of resistance to the particular bacteriophage strain, and one way to avoid or minimize this is to develop compositions comprising more than one bacteriophage strains, preferably each having high lytic activity against a specific bacteria.

Exemplary Bacteriophage Cocktail

The purpose of this study was to produce an exemplary bacteriophage cocktail against *Staphylococcus aureus, Pseudomonas aeruginosa*, and *Acinetobacter baumannii* strains using bacteriophage strains that display broad activity against a range of these bacteria and that may be used in the management of a wound infection.

After testing individual activities of certain bacteriophage strains against the bacterial strains, a bacteriophage cocktail was prepared having the following composition: F44/10 in a MOI=10, F125/10 in a MOI=10, F770/05 in a MOI=1, F510/08 in a MOI=10, and F1245/05 in a MOI=10. See FIG. 1.

This bacteriophage cocktail was tested in vitro against *Staphylococcus aureus* 743/06, *Pseudomonas aeruginosa* 433/07, and *Acinetobacter baumannii* 1305/05 strains. The viable bacteria counts were determined for each bacterium individually in growth curves at 1 hour intervals for 24 hours. In vitro application of the bacteriophage cocktail lead to a significant reduction of *Staphylococcus aureus, Pseudomonas aeruginosa*, and *Acinetobacter baumannii* bacterial counts (See FIGS. 4-6, respectively).

A single inoculation of the bacteriophage cocktail was sufficient to reduce *Staphylococcus aureus* 743/06 by 5 log units when compared with the control culture of bacteria, as illustrated in FIG. 4. A similar decrease had been observed for the activity of the two *Staphylococcus aureus* bacteriophage strains combined. During the second and sixth hour of incubation, the efficacy of the cocktail was lower than the two bacteriophage strains F44/10 and F125/10 together; however 24 hours later, the difference between the two cultures was significant. Bacterial counts started to decrease and at the end of the incubation period (24 hours), viable bacteria were at $6.8\times10^8$ cfu/ml (a reduction of 93.1% when compared with the control culture).

The bacteriophage cocktail was also tested against *Pseudomonas aeruginosa* 433/07, as illustrated in FIG. 5, presenting a reduction of the bacterial counts of almost 4 log units at the 2-hour incubation period. At the end of the culture incubation time (24 hours), bacteria counts were at $3.9\times10^8$ cfu/ml and, while slightly higher than when both bacteriophage strains were tested together, this represents a 91.9% reduction of viable bacteria when compared with control culture of bacteria *Pseudomonas aeruginosa* 433/07. This difference was not sufficient to associate an inhibitory effect of the cocktail on *Pseudomonas aeruginosa* bacteriophage strains F770/05 and F510/08 lytic activity.

The bacteriophage cocktail also was tested against *Acinetobacter baumannii* 1305/05 strain, as illustrated in FIG. 6. At 2 hours of incubation, the bacteriophage cocktail had reduced the bacteria counts by approximately 4 log units when compared with the control culture of bacteria 1305/05. At the end of the culture incubation period (24 hours), bacterial counts had reached $8.6\times10^8$ cfu/ml, which represents a reduction of 92.8% when compared with the control culture. These results indicate a better performance of this bacteriophage in the cocktail.

The results of the in vitro application of the bacteriophage cocktail indicated that there was no inhibition of each bacteriophage's infecting ability due to the presence of different bacteriophage of distinct bacteria.

Results Using the Rodent Model

To recap, studies conducted in rodents were approved locally by the Animal Ethics Committee of the Instituto de Medicina Molecular and nationally by the Portuguese General Directorate of Veterinary Services (Direcção Geral de Veterinária), in accordance with Portuguese law. All animals were maintained in accordance with European Directive 86/609/EC, Portuguese law (Portaria 1005/92), and the Guide for the Care and Use of Laboratory Animals (NRC 2011). A previously optimized rodent wound infection model in chemically-induced diabetic Wistar mice was used (Mendes J J, et al. 2012. Comp Med 62:1-12).

As noted above, FIG. 2 illustrates the study protocol. Briefly, after induction and establishment of diabetes, treatment was administered based on the lysis curves of the bacteriophage strains and similar to antibiotic posology, i.e., every 4 hours during the first 24 hours and then once a day for 5 days. Doses were based on the results obtained in an epidemiological study done previously in a range of patients collected from several Portuguese hospitals (data not shown). In this study, it was concluded that the concentration of bacteria that infects diabetic foot ulcers ranges from $10^6$ to $10^8$—the in vitro assays indicated that the MOI is 1 or 10, depending on the bacteriophage strain, such that the phage concentration was $10^7$ to $10^9$ per $cm^2$ of ulcer.

The choice of an infected chronic wound model was based on the fact that bacteriophage only replicate in their specific live bacterial host, thus it did not make sense to study models where infection would not be chronic. The primary endpoint was microbiological decrease in the wounds. Wound closure also was measured although differences in wound closure do not always reflect the real decrease in the dermal and epidermal gap, as when comparing histopathology to microbiology results.

To overcome problems of bacteriophage waste and the appearance of bacterial resistance, which might occur in the animals models associated with environmental conditions and the extension of treatment, larger numbers of bacteriophage were used in the in vivo experiments, that is, to inoculate the wounds and treat the animals. The number of bacteriophage particles present in the exemplary cocktail for in vivo use was increased by 1 log.

Microbiology Analysis

Figure 7:
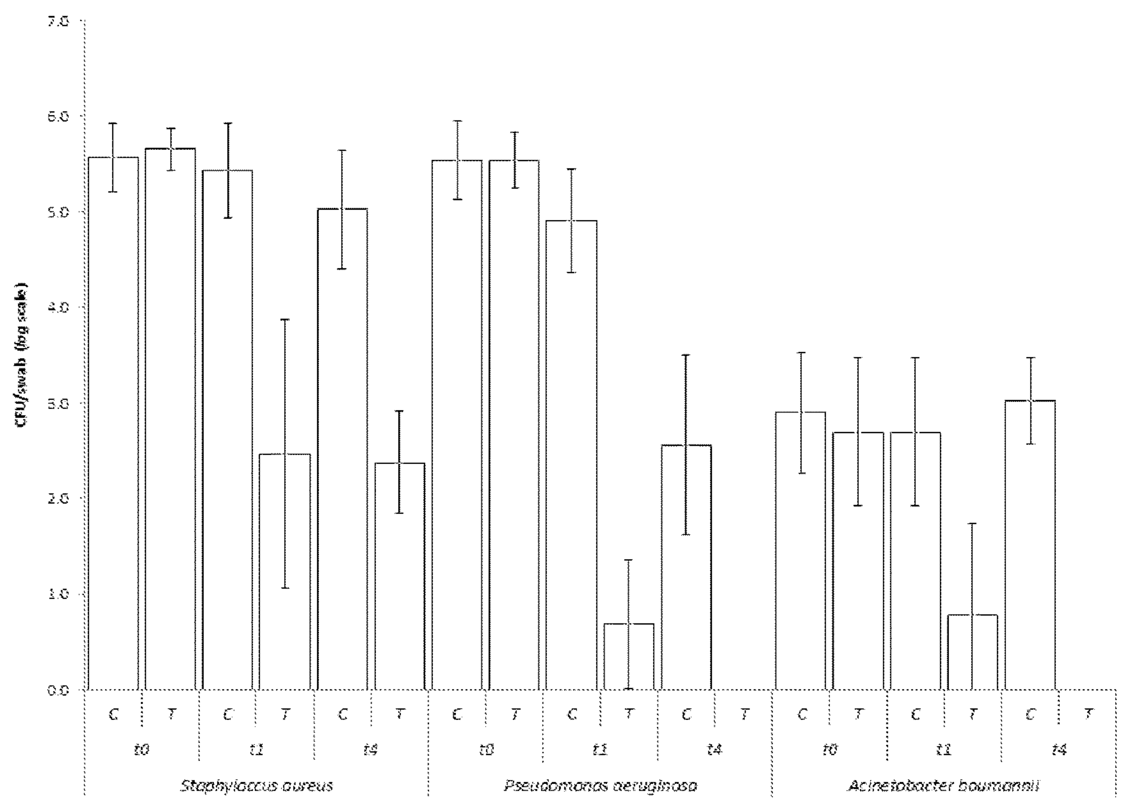
FIG. 7 illustrates results of microbial load analyses for control (C) and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention.

FIG. 7 illustrates results of microbial load analyses for control (C) and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention.

After induction therapy (t1), there was a statistically significant difference in colony counts in selective media between control and test subgroups in *Staphylococcus aureus*-inoculated, *Pseudomonas aeruginosa*-inoculated, and *Acinetobacter baumannii*-inoculated groups. At day four after treatment initiation (t4), there was a statistically significant difference in colony count in selective media between control and test subgroups. From t0 to t4 in *Staphylococcus aureus* and *Pseudomonas aeruginosa*-inoculated control subgroups, there was a tendency for microbial load reduction. That is, the bacteriophage-treated animals showed significantly lower counts than the control animals in all three groups on t1 and t4.

Wound Closure Kinetics (Planimetry)

Figure 8:
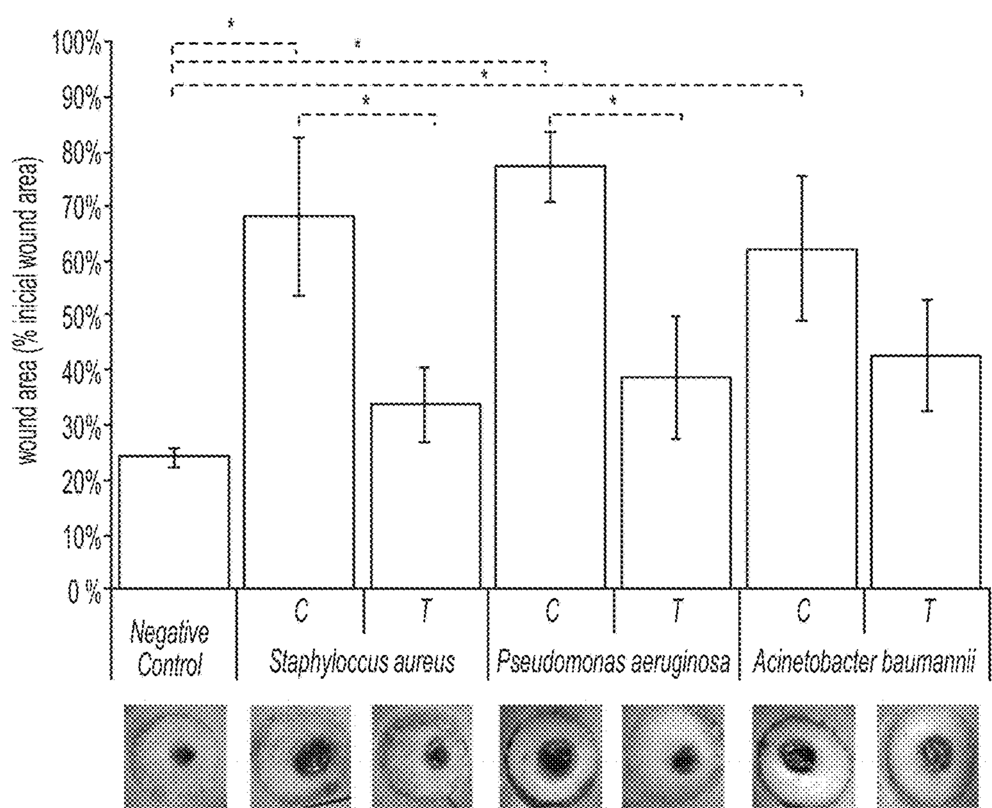
FIG. 8 illustrates results of wound closure analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention.

FIG. 8 illustrates results of would closure analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention. Wound area was assessed on t1 and t9, and the differences between the two timepoints calculated.

Planimetry analysis of wounds in the rat model showed a statistically significant difference between the negative control group and all the inoculated control subgroups wound areas, with a tendency for wound area reduction between control and test subgroups in all groups; and a statistically significant difference between control and test subgroups wound areas in the *S. aureus*-innoculated and *P. aeruginosa*-innoculated groups. That is, bacteriophage treatment reduced wound size in both *S. aureus*- and *P. aeruginosa*-infected wounds ($p<0.05$).

Histological Analysis

Figure 9:
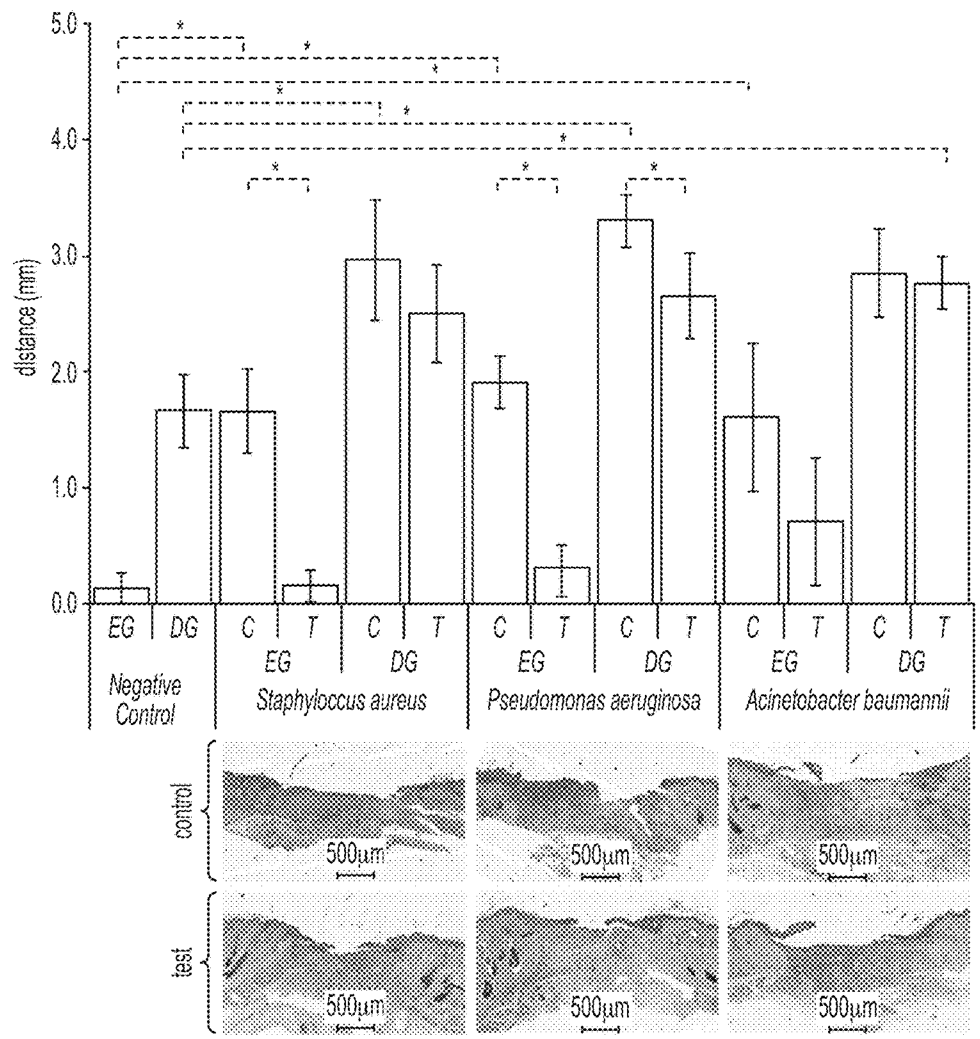
FIG. 9 illustrates results of histological analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention.

FIG. 9 illustrates results of histological analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a rat model of an exemplary phage cocktail composition in accordance with the instant invention.

There was a statistically significant difference between the negative control group and all the inoculated control subgroups in both the epidermal gap (EG) and the dermal gap (DG). There was a statistically significant difference between control and test subgroups EG in the *Staphylococcus aureus*-inoculated and *Pseudomonas aeruginosa*-inoculated groups ($p<0.05$). In DG, the difference between test and control subgroups only obtained statistical significance in *Pseudomonas aeruginosa*-inoculated group. These results correlate with the fact that *Pseudomonas aeruginosa* enters more deeply into tissues than *Staphylococcus aureus*. *Acinetobacter baumannii* is a colonizer appearing later in the process in patients which is why it is important for the bacteriophage cocktail, in certain embodiments, to comprise this bacteriophage.

Results Using the Pig Model

Similar results as those illustrated above were obtained using a pig model. To recap, a previously optimized pig wound infection model in chemically induced animals, as described by Hirsch et al. (Hirsch T, et al. 2008. BMC Surg 8:5), was modified to fit the needs of the instant study. Three animals (negative control, inoculated-control, and inoculated-test) with a total of 48 excisional wounds (12 negative control wounds, 12 *Pseudomonas aeruginosa*-inoculated wounds, 12 *Staphylococcus aureus*-inoculated wounds, and 12 *Acinetobacter baumannii*-inoculated wounds) were used. As noted above, FIG. 3 illustrates the study protocol. The same dosing and dosing schedule was used as in the rat model, described above.

Microbiology Analysis

Figure 10:
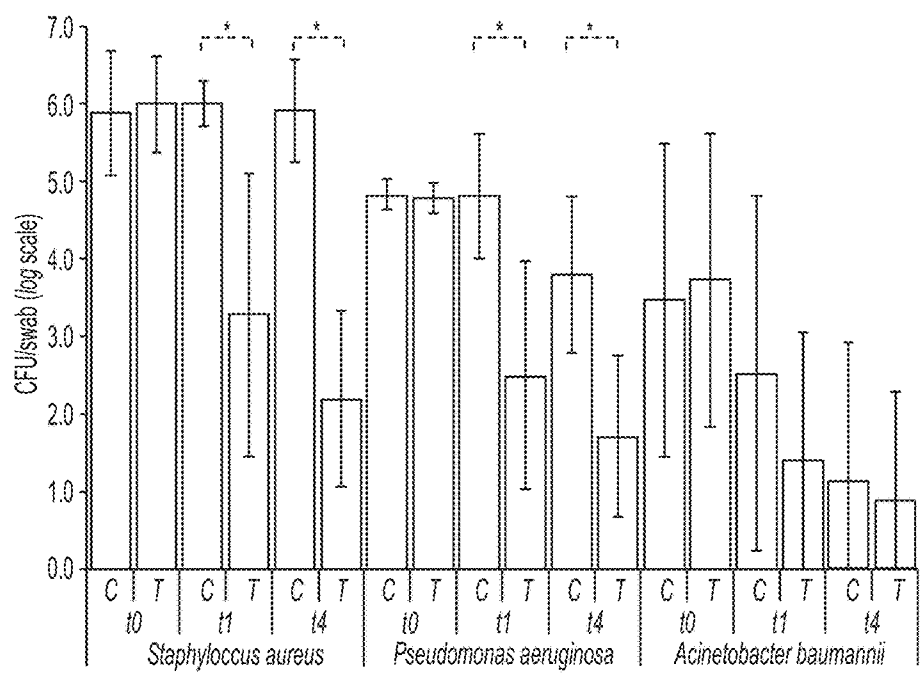
FIG. 10 illustrates results of microbial load analyses for control (C) and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

FIG. 10 illustrates results of microbial load analyses for control (C) and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

After induction therapy (t1), there was a statistically significant difference in colony count in selective media between control and test subgroups in the *S. aureus*-inoculated and *P. aeruginosa*-inoculated groups, and a tendency for microbial load reduction in average colony count for the *A. baumannii*-inoculated test and control subgroups ($p<0.05$). At day four after treatment initiation (t4), there was a statistically significant difference in colony count between control and test subgroups in *Staphylococcus aureus*-inoculated and *Pseudomonas aeruginosa*-inoculated groups. There was no statistically significant difference in average colony count in *Acinetobacter baumannii*-inoculated test and control subgroups, although there is a trend for a decrease in colony count.

Wound Closure Kinetics (Planimetry)

Figure 11:
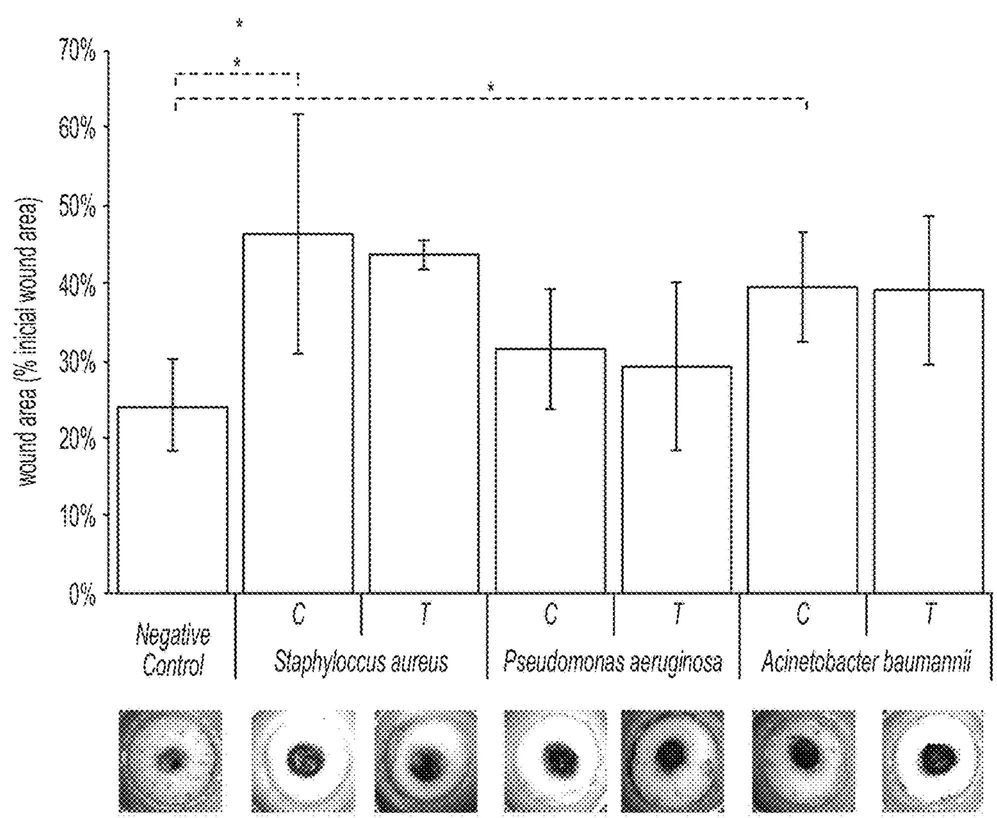
FIG. 11 illustrates results of would closure analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

FIG. 11 illustrates results of would closure analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

Histological Analysis

Figure 12:
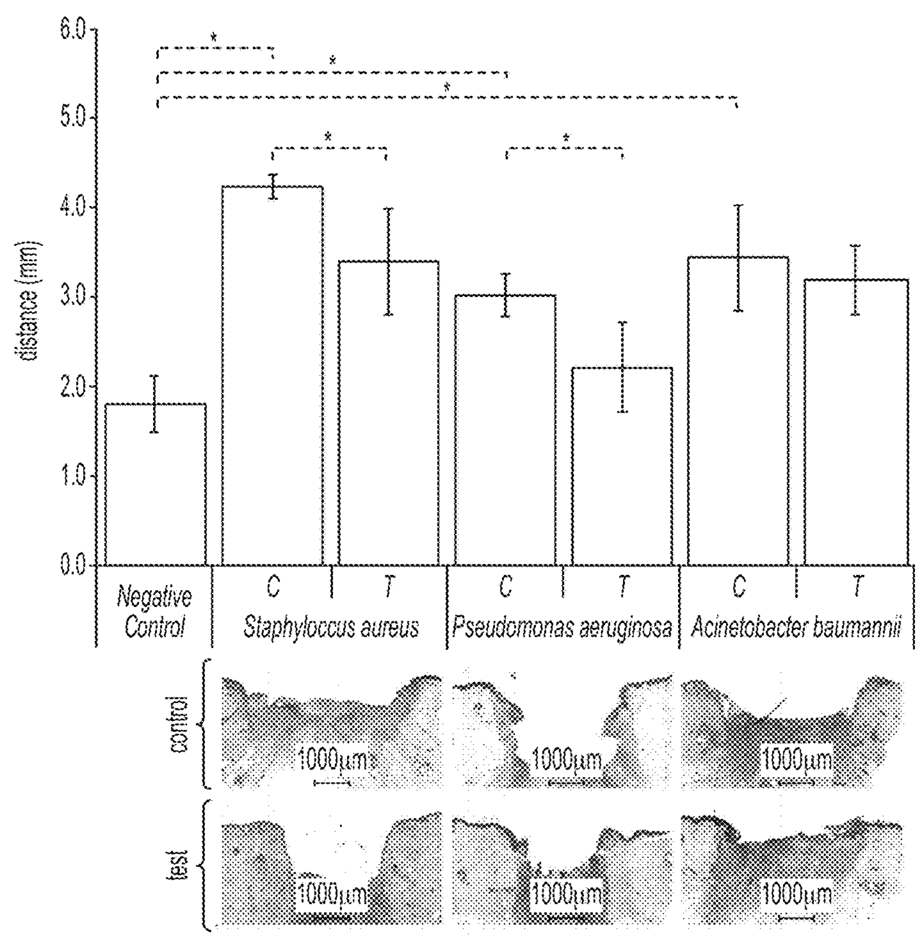
FIG. 12 illustrates results of histological analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

FIG. 12 illustrates results of histological analyses for negative, control (C), and test (T) groups for *Staphylococcus aureus*-inoculated, *Pseudomonas aeruginosa*-inoculated, and *Acinetobacter baumannii*-inoculated animals, demonstrating in vivo efficacy in a pig model of an exemplary phage cocktail composition in accordance with the instant invention.

There was a statistically significant difference between the negative control group and all the inoculated control subgroups in EG. There also was a statistically significant difference between control and test subgroups in the *Staphylococcus aureus*-inoculated and *Pseudomonas aeruginosa*-inoculated groups with respect to EG ($p<0.05$).

Discussion of Results

Based on previous rodent studies (Mendes J J, et al. 2012. Comp Med 62:1-12), it was known that the bacterial colony counts in tissue cultured from infected wounds at t4 are, on average, 7.54±0.19 log(CFU) per ulcer. The instant study used high bacteriophage doses ($10^8$ to $10^9$ pfu per administration), which yields a multiplicity of infection of 10 to 100. It is believed that this initial dose is sufficiently in excess of the target bacterium population to cause reductions without the need for bacteriophages to replicate and complete their life cycle. This is in contrast with previous bacteriophage therapy studies that employed relatively low bacteriophage doses and mainly relied on active therapy, which involves phage infection/replication cycles to reduce the target bacterium (Loc Carrillo C, et al., 2005, Appl Environ Microbiol. 71(11):6554-6563). These processes of active and passive bacteriophage therapy have been described for in vitro and in vivo studies (Cairns B J, et al., 2011, PLoS Pathog. 5(1):e1000253; and Hooton S P, et al., 2011, Int J Food Microbiol. 151(2): 157-163).

All three outcomes were improved by bacteriophage treatment in animals infected with *S. aureus* and *P. aeruginosa*, and bacterial reduction was observed in those infected with *A. baumannii*. Without being limited by theory, this can be explained by studies (e.g., Simoes L C, et al., 2008, Appl Environ Microbiol. 74(4): 1259-1263) in which the presence of *Acinetobacter* spp. in a biofilm community was found to facilitate surface colonization by other species, namely *Staphylococcus* spp. Results herein are in line with this finding, in that excess bacteria growing in non-selective media in *A. baumannii*-inoculated groups were determined to be primarily *Staphylococcus* spp.

In the instant work, bacterial counts were assessed at t4 (day 4 after treatment initiation), and colony counts were significantly different for *S. aureus* and *P. aeruginosa* test conditions compared to control. especially with respect to *P. aeruginosa*. These findings are in agreement with previous studies (e.g., Mendes J J, et al. 2012. Comp Med 62:1-12; and Fazli M, et al., 2009, J Clin Microbiol. 47(12): 4084-4089). In particular, Fazli et al. used confocal laser scanning microscopy of clinical wound-biopsy specimens to demonstrate that the distance from *P. aeruginosa* aggregates to the wound surface was significantly greater than that of *S. aureus* aggregates, which led to an underestimation of the former in swab samples. This observation supports the possibility that factors intrinsic to each pathogenic bacterial strain can contribute to differences among studies that compare cultures grown from swabs and tissue samples.

Planimetric assessments revealed statistically significant differences between the control and test groups treated with *S. aureus* and *P. aeruginosa*, and the same trend was observed for *A. baumanni*. These results were similar to the EG and DG measurements in harvested histological specimens.

Importantly, the results obtained in the rodent model were largely corroborated by experiments in swine, as pigs are considered the ideal large animal model for studying cutaneous disease (Greenhalgh D G., 2005, J Burn Care Rehabil. 26(4): 293-305). In both models, there was a significant reduction of bacterial counts at both time points (t1 and t4) for *S. aureus* and *P. aeruginosa* infections.

Significant results were observed in the *S. aureus*-inoculated and *P. aeruginosa*-inoculated test animals with regard to EG measurements.

Accordingly, this study suggests that bacteriophage-containing TAT provides a viable treatment for DFIs, including infections caused by drug-resistant bacteria, offering an effective and novel therapeutic approach for addressing the serious problems associated with DFIs and other chronic skin and soft tissue infections. That is, bacteriophage treatment effectively decreased bacterial colony counts and improved wound healing, as indicated by smaller epithelial and dermal gaps, in *Staphylococcus aureus* and *Pseudomonas aeruginosa* infections, and thus topically administered bacteriophage treatment is effective in resolving chronic infections, especially when applied in conjunction with wound debridement.

6.1.9 TOXICOLOGY PROGRAM FOR FIRST HUMAN STUDY

A 4-week dermal irritation study in mini-pigs, as shown below, is proposed to support an initial clinical study. If necessary, a 4 week intravenous (iv) study in rats also can be carried out, although it is believed that the iv study will not lead to any conclusion as the bacteriophage strains do not replicate if they are not in the presence of specific bacteria; the iv study, however, can confirm this belief and also that the bacteriophage strains are safe when given in much higher quantities (as using the same dose in an iv study as topical application reflects a much higher dose when compared to maximum absorption possible).

4-Week Dermal Irritation Study in Minipigs, 4-Week Recovery Period (GLP)

The study design involves 5 female minipigs, where the dose route is dermal (2 sites/side; wrapped/washed) with a frequency of once daily. The dose preparation is to use as received. Observations are made twice daily (mortality/morbidity), while a detailed clinical observation is made weekly, including measuring body weight. Physical examinations are conducted by a staff veterinarian on all animals prior to initiation of administering an exemplary phage cocktail composition in accordance with the instant invention, as the test article (TA).

To evaluate skin reaction, each animal is evaluated for erythema and edema daily prior to each dose beginning on Day 2. Any non-test site lesions also are noted and described. A Draize scale for scoring skin irritation is used, as follows. For erythema and eschar formation—0 indicates no erythema; 1 indicates very slight erythema (barely perceptible); 2 indicates well-defined erythema; 3 indicates moderate to severe erythema; while 4 indicates severe erythema (beet redness) to slight eschar formation (injuries in depth). For edema formation—0 indicates no edema; 1 indicates very slight edema (barely perceptible); 2 indicates slight edema (edges of area well defined by definite raising); 3 indicates moderate edema (raised approximately 1 millimeter); while 4 indicates severe edema (raised more than 1 millimeter and extending beyond area of exposure). If there is no necropsy, the animal is returned to stock.

Punch biopsies are performed for histological analyses. Three samples (naïve, placebo, TA) from the left side are collected on day 29; 3 samples from the right side are collected on day 57; all samples are preserved, processed to slides, and microscopically evaluated. Formulation analysis involves a certificate of analysis, provided by a third party.

4-Week Dermal Toxicology Study in Rats, 4-Week Recovery Period (GLP)

The study design involves a dosage schedule for administering an exemplary phage cocktail composition according to the invention, as presented in the table below.

| | Main Study | | Recovery | |
|---|---|---|---|---|
| | Males | Females | Males | Females |
| Vehicle Control | 10 | 10 | 5 | 5 |
| Mid Dose | 10 | 10 | 5 | 5 |
| High Dose | 10 | 10 | 5 | 5 |

Additional animals/sex/treatment group are included as replacement animals.

The dose route is iv bolus, with a frequency of once daily. The dose preparation is to use as received. Observations are made twice daily (mortality/morbidity), while a detailed clinical observation is made weekly, including measuring body weight. Food consumption occurs weekly as well.

Ophthalmology tests are performed on all animals pre-test and on all surviving main study animals at termination and recovery. Clinical pathology tests, including hematology, coagulation, clinical chemistry, and urinalysis, are performed on all surviving main study animals once at the terminal or recovery necropsy. Necropsy tests are performed on all main study and recovery animals; TK animals are euthanized and discarded. Organ weights are determined for adrenals, brain, heart, kidneys, liver, lungs, ovaries, pituitary, prostate, salivary glands, seminal vesicles, spleen, thyroid with parathyroid, thymus, testes, and uterus.

Slide preparation and microscopic pathology is performed for all animals in the vehicle control and high dose groups, as well as for all found-dead animals, and includes the preparation of a full set of standard tissues (approximately 65) and target organs in low and mid dose groups, and for all recovery animals. Slide preparation and microscopic pathology also is performed on gross lesions from all animals.

Standard statistical analyses are used. Standard parameters for toxicokinetic analysis also is used, such as AUC, $t_{1/2}$, $t_{max}$, and $C_{max}$.

6.1.10 CLINICAL STUDIES

Clinical Trial/Proof of Concept

Figure 13:
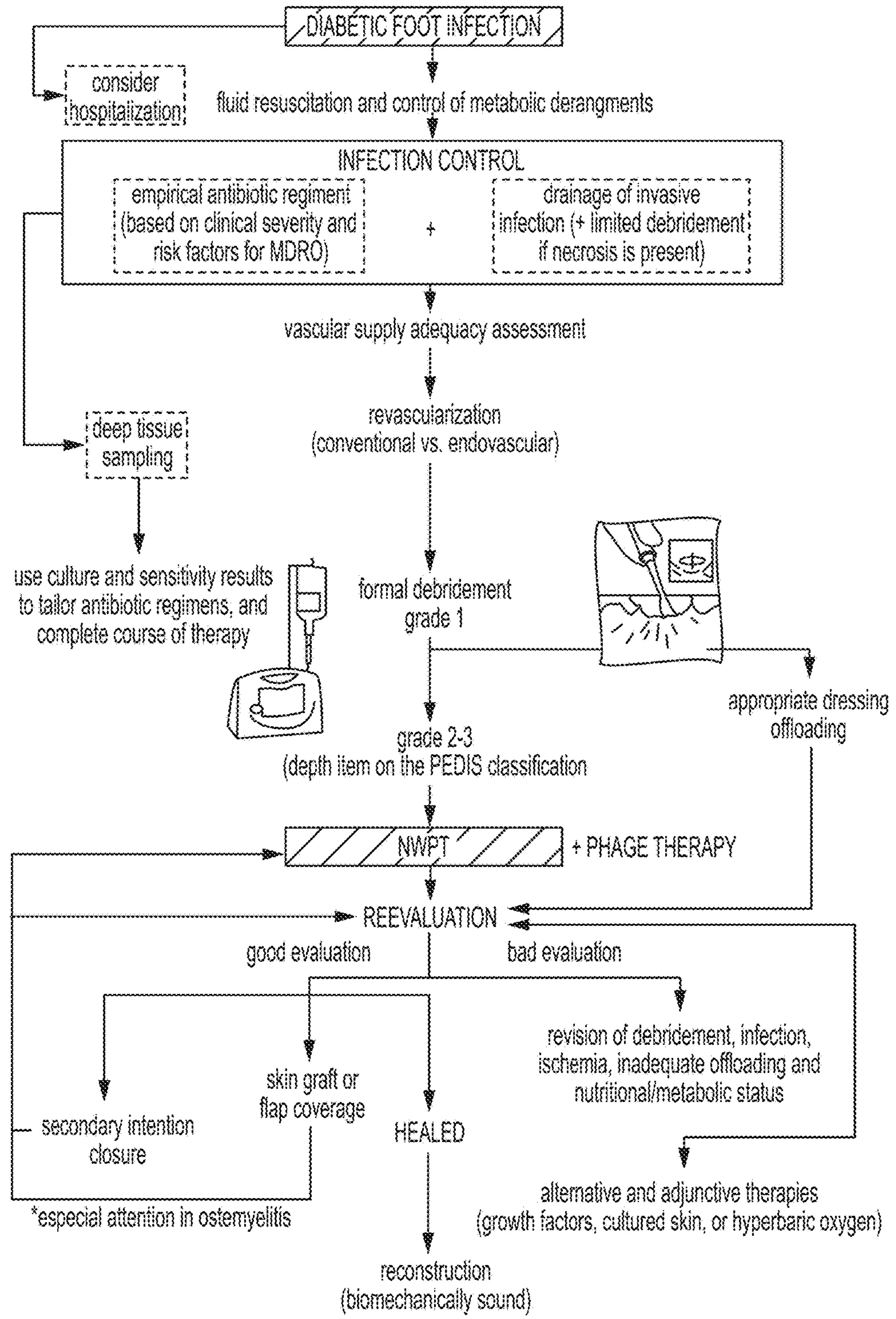
FIG. 13 illustrates diabetic foot infection classifications and application of phage therapy thereto using exemplary phage cocktail compositions in accordance with the instant invention.

FIG. 13 illustrates diabetic foot infection classifications and application of phage therapy thereto using exemplary phage cocktail compositions in accordance with the instant invention. Basically, a bacteriophage cocktail composition in accordance with the invention is applied in grade 2-3 ulcers based on the PEDIS classification. Administration involves use of a topically-applied liquid formulation after debridement of the wound.

Figure 14:
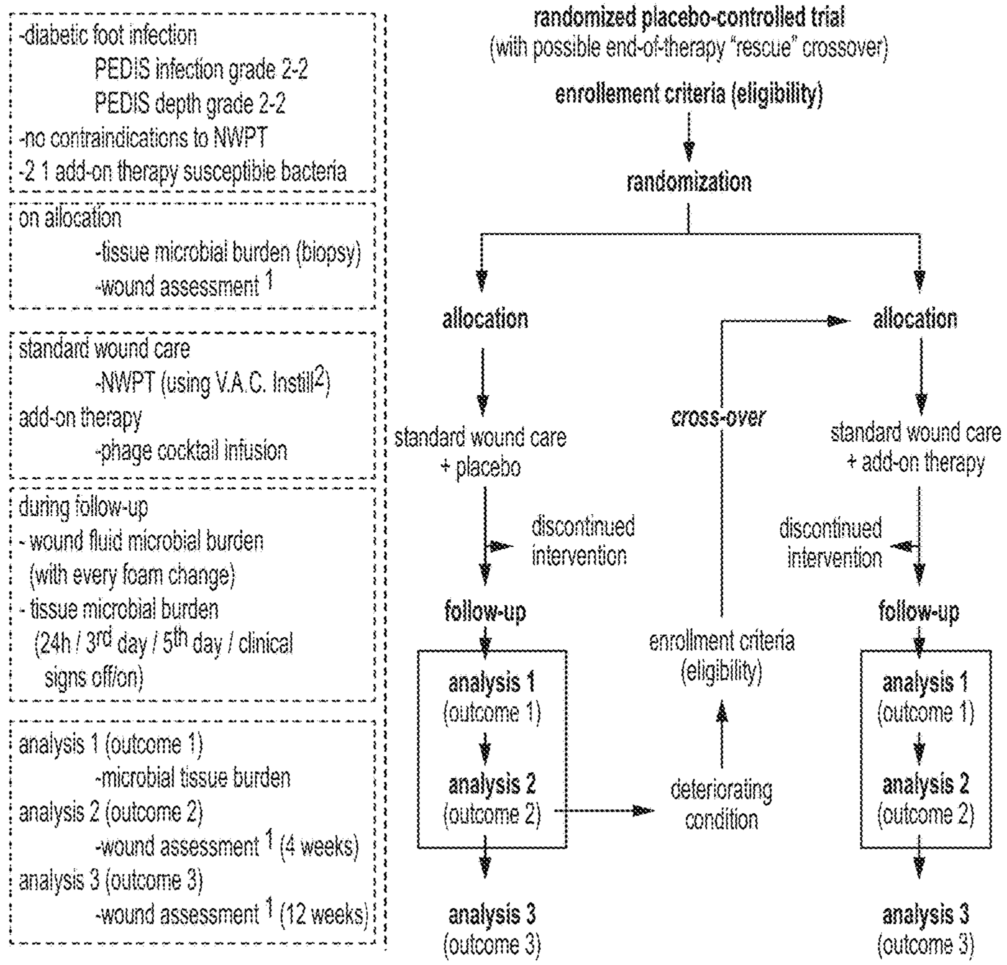
FIG. 14 illustrates a clinical study design for exemplary phage cocktail compositions in accordance with the instant invention for use in therapy for diabetic foot ulcers.

FIG. 14 illustrates a clinical study design for exemplary phage cocktail compositions in accordance with the instant invention for use in therapy for diabetic foot ulcers. The study type is interventional, with the intervention model of parallel assignment; the study design involves randomized allocation with open label masking; endpoint classification includes safety and efficacy, while the primary purpose is for treatment. Primary outcome measures include microbial tissue burden (biopsy); wound fluid microbial burden (time frame: with every foam change); and tissue microbial burden (time frame: 24 h/3rd day/5th day/clinical signs off/on). Secondary outcome measures include wound assessment in each follow up visit (time frame 4 weeks and 12 weeks).

After the screening visit and debridement of wounds, the eligible patient population randomly receive placebo or a bacteriophage cocktail composition in accordance with the invention at $10^9$ phages/cm$^2$/application for 4 h/4 h the first 24 hours and then once a day for 5 days. Safety and efficacy of the drug is compared to the placebo group; however, if a patient is determined to be at risk of requiring an amputation, the patient also can be included in the therapy group.

Criteria involve the following inclusion and exclusion criteria. Inclusion criteria include a clinical bacterial infection at the ulcer site of grade 2 or 3 according to PEDIS classification and no contraindications to negative wound pressure therapy. Exclusion criteria include topical application on the wound of any agents for advanced wound care (e.g., use of a growth factor) within the prior 7 days.

Certain modifications and improvements will occur to those skilled in the art upon a reading of the foregoing description. It should be understood that all such modifications and improvements have been deleted herein for the sake of conciseness and readability but are properly within the scope of the following claims.

All publications, patents, and patent applications cited herein are hereby incorporated by reference in their entirety for all purposes.

What is claimed is:

1. A method of treating or reducing the incidence of a bacterial infection in a subject in need thereof comprising administering to said subject a therapeutically effective amount of a pharmaceutical composition, said pharmaceutical composition comprising a pharmaceutically acceptable carrier;

a first and a second purified strain of bacteriophage, each of said strains having a genome which comprises at least 99% sequence identity to the nucleotide sequence selected from the group of consisting of SEQ ID NO:1 and SEQ ID NO:2, and showing antibacterial activity against *Staphylococcus aureus;* a third purified strain of bacteriophage having a genome which comprises at least 99% sequence identity to the nucleotide sequence SEQ ID NO:3 and showing antibacterial activity against *Pseudomonas aeruginosa;* a fourth purified strain of bacteriophage having a genome which comprises at least 99% sequence identity to the nucleotide sequence SEQ ID NO:4, and showing antibacterial activity against *Pseudomonas aeruginosa*; and a fifth purified strain of bacteriophage having a genome which comprises at least 99% sequence identity to the nucleotide sequence SEQ ID NO:5 and showing antibacterial activity against *Acinetobacter baumannii;* wherein each of said first, second, fourth, and fifth bacteriophage strains is present in the composition in an amount about 10 times that of said third bacteriophage strain; and wherein said bacterial infection is a *Staphylococcus aureus* infection.

2. The method of claim 1 wherein said bacterial infection is diabetic foot infection.

3. The method according to claim 2, wherein said treatment comprises topically administering said composition to a cutaneous ulcer associated with said diabetic foot infection, and/or wherein said administration follows mechanical debridement of said ulcer; and/or wherein said administration comprises use of at least one of a dressing, an instillation device, and a negative pressure wound therapy device; and/or wherein said pharmaceutical composition is administered every 4 hours or every 6 hours for an initial 24 hours, and following said initial 24 hours, said pharmaceutical composition is administered every 12 hours or every 24 hours for at least 3 or 4 additional days; and/or wherein said method is used in combination with a standard therapy for diabetic foot infection, said standard therapy selected from the group consisting of extracellular matrix replacement therapy, moist wound therapy, negative pressure wound therapy, arterial revascularization therapy, hyperbaric oxygen therapy, administration of an antibiotic agent, and administration of a growth factor; or wherein said method is used in combination with a non-standard therapy for diabetic foot infection, wherein said diabetic foot infection is refractory to a standard therapy.

4. The method according to claim 1, wherein said subject is a human.

5. The method according to claim 3, wherein said extracellular matrix replacement therapy comprises use of bioengineered tissue;

wherein said antibiotic agent has antibacterial activity against at least one of *Acinetobacter baumannii, Pseudomonas aeruginosa*, and *Staphylococcus aureus;* wherein said antibiotic agent is administered via systemic administration;

wherein said growth factor is at least one selected from the groups consisting of platelet-derived growth factor, granulocyte colony-stimulating factor, epidermal growth factor, fibroblast growth factor, nerve growth factor, and vascular endothelial growth factor; and/or wherein said growth factor is administered topically.

6. The method of claim 1, wherein said composition is formulated for topical application to an area of non-intact skin.

7. The method of claim 6, wherein said area of non-intact skin is selected from a diabetic ulcer, a cutaneous ulcer, a chronic ulcer, a burn wound, a cellulitis sore, an erysipelas lesion, a decubitus ulcer, and a pressure sore.

8. The method of claim 7, wherein administration of said composition provides said third phage strain in an amount of about $10^7$ phage particles/$cm^2$ of said area.

9. The method of claim 7, wherein administration of said composition provides said third phage strain in an amount of about $10^8$ phage particles/$cm^2$ of said area.

10. The method of claim 7, wherein administration of said composition provides said third phage strain in an amount of about $10^9$ phage particles/$cm^2$ of said area.

11. The method of claim 1, wherein said bacterial infection is an infection further caused by *Pseudomonas aeruginosa.*

12. The method of claim 1, wherein said bacterial infection is an infection further caused by *Acinetobacter baumannii.*

13. The method of claim 1, wherein said bacterial infection is an infection further caused by *Pseudomonas aeruginosa* and *Acinetobacter baumannii.*

* * * * *

SEQUENCE LISTING

```
<160> NUMBER OF SEQ ID NOS: 5

<210> SEQ ID NO 1
<211> LENGTH: 137360
<212> TYPE: DNA
<213> ORGANISM: Unknown
<220> FEATURE:
<223> OTHER INFORMATION: Description of Unknown: Bacteriophage F44/10

<400> SEQUENCE: 1

aatttcatta gaaaagaatt tttttctttt tctatagtat ctttcttgtt atcgtattct      60

gaatacatca taaattctat aaatatacta tttctgtcag atgaaaacat atctatagaa     120

aacggacaat caaaacttat gtcatcttta ttaatactaa aacattcagt aacatttaag     180

tcatttattt catatacctc aaagtatcca tcaactcttt taagttctat agcactatta     240

tatctataat aacgttgttc ctctattaac ttatcttttg ttagataggg atattcattt     300

ataaatatag gattacttgt tccatagtta tttttaatat attcagcatc ttctaaggaa     360

tcagtataac ctaaaacttc gtaacttgtt gtatacacag tatcctcttc ccacaagtca     420

tagtccattt cctctatttc ttcctctagt atataaattt ttttcatata ttactcccaa     480

acaccaataa gatttttaag tttagctata acttcttctt ctgtttgata agaaaatact     540
```

```
cctgtaatgt gtccatagtt acctataatt tcataatcct gtgtaccatg tttgtctact    600
agatatgagt tacccataac atttaaacta tcctccgagt aactgaaatt tatattatag    660
tctactaaaa aattaataat ttttttcatt tacataacct ctcctatcgg atattgtcct    720
aacattcttg ttccattttc gttatagaag gtatattcta ctacaataat attcattata    780
tcgacatata tagcttctat ataaggtgta atattctctt cttcttgtat gtgtttacct    840
ataatattat ataataattc agagtgtatt cttttatctc tcattataga cctccgtaag    900
aaatgataca gtcttatctt ttaaagattt ttctactagt tccatagcat ctttataatg    960
ttttatatta gattcattag acttcagttt atcttttact tcttgaatta gaggttcaac   1020
tttagtaact aaatcttttt tattttctat actcacattg cttcttttat tatctaatac   1080
ttcctttggc atatacttaa cttttgcaaa gtctttatag ctaacattta agttatctaa   1140
atcatctaat aaatcattat aatattctaa atgattatag aatgtgtaaa acttaacaag   1200
gtctttacct gctagctctt ctttttttag tatattattg atattaccaa taacagaata   1260
tgctataggc ttaaaattag ccctaacata agttaaaaat ataaaatcat cataaaacaa   1320
gtctaaaaca gttttattga atctagtatt tttagcttgc tctaattgag cacataaatt   1380
aagaacatta tcaaacccac tctttaatac caaagagata aatctttcca ctgcatagta   1440
cctagatact tcagtatgtt tgcttgcttt ttcactattt ctaaaaatag tatctgataa   1500
aggttgaact actaaactca tataatcttt atctgaatat tcatccgatg ttccttgata   1560
agtacttcca aattctattg tagataataa aaaacttttt tctaaattca ttataacatc   1620
ctccttttac ttgttattat aatactaaca catatgttta ttaatgtcaa acattaaata   1680
tcttctgttg tgtcaacttc atcttgtata tacttaaagt attcataaat tttaaatagt   1740
ataactccta gtgttattaa tcctaaaata tatttcataa caatcctcct taaaagtatt   1800
tatccttccc atcctgataa agcatccata gccatatcat actcttcttc atttttagtt   1860
cttataattt tctctatttc tttttttgct tgtttagagt tcataaaatc aatatctact   1920
gtatctaaat ttgtataatc aatattttct ctaataaagt tcttttgact tggtgttata   1980
gaattaactc gtacgttttc gtgatttaaa aattgataga agtccatact attcaccttc   2040
ttttaaacag tctgccatat cttttaaagt attaagtaca tatttcaaat ctctataata   2100
actatcagaa aaactaataa cagcatatgg tgtcatatca ctatagtgtg cacaatcaaa   2160
acctaatacc ctatagtcac cctcatgttc atcgtatgtt atacctccat gggaacaatc   2220
ttctatacta ttaaactgtt ctttggttat attcgtaggc acattaatat aaccatttag   2280
atgtcctgaa tgagggtgac gtttaacagt taggtttatt cccttataat ctatatttaa   2340
agttaagtcc tctcctaata tattatcctc tttatctata atttccataa tatgttctgg   2400
agcttttcca aacatcataa ttcctccctt ttctttatac tcttactata cactactttt   2460
tctattttgt caacaaaaaa aggctactaa ttaaagtagc ctaagaatta attatttagc   2520
attatatttc cattgccaat aaccattttt ctgtgagaac tcaaagtgaa aaccgtcata   2580
gtcaaattca atattatagt ctccatcttg aagtggtttt gaatttagta caggactatt   2640
actctttgcc aattctgcta gaaactcatg atttactttt tccatagggt ttattcctcc   2700
taattattct tacagtacta atatatcaca ggtctttttc taggtcgttt ttaaatttct   2760
cctcataaga actagcataa gttacttcat aacctattac cttagtataa tctatgcaaa   2820
gtaatttata attggacttt attttaatat cctctgattg ttctatttta ttgataactt   2880
```

-continued

```
catttagctc attcgaagag taatgtttat tatcaacttt tattgttttt ccttgggtat   2940
agatatcaat ttcttgtatc atcatttcat ccttttgatt attcattatt tgattataag   3000
tctctaaatc atcaatgtta tctgtatctg aacctttttac taaccattct cctctcttct   3060
taaggaggtc atcaaatttc tcatgttctt taattatctt ctctacttca ctcggtatta   3120
gaacagctct agcgtaattt atatgccaca tagacatatt atcaataaga taattaacca   3180
ttcttataag ttccttctca tttgccatat accaacctcc ttatatctaa tactaatata   3240
agagaaaagc agacttatta aaagtctgct tctgtaccta attctaatct tttatttttc   3300
atatgaggaa tcattttctt atctcctgtt aatagagata attctctagc tttttcttta   3360
gataatgtta atagtccatt ataattatct actttcttat tatattccat aattaagcgc   3420
tctagctcat atgatatatc ttcgagttct cctgatttaa ctccaagtaa ctttctatac   3480
atatcataat cttcagaaag actttctact ttatttttag atacagaatc ataaactgct   3540
tgtaaattac cttcttcaat aagtttaaag ttatgttcac ctatgattaa ttcctcctca   3600
gaagaatcaa gcgttactaa tccgcttgta ttacctgtaa agtcaccttt ataatctaca   3660
acaatacctt cagttacttt gtcacctaat tcaatagtcc catcttcatt ttctttaaat   3720
ttatgagcat catatacttc tactttgtca cctaatctca aatcttgagt taagttatgt   3780
ttaccaataa ttctatccat tactcaatct ctcctttatt aatagggtct tgtgttaaga   3840
acatttctag attctctttt gtaataggta accaaaaata tttactttcc ggaattgtaa   3900
ttgtatagaa atcctcatct ttgttaactt taatattaac atctgtaaac tcatcctgca   3960
ttaaccaatg agttacagtt aagttatatg aaccatcact aacataccct aaatcaatat   4020
catgtctaaa agccaaatct tctaaatgtt ctaataaatc gttcttttca ttatgttttt   4080
cttcttctgt attattttta attgggttaa ttaactctgt gcaaacaata tcgtacaatt   4140
caccatctgt aacctcatag ttcttttcaa ttaatacatc ttgtatttta ttgattgagt   4200
ttgtaactac tttcccatat tcttcttctg taaacttaca tttatctaaa tcaacatctg   4260
taattaattc tgcaatccat ttatttaaaa ttgatactgc cattgttcta gaaataatac   4320
tgtcgtatac catatttatt taatctcctt atttaggtga atgtggtctt ctaatgaaaa   4380
atcaaaaggc gctacaccat ttcttttatt atttgtttct tttttaagta taacataagt   4440
tagtgaaaaa gtcaagatag ttactacaac cattgataaa aatttaatca ggtttttcat   4500
aattactcta actccttaag tttatttttt actttctctt tatcgtactt ataatcttta   4560
ctagagtttt cattttttc tttctcttct tcattaagtt ctctatactg agcctcttct   4620
acctcttgtt ctttattatc attaccttct tctgcttttt gaatttctac atttttacta   4680
ctaccaccat ttaccttttt tctaaaaaga aaccaaagta ttaataaaat gatgagtaaa   4740
ataataatgc ttaatacaac agcccaaata ttattaacca ttacaaccta cctccgaata   4800
gtttttttac ggctcttaag ttttcagatg aatcattatt tatatcaata cctatgctag   4860
aatcaaaaat tacagcatta tcaagtatat gctctgtcaa tttattaccg taactacttt   4920
tacttaccac actaccataa ccatgattag ttaggtcaac catatcaggt tcaacttcta   4980
gtactctaaa agatattcta cgtaagaatg aaggatttac caagtaaaag gaagatttaa   5040
aaacatttaa tctttgataa gaatgtttta tattaacaac aaaccctgtt aacttatttt   5100
catattctga atttgataac ttacctaggt aaaggtttat actatatcct tttgtttcta   5160
atgtttgaat agcacttaac attatagccc ctctataagc aaggttttca gggtcttcca   5220
tccaactaat actagaatta taaaatacat caataacttt cttctctgct ttaactcttt   5280
```

```
gctgagacat catagaatta ggtaaccctt ttatagcatt aggtacgtga ggttgatacc   5340
cttccggagc tacgacaggt tttcttttta ctgacttatc cattctaaat aatgcatctg   5400
tcattttttt aagtttaact accatatcat atgattctct atcaccctta accattaagt   5460
tataggcttc ttgaaaacta tgagttcctg taaaatcata gctacctgta tctgatgaat   5520
tttctctacc tgaaactcta ttctttttta aagcagaaaa gaaatcaggt agaccatcat   5580
atttaattac atttaattct gagttatcta ttaatcgtct acccattgat tttcctccta   5640
ttctaatcct aacttatcca taattgtatc aaagtccatt gaatcttttg atgtactatt   5700
agattttcta ggttcctgtt taggttcttg ttgcatacct aaaagctttc ttgttgcttc   5760
tgtatatctg ttaccttcag gtaaagagct aataaattga ttaatctcat ctttcggtac   5820
agatttaaag ataatacttt ctacaacaaa ctcatcttcc attactccat ctaatttact   5880
accattaata attgcacgca ttgagaatac ataaggtaat ccttttttcat cattctcatg   5940
tcttaattgt tgtacaaagt ttactaagtc ttcattgctt gatagttgat gttccacctt   6000
agtatcatag tcaaattcaa cttgagcaaa gcggtctaat gtagctccat ctaattgttg   6060
tctacctaca taaatatggt ctgctcctgt tcccatagta ttacctgctg acacaactct   6120
gaaatcttca tgagctgtta cacgtccaat agggaagtca aagtatttat ttgcaatagc   6180
tgaattaaga attaatagta cttcaggaat agatgcatcc atttcatcta agaagaataa   6240
cccacctttt gtaaatgctt tatagaattg agtttcatga aacttaccat ttgcatcaat   6300
aaatcctgtt aatttaaatt cttgagtaat tgcattacta aaatagaaat ctaaatctag   6360
ggcttctgct acttgttcca atacatggtt cttacctgaa cctgctccgc cttttaaaaa   6420
tactggaata ttttggttaa ctaactttag tatatcttga tatctgtaat ggaagattcc   6480
tgagatatct ttaattgttt ttccttcttg ttgtaattca attttaactg gtaaattact   6540
aagttgttct tctacatact cttcaatttg ttttttaaca tcagtaataa taatttctct   6600
actctcagtt cctgctttct caacaattgc atctacaatt gcttgttcat acggattaga   6660
gtttttctct cctagttttt ttgctaaatc tgctgttgtt tccatttgtt gctctaccaa   6720
tctctctaat ctttcaatag tatcttgctt tgccatattt atcattctcc tttgatttgt   6780
tatacattta ttatattaca agtatttgaa tttgtcaaca actttctaaa actttttttag   6840
ttgctaataa aaaaatacct tacacctata acttaacata gggtaaggta attgtcaaca   6900
cttttgttaa aaatacatta atttaaaaaa atcatcaata tctttagttc catgtgtatc   6960
catatcatac ataaacatac aattatatgt atgactattc attatttcta acatgttatg   7020
catagaagtt gcattattga attcctctaa atcaatagtt accgtaagtt cttgaccttc   7080
ataaagtatg tttgctatat aatatttcct aacaccttcc attgttccat gggaagtttc   7140
attatgatta agtacttcta cacctagtga aggtaaatat tctgaaaagt aatatttaca   7200
gaaatatata aaattgtctg ttcttttaga cacgagtact atctccgtac tttatatttc   7260
tttctaatcg tacataatat gttttaattt tttgtacttc tttatctact gcatcctttc   7320
ttcctaacct tgtagtatat tttacaatat taaatatcat agaatcaaca aagccatcat   7380
aagaaaaatg ttcttctaga aaagaaataa catccttact acctttataa tgttcaggta   7440
aatgtgcatc tacttgtata ttataataat cttctaaaag acctatactc tcaccaagac   7500
tagataaagc gtaacctaaa tcatttgaat cattagacca ttctttagat actgatagtg   7560
catcttctat aattgttact tttaatttat ctaaataatc ttctacttga gcttgtgttt   7620
```

```
tcataaattc ttttgcgttc atgtaatacc ctcctaaatt atataaaaaa aacaccctgc   7680
ttggatacaa gcaaggtgaa aaaggaaaga tattatggaa gtgtactatc taagtacacc   7740
tcataatata acagttttcc ttgctagtta ttacttattt tttaaggtct tcttctttga   7800
caaacactcc gttaataagc ttacctttcc tttcttttat ctcatcataa gccatatcaa   7860
tacactcttc aatatctata tctaactgta aacatagtac tgttaatact acaaaaatat   7920
ccccaacact atctcttgtt acatggtcat tacttttagc aatacctgaa gctaattctc   7980
ctgcttcttc taataatttt aacatttgac cctcgggttt acctgtttgt aagtttctat   8040
cttttgccca ttgtttaata agttctactt tttccattat tctatatctc ctttaatttc   8100
tgtatctttg ataattaggt tatcagagtc acttgttaca tttaagttat cttcaactaa   8160
ttcatgtaga ttattagtaa tatcttcttc atacctataa cctacacgaa cataagcttt   8220
aactctgata tctatattaa cataatcttc ttggaatttt tccatttcta acttccttta   8280
ttatatcata ttattatact attgtcaatt aatctgagta gtttccttta gcaagttgat   8340
actttttgtg taattcttca tataattctc tcataccttc gtagtttctc atatcatctt   8400
ccaagaaact aagataatct aataatactt ttacatcctc aggttctaaa gttataactg   8460
gttttaccat taggcaacct ccttaaattc ttctttattt attttcttaa tatctttttc   8520
taatgcttct tttaattcat taggtaattt ataggcatca attgattgtt gttgacctaa   8580
tacatatcca ttatctgtga tacgtatttc cactgtaaac catgaattat ctaaatcttc   8640
ttctaatctt gctaataata ttaaacaact attttttaaa attctattag catacccgcc   8700
aacacaatga gataacattt taccttcatc tttaagttta cttacagtat ctgcaggaag   8760
gaattttact tttctaccat cttttaattt ataagtttta tcaattattt tttctaattt   8820
attatcatat ttagctttaa gttccgcatc atctaattgt tgttgtatag attgtttctc   8880
atctgtaact atatcatgtt ctagttttaa tgagaatggt gttaggttaa cactttctaa   8940
tgttctataa ccttctctta ttaatattga taaatcatgt aagtaatcta agtaatagtt   9000
atctagtgca tatcctgtta tacgttgtct gtcttgagca tctacatcta aatagtgagt   9060
catctttttg tagttagcaa aagatataga taatatttca tttacaatag gttttacttt   9120
taaagcattt gtaacatctc ttgaatctct aaccattaaa aaggtatcgt caaataattg   9180
gtgtaaatta acttcattgt gtaaatgatt atagttctta tagagagtat tagcaaatct   9240
taagtaatta ccttgctcaa atttatttaa agttagtagc tttttataag tctgttttgt   9300
aagattgaag gcttcatgaa ctttccattt agggttttta ggtatatgga atagtaatgc   9360
atttctttca aataatccaa attcttctaa gttatttatt ttatcaatat ttttaacaat   9420
atctgttaaa gttattaagt aattagaagt tgaattttct cctataaaaa tcctatactt   9480
atcccctcta taatttatat gaccataaac atctatatta tcaggacacc aactagaaaa   9540
atcaaaatta tgatgctcta atgtttgttc tattatcttt attataattc ctctatttaa   9600
gttaggttgt gaatagtttt ttaaaataac atttaataaa acagataatg tcaattcatt   9660
tttgtattca cttttactaa tatcatcttt atataggttt aaagctattt ctttattaac   9720
aagactatct gttaagaaaa ccttgactgc tcctgtctta acgtcaaatg aacttttatt   9780
ttctaaaacc catttgttac ccatattatg cttatccctg atatgtctaa ctttaagacc   9840
aaaagatgaa ttattctcag tacttgggtg catgtaccaa acacgactat acaatgaatc   9900
tgacatttcc ttataatact cactagaacc tttttctata tcttcattca taacaataat   9960
agatgaattt ataagaacat atttaccttg gtctagtaca tccatgatat cattatttaa  10020
```

```
actatctact gcttccttat actcatctaa ttgtctagct tcatatcccc ataaacggtt  10080
ttcattttct aattctttaa ttttttcttc aacataccct ttagattgta tttgttttct  10140
acgtctacta ccatataaag gaaaatcttt tctttctcct ctatcagctt caatatactc  10200
tttgtaattt cttcctttat tattaccaat cacaccttca actaattttt caactgtttc  10260
ataggggtca ccttcaaagt ttgttacttc tttattacca catagggcta aaaataaatg  10320
tatttctgta gctgtatcaa aactaaatat attatgaata tctctaaata attctttaga  10380
acctaagtta attatattat ttttcttttt cttaagaaat acatcttctt ctcctatata  10440
gatacatcct ttattaacct taggtaaatt aataatttct tgttctgtta atccttttttg  10500
tttataagtt attgccattt aaaatcactc cttatttgtt atgtactaat cataccatag  10560
taaataatat ttgtcaacaa aaaaagaaga actttttaaa gttcttctaa atgagtttcg  10620
tatataactt tttgaatttt atttaatggt tctaaatcta aattcctaat aagtttttca  10680
tactttcttg aatttttaaa attgatagta tttggcatag caagagcttc atcaacatct  10740
ttagtatagc ttacaacatc tgaatagata tctacttctt ttacatatag accttgagtt  10800
aaactcctaa atactacctc attatgtgct ataatttctt ctttcttttc tatgctcatt  10860
tataaacctc ctggtctact ctacacaaac aagtacgtat tctaaattag ttaaagaaac  10920
tgatttaata ttgtttaatt cttgtaattt cttaatttcc acatcatagt tcttacttat  10980
agtccataat gtctctcctg ctcttacttt gtgataatat ttatttccct ctttgataag  11040
gtcattcaat attacctacc tccttgagta ataattagct tgtagataac atataagtat  11100
aagaacaaag tttacaaatt cagtagctat aatatgaaca taggtatgtg ttaaaaccat  11160
acttacaatt aatgaagcta atcctaatcc aataataaga aatagaaatc tatttgttcc  11220
ttctgcactt ttagttttat aaaaggttgt tatctgagtt acatacgcaa ggataatagt  11280
aatagttgct acagtttgtg ttaaggctgt aaagtcactt aataaaaata gtaacagtga  11340
gaacacaata ataaaaggta tagagaaata gtcctttttt ctatatgaag ctactaataa  11400
gcaaacaata cctagagtta aattaagacc aactgatact acttgaaaca tcgtagcatc  11460
agttagaagt aaattgtaaa aactaatacc tactgtagct acaattaaat accaaaaata  11520
actactaaca cctttaacac tatctgactt aactagggct attaaacctg gtatataacc  11580
tactgtaact aatatagcat ataatatact taagtaatgt gataaattat ccatcttgtt  11640
cccctaattt ctctaatcta ttagtaactt cttcccatga aataaatcct tctccgtttg  11700
ttaattctaa aaccatacca tacacaaatt ggtttgtact aaattcagct ctgtcagggt  11760
cattgtatgg tttaccatga ccctgtctaa tatcagagca gtagattaat acgggttttt  11820
ttaaaatata ttcctgctct ccaatttgtc cttgtaaaat atcatatgtt tctgatagtt  11880
catctatctc attgaactta aataactcag actgttcttt taattgtttt attgtttctt  11940
gtgcttgatg tttcatacct aataaaatac ctagttctgc aattgttcct aatccttcat  12000
taagaacatc aaatacaaaa atatctgatt cttgcatagc cttaaagtca ttagttaaaa  12060
tacgttctgc tagcttagtt tgttctgcat tagctttatc atttattgac ttatctttgt  12120
gagggctata cggagttact cctacaatgc catctacttc tttatgttgt ttatctctgt  12180
aatctaccat agcttcattt aggatatgtc cacccatata aattactttg tctttaattt  12240
tattaaccat ctatagtatc tcctttttct tctaaaattt ctcttaaaat atgtggcatt  12300
tttttcttaa tttgtttatc tactattttc agtatatttt ctttttcttc ttccataata  12360
```

```
tcatcaacaa agttttgacc tacttgtttc ataattagac cgaagttttc taattctaaa  12420
tcatcttcag ataatctatc ttcttctata gccctaaaaa tcattttttc cattcttgct  12480
cttgtaatgg cataatctgc cactgactcg ttcttttta cttctgtttt catttttga  12540
cgactaaatt ctttaaactc attagatact aatttaaagt agtcatcata ttctgattta  12600
ccatctaagt atttaattac tataccttca cccttatcag gtttaactgt catgtcagat  12660
tttcctacta attcttgaat ttcttcaggt tttaaatcat ttaagtagtg agatggttta  12720
gctactagca aagttttaac tgtttttaac cctaaatgat gtgcaattac attcatgtct  12780
tctattgata aataaacttc attttcttta tcataaacat caaatacata aaaattgttg  12840
taaaattctt ctttgtactg aatcttatgt ttgactaacc attcaccaaa aataatgtat  12900
ttttctaagg ctgatacgta cgtatttctt acatttatat tttcatgtac ccaatcataa  12960
aaaccattta aagtttcatt ctcatttaat tttttctac gtgaaaaaca tactaattca  13020
ccattttcta ctgtgaagct tgcattactt ccatctaatt tttcttgtac aactagacct  13080
ctttctttaa atttatctag tacaatacct ttatttttta ctttagtata cgatttcatt  13140
aattatcctc ctttgaatta tgtactatag aaaacaaaat aagacttaca ctagctaaaa  13200
atgctaatac tactaaacca ggtaaattaa gaactgttga taagaataat gatattgcac  13260
ttataacata aactagaccg cttagaaata aagttaataa tacaattgtt ataagtttca  13320
ccaaccaatt attattaata aataccttag ctaaataatt cataaaaaaa tcctccttag  13380
ttattataga ataactatac cataactaag gggatttgtc aacatattat tttaccattt  13440
aaaattgtct gcatattgtg caagcttaga gcggaaatta actgtaaaat tatgaaatac  13500
tgctccttca taatttttaa agtattccat ataatctcca aaacctgatt tactttcgtt  13560
ctttaaatct atttgtttaa aattaccttc tactattaca gtagaatttt ttgtatgaac  13620
ccttgtaaga acttttttaa gttcactgcg tttaaagttc tgtgcttcat ttataattat  13680
agtagcatct cttagatttc cacctcttag gaataaatgg gatatttgag atacccaaca  13740
atctcctagt ttatcttctt taacattatc ttccatcatt aacatttcag ttatttgttg  13800
ttcaggattc atattaagtt caataagggc atcgtgtaat cccatgaaat aagccatttc  13860
tttttctgtc tgattacctg gtctgcttcc taaatcttct gatactggtg aaattataaa  13920
tactagcttt ctatttttat taagatagtc tgcgtaagca caggctactg agcacattgt  13980
tttacctgta ccggcttgac tctcattcca aagtatttca acattatcat taaagaaatc  14040
ctcacagaaa tctaactgct cggttgtagc tttttcaagg aattcattaa agattagatg  14100
ttctcccatg ttgtatctta cattaggata atcttttaac ttaaagtcta actcttttag  14160
ttgtattgcc atattttaaa gttcccctat ctataaatag ttttactctc ttttaatata  14220
gtactaattt ccgatatatt ctcctgttga agagcaataa ttactacatt cacattcagg  14280
gtagttatca caaacatctt catcttctac atcatcataa ccaatatcat aattattata  14340
attaaaatct acaatacaat tttcactatt acctttagat aatcctgtat aaataatatc  14400
atccacagaa tcccaatcgt tatctgccaa gtaatttaca ctatctagta ctgattcatt  14460
atcaggtaaa taaatactac cgtctgaaaa tttaattaaa atatcacctt gaggtaaggt  14520
atcattaatt aaatcaatct ctgtttcttc ttcaatagtg aatacagttc cttctaatct  14580
ttccggtgta gtatgtgtta aatgttttac agtatcccct gattcttcat agaatcctac  14640
tgcattcata tctttattat attttgcaat aaatttacca ttgtcactta ccaaatattg  14700
actagttgca ttatagtcgt ttgcgtcatc tactgtcatg caagggttat aatctttaac  14760
```

```
ataataacta attttcctaa catctgctgt ttgtactttc ttaccttcac ctttaattac  14820
tgaattaatt ttcttcataa tattttctcc tttttatata tcaattgatt tttttgcaag  14880
attatcggca tagtcattcc atttgtcatt tgaatggctc tttactttta caaagtttat  14940
atctattact ttttggtatt ctcgtatcat attaatatat gttttactta gaatatttct  15000
tgcagaccaa gtaccttcat accaatgtat taaaccaata taatctatat aaactattgc  15060
ctgattgtat cctagtttta tagcctcttc aataccataa caacaagcca atatttcacc  15120
cgcaacatta ttatacttta ttaatcctgg tttgtcaaca cttttactaa tttccgatat  15180
tatatttcct tctttactta ccaagacagc acctgagcct actttacctt tattatatga  15240
ggagctaccg tctgtgtata tatttacact atcctgcata cttataatcc tccataaatt  15300
gagggaattc acaatctgaa tagacttctc tgcaaaaaga tactgagata tagttaaaat  15360
caaaacattt gaaacagtgt tcttgaactt ctttttttatc tttagcaatc acattaaatt  15420
taaaaccatc agctatgact gtaaatactc cttttttcat aaaacaaata cctccactaa  15480
ttttatttta aattaataac taactcaata aatgatttaa tagttttatt tttaccttca  15540
tcaatatctg aaaagaaatt aattaaactg tcatcctcat caaataaatc ttcaacatca  15600
tcaaatttat ttaatatgtc tgtaacactg taaccctctt ctgatatata ctcatgtaag  15660
tcttctccat cttctgacag tgttgcttct attttaccat ttttactttc aattaaatat  15720
aaagtattta atactttaac agaatctaca actacactgt agttactaat agtaggatac  15780
tctgtataaa gtatttctat attagtattc atataactat caattacaga gttaactgta  15840
tctcttttta gctcagatac attatgtttt cgtatagtag ggaattcttc atcatattct  15900
actaattctt ttctatctgt attcaataac ttgtctaaag aagacaacaa tactatttta  15960
tattggttat caggaagact gtctgtaatt tccattattg ttaaaaacgt atcttcacct  16020
agaactttgt ttatatcttg taattcaaat gaatctacca tttcaatagt atcatctata  16080
tcatctgtag tcattaaaaa attaactaaa ttattattct ccatcgtctt cctccaattc  16140
tttaaataac tcttttcctg gagtatttaa cgctttctct aaccgcatta aattagcact  16200
tcttggtttc ttttttccat actcccaata agatataaga gagtaatgaa cacctatctc  16260
agaagctaga cttcttaacg tatgtccttt ttctactcta attttttgaa ggtttagagg  16320
tttactttcc ttttttttcat ccataattat ttctcctcta cttttaaaaa tttaaaatcc  16380
tcagattctt ttgcattttt tagtatatac tcttgtgatt tatttcttgc ctctgcctta  16440
cttttagcat ataactctat atgaaataca tgaggttttt ttaaagacgg tgactcgtat  16500
ctccaataaa ctttaaaaag tagtgtttct ttttttaaaa cattaattcg aaaccatctt  16560
ttaaatttat tcattcatta tcctcctcta tttatttgtt aaactaatta tagcatagtt  16620
aacttatgaa gtcaactata atatacaaaa aagactaaga aattaatctt agccttaata  16680
tattaataac tattatgtgc gttgtggtat gcaagagctc ctgatgttga accgtaacgg  16740
tcaatcatat attgttttgc acctttagtt tgttctgcta tagaaccacc actccatgat  16800
ttacctaatc cttggaatag tccttgagct cctgatgatg cattaacagc attagggttc  16860
attgtagatt cacgcatagc aatttcaatc attgcctcgt ctccacctgc ttgtctaatc  16920
tgttctgcta cagagcctcc tgtagaacta gttgattgtg taggttgttt agtttccttt  16980
tgaactggtg ctgatgttgt ttgtacttct tttttagtat cttgtttatt ttgagtatca  17040
aattgtgctt gttgttggtc tactttttgt tcaggtgttt gttcttctcc tgctaatcta  17100
```

```
gatactgtat tatctacttg agttgagcct gaatggtatt cataaccaaa gttaccatta  17160
taattataga aatgataagt aaattcaccg tcactaaatg agaaatcata attaccttct  17220
tgaattggtt ttgtattgac ttctgctgaa tttgatttag cctgttctgc taacttatta  17280
taatcaattt cgtctgcact agcttcgttt gtagcaatac ctccaaaagt aatagctgta  17340
cctaatgcta atgttgcaaa aattgttttc ttcataaatt taaaactcct taaataattt  17400
tttagaattg tttatttgta aaccgacata agtaatcata acatatatct ttaaataacg  17460
caagtataat atagcactaa ttagtgtaat attattaagg ttttattaca aacattacag  17520
ttatcagata attaaataca aaaaaaagag aggtattaac ctctctaatt tattattttc  17580
ctgttacatc tacaatagtt ccgtctccgc caatttgaat aggttgttta ccatcccatt  17640
tttcaattaa ctgttgacgt aatatcttat cagataagga agattctcta atctcattgg  17700
ctttttttatc accattagcc tctacttctt ttttcttagc attttgttca gcaatttgtt  17760
tatcaacttt agtacgttct aattcttggt tagctttaac tcgactgtca attgcttttt  17820
gagtattctt atctgcttta gggctagata atgcaatgtc ctcaattaca aatccttgtt  17880
tttctaagtt gtcattcaag ctatctaaag tatctttttt aatttcccct gttttaactc  17940
caaatgcatc aattacagaa tacttagata ctgcttgacg gacattatct tgtacccgtg  18000
aacgtaaata tcctttttct agttcttcga tatctgcact accaaaacga ttaaataaat  18060
ctacagcttt agttgcatct actttataag atacatcaat atccatttgt aaattcttgc  18120
catctgaagt tgctacattt aaatctttat atttatgtgt ttgtgtttta gttgggtatt  18180
tatttacctt atcaaaaggt gctgttaaat gccaacctgg tgatttagta tcttccttaa  18240
caccatttac tgagtataca actccaacat gaccttgtgg aatcttagta atacacatta  18300
ataaaataat aaaccctata attgctaaaa accctaatac tcctgaaata actactgact  18360
ttctcattac atttctcctt tttctatttc ttttattaag ctatttaaag ctttttcctc  18420
ttggtctatt tcttgtttat cggctctagt tacaattgat tgtctacggt catttaagaa  18480
ttgtttttta tactttacat attgttctaa accgtattca tctaatgtac cttgcctaac  18540
taattccctg tattgttttc ttatgttact cttcttctct ttcattgaaa gaaaatcaaa  18600
taaataactt ataccaaaac ctacaaggac tagaaaaaca ataaaaatag caaaatatgt  18660
taaaagtagt gccatgtaat tcctccttta tttgattaca tatataacta tacactatgt  18720
atttaatttt gtcaacactt ttttgcaaaa aaaaatagac ggattttaaa tccgtctaaa  18780
tttatattct atttgaatac tccccaggca acgccaggta tttgattagg tggaacacct  18840
tgacaagttc taacagggca atatactctg ttaccgttgt aagcattata acctatccaa  18900
atatgacctg cttggataca aacttcgtca tatacaattg tagcccctgc cggtaagtta  18960
ccgcctactg gagcatttaa gaatggagaa cctattctgg ttactatagg ttggttacca  19020
ttaacaaatg ttgcgctttc cggtttatac caagttccga actggttctt tttccaagaa  19080
cctgtaactg gtctagttgc cggtgtactt gcactacttg ttttaccatc tttaactaca  19140
gtagagcttg aagttccgtt actcatgtag tttttaattt gtttaatgaa gtaatctttt  19200
aacttattca ttattgcttg tgatggtctt ccttgtgtta ctgggttaaa tcctgtatga  19260
agaaccatcg aacggtgagg gcaggcagtt ggtacaaatt ccatatgcaa tcttacagtt  19320
ttacggttag gagtaagacc ccattcttta aatttctctg ctgtaaattg gaatactgct  19380
tgttcatttt taaggaattg agcatcacta gcactcattg attgacagac ttcaatacct  19440
gcaaatctaa agttacctga gtttgctcct gttccatccc ctgtgtgcca agcaatttga  19500
```

```
ttcttagcat ctattgcttc ccatacataa ccttcagagc catagtaatg agcaatacca  19560
ttagcatatc tagcataacc tgcattagct aatgaattct cgtattgttg tcctgaagaa  19620
cgacctgcat cgttgtgtat taccattcct tcaggttttt taccacgttt atccattgta  19680
tagttaatgt gattcttaga aacttttagt gttgctttct ttttaggtgc aggtgtttta  19740
cttgcgcttt tcttagctgt ttcttttta acagtagttc ctgcttttac aggtatttca  19800
atgaagtgag ttaatccgta ataattatct acacgttttg taggtttttt attagcataa  19860
ccattccagt tttgctctaa aatagtaaat gtagaagtat tacctccatc atatacaata  19920
cctatgtgac cccactgttc ataactaccg gatgtaaata ccgcaatcca accttttta  19980
ggtacagtag aaggtttatt ttcatgtatt ttaaatccag taccataact ctgtttaatt  20040
tggtctttag cattacccca agttctaact ttattatctg ttaaccataa aacatagtct  20100
gtaataaggt cttgacattg agcgtgatag tagccatctg cgtcaatggc tcctgcttcc  20160
attacaccaa atgacgggtc ataacttgta gctttttaa ctctgtaagg gctatctact  20220
gttccttttg cataagcgtc taaacgttta tttatttctg cttgagtctt agccattact  20280
taacttcctc ctctgcaaat actttaccat gttcctcggt atcttcttca tcttgagaag  20340
gtgctgaacc accatcaatt tcatcttcaa tagcaggtac ttcatcacta tcatctgtgt  20400
caggttctgc attgttttcg tagctgtcta tctcaaaagt actagcgtta tttgcgtttg  20460
tttgccattg aacgaactca ttagggtctt tactatcacg aggtttaacg taatctgttt  20520
gaacaatatc actgtctcta agacctttag tattattatc aacaataata cctaaacctg  20580
ctaataatgt tagtatagaa cctacaatat ttacaccttg ctcaatttga gctgagtagt  20640
ctaaaccgaa agcacctgta atttggttag caaataatgc tactgctgat ataattgcta  20700
cccaaaatgt tttgctctta gttcttgtgc taaggtttat tcctccaaca actttaggtt  20760
gtttagtttc attagccatt aaaaaaccga cctttctatt atatttattt ctaacaataa  20820
tataacagta ggtcggtcat gtttatctat attaatttaa cacttactca ttaatttggt  20880
ttagtttttt gataacttca gacatttgtt tgttatctaa atcttctaat ttagtttccg  20940
gaagtagctc taacttatcc caaacttctt ctttattaga tactttatta ttaataattg  21000
ccttaccaac taaactttcc gtataaatata attgttttgc tgatgccatt tgtatctctc  21060
cttttaaata tgtaaagtat atagctagta tcgtatccta ggaacaaaca cttgcgctat  21120
atactcaatg aaatcctacc ctcattcgag gacacagcaa accggttcgt caaccgcaca  21180
tatgaattct aagatttcat ttatgtaaaa cacaccctct ttgatttgca caaagactaa  21240
gggttttgga gacccttgta ctactaatta tactaagggt gtttattatg gtttctattg  21300
gatttgaacc aatgacacct agagcttcaa tctagtgctc taccatctga gctaagaaac  21360
cttaaaacga cccatacgag actcgaactc gtactctctg ccgtgacagg gcagtgtgtt  21420
aaccagttac accaatgagc caaaattata atgctatacc ctaaccttac cttaatgtat  21480
agcaggtttt ctcttaggct cgaagcaacg attattacca ctcataacaa ctatatatta  21540
agtgaaagga ggtgaaatga acaaaacgtg gtaattggta cctaagaagg taatatgtat  21600
aatctacaag gagtaagtta ttggttcata aaggagtgtg aacaataaat acatgaaaga  21660
gtgaaagttt actccctgta gattcttttt taattatcaa tcaaaggagg aaactgataa  21720
ttgttaataa taaactataa agaggaaaat atttatagtc acattctgat ataatgcaac  21780
taaatatcca agcataaccc gtctcacgag gaacctacct ataagacctg ttattaagtg  21840
```

```
aatcactacg attgactcta ttaaggagct accttaagtc catctcacgc aatttaaaag  21900
ggacttacaa accgtaaaac ggtaataagt ttattaaata atgtgatatt aacatattag  21960
ttaataactt tcacatggtc gaagaaaagt aaatttattt gattaccaaa ttatttttat  22020
caaatatagc tcttttgaac ctgtagattt atgctactca tactgataac ctctattatc  22080
taacacattt ctgtgctcca actacagtta gtcgttacag cgtatctttc taggattccg  22140
ctaagaccct agaaagaaat taaaccctag ccgttatcat actctacaga ccttataagt  22200
aagtaccaag tataccaatc gtatttaaca atactaatga cgacccatcc taccgatata  22260
tctccgataa gttttgattc gtttgattat cttgtacctt atgactacca aatcattatt  22320
cagtcactat gctcagatat ttagttgtat tatttatata ttaattataa catagttttt  22380
attacttgtc aagttaattt caaaaaaatt atagaagtag ggacgcttac ctacttccat  22440
ttaatttaca caaggatgat aacattgtta ttgttttata ctggaaaaca atgtaagaaa  22500
aacagtgatg tgtaaggtat ttgttttatt gttaattaca ttatagcata tactgatacc  22560
tttgtcaagt taatttaata ctttttaaa atattagtta tcttttgtta attcttcctg  22620
aatagcatcc catcttcttt ctgcttcact acgattatct tctatatgtt ttgtagtttt  22680
acaacatttg atacaatata tatctttgat atgaccttct tctcttttat ttgctctttt  22740
tcttggtact ttgaatacat ttccacattc tttacatatt aaacttgagt aaaacatttt  22800
ttgtcttttc ataattaatc aattcctttt ctcttttatt tgataattta actatatact  22860
atattgataa ataagtcaac agttttctaa aaataattta aattattttg aagaatcctt  22920
taatatcaag ggttacaaga gaaaaagtac gtatttagaa aataaggagt actcctatta  22980
tatataatta tattctgata tagagtaata aataatatta aatatataat tataattaat  23040
aaggttggga aaattgatat aaacataact gatattgctt atagatactc agtataaaag  23100
taaaatccct tagtatcagt acttacaggc aaaaaagtac gtatttagaa aataaggaac  23160
tctcctatta tagttatata tattaattac tattattaat tactatttaa atatataatt  23220
ataattaaca atgttagaaa gtcaacaata gtataaataa aaaagtgact acttaaagtc  23280
actcaataat tagaatacta ttttaaaaga ttctattctg tttggattaa tatatacttg  23340
aggtgaagtt atagcacttt cagtatatac ttttatagag gtttcatcca ttcctcttaa  23400
catataatct atatcttgcc tattgtaact cttttcatca gtagatacta aaaagtattt  23460
agctccactt gacattgtta tttcaatatg ttttgacatc tacaatctct cctatgcaaa  23520
tttgttaaag acaaaggata atatagctcc tagaacaagt aaaagaactt tctcagttgt  23580
atccttcttc ttagtatcct tagtttttgt acttccagca agttctgaaa tcttttcatc  23640
aagtctttct aattggacgt aaattgctga ttgtttttca ctattgacag ctacatcttt  23700
atctatacta actatcattt ttcttagttc agctacctca acttctaaat ctttgaaagt  23760
ccctctatct atataattac cttcttgtat cttagactta atagtttcta cttgagaaac  23820
aaggttgttt atctccttat ccaactagaa tcacctctaa ggtctaaccg tttcagattc  23880
agaatggata tcataatttt ctaagaaatc attgataatc tccatataat tatccgtaac  23940
gacttttccg taagatgttt ttgtatcaat ttcaaaccta agcttaccaa aactttggag  24000
gtctaattct tttattacaa tattagggtc atcagaagga aggtaataat agtcgaagta  24060
tataattgag ccatttatta atactctgtc tattctatag acgtggaaat agcgtctgtc  24120
tcttttaaaa tgggctagtg catctttaaa ctctaactta aggatatcct tatatttagt  24180
caaagtggta acctccttac tattaatttt taaatttact tattttgtgg tataatagtt  24240
```

```
atgataaagg cagttattat aattatatta agaataatga taataattat tttttctgag  24300
aaaataagcc aaatactaaa aacagataaa gcatagatag ctgatagata tactatatta  24360
agagttacct tacttttatc ttttctatag atagaataac ctaaagacgt tgtaacacca  24420
ctaagtataa aataatagaa acaaaaaaga ggtatagaca gaaaaaaaga tacgataatc  24480
attgttaaac acctatttct ttttgaccta ttatttctag aacttttaga ttacaccact  24540
aatataacat taaaagccag tcataaaagt caattgttag attaataata taataaaaaa  24600
agacaatagg aggttaaagt ggttgaataa taacatagct atattcatat tcaaaacact  24660
ggttatcatt atattcttac tactaatttt gtctgttatt aattccttgt cccttattta  24720
ctcaataaga ccgagtgtag ttatgacata ctttatcttt ggtggtattg tttctaatgt  24780
cgcacttact gtaacagata agttcttact gaagaaagaa gaccccctac ctgaatatgt  24840
tcttaaaaaa gtagagataa atgataaaga aataagaata atcaagaaaa tcatagaaag  24900
taattacgga ataacagcag aagagataaa agttagggct aaagcacaaa gaagaataga  24960
ggaagatagt aaaaaggaag attacgatga aaacaaagaa agaaattaaa gaacaaagga  25020
aagagcttaa ggatggtgct acatctgttt ctttagtaaa aaaaggagat aagagaatag  25080
ctagccctag tagaatttgt agtctatgtg gtcagcagtt atcaggtatg aattacacta  25140
aaggaaaagc attatcaaaa gttaatcatt ttcatttaca gtattctaag tatatttatt  25200
ttgatatttg cgcagatatc aacaattgtt ataaaaattt aagaaaacga ggtgaaatgg  25260
attgagtgca gaaaatatta gagatataat taacaagaaa aagttagaag aagaggatac  25320
aagaaaatat atagctgatg gatttatgaa tggtatcggt aaattaatgt acgaattcaa  25380
taaaaaagta gataataaag aaatagaagt taaagaccct aatgatttat ataaattatt  25440
tgtgatattc tctcaaatgc aaaatatggt caatgaaact tctgaaggtg gagcaatacc  25500
tcaactatct agacctcaac aggaattatt tgatgagatt acaacagaag atagtaatgg  25560
agaatctaca gttgatttac agaagatatc agaaatgtca gcagaagata ttacagcaat  25620
gatttctgaa aaggaaaaag taatgaatga ggaaaattca gaaacattct aaggagaaag  25680
atataaatgg atggaaaaga actaattaag atagcacaag aaacatttca aactgaaaaa  25740
ataacaagag aacagataga ccatataatc aatatgctaa acccttctac ctatatgctt  25800
aagtatcata cactgagagg tcatcctata acttttagta ttcctaacag ggatagaagt  25860
aaagcacagg ctcatagacc ttggcaaact aggattgtaa atgatactca tcctaataag  25920
gctgtaataa aatcacgtca gttaggtctt agtgaaatgg gtgtaatgga aatggttcat  25980
tttgcagata tgcatagtta tgctaacgca aagtgtctgt atacattccc tacaaatgaa  26040
caaatgaaaa aatttgttca gtcacgtttg aaccctgttt tagagaaaga atattttaga  26100
gacattgttg attgggataa agactcgtta ggttttaaaa agataagaaa ctctagttta  26160
ttctttagaa caagttctaa agcaagtacc gtagagggtg tggatattga ttatttatct  26220
ttagatgagt atgatagggt aaacttatta gcagaatcgt ctgcactaga atcaatgtct  26280
tcatcacctt ttaagattgt gagaagatgg agcacacctt ctgtacctgg gatgggtata  26340
cacaaattat accaacaatc agaccagtgg tattacggtc atagatgtca acattgtgat  26400
tacttaaatg aaatgagtta taatgattac aaccctgata atcttgaaga aagtggaaat  26460
atgttatgtg ttaatcctga aggtgtagat gagcaagcta aaacagtaca gaatggcagt  26520
taccaatttg tttgtcaaaa atgtggtaaa ccattggata gatggtataa cggtgagtgg  26580
```

```
cattgtaagt accctgagcg tacaaaaggt aataaagggg tacgaggata cctaataaca  26640
caaatgaacg ctgtatggat ttctgctgat gaattaaaag agaaagaaat gaatacagaa  26700
tctaagcaag cattctacaa ctatatttta ggttatcctt ttgaagatgt taaacttaga  26760
gttaatgaag aagatgttta tggtaacaaa tcacctattg cagaaacaca attaatgaaa  26820
cgagatagat attctcatat agctattggt atagattggg gaaatactca ctggataact  26880
gttcatggta tgttacctaa tggtaaggta gacttaatac gattattctc tgttaaaaaa  26940
atgacaagac ctgatttagt tgaagcagat ttagaaaaaa taatttggga aatatctaag  27000
tacgaccctg atattataat tgcagataac ggggactcag gtaataacgt tttaaaactc  27060
attaatcatt ttggaaaaga taaagtattt gggtgtactt ataaatcttc tcctaaatct  27120
acagggcaat taagacctga atttaatgag aacaataata gggttacagt agataaatta  27180
atgcagaata aaagatatgt acaagcactt aagacaaagg atataagtgt ttatagtaca  27240
gtagatgatg atttaaaaac tttcttaaaa cattggcaga atgttgttat tatggatgaa  27300
gaagatgaaa aaactggaga aatgtaccaa gttatcaaac gtaaaggtga cgaccactat  27360
gcacaagcaa gtgtctacgc ctatatagga ttaacaagaa taaaagaact tcttaaagaa  27420
ggaaacggta caagctttgg ttctacattt gtttctactg attacaatca agaaggaaat  27480
aaacaattct actttgatga atagaggtga aatagacttg acagataaat tattttatgg  27540
tacaattagt aatgaagaaa ttaataaaag tgtattgaat ttgttattgg gtgaggaatt  27600
atccttagat tatgtttcta aaaatagtga tactttagat gttaaatatg aacatgttta  27660
taaatctcta ggattcgata atttctttga ttgtttttta tatgctaata gagagcctga  27720
aatagtccat aaaggtggag ataaaaatct tggtggacta aataaggtta aacgtactgt  27780
tattcgtaat ggtaaagaaa tggaaatgac agtttacgaa gatggtaata aagagaacga  27840
tagtaaagaa aaacaagaag gaaaagaaga agttagtaga agtgcagtag gagcaagggc  27900
tatttctaat ggtgaagaag gaaaggtaaa ccctaaaaag gtagcaaatt cattatctaa  27960
tttaagtaaa aaaggtgtag atgtatcaca tattaataca aactcatcat tgtataaaga  28020
gtttgttgat gataacggtg atacattagg aattacatct tttaaacgaa ctgaaaatga  28080
tataatatta gaatcttatg caagttcaca tgattcagat ggtgtaggag caagagctat  28140
tatggaatta ttacgtttaa gtattaagga aaataaaaat gcagttgtgt atgatataga  28200
attacctgaa gcagtagagt atttaaaaac tttaggattt aaacctaata aagatggata  28260
catcttaaga aaaaaagatg taaaacaatt cttaggtgat tatagtgatt ttatttagca  28320
ctatagtcat ctattctatt gtatttattc tatatattgt attaaaaaca atttatataa  28380
agtctaatat gagtagaata gataacacaa ctgaattatt aaaaatatta caggaagata  28440
ttgaaggtaa gataaaaaag gaaggaagaa ataaatgact ttagaagaaa ataaattaac  28500
attagaagaa tcaataactc cacttagcaa agaggagaaa gaagatagta ttaaagaatt  28560
tagcagttta ttatgtgaaa tggtaaatag actatataag tcttataatg tatttagaca  28620
agaccctatg gatgaaactc aacgtctaga tggctcttta atggtctttc aaagtagatt  28680
aaatgaccct ttaacaggag atttacatga taagatgtat aaacttgctt tttcaaaacg  28740
tattgatatt ttcgaagcta ataagcaatt tagaaaagat gtagaagcag gtaaagcaat  28800
tgagttaggt gatgtagcta ttatagatac agcattaagt aacatccttt caggcaatga  28860
gttccaagga agtatttcat ttatgcttag aaaagacttt gaagaaaaag aacgaattag  28920
aaaagaagaa gaagagaaac ttaataactt ataaaaggga agaattatga gactatataa  28980
```

```
aatgaggtat cataattgaa aaagaaacca caaggcaatg aggtaatcat aaccataata  29040
acggttatga tagcagtatt tgtagtcatt atgaccatat tttttaataa atatcaagat  29100
gctaaagaag ataaagatag atatcaaaga ttagtagaga tttataaaaa agcagatgat  29160
aatgatggtg agactaaaaa gaaatatgtt aaaagattaa ataaggctga agaagaactt  29220
aaaaaagtaa aaaagaaaca aattataaag attataataa gaagtcaagt aaagaaagac  29280
aaaaagaaga taaagaaact agagagaaaa tatatgatgt aactggtgat gatgacttaa  29340
tattagtaaa aaataatatt gagtttagtg ataaagtaga caagcccgaa atacttatta  29400
gtgaagatgg aattggtacg ataactgttc ctgtagatag tgggtatgaa aaacaaacag  29460
taggttctat tattactagt gtattaggtt ctcctttcct atcacctggt tcaaatagta  29520
tagatggttt aagtgttatt aacgataatg tttatccaaa tacagtagat agcatagtag  29580
aagatacaaa accttctatt aacttaccaa cggataatcc tattataaca aatccagttg  29640
aaccaactat accttcagat attatacctc ctattgataa tccttcagtt ccgatatctc  29700
ctgagaaccc aggagataat aatcaaggaa atacagataa tccaaatcct cccccctccag  29760
ggtacacaga tgaagatggt ggaagaggct ccggtggtgg aggaaattct gaaccaccat  29820
caacggaaga accttcggat aatggtaaca ccggaggagg agattgggaa gaaaaacctg  29880
acccaggaga agaaccttca gataatggta atacaggagg aaatggtgga gaagttacgc  29940
ctgaacctga acctgaacct gaacctgaac ctgaacctga acctgaacaa ccgaatgaaa  30000
atcctgatga aggtaatgaa gaaaaaccat ctgaaccgtc tgacaatcct gatgaaaatg  30060
gaggatggga aactgaacca actgaacctg agtcaccttc agagccggac gataaagtgg  30120
acgaagaaga taaaaatgaa gatactacag atgataaaca gcccactgaa caaccggacg  30180
ataacaacat agataatgaa gataaaactg aagaggagta attactcctc ttttttgttt  30240
gctatattaa ataagagcta aatataaaaa aattgaacat tacggtggtg aaaactttgt  30300
taggaatgaa tattataacg tcactatcag tagtatttac ttgtttaagt cttttaactt  30360
taatgatttt tgttcatagt aagttctcta gtaaaaacgt ttttgttttg tatgtaattt  30420
atgctataat aggaataggt acatacatag ttttaactat gtttcaaaca acatctgtac  30480
ttattaagaa tgatgtaata gattccatag aaaatactga acattatatt ggattcaatg  30540
accctataat tatatttact ataagtttta taggtgcaat acttggagga atttggtaca  30600
agatgatgaa aattattaaa aagagtaact ttaaagataa aaaataaaaa agacggtgaa  30660
taggttgata ttctctaaag ataaaaaatg ggatgaagca aaagatttca tcaaaggtca  30720
aggtatgcaa gataattgga tagagattgt agattattat agacagatag gtggaaaaca  30780
cgtagctgtt tttattgctt taaacaaagt aaaatacatg attctagaag caacaaaaga  30840
caataaggta atattagtag ataaagataa taatatacta ttagaagatt atgatattgt  30900
tatggaaagt aagaagatgt tttattacat tgaagaaccg ttcgaggtta aaataaatat  30960
ccctcaacat attagagatg taacttataa taatactgtt gtattaacta cagtaagagg  31020
gagtagaggt gactagtaat tggcagattt atttaagcaa ttcagattag gtaaagacta  31080
tggtaataat agtaccattg ctcaagttcc tattgatgaa ggattacaag ctaacattaa  31140
aaaaatagaa caagacaata aagagtatca agatttaact aagtctttat acggacagca  31200
acaggcttat gcagagccat ttatagaaat gatggatacg aatcctgaat ttagagataa  31260
gagaagttac atgaagaacg aacataactt acatgatgtt ttgaaaaagt ttggtaataa  31320
```

```
ccctatcctt aatgctatca tacttacacg ttcaaatcaa gtagctatgt attgtcaacc  31380
tgcaagatat tcagagaaag gtttaggttt tgaggtaaga ttaagagacc tagatgcgga  31440
acccggtaga aaagaaaaag aagaaatgaa acgtatagaa gattttattg ttaatacagg  31500
taaagataaa gatgtagata gagattcatt tcaaactttc tgtaagaaaa ttgttagaga  31560
tacttacatc tatgaccaag ttaactttga aaaagtattt aataagaata ataaaactaa  31620
attagaaaaa ttcatagcag tagacccttc tactattttt tatgcaacag ataaaaaagg  31680
taaaattatt aagggtggta agagatttgt tcaagtagta gataaaagag tagtagctag  31740
ttttacttct agagagttag ctatgggtat aagaaaccct agaactgaat tatcttcttc  31800
aggatatgga ttatcagaag tagagatagc tatgaaagag tttattgcct acaataacac  31860
tgaatcattt aatgatagat tcttctccca cggtggtact actagaggta ttttacagat  31920
acgttcagac caacaacaat cacaacatgc attagagaac tttaagcgtg aatggaaatc  31980
tagtttatca ggtatcaacg gttcatggca aataccagtg gtaatggcag atgatattaa  32040
atttgtcaat atgacaccaa ctgctaatga tatgcaattt gagaaatggt taaattacct  32100
tatcaatatt atatctgctt tatatggtat tgaccctgca gaaattggtt tccctaatag  32160
aggaggagct acaggttcta aaggtggttc tactttaaat gaggctgacc cgggtaaaaa  32220
acaacaacaa tctcaaaata aaggtttaca acctttactt agatttattg aagacttagt  32280
taatagacat attatatcag aatatggaga taagtataca ttccaattcg taggtggaga  32340
tactaagagt gctactgata aacttaatat tcttaaacta gagactcaaa tatttaaaac  32400
agttaatgag gctagagaag agcaaggtaa gaaacctatt gaaggtggag acattattct  32460
agatgcttca ttcttacaag gaacagccca attacaacaa gataaacaat ataatgatgg  32520
taaacaaaaa gaacgtttac aaatgatgat gagtttacta gaaggagaca atgatgattc  32580
tgaagaaggg caatcaacag attctagtaa tgatgataaa gagataggaa cagatgcaca  32640
aataaaaggt gacgataatg tttatcgtac tcaaacatct aataaaggtc aaggaagaaa  32700
aggagaaaaa tcttctgact ttaaacatta attaataagc ctagaataaa tctaggcttt  32760
gtttattttt ttcgtaattt aattttgata aatgtaataa ctatgatata ctatatgtaa  32820
ttgatattaa tacataaaaa atattaatat ttcacttaca agttattatt gttatattat  32880
taacgtaaaa gtaaataaaa taacaagtgg aggtgtagac acctttggaa gaaataaaat  32940
ttaatgcttt tgtacctatg gatttgaaga aatctgtatc aacagcttct gatactaatg  33000
agtattctat cgtttcagga tgggctagta ctccaagtat ggatttacag aatgatatag  33060
ttaatcctaa aggaatagat atagagtatt ttaagtcaca agggtacatt aattatgagc  33120
atcaaagtga taaagttgta ggtataccta cagagaattg ctatgtggat atagaaaaag  33180
gtttatttat tgaagcaaag ctatggaaga atgacgaaaa tgttgttaag atgcttgatt  33240
tagctgagaa attagaaaaa tcaggtagtg gaagacgttt aggtttttct attgaaggtg  33300
cagttaaaaa acgtaatata aatgacaatc gagttattga tgaagttatg ataaccggag  33360
ttgcattagt taaaaaccct gctaatcctg aagcaacatg ggaaagcttt atgaaatcat  33420
ttttaactgg tcatggtaca tcacctgaca ctcaagttga tgcaggagct ttaagaaaag  33480
aagaaatagc atctagcatt acaaatttag cttacgtcac taagattaaa gatttaaaag  33540
agtttaatga tgtatggaat ggcgttgttg aagatttgag taaatctaat agtatgggat  33600
atgaggaatc agtccttacg ttacaactag ctaaaggttt atctcgtaaa gatgcagaac  33660
tagcagtaat ggatataaac aaacaaaaac tagaataggt aaggagaata cattctatga  33720
```

```
gtaaagaaat gcaaaatatt ttagaagagt atgataagtt aaatgctcaa gaggcagttt  33780
cgaaatctgt agaagatgat gaaaagaata cagtagaatc taccgaagag caagtagcag  33840
aaacaactga agaacctgct aaagaacctg aaaaagtatc tgaggaagat gctaaagaag  33900
cacaagagca aggtgaaaaa gttgaatctg aagaggtagc agagggcaat gaagatgagg  33960
aagttgaaaa atcagctaaa gaatcaaaag accctgtaga ccaaaaagat actaagacag  34020
aaaataaaga caacgagaaa cgtaaaaata aaaaagataa aaaagaagat tctgacgatg  34080
aagataaaga tactgacgat gataaagata agaaagaaga taagaaggaa aaaacttcta  34140
aatcaatttc tgatgaagat atcacaacag tatttaaatc tatcttaaca tcttttgaaa  34200
acttaaataa agagaaagaa aactttgcta ctaaagaaga tttaagtgaa gttagtaaat  34260
ctattaatga gttatcagca aaaatttctg aaatccaagc tgaagatgtt tctaaatcag  34320
tagacactga tgaagaagct gtagaaaaat cagtaacatc tacaaacgga gagcaagaaa  34380
aagtagaagg ttacgtttct aaatcagtag acactgaaga acaagctgaa actggtgaag  34440
caaaatcaga agaagctgaa gaagtacaag aagataacac atttaaagga ttaagtcaag  34500
aagaacgaac taagttcatg gattcttaca aagcacaagc taaagaccct agagcttcta  34560
aacatgactt acaatcagct taccaatctt acttgaacat taacactgac cctactaatg  34620
catcagagaa agatattaaa actgtaaaag actttgcaca aatttaatta atgcacaaag  34680
ttgtgttata ttatacggtg taactaaaga atataaatag ggtacatttt actgtaccct  34740
acataaaata aaaagaacac aaatgaaagg tgataaattt atatgactat cgaaaagaac  34800
ctgtcagacg ttcaacaaaa gtacgctgac caattccaag aagacgtagt aaagtcattc  34860
caaactggtt atggaatcac tcctgataca caaattgacg caggagcttt acgtagagaa  34920
attttagatg accaaatcac aatgttaaca tggactaatg aagacttaat cttctatcgt  34980
gatatctcac gccgtcctgc tcaatctaca gtagtaaaat acgaccaata tttacgtcat  35040
ggtaacgtag gtcactctcg tttcgttaaa gaaatcggag tagcaccagt atctgaccca  35100
aatatccgtc aaaaaactgt atcaatgaaa tacgtttctg atactaaaaa tatgtcaatt  35160
gcatcaggtt tagtaaataa cattgctgac ccatcacaaa tccttacaga agatgctatc  35220
gcagttgttg caaaaacaat tgagtgggct tcattctacg gtgacgcttc attaacttct  35280
gaagttgaag gtgaaggtct agagtttgat ggtttagcta aattaattga caaaaataac  35340
gtaattaacg ctaaaggtaa tcaattaact gagaaacact taaatgaggc ggcggtacgt  35400
atcggtaaag gtttcggtac agctacagat gcttacatgc ctatcggtgt acacgcagac  35460
ttcgttaact caatcttagg tcgtcaaatg caattaatgc aagacaacag cggtaacgtt  35520
aacactggtt acagcgtaaa tggtttctac tcatctcgtg gattcattaa attacatggt  35580
tctacagtaa tggaaaatga actaatctta gatgaatcat tacaaccatt accaaatgct  35640
ccacaacctg ctaaagttac agctactgtt gaaactaagc aaaaaggtgc ttttgaaaat  35700
gaagaagacc gtgcaggatt atcatataaa gtagtagtta actcagatga cgctcaatca  35760
gctccttctg aagaagtaac agctacagta tctaacgtag acgatggtgt taaactttca  35820
attaatgtta acgctatgta ccaacaacaa ccacaattcg tttctatcta ccgtcaaggt  35880
aaagaaacag gtatgtactt cctaatcaaa cgtgtaccag ttaaagatgc acaagaagac  35940
ggaacaatcg tattcgtaga taagaacgaa acattgcctg aaacagcaga cgtatttgtt  36000
ggtgaaatgt caccacaagt agttcactta ttcgaattac ttccaatgat gaaattacca  36060
```

```
ttagctcaaa ttaatgcttc tattacattt gcagtattat ggtatggtgc attagcatta  36120
cgtgctccta aaaaatgggc tcgtattaaa aacgttcgtt atatcgcagt ttaatagaat  36180
aagaaaaact gaatacaaga gaatagggat aaacttaggg tttatccctt ttttattaaa  36240
ataaacttga agggatttaa taaatatgtt atactataag aaactattag ataaaaaaat  36300
ggctactgtt tatggtacag tggagattga caaagatgga gtagttaaag gattaactaa  36360
agagcaagaa aaagaatttg caaatgttcc aggttttgaa tttgaagaag aaaagaaaac  36420
tactagaaaa caatcagctt ctactagtaa agaagaagag cctaaggaag aggaaaagaa  36480
agcctctact agaaaaacta caagtactac tagaaaatct acagcacgta aaacaacagc  36540
caaaaaagat gaaaataagt aaagggtgaa ttaaatggtt aactcaatgt ttggagggga  36600
cttagaccct tatgaaaaat cattaaacta tgaatatcct tatcatccta gtggtaatcc  36660
taaacatata gacgtaagtg agatagataa tttaacatta gctgattatg gatggtcacc  36720
ggatgcagtt aaagcatata tgttcggtat cgtagttcaa aatcctgata caggacagcc  36780
tatgggtgat gagttttata accatatatt agaaagagcg gtaggtaaag ctgaaagagc  36840
attagatata tctatactac ctgacactca acatgagatg agagattatc atgagacaga  36900
gtttaatagt tatatgtttg tacatgctta cagaaaacct atattacagg tagagaactt  36960
acagctacag tttaatggta gaccaatata taaataccct gctaactggt ggaaagtaga  37020
gcatctagca ggacatgttc aattatttcc tacagcactt atgcaaacag gacaatcaat  37080
gtcatatgat gctgtattca atgggtatcc tcaattagca ggtgtatacc cgccatcagg  37140
ggcaacattt gcacctcaaa tgatacgatt agaatatgta tcaggtatgc ttccacgtaa  37200
aaaagcagga agaaataaac cttgggaaat gcctcctgag ttagaacagt tagttataaa  37260
atatgcattg aaagaaatat accaagtatg gggtaactta atcattggtg ccggtattgc  37320
taataaaaca ttagaagtag acggtattac agagacaata ggtactactc aatcagctat  37380
gtatggtgga gctagtgcac agatacttca aataaatgaa gatataaaag aactattaga  37440
tggtttaaga gcttactttg gatataatat gataggatta taaggagggt tagaaaatgg  37500
aaaaaccgta tatgatagga gccaactcta accctaatgt tattaataag tcaacaacat  37560
atactactac aacacaagca gatgaacaag ataaacctaa gtatactact agactagagt  37620
ttgatacgat tgacatgatt aggtttatta atgaccgagg tataaaagta ttatgggaag  37680
aagcatattt ctgtccttgt cttaatcctg atacaggaca tcctagggta gattgcccta  37740
gatgtcatgg taaagggatt gcatatctac ctcctaaaga gactataatg gcaatacagt  37800
ctcaagagaa aggaactaac cagttagata taggtatatt agacacaggt actgcaatag  37860
gtaccactca attagaaaag agaatttcct atagagatag gtttactgtt cctgaggtat  37920
tgatgcctca acaaatgatt tattttgtga ataaagatag aattagaaaa ggtatacctc  37980
tatactacga tgtaaaagaa gtaacttata tagctactca agatggtaca gtctatgaag  38040
aagattatga aattaagaat aacagattgt atttaaatga aaaatatgag aaccatacag  38100
taactttaaa gatacttatg actttaagat atgtagtatc agatatacta aaagaaagtc  38160
gttatcaata tactaagttt aatcaaccta aatcaaaatt tgaaaactta cctcaaaaat  38220
tacttcttaa aagggaagat gttattgtac tacaagaccc ttataaagtt aatgatggca  38280
tagaagaaga cctagaaatt caagtagatg accctaaggc ttcagcatct aatcctagta  38340
atttaggtgg attcttcgga ggtgcattta aataatgcca gttcacggaa agagacctaa  38400
tttatttaaa aataaaaact ataagcaggt aggtaagaga acaattgatg gtatgcgttc  38460
```

```
agaagttctt gataaattac aagcaacagc acagcaagta gagaatacta gtattaaacg  38520
tatgcctact tacctacaaa taacagagaa aaagcttgaa aaagaaggag tagtagacct  38580
taaaaaagct tttgctcact catctaaaaa gaaaactagt aaagatggcg gatggtattt  38640
aactgtacca atccgcatca aaactagtag aatgaataac agtacttacc aagatatgag  38700
aactttaaaa gtagataaag gtacaggttc agtctctaag ataactgatt acctagaagg  38760
acgtagaaag aatgtaagcc atccttcaat gaagcctgaa cctatgactc ataatatgac  38820
taaagttaaa agaggaaagc aatcttctta ctttatattt agaactgttt ctagtaagtc  38880
acctgctagt tcttggatac ttaacagaga taaagttaat gaagataact tctctaaaac  38940
aactctaaaa actgttaagc aattaatgaa ctggaagatg aaaaatttaa attaagagga  39000
gggttagtat taaatggcaa taacatcagt tgattcatat ttattatcag aaataaagcc  39060
tagacttaac actgtgctag agaattgtta tattatagat gaagttttaa aagactttga  39120
ttatcaaact agagagagct ttaaagaagc tttctgtggt aagaatgcac aacatgaagt  39180
aacggtagga tttaacttcc caaaatttaa aaataactat gaagctcatt acttgataca  39240
attaggtcaa ggacaagaga caaaaaactc tttagggagt attcagtcat cttactttga  39300
ggcaacagga gataccttag tcgaatcttc tacagcaata agagaagatg ataagttagt  39360
ttttactgtt tctaaaccaa taggagagtt aataaaggta gaagatatag agtttgctaa  39420
atacgataat ctccaagttg aaggtaataa ggtatcattt aagtatcaaa caaatgaaga  39480
ttatgagaac tacaatgcta acattatatt taccgaaaag aaaaatgatt ctaaaggttt  39540
agtaaaagga ttcacagttg aagaacaagt aacagttgta ggtctttcat ttaatgtaga  39600
cgttgcaaga tgtttagatg ctgtactgaa aatgatttta atatctatga gagatagtat  39660
agaagagcaa caaacattcc aattacagaa tttgtctttt ggtgatattg caccaataat  39720
agaagatggt gactcaatga tttttggtag accaacaatt attaagtaca caagttctct  39780
agatttggat tatactatta cacaagatat taataaacta acttttaaag aaagaaagga  39840
ttggaagtag gatggctaga aaaaagacac ctgaaaataa cactcctaaa tttaatggtt  39900
atgttcatat agatacattc cttgatactg caaaaaccct ttttaatatg aaggattcac  39960
aagtagcagg atttaaagct tatatggaag gtagtcatta tttgtttagt gagcaagaat  40020
tcttaccatc attagagaag tatctaggta ggaaattaga tatataataa cattcagata  40080
aggagaatta aatatggcag tagaaccatt cccaagaaga cctattaccc gtcctcatgc  40140
atctattgaa gtagatactt caggtatcgg tggctcagca ggttcaagtg aaaaagtatt  40200
ttgcttaatc ggtcaggctg aaggcggaga accaaataca gtttatgaat tacgtaacta  40260
tgcacaagct aaacgtttat tccgttcagg agaattactt gatgcaatag aattagcatg  40320
gggttctaac cctaactata cagcaggtaa gattttagct atgcgtatag aagatgctaa  40380
acctgcttca gcggaaatcg gtggattaaa agtaacatct aaaatctatg gtaatgttgc  40440
taacaacatt caagtaggat tagaaaagaa tacattaagt gattcattac gtttaagagt  40500
aatcttccaa gatgaccgtt tcaatgaggt ttatgataat atcggtaata tcttcacaat  40560
caagtacaaa ggagaagaag ctaacgcaac tttctctgta gaacatgatg aagaaactca  40620
aaaagcaagt cgtttagtat taaaagttgg agaccaagaa gttaagtcat atgatttaac  40680
tggtggagct tatgactaca ctaatgctat tattacagac attaatcaat tacctgattt  40740
cgaagctaaa ttatcacctt tcggagataa gaacttagaa tctagtaaat tagataaaat  40800
```

-continued

```
tgaaaatgca aatatcaaag ataaagctgt atatgtaaaa gcagtttttg gtgacttaga  40860
aaaacaaaca gcttacaacg gtatcgtatc tttcgagcaa cttaatgcag aaggagaagt  40920
accaagtaat gtagaggttg aagcaggaga agaatcagct acagtaactg ctacttcacc  40980
tattaaaact attgagccgt ttgagttaac taagttaacg ggcggtacta atggagaacc  41040
acctgctaca tgggcagaca agttagataa atttgcacat gaaggcggat actacattgt  41100
cccattatca tctaaacaat cagttcatgc agaggtagct tcttttgtta aagaacgttc  41160
tgatgcaggg gaaccaatga gagctattgt tggtggagga ttcaatgaat ctaaagaaca  41220
attgttcggt agacaagcat cattatctaa tccacgagta tcattagtag ctaactcagg  41280
tacttttgtt atggatgatg gacgtaaaaa ccacgtacct gcttacatgg tagccgtagc  41340
tctaggtggt cttgcaagtg gtttagaaat tggtgaatca atcacattca aaccactacg  41400
tgtaagttca ttagaccaaa tctatgagtc aatagactta gatgaattaa atgaaaatgg  41460
tattattagt atagagtttg ttcgtaaccg tactaataca ttcttcagaa tcgttgatga  41520
cgtaactaca ttcaatgata aatcagaccc agttaaggct gaaatggctg ttggggaagc  41580
taatgacttc ttagtaagtg agcttaaagt tcaacttgaa gaccaattta ttggtactcg  41640
tactatcaat acaagtgctt caatcattaa agactttatc caatcttact tgggtcgtaa  41700
gaaacgtgat aatgaaattc aagacttccc tgctgaagac gtacaagtta ttgttgaagg  41760
taacgaagca agaatttcaa tgacagttta cccaatcaga agcttcaaga aaatttctgt  41820
tagcttggtt tacaagcaac aaacattaga agcctagtct aggtgatgga gtacctggat  41880
taggtactcc tattaatata atttgaatac tttaggagag tgaatacaga tggcatcaga  41940
agctaaacaa accgtccata ctggtaatac cgtcctactt atgattaaag gtaaaccggt  42000
aggaagagca caatcagcat caggtcaacg tgaatacggt acaactggtg tatacgaaat  42060
cggttctatc atgcctcaag aacacgtata tttacgttat gaaggtacaa ttacagtaga  42120
acgtttacgt atgaaaaaag aaaactttgc agatttagga tatgcttcac ttggtgaaga  42180
aattcttaag aaagatatca ttgatatttt agtggtagat aacttaacga aacaagttat  42240
tatctcatat catggttgct ctgcaaataa ctacaatgaa acttggcaga caaatgaaat  42300
tgtaacagaa gaaatcgagt tcagttacct ttaactaata gaggctatgt ttggtgacaa  42360
gcatagaaaa cactttaaat tgcgtgaaag tcttaaagac tagataacta caacgtaact  42420
cgaaagggta agcgtgaatg ttgagaaatc agaaaaaata tctagtatag tataaggtta  42480
aatcctaagt acagtaaaat agatgatacg caggcaagcc tacaaatgtg ggaagcttca  42540
acgactataa taggtgagtc ttagttacac attaagatta tggtatagtc tactcccttt  42600
aaaatatatc gaaagatagg gtacaaagga cagcatcaga taaagctaga acttaaattt  42660
cttattaaga ccaacaataa aagttggtct tatattttat acttgctttg tctgaggcag  42720
tgtgctataa ttaaaataca aggaggtaat aatatgggaa aaaatcaata tacatttaat  42780
attaaagaaa ataaaaataa atggtatgaa tggtgtaaac tacaaaacgt aaaaccttta  42840
gtagaatatg aaaatgcaca acaaatattt tattttgaat ttcttgaagg taaatttaaa  42900
ggactaatag gaaaaacata ttgggctagt ataaatagag gttctaatat gcgtatgagt  42960
tgtttaacat cagaaagtaa agataaatat ttaaaaaatt taggaaaaag aaaaggtata  43020
gaggtagtag aagactataa gggtggcaga aaattaaaac ataaatttat agttttagaa  43080
ggtaagtacc aaggatgtga agggtatata actttaaatg atttagagaa tttaggtaga  43140
gtagataata gaagtttatc tgaaaaagga aggaaacaat actttgataa acaggcaaga  43200
```

```
cttagagatt gtattattct agagtaccct aaagactata gaataaaaac taaagataag  43260
atagtagtaa aagataaaga agggcatgtt cataatatta ttgttcagga ctttttttgag  43320
aaatcatctt tattggagtt atcttgtgct agtgaaggag agaaaatagt taaagaaata  43380
cttactaaaa attctataaa atttgaaaaa gaaaaatcat ttagaaacaa agaaggtaaa  43440
gtacaaagat ttgattttta tattaatgaa aataataaag aatatgcaat agagtacaat  43500
ggtgcacagc actacataga ttctacagga tatcttaaag atactttgga aacaacccag  43560
aaaagagata aactaaaaaa agaatacagt aaagataaag gtataaattt attaattatt  43620
ccttacacaa taacagataa gaaagaaatg gaaaaaatta ttttaaattt tttaaacaaa  43680
taacccttga cactccctca agggatatgt tattataata acaggttagg agtaataagt  43740
atgaataata ggcaagctaa actaaaagga tataaccaat ttcattatta tgattttcca  43800
acaactaaag gtaagtttaa agatataatg aaaagaaaat ctagaacaga acttaaaaaa  43860
gatttacaaa aagaaaggaa gtattatctt gacaaataag agaaaaacga taggtaagat  43920
gagtaacaca agagcaacat ggaatattaa tccggtaact aaagttaaaa aagataaaac  43980
aaaatattct agaaaaaata aacataaagg tcttgacaat tataattaac taaggtatat  44040
tattagtata acaaaaaaag gagatgttat aatatgagaa tttatataag taatgactat  44100
aacaaagagc tattagataa atgtttatca gatattaaca aagataaagg taatataaac  44160
tacagtatta attatggtga aggtaacatt aaagaagcag atgtagaaat tattaaacta  44220
gataagaatc tattagaaac agaatcaaga gcatttgctt attcgaagtt tgttgaagat  44280
tgtatatttt tatttcctta taagattgct ttacttagag gggtaaaat agagttaaga  44340
tttgattgga atgaaatatt ataacaaaaa aaggagatgg atatatgagt acattttggt  44400
cagaaagaag aacaactaat aaagataggc aagttaaaaa acattatact caaatgagta  44460
tgtatgaaag aaagaaatgt gtagagttat tacaagagac aattactgaa aatagaatta  44520
ttaattttac acgacatagt gcaaaaaaag ttaaaggtaa accaacaaca aatataccta  44580
aattaatagg ttttattttt aaaaataagt ttgcctacga aaatatcata gagtacaata  44640
acacagatta taatggtaat attgagagga gaattgttgt taaacatccc aaagttataa  44700
ctgtagaagg aaaacttagc tatcagtttt tgacaattag tcttgaagat gctagagtta  44760
ttacggtgtg gtataacagt gtagatgata cacatagaac actagattta aattattata  44820
gtaaagactt gacaattcaa taaggaggag ttataatggg attaacaata gtaaatggtt  44880
atttctttct atcaagtatt atatttattg tagtaagtat actaaatgga aaaggtacag  44940
ttacaaggga atcactagct atgagtcaag cattagtgat aataacatcc attcaatttt  45000
tagcattttt aattataaat ggcatttatt actcattaaa atatatgtaa taaaaaggag  45060
tacaaatgga aatatacatt gtaatagact taagaggaag cacagaagaa gaaacaagta  45120
tggattttaa agcttttaga aaattacaag atgctataac atatgtagat ggtaatggta  45180
acagggattt acatataatt cctctagaat tagaataaaa gtattgacaa attaaaacta  45240
ataaattata ataaaggtat aacaaattaa aggagaagat ataaaatgtc acaagataaa  45300
ttaagagcaa tttacacaga aatgaaagta gaattacaca aatttcctaa agaggtagat  45360
gtaacaagta aatcaactgc aattgcaatc aatcagattt tagataaatt caaaacatta  45420
acagaacaag caggaaagat tactagaaaa tatttagaag gtcaagaaat attaactatt  45480
gattatgagt actatgattc attacaagaa tactatattt acctacttag aaatagtgaa  45540
```

```
aaaattgaac aaagtttaca agaaattact aagcgtacag gtgaatatgt aaagtaattt  45600
tgatttaaaa acaaaatatg atatactatg tttaaagtag taagcctaca ctagtccgtg  45660
ttatattaat attgaatcgg ataagcgtag gctttattaa tatttaaaaa aaggaaggta  45720
tatcatatta tggcagaaga aattaaaaag gaacaagatg tacaagaaac aactaaagaa  45780
gaaaaaaaag atgttagcaa aatgacaccg gaagaaatag ataaattaaa atatcaagac  45840
aagcaagaaa aagaacaagt tattaacaaa gttattaaag gtgttaatga tacttgggaa  45900
aaagaatata actttgaaga attagactta agatttaaag ttaaaattaa attacctaac  45960
gcacgagagc aaggtaatat atttgcgtta cgttctgctt acttaggtgg tatggatatg  46020
taccaaacag accaagtaat tagagcatat caaatgttag ctacattaca ggaagtaggt  46080
attgaagttc ctaaggaatt ccaagaccct gacgatattt ataacttata tcctttaact  46140
gttatgtatg aagattggtt aggattctta aactcctttc gttactaata gtatagaaac  46200
actagataaa gatatagaac gattgggcgg tatggaatca attgttaaac aacctttatc  46260
tagaaatcta tgggctatta tgaaagagtt taatgtttta cctactgagc aaagatttaa  46320
ggacttagat gattatcaga tagagtttat tattgggaat atgaacagag atgtttatga  46380
acataacaaa caacttaaac aagctcaaaa aggtggaaaa ttcgatagtc aatttgaaga  46440
tgatgatagt agttggtgga atgaatctca tgaagacttt gacccagtac ctgatttctt  46500
agatgctgat gatttagcac aacagatgga agctaaatta tccgatagag ataaggaaga  46560
aagagctaag agaaacgatg cagagttaaa tgatgaaaca gaaggactta ctacacaaca  46620
tctagctatg atggaataca tcagacagaa acaacaagaa ttagatgatg aagtaggaaa  46680
tggtaagact agtgaagatg acgctactat atcacaagat agcgttaata aagcactaga  46740
agacctagat gatgactggt atatgtaaag ggtggtaggt gatactacca tccttatttt  46800
tttaaaatgg atggtgaata atgatggcaa tgaatgacga ttatagattg gtcttgtccg  46860
gtgatagttc ggatttagag aatagtctaa aggcaataga actttatatg gattctttag  46920
agtctaagaa tattgatgct cctttagata atttcttaaa aaaattaaaa gtaattgcta  46980
aagaagttaa aaatgtacag aacgcaatgg ataaacaaga tggtaaatct gttatatctt  47040
ctaaagacat ggatgaatct attaaatcca ctcaatctgc tacaaagaat ataaatgaat  47100
taaagaaagc tttagatgac cttcaaaaag agaatatatc taaaggtatt gcacctgacc  47160
ctgaagttga aaaagcatat gctaagatgg gtaaagttgt agatgaaact caagaaaaac  47220
ttgagaaaat gtcttcacaa aaaataggtt ctgatgctag tattcaaaat agaattaagg  47280
aaatgaaaac cttaaatcaa gtaactgaag aatacaataa aataagtaaa gattctagcg  47340
caactaaaga ttatacaaaa cgattaagag ctaatcgtaa tatgactaga ggttacatgg  47400
agcgttcaga aggaacagga cgtttgacat atgaccaagg tgcacgagtt agaagtgaac  47460
taggtaaagt aagttcttat gagagccaaa gaaaacaaaa ccaacgtaat ttgggacaag  47520
caagagaaca atatagcaac tatagaaacc aacaacaaga cttgactaaa cgtagagcta  47580
gcggtcaaat taataaggca caatatgaac aagagttagc ttctattaaa caggaaatga  47640
aagctagaga agaacttata tctaactatg agaaattagg agcagaactt gataaaacag  47700
ttcagtatta taagggttca gttcaaaagg atttccaatc tagagacgta gaccaacaaa  47760
gaggaacatt tggtagaatg gttcaagaac gtttgccatc tattggttct catgctatga  47820
tgggtactac agctatggct acaggtttat acatgaaggg tgcctcacta agtgaaacta  47880
atagacctat ggttacatca ttaggtcaaa attccgataa tatggatata gattctgtaa  47940
```

```
gaaatgcata tggagacttg tcaattgata acaaattagg ttataatagt actgacatgt  48000
tgaaaatggc tacttcatat gaagcatcag taggacataa aagtgatgag gacacaatgg  48060
caggaactaa acagcttgct attggaggac gttctttagg cattaaagac caagaagctt  48120
atcaagagtc tatgggtcaa atcatgcata ccggcggagt aaattctgat aacatgaagg  48180
aaatgcaaga tgcattctta ggtggtatta aacagtcagg tatggttggt cgtcaagatg  48240
aacaacttaa agcactaggt tctatagcgg aacaatcagg agaaggaaga actctaacta  48300
aagaccaaat gagtaatctt actgccatgc aatctacttt tgcagagtca ggaagtaaag  48360
gattacaagg tgaacaaggt gccaatgcta ttaacagtat agaccaagga cttaaaaatg  48420
gtatgaatag ttcttatgct cgtatagcaa tgggatgggg aacgcaatac caaggtcttg  48480
aaggtggata tgatttacaa aaacgtatgg atgaaggtat atctaatcct gaaaacttga  48540
cagatatggc tgatatggct actcaaatgg gtggcagtga aaaagaacaa aaatacctat  48600
ttaatagaag tatgaaagaa ataggcgcta acctaactat ggagcaatct gatgaaatat  48660
ttaaggactc taaagaagga aaactgtcta aagaagagtt agctaagaaa gctaagaaaa  48720
tggaaaaaga aggtaaaaaa gaaggagaag ataacgccac tgattataaa gaatctaaat  48780
caggaaaaaa tgaccaaaat aaatctaaga ctgatgataa agcagaagat acttatgata  48840
tggctcaacc actaagagat gctcatagtg ctttagcagg tcttcctgcc cctatatatt  48900
tagctattgg tgctatagga gcatttacag cttcactaat tgcatctgca agtcaatttg  48960
gagcaggtca cttaattggt aaaggagcca aggacttag aaataaattt ggtagaaata  49020
aaggtggtag ctccggtggt aaccctatgg caggtggaat gcctagtggt ggtggttcac  49080
ctaagggtgg aggctcacct aaaggtgggg gcactcgttc tactggagga aaaatacttg  49140
atagcgctaa aggtcttgga ggattcctag taggtggcgc aggatggaaa ggtatgtttg  49200
gcggggagtc taaaggtaaa ggatttaaac aaacatctaa agaagcctgg tcaggtacta  49260
gaaaagtatt taatagagat aatggtagaa aagccatgga taaatctaaa gatatagcta  49320
aaggtaccgg tagtggtctt aaagatatct ataatgatag tatatttggt aaagaaagaa  49380
gacaaaacct aggagaaaaa gctaaaggtt ttggtggcaa agctaagggt ctctatggta  49440
agtttgctga taagtttggt gacggaggta aaaatggtat cctttcacaa tcaccaaaag  49500
caggtggaag tggcataggg aaacttggaa aacttgcagg tggacttgga aaaggagccg  49560
gagttttagg tgttgctacg tctgccttat cattaatacc tgctttagct tccggagata  49620
gtaaagctat cggcggagga ataggctcta tgggtggagg aatggcaggt gcatcagcag  49680
gagcttctat aggagcttta tttggtggtg taggtgcaat ccctggagct ttaataggtg  49740
gagctatagg ttctttcggt ggaggagctg ttggtgaaaa agtaggagac atggctaaga  49800
aggctaacac taaagaagga tggaacctag gatggactaa tggagataaa gacggtaaga  49860
ataaattcca agattcttta ttaggaaaac ctatatctaa agcatggagt ggtataacag  49920
gtctctttga taatgacgct gaagcatctg aagaaaatag caaagataag aaaaaaggcg  49980
ttaaaggtgt taaaggggat actaagaaga aagaaaaaat gacagcagaa caacttagag  50040
aaaaaaataa ccaatctgaa actaagaacc ttaaaatcta tagtgattta cttgatagag  50100
ctcagaaaat tattgagagt gctaaaggta ttaatataga tggaggaact tctgatagtg  50160
gttctgatag tggaggctct gcatctgatg taggaggaga aggtgcagag aaaatgtata  50220
agttccttaa aggaaaagga ctatctgata accaggtagg agctgttatg gggaacttac  50280
```

```
aacaagaatc taaccttgac cctaatgcta agaacccttc aagtggagca tttggtattg  50340
ctcaatggtt aggtgctaga aaaacaggat tagataactt tgctaagtct aaaggtaaaa  50400
aatccagtga tttagatgtt caattagact acctatggaa agaaatgcaa tctgattatg  50460
aaagtaaaaa cctcaagaat gcaggttgga gtaaaggtgg aagtctagaa cagaatacaa  50520
aagcatttgc taccgggttt gaacgtatgg gagcaaatga ggctatgatg ggtactcgtg  50580
ttaacaatgc caaggaattc aagaagaaat atggaggttc cggcggagga ggcggagggg  50640
gcgctatgtc ctctacttac caagaagcta tgagtaaccc tgtattaacc actggttcca  50700
actacagagg ctctaacgat gcttctaatg cttctacaac taacagaata acagttaatg  50760
ttaacgttca aggcggaaat aatcctgaag aaactggaga cattatcgga ggaagaatta  50820
gagaagtttt agacagcaac atggatattt ttgcaaatga acataagaga agttattagt  50880
gattttgtat tgacacaaga gtagtatagt agtatactac tcttatacat ataaaaataa  50940
aaggaagtat gtgtatatga aaagattaag aagacctaag gtaagaatag agatagttac  51000
agatgataat acatttacat taagatttga agatacacgt gactacaatg gtgatgagtt  51060
tggagctaaa cttttaggct ttcaaactaa aaactctatg gaagatgata gttctgtatt  51120
ccaaatcaat atggcaggag atacttactg ggataagtta gttatggcta atgatataat  51180
cagaatattt attacaccta atgatgaccc taatgataaa gaaggtcgtc aagaacgttt  51240
aatacaagta ggtatggtat cacaagtatc aaaagtaggt agctatggta atgaccaaac  51300
tcaatttaga ataacaggtc aatcttttgt aaaaaccctt atgaaatttg gattaggtgt  51360
tattcaagag gttcaagctg tattacctga agtaggttgg cttattgatg gtgatgggga  51420
taatgaagta aaatttactg gtagttcggc acatgaagtt atgacaggta ttatccgaag  51480
atttgttcct tatatgaaat ataactatac agaaaaaaca tataatacaa tagatagtta  51540
ccttgattat gatgatttaa gtagttggga tgaatttgaa aatctgacag aagtatctgc  51600
ttttactaat tttgatggct cattaaaaca gttgatggat atggtaacag ctagaccttt  51660
caatgagtta ttctttaaaa actccgaaaa aacaccaggt aaagcacagc ttgttttaag  51720
aaaaactcct tttaatccta ctgagtggag agctttggat atgattaaag tacctactga  51780
agactttatt gaagaggatg tgggtaaaag tgacgtagaa acatactcta tatttacagc  51840
tacacctgca ggtatgttaa aagaacttaa tggtgatgta ttttctaaac cacaatttca  51900
ccctgaattg actgatagat atgggtatac taaatttgaa gtagagaata tctatcttag  51960
tactaaatca ggttcagcta ctgaagactc agattcttcg ggtgatgata atggtactga  52020
aagaggaact tattctaaaa ttatgaaaga tttaagtaac tatggaagag ataatatatc  52080
taaaggtata gataagtata caagtaaatt atcctcaaaa tataaaaact taaaaaagcc  52140
caagctaaaa aaattataga gaagtttgtc aaagaaggaa aagtaacaga aaaagaatat  52200
gaaaagataa caggtaataa ggtagatgat gaattaacat cagataacag accgaagttg  52260
acaaaagata aattaaagag tatactaaaa gagaagttta aaacacaaga tgattttaat  52320
aattctaaaa aaagaaaaaa gctaaaacag atgcacttaa agaattgaca actaaatatc  52380
gttttggtaa taaaacacat gctacaactt tgttagatga atatattaaa tacaaaggag  52440
aaccacctaa tgatgaggct tttgataaat atcttaaagc tattgaaggt gttagtaata  52500
tagctacaga tacaggttca gatgcaagtg atagtccttt agttatgttc tctagaatgc  52560
tatttaactg gtatcatggc aaccctaact tctatgcagg agatattatt gttttaggag  52620
accctaagta tgacctaggt aaaagattat ttattgaaga taagcaacga ggagacactt  52680
```

```
gggagttcta tattgaatct gtagaacata aattcgatta taaacaaggg tattatacaa  52740
ctgtaggagt aactagaggt ttaaaagatg ctattctaga agacggtaaa ggtagtcctc  52800
atagatttgc aggactatgg aaccaatcat cagacttcat gggaggtctt atgggtgaag  52860
atacttctaa agaacttaaa gaaaaaggtg tatcagagaa acaaagcagt ggagataaag  52920
acggtggctc tgatagtggt ggcgctcaag atggtggctc tttagattca cttaaaaaat  52980
ataatggcaa acttcctaag catgacccaa gttttgttca acctggtaac cgacattata  53040
agtatcagtg tacatggtat gcttataata gaagaggtca attaggcatt cctgtgcctt  53100
tatgggggga tgccgccgac tggataggcg gtgctaaagg agcaggttat ggagtaggta  53160
gaacacctaa acaaggtgct tgtgttatat ggcaaagagg agtacaagga ggtagtgctc  53220
aatatgggca tgttgctttt gttgagaaag ttttagacgg aggtaaaaaa atatttatct  53280
ccgaacataa ctgggctact cctaatggat atggtactag aacaatagat atgagctcag  53340
ctataggtaa gaatgctcaa ttcatttacg ataagaaata aaggaggata gtctatggca  53400
acagataaag aagctaaaga tgttattgac aagtttatag ataatgtatt taattttgat  53460
gtattaacta tggaaagagt taaagaaaaa gatgaagaaa ttaaaaaaat aactacagat  53520
gatatgtatg aaaaggttgt gtatatacga ccttatgttg gagtaataca aagccttaac  53580
cctcaacatg tacagtatga atcattttct aataatggtt atgatataga ggcagaatta  53640
agtttcagga aagtaagtta tttagttgat aaagggtcta tacctacaga ttctttatct  53700
actttaacag ttcatttagt agaaagaaat caagagctat taatagatta ctttgatgag  53760
atacaagatg tgttgtacgg agaatatatg gaagaagaat atgtattcga tgaagatgta  53820
cccttaagta cgatactagc attagactta aatgataatc ttaaatcctt atcaaatata  53880
aagtatatgt tcaaaggtgc tcctaaagag aatccatttg gaacagataa agatgtttat  53940
atagatactt ataacttatt atactggtta tatttaggtg aagatgaaga gttagcatac  54000
cctatgaata ttaattattt ctttacagag ggtagattct ttactatatt tggtaaaggg  54060
cataagtaca aggtagatgt tagtaaattt atagttggag atatattatt ctttggtaga  54120
agtgatacta atataggtat ttatgtaggt gatggagagt ttatatctat gataggtaaa  54180
tttcctaaag atgaaacacc tataggaaaa tataaacttg atgattactg gaatgaattt  54240
aacggaagag ttatgagatt cgatgaagag gtgtatattt aatggtagta agattccaat  54300
cttccatggg aagaagttta aaaagagtag attcagatga tttaaatgta aaaggattag  54360
ttttagctac agttagtaaa attaattata aatatcaatc agtagaagtt aaagttaaca  54420
acctaacttt gggaagtcgt ataggtgacg atggtagctt agctgtacct tatcctaaat  54480
ctttcatagg aagaacaccg gaaggaagcg tattcggtac aaaacctctt attactgaag  54540
gttctgtagt attaataggg ttcctaaatg atgatataaa tagccctata atcttaagtg  54600
tttacggtga taatgaacaa aataaaatga ttaatacgaa tcctttagat ggaggtaaat  54660
ttgatacaga cagtgtttat aaatatagta gtgcactata tgaaatttta ccatctttaa  54720
attataagta tgatgatgga gaaggtacaa gtattaagac ctataatggt aagtcattct  54780
tctccatgac atcaggtgaa gaagaaaaac ctcaggcaac agatttttac actggaactg  54840
agtatcaaga tttatttact tcttattatg gtaataagac attaattgag cctagaatac  54900
aaaaggctcc taatatgtta tttaaacatc aaggagtttt ttatgatgat ggtacaccgg  54960
ataatcatat aactacttta tttatatctg aaagaggaga tataagagct tcagttttaa  55020
```

```
atacagaaac acagaaaaga accacacagg aaatgtcaag tgatgggtct tatagggtta  55080
tcaaacaaga tgacgattta atgttggatg aagctcaagt ttggattgag tatggtatta  55140
gtgaagataa taaattttat attaaaaatg acaagcataa atttgaattt actgatgagg  55200
gaatctatat agatgataag cctatgttag aaaacttaga tgagagtata gcagaggcta  55260
tgaagaattt gaatgaaata caaaaagaac tcgatgatat aaactacctt ctcgagggtg  55320
tgggtaaaga caatttagaa gaattaatag agtctacaaa agagtctata gaagcttcta  55380
aaaaagcaac ttcagatgtc aatagactta caactcagat agcagaagtt agtggtagaa  55440
ctgaaggtat tataacacag ttccaaaaat ttagagatga gacttttaaa gatttttatg  55500
aagatgcttc tactgttatt aatgaagtaa atcagaattt ccctactatg aaaacagatg  55560
ttaatacctt aaagactaaa gttgataacc tagagaaaac tgaaatacca aacattaaaa  55620
ctagattaac agaactagag aacaataata acaatgccga taaaataatc tcagatagag  55680
gagagcatat aggtgctatg atacagttag aagaaaatgt tactgtaccg acaagaaact  55740
atatgccaat accttggagt aaagttactt ataataatgc agagttttgg gattctaata  55800
atcctactcg attagtagta cctaaaggaa taacaaaagt aagagttgca ggtaatgttt  55860
tgtgggactc taacgccaca ggacaacgta tgttgagaat attgaaaaat ggtacttata  55920
gtctagggtt accttataca agagatgtag ctatatctac agcccctcag aacggtacta  55980
gtggagttat tcctgttaaa gaaggagatt actttgagtt tgaagctttc caagactcag  56040
aaggtgacag acaattcaga gcagaccctt atacatggtt tagtattgaa gctatagaat  56100
tagaaactga aactatggag aaagacttta tgcttatagg acatagagga gcaaccggat  56160
acacagatga gcacacgata aaaggatatc aaatggcttt agataaaggt gcagattata  56220
tagaattgga tttacaatta acaaaagata ataagttatt gtgtatgcat gattctacta  56280
tagacagaac aacaacagga acaggtaagg taggagatat gactttatct tatatacaaa  56340
ctaactttac atctcttaat ggtgagccga taccatctct tgatgatgta ttaaatcatt  56400
ttggaacaaa agttaaatat tatatagaaa ctaaacgtcc gtttgatgct aatatggata  56460
aagaattatt aactcaatta aaagcaaaag gattaatagg aatagggtca gagagattcc  56520
aagtaattat tcaatcattt gctagagaat cattaattaa tattcataat caattctcta  56580
atataccttt agcttattta acaagtacat tctctgaaag tgaaatggat gattgtttaa  56640
gttatggttc ttatgctatt gctcctaagt atacaactat aactaaagaa ttagtagatt  56700
tagctcatag taaaggtctt aaagtacacg catggacggt aaacacaaaa gaagaaatgc  56760
aaagcttaat acaaatgggt gtagatggat tctttacaaa ctacttagat gaatataaaa  56820
agatttaata ttaaagacct attaatttag gtcttttttt agttgtaatt taaactagtt  56880
cgtgatatat tagtagtatg agatttatat acatactgaa aaggagagga taaaatgcca  56940
caatcagatg gaataagtaa tcttcataga atagctttac gcttccctaa agaaggcggt  57000
ggttatgata tgtatagatt taaagttaac cccgagaact acacaataga ttcaccacaa  57060
cgtacgacag caattaaaac aaaatcagat attgtaatag aagattatgg taaagacata  57120
gaagttatta acttcacagg tacaactggt tttagacctg ttagagaagc agacggatta  57180
aaaacaggta agcagaaaat ggaagagtta caaagtagag ttagtgaata tgctatgcaa  57240
ggtggtagtg gtaatgtaag tggttcttac ttacaatttt ttaactttac agatgatagc  57300
tactataaag ttcatttagc tcctcaaggg ttaaagataa ctaggtctaa agatgaacca  57360
ttacttttta gatatgaaat aacattagta gttattggtt cgttaacaga agcagataga  57420
```

```
agtgctgtaa caacagaaga gtttggtaat gttaaaccta atgcttctca aagagtagat  57480
gagggtataa aagaattaga taaaaatgct cgtaaaacga gagatagaaa taatcaagaa  57540
atatctaaaa gagaaaatac aatacctaaa tctacaggag ataatacgaa tgagggtaat  57600
agacttaagc aaagcttccc tagtagttct atatataatc ctagacaatc tactaacgga  57660
ttaaaaggga atattgacaa tatggctctg ataataggtt acggtgatgg aggtgtatct  57720
agctaatgaa taattttata ccacaacctc aaggtctact cagattttta aatgccctag  57780
atgcagattt aacttcttct cacatgaatt tactggatga agaggtatca tttgtatcta  57840
aattttacac accacagcta caattaagtg aattagcaaa aaaagtattg acaaatataa  57900
agacagatga tatacctgta ttagaaagag aatttaatga taatacaatt atccataaag  57960
ctaatgatac attactaaaa gtacaggctc caagaatgta tatgattcta cagtctattg  58020
tgcttgaagc atatgctatt gttaattgct ttgtagaaaa tccaagctct ttaaaatact  58080
taactgaaga agatgttagt ataacacgag aaaatttaaa ttatgtagct gactacttag  58140
gtaactatga tgactacaat agtgttgtct tagacttaag agatttagac ttatgtttta  58200
gtgctataga attacaatta cctctaatta aaaaggaggc taatgtataa tgagatttaa  58260
gaaacacgta gttcaacatg aagaaacgat gcaagcaata gcacagagat actatggtga  58320
tgttagttat tggatagacc tagtagagca taataatcta aagtatccct atttagtaga  58380
aactgatgaa gaaaaaatga aagaccctga acgattggct tctacaggtg atacactgat  58440
tatacctata gaatctgatt taacagatgt atcagcaaaa gaaattaatt ctagagataa  58500
agatgtacta gttgaattag ctttaggaag agatttaaat attactgcag atgaaaagta  58560
ttttaatgaa catggtacta gtgataatat actagcattc agcacaaacg gtaatggaga  58620
tttagatact gtaaaaggca tagataatat gaaacagcaa ttacaggcac gtttattaac  58680
tcctagaggt tctttaatgc tacatcctaa ttatggttca gatttgcata atttatttgg  58740
tcttaatata cctgaacaag ctacattaat agaaatggaa gtattgagaa cattaacatc  58800
agataataga gtaaaatctg ctaatctaat tgattggaaa atacaaggta atgtttattc  58860
aggtcaattt tcagtggaaa taaaatctgt tgaagaatca ataaattttg tcttaggaca  58920
agatgaggaa ggaatttttg ctttatttga ataggaaagg attaaattat gaaaactaga  58980
aaattaacta acatactatc aaaattaata gataagacaa tggcaggtac aagcaagata  59040
acagacttta ctcctggttc agcttcccgt tcattattag aagctgtatc attagagata  59100
gagcaattct atatcctaac aaaagaaaat attgattggg gtatacaaga aggtatcatt  59160
gaagcttttg attttcaaaa aagacaatct aaaagagctt atggtgatgt tactattcaa  59220
ttctaccaac ccttagatat gagaatgtat atacctgcag gaacaacttt tacttcaaca  59280
cgacaagaat atcctcagca atttgaaaca ttagttgatt attatgcaga gcctgattct  59340
actgagattg ttgttgaagt ttattgtaaa gaaacagggg ttgcaggtaa tgttcctgaa  59400
ggaacaatta atactatagc atcaggttct agtttgatta gaagtgttaa taacgagtat  59460
tcttttaata caggaactaa agaagagagc caagaagact ttaagcgcag attccactct  59520
tttgtagaat ctagaggtag agcaactaat aaatcagtaa gatatggtgc attgcagata  59580
cctgatgtag aaggtgttta tgtttatgaa gaaacaggac atattacagt atttgctcat  59640
gatagaaatg gtaatttatc agatacctta aaagaagata taatcgatgc tttacaagac  59700
tatagaccaa gtggtataat gttagatgtt acaggtgtag aaaaagaaga agttaatgtt  59760
```

```
tctgctacag taactatatc taataaatct agaattggtg atacattaca aaaacatatc  59820
gaaggtgtta ttagaagcta tttaaataat ctaaaaactt ctgatgactt aataattaca  59880
gaccttattc aagctataat gaatattgat gatgtactaa tatatgatgt gtcatttgat  59940
aacctagatg agaacattat agtaccacca caaggaatta ttagagcagg agaaataaaa  60000
gtagaactaa agtaaagaga ggtgaaactt aagtcgtggc taattttta aagaatcttc  60060
atccattatt aagaagagat agaaacaaaa aagataatca agaccctaac tttgctctca  60120
tagatgcact caatgaagag atgaatcaag tagagaaaga tgctatagaa agtaaattac  60180
aatcctctct aaagacatct acaagtgaat atttagataa gtttggggat tggtttggag  60240
tttatcgtaa gactgatgag aacgatgatg tttatagagc aagaattata aaatatttac  60300
tcttgaaaag aggaactaat aatgctataa tagatgctat aaaagattat ttaggtagag  60360
atgatattga tgtaagtgta tatgaacctt ttacaaatat tttctatacg aacaaatcac  60420
atttaaatgg tgaagaccac ttaatgggat actattatag atttgctgtt attaatgtct  60480
ctataggtga ttatttccct gtagagatta tagatgtaat taatgaattc aaacctgcag  60540
gtgtaactct gtatgtcact tatgatggag cttctactat tagaggtgga gcaattatta  60600
agtggttaga tgggttacct aaaatagaaa cataccaaga gtttgatagg tttacaggat  60660
acgatgatac attctatggt catattaaca tgaatcaaag taaagatact gataatagta  60720
catcagatat ttttaaaaca aaccatagct taattaatag tttagatgtt ttaacaggtt  60780
cctctagcgt aggtagacag tatgttaact atggatatat aacatcatat gtttataatc  60840
caggtatgac atcttctgta aatcaaataa gcgctagtac agaaggtaga gggcaagaag  60900
tacctactga ctattatatg tatactagta ctaagaataa caatacagta gaacttagta  60960
tgcaaactac ttccggtgtg tcttatttat ataataactt taattttagg gattatatga  61020
gtaaatatag acctcaagta aatttacaat ctgatgaggc tagaagaatt gtatctgatt  61080
atataaaaga attaagtatt gattattatc tcagtgctgt aatacctcct gatgaaagta  61140
tagaaattaa attacaagtt tatgattttt ctattaatag atggcttaca gtatcaatta  61200
ataatttatc tttctatgaa aaaaatatcg gtagcaatat aggatatata aaagattatt  61260
taaacagtga attaaatatg tttactagat tagagataaa cgcaggtaaa agagattcag  61320
tagatattaa agttaattac ttagatttaa tgttttatta ctatgaacga ggtatttata  61380
caataaaacc ttataaagcc ttagtagaaa attatttaga tatatctaga gagacttacg  61440
tagaggcatt taaaatatca tcgttatcta atggagatat tataactaaa acaggttatt  61500
tacctatagg ttatctaaga gtatcaggag acattgataa cttaagtaac catatagaaa  61560
ttattaccat agataataat actaatagta ttacaagtac tcttttagaa gatgactcta  61620
atagtttgat attatcatat ggtaacgtca aaaccaatat acacagtttt gaattaaata  61680
gtgatgcttc aatttcaaat attaaatttg aatactctta ttatggtgat gcttgggaag  61740
aactgacagt attaactgaa atatctgagg gtgaaactat agtacctaat atactaatag  61800
atttatatgg attacagaca gtagattatt ctaatataaa tccaatgtca aaagtatcat  61860
tacgttctat ttggaatgtt aaattaggtg aacttaataa taaagaaggt tctttatcaa  61920
atatgcctaa cgattatttt aatgctgtat ggcaagatat agataaacta tcagatattg  61980
atttaggctc tatgagaatg attaaagaca ctgagggtgg agtatttgat ggagctacag  62040
gtgaaattat taaagctact ttatttaatg ttggtgtata tactgattta gatatgttag  62100
cctacacttt aactaactat actgaaccaa taactttagg ttctagtcga ttaataagtg  62160
```

```
aacttaaaga agaactatta acatcagaat catttaatgt cgataataga attaaagtaa  62220
ttgactcaat atctgagcag ttacctaata acaatatatt aagtaactct taccaaacac  62280
aaactattac acagaatgga tttgctaagt ataatttgaa agaacctata gagcagagaa  62340
aacaatacaa tctaagaata catggagatt ttaaagaagg attagaaaga ttagctatag  62400
gtaattctaa tggttcattt aatgaagtat ttgtttaccc tgaaaatatt aaagatggta  62460
tagtagatat tacttacact tctagagatg ataattacgc agaagggaaa caaagactta  62520
ataatgatta tagagtttac gctcaaccat acgatagtga agtagtaaca atttacagtt  62580
tagagttaat aaaagtttaa taaataagtt gacagaaagt taataaatatg gtatacttat  62640
aaagtaatat ttagtgggta taccatgtta tattaataaa gaaaacaaca gatgaaagga  62700
attaaaaaat atggcaattg caacgtataa ttctcatgtt gagttagcaa aatatctagt  62760
tagtaaagct gattcagttt acttaacaat tggaaagagc acaccgtggt ctaatgaaac  62820
aaacccaccg caacctgatg aaaatgcaac agtattacag gaggttatag gatacaaaaa  62880
agctactaaa gtaactttag ttagaccttc taaatcacct gaagatgata ataagaattt  62940
aatttcttat ggtaataaat catgggtaga agtaacacct gaaaatgcta aagatgaagg  63000
agctaaatgg gtttacttag aaagcagtat tgttggtgac gaactacctc ttggaacata  63060
tagacaagta ggatttgtta tggacttagt agcaaaaagt ggtattagta aatttaactt  63120
agtacctagt gaagtagaat caactggaac attattattc tttgataata aacaattcca  63180
aaatagaagt gagcaaacaa ctgctaaaga aagatttatt gtagaagttt aaagaaaggg  63240
agataattct aaatggcaat taattttaaa ggttcacctt atttagatag atttgacccg  63300
tctaaagata gaacaaaagt attatttaat cctgatagac ctctacaaca ggcagaatta  63360
aatgaaatgc agtctataga ccaatattat ttaaaaaatc taggagacgc tatttttaaa  63420
gacggagata aacaatcagg tcttggattc acattatctg aagataatgt attgacagta  63480
aatcctggtt atgtatatat caacggtaaa ataagatatt acgataatga cgattcagtt  63540
aaaataactg gcgtaggtaa agaaactatc ggtattaagt taacagaacg tattgttaca  63600
cctgatgaag atgctagcct actagaccaa actagtggag taccaagtta cttctctaaa  63660
ggtgcagata gattagaaga aaagatgtca ttaactgtta atgaccctac atcagcaact  63720
atttatactt tcatggacgg agatttatat atccaatcaa ctaatgctga gatggataaa  63780
atcaataaag tattagctga acgtacttat gatgagtcag gttcatataa agtaaatggt  63840
tttgagttat tctcagaagg taatgctgaa gatgatgacc acgtttctgt agttgtagat  63900
gcaggtaaag cctatgtaaa aggttttaaa gtagataaac ccgtatcaac aagaattagt  63960
gtacctaaat cttatgactt aggaacagca gaaaatgaaa gtactatctt taataagtct  64020
aataattcta ttagtttagc taatagccct gtaaaagaaa ttagacgtgt tacaggtcaa  64080
gtacttattg aaaaagaacg agttacaaga ggagcccaag gtgatggtca agattttctt  64140
tcaaataata cagcatttga aattgtaaaa gtttggactg aaacaagccc tggagttact  64200
acaaaagagt ataaacaagg agaagacttc agattaacag atggtcaaac gattgactgg  64260
tcacctcaag gtcaagaacc ttcaggaggt acttcatact atgtttctta taaatataat  64320
aaacgtatgg aagtcggtaa agattatgaa gtaacaactc aaggagaagg gttaagtaag  64380
aaatggtata ttaattttac acctgaaaat ggtgctaaac ctattgacca aacagtagta  64440
ttagtagatt atacttatta cttggctcgt aaagattcag tgtttattaa taagtatggt  64500
```

```
gatattgcaa tattacctgg tgaacctaat attatgagat tagttacacc accattaaac  64560
acagaccctg agaatttaca attaggtaca gttacagtat tacctgattc agatgaagcc  64620
gtatgtattt catttgcaat cactagattg tctatggaag acttacagaa agttaaaaca  64680
agagtagata acttagagta taaccaagca gtaaatgcct tagatgatgg tgctatggaa  64740
ggacagaacc ctctaacatt acgttcagta tttagtgaag gtttcattag tcttgataaa  64800
gcagatatta cccatcctga cttcggaata gtatttagtt ttgaagacgc agaagctact  64860
ctagcttata cagaagccgt taaccaacct aaaattattc ctggagatac aacagctcat  64920
atttggggta gattaatttc agcaccattt actgaggaac gtacaatcta tcaaggtcaa  64980
gcatcagaaa cattaaatgt taacccttat aatatcccta ataagcaagg tgtacttaag  65040
ttaacaccta gtgaggataa ttggattgat actgaaaatg ttacaattac tgagcaaaaa  65100
actaagaaag taactatgaa acgattttgg agacacaatg aaagttacta cggtgagact  65160
gaacactact tgtactctaa tttacaatta gacgcaggtc aaaagtggaa aggtgaaact  65220
tacgcttatg acagagagca tggtcgtaca ggtacattac tagaatcagg cggtcaacgt  65280
actttagaag agatgattga attcattaga attagagatg tatccttcga ggttaaaggt  65340
ctaaacccta atgataataa cttatattta ttatttgatg gtgtaagatg tcctattact  65400
cctgcaactg gttacagaaa aggttctgaa gatgggacta ttatgacaga tgcaaaagga  65460
acagctaaag gtaaatttac tattcctgca ggtattcgtt gtggtaaccg agaagttaca  65520
ctcaagaatg ctaactctac aagtgctaca acttacacag ctcaaggacg taaaaaaatc  65580
gttcaagata ttattattag aactcgtgta acagtaaact tagtagaccc gttagcacaa  65640
tcattccagt atgatgagaa cagaactata tcatcattag gtttatactt tgcttctaaa  65700
ggagataagc aatctaacgt tgttatccaa attagaggta tgggtgacca aggttatcct  65760
aataaaacaa tctatgcaga gacagttatg aatgcagatg atattaaagt atctaataat  65820
gctagtgctg aaactagagt atactttgat gaccctatga tggcagaagg cggtaaagaa  65880
tacgctattg ttattattac tgagaacagt gattatacaa tgtgggtagg tactagaact  65940
aagcctaaga ttgataaacc taatgaggtt atctcaggta atccatatct tcaaggtgtg  66000
ttattcagtt catcaaacgc atcaacatgg actcctcatc aaaactctga ccttaaattt  66060
ggtatctata cttctaaatt taatgaaaca gcaacaattg aattcgaacc aattaaagat  66120
gtatctgcag atagaatagt tcttatgtct acgtacttaa ctcctgagag aacaggatgt  66180
acatgggaaa tgaaattaat tctagatgac atggcatctt ctacaacatt cgaccagttg  66240
aaatgggaac ctattggtaa ctatcaagac ttagatgttt taggtctagc aagacaagtt  66300
aagttaagag caactttcga atctaataga tatatctcac cattaatgag ctctagtgat  66360
ttaacattca ctacattctt aacagagtta acaggttcat atgttggtag agctattgat  66420
atgacagagg ctccttacaa tacagtaaga tttagttatg aagctttctt acctaaaggt  66480
actaaagttg ttcctaagta ttctgcggat gatggaaaaa cttggaaaac atttactaaa  66540
tcccctacaa ctactagagc caataatgag tttacacgct atgtcattga cgagaaagta  66600
aaatcatcag gaacaaatac taaactacaa gttagattag atttatcaac tgaaaatagc  66660
tttttacgtc ctcgtgttcg tagacttatg gttactacta gggatgaata aactagaggg  66720
gttgattgac cctctttat ttaataagga gagatttata tgcctagaga agttagagac  66780
ccttattctc aagctaaatt atttatacct acagttgagg aaaaatcaat taaggaatta  66840
gaaaaaacat acaaagaaaa aattgatgaa gctactaagt taatcaatga attaaagaaa  66900
```

```
gagagaggag aaaaatagat ggcatttaac tacacgcctc ttactgaaac acagaagtta  66960
aaagatatgt atcctaaagt taatgatata ggtaactttt taaaaacaga agttaacctt  67020
agtgatgtaa aacaaatatc acaacctgac tttaataata ttttagcatc tatacctgat  67080
agtggtaact actatgtaac taattcaaaa ggtgctccta gtggagaagc tacggcagga  67140
tttgtaagat tggataaacg aaatgtaaat tattataaaa tttattattc accatatagt  67200
agtaataaaa tgtatatcaa gacttatgct aatggtactg tatatgattg gattagtttt  67260
aaattagatg aaggtaactt atacaatgaa ggtaatactt tgaatgtaaa ggaacttact  67320
gaatctacaa ctcaatatgt aacactagtt aatcctccaa aagagaactt aaatacaggt  67380
tgggttaatt acaaagaaag taaaaatggt gtttcttctt tagtagaatt taacccagtt  67440
aactctacct caactttcaa gatgataaga aagttaccag tacaagaaca aaagcctaac  67500
ttattgaaag atagtttatt tgtttatcct gaaactagct cttcaaatat taaaacagat  67560
aattggaata cacctccttt ttggggatac acagctaata gtggtcgttc aggggttaga  67620
tttagaggag agaatactat acagattgat gatggtagta gcacatatcc tactgcaatg  67680
actaatagat ttaagatggg taatgagctt tctgtaggtg atacaattac tgtatctgta  67740
tatgctaaaa ttaatgaccc tgcattactt aaagataact tagtttactt tgaactagcg  67800
gggtatgata tggtagatag aactgataat ccttatacag gaggacgtag agaaataaca  67860
gcaagtgaga taacaactga gtggaaaaag tactccttca cattcacgat acctgaaaat  67920
acaattggag catcaggcgt taaagttaat tacgtatctt tactcttaag aatgaattgt  67980
tcatctagta aaggtaatgg tgctgtggta tactatgctc tacctaaatt agaaaaatca  68040
tctaaagtta caccgtttat cacacatgca actgatgttc gtaagtatga tgagatttgg  68100
tctaactggc aagaagttat tagtaaagat gaattaaaag gtcactctcc tgtagatata  68160
gaatataatg attactttaa gtaccaatgg tggaaatctg aagttaatga aaagagttta  68220
aaagatttag ctatgacagt acctcaagga tatcatacat tttattgcca aggctctatt  68280
gccgggacac ctaggggacg ttctattaga ggaaccattc aggtagatta tgacaaaggt  68340
gacccctaca gagctaataa gtttgttaaa ttattgttta ctgacacaga aggtatacct  68400
tatacattat actacggagg gtataatcaa ggttggaaac tcttaaagca atcagaaact  68460
tctactttac tatgggaagg tactttagat tttgggtcta cggaagctgt taacttaaat  68520
gactcattag ataattatga tttaattgag gtaacttatt ggactcgttc agcaggacat  68580
ttttctacaa aaagattaga tataaaaaat acatcaaatt tactgtatat tagagatttt  68640
aatatttcaa atgatagtac aggttctagt gtagactttt ttgaagggta ttgcactttt  68700
cctactagaa catcagtaca acctggtatg gtaaaatcta taactttaga cgggtctaca  68760
aatacaacaa aagtagcatc atggaatgaa aaggaacgta taaaggtata caatattatg  68820
ggaattaata gaggataaag aaaggtggaa taaaaaaaac tatggctgtt aaatatgata  68880
taggtaataa tgagatagta ttacatttaa gagaaggtaa atatataaca gggtttacaa  68940
cagtaggagg gtatgataag gagttaggac aagtaaaagt taatagagaa atcttacctg  69000
cttacttctt tgataatttt gcctatgaaa gatacttgta ttatagtaaa cctgaagagg  69060
ttatagagaa taaaaactat gtaccacctc aaatcaataa tggtgatgag gaatctcaac  69120
aaaatactgt acctaaagaa caatatgata gtttaaaaga agaactagaa cttatgagaa  69180
aacaacaaga agctatgatg gaaatgcttc aaaaactctt aggtcaaaag gggtaataat  69240
```

```
aaatggcatt aaattttact acaataacgg aaaacaatgt tattaaagac ctgactactc  69300
aggtcaataa cattggggaa gaattaacaa aagaaagaaa tatatttgac attacagatg  69360
atttagttta taattttaat aaatcacaga agattaaact aactgatgat aaaggattaa  69420
ctaaatcgta tggaaacata acagctctta gagatataaa agaaccaggt tactactata  69480
taggcgctag aacattagca acattattag atagacctga tatggagtct cttgatgttg  69540
ttttacatgt agtacctctt gatacttcta gtaaggtagt tcaacattta tatacactat  69600
ctactaacaa taaccaaatt aaaatgttat atagatttgt ctcaggaaac tctagttcag  69660
aatggcaatt tattcaagga ttaccgagta ataaaaatgc tgttatatca ggaactaata  69720
ttctagatat agcttcacca ggtgtttatt ttgttatggg aatgacagga gggatgccta  69780
gtggtgtaga ttcaggtttt ttagatttaa gtgtagatgc taatgacaat agattagcta  69840
gactaactga tgctgaaact ggtaaagaat atactagtat taagaagcct acagaagtat  69900
acacagcttg gaaaaaagaa tttgagccaa aagatatgga gaaatattta ctaagtagta  69960
tcagagacga tggtagtgca tcattcccac tcctagttta tactagtgat aataaaacgt  70020
ttcaacaagc tattatagac catatagata gaacaggtca aacaaccttt actttctacg  70080
ttcaaggtgg tgtatcaggt tcccctatgt ctaatagttg tcgaggtcta ttcatgtcag  70140
atacacctaa cacttctagt ttacatggtg tctataatgc tataggtaca gatggtagaa  70200
atgtaacagg ttcagtggta ggaggtaatt ggacttcacc aaagacatca ccttccccata  70260
aagaattatg gacgggagca caatcattcc tatctgtagg tactactaag aatctagcag  70320
atgatattag taattactct tatgtagagg tttatactaa acataagaca gtagagaaga  70380
ctaaaggtaa tgatgactcg ggtacaattt gccacaagtt ctacttagat ggtagcggta  70440
cttacgtttg ctcaggaact tttgtttcag gagatagaac agatacaaaa ccacctgtta  70500
cagagttcta tagagtaggt gtatctttca aaggttcaac atggacgctt gtagatagtg  70560
cagtacaaaa tagtaaaact caatacgtta caagaattat aggtattaat atgccataga  70620
ctaggataag tttcctagtc tttttttctt gacttgaaaa ggattctatg gtatactata  70680
actcgtgtaa ggatataagg agattaaaat gagattaaga attaagaact tatataccta  70740
tgtagaattt gaggaggatg ataaatactt aaaagatata tttttaaaga gagttcatac  70800
aactatagga gcaaggcaag aaggttttca gtatagccct gcttacaaaa gaggcagttg  70860
ggatgggtat gtagactttt atgtttatga ggaagataaa ttccctactg gacttttatt  70920
taaaattgag ttattattag gtgagctaca atcaagatat aacttccagt ttgaaacaat  70980
tgatgagcgt gatgaaagtt tcttatctga agaagatatt gatgacgaga taacattgct  71040
tgataataat gtaggtcaaa ttaccttacg agattatcaa tatgaggcag tgtacaacag  71100
cttaacattt tacaatggta ttgctcattt agctactaat ggaggtaaaa ctgaggttgc  71160
tagtggtatt atagaccaac tattacctca attagaaaaa ggtgaaagag tagcattctt  71220
cacaggctct acggagatat tccatcagtc tgcagataga ctacaagaac gtttaaatat  71280
ccctattggt aaagtgggtg caggtaagtt tgatgttaag caggttacag ttgtaatgat  71340
acctacttta aatgcaaacc ttaaagaccc aacacaaggg gtaaaggtta cacctaaaca  71400
aaatattagt aaaaagattg ctcaagagat attaccgaaa tttgaaggcg gtacaaatca  71460
aaaaaaatta ctaaaagtat tacttgataa cacaacacct aaaacaaaag tagaacaaaa  71520
cgtattaagt gccttagaga taatttacca aaatagtaag acagatgcag aagttttatt  71580
aaacttaaga aatcataatg cacattttca aaaaattgtt agagaaaaaa acgaaaagaa  71640
```

```
atatgataaa tatcaagata tgagagattt tttagactca gttacagtta tgatagttga  71700
tgaggcacac cattctaaat ctgattcctg gtacaacaat ctaatgacat gtgaaaaagc  71760
tttataccga attgcattaa cagggtctat agataaaaaa gatgaattac tttggatgag  71820
attgcaggct ctattcggta atgttattgc acgaactact aataagtttt taattgatga  71880
aggtcattct gctagaccaa caataaatat tatacctgta gctaatccta atgacataga  71940
tagaattgat gattataggg aagcttatga taaaggtata acaaataatg attttagaaa  72000
taaacttatt gcaaaactaa cagaaaagtg gtataatcaa gataaaggta cattgattat  72060
tgtaaacttc attgaacatg gagacacaat atcagaaatg ttaaatgatt tagatgtaga  72120
gcactacttc ttacatggag aaatagactc tgaaactagg agagaaaaat taaatgatat  72180
gagaagtggt aaacttaaag taatgatagc tacatcactt attgatgagg gtgtagatat  72240
atccggtatt aacgcactaa tattaggtgc aggaggcaag tcattaagac aaacattgca  72300
acgtattggt cgtgctttgc gtaagaaaaa agacgataat acaacacaaa tatttgattt  72360
taatgatatg acaaatagat tttatatac tcacgctaat gagcgtagga aaatttatga  72420
agaggaagat tttgaaataa aagacttagg aaaataggag ggtaagagat ggcaacaaaa  72480
acacaaagaa agctatacca atatctagag gaaaatgcta cagaaaataa atttcatatt  72540
tctactaaga aagagttagc agattctcta ggtgtttcca tctctgctct atccaataac  72600
cttaaaaagt tagaagaaga aaataaagtc gttactgttt ctaaaagagg aaaaaacggt  72660
ggagtaataa taactttagt tagagagtat gacacagaag aattgaaaga atttaataat  72720
tctacagata atattattac ttccgattta cagtatgcta aggcattaag agaaaagcac  72780
ttcccttctt atagatatga gagaaaagaa caacgtagac gtactaagat agaaatggca  72840
caatacaatg ctattaagga tgagaagaga agaattatag cagatatgaa tttctattca  72900
gaaggtcttc cttacccttc taaagatatt tttaatatgt cttatgaccc ggaaggtttt  72960
tataaagcat acatcttatg taagttatat gaccaatatg ctatttctca tatggatgct  73020
aaacatacaa gtcatcttaa agcaatgagt aaggcaacaa ctaaagatga atatgactac  73080
catcaacata tgtctgaata ctatagaaat aaaatgattc aaaatttacc tagaaatagt  73140
gttagtgata atttctttgg tagtaaaatg tttaatactt tttataattt ttatttaaaa  73200
ataaaagata aaaatattaa tgtatttaaa tatatgaaaa acgtatttaa aaatgtaaca  73260
ttttattacg agaacggtat gcaacctaat ccaatacctt ctcctaactt ctttagttca  73320
gataagtatt ttaaaaacta taataattat attaaaggaa taaaaaaagg cattaacagt  73380
acgaatagac acctaggtga tacagacagc atcattaatt catcagacta tgtgaaaaac  73440
cctgctgtat tacatctaca ccaactatat actacaggat taaattctac tttacatgat  73500
attgatacta tgtttgaaca agccttagac cttgagaatg cttcttatgg attatttgga  73560
gatatgaaac atattatctt actacagtat aattctatga ttgaagaaga aattaagaat  73620
ttacctatag aagagaagga tattattaat aaatatgtaa aacaatgcat aattaataat  73680
tactcaccaa caagtatttc accatctgca agattatcaa tgtttactat gcagaaagag  73740
catatagttt ataataagca attaaataag ggaatcaaga gagaggattt attaccatta  73800
agtctaggag gtatagtgaa taaagattca ttaagtagta tggatataca aaacttagaa  73860
cagaatggca atgaatacct atatatgaga caacatactt caacttatta tatactaaga  73920
atgtttggtg actatttagg gtatgaggta aatttaagag aagtaaaata tattgtagag  73980
```

```
aaatataatt taattgataa aataccattg acaaaagagg gtatgttgga ttataataaa  74040
cttatacatt tagtagagga agaggttaat aactatgagt aagaagataa aggagcttat  74100
ccttcataaa tcaatgaagg atatacattt tgcaagagaa gtattagata acttacctaa  74160
gaacttattt tcagcagagt ctgaagacat gggttactta tttacagcca taaagagaac  74220
agcacatatt tccgataaga tgtcaaatga agcattagca attaaagtag aacagcttat  74280
gggtaataac aaggaagatg aggagaaagt aaccaagaca ttaacttact tagaagattt  74340
atataaagta gacgttaatg aaaaagatga atctgttaat tatgaaatag agaagtatat  74400
taaaacagaa atgtcaaaag aagttttagt taaatttatt gcagaaaata aacaagaaga  74460
ctctgataat ctacatgaac ttgtagacaa actaaagcaa atagaagtaa gtgacatctc  74520
aggaggtaat ggggagttta ttgacttctt cgaagataca gaaaagaaac aagaactatt  74580
gagtaattta gctacaaata aattctctac tggatttact tctattgaca accatattga  74640
aggtggtata gcaagaggag aggttggatt aatcatagct cctaccggta gaggtaaatc  74700
attaatggct tcaaacttag ctaagaatta tgttaaaagt ggattaagtg ttttatatat  74760
tgccttagag gaaaaaatgg atagaatggt tttgcgtgct gagcaacaaa tggcaggagc  74820
agaaaagagt caaattgtaa atcaggatat gtctttaaat aataaagttt atgatgcaat  74880
acaaaatcat tatcagaaga atagaaagtt attaggtgac ttttatattt ctaaacatat  74940
gccgggtgaa gttacaccaa accaattaga gcaaattatt gtcaatacaa caattaagaa  75000
agataaaaat attgatgttg ttattattga ctatcctcat ttaatgagaa atccttatgc  75060
taaatatcat tcagaatcag atgcaggcgg aaaattgttt gaagatattc gtagattatc  75120
acagcaatat ggatttgttt gttggacgtt agctcaaact aaccgtggtg cttatggttc  75180
agatgttatt acaagtgagc atgtagaagg ttctcgtaaa attgtcaatg ctgttgaggt  75240
gtctttagca gtaaaccaaa aagatgaaga attcaagagt ggtttcttaa gattatattt  75300
agataaaatt cgtaatagct ctaacacagg agaacgattt gttaatctta aagtagaacc  75360
aactaagatg attgtaagag atgaaacacc tgaagaaaaa caagagcata tacaattgct  75420
atcagataat ggaaaagaag acacaagtaa atttcaaaat aaagataata aaatagaagc  75480
tataaataac acattcggag gattaccggg agtttaattt tttaaaatat accacttgac  75540
attttatatg ttaggtggta taattatttt ataaagaata aaggagagat taataatgaa  75600
atttgtattc tttacagata gtcattttca cctatttact aactatgcta aacctgataa  75660
tgaatttgtg aatgatagat ttaaagaaca gatagaagca ttacagaaag tttttgatat  75720
tgctaaaaaa gaagaagcaa cagttatatt tggtggagat ttattccata aacgtaactc  75780
ggtagatact agagtatata acaaagtatt tagtacattt gccaaaaata atgaggttcc  75840
tgtattatta cttagaggta atcatgatgc tacaactaat tcattatata ctgattcaag  75900
tatagataca tttgagtatc tacctaatgt aaatgtaata aaatcattaa atacaatttt  75960
aaaagataat gttaatattg tgtttactgc ttatggggat gagacgaagg aaataaagac  76020
atacattaat agtaattatg ataaagatat ggtcaatata ctagtaggtc atttaggtgt  76080
agaaggttca ttaactggaa aaggctctca tagattagaa ggggcatttg gataccagga  76140
tttattacct gataaatatg atttcatttt actaggtcat tatcaccgta gacagtattt  76200
ccaaaatccg aatcattttt atggtggctc attaatgcaa caatcatttt ctgatgaaca  76260
agaagctaat ggtgttcatt taatagatac agacaaaatg actacagaat tcattccaat  76320
tcatacacgt agatttatta ctattcaagg agaagatatt cctgataact ttgaacaatt  76380
```

```
aatagaggaa gataatttta ttagagttat tggtacagca aatcatgcta aggttttaga  76440
aatggatgac agtatgaaag ataagaatgt tgaagttcaa attaaaaaag agtatactgt  76500
agagaaacgt attgatagtg atgtatctga tgaccctcta acaattgcta gtacctatgc  76560
taaacaatac tcacctgaat cagaacaaga aatccttgaa tgtttgaagg aggttttata  76620
atgaaaaaat atagagaata tctaaataag acagatgcag aaaatttagc agaggattgg  76680
gagaaagtaa ccgaagattt atggaaagtg tttaaagata tgaaacctaa aattaataca  76740
ttagatatca gtaatgtagg aagtaaagat ttagataaaa gtaaacctat actacaattc  76800
caagattcag atggagtaat agagaatatt tgtaatgttg aaggtttaga agatggtcta  76860
agtaaaatga aaaagatttt tgatgatagt aattttgaaa agcattatta caatagagta  76920
gtagaccatg atgggtatta ctggattgat tatggttctc atcattgttt ctttagagtt  76980
acgaaagggg ataagtaatg gttgtattta aacaagtaga agttaataat tttttagcaa  77040
ttaaagaagc tacactagag ttagacaata gaggtttaat tctcattgag ggtgagaata  77100
aatccaatga gtcatttcat tcaaacggct caggtaaatc aactttaata tctgccatta  77160
cttatgcttt atatggtaaa actgaaaaag ggctaaaagc ggatgatgta gtaaataata  77220
ttgagaagaa aaatacgtct gtgaaactta agtttgatat cggggaagat agctatttaa  77280
ttgaacgtta tcgtaaggac aaagagaata agaataaagt aaaattattc gttaatgaaa  77340
aagagattac aggttcaaca aatgacgtta ccgataaaca aatacaagac ttatttggta  77400
ttgagtttaa tacttatgtt aatgccatca tgtatggtca aggtgatatt cctatgttct  77460
ctcaagcaac agataagggt aagaaagaaa ttcttgaatc tattactaag acagatgtat  77520
ataaacaagc gcaagatgta gcaaaagaga aagttaaaga agtagaagaa caacaaaata  77580
atataagaca ggaaatctat aaactaggtt atcagttatc tacaaaagat gagtacttcc  77640
aaagagaaat agaacaatat aatcagtata aagaacaatt ggttcagata gaaaatagta  77700
ataaggaaaa agatagatta agagaacaag aggagaagca aatagaagct caaatagagc  77760
aattagcttc acagatacca acaatacctg aagatgaatt taagcactca gaggagtata  77820
ataaagcctc tcaaagccta gatttacttt ctaataaatt aacggagtta aatcaagtat  77880
actcagaata taataccaaa gaacaagtac taaaatctga aatagctaca ttaagcaata  77940
gtctaaatca gttagatata aatgaccatt gtcctgtttg tggctcccct atagataatt  78000
ctcataaatt aaaagaacag gaaaatatca gcaatcagat tgagaataag aaacaagaga  78060
ttactagtgt attagaaatg aaagatacgt ataaagaagc tattgataaa gtaaaagata  78120
aatcacaaga aattaaagat aaaatgtcac aggaagacca acaagaacga gagcacaata  78180
ataagattaa cagtatcatt caagaggctt ctaggattaa atcagacatt agttcattag  78240
agaataataa aacttattta aaagtgaaat accaacatca atctgttcaa ggattagaga  78300
gagaagaacc aagtaaagaa aaacatgagg aagataaaaa agaattacaa gaatctattg  78360
acaaacatga agagaatata gtacaattag aaactaagaa agggaaatat caacaagctg  78420
tagatgcttt tagtaataaa ggtatacgtt cagtagtgtt agactttatt acaccattct  78480
taaatgagaa agcaaatgag taccttcaaa ctttatcagg ttcagatatt gaaatagagt  78540
tccaaactca agtgaagaat gctaaaggag aactaaaaga taagtttgat gttattgtta  78600
agaataacaa gggtggaggc tcctacaaat ccaattcagc aggagaacaa aaacgtattg  78660
atttagcaat tagttttgca attcaggatt taattatgag taaagatgag atatctacga  78720
```

```
acattgcact ttacgatgag tgttttgatg gattagatac tatcggttgt gaaaacgtga  78780
ttaaattatt aaaagataga cttaatacag taggaacgat atttgtaatt actcataata  78840
ccgaacttaa acccctattt gaacaaacaa ttaaaatagt aaaagaaaat ggagtatcaa  78900
aactggagga aaaataatga aattaaagat tttagataaa gataatgcaa cacttaatgt  78960
gtttcatcgt aataaggagc ataaaacgat agataatgta ccgactgcta atttagttga  79020
ttggtaccct ctaagtaatg cttatgaata caagttaagt agaaatggag aatacttaga  79080
attaaaaaga ttacgttcta ctttaccttc atcttatggt ttagatgata ataaccaaga  79140
tattattaga gataataacc atagatgtaa aataggttat tggtacaacc ctgcagtgcg  79200
taaagataat ttaaagatta tagagaaagc taaacaatat ggattacctg ttataacaga  79260
agaatatgat gctaatactg tagagcaagg atttagagat attggagtta tattccaaag  79320
tcttaaaact attgttgtta ctagatatct agaaggtaaa acagaggaag aattaagaat  79380
atttaacatg aaatcagagg aatcacaatt gaatgaagca cttaaagaga gtgatttttc  79440
tgtagactta acttatagtg acttaggaca aatttataat atgttgttat taatgaaaaa  79500
aattagtaaa tagtaaggaa ggatattatg aggtttgaag actttttaac ccaagaatta  79560
ggagaaccaa aagaaaatac tataggtgag ctaagatact gttgtccgtt ttgtggagaa  79620
aaaagttata agttctatgt taagcaagcc ctagactcta gtaatggtca gtatcattgt  79680
aaaaaatgtg atgaaacagg caaccctatt acatttatga agacttatta taacattaca  79740
ggtaagcaag cttttgattt attagagtct aagaatatag atatagagag agccccttta  79800
cttacaacta ataataagga tttaacagaa tcagagaaac ttatattaat gcttagaggt  79860
gtgcaccaag ataaaggaac tactagtatt aaacctcctc gattacctga aggatataaa  79920
ttattaaaag ataatttaaa taataaagag attatacctt ttttaaaata cttaaaaggt  79980
agaggtataa ctttagaaca aatcattaat aacaatatag gctatgttat taatggtagc  80040
ttttataaag ttgacgggga atccaaagta tcattaagga atagtattat atttttttact  80100
tatgataaca atggaaacta ccagtactgg aatacaagaa gtatagagaa gaacccttat  80160
attaaatcta ttaatgctcc tgctaaacaa gatgaagtag ggagaaaaga tgtcatattt  80220
aatttgaata tagcaagaaa gaaaaagttc ttagttataa ctgaaggtgt atttgatgct  80280
ttaacctttc atgaatatgg agtagcaaca ttaggtaaac aagtaactga gaatcaaata  80340
aaaaaaataa ttgattacgt tagtatagat acatcaatat atattatgtt agacactgat  80400
gcattagata ataatataga cttagcttat aagttaaaaa cacattttaa taaagtttac  80460
tttgtaccac atggtgatga agatgcaaat gatatgggaa caaggaaagc ttttgagtta  80520
ttaaaacaga accgggtgtt agtaacacct gaaagtatac agagttacaa aatacaacaa  80580
aaacttaaac tttaggcttg accttagaga agttttatgt tatactagta attaagtaat  80640
taataaagga gaaaaaaata atgtcaaata gtaaaaaaga tattttagaa tttgtagatg  80700
aatacattac agctttaaga gttggtaatg agcaacgaca acaccaatta gaagaaatgg  80760
gtaaagaaga aacagcaaca ttaacagatg tagctaaagc tattactaac cttatgttag  80820
gtgttaatga gcagatgaca gacttagaat ataataacga gttaaactta aatattttaa  80880
ttgacgcttt atataaagca gagcttatta atgaagatgt attagactac attcaagaat  80940
caattgataa atcacaagaa gaacctaaaa atgaagaaga aaaaggagaa caagaataat  81000
ggaaaaaaat attagcacac acacaaaagg tattagtcaa gcagacatgg agaaatggat  81060
tgaagctgta gtacaaggaa ctgttgatgg taaacaagtt gatgagaaaa cagctaaaca  81120
```

```
attagataga attggttcac gtagtgtttc tttagaagaa gcaactcgta ttgctaaagt  81180
tcttaatgct gtaacagctc aagaggttac aggagacttt aatgatgcat ttaatgcaat  81240
tgacttaatg atgattatca tggaagatga gctaggagta actcaagaaa aagtgggtaa  81300
agctaaagat aaactaaatg aaaaacgaga agcttaccta aaagagaaac aagaagaatt  81360
acgccaaaaa caacaagaag aggcacaaaa agaaactgaa tctgacagca atgagaaagt  81420
aattcagttg aagaaaaatg acgaacagta agaaaaaagg ggatacattc gaacgtaaaa  81480
tagctaaaga attaactgct tggtggggat accaattcaa taggtctcct caatcaggtg  81540
gtgcttcatg gggtaaagat aataatgctg tcggagatat agtagtacct caggaagcta  81600
attttccttt agtagtagaa tgtaaacata gagaagaatg gactatagat aacgttcttt  81660
taaacaacag agagccacat acatggtggg agcaagtcat taatgatagt agcaaggtgg  81720
ataagacacc ttgcttaata tttactagaa acagagctca gagttatgtt gctttacctt  81780
atgatgagaa agtatatgaa gatttgagaa ataatgaata ccctgtcatg agaacagatt  81840
ttattattga taatattaga aaagataaat ttttttatga tgtacttata actaccatga  81900
atgggttgac ctcatttaca ccttcttata ttatatcttg ctacgacaaa aaagatataa  81960
aaccatacaa gaaggtcgag tctaatttat ctgaggtaag taagcatgaa gatgaattga  82020
ttaatgacct tcttagtgat atataaggaa ggtaagataa gtatgacaag taaagaaaga  82080
ccattaatcg tatatttttc aggtacaggg caaacagaaa gattagtaaa taaaattaat  82140
attaataatt catttgaaac atttagggtt aagagtggaa aagagaaagt aaataaacct  82200
tttatactaa taacacctac ttatatgaaa ggtgcaatac ctaaacaaat agaaagattc  82260
ctagaaatta atgggagccc taaagaagtt attggtacag gaaataaaca atggggctct  82320
aatttctgtg gagcaagtaa aaagatttca gagatgttta agattccttt aattgctaaa  82380
gtagagcaat caggacactt taacgagata caaccaatat tagaacactt tagtaataaa  82440
tataaagtag cgtaaaggat gagagatata tggcaacata tggaaaatgg attgagttaa  82500
ataatgaaat aactcaatta gatgacaatg gaaaaaataa actctataaa gaccaagaag  82560
ctttagatga gtatttaaaa tatattgaag acaatacaag aaagtttaat agtgaagtag  82620
aaagaattag agtattgaca aaagaaggaa catatgataa aatatttgac aaggttcctg  82680
atactattat tgatgagatg actaagttag cttacagttt taattttaaa ttccctagtt  82740
tcatggcagg gcaaaagttt tatgaatctt acgcatcaaa acagtatgat gaaaacaaaa  82800
aacctatttt tgttgaagac tatgagcaac ataatgttcg agtagcttta tatttatttc  82860
aaaatgacta tgtaaaggct agagaattac tagtacaact tatggagcaa acattccaac  82920
catctacacc tacgtataac aactcagggc aagctaatag aggtgaacta agttcatgtt  82980
atctatttgt agtagatgat tcaattgagt ctttaaactt tgttgaggat agcgtagcta  83040
atgctagttc taatggtggc ggagttgcaa ttgatttaac tagaattaga cctaaaggag  83100
ctccagtacg taatagacct aattcaagta aaggtgttat tgcttttgct aaagctattg  83160
aacataaagt tagtatttat gaccagggcg gtgtaagaca gggtagtggt gcagtttacc  83220
taaatatatt ccacaatgat atcttggatt tattaagctc taagaaaatc aatgccagtg  83280
agtctgttag actagataaa ttatctattg gtgttacaat ccctaacaaa tttatggagt  83340
tagttaaaga aggtagacct ttctatactt tcgatactta cgacattaat aaagtgtatg  83400
gtaagtattt agatgagcta aacattgatg aatggtatga taagttatta aataatgata  83460
```

```
gtatcggtaa agtaaaacat gatgctagag aagttatgac agatattgct aaaacgcaat  83520
tagaatcagg ctacccttat gtattctata ttgataatgc taatgataat cacccattga  83580
aaaacctagg taaagttaaa atgagtaact tatgtacaga aatttcacaa ttacaagagg  83640
tatcagaaat ttatccgtac tcttacagta atcagaatgt tattaataga gatgttgttt  83700
gtacattagg ttctcttaac ttggttaatg tagttgaaaa aggtttattg aatgaatctg  83760
tagatattgg tacaagagca ttaacaaaag ttactgatat tatggattta ccttacttac  83820
ctagtgttca aaaagcaaat gatgatatta gagctatcgg tttaggttca atgaatttac  83880
atggactttt agctaagaat atgattagtt atggttctag agaagcatta gacctagtaa  83940
acagtttata tagtgctatt aacttccagt ctattaagac atctatgtta atggctaaag  84000
aaacaggaaa accatttaaa ggctttgaga agtctgatta cgctacaggt gaatactttg  84060
taagatatat tagagaatcc aatcaaccta agacagataa agctaagaaa gtcttagata  84120
aggtttatat tccaacacaa gatgattggg atgaattagc taaagcagta aaagtacatg  84180
gcttgtataa tggttataga aaagcagaag cacctactca atctatatct tatgtacaga  84240
atgctacaag ttctattatg ccagtcccta gtgctataga gaatagacaa tatggagata  84300
tggagacata ttacccaatg ccttacctaa gtcctataac tcagttcttc tatgaaggag  84360
aaacagctta taagattgac aataaacgta ttattaatac aagcgcagtt gttcagaaac  84420
atacagacca agcagtgtct acaatacttt atgtagagtc agaaatccct actaataaac  84480
tagtatcatt atactattat gcttgggaac aaggattaaa atcattatac tatacacgtt  84540
cacgtaaact ttctgttatt gaatgtgaaa catgttcggt ttagaaagga aatagatatg  84600
gatattacac aaaaagtaaa acaacataat aaaaatgctg tattaaaagc aacaaactgg  84660
aatattgaag atgacggtat gtctgatatt tattgggagc aaggaatctc ccaattttgg  84720
actcctgaag agtttgatgt atcaagagat ttaagttctt ggaatagttt aactgaaagt  84780
gaaaagaaca cttataagaa agtccttgca gggctcacag gtctcgatac aaagcaagga  84840
ggagaaggta tgaacttagt atcctaccat gaaccaagac ccaaatacca agctgtattt  84900
gcgtttatgg gtggtatgga agagatacat gctaaatcct atagtcatat ctttacaaca  84960
ttactaagta ataaagaaac aagctatcta ttagatactt gggtcgaaga aaatgacttt  85020
ttaaaagtaa aagctcagtt tatcggatat tactatgacc aactattaaa acctaaccct  85080
actgtatttg atagatatat ggctaaagta gctagtgcct ttttagaaag tgcactattc  85140
tactcaggat tttattatcc tttacttctt gcaggaagag gtcagatgac acaatcagga  85200
gctattattt ataaaattac tcaagatgaa gcttaccatg gttcagcagt aggattaaca  85260
gctcaatatg attataatct tctaacagaa gaagagaaaa aacaagcaga taaagaaact  85320
tatgaattat tagatattct ttacactaat gaagtagcgt atacacatag tctatatgac  85380
ccactagaat taagtgaaga cgtaattaac tatgttcagt ataattttaa tagagctctt  85440
caaaaccttg gaagagagga ctattttaat cctgaacctt ataaccctat tgtagaaaat  85500
caaactaatg tagacagatt acgaaatgtt gatttcttta gtggtaaagc agactatgaa  85560
aaatctacaa atatcaaaga cattaaagat gaagatttct cattcttaga tagtaaagaa  85620
tacaatactg ccaaggaatt cctataaaaa ggagaaaaga tattatggat agaaaagaag  85680
caatggattt actaagtaaa gcagaaatat tatttaaaaa acatgatgag ttttcatgtg  85740
taagtgatat taatgaccct atgaagttat tcagtagctc taaggatgct aaagctgatg  85800
atacgtctaa gtcttttcag ctagagttta tgcatgatat gaccatgtat actttatctt  85860
```

```
atggctcagg acagttaaaa cttattgatt tagcagaagg ttatgaagca caaaaagcta  85920
cagtagttaa ctcatttccc gaaattatta aaacattaga aaaggatgat tcagaagatg  85980
gaaaaaatga atagtttagt agatttaaat acagcaatta gacaaaagaa agatgttatt  86040
gtcatgatta cacaagataa ttgtggtaag tgtgagattt taaaaagtgt aatccctatg  86100
tttcaagagt caggtgacat taaaaaacct atcttaacat taaatctaga tgctgaagat  86160
gtagatagag aaaaagctgt taagttattc gatatcatga gtacaccagt attaattggg  86220
tataaagatg gtcagttagt taaaaagtat gaagaccaag ttacacctat gcaattacaa  86280
gaattagagt cactttaatt tggaatttcc tactatctgt gctatactat aatagtacaa  86340
ggtagtagga tttttaatg gaaggaagat gacatatcgc aaagaataaa acattaacga  86400
tatataatag tgatagatat tttaatatac acacaaaaga taaagataaa attaatgagg  86460
ctattaaagt cacacatggt aatgaagaag aaattgagaa gaatatggat gaattaatat  86520
ctaagtctag acgatatatc atgagagatg aaaatcatta catgttattt aatgagaagt  86580
ataataatga tagacttata gaaaaagtat gtaaacatgg cggtaaagtt acatactata  86640
ctgattcagt attaccttat tatgttttaa aagacttatc tagtcaccct gactcagaag  86700
ttgtttatcg tatgcgcaat ggttttactg caaaagaagt agataatata gctttatcat  86760
tcatgggtac aaaagttatt attgatattt ctgtagtatt tccttatgta aacccttatg  86820
atattattag aagtttacat gatattaaaa caaatgtaga tgaagttcat ttatcatttc  86880
cacgaatatt agaggtagat gaaaaacaag aaaagtttta tttctttgat ggtgaagctt  86940
atgatttaaa acctgaatat aaagtcgatt ttgcagataa aattagagta tctttatcag  87000
tatggaaaat gtatatctat atcttaacaa gtagtcgtga ttttgaggat gtagacaatg  87060
taattacgaa attaaaacaa caacgaaaga ttaagatata aggtgattat atgagtacag  87120
caaatagaag agatatagca agaaagatat cagagaatac aggttactat atccaagatg  87180
tagaggaaat actaagtgca gagacagatg ctatttctga cttactagaa gaaggatata  87240
ctaaagtaaa gaatcataaa tttatgcaaa tagaagttat tgaaagaaaa ggtaaaaaag  87300
cgtgggatgg tctgaataaa gaatacttcc atttacctaa tagaaaagct ataaaattca  87360
aaccactaaa agaactagaa gaggttattg atagacttaa tgaagaagag aaataattct  87420
cttcttttt tattgacaag gtttaaaata tatggtatag tattattaag ttaaaaaagg  87480
agaggaatta aatgaaagta ttaatcttat ttgaccacat tagagaagag catttttctg  87540
taagtaaaga tgggagtgtg aaatctaatg tactaaatac acctaatgga aaaacactta  87600
agaaattact tgagaagtgt tctaacttaa agagagataa gacaaacaga gattatgata  87660
ttgattttct ctacaatgca gtacctacac ctatcagaaa tgactacggt aaaatcatta  87720
aatatcaaga tgttaaacaa gcagaagtaa agccatacta tgagagaatg aacaatatta  87780
ttattgataa ttcttatgat atggtaattc ctgtaggtaa actaggtgtt aaatacctat  87840
taaatgttac agctatcggt aaagtaagag gagtcccaag taaagtaact attgaaaatg  87900
aaacatcttc tcatgacgtg tgggtattac ctacttacag tattgaatat actaatgtaa  87960
ataaaaatag tgaacgtcat gtagtatcag atttacaaac agttggtaag tttgtagagc  88020
aaggagaaga ggcatttaaa cctaaggaag tatcttacga gttggtagat aacattgaaa  88080
gagtaagaga aatattcaat aaggaagtaa agaacgacaa ttatgatggc gtagatatta  88140
ccgcatggga cttagagact aactcattaa aacctgataa agaaggaagt aaacctttag  88200
```

```
tactatctct atcatggaga aacggtcaag gtgtaactat acctttatat aaatcagact  88260
ttaactggga aaatggtcaa gatgatattg atgaagtctt agaattgctt aagaattggt  88320
tagctagtaa agaagacatt aaagtagcac acaacggtaa atgatttgct gttgtaaaat  88380
ccctctcata tcgggcatag ctttaagaag ctgataagag aacctaagtc ctgtaataag  88440
gatagtggta atcccgagcc tacattattg gtgacaatag atggggtgta gagactgagc  88500
tgaggttttg tagaccaagg tgagacatag tgtatcaact taatagaggt ggtacagtga  88560
aaaaagatta tatgacatca gttaaaaata acaaaaaagt atgtagaaga tgtaatgaag  88620
aattagactt atctaatttt aaaacatata aaaagaatga taaaatttat tatcagagta  88680
tgtgtatacc ttgtagaaag gaatacaata aattagataa aactaaaaat actattaaaa  88740
aatgttatga taaaaatgga gataagtatc ggaaacaagg taatgagtat aacacttctg  88800
atagaggaag agaactaaat aaaaagcgtt caagaaaata cagagaaaat aattctttaa  88860
aagctaaagc tagaaactct gtaagaactg cattaagaaa tggttctcta ttaagaccta  88920
gtaaatgttc agagtgtaat aaggaatgta ttcctgaagc tcatcatcct gattataaca  88980
aacctttaga aataaaatgg ttatgtaaat catgtcatga agatacacat cataaaaaat  89040
aatcacacta tgtaaatgag ggacatcaag cccatttagg taactacaaa caaacctaat  89100
ggtaagggct tatgaaggta tagtccgttc tgtatagaaa tatacaggct aaaacgaaat  89160
atgatattaa attcttaatg agtactgaaa actttaaaga ttttgagagt attcaggata  89220
ctaaagtagg ttggtaccta gccgttaccc aggaagttaa agaatcttta agattatctg  89280
atttagctta cgaggttacg gatgtcggag gatatgataa accattagaa gactttaaat  89340
tatggtttgt tactaagtta ttaagattct tctcagataa aattaaagag atacagaaag  89400
aaaataaaaa aattgctaag aaagagtatg atgttaaagc tcctgaatat aaagaatggt  89460
tagagaataa actaaatgaa acagtagtag aactagatga tactgagaag aaatttagag  89520
tcagtgaatt agagaaaaag tatattcaac taggtctttc acctgaaatt gtaaatatga  89580
atttagttat gaataacgat gagtttataa gtattgcaga acaatcacct gagtacatgg  89640
ggttatctga ctacgctaag tcttacacat taaatactgc aattaattta attaatgagt  89700
atagagatgt aaaagatgta gttaatgata ttgatggagg taactttaat tatgattggt  89760
tccctattga gttaatgcat ccatatgctt caggagatac tgatgtatgt agaagaattc  89820
attgtgatgt agttaaaaaa cttaaagaac aagatagacc taaatcaatg catttattag  89880
aagttaatta tccaagactt actaagtctt tagctaggat tgaatcaaat ggtttatatt  89940
gtgacttaga ttatatgaaa gaaaatgatg agtcatacga gtctgagatg gctaaaaatc  90000
atgctacaat gagagagcac tggctgtta aagaatttga agaataccaa tacaatcttt  90060
accaaatggc gttagaagaa catgagaaaa agccaaaaga tagagataaa gatatccatc  90120
agtatagaga taaatttaaa gatggtaaat ggatgttttc cccaagttcc ggagaccata  90180
aaggtagagt aatttatgat attttaggaa ttcaattacc ttatgataaa gaatatgtta  90240
aggaaaaacc atttaatgct aatgttaaag aagcagacct tacttggcag gactataaaa  90300
cagacaagaa agctattggt tatgcgttag ataatttaga attaaaagat gatgttagag  90360
aacttcttga gttacttaaa tatcatgcta gtatgcagac aaaacgtaat tcatttacta  90420
agaaattacc taatatgatt aataaacaaa aacgaacatt acatggttct ttttctgaga  90480
caggtacaga gacatcaaga ctaagtagta gtaaccctaa cttgcaaaac ttaccggcac  90540
acacatcaga tgtaaacaag tttgattaca aacatccaat taaacgttca tttgtttcta  90600
```

```
gatttgaaaa tggagtacta ctgggagccg actatagcgc cctagagatg cgtattattg  90660
gattatttac taaagaccct gatatgctac aatcattctt aaatggggaa gatattcata  90720
aggctactgc aagtattgtt tataataaac cagtagaaga ggtaactaag gaagaacgac  90780
aagcaactaa agcagttaac ttcgggttag ccttcggtga atcacccttc tcatttgcag  90840
gtaaaaataa tatggaagta agtgaagcag aagaaatatt tgaaaagtac ttccaaacaa  90900
aaccaagtgt aaaaacttct attgacaatg tacatgagtt tgtgcaacaa tatggttatg  90960
ttgatacaat gcacggacat agaagattta tccgttcagc ccaatcaaca gataaaaaga  91020
taaaaaatga aggtctaaga cagtcattta acactattat ccaaggttca ggtagtttct  91080
taacaaacat gtctttaact tacttagatg attttatcca atctcgtaac ttaaaatcaa  91140
aagttattgc cacagtacat gatagtatct taattgattg tcctcctgaa gaagctaaaa  91200
ttatggctaa agtgacaatt catattatgg aaaacttacc atttgatttc ttaaaagcag  91260
aaattgatgg aaaagaagta caatacccta ttgaagctga tatggaaatc gggttaaact  91320
ataatgatat ggttgaatat gatgaggaag aaatagatac atttaattct taccaaggtt  91380
atattaagta tatgatgaat ttacagacct tagaagatta taaagagtca ggtaaactaa  91440
cagatgaaca atttgaaaag gctactaacg ttgttaaaag tgaaaaacat atttaccaag  91500
aaatttaata aaagtattga caatatattt aacttatgtt atactatata ggtaataaat  91560
ataaggagga aaaagagtga atacaggaga gattagattt aatcgttcta tggatgaatg  91620
gattataaca agtatgtacc aggatgagct aggtgatatg aatattgttg ttacattcta  91680
taatagagaa gaaaataaac acggttctac agttttaccc acagagtcat ctactggaga  91740
agtaacagag gaattggcaa atcttgaaga agaatatcct ctagctttac ctttaagtag  91800
tatctcagtt aatatttaaa aggaggaact gataaatgga aatacacatt gattccctag  91860
attttacaaa ctttactatt aaagatagaa atgggaactc acaagagttt gatattacag  91920
atgagttaag aattacagag tatacaatac aagaggactt tatgcaacaa tcagctaaat  91980
atgctttttg ggcttctata ttagagaagg taagagcata ttctgaaatg gaacaaagaa  92040
atctagaaac aattggtagt aagctaaacc ttacaattag acaagagtac gaacaacaag  92100
gtaaaaagcc tactaaagat atgattgaat ctagtgttta tattcatgat tcttaccaac  92160
aacaacttaa agttgttgag gcttggaatt ataaagttaa acaacttcaa tatgttgtaa  92220
aagcttttga gacaagaaga gatatgatga ttcaattagg tgcagaatta cgacaaacaa  92280
ataaaaatgg tggaattact aatccatttt cacattaaaa aataaagtaa agaatataat  92340
tgacaaatat aaaaaactat gttataataa ataagtaaat taattaaaag gagaaaagat  92400
aattatggat ttcaatcaat ttattaacaa tgaggcaagc aaattagaaa gcaataacag  92460
ttcttttaac aataatgtag agagctacaa acctaaaaac cctgtactac gtttaggtaa  92520
tattaaagat gcaaacggaa ataaggttgt taaagaaaat gcttttgtac gagtattacc  92580
tcctgcacaa ggaacaaatg ttttctttaa agaatttaga acaacaggta ttaactattc  92640
taagaaagat ggttctcaag gattcacagg attaacatta cctgcagaag aaggttcatc  92700
tgtccttgac ccgtacattc aggactggat aacaaatggt gttcaattta gtagattccc  92760
taataaacca ggagtacgct attacattca tgtgattgaa tactttaata acaatggtca  92820
aattcaacca aaaacggatg ctcaaggaaa tgtaatgatt caacctatgg aattatctaa  92880
cacaggatat aaagaattat tagctaactt aaaagatact atgttaaaac catcacctaa  92940
```

-continued

```
tgcacctcat agctttatct cagcaaatga agcattctta gttaatattg ttaaagctaa  93000
gaaaggtgaa atgtcatgga aagtaagtgt ttatcctaat gctcctttag gtgcgttacc  93060
gcaaggttgg gaacaacaat tatctgacct agaccaatta gcaaaaccaa cagaagaaca  93120
aaatcctaat tttgttaact tcttaatcaa taatgttaat aacacagagt taagtcatga  93180
taactttaaa tttaaccgtg aaacaaatgt cttaggtgaa gaaccttcag agcctaaaca  93240
agcacctacg caacaagatg tagatagtca aatgccaagt aatatgggag gacaacctaa  93300
tcagcctcag caaggtcaag taggtcagta tgcacaacaa ggtcaaagta atggtcaagg  93360
acagcagtta caaggtacac aacaacctat caataacacg caatttggtc aaggaactcc  93420
ttcaggacaa caaccaagta acacaggttc tgttgattgg gataacttag cgcaacaaca  93480
atcacaacct gattcaaacc cattcaatga ttttgatgtt agcagtgttg atgattcaca  93540
ggtacctttt gagacacaac ctcaaaatac acaacaagca cctgaaccac accaaactac  93600
acaagagcct ccaaaacaaa aacaaacgca aagtattgac gatgtattag gtggtctaga  93660
cttagataac ctataagata tagagtgcct tagagcactc ttttatttga gatataatta  93720
ctaggaggat attaaatggc aagagcaaaa aaaggtaaag aagtagattt aacagattta  93780
aatacaattg atttaggtaa agaattagga ttaacattgc tatcagatac aaacagagca  93840
gatattaaaa acgttatacc tacaatggtt cctcagtatg actatatttt aggtggaggt  93900
attccattag gtcgattaac agaagtttac ggtttaactg gtagtggtaa atctactttt  93960
gcagttcact tatctagaat tgcaacacaa ctaggtgtta tcactatttg gattgatatt  94020
gaaggaacag cagataacaa tcgtatggaa caacttggtg tagatgtttc aaaactattc  94080
tctattcaat caggagaagg tagacttaaa aatacagtag aattatctgt agagcaagta  94140
ggtaaagaat tagaatactg gattgacact ttcaatgaaa agattccagg agtacctatt  94200
gtatttattt gggactcatt aggggctaca agaactcaga aagagattga tggcggtatt  94260
gatgagaagc aaatgggtct caaagcatca gctactcaaa aagtaattaa tgcagtaaca  94320
cctaaactaa atgatacaaa cacagggtta attgttatta accaagcccg tgatgatatg  94380
aacgcaggta tgtatggtga ccctattaaa tctacaggtg gtagagcttt tgaacatagt  94440
gctagtttac gtattaaggt tcataaagca tctcagttaa aacagaagag tgagttaact  94500
ggtaaagatg aataccacgg tcacattatg cgtattgaaa ctaagaaatc taaactatca  94560
cgaccagggc aaaaagctga agcagactta ctatctgatt atatggtagg taaagaagat  94620
gaccctatct tattaaatgg tatcgactta gaacataccg tatataaaga agcagttgaa  94680
agaggtttaa ttactaaagg agcatggaga aactatgtta cattgaatgg tgaggaaatt  94740
aaacttagag atgctgaatg ggttcctgta cttaaagata atagagagtt atatctagaa  94800
ttgtttagta gagtttatgg agaacacttc cctaatggtt actcaccatt acttaataac  94860
aaagtaatcg taactcaatt agaagagtat caagctcttg aaaactacta taaagaatgg  94920
gctacagata ataaacaaga agaacaagag gaagaactaa aaggagaatc tcaagaaaag  94980
gattctgaat aatagatgga taatttaata gataaaaaca tgagtcaggt aaaagaatct  95040
ttggggaacg caaattcctc agatgttctt cctttacctt ataaagatat agcaaagaaa  95100
tttgaagaag taaaagaaaa aggtgaatca attatcattg aagaaggtgg attcccttat  95160
acagattcta cagtgatgta tatagaacat gtaacagata gatgggcagg aggatattcc  95220
ttaattagac atgaaggtga ggaagttaaa gtacctaaga ctatccattt ctctgatata  95280
tatgttaaag ataaatcaca caaagtaaga ataatcttcg agggggctaa tccttatgaa  95340
```

```
gaaagctaat aatggtaata gatatgtaat agatatagat ggtatacctg ttgattttga  95400
aagagattta gatagtttac ttaataggta taaaaacctt agatggtctt tatatcatag  95460
atacgcaggg attttatcta atgattttga aagacaagaa ctaagagaat atattgatga  95520
gcaatttatt aaattagtta aagaatataa tattagaagt aaagtggatt ttcctggata  95580
tattaaagct aaactaactt taagagttca aaatagttat gttaagaaga atgaaaaata  95640
taaacgtact gaaattatcg gtaaaaaaga ttatacagta gagtccttaa cagaagattt  95700
aaatgaagac ttcgaggata atcaaattat gagttatgta tttgatgata tagaatttac  95760
agaggttcaa agtgagttac ttaaagaatt acttattaac cctgaaagag aagatgatgc  95820
ctttatcgtt tctcaagtag cggaaaagtt tgatatgaaa agaaaagaag tagcaagtga  95880
gttgacagaa ctcagagact atgttagatt taaaataaat gcataccatg agtactatgc  95940
taagaaagaa ttaaataacc atagagttaa tactgaaaat catatttggg aaaactagtt  96000
acagtgcctt ccttgtgtta tattattatc gagaattcaa taataaagca tagggaaggc  96060
tttttctat gtcttataga atgctttaaa atagattact aaaataaaga ttggagatta  96120
agcttatggc taaaaagaat gttaatgatg tattacaaca agaatctgtt acagtagcag  96180
ataagtattt acaagttaaa gttaaccgtg acggttatac tcgtacacat gaaggacaat  96240
atgcgtacaa agtagtttca gagggagaag aattattctt ataccctgta caaacagatg  96300
gtaaaggtac attaaatgta atgaagaaat cacctattgc ttacactgat ggagacaata  96360
tccatttcgt agtaaacaca gtagtagacc cttataatca ctcatttatc cgtactgaag  96420
atattaaagg attagataaa ggtaaacaac ttattcaagc tttcttagct ttcgttgaag  96480
accgtttcaa atttggtgtt tataacgtat ttgttgcaaa caacaaagag gatgtattat  96540
ctattgtaga ccctacagat aatgatgcag atgaagttaa agatagttta gagcacgcac  96600
atgaagatgt aattgcggat ttccctgcta gccctgctcg taaggacgtt aaaggcgtag  96660
attcaggaga aggtcaagga gacacttcag aaccatcagc acctaagaac gttcaagtta  96720
ctcctaagga agacggagca gacgtatcag cagaataata tatagataag gatggtaaat  96780
ttggctaagt taaatttata caaaggtaat gagttactaa acagcgtaga aaaaacagaa  96840
ggaaaatcaa caatcacgat tgagaattta gatgctaata cggattaccc taaaggtact  96900
tttaaagtat cattctcaaa tgattcagga gagtcagaga aggtcgatgt tcctcagttt  96960
aagacaaaag caattaaagt tatttcagtt acccttgacg ttgatagttt agaccttaca  97020
gttggagata ctcaccaact atcaacaact atcacgccta gtgaagcatc taacaaaaat  97080
gtgtcatttg aatcagacaa atcaggtgtt gctagcgtaa catcagaaga cttaattgaa  97140
gcagttagtg caggaacagc taatgttact gtaactactg aagatggtag tcacactgat  97200
attgttgctg taacagttaa ggaacctatt cctgaagcac ctgcagacgt aacagttgaa  97260
cctggtgaaa atagcgcaga tattactgta taagaggaca ataaagaatg gaaaagacat  97320
taaaagttta tagtaatggt gaagttgtgg gctctcaagt agctaataac gatggagcta  97380
ctacagtatc tattacaggc ttagaagccg gaaaaactta tgctaaagga gattttaaag  97440
tagcatttgc taatgattca ggtgaatcag aaaaagtaga tgttcctgaa tttacaacta  97500
aaactcctac tgaagaacct tcaggagacg cataataatt aagaccaact aaaaagttgg  97560
tctttttta ttgacaattt ataatatcta tgatacacta tataagaatt aagaaaagga  97620
ggggaaagta atggatattc caacaatatt atttagaaat ccatatgatt atacgaaagt  97680
```

```
aaaaaaatta atggaaaaca aagagcagta tattgtagta aagtttgatt ctgtttctgt  97740
tcataattta aatgttcaag gtatgatgaa tgtcatccaa gattacctac acatctatgg  97800
ttacagagtt aaagagtacg gacaagaaaa ttcttctaaa gatgatgaaa gagacgttaa  97860
aggctactta tatgaaagag taggtgagta gggtatggga attatagtaa actccaacca  97920
tattcaatca gacactttat atgagtatga tagctttttt gatattgaga aagtagatac  97980
atttgaagaa ggattgcttt caatacagga tgagccaact gttttagcag gattcatcta  98040
tgatgatatc acatttaata aggtcattaa ttctaattca gatattgatg actatattaa  98100
gaataatgat atttattatg tctctgatat aggattactt cctgatactt ttatcactgt  98160
tgattctgat agaaaatatt attcattatt acaacagata actgagttaa gtaaagaccc  98220
ttttcctaaa tgggtagagg atgatgcaaa aggtttaact aagtattata actttcaaga  98280
ttttgaagat gtatttgatt taaatagttt ttacaaaaaa gaagttgaca tggtaagaga  98340
aaagtgctat aataatggta atgtatattt attatatgag gttctgcctg attataaatt  98400
acctctagct tatagtttac tttcaaacaa ggagcatggt attgttatta tcggttcaca  98460
gacacgttct aataatgata tactgacttt ttatgttaaa ggtatggatg ctaaggcaat  98520
agctagtatg ttcaatgtag aacatgatta tgattctaat attttccata catttgtaaa  98580
cagtcacatt aatattttag gaaatcaaat aactaagttt ataagagaga aaggaagcag  98640
ttatgagtaa ctataaaaca atagaagaag tacaagcagt tattattggg gtattattta  98700
aagatgaagg taaaattata acatctaagt ttaataaaat tactaaagag tttggtttag  98760
atagaatcgg taaagatgac cttaaagaaa ttgtagagga tatccgacaa gacgcttatc  98820
taaatgaact taaaaacaaa gcaattaaag gtaaagtaac gttaggtgat ttaaaagatg  98880
ttgcagataa ccaagtattc gaaggtaata actaccatga agaagtatct acttatgtag  98940
tagctaaaga aaaagaattg tctcacttaa gagaacagcg taagcacaat aggcatactg  99000
catacctca aattatgttt gatgaactta aagaacatat ggttaaggaa ttacaagggg  99060
aaacattagt agaacatcac ggaagtaaag ctaatattaa tgatacagag ctaattgtgt  99120
tactatcaga tttccatatt ggaagtattg tatctgatat gactaatggt aaatatgatt  99180
ttgaagttct taaagcaaga ttaaatcatt ttattaatac aacagttaaa gaaattgaag  99240
atagagaaat ttctaatgta actgtttact ttgttgggga cttagtagaa catattaata  99300
tgagagatgt taaccaagca tttgaaacag agtttacttt agcagaacaa atctctaaag  99360
gtactcgatt acttattgat atcctgaatg tactatctaa tgtagtttca ggagaactaa  99420
gatttggtat tattggtggt aaccatgacc gtatgcaagg taacaagaat cagaagattt  99480
ataatgataa cattgcttat gtagtgttag attctttatt gttattccaa gaacaaggac  99540
tattaaatgg tgtagatatt attgataatc gtgaagatat ttatactatt agagatacct  99600
ttggcggtaa atctattatc attaaccacg gagatgggtt aaaaggtaaa ggtaatcata  99660
tcaataaatt tatcttagat agtcatattg acttattaat tacaggtcat gtacatcatt  99720
tctcagtaaa acaagaagat tttaatagaa tgcacatcgt agcttcatct ccgatgggat  99780
ataataacta tgctaaagag ttacatttat caaaaactaa accttcacag cagttattat  99840
tcataaataa ggaaaataaa gatattgata ttaaaacagt atttttagat taaggatggt  99900
taataaatgg atacaatttt tattataggt gtagcgttta taacttttgc aacatttaac  99960
atagtcttta gattatttga tttatggact acagagaaaa aaatggtaag tcaaggacaa 100020
cctccactaa gtaactttga gtactatcat gtgatagtac cttacttagt aggtgttatt 100080
```

gttattatac tgagtattat ttttagggat tccttgtatt ccgcacaatc agggttcggt 100140
gttattatta caagctttat ttacatgcta gtttatgtta taattggtct tgtagggtca 100200
tttgtactta caatattcca agctagaaaa gctagacagt atcaaacaca ggaggataat 100260
aatgaagttc aatgatattt atgagcaatt aattaaaaat gatacagtac aaaacattca 100320
tgagtctcaa gatgacaaag gaaatattta tacaatacag tttgataaag gtaatgataa 100380
gtatttattt aatgttatta atgatggatt cttgaaagaa atgacaaatg gtatggtaga 100440
ccatcctgaa ggtcagccat attcagtaag tttaatcaat aaagaaacac ctagtatgtc 100500
agtgaaacaa tatttaacag atgtagaaga tattgtacct actattagaa aaatggaaaa 100560
ggatttctta tagagtcaag tctttacttg actcttttta ctatatatgg tatattaata 100620
tagaggtgac ttaaaaatgg attttaattt tagtgctttt gataatagct cattagcaat 100680
gagaattagt gagggtgtat actatttcaa tgatacgcct tattacttta ttgagcatgt 100740
agaagaagaa atgtctgagt atgttattgt atatgacata catgacagag aggaaaaaga 100800
aaatcctcag aagaaatata gaatagaacc ttaccaacgt acaataccgg gaggaacacc 100860
tcttagtaat ttaattaaga gtatgatgcc tcaacgtaag tatcctaaga aggttacaga 100920
agaccctata tttgtagcta atgttattcc tttaggaaca gatacagtaa caggtaaaac 100980
cggtaaagga ttttttgaaa gagataagga tagaactatc tattctcaaa aggaaccaac 101040
taaagtcgtt catggtcaat acacaggtgt ttttataggt ctaacaagtg ttaagtggaa 101100
tagaacatat accccttag aaagtgttgt tgagtactac aaaagggtta aaggagatag 101160
gttaaatgtc taatgatgta gttaagttct atgaaaaaga tattaaagac cttatcagaa 101220
ctaaaaaaca catgttcaaa gacgatgaaa taactagtga tataaacgat atacgaatct 101280
ttaatgagaa agtcatttgt caaggtaaat gtagaacaga ttgtttagtg ttagaccgta 101340
atggtacagt aatgggtata gagataaaaa cagaacgaga ctctacacaa agattaaata 101400
accaattaaa atattatagt ctagtatgta agtatgtata tgtaatgtgc catgacaaac 101460
atgtacctaa agtagaacaa atacttaaaa ggtataaaca taatcatgta ggtataatga 101520
gttacattag ttttaaaggc aaacctgttg taggcaaata caaagatgct acaccatcac 101580
cacatagaag cccttatcat acaatgaata tattatggaa gacaaactta atgacaatac 101640
ttagattgat tagagaccct catacgtata gaacagggta tagctataat gctagtggta 101700
gatatagtgg aggggaaggt aatttctccc aaacaactca aagtaaaaga atgaaaaaac 101760
ctgctattat taaccaaata attcattatg taggggtaga taatacttat aaactcttta 101820
caagaggtgt tatctatggt tataataata ggtgggaagt tatagaagaa gatttcttta 101880
atactatgaa gaatggggta agagtaatta atgagcaaag acaaaccaaa tagacgtaaa 101940
gagatacagc atcaacctgt taactttgcc cctacgaata ctttaacagg agctaataat 102000
agtttctttg ctaaaaatcc ttcagagcct aaagatgcaa catctgttat tgaatatcgt 102060
atactattta ttaaaagatt tgataacgta acaagtacag atgtgaaatt acagaaaaag 102120
tatgcactaa atcttattag tgaagcactt gatgttaaag aaacttactt gtctcttaag 102180
caaaaaggaa aaaaaacaga atctattttg catacagata gagtttatta tgttcataga 102240
ggtaaaaaac ttattggaaa gtgtagtatc agagagcaaa gaacatttaa gggtaaacat 102300
ttgatattta tattcaaaac aagacataga gttaaagcag aaaggaaaga taaataatgt 102360
taaaaggatt ttcagaacat gtagacaaac ctacaactag taagacctta tacaagacct 102420

-continued taacaagtgg taaagtagaa ttactaggtg tatcttacga tagtgattac ttcccttcag 102480
gtgttacagt acaatcttac attgaggata taggtaatga agatgagggt ctacagtttg 102540
ttaataaggt aaatgtagta gaatcaatga aacaggctgt agtaggtatg aataatcaat 102600
taggttcttc aggtcttggc tatgtgagaa ctgaacaact taaaaaagag ttggaagaga 102660
ctggactaat gacagattta cttgctagag gtactaactt aacctctact aagaaagtag 102720
atattgtaag tacttttatt gagcctgagg taacatacca aaatattact atagctaaag 102780
atattaaact acgtttgtat aaagtagaag aagaatcacc attaaatggt tacactcata 102840
ttgtatactt acttactaca gaaaaactat atgatggtca aacactcttc ggtatgctct 102900
ctaaaaaaga taagttatct aaaggagata ctgataaatt attagcattc ttcagaaaca 102960
atagtttaat aagtaaaagt gtattttgtg ttaagttatt aagtaaagac tactacttta 103020
atttatataa tacacatgag acagggatat tctttttaga agacacagat gttattacta 103080
ttgcttgtgg tcagtcatat gttaaagtta acactaaaga tattaagtct agttatgtta 103140
aaattgaaga taagactcat aaattaactg agctagtaat taacctaaag ggtgacgaca 103200
cattaactat tttattctag gaaaatgtta taaatatgtg ataattaagt ataaatatac 103260
gttatataag aagttttcat aatgttttta atacagaaac tagttaagtt ttttctactt 103320
gctctagttt ctgtgaaatt atatttatga aaagttaaaa tatcttttag gtaaaggctt 103380
tgtaaatagt taaaaaatat attaaaattt tatacaaagt agttaataaa attatattac 103440
atttatatat tatgaaataa taacagaaat tgtgatatat tatatagtgt aaccttgaaa 103500
cagttgatgt tgtagggttt gtttatgttc gttaaactgg tttcaaaaca tcagttacca 103560
taaataaatg acagttaagg agagctatat aatggctaga aaaaagaatt tacgaaataa 103620
aaacagtgat ataaaagttg ttcctgataa agaaaaagaa agtatattat ctaagctata 103680
ccataataaa ttactacgtt ctaaggtaga taatgcatta gatgaagata tgagttatga 103740
tgatattata gaactatgta aagaatatga tttagaattg tctaaatcag ctattacaag 103800
atacaaaagt aaaagaaaag aagctattga aaatggttgg gatttaggag aattaattga 103860
taaacgtaaa aaaacaagtg taaaagatat taaggaaaaa gaaactccta tattagaaga 103920
ggagcaactt tctccattcg aacaatcaaa acatcacaca caaacaattt atgatgatat 103980
tcaagtacta gatatgatta tttctaaagg tgcaaaagga ttagagtttg tggaaacttt 104040
agaccctgct ttaatgatac gtgcaatgga aactaaagat aagattaccg gaaatcaatt 104100
aaaaggtatg tcatttattg gacttagaga attacaatta aaacaaacag ctcaagatac 104160
agctatgagt gaagtattat tagaatttat acctgaagag aaacatgaag aggtattaca 104220
acgattagaa gaactacaaa atgaattcta caaaaatcta gatttagatg aggaaagtag 104280
aaaattaaaa gaagctcttg atagagtagg ctatacaatt tagatagtga ggttagagta 104340
atggcagatg agattagttt aaatccaata caagatgcta agccaattga cgatatagta 104400
gatatcatga catacttaaa aaacgggaaa gtactgagag ttaaacaaga caaccaagga 104460
gatatccttg ttagaatgag tccagggaaa cacaaattta ctgaagtatc tagagactta 104520
gataaagaat cattctacta taaaagacat tgggttctct ataatgtatc tgttaactct 104580
cttataacat ttgatgttta tctagatgaa gaatattcag aaacaactaa ggttaagtat 104640
cctaaagata ctattgtaga atatacaaga gaagaccaag aaaaagatgt tgctatgatt 104700
aaagaaatac ttacagataa taatggtaat tatttctatg cacttacagg agaaacaatg 104760
ctctttgatg aaaataaatt aaataaagtt aaagattagg gttgacagct tctatagttt 104820
atgatatagt atatgtatac taaaaataaa ggagctaaca attatgttta tttcattaaa 104880
tcaagaagag aaagaattat taactaaaga ggaaagtaaa tacacaccac tagaaacatc 104940
aagagagttt aacacaccta aagaagaatt cattgtaaca agttataacg aaggtaaacc 105000
cttagattac attgcaaaag aagctaaggt aagtatggga ttaatttaca cagttctaaa 105060
ctactataaa gtaggtaagc gtaataagaa atcacctgta gaagaaagaa ttgcacatat 105120
cttaaaagat aaaaacttag tcaaagagat tattaaggat taccaatata tgaatttaca 105180
ggacatttat agtaaatata atcttcataa gaatggttta tattacatct tagatttata 105240
ccatgtagaa agaaaatctg aacttaagga caaagcatta gaagaggata atattgtcgt 105300
tgagtaagta aagaggttat aatatgagaa ataaaaaatc atttcaagag cagttaaatg 105360
acatgcgtaa taaagagaaa tgggtatctg aagaggagtt cactgaagaa gtggctcctt 105420
ctgaagaacc tgaagtagaa gaagaaaaac tatatacttt aaatgagtta aaagagaact 105480
tactagatgc tcaaggatta aaagatgttg tagctgattt tcctgcatct aaagatttat 105540
atgaacctaa taaactatat atttgtacaa taccaaaagg atatcgttct acagaagtac 105600
aaccaggtca atatattggt atcagtacag gattattatc agaatcagaa gattttagtc 105660
atttaagagg tcaaatgcct agaaatcttt atgaaacttc tcatgtttta aaacctttag 105720
tacgtattaa taatacaaat ctcgaatatc aacagcatga gttacttgaa gatattaaag 105780
atgacaagaa gatatacgat gttgaattag aagacctgag attagtaaca ggagaagaaa 105840
tatcccattt agaaattgtc gatagtaagt tttttgaaag tcgtattaat gaaattctag 105900
accgctatac tgaattaacg gattccgatg atttgcttat atactatagt aaattacgag 105960
aattagttgg tagtgacaaa atgatttatt gttcactttt agataaatgt gttaaaatta 106020
tagattaata gttagtctcc tcttatatta taactgtaag aggagacatt tttgtataga 106080
ggtgttaatt atgtcaagaa aagcaagtat attctatata ctagtggtta ttgttttggc 106140
tttttctatt tcatcttatt atatatcttc tttcatgtat cacgacaaag caaagaatga 106200
agtctctact gagttatcaa acacgggaaa gattaaagaa gaaaagaacg tagaatttgt 106260
cggtgactat acacttaaaa aagtggaaaa taataaagct tattttatgg aaacattacc 106320
tacttaccta cccggtagaa caggagataa cagcatagat atgaggtact acaaaacaag 106380
tagatttaaa gaaggggtaa atttcaagct tattagggta tatactgaag atggggaaga 106440
taatccaatt cataagtata ggtttgaagc agtaccaacc aaaaagtaat aaggaggtga 106500
cttaaatgac aacattaatt gtcgtcatct ttattgctat catttattac ttatggaaca 106560
gtgattgagt caagttaatt cttgactctc tttttgtttt atggtatatt aatatataga 106620
aaggagagat taattatgga aatggcagat ttagaaagat tcgatacgtt tgtaagatta 106680
gtttcagatg atgagctttc ggaggagaga gcattagaat taagtgtaga cttattaaat 106740
ccgatactag aaggaggtac agcttaccaa gctaaaaaac gcattagaag taagttcggt 106800
aaaatagaag caaaaaactt taaaagaaat tataaattct tactcaagtc gatagctcaa 106860
atagaccaaa ggagatagga caatgataga aagggaaaag ttagttaaag aaattgaaga 106920
tgctaataga gacatacaat tgaggttaaa agaagtagat gattataagg atagtatacg 106980
ttctaaagga acaagaaact atgtatctac taaggtatta gattcagtta tggtagggct 107040
aattataagt ttctttattc ttgtaatgtt acgtgtactt gaatattttg taacaggtaa 107100
tgctgtttat tcacctttag cacccgcagt tattattatg tttgttttag ccttaggtac 107160
atggaaagta agtaaaatga ataaaatagt atcctatagg ggaactatta agatgtactg 107220
ggaattaagt aatgctgaac agaaccaagc taaggtattt aagtatccta atgatgaagt 107280
agatattgta tcaaaacata acttaagaca aataactttt agtgagatta atatacttca 107340
tcttaaatat atgagatata ataaggcagt agaacagcat actaagttat ctaaagaact 107400
ttttaaaaaa gataaagaaa ctgttgacaa gaataaataa gtgtagtata gtattactaa 107460
aggaggagag atattatggt tatacctagt attaaagcac aaaacaaatt caagaatgaa 107520
ttagagtatt ataagcaagg tcacattagt gaaagtaaaa tgttagaatt agcttttgat 107580
tacattcaag aattagaaca aaataatgaa tacgttacta atttgctaga agaggagaga 107640
tacggtgagt aaatttattg gagtgtactt atttaattta ttagtagtag cactaattta 107700
cacagtagga tttttattct tttatggtgt agctagctta gttattattt taactcatgc 107760
tactattgac ccgttcgtat tagctacttt cttaggaata ggattcttag ttattagaac 107820
tgcacacaga atcatggcac gagtaattaa tgatgcagta gctaaagcta ttaaggataa 107880
agaaaatgaa taaaggggaa tttattatgg ataaaacatt accaaagttt agtgtatatg 107940
aagttattgt aaagactgta attatgacac caacagaagg aagttctgac ctagaatcat 108000
tttacttttc aactagagag ttagcagaaa gatttgttga agaaaataca gtggaaacaa 108060
aaaacggtaa acgtgtatct tttgctgtta aagaacgtaa agtaaatcaa ccaggctaac 108120
attaatttgt tagctttttt tattgacaaa tcattttata tagtgtatag taatattata 108180
cagaaaagga ggaattatta tgaaagtttc agaagaagta aaacagagtt atctagagaa 108240
tagagctaat actaaaatgg ataagataag ttggtctgag ttaaggtcta gtcctttagg 108300
tattacctta ggtgatatta tattttatag tgtggttatt atagataaca ttatagctat 108360
tattttaact ttaaccttaa taggtactat tactgactca attgagagta ctttagccca 108420
aataatcgta gggatgttca taatcattac tatatatgga atcctatcag cgttaatacc 108480
tattctagtt cataaagctg tatcaccggg atggagctat actgaatgga atgaatccta 108540
ttacatcaga ttacctggag aagagaacta caagtactat agtaaatggt atttagattt 108600
attaggagtt aaagaatttt actataagag agacaatgga gaagaagtaa aagaaaaaat 108660
atatcatggg cttttcaagc tgaagtaaaa agacctgaag atgttaacca ctggaaaaac 108720
caattgctta ctaatagacc tttaacaatt ttagaatata aaaaattaaa gaaattagat 108780
aaggaaagtg aaattaggaa acaagaagat ttagaagaat ataaacaata caatagtaat 108840
taaagaggtg gaaagcaatg ataagctcat ttgatagtat actacttgtc atatacatta 108900
ttatagcttt tgcagtagct atggcaatta tctacttagt atttaaaggt atgactattc 108960
tactagataa gctaatgatg ttattattaa gtaaaactac attagatgta gaagcttgct 109020
ctatgataat ggcagtcatc agtacaattg tgtttggaat tattgtactt ttaatatggc 109080
tagcagtaaa taatatttta ctataaggag atttactatg gattttaatg actttataaa 109140
cagtgaatcg gatagggtag gtaagcctaa acaaaagaag aaggtagaga ataagctacc 109200
ttcttctact cctattgaag ataaggaaaa gaaattaaaa gagataagaa agaaatcatt 109260
atatattgat ttaaggagaa aaagaaatga ctaaagaaac aaatgtactt tacaaagata 109320
agtatagaga ttatactata gttgtaagat tagcagggaa tattattgtt actgaagtag 109380
ataagaaaca taaaacagca tttacaccta ttatatttga caatggtgta gaaggcgtag 109440
agcttgtaat gcgtataggt tctgtagagc ttagcatgac agatttacgt gagttcacaa 109500
aggaagtatc tacagctcag aaagctttag aatattttaa taaaaaactt tatattaaag 109560

```
gcttgacaga tgaagcattt taatatatac taaaagtata aataaaataa agaaaagagg 109620
aatgattatt atgttattag gaattttatg gtttatatgg ggatttgtat cgtactttgt 109680
attgatgttt ggaattgagt tttggaaaga tagatggatg ccaggtgtta tcggagcagg 109740
agctttacta ctattcttat tttggattat gaaatctatt cataatgcta tgacagtagt 109800
atacttgtat taggaggttg tatagatgat tgatatacta gttattcact atgaagaaac 109860
aaataaacgg gttttaaaag aaacaataca aacaatacaa aatcatttaa atgatgaaca 109920
tggtttggtt aagatgacag caacaaaact tagcagagag aatatagaga aaagatttaa 109980
taactataat atagtcattg cagaagatga ccctgataat tcttatcatt acggtgaagc 110040
tgtagaagac gcagatttta ttatagacat accaatttca tatttagata tacatgcagg 110100
aatagaatgg gatgttgata atcctgtaga tatgctagat aggaatcctg attttataga 110160
agctgtaaat aaactaaatg aagacttaat gttataagga ggaaatagaa tgctaaatga 110220
aaaactaaaa aacctggaag atacaaaagt atacatgatt aatagtattg caagtttact 110280
aagcgcaagt acaggaaaat caagtaaagt attttttgat gaaggaacta ttaaaattgt 110340
aagtggtgaa acaaaagcag tagaagttat tgataactta gttcaccctc actcaggacg 110400
tttacctatt aaaacaacag aacgtattgc gctaggtaga ttaacagatt ctttacagtt 110460
tgttatctca gaaatagaag tagttaaaga ccaaattata gatgaagaaa atgaagctta 110520
cattgatttt gtgatggaag actggaactg ggattaatgc ctatggactt attaactatt 110580
gcttctgttg cttttatagc tgtagtcatt attgatttga ttaatgatga tatgagctat 110640
atgcttactg gtactgcaat cttaataaat atttgggcgg gattttatgg atggtttttc 110700
ttactacaag caggtatgtt acttttctta ttattagcta ggaaggttaa agatgataag 110760
gagtcaatac tatattccag tgcttcatta atatgtgcac taggaatgat aataaatctt 110820
ctttcatttt cttaaaaata agtattgaca cctttgtact tttgtattat acttagtata 110880
taacaagtac aggagatgat taatatgagt aaagaaacaa tcagaagaca attttcaaat 110940
gcaattgaga ttatggcaac aactaaagaa tggtggaact tccctaaaag ttttgatacg 111000
aataaagaat ttaaaattaa aacttttaaa aatgatacac ttgtatttga agttagagaa 111060
ggtagtagaa acttaggaag ctttgtagtt tttacaaaca ttgattttga ttatgataaa 111120
ctagaaggaa cttcaacaca atatatgatt aattactttg ctaagaaatt aactaaagat 111180
atgtttaact atcataagtt acaattatag taggaggtgg aaagatgaga gaagagttaa 111240
aacctttaa taggaaacaa gttaatgtta aagggtattt agatgatgtt aagtactcaa 111300
agcgtagaag acataagggt aatcaacatg ggtgtgttaa aatcacagtt actgatgtaa 111360
agattaatgg tatacctatt gaccacgtta acattgaagt tggtatctct ttctatgaaa 111420
aactaaagga gcttcaagga aagagaatcc aatttgtagg cactgtttac aagtatgtta 111480
aacatgctag agggcgcaaa ggtagaatta aaggatttta taaagaggat tatagcgtaa 111540
ctttagataa gaagttacaa aaggaggaaa aataatgact gaatggtatg ctttatgcta 111600
ttatgataaa gtaggtaaaa agaaaatacc taggcaagtt agagcgcaca gagatatttc 111660
agtattagaa gaattaaaag aaagattaga agaaagaaat cctaatacag aatactctat 111720
aaaaacaaca aaagaatttg atgaggagag ataaggatgt taacaccaca acaaaaagat 111780
tcattaaaag aacaacaaaa gaaattaagt aaaaagaaga aataactgtt gacaaatgag 111840
tgtgcatagg ttatacttaa gttaacaaat aaagaggagg tatgacctat gttattcata 111900
```

atttttattc tagcagtatt ctttgtacta ggatttatta acggatggaa ctcagaagac 111960
taaaaaagga gtggttatag tgaagttaga agataaagta ttagaaagaa ttgattctct 112020
tggaggtaag ttaggtgata ttagccaaca tgcttgggaa gctttagtaa agtaccaaat 112080
tatatatggt attatagacc ttatagtagg tattgtagtt atagcattaa ctttattttt 112140
atggaaggta tttattaatc aacataagaa ggtaaatgat atggatagag atgatgatta 112200
tagtttacta tttgaagatt gtgaagattt atcaggcata ggtttgtttt atgtaatagt 112260
tacatcatta atatcactat ttgcatttat atacttaatc tatggaatac ctatggatat 112320
tataaagata ttaaaccctg aagtatttgc agtaaaagac ttaatagaac aagctaaagg 112380
aggaaattaa tatgaaacaa agagatttcg aatttgaaga ggattttgta ttaacttatg 112440
aatgtgagga ttgcaaacat ttcgaggatt ggggtcatga tgaagagcct gaagaatgca 112500
gtgaatgtgg tagtagtgac ttaattaaca atacaagtca tgaagacact gagtgtgata 112560
tgtgtaaagg atacattgat atgtggcaag atggttatag atacatggga gataataaag 112620
cataccttga aaaagaagat tcaggtttaa tttgtgaaga ttgctatgag aaattagata 112680
tttaataagg aggaatttat atgaataaag cagtagaaca agcaagtaac gcagtaggtc 112740
aaggattttc agccatggta tggcatcaag tattagtagg tctagggttt attttattag 112800
ggttgatatt atccttacta gtttgggtac tagtgaaaaa atttcatgta ccttttaatc 112860
acccaacagc ttttgttgta tattcaatta tgttagttag tattgttgct agttttattt 112920
ggggcggttt acatgtaatt aaccccgagt attacgctat cttagaactt aaaggtttta 112980
taaagtagga ggaattctat gactaaagaa gagttagagc aaagagtaaa agaacttgaa 113040
gcagagaata aagaacttaa aaaacaaata gaacgttttg aagacgaggg aggaaaaaca 113100
aaagatgaat agtagacaaa agaaaatttt aacattaaca gtaagtaact ttttaattct 113160
agccttagat actgtagcac taattagata taaaaaaggt aaaattaaac aagagaatta 113220
taacacaggg caaattacaa gaatgatagc tacaacagct aactcattag gtattcttta 113280
cttagaagag caagagcgta aagaagttaa agatattaaa gtaggtactt ttgaaattgg 113340
agccttaaaa agatttacaa ataataaata aaaaaagttt aagaaaccta ttgacattag 113400
gtttctttta ttatatacta atattataag aaataaggag gttaacttat gaaaggtatt 113460
atcatatttt acaaggaaga gaccaaagag gatttaggat attttcttgg gtttataaac 113520
tttaagctag aaggattatc ttacacaact gaaggtactt tagtagataa tgatgtagta 113580
gttttaaagg ataaccaaat taatgaggat aatttagagc agtttagtat gtcaaacaat 113640
aatttagtta ttggaatact aggtcattca tctctttcag tacgcatcta tgaaaaaggt 113700
attagacaag agtttgatag agtagaagaa tatttagagg agttgagaca ataatgatat 113760
ttatattaat ttttggttta ctatttattt tatctttact aggtattttt atttattcta 113820
tagttttacg aaagaaaaaa caattaatag aagaaagaga atcatttggt atttataata 113880
gaacaaaaga aaaactgggt gatgtaacac gtttagggta tgaggaagat gtatataagt 113940
taatccataa ccaatctaat aaaacaatca tagaggataa aaagagtaaa gttgtagata 114000
caattaaaaa gatgtatgaa ttagaattaa catctgtaga tgtttctaag gtagaaggat 114060
tatctccact tgatacagaa cctatgacaa atatgaaatt actttcatat aagctagata 114120
gagaaggatt atatagttta agtaaattta tttaggagtg atacaatgga atttatagat 114180
aaaaataatg taattaaagc ttatgatata ccaaatgttt atttaaaagg ttatgtatta 114240
caggcatgtg ataaaaatgg agatacaaca gcttatgatg gttatgacca aatacactat 114300

-continued aaagaaggta gagtattaac attccctttt gataaaccat taagaaagat aaatgtacta 114360
tcaggatatt acaaactatt taaaaaggag gacataatat gatttatttt gttagtgatt 114420
tacatttcgg tcatgataat attagagaat tcgaagcacc tacaagaagt cactggaact 114480
cagtagaaga aatgaatgaa ggtttaattg agttgtggaa taatacaatt acaaataacg 114540
atattgttta taacattgga gacttctttt tcaatatgaa accttctaaa gtagaagata 114600
tacttaatag actaaattat aaagagatga tactgattgc aggtaaccat gaccataaga 114660
aacttataaa actatatgaa cgtaatggta ttacagtaaa gtacgcagac atgattaaaa 114720
aggatggtaa gagattttat ctaagccatt atcctacact aataggtaga aaaaacatgt 114780
ttaatattca tggtcatata cactcacaat taatgggtac tgaatatcac atcaatgtag 114840
gttatgatgt agagggtaaa attgcctata gttttgatga tattataagt agagcaggtg 114900
aatataatgg agaaattcaa aggtaaagat ttatataaaa ctagaattag aaaacaaaca 114960
attaaaaatt tagttataaa aacagagaag ctacataata aacacggaaa gtatagacct 115020
attggtcatg tttattatta tccaaaaaca aaagagttta ctttatctaa acctgagcag 115080
aaaatattta tagagtatat gaaggcatta ggttttagtg ttaaacataa gagacgtaag 115140
aaaataatta tagtatacaa gaatgtgtta gatgaatatc ttagtatgta tcaggaagca 115200
attgaaagta cgtgttgaca attaaggtat actatgctat agtatagaaa aggaggttaa 115260
ctgatgaagc attttatttt gattttaggt attgtaattc tagttattgc attaggtatt 115320
gttttacctg catggatttt acaattagta ttatctgcat tcggtgttaa agtaagtatt 115380
tgggtatgta tcgggatatt tattttaatc agtgcagtag gaagtatgtt tagtagaaat 115440
taaaggagga actataaatg gcaaaatatg aatcaaatat caatggagaa aattatattg 115500
caacaccgtc acaagcttta agagaggcat tggcagaatt aattagagaa gaaaagaatt 115560
ttgcagagta tcaaactaag ggtgaggaac agtatgaatc acagttacaa ctaagacact 115620
ttgattcaat gatttctcag tatgaagagg ctattcgagt actagaggat agatattcac 115680
ctcagatttt tattccaaaa gataataagg aggaaaagta attatgaaag cagaatcaat 115740
agcaagattt tttcaggata aggtattaca aatagaaggg tataaagtaa gattcactca 115800
agctagttca tcatatattt tagatataga tactatggat gaatcagtat tgtttttaga 115860
tactgtagtt ttcactctat caggcaagta cttattagat acgcacatta caattaataa 115920
acctgagaca ctaagttcta atgaattata cacagagatt agtaataaac tacaagagat 115980
tgtaggagac caaactaaaa cagatataga gttatcaaaa tactttaagg aggtaaaata 116040
aatgagttca gaagctatta caaatcattt attaaattta aatcaaataa aaattaaaga 116100
atataatatt catgcttaca ttaaaaaatc tgtttgttcc ggtattgaaa atgcagattt 116160
tgaagtaaga ataaactata tagcagacaa agaccctaac tatattagaa ctattaattc 116220
tattattttt gttgattaca gtaaccgtaa tccaaaagaa attttactac agtttaaaga 116280
aaaaattctt tctattgtaa aagaacaggt agagattgat aatgatttta ttgaggctat 116340
taaagatatt aatacaaatc atgaactaga gaaattagaa ccttttatta ataaagaata 116400
ctattctatg tttaagtcat ctattgaaaa agaggtacca gtagctttat catctgaagt 116460
acttaataga tgtacaggta aaacaagcac actagcttat ttagctattg aaaaggattt 116520
acctttaatt gtgtctaaca attctatgat gaaaatgctt aaaaaagatt acccttctgt 116580
taaagtttcg tctgttgaag atttctcaaa ctataatatt aaaggtgaaa ttgtacttat 116640
agatgaagta gatgtagacc agttatatag tgcagataga gtttctgttg atgcactact 116700
agtaggtatc ataaaaaatt aaataaattt gtaaatacct gttgacagca ggtatttttt 116760
atagtatact ttagatgtaa agaaaaagga ggtagtaata tggttggtat tataatttta 116820
attgtcggtt taatattatt tttagctagt ggatataaat tagttttagg taaatattat 116880
gatgacatag atttaaagat gttatttaca atctttggta ttggtgctat actattactt 116940
acaggattta tattataaag gaggaaatta caaatgaact ataaagaagt actagaagtt 117000
attaaaaaga ataagccatg taaggttaga tttactggaa gtattttagc aatcgttaat 117060
aaggaattta atgcagatac tgataaaggt atactacaaa ttgatgtatc aaatattaat 117120
aaaaatgact acattaagtt acaacagtat tgtttagaaa gagatgatta tactgtagca 117180
ggagctattt tattttaagg aggagtaatt atgaattata gagattttat tacggattgt 117240
attagttgtg gttataaagt ccacattagt gttactgaga aaagagttca cattatttca 117300
gaaatgacat cagcatctta tccaaagaaa gaaattaatt tggatgaatt acaagcttat 117360
gtttattata tgaataattt tggaagtcag attacaacgg agggattata aatggaatta 117420
gttattaata ttatagcagt attaattggt atgtatggta tttactttta tgttacaaaa 117480
tttagtactg gtctatcagg tatcttaatt gtactaggta tggctgtagg tctttacttt 117540
tacttagatt acttaaatgt tagagagaat gttattcgat tagtatctgt aatgtttggt 117600
gctttcttat ttagtatcga gatgatttat aataagatta tgtttgaaat taaaaaatct 117660
aagtatgata agactgttag aacgtacaga ggagaccaat aagaatttta ctataaagag 117720
tacttaaaat aggttaagtg ccctatatgg taccttaaaa tggcttagaa ttgaaattaa 117780
ggagatgaaa agttattata gctactaaat atattgtatc tattgaacga tggtaaataa 117840
ggaggagtag ttatgaatgc taggaaagca cgtaagaaca ctaaaaatca taaagactct 117900
agtgtagtaa ctaaggagca acacctaact tatatctata ataagataaa ctacttgatt 117960
gcaaatagta gtagtcaggg taagacatat gtggtaatga acctaagaac aggttatcct 118020
gacgagttct ctttatctaa attaaaatat ctaaaagaaa ttaaacagca ctataaagac 118080
ctaggattta ccgtacaaac tcaagtaaga aagtcacggt ggtcagagaa aagtataatc 118140
aggtactact ttaacttagg ttatatagat agcgtgttag ttcctattat acacattagt 118200
tggtaattac aaggaggaat agttatggat aatccaaact taaataaaaa gacactgaga 118260
gctgtaataa gagaaatgga taaagatata gaagaaagag cagaagcatt aagaagagaa 118320
gagactagat taagtattgc tagggataat agaaaaaggc tttacattga attagagtct 118380
atactagagg aggaataatt atggatttta atttgaaaga ctatgctgta agacctataa 118440
cagacaaaga aggaaatatg gtagtaagaa cagtgtatgt gtgtttaaag agagaataca 118500
gtgattgggt agtagataaa gtatatggta gacaagagag ttctgaaacg tggttaaaat 118560
ttatgcaaga aattagaaac atagagagag caaaactaag agtggagaaa tggcaagtta 118620
attagaataa ttagttaaag gagggaaaga tatgagttta tcagaattat tagagtatca 118680
taaaaatagt ggtaaggaac gagcagagta tataagtgat aatggtaatt gtagagtagc 118740
tattatgcat tatgataaat gggcagttgt aggagattta gagaatgcag tctttacaat 118800
tgagaagtaa tagttatgta cttatttgct aaaataatta ttatatctat tgatgttata 118860
cccttaatgt ctattattgt tgtacagtta attacagatt ataatgatag acattaagta 118920
tcgaatattg ttgactagta agaagaagaa aatattacta ttaagaagtt aaagttaccc 118980
gggaatattg ttgactaaca ataataagaa gaaaaaaata ttattactat taagtacctg 119040

```
ggaattcttt tacctctccc actcagccta ttacttacta ccgacttccc taactactta 119100
ttctatagtt atagtattca tttattatac aatacttaaa ctatagtatt ctaaccttaa 119160
tctatgctga agcggtatta atctattgtt attatataat aatcttatct aatagtggta 119220
taatctaggt tattacatta gaatgattct aatctagtat tttaatcttt agaccctagg 119280
aaaagtggta ctaaaatata gaaccctata ggtacgggat tcttattttt aaaattacta 119340
aaaagtatta ggttttccct agggtaaagt tttaatgtac ttaaaatcgt aagtagctcc 119400
ttatcattta ggtctgttta attgagaata ttagaagata tccgcttcaa ttacaattaa 119460
gtgttgacaa tcatgaagcg gtatgttata cttagtatat aaattaatag gagatgaatt 119520
aaatgattat accattaatt atactcatga tgaccttcgg tacatttgca ttcagttatg 119580
ttgcacatga tgcatacagg gtagatgaaa aaggtatcat gtatgctatg gtagttggta 119640
ttgtagttat aaatgtaatt ggtttagaaa tgataattgt agaatgttta tagaggagat 119700
gatttaatat gattgatatt tatttacaca gtgaatatga taaagataag ttaaaattta 119760
tccttaaagc aataagggat ttttctccta gagaattaac ctacgatttt aggaatccaa 119820
aagcggatgt tagtatccag gaactactag gagatgacat agacatattt gaatctatag 119880
cattagatta ccctaatgat attaatatcc ttgtaggaga tagtggatac tcgatagttt 119940
atcagaatga ttttcttaca attagtggat tgagtacggc tatgaaggag gtaataggat 120000
gataggattc acaatattaa gtacaataat ggttatctta gttatagcta tgtacactca 120060
ggtgttagta gatatgattc agtcaatcag gtatgataga tttgataagg tacttaacat 120120
agtaacgttt atagttatga cagttgtact agtatcaggt attttaatta tgtttgacat 120180
ttagagctta tttaagaagc ggttaagtag ttaaggataa attggtctag aaatatacta 120240
ccgcttctct atggctcttt aaataggctt agaattgaaa ggagatggaa taatgaaagc 120300
aattgtatat tgtgctaaaa gatatagtaa gcatacactg aagcatattt tagaggaatt 120360
agaagcggag aatagtgact taacatttag tacagaaata tcagatttag gggaagtaga 120420
tattgttgta caacatacta aattaccttt ctcagaacta atggatttgt gtagtaaagt 120480
aagtaaaggg tctgaccgct tctatgtatt tgttggtaat cactcagggt attatataaa 120540
cggtgattta tatatcaacg agataggtaa gtttattaca tctagagaaa ctaatgttat 120600
gatgtagagg aggagatatt atgatagaaa ttagattagt tgaaggctat gataaaagtc 120660
agttgaagtt tatgttaaag aaaattaaga gagtagcacc tagggaatta acttatgata 120720
tagaagcggg gatagattcg gtagatgtta atattgaaga tgtacttcct cataaatcac 120780
cccaggagta tgaaagatat tcaatgttac ttgaagaaga cttatggata gttatacttg 120840
agtcaggtta tatagcttac tgggatggaa agaagtatgg tggtgaagct ttagatgata 120900
ttatatataa tatgtttaaa gggagaggga gactataatg atagaagtat ttttaagtaa 120960
agattatgat aaggatttac tcaaagctta tttagagtat attagaaagt ccgcttcaag 121020
agagttaaag tataatacta accatactaa aggaacggat gttaatattg aaaatattat 121080
tagttatact aatcaagagg ttcatcattt tagctcttac ggtatgtata gagatgactt 121140
atgtgtattc atagataata caagagtatc tgagtatctt aatggtgaac ctgtaggggt 121200
agatacaata tataaatata taaaggagat gtaatggatg tttaaagtat attatacagt 121260
ttatcataga caaagtatga agactattaa ggataagtta gatagaagcg gtttaatcta 121320
tttcttatat gaaacttggt ataaagatat aaataatgta tgtccttcta actataaccc 121380
```

ggaatttggt agtcttaata aagatataga catagataga ttaattgaag cggttaatga 121440
agaagggata ctacttatta accatggtaa ttatgttaca gtagaagagt ggtaggatgt 121500
tgacaaatca taagtagtgt ggtatgatta aggtagaaat tttacgataa actcgtagga 121560
taaaaccgta ggataaaaaa ggaggataga atatgataga tattgagata aaaatttggg 121620
atgaaaccct taggatgcag gttgaagaag aggatgtact ttccttctta tctaagttta 121680
aaaataaaac aacaggtgat aaagaagaat cttatggagt agggttagat gaatctaaat 121740
ggaaagtaca cccattctat acacgttatg aggtacaccc tgaaggatac gttaggttga 121800
aggatactaa aacacctgta atatttacta agtatagaaa agaacttcac cataaaccac 121860
agtttattag ctctaatata atggatgatg aaggtaagca tacagtagct ctacataagt 121920
tagttgctga tacatttata cctattccat ggtatttaca gggatataac tatacagatt 121980
tatcagtagg cttgaaggat ggagattatg aaaataaaga agcggttaaa gcatataact 122040
tagcttggta tgtaggaagg atacgaggta atgctccaat gattaaactt atggacttag 122100
aagatgatag agtattatac tttgctagta ttcctcaaat agagaacttt attagagata 122160
ataaattaga ccctaaacgt tttaattaca aaactgaata aatgataagt agagagggct 122220
taagtagtcc tcttttattt aggttagaat aattagtaag tagctcctcg taatactaag 122280
tagttcctga ttttttgata tagttgtaag tagtcccctg gtaatccccc cagtttatcc 122340
caaccgcttc aagcagaccg caataagaat ccccaggaat tatattccca gggatttcta 122400
taattttttt atttaattaa gatatgtttc aatatattct tcataaattg cacttgctaa 122460
atcattgtac ccgtcttttt gtttttcctc cattaaccaa ttgtaatcta cacttaaact 122520
gaataaataa tctttttctt ttacatcaat taaatttctt aattcattct caaagatatt 122580
aacttgatac acatagttta cttttttaa taggttgtgc acctctttat tcaattcttc 122640
tttagttccc tcaaatttaa attccattgt tatcaatcct tttcatttag ttgttaaggt 122700
gtttgattac cttacaaata ctattatatc agattgagga taaattgcaa taggtttttg 122760
aaactttttt aaattctttt tgtgttgact tgatcgacct ataacaacta tttagtaggc 122820
ttttttgaat atgtttttc tgtttcttcc attataaaca aaaaatagg tcataaaact 122880
ttttaaaaga atttgtaaat atgtattgac ttattaatca tatgatagta atataaaggt 122940
acagcaaggg aacagcaaca agatattaga attatataaa aaaattattt aattggagat 123000
gatttaaatg gatgtaaaag aaattgcaaa tactataatg gagttgtggc aaatggacgg 123060
ctacagatgt acagaaccac cattatatga aagcacatta aaccatacac gcacatatac 123120
ggctttaatc gtaagcatta aaggaaacta tgacactgtt caaatgttcc gcaaaacgcc 123180
tataatgagc atgagagggc aagcccaacc ggctagtatg ttagtaaatg taattgatga 123240
tgtgattata atcgtatatg aaaatgttgt ttacggggta cagaataaag aaataaaatt 123300
tattgaagaa atttaaaaat aggggttgca ataccctta agatgtagta atataataga 123360
tgtaagggat agcaacacac cttaaaaaac tttttaaaaa gttaaaaaaa gtgttgacac 123420
cttacaagat acatgttatt attagtatag aagttaagac aagccacata gcaaataacg 123480
aaattaaata aaaaaattat agaataggat ttgattatta tgacaaacaa aaattactta 123540
tatgaagaag ctcacacagt acaagggaac gaaattacgg ctttcagaat tccaaatgac 123600
gcaaacggca acccacgtta tgtagtgcat ttcatggatt taaatattaa actagcagac 123660
tatgacaaca tcaataaact ttacggattt aataaatatc gtgctaaatg gtttggcggt 123720
ggtgtagtat tccaaagcta taatatagaa gatacattaa attttgcact agataaagtt 123780
aaagaaatag aagcggttaa gaattaaaac cgcttctgaa ttaaataaaa aatttatata 123840
aaaaggatat gataatatga aatttaaaat agaaaaaaat aacagtgata taaaaacttt 123900
atggaattta gctaaaaatg gatatatgag ttatcaaact gtacacaata tatttaaaaa 123960
tgaatcagat gaatttatta tatttaacag taaacaaact tataataaat ttatggaatt 124020
aagatataat agaagtgcaa tccaatagta taaaaaaatt atacaattcc ctgggattaa 124080
attcctaggg atttttattt gttttaattt atataaaaaa attatttaat aaataagtta 124140
gtgtaaaatt gactattgac aaggttgtat tttttatggt ataatgaagt gaagaccttt 124200
tttagtataa aaaaattatt atataaaaaa tttatattaa atggttttaa agcgggtctt 124260
tctcccaacc ttgtcattta tatagcggaa gggttaggct ggttaccgct gttttacttt 124320
ctatatatag aatactatga ataatggtaa ttgtcaacac ctttcagaaa cttttttttac 124380 tttcttttat tattatataa aaaaattata catattttag ggctccactt ccattatata 124440
ataattcggt attaatgtca atagataaat gtaaaaaagt tttttaaatt aatttcatta 124500
aatccattga cttgtgtttc tttctatagt aatatatagg tataccaaca agggaggcaa 124560
tacaaatgct aaaattcaaa tggaaaaaca aaacaattaa atcaactcaa aaaacggata 124620
acattctatt acttattata ggtggtttag ttgcaacaat cacacctaaa cttgtaaact 124680
ggtttttact actacaagat aatataaata tttttttaag ataactattg acaacctaga 124740
aacaacatgt taatattaag ataacaaata aatcaataaa ggaaatgata aaaatgaaaa 124800
aaatcacaac aactttaaac ttaatcggca tgaaaaataa tgaaaggttt acagaagagt 124860
taaaaaacta ccgtcaagat gttactttct tgaaagcaaa taaaattgta aaatattcaa 124920
aataaggctt gacaacttaa acactacatg ttattattaa ggtacaaggt aagggaagcg 124980
gtcaaccgct tccaacctaa ataaaaaagt ttaaaaaaac tattgacagt cacttgaaac 125040
catgatatta ttaagataac aaaaaacaaa cagaaaagga attgattata atgaaattta 125100
tcaaaactat cgaaaactta ttaactaaag cagaaaacaa agggcaagca attttaaacg 125160
gtcgttatta tgacggatat agaaacggtg agcttgaaga aaaatacgca atcgaaattg 125220
agggaaacaa attagttatg cgtcactggg gaacacaaac aattgagatt gacttaggta 125280
tgaaagaaat tgtttcatac tatggagaaa gcaactcaga ccgtgacagt ttaaacacac 125340
ttgtatattg cttaggaatt gcgccaaact ttagatactt accaagcaaa gacttattta 125400
tttacgaaaa ttaattaaat aaagggcttg acttccaagc cctaccatgt tattattaaa 125460
ttgtaaggta atcaagcaca acgacaaaat aaactgaaaa ggaattgatg aaaatgttca 125520
aattacaaaa taaagtggaa attatcgtac ctaaatatac taatagtggt aaagagattt 125580
caagccctgc aattaaagaa gcggttaaca atgcaactaa aatatgtgga ggttgtacga 125640
taactgaaat caagggacaa tggtggtcag acgatgaaca acgtattatg gaagatgaca 125700
acttaaatct tgagtggtac tatgacaaag gtatgcaaga catgaacgac caacaagggt 125760
tattacaagc cttatcaaag attgctagac aattgattgt attctatgaa caagaggcaa 125820
tcagtataaa aattaatggt acactatata ttatagatta tgaagattta gatttattat 125880
cttatgactt atatgaatta atgtttaaaa attaaataaa aattttatat aaaccgcttc 125940
ggattaaatt cttgaagcgg ttttttatgt aaaatttatg cttgacaaat gtattaaaaa 126000
atgagataat agagtgacaa cttttttttag tataaaaata atattatata aaaaagttat 126060
agagttttta aggctccaag tccattatat caattttact actggttgtc aatactttct 126120

```
tttttatat aataatttaa ttatcttaaa gataccgtcc acctccatta tctcaaattt 126180
tgcccccaaa gtcaagaact ttctttcaaa taatttattt aaaaaagttt ataaaaaggg 126240
ttgacttatt ttgtactata gtgtaatata taaagtgtag taaggaagcg gaggaaataa 126300
cctaaaaaaa gaatttaaaa aacttttaaa aaggtgttga caaacttcca aatacatgat 126360
aatattaaga tagttagaaa aacaaaaaac gaaaaggaat tgataattat gaacagatta 126420
gaaatagtaa aagatacggc aatggaatat atccttatga tggataacag tgttatggac 126480
ggcgttatga cacaagagga atacaacgaa gcggttagct ttgaaaaggt gtatgactat 126540
actctatcag aagcaaatca agaatgtaaa ttcttaggtg gtaaggtttt aactttccta 126600
gtacatgaag caatcgaaga atacgcataa aaaaacttaa taaaaggggt tgaatgtcaa 126660
cccctaccat gttaatatta atatatacca aatgagagga attgataatt atgagatacg 126720
aaatcgtaac attagttaat ggagaattat tcatgtttgc aacatttaag aaagcagagg 126780
cagaaaataa atatcaagaa tggtgtgact tgtacggtca agaaaatgtg agcatggaaa 126840
aaaattaaaa taagcggttg acaaactaac cgcttcatgg taatattaaa ctatactaaa 126900
gaaaaggaaa tgattacaat gacaaaaaca atcaaacaat tagaaagcca acttgaaaga 126960
ctagaaagaa aatcagatga gcaactagca aacggatatt atgaagcctt tgaaagaact 127020
tgcgcacaaa ttagagaatt agacctacaa atcgaattaa aaaagaattc agaaactgtt 127080
taaaaaaatt aaataagggg ttgacactta accccttaga tgttattatt aatacataag 127140
gtaaaacaaa taaaggagga aaacaaaatg atgatttgga tattgatttt tatggtaatc 127200
ccttttgtac ttggattcat taacggttgg aactcagaag aagaaaatta aaaaaagtgt 127260
tgacacttta aaaaatacat gttaatataa atatatacta aagaaaagga attgataaaa 127320
atgaaattat taaacagaga caatgaaatc gtaattagca tagcaacatt agagagcgta 127380
aaacaagcct taatttggga atacatcgac cacatagata ataacatcct agacagtgaa 127440
atctatgacc aagaagcggt tgtcgttact tctaagactc tacaatcaat aaaatttgca 127500
gacactatgg aagacctgca ggaatacatt gcagatatca attggaaatt agtttaaaaa 127560
agttttaaat aactgttgac accttagcaa atagatggta atataagagt ataaagaaaa 127620
acaaaaaaac gaaaaggatt tgattataat gacaaacaca ataaaaggat ttttacaaac 127680
agaagaagca agcacagtta aggacgtagc aactcacgga gtacaaagcg gagcaattgg 127740
cagattaatc tatacatcgg acgtagtaaa attctttgat agacattatt cagatattga 127800
agcggtagta ttagacttct tagaaggctt tacaggtcaa agatactatg acctattaga 127860
ttatgacttg atgagagaac tcgaagagca tgcaaatgta gagtttgaag acgaagacga 127920
atataataat attcaatttg acttagcaga aaatattgct tctgatgaga ttgaaggatt 127980
cgaagacatg gacgaagccg agcaggcgga tgcagttatc gaagctatgg acgatgtaga 128040
attagagata ctagacacgg ataaggtgca gtttgttaac ttagcagttg agattgtagc 128100
acaacaaatg caagaagcat aagaccctgc aggaagcaca cagagacaca cagagaagct 128160
taaccgcttc tctaatataa aactattagg agatgttgaa catgacaatt aaagagatta 128220
taaaccaatt acaagcagta gaaaataagg aacttgaact attcgtatgt gacaaggaag 128280
gaaataacat ttcaattaaa gatattactt tgtttgatag tgaagcggag cacacagaaa 128340
acaacccatt agggattaac tattaggagg tttataattg aacattagag aggttcataa 128400
tgtcgttaag agtgcaaaga gcaaactcct acaggagcag aataatatta ataatgtaat 128460
gatagatgac tacatcacag aagagcttca cagacgcaca cagagaagcg gaacaataca 128520
```

gatgaacaat aacaccgctt catatagtaa tggctcatat ggtagcttag aagagattag 128580
agaagcttat gacctatctt cattatctac taatgagatt aaagaactgc ttgaaacatt 128640
tgtttaaatt attttatcaa aacgctttac aactatttaa tttgtatgat ataatgaact 128700
taacaaatta aaagaaaagg aaatgatgaa catgagagac ttacaagaaa gaaaaagaga 128760
attgaaaaca ttactattta acttagctat agagaagaac agagcaactg acgagacact 128820
aagaagtgta ttagaagaag cccatcaaga ggtaggaaac caactaagaa aagtaagaaa 128880
agaaattgaa attttagttg aagaaaaaga aagagaattt tggaacgatt tcgactttaa 128940
tggattagac taagagggaa taaaatccct cttttatttt tatcctatta tataattttt 129000
ttatattata cgggggcagg ggtaaaatgc cactcaatgg gggtgggtct atataccccct 129060
atggtctacc caggtactta ttttttgggg aaaattatga aaataaatat tctaaaagtc 129120
aacaccccccc tattataagt caacattaca accctaccct ataagtcaac aatttataat 129180
ataaatagat agcccttaaa tataaagtca acatatctaa aataaaaaag ccacccctttt 129240
aggagtgact tagtgtttta atattttatt tcttctccta aaatgagttt gttttgataa 129300
ctacctaatc ttgtatatat cttactatta gggtctgatg aatttatact atttgtgcta 129360
ccataagcta tacaactatc taaccacata tgactacctg atgaagtttg gaaatctttg 129420
ccttggtaac tttcgaaagc ggtacatcct aaattccaag attctgtacc ttcatttaca 129480
tctgcgacat taccgccatc atttctagca taaataccgt ttactcgtat agctttaaga 129540
ccatcatgag ttgtggaacc attatttgat ttagtacctg ctgttccttt ttcgaatcca 129600
ttttctaaag ctgtacaatt aatttcaata actaaaggtt tagagctatc tgcacctata 129660
tgataattaa atccatccat atagttatta ttagctacac tattattgac gataacttct 129720
ttacctccaa caatttctaa accattacca ttgacttggg aagcatagct cagtacacag 129780
ttattaatat atacgctatt gtcttggttt aattcaaacc tagcaggtct agctccaccg 129840
tacagattta aattttcaat ataaaagtca gttggtacac tagatactat taggtgttgg 129900
gatgataata gcggtacaac ttttttgtta ggttctatgg aaccgttatt aacataaact 129960
tttgtaccat cagagtacca agaaaaaagt gtcgtatcta ctttatctaa ggaggtaaca 130020
tttgtaaact ccctatcatt attaaaatct actacccttc taacggcgga acgtgtaaat 130080
tcataagtgc tatctctacc tgatgtttta gtccaagttg gctcatctgc cataaataag 130140
tttacatttg agcccaaacc aataatatta atactcttat tacttattgg tggaagcaat 130200
gtgcctccta ctctaaagta atccccgtca ctaacataaa gtgtatcccc attatttatt 130260
atgccttgag cttttttaaa tgttttaaag gggttgatt gagaaagacc gtcattagta 130320
tcattaccat tttctccatc aacatagtaa gatttacctc ccctaagttt aaagttctcc 130380
atatttaaag aagtggaaaa cttacctaaa ccatctgtaa aaatattatt gacaagcggg 130440
tggtctttaa ttaagtaatc tacaggagtg aaaacaggta ttttatacga tgtttctttt 130500
ttcatagaaa ttttcatatt atcaatttct ttgattaatc ctttaatgaa ttcctcatta 130560
ttaactgttt gtattttctt agtagaagaa ccatcaaaaa gtagaaactg ttttatattt 130620
acaggtgaag taacttgtct tgtatctatt cttaaactaa ttttgcttga attttccggg 130680
atatttatat tattaattgc aaatgtcgtg tcatttattt tattaagttg agtaattgtt 130740
tgtatatatg aaccatcaga atcttgtatt gaatactcaa atgatgcttt cgggtcaggt 130800
acgtcatctg ttattatttt agcactaaat gttttacctg gtgcaagttt ttcaacagct 130860
ttaactgtgt aaaataacca accatttgaa ttaagtgtaa aagaaccatc ggggttcatg 130920
gtattttccg gtatactgtt tctaattgta atattagaga aatatgtttt atctactgtt 130980
gatgggtata aacgaatgtc ttctccatta tcagggtaca ctattaaact atcttccatt 131040
gttttattta cttcttgtaa attagagtca ctaggattaa caaaaactct caatgaatct 131100
aattgttctt cggtaaatct atcaaaagta aagtctttac ctggttcccc tgttttacct 131160
ggctctcctg gttttcctgg ctctcctggt tttcctggct ctcctggttc acctttaatg 131220
gacttaaccc attcttcttc tgtacctgta aaaccattat ctactgctat atcataagct 131280
gttttaggtt taacagttaa gatgtcttta gcataaaaag taatttcttt gtaagaagat 131340
tctaatgtag taaattcagg aactacagtt ttttccgact catagttatc cccttcccaa 131400
gaaacataaa actccccttg agggtactta gtatgaggtt ttaaatttgg tataataact 131460
gaaccttgct cagtatatac attataacct atggctagta tattgccttc tttatcataa 131520
gcttttaaat gtggcattta taaatctcct attctaatgt gttagtacat ataatatatc 131580
aaattgaata aaagaagagt attagttacc cttctttatg tttatatcgc agtctacgat 131640
attaagttca tgaatagtaa tcatatccat tccatcgaat cctcttgggt ctcctttaat 131700
gaactcttgt tctcctctat aattagtctc ttccctatac ccttcttctt taatacgttt 131760
aattaatttt tccttatttg tatatacatt gtcttctcta aaatgaaaat tatcttcata 131820
aggttcacaa ttatcatgtt ctacttgata tagtttcatt catttgtcct cctttactct 131880
ctataataat catatatttc taagtaaggt gaaaatggtg aatcacctct agtattaata 131940
ataacttcac cttcatgttt acttatctct gtaagctctt ctagactatt aatttctaca 132000
caccatcgtt ctagtgtaaa tggattacct ttttggtcta caagttctag tttctttata 132060
taggcaccct ctataggctt tttattaatg gtgcttgtcc tatctataaa aaattccatt 132120
agttttcctc cttttcataa gaccattcac catattctgc gttaaaatgg gctgtatccg 132180
taccctcgtc ttcatattct acactatacc atgcatcctc ttctgtttct gcatctatat 132240
atcttacttc ctctgtagta ataaatacgtt ttactttaaa tctctccata ttagttttcc 132300
tccttatatt ctttataact tttaataaca atcttacaga tacctctatt aacagctaaa 132360
aacaataaaa atgataacag agttataact gctctagtat ctcctgtgaa aggtaatact 132420
ttaaatagta aaacactttc taaaacactt gtagctgtga tagttgttag gtataagata 132480
gttagtaaat aatcttttaa ttttagctta acaaaaggtt ttttattatc ttgagttctt 132540
actataccat atagaattat aaaccattct acagttacga gcatagttat aaagtaatta 132600
tttatgtcta atgcatataa accataaatg atacctgcag gaataccaat aatgaatgct 132660
aaaaatacag agagtataat tagcattata agaagagcta caaggaatcc taagccttgt 132720
tttgagtact ctagtgtatt ctttcctatg gctttaaaga atgttttatt catctgctac 132780
ctccttgtaa tatacagtat ctatatggat aatattgtct ttgaaccata tagatgtatc 132840
acctttgtta gattctaaaa atttaacacc attaaaaaca agacccccga taaaagaatt 132900
taaattagtt ttagtatctt tttgctttat aatagtagaa gtccctgata catcatgaat 132960
ccttataaaa ttaatatctt tttttacttc ctcttcttta tgttttttaa atatcattat 133020
tcttcctcct ttatattctc ttctaatatt tgttttaacg tctgacaatc tttttggtct 133080
aaagtattcc aactttctag attttgtaat tgatagtgaa attcatttac aatttcatcg 133140
aaggcttctg ctttttggta gacttcttgt aactcttcta attctttttc attatcaata 133200
caccagtagt tctcgttgtc agttataata tcttgaattt tatttttata ttcataagcc 133260

```
attatttatc cctcctcttc tatagaatta ctttccgtaa tagttacctc tagcatgtta 133320
ttgtaatact cattcttttg attgatattg tagtagtcat tatattcatt aaagtctaca 133380
taagtgtatt catttgtatc atcatcataa ataatatcta tagctgtaat atctgagtat 133440
gctgtaatca tttcataagc atttgtatta tccggataag caaaaccaac ttgagatatt 133500
tctttagggt tatcaataag aataccaaaa taagtacatc tacgtgttcg acttatatgt 133560
gaagtaccat agtaatctat accttctgta attccatcta catggaacct tttacatctt 133620
ttaggttcta gtcttacaac atcacaattt tctaatacta aatcaatata ttttatattc 133680
attttaattc tcctctttat ttaaacctat tatatacgca atggactcta acatcttcca 133740
ttactttacc taatagattc tgacctttcc agttgctttc atctaatatc ttagggtcat 133800
ttgctttaat acctacaccc catattttat catagggtga tgcttctacg aaatctttac 133860
gtaaatctgt atctagtatt ttttgtttta agtgtgtagt cataaattta tctttaacca 133920
cttctaccat aatgtcatat ctcaccttat tccattgctc ttcattaaaa ttacgaactt 133980
tacgacctag acttttagca tggttcggat gcttagcatt taatatttct cctgctattt 134040
gccagtcttt aaaatattga gctttacgcc acataaaggc ttgttctgag ttattaaatg 134100
ttcttccttt gtgtttaaat gttattgggt aaaagttaga atagatatct tccttacccc 134160
aaaacataat gtattcttta gtctctttca tattatctct cctttaattc cataatgatg 134220
gtaatacgat tttaaagtta tctagaattt tgttttgtac ctgttcaatc tcgtcctcat 134280
tatcaacatc aaagctatcc attgattcgt ggtagaattg aattaaactt aatatatgct 134340
ttatcatatc tatctgtgtt ctttcttttc cttctatatc agtaaatgta tggtactcca 134400
tatccacatg attactactt tctacaaaag catttaaatc agcatatagt tgaataaaga 134460
aggacatatc atagttccaa tatttaggtt catttctacc taattcttta ttcatttttt 134520
tgtatttttt attctttttt aatccaaaaa cttctttttc aaagtcattt aatttaagtc 134580
ctttaaaata tcttttcttc atgagtttcc ctccaattta ataaaaggta aatctatatc 134640
cctgaataca gcacctacat cacacattaa catgtctcca ttaatttcta cttctccact 134700
gtcagttggt gtatgaccac atacataggt aaaaccatct tttctaggtt gaaagtctct 134760
tgaccatatt aattggtcaa ttgtttgttc ttctacaggc ttccaactaa ccccgcctga 134820
atgagagaat atatacttgt cttctttata gtactttcta caattaacca taagtatttt 134880
aaattttcta tagtcgtctg attctttaag tttctttagt tcacttttaa taaaatcata 134940
attacttctt aggttttctt ctacactact atactttaaa gttaccgtac tcacaccgta 135000
agagttaagt gtttctatac aatatcttga gagccattca atatcataga tacttaatcg 135060
gtctacgttt tccataacat tataaaactc atcatcatgg ttccctaaca gagttactac 135120
attatcatca ttagacatta aatcaaatat atagttaaca acgtcttttg accttttacc 135180
tctatctaca taatccccta aaaatactat tgtttcttta ggttttcttt cattgtttat 135240
tttatccata attgttaata atttttggta ttctccatga atatcgggaa caacgtatat 135300
agccatctaa tctcctcctt attgtatata actatcttac catacttagt aaaaaaagtc 135360
aataaaaaaa cacctattaa tttaataggt gtttatcatt taatgttatt ttaaagtatc 135420
attaccatgt gctaattttt tatcatctat tgcatggtca ttataaatat atttaacctc 135480
tatatactgg tcttcacttt tcagtgcatc tactatagaa gcattattag ttattgagct 135540
tgttctaggg taagtaaatt tttgaccgtc agataaaata atagtaacat caacttcaaa 135600
```

```
gttaacaggt agtctgtatc cataatcttc caaataatta ataaagttat taagagaaaa 135660
tggtttatac ttgccatcta aggtatagtc aatatattca tttaatgcat cagtaagttc 135720
tgattctgtt aactccattg tatcataatc tttttcgtta tagaatacta caacattatg 135780
ttgttctata ctagaatctc cgtctttata cttagatata aaaaatccaa tatttccttt 135840
atgctctaaa taatctgctt tcataatttt aaatacttct tctgctatag gttttgctaa 135900
tagtgttacc cattcacctt tttctgcgtc ataaacacta ggtagtacgt ttaccatcat 135960
ttaaatctcc tcttcttaat ttattggttt aaaccacaat ttactcttat cacttggttc 136020
tgtttcacta actacgaaag agttagaatc aatgtttaaa gtattaaaaa caatttcttg 136080
tttgtcttca ttactttttg ttgtaaattc gggaacatct gttaatatag actctttacc 136140
attaatagtc catgatattt taaaagaccc ttggctatac actgtattcg gtgtcagttt 136200
ttcaattata attttagcgg atgcacctgt aatttttttct gaagatttta ataatttacc 136260
tttggaatca tataagttta atgttctctc cacaaatttt atctccttta ctatattttg 136320
tacaattaat ataacaaaaa aacacctatt agtttaaata ggtgtccgac agagctcccg 136380
tacttagatt acggttaata atattttacg acaactatat gagaccctct gtcgttgaaa 136440
ctcttgtcac tgcgttattc cacaagatat tttagaaggt agcttgtgga agaagattgt 136500
ttttaaaggt acaattagcg tttttaagcc tattcgatac ccaggacact atgtccgtac 136560
taactattac gtcaataaag gttctacggt ctcaattacc tactctttat tgttaaaact 136620
aaaattaagc ttgagtgctc tagaagccaa aatcaattaa ttaactatag atacggaatg 136680
gagggacact accatccgga gtctacggtc agatacaaag cctctgccgg gcaacatacg 136740
gtatctctcg tacatcaggt tgactagacc tttagagttt ttcactcctt ctcttataac 136800
cagtaactta ggagaaatag gttttactta gtagatatga aacaataaat ccacatacaa 136860
tattaaatca tagtcaagtg attgcacata tgtctaatac ctataagttt tttgctagcc 136920
tggtatatgg actctgcagg attcgaacct acagtcaaac cgttatgagc ggttggcttt 136980
acctttaagc taagagtcct agaaatatcc tgagagagga ctcgaacctc aacgactagg 137040
tagctacatc tagccaatgc cattactcag gattgctagt aacgctaaat agaattataa 137100
cgttaccgta gacctttttct acgcttggta gataggtaaa atataatgat ttcaaagtac 137160
ccatatagtt aggctcttat tctcattata aggttaaaaa ggctaactgt gtttagcatt 137220
atataagagg ctttagttaa ctactatact aatagtatac cataaataat acttaatgtc 137280
aagttaattt atcaattgaa tccataattt ttgatgtact tcttatatcc gcttctttac 137340
tgtgtttaag aagatatttt                                             137360
```

<210> SEQ ID NO 2
<211> LENGTH: 144994
<212> TYPE: DNA
<213> ORGANISM: Unknown
<220> FEATURE:
<223> OTHER INFORMATION: Description of Unknown: Bacteriophage F125/10

<400> SEQUENCE: 2

```
ctttgttcaa attcctatat ttagtttaat accaatacta aggtataaat tagaagaaca    60
aggtatagga ttaatagaaa cagaagaatc ctacacaagt aaaacgtctt ttattgataa   120
tgaaaaacca atcaaacata atgtttataa aggtaaaaga gtaaaaagag gtctctttaa   180
aacagaagag ggtagaatat taaatgctga tgtaaatggt gcatttcaaa taatgaaaaa   240
agtattccct gatgtagaaa taccaaggga taatgggttt gtgtataacc cattcttaat   300
```

```
aaattgttaa aaaaacaaca aaataagaaa aaatttctca aaaagtagca ttatgtgaag    360
agaagtgtta cattattatc gagaattcaa taataaagca tagggaaggc tttttctatg    420
tcttatagaa tgctttaaaa tagattacta aaataaagat tggagattaa gcttatggct    480
aaaaagaatg ttaatgatgt attacaacaa gaatctgtta cagtagcaga taagtattta    540
caagttaaag ttaaccgtga cggttatact cgtacacatg aaggacaata tgcgtacaaa    600
gtagtttcag agggagaaga actattctta taccctgtac aaacagatgg taaaggtaca    660
ttaaatgtaa tgaagaaatc acctattgct tacactgatg ggacaatat ccatttcgta     720
gtaaacacag tagtagaccc ttataatcac tcatttatcc gtactgaaga tatcaaagga    780
ttagataaag gtaaacaact tattcaagct ttcttagctt tcgttgaaga ccgtttcaaa    840
tttggtgttt ataacgtatt tgttgcaaac agcaaagagg atgtattatc tattgtagac    900
cctacagata atgatgcaga tgaagttaaa gatagtttag agcacgcaca tgaagatgta    960
attgcggatt tccctgctag ccctgctcgt aaggacgtta aaggcgtaga ttcaggagaa   1020
ggtcaaggag acacttcaga accatcagca cctaagaacg ttcaagttac tcctaaggaa   1080
gacggagcag acgtatcagc agaataatat atagataagg atggtaaatt tggctaagtt   1140
aaatttatac aaaggtaatg agttactaaa cagcgtagag aaaacagaag gaaaatcaac   1200
aatcacgatt gagaatttag atgctaatac ggattatcct aaaggtactt ttaaagtatc   1260
attctcaaat gattcaggag agtcagagaa ggtcgatgtc cctcagttta agacaaaagc   1320
aattaaagtt atttcagtta cccttgacgt tgatagttta gaccttacag ttggagatac   1380
tcaccaacta tcaacaacta tcacgcctag tgaagcatct aacaaaaatg tgtcatttga   1440
atcagacaaa tcaggtgttg ctagcgtaac atcagaaggc ttaattgaag cagttagtgc   1500
aggaacagct aatgttactg taactactga agatggtagt cacactgata ttgttgctgt   1560
aacagttaag gaacctattc ctgaagcacc tgcagacgta acagttgaac ctggtgaaaa   1620
tagcgcagat attactgcat aggaggacaa taaagaatgg aaaagacatt aaaagtttat   1680
agtaatggtg aagttgtagg ctctcaagta gctaataacg atggagctac tacagtatct   1740
attacgggct tagaagccgg aaaaacttat gctaagggag cttttaaagt agcatttgct   1800
aatgattcag gtgaatcaga aaaagtagat gttcctgaat ttacaactaa aactcctact   1860
gaagaacctt caggagaagc atagtaatta agaccaacta aaaagttggt ctttttttat   1920
tgacaattta taatatctat gatacactat ataagaatta agaaaaggag ggaaagtaat   1980
ggatattcca acaatattat ttagaaatcc atatgattat acgaaagtaa aaaaactaat   2040
ggaaaacaaa gagcagtaca ttgtagtaaa gtttgattct gtttctgttc ataatttaaa   2100
tgttcaaggt atgatgaatg tcatccaaga ttacctacac atctatggtt atagggttaa   2160
agagtacggg caagaaaatg cttctaaaga tgatgaaaga gacgttaaag gttacttata   2220
tgaaagagta ggtgagtagg atatgggaat tatagtaaac tccaaccata ttcaatcaga   2280
cactttatat gagtatgata gctttttga tattgagaaa gtagatacat ttgaagaagg    2340
attgctttca atacaagatg aaccaactgt tttagcagga ttcatctatg atgacatcac   2400
atttaataag gttattaatt ctaattcaga tattgatgat tatattaaga ataatgatat   2460
ttattatgtc tctgatatag ggttactccc tgatactttt atcactgttg attctgataa   2520
aaaatattat tcattattac aacaggtagt tgagttaagt aaagaccctt ttcctaaatg   2580
ggtagaggat gatgcaaaag gcttaactaa gtattataac tttcaagact ttgaagatgt   2640
```

```
atttgattta aatagttttt acaaaaaaga agttgacatg gtaagagaaa agtgctataa   2700
taatggtaat gtatatttat tatatgaggt tctgcctgat tataaattac ctctagctta   2760
tagtttactt tcaaacaaag agcatggtat tgttattatc ggttcacaga cacgttctaa   2820
taatgatata ctgacttttt atgttaaagg tatggatgct aaagcaatag ctagtatgtt   2880
caatgtagaa catgattatg attctaatat tttccataca tttgtaaaca gtcacattaa   2940
tattttagga aatcaaataa ctaagtttat aagagagaaa ggaagcagtt atgagtaact   3000
ataaaacaat agaagaagta caagcagtta ttattggggt attatttaaa gatgaaggta   3060
aaattgtaac atctaagttt aataaaatta ctaaagagtt tggtttagat agaatcggta   3120
aagatgacct taaagaaatt gtagaggata ttagacaaga cgcttatcta aatgaactta   3180
aaaacaaagc aattaaaggt aaagtaacgt taggtgattt aaaagatgtt gcagataacc   3240
aagtattcga aggtaataac taccatgaag aagtatctac ttacgtagta gctaaagaaa   3300
aagaattgtc tcacttaaga gaacagcgta agcacaatag gcatactgca taccctcaaa   3360
ttatgtttga tgaacttaaa gaacatatgg ttaaagaatt acaaggggaa acattagtag   3420
aacatcatgg aagtaaagct aatattaatg atacagagct aattgtgtta ttatcagatt   3480
tccatattgg aagtattgta tctgatatga ctaatggtaa atatgatttt gaagttctta   3540
aagcaagatt aaatcatttt attaatacaa cagttaaaga aattgaagat agagaaattt   3600
ctaatgtaac tgtttacttt gttggggact tagtagaaca tattaatatg agagatgtta   3660
accaagcatt tgaaacagag tttactttag cagaacaaat ttctaaaggt actcgattac   3720
ttattgatat tctgaatgta ctatctaatg tagtttcagg agaattaaga tttggtatta   3780
ttggtggtaa ccacgaccgt atgcaaggta acaagaatca gaagatttat aatgataata   3840
ttgcttatgt agtgttagat tctttattat tattccaaga acaaggatta ctaaatggtg   3900
tagatattat tgataaccgt gaagatattt atactattag agataccttt ggcggtaaat   3960
ctattatcat taatcacgga gatgggttaa aaggtaaagg taatcatatc aataaattta   4020
tcctagatag tcatatcgac ttattaatta caggtcatgt acatcatttc tcagtaaaac   4080
aagaagattt taatagaatg catatcgtag cttcatctcc aatgggatat aataactatg   4140
ctaaagagtt acatttatca aaaactaaac cttcacagca gttattattt gtaaataagg   4200
aaaataaaga tattgatatt aaaacagtat ttttagatta aggatggtta ataaatggat   4260
acaattttta ttataggtgt agcgtttata acttttgcaa catttaacat agtctttaga   4320
ctatttgatt tatggactac cgagaaaaaa atggtaagtc aaggacaacc cccgctaagt   4380
aattttgagt actatcatgt gatagtacct tacttagtag gtgttattgt tattacacta   4440
agtattattt ttagagattc cttgtattcc gcacaatcag ggttcggtat tattattaca   4500
agctttattt acatgctagt ttatgttata attggtcttg tagggtcatt tatacttaca   4560
atattccaag ctagaaaagc tagacagtat caaacacagg aggataataa tgaagttcaa   4620
tgatatttat gagcaattaa ttaaaaatga tacagtacaa aacattcatg agtctcaaga   4680
tgacaaagga aatatttata caatccaatt tgataaaggt aatgataagt atttatttaa   4740
tgttattaat gatggattct tgaaagaaat gacaaacggt atggtagacc atcctgaagg   4800
tcagccatac tcagtaagtt taatcaataa agaaacacct agtatgtcag tgaaacaata   4860
tttaacagat gtagaagata ttgtacctac tattagaaaa atggaaaagg atttcttata   4920
gagtcaagtc tttacttgac tctttttact atatatggta tattaatata gaggtgactt   4980
aaaaatggat tttaatttta gtgcttttga taatagctca ttagcaatga gaattagtga   5040
```

```
gggtgtatac tatttcaatg atactcctta ttactttatt gagcatgtag aagaagaaat   5100
gtctgagtat gttattgtgt atgacataca tgacagagag gaaaaagaaa atcctcagaa   5160
gaaatataga atagaacctt accaacgtac aatacctggg ggaacacctc ttagtaactt   5220
aattaagagt atgatgcctc aacgtaagta tcctaagaag gttacagaag accctatatt   5280
tgtagctaat gttattcctt taggaacaga tacagtaaca ggtaaaaccg gtaaaggatt   5340
ttttgaaaga gataaggata gaactatcta ttctcaaaag gaaccaacta aagtcgttca   5400
tggtcaatat acaggtgttt ttataggtct aacaagtgtt aagtggaata gaacatatac   5460
ccctctagaa agtgttgttg agtactacaa aagggttaaa ggggataggt taaatgtcta   5520
atgatgtagt taagttttat gaaaaagata ttaaagacct tatcagaact aaaaaacaca   5580
tgttcaaaga cgatgaaata actagtgata taaacgatat acgaatcttt aatgagaaag   5640
tcatttgtca aggtaagtgc agaacagatt gtttagtact agaccgtaat ggtacagtaa   5700
tgggtataga gataaaaaca gaacgagact ctacacagag actaaataac caattaaagt   5760
attatagtct agtatgtaag tatgtatatg taatgtgtca tgataaacat gtacctaaag   5820
tagaacaaat acttaaaagg tataaacata atcatgtagg tataatgagc tacattagtt   5880
ttaaaggcaa acctgttgta ggtaaataca aagatgctac accatcacca catagaagcc   5940
cttatcatac aatgaatata ttatggaaga caaacttaat gacaatactt agattgatta   6000
gagaccctca tacgtataga acagggtata gctataatgc tagtggtaga tatagtggcg   6060
gagaaggtaa tttctcccaa acaactcaaa gtaaaagaat gaaaaaacct gctattatta   6120
atcaaataat tcattatgta ggggtagata atacttataa actctttaca agaggtgtta   6180
tctatggtta taataatagg tgggaagtta tagaagaaga tttctttaat actatgaaga   6240
atggggtaag agtaatcaat gagcaaagac aaaccaaata gacgtaaaga gatacaacat   6300
cagcctgtta actttgcccc tatgaatact ctaacagggg ctaataatag tttctttgct   6360
aaaaagcctt cagagcctaa ggatgcaaca tctgttattg aatatcgtat actatttatt   6420
aaaagatttg ataacgtaac aagtacagat gtgaaattac agaaaaagta tgcactaaat   6480
cttattagtg aagcacttga tgttaaagaa acttacttgt ctcttaagca aaaaggaaaa   6540
aaaacagaat ctattttgca tacagataga gtttattatg ttcatagagg taaaaaactt   6600
attggaaagt gtagtatcag agaacaaaga acatttaaag gtaaacattt gatatttata   6660
ttcaaaacaa gacatagagt taaagcagaa aggaaagata aataatgtta aaaggatttt   6720
cagaacatgt agacaaacct acaactacta agaccttata caagacctta acaagtggta   6780
aagtagaatt actaggtgta tcctacgata gtgattactt cccttcaggt gttacagtac   6840
aatcttacat tgaggatata ggtaatgaag atgagggtct acagtttgtt aataagataa   6900
atgtagtaga atcaatgaaa caggctgtag taggtatgaa taatcagtta ggttcttcag   6960
gtcttggcta tgtgagaact gaacaactta aaaaagagtt agaagagact ggactaatga   7020
cagatttact tgctagaggt actaacttaa cctctactaa gaaagtagat attgtaagta   7080
cttttattga gcctgaggta acataccagg atattactat agctaaagat attaaactac   7140
gtttgtataa attagaagaa gaatcaccat taaatggtta cactcatatt gtatacttac   7200
ttactacaga aaagctatat gatggtcaaa cactattcgg tatgctctct aaaaaagata   7260
agttatctaa aggagatact gataaattat tagcattctt cagaaacaat agcttaataa   7320
gtaaaagtgt attttgtgtt aagttattaa gtaaagacta ctactttaat ttatataaca   7380
```

```
cacatgagac agggatattc tttttagaag acacagatgt tattactatt gcttgtggtc   7440
agtcatatgt taaagttaat actaaagata ttaaatctag ttatgttaaa attgaagaca   7500
agactcataa attaactgag ctagtaatta acttaaaagg tgacgacaca ttaactattt   7560
tattctaaga gaatgttata aatatgtgat aattaagtat aaatatacgt tatatgagaa   7620
gttttcataa tgtttttaat acagaaacta gttaagtttt ttctacttgc tctagtttct   7680
gtgaaattat atttatgaaa agttaaaata tcttttaggt aaaggctttg taaatagtta   7740
aaaaatatat taaaatttta tacaaagtag ttaataaaat tatattacat ttatatatta   7800
tgaaataata acagaaattg tgatatatta tatagtgtaa ccttgaaaca gttgatgttg   7860
tagggtttgt ttatgttcgt taaactggtt tcagaacacc agttaccata aataaatgac   7920
agttaaggag agctatataa tggctagaaa aaagaattta cgaaataaaa acagtgatat   7980
aaaagttgtt cctgataaag aaaaagaaag catattatct aagctatatc ataataaatt   8040
actacgctca aaggtagata atgcattaga tgaagatatg agttatgatg atattataga   8100
attatgtaaa gaatatgatt tagaattgtc taagtcagct attacaagat ataaaagtaa   8160
aagaaaagaa gctattgaaa acggttggga tttagaagaa ttaattgata aacgtaaaaa   8220
aacaagtgta aaagatatta aggaaaaaga aactcctata ttagaagagg agcaactttc   8280
tccatttgaa caatcaaaac atcacacaca aacaatttac gatgatattc aagtactaga   8340
tatgattatt tctaaaggtg caaaaggact agaatttgta gaaactttag accctgcgtt   8400
gatgatacgt gcaatggaaa caaaagataa gattaccgga aaccaattaa aaggtatgtc   8460
atttattgga cttagagagt tacaattaaa acaaacagct caagatacag ctatgagtga   8520
agtattatta gaatttatac ctgaagagaa acatgaagag gtattacaac gattagaaga   8580
actacaaaat gaattctaca aaaacctaga tttagatgag gaaagtagaa aattaaaaga   8640
agctcttgat agagtaggct acacaattta gatagtgagg ttagagtaat ggcagatgag   8700
attagtttaa atccaataca agatgctaag ccaattgatg atatagtaga gattatgaca   8760
tatttaaaag acggaagagt actgagagtt aagcaagaca accaagggga tatccttgtt   8820
agaatgagcc cagggaaaca caaatttact gaagtatcta gagacttaga taaagaatca   8880
ttctactata aaagacattg ggttctctat aatgtatctg ttaactctct tataacattt   8940
gatgtttatc tagatgaaga atattcagaa acaactaagg ttaagtatcc taaagatact   9000
attgtagaat atacaagaga agaccaagaa aaagatgttg ctatgattaa agaaatactt   9060
acagataata atggtaatta tttctatgca cttacaggag aaacaatgct ctttgatgaa   9120
aataaattaa ataaagttaa agattagggt tgacagcttc tatagtttat gatatagtat   9180
atgtatacta aaaataaagg agctaacaat tatgtttatt tcattaaatc aagaagagaa   9240
agaattatta actaaagagg aaagtaaata cacaccacta gaaacatcaa gagagtttaa   9300
cacacctaaa gaagaattca ttgtaacaag ttataacgaa ggtaaacctt tagattacat   9360
tgcaaaagaa gctaaggtaa gtatgggatt aatttacaca gttctaaact actataaagt   9420
aggtaagcgt aataagaaat cacctgtaga agaaagaatt gcacatatct taaaagataa   9480
aaacttagtc aaagagatta ttaaggatta ccaatatatg aatttacagg acatttatag   9540
taaatataat cttcataaga atggtttata ttacatctta gatttatacc atgtagaaag   9600
aaaatctgaa cttaaggaca aagcattaga agaggataat attgtcgttg agtaagtaaa   9660
gaggttataa tatgagaaat aaaaaatcat ttcaagagca gttaaatgac atgcgtaata   9720
aagagaaatg ggtatctgaa gaggagttca ctgaagaagt ggctccttct gaagaacctg   9780
```

```
aagtagaaga agaaaaacta tatactttaa atgagttaaa agagaactta ctagatgctc   9840
aaggattaaa agatgttgta gctgattttc ctgcatctaa agatttatat gaacctaata   9900
aactatatat ctgtacaata cctaaaggat atcagtctac tgaagtacaa ccaggacaat   9960
atattggtat tagtactgga ttattatcag agtcagaaga cttcagtcat ttaagaggtc  10020
aaatgcctag aaatctttat gaaacttctc atgttttaaa acctttagtc cgtattaata  10080
atacaagtat cgaatatcaa cagcatgagt tacttgaaga tattaaagaa gacaagaatg  10140
tatatgatgt tgaattagaa gacttgagat tagcaacagg agaagaaatt tcttatttag  10200
agattgttga tagtaagttt tttgaaagtc gtattaatga agttcttgat ttttaccatg  10260
aactaacgga ttccgatgat ttgcttgagt attataacaa attacgagag ttagtcggaa  10320
atgatagaat gatttattgt ccgcttttaa ataaatgtgt taaaattata gattaatagt  10380
agtctcctct tatattataa ctgtaagagg agacattttt gtatagaggt gttaattatg  10440
tcaagaaaag caagtatatt ttatatacta gtggttattg ttttggcttt ctctatctca  10500
tcttattata tatcttcttt catgtatcac gacaaagcaa aaaatgaagt ctctactgag  10560
ttatcgaaca caggaaagat taaagaagaa aagaacgtag aatttgttgg tgactacaca  10620
ttgaaaaaag tggaagataa taaagcttat tttatggaaa cattacctac ttacctacca  10680
ggtagaacag gagataacag catagatatg aggtactaca aaacaagtag atttaaggaa  10740
ggggtaaatt tcaagcttat tagggtatat actgaagatg gagaagataa tccaattcat  10800
aagtataggt ttgaagcagt accaaccaaa aagtaataag gaggtgactt aaatgacaac  10860
attaattgtc gtcatcttta ttgctatcat ttattactta tggaacagtg attgagtcaa  10920
gttaattctt gactctcttt ttgttttatg gtatattaat atatagaaag gagagattaa  10980
ttatggaaat ggcagattta gaaagatttg atgcatttgt aagactaatt tcagatgatg  11040
agctttcgga ggaaagaata ctggagttaa gcgtagactt actaaacccg atactagaag  11100
gaggtacagc ttacagagct aaaaaacgta ttaaaagtaa atttggtaag ttagaagcaa  11160
aaaactttaa acgaaactat aaattcttac ttaagtcgat agctcaaata gaccaaagga  11220
gataggacaa tgacagaaag ggaaaaatta attaaagaga ttgaagaggc taacagagac  11280
atacagttac agttaaaaga agtagataat tataaggata gtatacgctc taaaggaaca  11340
agaaattata tctctacaaa ggtattagat tctattacgg ttggtttcat agttagtttt  11400
ttaatactca ttataatgcg tgtacttgaa tactttgtaa caggtaatgc tgtttattca  11460
cctttagcgc ctgcagttat cattatgttt gttttagcac tcggtacatg gaaagtaagt  11520
aagatgaaca aaatagtatc ttatagagga actattaaga tgtactggga gctaagtaat  11580
gctgagcaaa aacaagctaa ggtatttaag tatcctaatg atgaagtaga tattgtatca  11640
aaacataact taaggcaaat aacttttagt gagattaata tacttcatct taaatatatg  11700
agatataata aagcagtaga acagcatact aaattatcta aagaactttt taaaaaagat  11760
aaagaaacgg ttgacaagaa taaataagtg tagtatagta ttactaaagg aggagagata  11820
ttatggttat acctagtatt aaagcacaaa acaaattcaa gaatgaatta gagtattata  11880
aacaaggtca cattagtgaa agtaaaatgt tagaattagc ttttgattac atccaagaat  11940
tagaacaaaa taacgaatac gttactaatt tgctagaaga ggagagatat ggtgagtaaa  12000
tttatcggag tgtacttatt taatttacta gtggtagctc tagtttacac agtaggattt  12060
ttattctttt atggtgtagc tagcttagtt attattttaa ctcatgctac tattgacccg  12120
```

```
ttcgtattag ctactttctt aggaatagga ttcttagtta ttagaactgc acacagaatt  12180
atggcacgag taatcaatga cgcagtagcc caagccatta aggataaaga aaatgaataa  12240
aggggaattt attatggata aaacattacc aaagtttagt gtatatgaag ttattgtaaa  12300
gactgtaatt atgacaccaa cagaaggaag ttctgaccta gaatcatttt acttttcaac  12360
tagagagtta gcagaaagat ttgttgaaga gaacacagtg gaaacaaaaa acggtaaacg  12420
tgtatctttt gctgttaaag aacgtaaagt aaatcaacca ggctaacatt aatttgttag  12480
ctttttttta ttgacaaatc attttatata gtgtatagta atattataca gaaaaggagg  12540
aattattatg aaagtttcag aagaagtaaa acagagttac ctagagaata aagctaatac  12600
taaaatggat aagataagtt ggtctgagtt aaaagctagt cctttaggta ttaccttagg  12660
tgatattata ttttatagtg tagttattat agataacatt atagctatta ttttaacttt  12720
aaccttgata ggtactatta ctgactcaat tgagagtact ttagcccaaa taatcgtagg  12780
ggtgttcata atcattacta tatatggaat cctatcagcg ttaataccta ttctaattca  12840
taaagctgta tcaccgggat ggagttatac tgaatggaat gaatcctatt acatcagatt  12900
acctggggaa gagaactaca aatactatag taaatggtat ttagatttat taggagttaa  12960
agaattttac tataaaagag atagtggaga agaagtaaaa gaaaaaaata tatcatgggc  13020
ttttcaagct gaagtgaaaa gacctgaaga tgttaaccac tggaaaaacc agttgcttac  13080
taatagacct ttaacaattt tagaatataa aaaattaaag aaattagata aggaaagtga  13140
aattaggaaa caagaagatt tagaagaata caaacaatac aatagtaatt aaagaggtgg  13200
aaagcaatga taagctcatt tgatagtata ctacttgtca tatacattat tatagctttt  13260
gcagtagcta tggcaattat ctacttagta tttaaaggta tgactatttt actagataaa  13320
ctaatgatgt tattattaag taaaactaca ttagatgtag aagcttgttc tatgataatg  13380
gcagtcatca gtacaattgt gtttggaatt attgtacttt taatatggct agcagtaaac  13440
aatattttac tataaggagt tttattatgg attttaatga ttttataaac agtgaatcgg  13500
atagagtagg taatcctaaa caaaagaaga aggtagagaa taagctacct tcttctattc  13560
ctattgaaga tagagaaaag aaattaaaag agataagaaa gaaatcatta tatattgatt  13620
taaggagaaa aagaaatgac taaagaaaca aatgtacttt acaaagataa gtatagagat  13680
tatactatag ttgtaagact agcaggtaat attattgtta ctgaggtaga taagaaacat  13740
aaaacagcat ttacacctat tatatttgac aatggtgtag aaggcgtaga gcttgtaatg  13800
cgtataggtt ctgtagagct tagcatgaca gatttacgtg agttcacaaa ggaagtatct  13860
acagctcaga aagctttaga atattttaat aaaaaacttt acattaaagg cttgacagat  13920
gaagcatttt aatatatact aaaagtataa ataaaataaa gaaaagagga atgattatta  13980
tgttattagg aattttatgg tttatatggg gatttgtatc gtactttgta ttgatgtttg  14040
gaattgagtt ttgtaaagat agatggatgc caggtgttat cggagcagga gccttactac  14100
tattcttatt ttggattatg aaatctatcc ataatgctat gacagtagta tacttgtatt  14160
aggaggttgt atagatggat atactaatta ttcattataa agaaacaaat aaacgagttt  14220
taaaagaaac aatacaaaca atacaaaatc atttaaatga tgaacatggt ttggttaaga  14280
tgacagcaac aaaacttagc agagagaata tagagaaaag atttaataac tataatatag  14340
tcattgcaga agatgaccct gataattcgt atcattacag tgaagctgta gaagaagcag  14400
attttattat agacatacca atttcatatt tagatataca tgcaggagta gaatgggatg  14460
ttgataatcc tgtagatatg ctagatagga atccggattt tatagaagct gtaaataaat  14520
```

```
taaatgaaga cttaatgtta taaggaggaa atagaatgct aaatgaaaaa ctaaaaaacc  14580
tggaagatac aaaagtatac atgattaata gtattgcaag tttactaagc gcaagtacag  14640
gaaaatcaag taaagtattt tttgatgaag gaactattaa aattgtaagt ggtgaaacaa  14700
aagcagtaga agttattgat aacttagttc acccacactc aggacgttta cctattaaaa  14760
caacagaacg tattgcgcta ggtagattaa cagattcttt acagtttgtt atttcagaaa  14820
tagaagtagt taaagaccaa attatagatg aagaaaatga agcttacatt gattttgtga  14880
tggaagactg ggactgggat taatacctat ggacttatta actattgctt ctgttgcttt  14940
tatagctgta gtcattattg atttgattaa tgatgatatg agctatatgc ttactggtac  15000
tgcaatctta ataaatattt gggcaggatt ttatggatgg tttttcttac tacaagcagg  15060
tatgttactt ttcttactat tagctaggaa agttaaagat gataaggagt caatactata  15120
ctctagtgct tcattaatat gtgcactagg aatgataata aatcttcttt cattttctta  15180
aaaataagta ttgacacctt tgtacttttg tattatactt agtatataac aagtacagga  15240
gatgattaat atgagtaaag aaacaatcag aagacaattt tcaaacgcaa ttgagattat  15300
ggcaacaact aaggaatggt ggaattttcc taaaagtttt aatacaagta aagagtttaa  15360
aattaaaact tttaaaaatg acacacttgt atttgaagtt agggaaggta gtagaaattt  15420
aggaagcttt gtaattttta caaacattga ttttgattac gataaactag aaggaacttc  15480
aacacaatat atgattaatt actttgctaa gaaattaact aaagatatgt ttaactatca  15540
taagttacaa ttatagtagg aggtggaaag atgagagaag agttaaaacc ttttaatagg  15600
aaacaagtta atgttaaggg ttacttagat gatgttaagt attcaaagcg tagaagacat  15660
aaaggtaatc aacatgggtg tgttaaaatc acagttactg atgtaaagat taatggtata  15720
cctattgacc acgttaacat tgaagttggt atctctttct acgaaaaact aaaggagctt  15780
caaggaaaga gaattcaatt tgtaggtact gtttataagt atgttaaaca tgctagaggg  15840
cgcaaaggta gaattaaagg attttataaa gaggattata gcgtaacttt agataagaag  15900
ttacaaaagg aggaaaaata atgattaaaa gaagaaaaca tttagaccac tcattacagc  15960
ctgagaaagg atggagaaca gtacctttta atgggtatta tgaagcgcat cctacgggtt  16020
taattagaaa taaagtaacg aaaaagttaa ttaaaggtac acagacaaga aagaaccatc  16080
ctaagtggac tgctcatgag attgtatact taattaaccc taagaaaaca agttattcta  16140
ggggagtagt tattgcacat acattccctg aaatgattag ccaatcaaga ggagacctta  16200
agaacggtca tgtgtgtttt aaagatggtg accgaagtaa ttgtcatgta gacaacatgt  16260
ttattggtaa aggtaatgtt aacaaaaata tctataaatt aaatgattct tatttaacta  16320
gaaaagatat tgaagaggat gttaataatt tagttaatga aagattattc tctcaattag  16380
aattattgat taagaaaaat gaaccggaaa gaattacacc tagtaatcac tttattaaaa  16440
gagataataa tgtgttcagt atcacagatt tatctaaaaa ctcactagta gagtttgagt  16500
tagaaatcaa gaatattaag taaggtggtt atataaatga atgagtggta tgctttatgt  16560
tattacgaca aagtaggtaa aaagaaaata cctaggcaaa ttaaagctca cagggatgta  16620
tctgtattag aggatttaaa agatagatta gaagaacaaa atcctaaaga agaatacaag  16680
attaaaacaa caaaagaatt tgataaggag agataattaa tgttaacacc tcaacaaaag  16740
gattcattaa aagagcaaca aaaaaaatta agtaaaaaga agaaataagt cttgacaatt  16800
gagtatacat aggttatact taagttaaca aataaagagg aggtatgacc tatgttattc  16860
```

```
gtaattttta tattggcagt actgtttgta cttggattta tgaatggatg gaactcagaa  16920
gactagataa ggagtggttg taatgaagtt agaagataaa gtgttagaga gaattgattc  16980
tcttggaaat aaagcaggta acttaagtaa tcaagcaatg gagtcattag taaagtatca  17040
aattacgtac ggtattatag atattgttgt aagtatttta gttattgcac taacaatatt  17100
tttaggtaag gtttacctta aagaatataa gaaggttaaa atggatttaa aagaaagctt  17160
attgtatgat gactacgata ttctctcttt acgcaatagt tgcaggtata ccaactgata  17220
ttatgagatt aattaatccg gaagtttatg cagtaaaaga tttaattgag caagttaaag  17280
gaggaaattg atatgaagca gagagatttt gaatttgaag aggattttgt attaacttac  17340
gagtgtgagg attgtaagca ttttgaagac tggggtcatg atgaagagcc tgaagaatgt  17400
agtgaatgtg gaagtagtga cttaatcaat aatacaagtc atgaagatac tgagtgtgat  17460
atgtgtcgag gatatattga tatgtggcaa gatggatata gatatatggg agataataaa  17520
gagtatattg aaaaagagga atcaggttta atttgtgaag attgttatga gaaattagat  17580
atttaataag gaggaaatta atatgaataa agcagtagaa caagcaagta atgcattagg  17640
tcaaggattt tcagctatgg tatggcatca agtattagca gggttagggt ttattttatt  17700
aggattggta ttatctttac tggtttgggt attagtaaaa aaattccatg taccttttaa  17760
tcacccgaca gcttttgtag tgtactcaat tatgttagtt agtattgttg ctagttttat  17820
ttggggcggt ttacatgtaa ttaaccctga gtattatgct attttagaac ttaaaggttt  17880
tataaagtag gaggaattct atgactaaag aagagttaga gcaaaaagta aaagaacttg  17940
aagcagagaa taaagagctt aaaaaacaaa tagaacgttt tgaagacgaa ggaggaaaaa  18000
caaaagatga acagtagaca aaagaaaatt ttaacattaa cagtaagtaa ctttttaatt  18060
ctagccttag atactgtagc actaattaga tataaaaaag gtaaaattaa acaagagaat  18120
tataacacag ggcaaattac aagaatgata gctacaacag ctaactcatt aggtattctt  18180
tacttagaag agcaagagcg taaagaagtt aaagatatta aagtaggtac ttttgaaatt  18240
ggagccttaa aaagatttac aaataataaa taaaaaaagt ttaagaaacc tattgacatt  18300
aggtttcttt tattatatac taatattata agaaataagg aggttaactt atgaaaggta  18360
ttatcatatt ttacaaggaa gagaccaaag aggatttagg atattttctt gggtttataa  18420
actttaagct agaaggatta tcttacacaa ctgaaggtac tttagtagat aatgatgtag  18480
tagttttaaa ggataaccaa attaatgagg ataatttaga gcagtttagt atgtcaaaca  18540
ataatttagt tattggaata ctaggtcatt catctctttc agtacgcatc tatgaaaaag  18600
gtattagaca agagtttgat agagtagaag aatatttaga ggagttgaga caataatgat  18660
atttatatta atttttggtt tactatttat tttatcttta ctaggtattt ttatttattt  18720
tatagtttta cgaaagaaaa aacaattaat agaagaaaga gaatcatttg gtatttataa  18780
tagaacaaaa gaaaaactgg gtgatgtaac acgtttaggg tatgaggaag atgtatataa  18840
gttaatccat aaccaatcta ataaaacaat catagaggat aaaaagagta aagttgtaga  18900
tacaattaaa aagatgtatg agctagaatt aacgtcagta gatgtttcta aggtagaagg  18960
attatctcca cttgatacag aacctatgac aaatatgaaa ttactttcat ataagctaga  19020
tagagaagga ttatatagtt taagtaaatt tatttaggag tgatacaatg gaatttatag  19080
ataaaaataa tgtaattaaa gcttatgata taccaaatgt ttatttaaaa ggttatgtat  19140
tacaggcatg tgataaaaat ggagatacaa cagcttatga tggttatgac caaatacact  19200
ataaagaagg tagagtatta acattccctt ttgataaacc attaagaaag ataaatgtac  19260
```

```
tatcaggata ttacaaacta tttaaaaagg aggacataat atgatttatt ttgttagtga  19320
tttacatttc ggtcatgata atattagaga attcgaagca cctacaagaa gtcactggaa  19380
ctcagtagaa gaaatgaatg aaggtttaat tgagttgtgg aataatacaa ttacaaataa  19440
cgatattgtt tataacattg gagacttctt tttcaatatg aaaccttcta aagtagaaga  19500
tatacttaat agactaaatt ataaagagat gatactgatt gcaggtaacc atgaccataa  19560
gaaacttata aaactatatg aacgtaatgg tattacagta aagtacgcag acatgattaa  19620
aaaggatggt aagagatttt atctaagcca ttatcctaca ctaataggta gaaaaaacat  19680
gtttaatatt catggtcata tacactcaca attaatgggt actgaatatc acatcaatgt  19740
aggttatgat gtagagggta aaattgccta tagttttgat gatattataa gtagagcagg  19800
tgaatataat ggagaaattc aaaggtaaag atttatataa aactagaatt agaaaacaaa  19860
caattaaaaa tttagttata aaaacagaga agctacataa taaacacgga aagtatagac  19920
ctattggtca tgtttattac tatccgaaaa caaaagagtt tactttatct aagcctgaac  19980
aaaagatatt tatagagtat atgaaagaat taggttttaa tgtaaaacac aggagacgta  20040
agaaaacact tattatttat aagaatgcat tcactgaata cattagtatg tatcatgaag  20100
caatagagca gattgaagga gggacataat ggaatattta tttttattta taggtattgg  20160
catgataatt tggggtttca tagcacctta tcttgcattt gtagtttact ataaacatgt  20220
aagagaaaat cataatggat tcagtgatga ggaatctcta gaagaggcta cagtacttgg  20280
tatgggattc atgtttatag catttattcc tataggtata ctagttgtaa ttgaagaaat  20340
taagatttta ttcttttaag tgttgacaac tacaatatag tgtgttacag tataaaaaag  20400
gaggttaact aatgaagcat tttattttaa ttttagggat tgtaatccta gttattgcat  20460
tagggattgt aatcctagtt attgcattag gtattgtttt accggcatgg attttacagc  20520
tagtattatc tgcattcgga gttaaagtaa gtatttgggt atgtatcgga atatttattt  20580
taatcagtgc aataggaagt atgtttagta gaaattaaag gaggaattac aaatggcaaa  20640
atatgaatca aatattaatg gagagaatta tattgcaaca ccgtcacaag ctttaagaga  20700
agcactagca aaattaataa ctgaggaaaa gagctttgca gagtaccaaa ctaaaggtgg  20760
ggaacagtat gaatcacagt tacaactaag acactttgat gcaatgatat ctcagtatga  20820
ggaagctatt agagtactag aagataaata tagacctcag atttttattc cgaaagataa  20880
taaggaggaa aattaattat gaaagcagaa tcaatagcaa gatttttttaa tgacaaagta  20940
ttacaaatag aaggttataa agtaagattt ccgcaggcta gttcatctta tattttagat  21000
atagatactg tagatgaatc agtattgttt ttagacgctc aagtatctac actttcaggt  21060
aagcatttat tagatacagc tattacaatt gagagacctg aaacattaag tgctaaagag  21120
ttatatacag aaattagtaa taaactgcaa gctattgtag gagaccaaac taaaacaact  21180
atagaactat caagatattt taaggaggaa aaataagtgt ctaataaaac tattacaaat  21240
catttattaa atttaaaagg aataaacatt gaaacgtata gtattattgc tcgtatcaag  21300
aaacaaacta gttggggtga taaaggagat tcttttgaaa taagcataag ttataaagct  21360
gataaagacc ctagaacagt gagatatatt acaactgaaa ttactattga ttatagtagt  21420
aataatccaa aagaaatttt attacaatta aaagataaga ttttttctat tgttgaggaa  21480
caggtagaga ctgacaatga ttttattgaa tctattaaag aaattaattc aactaaagca  21540
ttagaaaaac taaagcctta tatcaataat gaatattatt caatgtttaa atcttctatt  21600
```

```
gaaaaggaaa tacctgtagc tttatcttct gaagtactca atagatgtac aggtaaaaca  21660
agcacattag cttatttagc actagaaaag gatttaccct tagtagtgtc aaatgaacct  21720
atgagaaaaa tgcttaaaaa taaattccct caccttagag tatcttctgc tgaagattat  21780
tcaaattatg atattaaagg tgaaattgta ttaatagatg aagtagatat tgaccagtta  21840
tatagtgctg ataaagtatc tgttgatgca ctattagtag gtatcattaa aaattaaata  21900
aatttataaa tacctgttga caacaggtat tttttatagt atactttaga tataaagaaa  21960
aaggaggtaa tataatgata cctataatag ttatacttat tggactcata ttattttat  22020
ctagtggtta taagttggta ttaggtaagt actatgatga tgtagattta aaaatactat  22080
ttaccatatt tggtgttggg attgcattac tacttggagg atttatatta taaaggagga  22140
aacaataaat gaattatgaa gaggtactaa gaactattaa ggaaaataaa ccctgtaaag  22200
ttagattcac aggaaatatt ttagcaattg ttaatgagga atttaatgca gatactgata  22260
aaggagtttt acagcttgat gtatcgaata tcaacaaaga gggctatata agattacagc  22320
aatattgttt agaaagagat gactatacgg tagtaggagc tattttattt taaggagagg  22380
taaatatgaa ttatagagat tttattacag attgtattag cggtggttac aacgtacaca  22440
tcagtgttac agaaaaaaga gtgcacatca tttctgagat gacatcagca tcttatccta  22500
aaaaggaaat taacttagat gaactacaag cttatgtgta ctatatgaat aactttggaa  22560
gtcaaattac aacggagggg ttataaatgg aattggttat taatattgta gcagtattgg  22620
tcggtatgta tgctatttat ttctatgtta caaaatttag tactggctta tcaggtattt  22680
taattgtttt agggatggct attggtcttt acttctactt agactattta aatgtcagag  22740
aaaatgttat tcgattagtt tcagtaatgt ttggagcttt cctatttagt attgaaatga  22800
tttataataa aattatgttc gaaattaaaa aaagcaatgt tcagaagact gttagagtgt  22860
atgataaaga gcagtaatga tttttaccat aaagagtatc taaattactt taagtgctct  22920
ctatggtacc ttaaaatagc ttagaattga aattaaggag atgaatattt atgtatcctg  22980
aaatagatgt agaaaaatta gcgtacaagc taaaaagtac gagagaatat ttagaaagca  23040
ttaaaataaa agaagtagaa atttatgaaa tctatcatct taaaacaggt aagttagttt  23100
ttaaaggtga atatattgaa gtaaaagaat tactgaggaa aatgtataaa gagaatttaa  23160
cacttgtaga tgtagataca atgttaagta ttggtaaagg atttattgat gtaattaaga  23220
atatatcagc agaaaatgta ttccaaataa catataaaaa ggagctctca acaaaatgat  23280
taaaatattt tcagaagtag ataaagaata caaacccatt attactgaaa agtttcctaa  23340
tggtgagatt aattttaaat acgatgattt aaagtattta gtagaagaga acttaagatt  23400
tgatgttttc tttaaatggg aaaatgacgc agatttaatg catttgtata tgtttactaa  23460
gtatttagag caactaggta ttaaagataa agctgaattt ttagagattg catatctacc  23520
ttatagcaga atggatagag tagaagaagg gcataataat atgttcagtc ttaaatacat  23580
tacagaattt attaataacc ttaattataa atcggtatgg gtagtagaac ctcatagtcc  23640
tgtaacagaa gaattactta ctaattctgt tgctattgat gttacactta aattattaaa  23700
tcagtatatt gaaatgtccg aagagcctgt aacaatagta ctacctgata aaggggcata  23760
cgatagatat ctatttgatg tagaacgtat cttaatggaa tctaatattg aatcatattc  23820
aattgtatat ggtgagaaga aacgagattt tgaaacaggt aagattaaag gtattaaaat  23880
aattaaagat aaaaatactt tatatgataa ttgtattata ctagatgact taacaagtta  23940
cggcgggaca tttgtaggtt gtaaaaaagc ccttgacaaa cttaaggtaa gtagtgtatc  24000
```

```
attaatattg actcatgcag aacgagcttt tgcagaagga gcattactta gctcaggatt  24060
taaagatatt attgtaacag actctatgtt ccctaaaaat aattgggaaa aagctattgc  24120
taaacataga gctagaatca acggaactga attacaaata aaagatatcg aaagatattt  24180
ataaaaggag aaaaacaaat tatgctaaac ccaactttaa tgtgtgactt ctataaacta  24240
agtcacagag aacaatatcc tgaaggtaca gaaattgtat atagtacatt agtacctaga  24300
agtaataaat attatgaaca cagtgataat attgtagtat tcggtattca atcacttgtt  24360
aaaaaatatt ttattgatat gtttaataaa gagttcttta acagacctaa agaggaagtt  24420
attaatgaat acaaacgtac agttaaattt acactaggac aagaaaatcc tgatgctaaa  24480
cacttagaac aattacatga cttaggttat ttacctattg atgtaagagc tttaaaagaa  24540
ggtactgttg ttcatcctaa cacacctgtt atgacaattg aaaatactca ctcagatttc  24600
ttttggttaa ctaattactt agaaacgatt attagtactc aaacatggca agcaatgact  24660
agtgctacac tagcatatga tatgcgtaaa atgctagata aatatgcaat ggaaacagta  24720
ggtaatattg aagcagtgga tttccagggt catgacttca gtatgcgtgg tatgagttct  24780
ttagaaacag ctcaattaag ttcagcaggt catgcaatta gttttaaagg cagtgataca  24840
gtacctgtag tggatttctt agaatcatat tacaatgcag acgtagagaa ggaaatggtt  24900
gttgcttcta tccctgctac tgagcactca gtaatgtgcg caaatggtaa ttatgaaacc  24960
atggatgagt atgaaacata taaacgtatg ttaacagaaa tatatccaac aggaattttc  25020
tctattgtat ctgatacttg ggacttttgg ggtaatatga ctaaaacttt acctagatta  25080
aaggatatta ttatggaacg tgatggtaaa gtagtaatca gacctgatag tggagaccct  25140
gttaaaatta tttgcggaga ccctgatgca gatactgaat atgaacgtaa aggtgcagta  25200
gaagtacttt gggatacctt tggaggtact gaaactgaaa aagggtacaa agtattagat  25260
gaacatgtag gattaattta cggagactct attaactatg aacgtgctca acaaatttgt  25320
gaaggattaa aagaaaaagg ttttgcaagt attaatgttg tattaggtgt aggtagtttc  25380
tcttaccaat ttaatactcg tgatactcac gggtttgcaa tcaaagcaac gtatgctaag  25440
attaaaaatg aagaaaaact tatctataaa aatcctaaaa cagatagtgg taaacgttca  25500
cataaaggtc gagtagctgt atataaagac ggttcatggg aagataactt aaccttacat  25560
caatggctaa acaaacaaaa tgttaatcaa ttagaaagag tatttgaaga tggtaagctt  25620
tatagagacc agtcgttaag tgaaattaga gaaataatta aaaataatta ataaatattt  25680
aaactcccta ttgacaaagg gagtttttta ttatatagta gggttatagt aaataaagga  25740
gtgaaagaaa tgatttataa aatatcaaaa cataattact atagtaggtt tgaatattca  25800
tcttatttac ctgatgaagg atttgcatac atagattatg tagatgtcat tcttataggt  25860
gtagataatc cgaggaagag aaaagttatt actttaaaag cagatgagtt taatcctagt  25920
gattttaagg ttggtcataa atataatatt ataaaaatac tatggtttga gaaatgggaa  25980
tggttacagc catagggagg agaggtatac aatgattata gataaattaa atggagttaa  26040
attagagatt ggcggtcatg ttgtatcatt tagtgtaagc aaatttaaaa cgattaatgg  26100
tgagagacaa ttacttgatt accaccatat caaaagacgt aaacagaaat attttagaac  26160
tactgaagaa ttctataatg agtacaaaga aataaaaccc gataagaatg aaatagatga  26220
aatgtttgaa tctttaggtt atgtagatac taaactagaa gatgtagtaa gaaaccaaga  26280
gaaagtgaca gagatattag gagttagtga acaatactta aaccaattgt cttataaggc  26340
```

```
tatagaggaa tatgtagaca aaatagttac cttagaaatt aaagaattaa aaggagaaaa  26400
atagtatgag taatagttgg gaaaaagaag gagttaacta ctgggaaaat gaagattgcc  26460
ctagagaata cttagagaaa gcatttatag aattagttga atacgtagaa ggtgttacag  26520
taccatctag agatgttcag cagttgagag aggataagct tagagaagat attggatttt  26580
atgagtatgt agcagataaa taaatacaca tctacctatt gacttaggta gatacttatt  26640
atataatagt atacaaggag atgaagtatg atgaatggaa aacaaattta tgtattttta  26700
agtgaccagt atagtaaaga tatactcagt ttacaattag gacttattaa ggaatggtct  26760
agaagagaac taacttattc agatgatgtc gggtcagatg cagatgttgt tatttgtact  26820
gatatagtaa gagatgattt cgtaaaaaaa ctaagtaaaa ataatagcaa tgcattattt  26880
gtgtttatta gttcttttta ttggataggt tataaaggcg gagaattttt tgttgcagtt  26940
caagactatg tgaaaggtat gtaagatatg aaaaaattat taatattatt tacattagct  27000
agtactttac tattagcagg atgtacaccg gataatcatg aaggaaaagt tttaggaaca  27060
ggagaatata gagagccaac tacttatatc aagtcaggaa gtgttactgt accagttatt  27120
ggtgaaatga aatactatgt agatttagaa acagataaag gtgaagaccg tgtttatctt  27180
aatagagaag tttatcataa atttgataaa ggtgatgatt tctctaatgt aggtaaaaaa  27240
gtatataaaa atgatgaatt aatatataaa ggggactaat tagtatgaaa caatttatac  27300
atgataaaaa agatagttat aatagtacaa atcgtaattt tgatattcaa tattataaag  27360
gtataccttt acaacaaatt gataggggat atggtcaagc aagagctagg agatttacaa  27420
taaataatac gaaccaaaat atatggatac ctatgacata tttaaaacct aatggtactc  27480
ttaaaaataa cattgatata gattggatac ttgttaaaga aaaatgtagt ttaaagaaag  27540
caggattagt aataaaaata aaaattacag gagatgtatt ataatgtata tattagaaag  27600
aacaattaga ggttttgccg gtcaaacaga agatatttta ccttattact ttaaaagtaa  27660
gaaagaaatt gttaattttt taaaactaat ggagttcctt aaagaagaaa caaattattg  27720
ggttaaaaag aacggtaatt atactattat aatcagggct aaaaggatat tatacattga  27780
agaacatata cagaagttaa aggagtggga gaatgactta tgatgtttat gtattatata  27840
aaagaggaga acctattgca caaggtagta tggaacattg cttagatgtc tattattggg  27900
aaagggtaca cggttatagt aataaaggtt atgaactatt acctatggga tatgaacagg  27960
aggaataact aatgataaat atagaacatg attatacaat aagaactgta gataatagaa  28020
agtatactta ctatagtaaa catgaatctc cagttacttt atataaaaat attataggta  28080
aagattgtat tgaagtaact aaatacggga aagataaaaa agttattata gctactaaat  28140
atattgtatc tattgaacga tggtaaataa ggaggtataa ctaatgaatg ctaggaaagc  28200
acgtaagaac actaaaaact ataaggactc taatgtagta actaaagagc aacacctaac  28260
ttatatttat aataagttaa actacttgat tgcaaataat agtagtcagg gtaaaacata  28320
tgtggtaatg aacctaagaa cagattatcc tgatgagttt tctttatcta aattaaaata  28380
tctaaaagaa attaaacagc actataaaga cctagtattt aatgtgaaaa cgcaagtaag  28440
gaaggcacag tggtcagaga aaagtataat caggtactac tttaacctag gctatataga  28500
cagcgtgtta gtacctatta tacacattag ttggtaatta caaggagagg tagttatgtt  28560
ttttaaaaaa aagaagttaa gcaatgtaga gaaacaaata agacaaaacc gtaataaaga  28620
agacaaagaa agaaaagaac atcaagataa gttagataca gatatgtata aaacatatga  28680
attagataaa attgtagaag aacatttaag aaagttaaac actatatccc ttgaagaatt  28740
```

```
ataattaact tcagtgtgtt tagggacaag acttgtttat tattactcaa taggtaagga  28800
ttggaataaa caagtatata gtttaaacga attagaatat atgaagaaga aatttaagaa  28860
attaggattt gaaactcaga taacaaacga agatataggg tttcaacctt atatttattt  28920
aagattatta tgggatgcat aagtaattat tattaaagga gggatagttg gtgctgtacc  28980
tctaatgact attattattg cacagttaat tacagattat catgatagac attaagtatt  29040
gaatactgtt gactaataag gaggatatat taagaagtta aagttacctg gtaatattgt  29100
tgactagcaa gaagaagaaa atattattac tattaagtac ctgggaaaac ttttacctct  29160
ctcactcagc ctattactta ctaccgactt ccctaactac ttattctata gttataatat  29220
tcatttatta tacaatggta aactatagta ttccacctgt aaactatgct gaagcggtag  29280
taatctattg ttattatata ataatcttat ataatggtac gttaatctag tatattacat  29340
tagaatgatt ctaatctagg attttaatct ttagacccta ggaaaagtgg tactaaaata  29400
taaaacccta taggtatggg attcttattt ttaaaattac taaaaagtat taggttttcc  29460
ctagggcaaa gttttaatgt acctaaaata gtaagtagct ccttatcatt tagggttcta  29520
taattgagaa tattgaaagc taatccgctt caattgtaat taattgttga caactatgaa  29580
gtgggtatgt tatacttagt atataaaata ataggaggaa ttaataatga atctgacatt  29640
tgaagataag ttagaagact tactaaaaaa ggtacgtagt ggtgagatag aacctatcga  29700
gtactctcaa gttaatgatg agcaccctaa tggtaaaact acttgtggcg ttacttttaa  29760
gtttgatatc gacacaccaa ctaaatagga atatgaagcg gttaattccg cttctcttac  29820
ttagagtata taagtaactg tatattgtaa gtaggagtaa tcaaatttag gagatgagat  29880
agatgataat attatttacg caggattatg ataaaaccct aatgaaagtg atattagggg  29940
atattaatac tatgagacct aattggaagt acagtgttaa ccatcctgag aaagaagagg  30000
atgttcatat acaagcttat gaaggggaag atatatttga tgatatagag gagttatcag  30060
atagtacaca ggatatagtt ataggtgtta ctgaagatga ttgtatatca gagtctcctt  30120
atgactttaa tggtgggctt agattagtca ctaaacatat taaggaacat atagagaaat  30180
tcttataggg agtgataata tgattgatat atacttagga gaaggttata ataaagaata  30240
cttgtctaag gcactcagat taatcaatga ccatgctcct agggagttaa gttatgattt  30300
taataatgta gaagcggatg ttaatattca cacgatgtta tatgttaaac ctgaagatag  30360
gtatgtctat aaggatatat cttatgactt cccgggtgat ttaattattt gtatagttga  30420
agatgatgct attgtgtatc accaaggtaa acaggtttca ggtattagta ttttaagaat  30480
aatagaagag ctcatttaag aagcagttaa gtaaaaaagg ataaattgta ctagaaaatg  30540
tataccgctt ctgtatggaa ggctgagagg gcttagaatt gaaaggggag atataatgat  30600
agagatatac cttagtgaaa attatgataa ggatttatta aaagcggaat taaaatggat  30660
taaggagacc gcttcaagag aactaactta tgatgttaat aggaatccta acttagatgt  30720
acatgttagc ccatttagat atactaaaga tgaagtaaaa gaaataagtt tacatcctca  30780
atttgaagac gatgtatgtg tatttatagc ggagacgtgg atacatgaat accatagagg  30840
taaatcaata ggcgtagata gtatggaaga atatgtaaag gagatgtaag tatgtttaaa  30900
gtatattaca cagtctacca taaaggtagt atgaaaacaa ttaaagataa gctagataga  30960
agtagtttaa tatacttctt gtatgatact tggtataaag atattagtaa tgtattccct  31020
aatcactata ataaagagtt tggaagtaat agtgatgata tagacataga taaacttatt  31080
```

gaagcggtta atgaggaggg tatattactt atcaatagag gtaattatgt tacaataaga 31140
gaatggtagg ataggataaa cttaggatag aaaataattt aggatgagtt acgataggat 31200
aggatacgat aggataggat acgataggat aggatacgat aggataggat agggggttaa 31260
gttaggatgg ttactttaac atacactatt attcataaag aatctgatag ggtaatagct 31320
agtggtttag atgagttaga ggttataaac ttagttcaaa ggatggtaaa tactaatcta 31380
gttactgata tatcattaga tgattatata cgcagaccaa gtggagatat agatgtactc 31440
aatttactag tagatattag aagacaaggc gtatttgatt tcaatcacac ttggcacgta 31500
ggataggagg gataggatga tagttatata tacagatgtt tctaaggatt atttaaaaga 31560
cgagttctta ccttggctta atgaaaggga tagatactta gaagactata aagatgaatt 31620
acctgaggat atagattcct cttatattgt atcagttgta tactgtaagg atatggaagg 31680
tctattagaa agaaaagaca ttgttattgg taatagctat aatgaacctg tagctttatt 31740
aggtgttcct gagtttttg gtaattatag taattatttc tactatagag gagaaagtat 31800
tagtaaacat gacctaggag aaattgttag gttaaaagct tggcaacgta tgggcggaga 31860
ttgactaagt agctctccct aatttcacta agtagctccc taggaattgc ctaagtagct 31920
cggtatgatt ttaccctaag tagctccctc tgttttctac tagtttattt taaccgcttc 31980
aggtgtctat atatagacgg ttggaataat agcagaccgc aaaaataaat acactaggat 32040
attattccca gtgtattata taattttttt atttaaatct ttttatattt ctatttattg 32100
ttattctact tacattatac atatttgata attcttcttg tgtaaaacct ttttcagtat 32160
ataatttata aatatttttt ctttcattat ctgttaatga tttaccacgt ttaaaattgt 32220
ttattgtttc atctttatga tgtaaattat tatgttctgt agggctaata cattgtaaat 32280
tatttatatg gttattttgt ttattgccat ctatatggtg tatatgataa tcttgattaa 32340
aatcattgcc aaaatattca tatactaaac gatgtataga atgatgttta taattaattt 32400
taactatttt atagccttgc ttatgattat gaggttttac taacttttca atcatataat 32460
aattaccgtg tctttttatt ctaccatagt tagatactga ataattaaat atattattaa 32520
tattattttc tatgcgtttc catttctcat taggtaaatt attaatacta ttataatctt 32580
ttaaattgta ttgtaataaa gtatcaattt taacttttct tgccttgttt atatcatctg 32640
tcatacgata aaagttattt ttatcttttt ttaattcctt atttgttttc tttgaatata 32700
ctttgttttc ttttatatag tattttgaaa acatttcaat gttatttata ttatgtttca 32760
tcttctcaac tccttaacta tattctacta tataataggt aatttgtcaa gttaaaaaag 32820
tttttaaaaa cctattgact tattactttt tagggtgtaa tatagatact gtaataaata 32880
acacgaaggg aattgatgaa aatggaaatc aaagaaattg ccgatacaat tatgtattta 32940
tttaatatgg atggttacag atgtgcagaa cctccattat atgaaagcac actaaaccac 33000
acacgcacac acacggcgtt aattgtttct attaagggaa actatgacac agtgcagatg 33060
ttccgcaaaa cgcctataat gagcatgaga gggcaaagcc aaccggctag tatgttagta 33120
aatgtaattg atgatgtaat tataatagta tatgaaaatg tagtgtacgg agttcaaaac 33180
aaagaaataa aattcattga agaaatttaa aaataggggt tgcaatcctc aagcatctat 33240
agtaatataa taggtgtagg ggatagcaac acacctcaaa aaaacttttt aaaaaagtta 33300
aagaaaagtg ttgacacctt ataagataca tgttattatt aagataacaa ataagacaag 33360
ccacttagca aataacgaaa ttaaataaaa aaattataga ataggatttg attattatga 33420
caaacaaaaa ttacttatac gaagaaactc acacagtaca agggcaagac attacggctt 33480

```
tcagaattcc aaacgacaca aacggcaacc cacgttatgt agtgcatttc atggatttaa  33540
atattaaact agcagactat gacaacatca ataaactata cggatttaat aaatatcgtg  33600
ctaaatggtt tggcggtggt gtagtattcc aaagctataa tatagaagat acattaaatt  33660
ttgcactaga taaagttaaa gaaatagaag cggttaagaa ttaaaaccgc ttctgaatta  33720
aataaaaaaa ttatataaaa aggatatgat aatatgatat tagaaataga aactaaacca  33780
gttaaaacat tgaaagcaat taaagacgat acaaaaaata ttaaaaatag tatagcagaa  33840
catttaggat taaatagaga acaatttaaa ttatcaaatg gtttaataac tttaaaaggt  33900
tattcagaag aatttaaatg ttggtataat ttaactagca caattggtaa ttttcctaaa  33960
tatttaaaat cagaattata taatgaatat aaattatatt gtaatgtaga attaaaaact  34020
aaataaatta aataaaaaaa ttatacaatt ccctaggatt agatttctag ggatttttat  34080
ttattttaat ttatataaaa aatttattta ttaaataaat tagtgtaaaa ttgactattg  34140
acaaggttgt attttttatg gtataatgaa gtgaagacct tttttagtat aaaaaaatta  34200
ttatataaaa aatttatatt aaatgatttt agaaccgctc tttctcgtta cctcgtcatt  34260
tatatagcgc aagggatagg caacttagcg ctttgtttta ctttctatat atagtatact  34320
atgaataatg gtaattgtca acacctttca gaaacttttt ttactttctt ttattattat  34380
ataaaaaaat tatacatatt ttatggctcc acttccatta tataataatt cagtcttaat  34440
gtcaatagat aaatgtaaaa aagtttttta aattaatttc attaaatcta ttgacttgtg  34500
tttctttcta tagtaatata taggtatacc aacaagggag gcaatacaaa tgctaaaatt  34560
caaatggaaa aacaaaacaa ttaaatcaac tcaaaaaacg gataacattc tattacttat  34620
tataggtggt ttagttgcaa caatcacacc taaacttgta aactggtttt tactactaca  34680
agataatata aatatttttt taagataact attgacaacc tagaaacaac atgttaatat  34740
taagatacaa ggtaagggaa gcggttgacc gcttccaacc taaataaaaa aagtttaaaa  34800
aaactattga cagtcacttg aaaccatgat attattaaga taacaaaaaa caaacagaaa  34860
aggaattgat gaaaatgttc aaattacaaa ataaagtgga aattatcgta cctaaggaag  34920
ataacaacgg cgttgagatt gcagacaaac gtattaaaga atatgtaaac agtatcacaa  34980
tggaagcggg cggttgcact attacagaaa ttaaggggca atggtattca gaagatgaaa  35040
agcgtatcat ggaagataac aacttaaatc ttgaatggta ctacattcca gaccgtgcaa  35100
aattcatgac agttgaatta aaaggcattg taagacgttt aattgaagtt tacggacaag  35160
aggcaatcag tattaaagtt aatggcacat tgtacattgt agaccaatca gacattgaag  35220
aattacacac aacattatta aatatcatga aataaaaaat ttatataaac cgcttcggat  35280
taaattcttg aagcggtttt tttatgtaaa atttatgctt gacaaatgta ttaaaaaatg  35340
agataataga gtgacgactt tttttagtat aaaaaataata ttatataaaa aagttataga  35400
gtttttaagg ctccaagtcc attatatcaa ttttgctact ggttgtcaat actttctttt  35460
tttatataat aatttaatta tcttaaagat accgtccact tccattatct caaattttcc  35520
cccaaagtca agaactttct ttcaaataat ttatttaaaa aagtttacaa aaagggttga  35580
cttattttgt actatagtgt aatatataaa gtgtagtaag gaagcggagg aaataaccta  35640
aaaaaagaat ttaaaaaaac ttttaaaaag gtgttgacaa acttccaaat acatgataat  35700
attaagatag ttaaaaaaac aaaaaaacga aaaggaattg ataattatga acagattaga  35760
aatagtaaaa gatacggcaa tggaatatat ccttatgatg gataacagtg ttatggacgg  35820
```

```
agttatgaca caagaggaat acaacgaagc ggttagcttt gaaaaggtgt atgactacac  35880
tctatcagaa gcaaataaag aatgtaaatt cttaggcggt aaagttttaa ctttcctagt  35940
acatgaagca atcgaagaat acgcataaaa aaacttaata aaaggggttg acattcaacc  36000
cctaccatgt taatattaat atataccaaa tgagaggaat tgataattat gagatacgaa  36060
attgtaacgc tagttaatca agaattgttt atgtatgcaa cattcaacaa gcaggaagca  36120
gaagcaaaat atagtgaatg gtgtgaactg tacggtcaag aaaatgtaag catggaaaaa  36180
aattaaaata agctgttgac aaactaaccg cttcatgata atattaaact atactaaaga  36240
aaaggaaatg atacaaatga aattattaaa ccaagaaaac caaatcgtaa ttagcatagc  36300
aacattagag agtgtcaaac aagccctaat ttgggaatac atcgaccaca tagattataa  36360
catctggaac aatgaacttg atgacacaga agcggttgta aaaatttctg gtattcttca  36420
atcaatcaaa tttgcagaca ctatggaaga cctgcaggaa tatattgggg atattggttg  36480
gaaattaatt taaaagaatt tcaaataact gttgacacct tagcagatag atggtaacat  36540
tagggtagtt aaaaaatact aaatgaaaag gatttgattt attatgaaaa aaaatgttaa  36600
agcaagcact attgaatggt tagaattgac tcaagggcat ggggagtttg atggtttcga  36660
tgaagaagat atggacttca gaaaactaga tgatgaagat attaaatggt attttgaaaa  36720
ttggtacttt acagaggaaa aacaagaaca gattatagac gaaataggtc aagaggaatt  36780
tgaagaagcc tattcagatg atattaaaga atacaacaat taatacagga agcacacaga  36840
gacacacaga gaagcttaac cgcttctcta atattaaact attaggagat gtttataatg  36900
acaaaattta aattgattga taaaaatagc ttttacgtaa atgacaatta caataacgaa  36960
acttatttaa cttctcaaat tgttctatca ggtgaagcgg gtagattgtt agatgatatg  37020
atagaagatt gtgaagacga acacgacaaa gacaattaca agaaactaga cactaacaat  37080
attgatgata ttgattatat attggaatgt gctaacgttt atatttaccc ttacaataaa  37140
acggaattta aatattaaaa taggagatgt tgaatatgaa cacaagacgg gcaaataaag  37200
cgttaaacga agcggttaga ttattagata agcaaataga agacacacag aagaccatgc  37260
aggagctaaa caaacaacta gaacaacaaa taaaagctaa acaggaacta atgacactag  37320
ttgacgttat gactggtgat gatgagtaat gaacattaaa gaagctcaca aggtcgttag  37380
gagtgcaaag agcaaactcc tgcaggagca ggagcacata acaaaccata tcatagagga  37440
ctacatcata gaggagcttc acagacgcac acagggaagc ggaacaatac agatgaacaa  37500
taacaccgct tcatatagca atggctcata tggtagctta gaagagctta gagaagctta  37560
tgacctatcg tcattatcta ctggtgagat taaagaattg cttgaaacat ttgtttaaat  37620
ttatttaaaa aagtttagtc aaaactattg caatatcttc agaatactgt ataatagtac  37680
ttgtaagata aataaaacaa agaaaaggaa tgattaatta tgaaagaaca aatcaaacaa  37740
tttgagaaag aattagaaat ggcggtaaat aacttattcg tattacatga ttgtggcgta  37800
tcacaagcaa agattgaaga acaaaaccaa aaagttgtgt accttaaagc tatcgttgag  37860
aacatgaaag cctacgaaga aatcagagtt gagccaaaga gtgaagagca atttttcaaa  37920
gaacttgaag aagaacttga agaagaagaa aaaattttaa aaggaattta agaggagggc  37980
aaacgccctt ctttattttt atcctattat ataatttttt tatattatac gggggcaggg  38040
gtaaaatgcc actcaatggg ggtgggtcta tataccccta cggtctaccc aggtacttat  38100
tttttggagg aaattatgaa aataaatatt taaaagtcaa caccctatat gataagtcaa  38160
cattataacc ctaccctgta agtcaacaat ttatagtata aataagaagc ccttaaatat  38220
```

```
aaagtcaaca tatctaaaat aaaaaaagag aaagaatatt attcttcctc tgaggtatta  38280
ttaataactt ctaattcatg aatagtaatc atatcttctc taaataatgg tacatcttct  38340
atattatctt tataatagta agtatacccg tcttgaaggt atccgcttat tttttcttca  38400
tagccttctg ctttaatacg tttaattaag ttctccttat ttgtgtaaac tttatcttct  38460
ctgtaagaat agttatcttc atagggttca caattatcgt gttctacttg atatagtttc  38520
atattagtta tcctcccttt cataagacca ttcaccgtat tctgcactaa agtgggctgt  38580
gtctgtaccc tcatcttcat attctacact ataccatgca tcttcttctg tttctgcatc  38640
tatatatctt acttcttctg tagtaataat acgttttacc ttaaatctct ccatttgttt  38700
ttcctccttt atattttcct ctagtatttg ttttaatgtt tggcagtctt tttggtctag  38760
agtatcccaa ctctctagat tttgtaattg ataaagtaac tcatttacaa tttcatcgaa  38820
ggcttctgct tttctatata cttcttctag ttctgtttct gctaattttc tatccccttt  38880
aatttgttct gctttagtta ctaagatatg ggctttattc atttcctcta taataaagtt  38940
tttatagttt tccattatta tttatccctt ctattttcta tccgttgttt tatctcttcc  39000
ctattgcggt ggtgctcctt actcatttct ttacgttcct tatttgttaa ccttattcta  39060
taaacaaggt aattaatgta tagggtgccg gctgaccata gtagcaagaa tgttattaga  39120
taagtccatg agatactaat ttctatcatt gtgattcctc cttatctatt gtaaaggatt  39180
tacctgttct agagaatagt ttaaacattt cttcttcaaa atgcccatca ctcatatctt  39240
tatctttcag catttcacag agtttgtccc atgcttctgc tttattataa attgtttcta  39300
cttctctatc tgtttcatca ctataatttt catatataat ttgtaataca aaatccttct  39360
catcgtaaca tttttcatta atatcatatc tcattataat tcctccttat attctttata  39420
gctcttgatg gctattttac aaatacctct atttacagca acaaatacta taaatgataa  39480
tagtgttata actgctctta catctcctgt aaaaggtaat aattggaaga gcaaatagct  39540
ttctaaaaca ctaatagctg taatggtagt tagatataat atagatagta agtaatcctt  39600
taattttagt ttaacaaatg gttttttgtg ctcatctgtt cttacaatac cataaagtat  39660
tataaaccac ataacaggta ctaactgtat aataaaatca ttatctatat tcaatgcatg  39720
tagagcgtaa ataataactg caggaatacc tataatgaat gctaggaata cagaaaatat  39780
aattaacatt atagggaggg ctacaagaaa acctagcccc tgttttgaat actctaatgt  39840
gtttttacct aggaacttaa aaaatgtttt attcatcttc ttcctccctg gaattacttt  39900
ctgtaattgt aatttctaac atattattgt aataatcatt cttttgattg atattatagt  39960
tatcattgta ttcattaaag tctacataaa tatattcatt tgcgtcattt tcataaataa  40020
tatctatagc tgtaatatct gaatatgctg taatcatttc ataagcgttc gtattatcag  40080
gataagcaaa accaacttga ggtatttcca taggcttatc aataagaata ccaaaataag  40140
tacagtgacg tgttcggctt atatttgaag tctctttata tgtaccgtag taatctatac  40200
cttctgtaat acctgatata tggaacctgc ttacgtcttt agattctaat cttacaacat  40260
cgcaattttc taatactaaa tcaatatatt tgatattcat tttaactctc cttttatatt  40320
aataattctt tccattcttt atcaaccttt ttaagttctt ttttattata gtctccatct  40380
ttagttacta cagtgttcca ttgaaacttc tgtaataagc taaaattatt tataatccat  40440
atattacttt tactataata catattatct tcaaatctta tatctttttc tataaaatat  40500
ttatatattt tatatcttct ttcatctgca cctgatattt taataatttc attagtattt  40560
```

```
aattgagtgg ataactggaa gataacatct tttactttca ataggtcttt aacattacct  40620
ctacctacat ggtcattata ataatcgtac ttaacttttt tcttttgttt tctatcatta  40680
actacaatga atatattata tacgatataa gctttaaaat gggtataggt agtaggtgct  40740
tctgaatcat cacattcttt tcttaggtct gtacattgta tttttaacat aatattattt  40800
gatatgttga ctacggtaga accatcatgt tttttattga gatttatctt atccatttta  40860
taattaccta cttattgtag atacaatgta ctcgaacatc ttccattact ttgcctaata  40920
gattctgacc tttccagtta ctttgctcta atattttagg gtcatttgct ttaagaccta  40980
ctccccatat tttatcataa ggtgaagctt ctacgaaatc tttacgtaca tctgtgtcta  41040
atattctttg ctttaggtgt gtagtcataa atttatcttt aactacttct accataatat  41100
catatcttac tttattccat tgctcttcat taaaattacg aactttacga cctaaacttt  41160
tagcatggtt tggattctta gcatttagta tttcacctgc tatttgaaag tcattaaagt  41220
atcttgcttt acgccacata aaggcttgct ctgagttatt aaatgttctt ccttgatgtt  41280
taaactttat agggtagaag ttagaataaa tatcctcttt accccaaaac ataatatatt  41340
cacttgtttc tctcataata tttctccttt aattccatag tgatggtaat acaattttaa  41400
aattatctaa tattttactt tgtacctgtt caagctcatc atatttatcc atatcaaaat  41460
catccatttc tttatgataa tattttatta agcttaaaat atgttttatc atatctattt  41520
gtgttctttc tttgccgtct acatctacaa aagtatggta ttccatatcc acatggttac  41580
tactctctac aaatgcgttt aagtcagcgt ataactggat aaagaaggac atgtcataat  41640
tccaatactt aggctcattt ctacctagtt ttttcttcat tttcttatat tttttattct  41700
tttttagtcc aaaaacttct ttttcaaagt catttaattt aagaccttta aaatattttt  41760
tcttcatttc ttaacctcca atttaataaa tggaaaatca atgtttctaa atactgcgcc  41820
gacatcacac attaatatgt ctccattaat ttctacttct ccactgtcag ttggtgtatg  41880
accacataca taggtaaaac catcttttct aggttgaaaa tctcttgacc atattaattg  41940
gtcaattgtt tgttcttcta caggcttcca actaacccca cctgaatgag agaatatata  42000
cttgtcttct ttatagtact ttctacaatt aaccataagt attttaaatt ttctatagtc  42060
gtctgattct ttaagtttct ttagttcact tttaataaaa tcataattat ttcttagatt  42120
ttcctctaca ctactatatt ttaaagttac cgtactcaca ccgtaagagt taagtgtttc  42180
tatacaatat cttgagagcc attcaatatc atagatactt aatcggtcta cgttttccat  42240
aatattataa aactcatcat catggttccc taacagagtt actacattat catcattaga  42300
cattaaatca aatatatagt taacaacatc ttttgacctt ttacctctat ctacataatc  42360
tcctaaaaat actattgttt cttcaggttt tctttcatta tttattttat ccataattgt  42420
taataatttt tggtattctc cgtgaatatc gggaacaacg tatatagcca tctaatctcc  42480
tccttattgt atataactat cttaccatac ttagtaaaaa aagtcaataa aaaaacctac  42540
cttagtaggt aggtaattaa aattatttat atgttaattt aatttcaaca tttttatact  42600
ttttacgacc atctgttcct gttgactcta gtgtaagaac agatacaaaa tctttaacct  42660
ccggtgttct gttattagtt gtaccttccg ttgcagtagg tactgttaac cagtaagggg  42720
agttagatgc taagcttgta ttattaacta gtgttttgcc attatattct aacttagtaa  42780
cagacttacc tgttaaatct aacttagttt tatctatatt aatcatgaaa ctttggtctt  42840
ctttccagta tatagctgtt ggtgtgaatg ttgctgtata cgtaccatca ccattactta  42900
caggtgttat agttcctgat gtatctcctg ttggtggtgt actggctgta gtatctttgt  42960
```

aacctacttg agtatattcc cctacaatat tagtttttgt tttatctaca tagataactt 43020
taatgtaatc tctcataaac tctagtcctt gagcattatc atctatagtt atgaaagcat 43080
ttaagaagtt ttgaacttcg gaaattctat tatatttgtt accatcttca taagcaggta 43140
aagtatacca gtaaggtgaa ttagatgtgt agccttcggg gtttatcaag ctcttaccat 43200
tataagaaac atttaatatc ttattagcag ttaagtctat atcatctgta ctcatgttca 43260
taacaaagct tgtatctttc ttccatctca ttccagttgg tctgattaat ttagaataaa 43320
caccattacc taaatcctta acagaagtgt caatagatgg tgggcttgct atagcaccta 43380
cagtaccttt actttctaag aatgattgta tagtgtatga tataaattca tgacctttag 43440
cattaggatg taagccatcc tccatgcctt ctttccaagc aaagaatgtt ttatttacat 43500
tgttatccca tactctaata ttactctccc tatataagtc taatacagga aatgaaaatt 43560
gttttgctat ttcttttata acatctacca attgtcctaa agtatatcct tgtccgtttt 43620
caacttcttt aaaaggatta ctttcaatcc taggtgttgg tgttagaaca acaataggta 43680
ctgtaggaaa aaccttagat agttgataat aagtataata gattgaacct gctactgtag 43740
tgtaagagtg ttctttagct gttcctaggg gttttgtttt acccccaact aaaccatagt 43800
catttgtacc taacataacg caaattaaat caggtttatc tgtaatagtg taggctacgt 43860
ttttacggtc ttggtagcct gttccacttg tacctttatt aacatttatt aatcctgttc 43920
tgtcagcaat aaattggtgg tagtttttttg ttgttcttgc atttacttcc gtaatactat 43980
ctcctatgaa tataactttc ttatctttca aaggtgagat agttgttgta cttggttgtt 44040
gtgttggttt attatcagct ataagcttat ttatttctgc cataaattct tcttttatat 44100
ggtcgttaaa ttgggtatct ataacatcct gtaaacctat aatattttct gcttttatat 44160
tcataggttc tacttcatta taagtaacaa taataagttt gtcctgggat gatgttaagg 44220
taacaaattt tggtatatct acttttattg attcttcacc attaatatcc caacaaattt 44280
taaagtgccc tgcttcgtat gttgtatcag gatttaaatt ctctataact atttgaccta 44340
ttgaatcttc tatgttttca cttgatttta aaagattatt ttcatagtca taaagcttca 44400
atttcttagt catatttact tctcctttta ttgaattttg tacaactata atatatcaaa 44460
aaaaatttaa aaaaacacct atttaactta aataggtgtc cgacagagct cccgtactta 44520
gattacggtt aataatattt tacgacaatt atatgagacc ctctgtcgtt gaaacgctcg 44580
tcactgcgtt atacctcaca agatattttg acagttagct tgtgagaaga agattgtttt 44640
ttattgtact tagtttatac actctcaaaa gtacatgtgt actatatatt tatacaccaa 44700
gcgtttggtg ttagatacgg aatggaggga cactaccatc cggagtctac ggtcagatac 44760
aaagcctctg ccgggcaaca tacggtatct ctcgtacatc aggttgacta aacctttaga 44820
gcttttcact ccttctctta taaccagtaa cttaagagaa ataggtttta cttagtagat 44880
atgaaacaat aaatccacat acaatattaa atcatagtca agtgattgca catatgtcta 44940
atacctataa gttttctgct agcctggtat atggactctg caggactcga acctacagtc 45000
aaaccgttat gagcggttgg ctttaccttt aagctaagag tcctagaaat atcctgagag 45060
aggactcgaa cctcaacgac taggtagcta catctagcca atgccattac tcaggattgc 45120
tagtaacgct aaatagaatt ataacgttac cgtagacctt ttctacgctt ggtagatagg 45180
taaaatataa tgatttcaaa gtacccatat agttaggctc ttactctcat tatcaggtta 45240
aaaaggctaa ctgtatttag cattatataa gaggctttag ttaactacta tactaataat 45300

```
ataccataaa ttatacttaa tgtcaagtta atttatcaat tgaatctata atttttgatg  45360
tgctacgtat atccgcttct ctactatgtt taaggagata ttttaatttc attaaaaaag  45420
aatttttttc tttttctata atatcttctt tatcattgta ttctgaaaac ataatgaatt  45480
ctatacctat actatttcta ttatgtgaaa acatatttat agaaaaaggt gaatcaaaat  45540
ttttatcatc tttattaata ctaaagtctt cagtaacatg taattcattt atttcagata  45600
tttcaaagta cccattaact cttttaagtt caagataact attatatcta aaataacgct  45660
gttcttctat taacttctct tttgttagat aaggatactc atttataaat ataggattac  45720
ttgttccata gttatctcta atatattctg cgtcctctaa agaatcagta taacctaaaa  45780
cttcataact tgttgtatac actgtatctt cttcccacaa gtcatagtcc atttcctcta  45840
tttcttcttc taatatataa attttttcca tatattactc ccaaatacca ataagatttt  45900
taagcttagc tataacctct tcttctgttt gataagaaaa tacccctgta atatgttcat  45960
agttacctac aatttcataa tcttgtgtac catgtttatc tactaagtat gagttattca  46020
taacatttaa actatcttct gagtaactaa aatttatgtt atagtctact aaaaaattaa  46080
taatattttt catttacata acctctccta tcggatattg tcctagcatt cttgttccat  46140
tttcattata aaaagtatat tctactacaa taatattcat catatctaca tatatagctt  46200
ctatatatgg tgtaatattt tcctcttctt gtatgtgctt acctatgata tcatataata  46260
attctgagtg tattctttta tctctcatta tagacctccg taaggaatgc tacagttttg  46320
tctttcaaag atttttctac taattccata gcatctttat agtgtttgat attagattca  46380
ttatacttaa gtttatcttt tacttcttga attagaggct ctactttatt aaccaaatct  46440
tttttctttt caatacttac attgcttctc ttattgtcta atacttcttt tggcatatat  46500
ttaacttttg caaagtcttt atagctaaca tttaagttat ctaaatcatc taataaatca  46560
ttatagtatt ctaaatgatt atagaatgta taaaacttaa caaggtcttt accagttaat  46620
tctccttttt ttagtatgtt attaatatta ccgataaccg aatatgctat aggcttaaaa  46680
ttagctctaa cataagttaa aaatataaaa tcatcataaa ataaatctaa aacagtttta  46740
ttaaatctag tatttttagc ttgctctaat tgagcacata aattaagaac attatcaaac  46800
ccacttttta gcactaaaga gataaatctt tctactgcat agtatcttga tacttctgta  46860
tgcttacttg ctttttcatt attcctaaat atagtatctg ataaaggttg aacaactaaa  46920
ctcatgtaat ctttatctga atgctcatct gatgttcctt gataagtact tccaaattct  46980
attgttgata ataagaaact tttttctagg ttcattataa catcctcctt ttatttgtta  47040
tttaaataat aacatatatt gataataatg tcaatactta tatatcttct tctgtatcaa  47100
cttcatcttg tttatactta aagtgttcat agactttaaa tagtataatc cctagtgtta  47160
ttaatcctaa aatatatttc atagtaatcc tccttaataa ccatgtttag ttacccatcc  47220
tgctaaagca tccatagcca tatcatattc ttcttcattt ttaattctta taattttctc  47280
tatttcttcc tttgctttct tagaactaat aaaatcaata tcagtatcct ctaggttagt  47340
taattctaaa ttttctctaa taaaattctt ttgacttggt gttatagaat taactcttac  47400
attttcgtga tttagaaatt ggtaaaagtc catattactc atcctttttta acgtattctg  47460
ccatatcttt taaaatactt agtacatact ctaaatctct atattggtca tctaatgacc  47520
ctataatagc atatggtgtc atatcccagg catgtgcaca gtcaaaccct aatactctct  47580
taccctcata gtcataatca tcgtaagtga tacctctatg agcacgtctt tctaaggagt  47640
catattcttt ttcattgata tctgaaggta aagttatata tccatttaga tgaccagttt  47700
```

```
cagggtgtct cttaacagtt agtttaactc ctttataata aatatcaaga cttaaatctt  47760
ctcctagaat attgttttct ttttctactt tttccataat gtattgaggt gcttttttaa  47820
acataatcag tcatctcctt tttatttata tctttactat acactatttt ttctattttg  47880
tcaacaaaaa aaggctacta attaaagtag cctaaatact aattatttag cattgtattt  47940
ccattgccaa taaccatttt tctgtgagaa ctcaaagtga aaaccatcat agtcaaattc  48000
aatattatag tctccatctt gaagtggttt tgaatttagt acaggactat tactctttgc  48060
caattctgct agaaactcat gatttacttt ttccataggg tttactcctc ctaattattc  48120
ttacagtact aatatatcat aggtcttttt ctaagtcatt tttaaaagtt tcctcgtagg  48180
aactagcgta agtaacctca taacccacta cgttagtata tcctacatat aatgacttat  48240
aattagattt tatcttaata tcttctgatt gttctagctt atttaagact tcatttaaat  48300
catctgagga atagtgttca ttatctattg ttattgtttt tccttgggta tagatatcaa  48360
tttcttgtat catcatttca tccttttgat tattcattat ttgattataa gtttctaaat  48420
catcaatgtt atctgtatct gaacctttta ctaaccattc tcctctcttc ttaaggaggt  48480
catcaaactt ctcatgctct ttaattatct tttctacctc acttggtatt aacacagccc  48540
tagcatagtt tatatgccac atagacatat tatcaataag ataattaacc attcttataa  48600
tctcttttc atttgccata taccaacctc cttatatcta ttattaatat aagagaaaag  48660
cagacttatt aaaagtctgc ttctttacct aattctaatc ttctattttt catatgagga  48720
atcgtttttt tatttcctgt taataatgat aattctctag ctttttcttt agataatgtt  48780
agtagtccat tataattatc tactttacta ttatattgtc tgactaagta ctctagttca  48840
tcttctatac ctgctagttc tcctgattta actccaagta actttctata catgtcataa  48900
tcttcagaaa gactttctac tttgttttta gatacagaat cataaactgc ttgtaaatta  48960
ccttcttcaa taagtttaaa attatattca ccaatgatta attctttttc agaagagtca  49020
agggtaacta aaccacttgt attacctgta aagtcacctt tataatctac aacaattcct  49080
tcagttattt tatctcctaa ttcaatagtc ccatcttcat tttctttaaa tttatgagca  49140
tcataaactt ctactttgtc acctaatctc aaatcttgag ttaagttatg tttaccgata  49200
attctatcca ttacttaacc tctcctttat taatagggtc ttgtgttaag aacatttcta  49260
agttctcttt tgtaataggt aaccaaaaat atttactttc cggaattgta actgtataga  49320
agtcttcatc attattaact ttgatgttaa catctgtaaa ctcatcttgc attaaccaat  49380
gagttacagt taagttatat gacccatcac taacataccc taaatcaata tcatgtctaa  49440
aagccaaatc ttctaaatgt tctaataaat cattcttttc attatgtttt tcttcttctg  49500
tattattttt aattgggtta attaactctg tacaaacgat atcgtacaat tcaccatctg  49560
taacctcata gttcttttca attaatacat cttgtatttt attgattgaa tttgtaacta  49620
ctttcccata ttcttcttct gtaaatttac atttatctaa atcaacatct gtaattaatt  49680
ctgcaatcca tttatttaaa attgatactg ccattgttct agaaataata ctatcgtata  49740
ccatatttat ttaatctcct tatttaggtg aatgtggtct tctaatgaaa aatcaaaagg  49800
cgctacacca tttcttttat tatttgtttc ttttttaagt ataacataag ttagtgaaaa  49860
agtcaagata gttactacag ctattgataa aagtttaatc gggtttttca tagttactct  49920
aactccttaa gtttattttt tactttctct ttatcgtact tataatcttt actagagttt  49980
tcattttttt ctttctcttc ttcattaagt tctctatact gagcttcttc tacctcttgt  50040
```

```
tctttattat cgttattttc ttctgctttt tgaatttcta catttttact attaccacca  50100
tttacctttt ttctaaaaag aaaccaaagt attaataaaa tgatgagtaa aataataatg  50160
cttaatacaa cagcccaaat attattagcc attacaacct acctccgaat agttttttta  50220
cagctcttaa attttcagat gaatcgttat ttatatcaat ccctacgcta gaatcaaaaa  50280
ttacagcatt atcaagtata tgctctgtta atttattacc ataactactt ttacttacca  50340
cactaccata accatgatta gttaggtcaa ccatatcagg ttcaacttct agtactctaa  50400
aagatattct acgtaagaat gaaggattta ctaagtaaaa ggaagattta aaaacattta  50460
atctttgata agaatgtttt atattaacaa caaaccctgt taacttatct tcataccctg  50520
aatttgataa tttacctaag taaaggttta tactatatcc ttttgtttct aatgtttgaa  50580
tagcacttaa cattatagca cctctataag caagattttc agggtcttcc ctccaactaa  50640
tactagaatt ataaaataca tcaataactt tcttctctgc tttaactctt tgctgagaca  50700
tcatagaatt aggtaatcct tttatagcat taggtacgtg aggttgatat ccttccggag  50760
ctacgacagg ttttcttttt actgacttat ccattctaaa taatgcatct gtcatttttt  50820
taagtttaac taccatatca tatgactctc tatcaccctt aaccattaag ttataggctt  50880
cttgaaaact atgagtccct gtaaaatcat agctacctgt atcggatgaa ttatctctac  50940
ctgaaactct attctttttt aaagcagaaa agaaatcagg tagaccatca tatttaatta  51000
catttaattc tgagttatct attaatcgtc tacccattga tttgcctcct attctaatcc  51060
taatttatcc ataattgtat caaaatccat tgaatctttt gatgtactat cagattttct  51120
aggttcctgc ttaggctctt gttgcatacc taaaagcttt cttgttgctt ctgtgtatct  51180
gttaccttca ggtaaagagc taataaattg attaatctca tctttcggta cagatttaaa  51240
gataatactt tctacaacaa actcatcttc cattactcca tctaatttac taccattaat  51300
aattgcacgc attgagaata cataaggtaa tcctttttca tcattctcat gtcttaattg  51360
ttgtacaaag tttactaggt cttcattgct tgatagttga tgttccacct tagtatcata  51420
gtcaaattca acttgagcaa agcggtctaa tgtagctccg tctaattgtt gtctacctac  51480
ataaatatgg tctgctcctg ttcccatagt attacctgct gacacaactc tgaaatcttc  51540
atgagctgtt acacgtccaa tagggaagtc aaagtattta tttgcaatag ctgaattaag  51600
aattaatagt acttcaggaa tagatgcatc catttcatct aagaagaata acccaccttt  51660
tgtaaatgct ttatagaatt gagtttcatg aaacttacca tttgcatcaa taaatcctgt  51720
taatttaaat tcttgcgtaa ttgcattact aaaatagaaa tctaaatcta gggcttctgc  51780
tacttgttcc aatacatggt tcttacctga acctgctcca ccttttaaaa atactggaat  51840
attttggtta actagcttta gtatatcttg gtatctataa tgaaagattc ctgagatatc  51900
tttaattgtt tttccttctt gttgtaattc aattttaact ggtaaattac taagttgttc  51960
ttctacatat tcttcaattt gttttttaac gtcagtaata ataatttctc tactctcagt  52020
tcctgctttc tcaacaattg catctacaat tgcttgttcg tacggattag agtttttctc  52080
tcctagtttt tttgctaaat ctgctgttgt ttccatttgt tgctctacca atctctctaa  52140
tctttcaata gtatcttgct ttgccatatt tatcattctc ctttgatttg ttatacattt  52200
attatattac aagtatttga atttgtcaac aactttctaa aacttttttt agttgctaat  52260
aaaaaaatac cttacaccta taacttaaca tagggtaagg taattgtcaa cacttttgtt  52320
aaaaatacat taatttaaaa aaatcatcaa tatctttagt ttcatgtgta tccatatcat  52380
acataaacat acaattatat gtatgattat tcattatttc taacatgtta tgcatagaag  52440
```

```
ttgcattatt gaattcctct aaatcaatag ttaccgtaag ttcttgacct tcataaagta  52500
tgtttgctat ataatatttc ttaacacctt ccattgttcc atgagaagtt tcattatgat  52560
taagtacttc tacacctagt gaaggtaaat attctgaaaa gtaatattta cagaaatata  52620
taaaattgtc tgttctttta gacacgagta ctatctccgt actttatatt tctttctaat  52680
cgtacataat atgttttaat tttttgtact tctttatcta ctgcatcctt tcttcctaac  52740
cttgtagtat attttacaat attaaatatc atagaatcaa caaagccatc ataagaaaaa  52800
tgttcttcta gaaaagaaat aacatccttg ctacctttat agtgctcagg taaatgtgca  52860
tctacttgta tattataata attttctaaa agacctatac tctcaccaag actagacaaa  52920
gcgtaaccta aatcatttga atcattagac cattccttag atactgatag tgcatcttct  52980
ataattgtta cttttaattt atctaaataa tcttctactt gagcttgtgt tttcataaat  53040
tcttttgcgt tcatgtaata ccctcctaaa ttatataaaa aaacaccctg cttggctaca  53100
agcaaggtga aaaaggaaag atattatgga agtgtactat ctaagtacac ctcataaatat  53160
aacagttttc cttgctagtt attacttatt ttttaaggtc ttcttctttt acaaacactc  53220
cattaataag cttacctttt ctgtctttta tctcatcata agccatatca atacactctt  53280
caatatctat atctaactgt aagcatagta ctgttaatac tacaaaaata tccccaacac  53340
tatctcttgt tacatggtca ttacttttag caatacctga agctaattct cctgcttctt  53400
ctaataattt tagcatttga ccctcgggtt tacctgtttg taagtttcta tcttttgccc  53460
attgtttaat aagttctact ttttccatta ttctatatct cctttaattt ctgtatcttt  53520
gataattagg ctatcagagt cacttgttac atttaaatta tcttcaacta attcatgtaa  53580
attattagta atatcttctt catacctata acctacacga acataagctt taactctgat  53640
atctatatta acataatctt cttggaattt ttccatttct aacttccttt attgtatcat  53700
attattatac tattgtcaat taatctgagt agtttccttt agcaagttga tactttttgt  53760
gtaattcttc atataattct ctcatacctt cgtagtttct catatcatct tccaagaaac  53820
taagataatc taataatact tttacatcct caggttctaa agttataact ggttttacca  53880
ttaggcaacc tccttaaatt cttctttatt tattttctta atatcttttt ctaatgcttc  53940
ttttaattca ttaggtaatt tataggcatc aattgattgt tgttgcccta gtacatatcc  54000
attatctgta atacgtattt caactgtaaa ccatgaatta tctaaatctt cttctagtct  54060
tgctaacaat attaagcaac tgttctttat aattcgatta gcatacccgc caacacaatg  54120
agatagcatt ttaccttcat ttttcagttt acttacggta tctgcaggaa ggaattttac  54180
ttttctacca tcttttaatt tataagtttt atcaattatt ttttctaatt tattttcata  54240
tttagattta agctctgcat catctaattg ttgttgaata gattgtttct cgtctgtaac  54300
tatatcatgt tctaatttta gagagaatgg tgttaagtta acactttcta atgttctata  54360
accttctcgt attaatattg ataaatcatg aagataatct aaatagtagc tatccagtgc  54420
atatcctgtt atacgttgtc tatcttgagc atctacatct aaataatgag tcattttttt  54480
gtaattagca aaagatatag ataatatttc atttacaata ggttttactt ttaaagcatc  54540
tgtaacattt cttacatcct gaaccattaa aaatgtatca tcaaatagtt gatgtagatt  54600
aacttcattg tgtaaatgat tatagtaatt atacaatgta tctgaaaatc ttaaataatt  54660
actctgttca aaattattta atgttagtaa ttttttatac gtttgctttg taagattaaa  54720
tgcttcatgt attttccact taggattttt aggtatatga aatagtaatg aatttctttc  54780
```

```
aaataattca aattcctcta agttatttat tttgtcaata tttttaacaa tatctgttaa  54840
gattgttaag taattagaag ttgaattttc tcctttgagt ggtttatatt tgtttcctcc  54900
ataatttaca cgcccatata catcaacctc atcaaggcac caactagaaa gtccaaaacc  54960
atcatttctt aatgtttctt caattatttt aataataaca ttcttactta aattaggtgt  55020
tgaataattt tttaaaataa catttaataa aacagccaaa tttaattcat ttttatattc  55080
acttttacta atatcgtctt tgtatagatt taaagttatt tctttattaa caagactgtc  55140
tgttaagaaa accttaactt ctcctgtttt aacatcaaat gaacttttat tttctaaaac  55200
ccatctattt cccatattat atttatctct aatgtgtcta actttaagac caaaagatga  55260
actattctca gtacttggat gcatgtacca agtactactg tacaatgaat ctgatatttc  55320
cttataatac ttactagagc ctttttctgt atcttcatta agtctggaag taatagatga  55380
ctttattaaa ccgtacttac cttggtataa gatatccata atatcattat tcaaactatc  55440
tactacttcc ttatactcat ctaattgtct agattcatac caccttaaac gggtttcatt  55500
ttctaattct ttaatttttt cttctacata acctttagat tttatttgtg ttatacgttt  55560
actaccatat aaaggaaatt cttttctttc ttctctactg gatgcaatat attctttgta  55620
acttcttcct ttattttctt caattacacc ttcaactaat ttttcaattg tttcataagg  55680
attacctgta aagtttgtta cttctttatt accacatagt gctaagaata aatgtatttc  55740
tgtagcagta tcaaaactaa atatattatg aatatctcta aatagttcct tagagcctaa  55800
gttaattata ttatttttct tcttcttaag gaatacatct tcttctccta tatagataca  55860
tcctttatta actttaggta aattaataat ttcttgttct gttaatcctt tttgtttata  55920
tgttattgcc atttaaaatc actccttatt tgttatgtac taatcatacc atagtaaata  55980
atatttgtca acaaaaaaag aagaactttt taaagttctt ctaagtgagt ttcgtagata  56040
accttttgaa ttttatttaa tggtttcaaa tctaaattac gaataagttt ttcgtacttt  56100
ctagaatttt taaaattgat agtatttggc atagcaagag cctcatcaat gtctttagta  56160
tagcttataa catctgaata aatatctact tcttttacat atagaccttg agttaaactt  56220
ttaaatacta cctcattatg tgctacaact tcttctttct tttctatgct catttttgta  56280
aacctcctgg tctattctac acaaacaagt acgtactcta aactagttaa tgttactgat  56340
ttaatattat ttaattcttg taatttctta atatctacac catagttttt acttatagtc  56400
cataatgtct ctcctgctct tactttatgg taatacttat tcccttcttt aataaggtca  56460
ttcaatatta cctacctcct tgagtaatag ttagcttgta gataacatat aagtataaga  56520
acaaagttta caaattcagt agctataatg tgaacataag tatgtgataa aaccatactt  56580
aatattaatg aagctaatcc taatccaata ataaggaata gaaatctgtt tgttccttct  56640
gcacttttag ttttatagaa tgttgttatc tgagttacat acgcaaggat aatagtaata  56700
gttgcaatag tttgtgttaa ggctgtaaag tcacttaata aaaatagtaa cactgagaac  56760
acaataataa aaggtataga gaaataatcc ttttttctat acgaagctac taataagcaa  56820
acaataccaa gagttaaatt aacaccaact gatactactt gaaacattgt agcgtcagtt  56880
ataagtaaat tgtaaaagct aatacctact gtagctacaa ttaaatacca aaaataacta  56940
ctaactcctt taacactatc tgatttaact aaagctatta gacctggtat ataacctact  57000
gtaactaata tagcatataa tatacttaag taatgtgata agttatccat cttgtcctcc  57060
taatttctct agtcttttta aaacttcttc ccaagaaata aacccttctc cattagttag  57120
gcttagcaca catccgtaaa taaattggtt cgtactaaat tcagccctat cagggtcatc  57180
```

```
ataaccttttt ccatgtcctt gacgaatatc agagcaatag attaaaacag gtttatttac  57240
aatattataa gcttctaaaa tatcatattg tgttaagggc tctaagtctc taaagtctat  57300
atcttcatat ttatcaataa ttttttgagc ttggtgtttc attcctaata aaataccaag  57360
ttctgcaatc gttcctagcc cctcattaag aatgtcaaat acaaaaatat ctgattcttg  57420
catagcttta aaatcattgt ttaagatacg ttcagctaat ccagtttgtt ctgcattagc  57480
tttatcgttg attgatttgt cctgatgagg gctataagga gttactccta caataccctc  57540
tacttgttcg tgttgtttag ttctatattc taccatagct tggttaagta gatgacctcc  57600
catgtaacaa accttatctt tagtataatt aaccatctat agtatctcct ttttcttcta  57660
gaatacctct taaaatgtgt ggcatctttt tcttaatttg tttttctata attttcatca  57720
tattttcttt ttcttcttcc atgatatcat caacaaaatt ttgacctact tgtttcataa  57780
ttaaaccaaa attttccaat tctaaatcat ctttagacaa tctgttttct tctatagctc  57840
taaaaatcat tttttccatt cttgattttg tgatagcata atctgctaca gaatcattac  57900
ttctaacttc tgatttcatt ttcttacgac taaactcttt aaattcctta gatactaatt  57960
taaaataatc atcatgttct gatttaccat ctaaatattt aataacaata ccttctcctg  58020
tattaggttt aacagtcata tctgattttc ctactaaatc ttgaatttct tgagggttta  58080
atttattaag ataaaaagat ggttctataa tcattaaagt ttttacagtt ttcaaaccta  58140
atgtttctga taaagaaatg acttctgaat aaggtaaata ggtttcacta tccttatcgt  58200
atacatcgaa tacataaaaa ttattataac actcttcttt ataatttacc ttatgtttaa  58260
ctaaccattc tccaaatata ataatacctt ctaatataga taaatctaat ttatctgtca  58320
tgttttcatg tacccaatta taaaaaccgt ttaatgtttc gttttcattt aatttttttc  58380
tacgagagaa acatactaac tcaccattct ctgtagtaaa acttgcgttg cttccatcta  58440
atttttcttg aactacaaaa cctctatctt taaatttgtc taaagataat cctttatttt  58500
ttactttagt ataagatttc attaattagt tatcctcctt tgaattatgt actattgaaa  58560
ataaaataag acttacactt gccaaaaatg ctaatactac taaaccaggt aaatttagaa  58620
ctgttgataa gaataatgct actgcactta taacataaac tagaccgcct aataataaag  58680
ttaataatac aattgttata agttttacca accagttatt attaataaat actttagcta  58740
aataattcat aaaaaagcct ccttagttat tataatataa gtataccata tctaaggagg  58800
tttgtcaaca tattatttta ccatttgaaa ttatctgcgt attgggctaa cttagaacgg  58860
aaattaactg taaaattatg gaatactgca ccatcatatt ttttaaaata ctccatgtaa  58920
tccccaaaac ctgatttact ttcatttttt aaatctattt gtttaaagtt accttctact  58980
attacagtag aattttttgt atgaaccctt gtaagaactt ttttaagttc actacgttta  59040
aagttctgtg cttcatttat aattatagta gaatctctta gatttccacc tcttaggaat  59100
agatgtgata tttgagatac ccaacaatct cctagtttat cttctttaac attatcttcc  59160
atcattaaca tttcagttat ttgttgttca ggattcatat taagttcaat aagggcatcg  59220
tgtaatccca tgaaataagc catttctttt tctgtctgat tacctggtct gcttcctaaa  59280
tcctctgata ctggtgaaat tataaatact agctttctat ctttattaag atagtctgcg  59340
taagcacagg ctactgagca cattgtttta cctgtaccgg cttgactctc attccaaagt  59400
atttcaacat tatcattaaa gaaatcctca cagaaatcta actgctcggt tgtagctttt  59460
tcaaggaatt cattaaagac tagatgttct cccatgttgt atcttacatt aggataatct  59520
```

```
tttaacttaa agtctaactc ttttagttgt attgccatat tttaaagttc ccctatctat  59580
aaatagtttt actctctttt aatatagtac taatttccga tatattctcc tgttgaagag  59640
caataattac tacattcaca ttcagggtag ttatcacaaa cttcttcgtc ttctacatca  59700
tcataaccaa tatcataatt attataatta aaatctacaa tacaattttc actattacct  59760
ttagataatc ctgtataaat aatatcatcc acagaatccc aatcgttatc tgccaaataa  59820
tttacgctat ctaatactga ttcattatca ggtaaataaa tactaccgtc tgaaaattta  59880
attagaatat caccttgagg taaagtatca ttaattaaat caatctttgt ttcttcttca  59940
atagtgaata cagttccttc taatctttcc ggtgtagtat gcgttaaatg ttttacagta  60000
tctcctgatt cttcatagaa tcctactgca ttcatatctt tattatattt tgcaataaat  60060
ttaccattgt cacttaccaa atattgacta gttgaattat agtcgtttgc gtcatctact  60120
gtcatgcaag ggttataatc tttaacataa taactaattt tcctaacatc tgttgtttgt  60180
actttcttac cttcaccttt aattactgaa ttaatttttt tcataatatt ttctcctttt  60240
tatatatcaa ttgatttttt tgcaagatta tcggcatagt cattccattt atcatttgaa  60300
tggctcttta cttttacaaa atttatatct attacttttt ggtattctct tatcatattg  60360
atatatgttt tacttagaat atttcttgca gaccaagtac cttcatacca atgtattaaa  60420
ccaatataat ctatataaac tattgcctga ttgtatccta gttttatagc ctcttcaata  60480
ccataacaac aagccaatat ttcacctgca acattattat actttattaa tcctggtttg  60540
tcaacacttt tactaatttc cgctattata tttccttctt tacttaccaa gacagcacct  60600
gagcctactt tacctttatt atatgaggag ctaccatctg tgtatatatt tacactatcc  60660
tgcatattta taatcctcca taaattgagg gaattcacaa tctgagtata cttctctaca  60720
aaaagatact gagatataat taaaatcaaa acatttgaaa cagtgttctt gaacttcttt  60780
tttatcttta gcaatcacat taaatttaaa accatcagct attactgtaa atactccttt  60840
tttcataaaa caaatacctc caccaatttt attttaaatt aataactaat tcaataaatg  60900
atttaatagt tttattttta ccttcatcaa tatctgaaaa gaagttaatt aaactatcat  60960
cctcatcaaa taaatcttca acatcatcaa atttatttaa tatgtctgta acactataac  61020
cttcttctga tatatactca tgcaagtctt ctccatcttc tgacagtgtt gcttctattt  61080
taccattttt actttcaatt aaatataaag tatttaacac tttaacagaa tctacaacta  61140
cactgtagtt actaatagta ggatattctg tataaagtat ttctacatta gtattcatat  61200
aactatcaat tacagagtta actgtatctc tttttagctc agatacatta tgttttcgta  61260
tagtagggaa ttcttcatca tattctacta attcttttct atctgtgttc aataacttgt  61320
ctaaagaaga caacaatact attttatact ggttatcagg gagactatct gtaatttcca  61380
ttattgttaa aaacgtatct tcacctagaa ctttgtttat atcttgtaac tcaaatgaat  61440
ctaccatttc aatagtatca tctatatcat ctgtagtcat taaaaaatta actaaattat  61500
tattctccat catcttcctc caattctttg aataactctt ttcctggagt atttaacgct  61560
ttctctaacc gcattaaatt agcgcttctt ggtttctttt ttccatactc ccaataagat  61620
ataagagagt aatgaacacc tatctcagaa gctaggctcc ttaatgtatg tccttttttct  61680
actctaattt tttgaaggtt tagaggttta ctttcctttt tttcatccat aattatttct  61740
cctctacttt taaaaattta aaatcctcag atgcttttgc attttttagt atatactcgt  61800
gtgacttatc tcttgcctct gccttgcttt tagcatataa ctctatatga aatacatgag  61860
gtttttttaa agacggtgat tcatatctcc aataaacttt aaaaagtagt gtttcttttt  61920
```

```
ttaaaacatt aattcgaaac catcttttaa atttattcat tcattatcct cctttattta  61980
tttgttaaac taattatagc atagttaact tatgaagtca actataatat acaaaaaaga  62040
ctaagaaatt aatcttagtc taaatcgtta ctaatagttt ccgttggcat tatggaagtt  62100
taaagctcct gatgttgaac cgtaacggtc aatcatatat tgttttgcac ctttagtttg  62160
ttctgctata gaaccaccac tccatgattt acctaatcct tggaataacc cttgggctcc  62220
tgatgttgga ttaacagcat tcgggttcaa tgtagattca cgcatagcaa tttcaatcat  62280
tgcttcatct ccgcctgctt gtctaatctg ttctgctaca gaaccacctg tacttttagt  62340
agctgtagtc ttagtttcta ctttaggagc ttctactgac ttaggagctt cttgagtagt  62400
tgtttcttgt ttaggttgtt ctactgcttt attttgtgta tcaaattgtg cttgttgttg  62460
gtctactttt tgttcaggtg tttgctcttc tcctgctaat ctagatactg tattatctac  62520
ttgagttgaa cctgaatgat attcataacc aaagttacca ttataattat agaaatgata  62580
agtaaattca ccatcactaa atgagaaatc ataattacct tcttgaattg gttttgtatt  62640
aacttctact gaatttgatt tagcttgttc tgctaactta ttatagtcaa tttcgtctgc  62700
actagcttcg tttgtagcca tacctccaaa agtaatagct gtacctaatg ctaatgttgc  62760
aaaaattgtt ttcttcataa atttaaaact ccttaaataa ttttttagaa ttgtttattt  62820
gtaaaccgac ataagtaatc ataacatata tctttaaata acgcaagtat aatatagcac  62880
taattagtgt aatattatta aggttttatt acaaacatta cagttatcag ataattaaat  62940
acaaaaaaga gaggtattaa cctatctaat ttattatttt cctgttacat ctacaatagt  63000
tccgtctccg ccaatttgaa taggttgttt tccatcccat ttttcaatta gctgttgttg  63060
taaaacttca tctgttaatg attcacttct gatatcatta gctttcttct caccttttgc  63120
ttctacttct tttttcttag cattttcttc agctatctgt ttatcgactt ttgtacgttc  63180
taattcttga tttgctttta ctctttcgtc aattgctttt tgagtattct tatctgcttt  63240
aggactagat aatgcaatat cttcaattac aaatccttgt ttttctaaat tatcatttaa  63300
gctatctaaa gtatcttttt taatttgtcc tgttttaaca ccaaatgcat caattactga  63360
gtacttagat actgattgac gtacattatc ttgtacacga gaacgtaagt aacctttttc  63420
taattcttca atgtcagcac taccaaaacg attaaataag tctacagctt tagttgcatc  63480
tactttatat gaaacatcaa tatccatttg taaattctta ccgtctgaag ttgccacgtt  63540
taaatcttta tatttatgtg tttgtgtttt agttggatat ttgtttacct tatcaaaagg  63600
tgctgttaag tgccaacctg gtgatttagt atcttcctta acaccattta ctgagtacac  63660
aactccaaca tgaccttgtg gaatctttgt aatacacatt aataaaataa taaatcctat  63720
aattgctaaa aaccctatta ctcctgaaat aactactgac ttcctcattt acatttctcc  63780
tttttctatc tcttttatta aactatttaa agctttttcc tctttgtcta tttcctgttt  63840
gtctgctttg gtaacaagag attgcctacg gtcatttaag aattgttttt tatattttac  63900
atattgttct aaaccgtatt cttctaatgt accttgccta actaattccc tgtattgttt  63960
tcttatgtta cttttcttct ctctcattga aagaaaatca aatacgtaac tcataccaaa  64020
acctacaagg actagaaaaa caataaaaat agcaaagtat gttaaaaata atgccatgta  64080
attcctcctt tatttgatta catatataac tatacactat gtattacgtt ttgtcaacac  64140
ttttttgcaa aaaaaataga cggatttaaa atccgtctaa atttatactt tatttaaata  64200
ttgttatact tttagtttct tcatactctt tcaacattct atctctaaga tttattgctt  64260
```

```
cttttatact atctacttga tatgattggt accttatatt atttcttgtt atagaaactc  64320
tatatttacc attagttctt tcttgtatgt tttttaatcc ttctagttta gagggtctat  64380
taactatatt ttcacttcta gtagtccatc tacaattttc cggagaatag ttaccatcat  64440
tatcttttct atctaattgg tatttatcag aaggtctttt acccatatca tataaaaaag  64500
attcgaaaga gtttttccat ctatcacaaa cttcaatacc tcttcctcca taatatggat  64560
aactgtcttg atttttgtta tagcatcttt ctttcatttt tctccatact gtatactcag  64620
gatgtttttt agaaccatta cgtgatttca tacaaccaca acttttataa tagtataatt  64680
gacttttaga taaaactcta tccataccgc aatcacataa gcataaatat aatttacctt  64740
taatcttatc tgaacctaca tattcttcaa caaataattt ttctattttt ttacctataa  64800
tattttccat aaaatctctc ctttgaaaat attataacat atatataagg ggtattgcaa  64860
ccccttttatt tattaacctt tgaatacacc ccaggcaact ccaggtacat gtgaaggtgg  64920
aacaccttga caagttctaa cagggcaata tactctgtta ccattgtaag cattataacc  64980
tatccaaata tgacctgctt ggatacaaac ttcgtcatat acaattgtag cccctgccgg  65040
taagttaccg cctactggag catttaagaa tggagaacct attctagtta ctataggttg  65100
gttaccatta acaaatgttg cattttccgg tttataccaa gttccgtact ggttcttttt  65160
ccaagagcct gtaactggtc tagttgccgg tgtacttgcg ctacttgttt ttccatcttt  65220
aactactgta gaacttgaag tccctttatc catgtagttt ttaatttgtt taatgaaata  65280
atcttttaat ttattcatta ttgcttgtga tggtcttcct tgtgttactg gattaaatcc  65340
tgtatgaaga accatagaac ggtgagggca ggcagttggt acaaattcca tatgcaatct  65400
tacagtttta cggttaggag taagacccca ttctttaaat ttctccgctg taaattggaa  65460
tactgcttgt tcatttttaa ggaattgagc atcactagca ctcattgatt gacagacttc  65520
aatacctgca aatctaaagt tacctgagtt tgctcctgtt ccatctcctg tgtgccaagc  65580
aatttgattc ttagcatcta ttgcttccca tacataacct tcagagccgt agtaatgagc  65640
aataccatta gcgtatctag cataacctgc attagctaat gaattctcgt attgttgtcc  65700
tgaagaacga cctgcatcgt tgtgtattac cattccttca ggtttttttac cacgtttatc  65760
cattgtatag ttaatgtgat tcttagaaac ttttagtgtt gctttctttt taggtgcagg  65820
agttttactt gcgcttttct tagctgtttc ttttttaaca gtagttcctg cttttacagg  65880
tatttcaatg aagtgagtta atccgtaata attatctaca cgttttgtag gttttttatt  65940
agcataacca ttccagtttt gctctaaaat agtaaacgta gaagtattac ctccatcata  66000
tacaatacct atgtgacccc actgttcata actaccggat gtaaataccg caatccaacc  66060
ttttttaggt acagtagaag gtttattttc atgtatttta aatccagtac cataactctg  66120
tttaatttgg tctttagcat taccccaagt tctaacttta ttatctgtta accataaaac  66180
atagtctgta ataaggtctt gacactgagc gtgatagtaa ccatctgcgt caatggctcc  66240
tgcttccatt acaccaaatg atgggtcata acttgtagct tttttaactc tgtaagggct  66300
atctactgtt ccttttgcat aagcgtctaa acgtttattt atttctgctt gagtcttagc  66360
cattacttaa cttcctcctc tgcaaatact ttaccatgtt cctcggtatc ttcttcatct  66420
tgagaaggtg ctgaaccacc atcaatttca tcttcaatag caggtacttc atcactatca  66480
tctgtgtcag gttctgcatt gttttcgtag ctgtctatct caaaagtact agcgttattt  66540
gcatttgctt gccattgaac gaattcatta gggtctttac tatcacgagg tttaagatag  66600
tctgtttgaa caatatcact atctttaaga cctttagtat tattatcaac aataatacct  66660
```

```
aaacctgcta atagtgttag tatagaacct acaatattta caccttgctc aatttgagct  66720
gagtagtcta aaccgaaagc acctgtaatt tggttagcaa ataatgctac tgctgatata  66780
attgctaccc aaaatgtttt gctcttagtt cttgtgctaa ggtttattcc tccaacaact  66840
ttaggttgtt tagtttcatt agccattaaa aaaccgacct ttctattata tttatttcta  66900
acaataatat aacagtaggt cggtcatgtt tatctatatt aatttaacac ttactcatta  66960
atttggttta gttttttgat aacttcagac atttgtttgt tatctaaatc ttctaattta  67020
gtttcaggaa gtagctctaa cttatcccaa acttcttctt tattagatac tttattatta  67080
ataattgcct taccaactaa actttccgta taatataatt gttttgctga tgccatttgt  67140
atctctcctt ttaaatatgt aaagtatata gctagtatcg tatcctagga acaaacactt  67200
gcgctatata ctcaatgaaa tcctaccctc attcgaggac acagcaaacc ggttcgtcaa  67260
ccgcacatat gaattctcag atttcattta tgtaaaacac accctctttg atttgcacaa  67320
agactaaggg ttttggagac ccttgtacta ctaattatac taagggtgtt tattatggtt  67380
tctattggat ttgaaccaat gacacctaga gcttcaatct agtgctctac catctgagct  67440
aagaaacctt aaaacgaccc atacgagact cgaactcgta ctctctgccg tgacagggca  67500
gtgtgttaac cagttacacc aatgagccaa aattataatg ctatacccta accttacctt  67560
aatgtatagc aggtttttat ataagctcga agcaacgatt attaccactc ataacaacta  67620
tatattaagt gaaaggaggt gaaatgaaca aaacgtggta attggtactt atataggaaa  67680
tatgtataat ctacaaggag taagttattg gttcataaag gagtgtgaac aataaataca  67740
tgaaagagtg aaagtttact ccctgtagat tctttttaa ttatcaatca aaggaggaaa  67800
ctgataattg ttaataataa actataaaga ggaaaatatt tatagtcaca ttctgatata  67860
atgcaactaa atatccaagc ataacccgtc tcacgaggaa cctacctata agacctgtta  67920
ttaagtgaat cactacgatt gactctatta aggagctacc ttaagtccat ctcacgcaat  67980
ttaaaaggga cttacaaacc gtaaaacggt aataagttta ttaaataatg tgatattaac  68040
atattagtta ataactttca catggtcgaa gaaaagtaaa tttatttgat taccaaatta  68100
tttttatcaa atatagctct tttgaacctg tagatttatg ctactcatac tgataacctc  68160
tattatctaa cacatttctg tgctccaact acagttagtc gttacagcgt atctttctag  68220
gattccgcta agaccctaga aagaaattaa accctagccg ttatcatact ctacagacct  68280
tataagtaag taccaagtat accaatcgta tttaacaata ctaatgacga cccatcctac  68340
cgatatatct ccgataggtt ttgattcgtt tgattatctt gtaccttatg actaccaaat  68400
cattattcag tcactatgct cagatattta gttgtattat ttatatatta attataacat  68460
aatttttatt acttgtcaag ttaattttaa aaaaaattat agaagtaggg acgtttacct  68520
acttccattt aatttacaca aggatgataa cattgttatt gttttatact ggaaaacaat  68580
gtaataaaaa cagtgatgtg taaggtattt gttttattgt taattacatt atagcatata  68640
ctgatacctt tgtcaagtta atttaatact ttttttaaaa tattagttat cttttgttaa  68700
ttcttcctga atagcatccc atcttctttc tgcttcacta cgattatctt ctatatgctt  68760
tgtagtttta caacatttaa tacaatatat atctttgata tgaccttctt ctcttttatt  68820
tgctcttttt cttggtactt tgaatacatt tccacattct ttacatatta aacttgagta  68880
aaacattttt tgtcttttca taattaatca attccttttc tcttttattt gataatttaa  68940
ctatatacta tactgataaa taagtcaaca gttttctaaa aaataattta aattattttg  69000
```

```
aagaatcctt taatatcagt acttacaaga gaaaaagtac gtatttagaa aataaggagt  69060
actcctatta tatataatta tattctgata tacagtaatt aataatatta aatatataat  69120
tataattaat agggttggga aaattgatat aaacataact gatactgttt ataaatactc  69180
agtataaaag taaaatccct tagtatcagt acttacaggc aaaaaagtac gtatttagaa  69240
aataaggagc tctcctatta tagttatata tatatattta ttactattat taattactat  69300
ttaaatatat aattataatt aacaatgtta gaaagtcaac aatagcataa ataaaaaagt  69360
gactacttaa agtcactcaa taattagaat actattttaa aagattctat tctgtttgga  69420
ttaatatata cttgaggtga agttatagca ctttcagtat atacttttat agaggtttca  69480
tccattcctc ttaacatata atctatatct tgcctattgt aactcttttc atcagtagat  69540
actaaaaagt atttagctcc acttgacatt gttatttcaa tatgttttga catctacaat  69600
ctctcctatg caaatttgtt aaagacaaag gataatatag ctcctagaac aagtaaaaga  69660
accttctcag ttgtatcctt tttcttagta tccttagttt ttgtactttc agcaagttct  69720
gaaatctttt catcaagtct ttctaattgg acgtaaattg ctgattgttt ttcactattg  69780
acagctacat ctttatctat actaactatc atttttctta gttcagctac ctcaacttct  69840
aaatctttga aagttcctct atctatataa ttaccttctt gtatcttaga cttaatagtt  69900
tctacttgag aaacaaggtt gtttatctcc ttatccaact agaatcacct ctaaggtcta  69960
accgtttcag attcagaatg gatatcataa ttttctaaga aatcattgat aatctccata  70020
taattatccg taacgacttt tccgtaagat gtttttgtat caatttcgaa tctaagttta  70080
ccgaagtctt ggaggtctaa ctcttttatt acaatattcg ggtcatcaga aggaaggtaa  70140
taatagtcga agtatataat tgagccattt attagtagac ggtctattct atacatatga  70200
aagaatcttc tgtctcgttt gaaatgagct agtgaatctt taaactctaa cttaagtata  70260
tccttatatt tagtcaaagt ggtaacctcc ttactattaa tttttaaatt tacttatttt  70320
gtgttataat agttatgata aaggcagtta ttataattat attaagaata aagataataa  70380
ttattttttc tgagaaaata agccaaatac tacaaacaga taaaacatag atagctgata  70440
gatatactat attaatagtt accttacttt tatcttttct atagatagaa taacctaaag  70500
aagttgtaac accactaagt ataaaataat agaaacaaaa aagaggtata gacagaaaaa  70560
aagatacgat aatcattgtt aaacacctat ttctttttga cctattattt ctagaacttt  70620
tagattatac cactaatata acattaaaag ccagtcataa aagtcaattg ttagattaat  70680
aatataataa aaaaagacaa taggaggtta aagtggttga ataataacat agctatattc  70740
atattcaaaa cattggttat cattatattc ttactgctat ttttgtctgt tgttaattcc  70800
ttatccctta tttactcaat aagaccgagt gtagttatgg catactttac ctttggaggt  70860
attgtttctg atgtcgcact tactatgaca gataagttct tacttaagaa agaagaccct  70920
ctacctgagt atgttcttaa aaaagtagag ataaatgata aagaaataag cataattaag  70980
aaaatcatag aaagtaatta tgatataaca tcagaagaga taaaagttag agctaaagca  71040
caacagagat tagaggaaga tagcaaagag gaagataacg atgaaaacga agaaagaaat  71100
taaagaacaa aggaaagaac ttaaagacgg tgctacaact gtttctttag taaaaaaagg  71160
ggataagaga atagctagcc ctagtagaat ttgtagttta tgtggtcagc agttatcagg  71220
tatgagttac actaaaggaa aagcattatc aaaagttaat cattttcatt tacagtactc  71280
taagtacatt tattttgata tttgtgcaga tattaacaat tgttataaaa atttaagaaa  71340
acgaggtgaa atggattgag tgcagaaaat attagagata taattaataa gaaaaagtta  71400
```

```
gaagaagagg atacaagaaa atatatagct gatggattta tgaatggtat cggtaaatta  71460
atgtatgaat tcaataaaaa agtagataat aaagaaatag aagttaaaga ccctaacgat  71520
ttatataaac tatttgtgat attctctcaa atgcagaata tggttaatga aacttctgaa  71580
ggtggagcaa tacctcaact atctagacct caacaagaat tatttgaaga gattacaact  71640
gaagatagta atggggagtc tactgtagac ttacaaaaaa tatcagaaat gtcagcagaa  71700
gatattacag aaatgatttc tgaaaaagag aaagtaatga atgaggaaaa ttcaaaaaca  71760
ttctaagggg aaagatataa catggatgga aaagaactaa ttaaaatagc acaagaaaca  71820
tttcaaacag aaaaaataac aagagagcag atagaccata taatcaatat gttaaaccct  71880
tctacctata tgcttaagta tcacacgcta agaggtcacc ctataacttt cagtattcct  71940
aatagggata gaagtaaagc acaagcacac cgaccttggc aagtccgtaa acatactatg  72000
cggactataa accttttcta aaattggaaa ctcctaacaa gtgaagttga ggacaatcaa  72060
ttgctaaatc gtaactaaga taaatatttt aattacgtaa atgcctaacg actaaatttc  72120
caagtaagca ataaaatggt attgtgtaga attggaagag agggaaaccg taacgaaaag  72180
gacttttacg cctaactgta aaagtatgat atagtctaat cccctaataa atatcgggaa  72240
accgagggta gtaaatgata gtaaatgaca ctcatccaaa caaagcagtt attaaaagca  72300
gacaattggg gcttagtgag atgggtgtaa tggaaatggt tcattttgca gatatgcata  72360
gctatgccaa tgcaaaatgt ttatatacct ttaattagag aggcttcacg tagcaatgcg  72420
tgttgaaaaa ccttgttaaa cggggaaacc cctaacgtaa agacgagggc aatcccgtgc  72480
taaatgttga ctaacctaat attatatgat atattagtta tagtcagcta aatgccgaac  72540
gactaaattt ctaggtaggt atctaaatgg aggtactgag aactagataa aaaaactact  72600
taaaataatt agacttaaaa aaatactgtt ggaaggagga tatttaatgg gaaaaaaatt  72660
aactaatact gagtttttaa atagagtatt tcagttagtt agtgatgaat actcattttt  72720
agaagagtat aaagggagac ataccaaatt aagatgtaaa cataatttat gtagttacga  72780
gtgggatgta gaacctggag ctttttttagg taataagaac aaagcaggaa gtagatgtcc  72840
tagttgttat ggtaatgtta ctaaaacaac agataaattt aaaaaagaaa tatacaattt  72900
aactaaagat gaatataggt tactttctga gtatattaat gctaaaacaa aagtaaaaat  72960
taaacattct aaatgtggta atactttttc tatgacacct aatactttta taaatggaag  73020
tagatgtcct gaatgtaacc ctcaaaaacc gtataataca gattctgcta aagataggat  73080
aaataaagaa acgaatggta cttttgaact agttagtgaa tacaaaggtt gttatgagct  73140
tatgaagtta aagcatcatg aatgtggaaa tattgtagaa ataaatatgc agagtattga  73200
tagcaataga ctaaattgtc cttattgtta taataggtct agaggtgaat tactagtatc  73260
ctcatttctt ctttcaaaaa acataccatt cgaagtccaa aaaagatttg atgggtttaa  73320
gaaatatcct tatgattttt atatagctga ttataatacg gttatagaat atcatggaga  73380
acaacattat aaacctatta agttttatgg tggagaagat agattggtaa ggcagaaaaa  73440
tatagattta aagaagaaaa attttgttga gggtaaaggt ataaattact tagaaatacc  73500
ttacacatta aacaatcaaa ataaagtaaa tgagttttta attaattatt ttaagtagaa  73560
gtaaagcaag gaacccttaa ccaaacttaa gggttatgat atagtctaaa ccgtatataa  73620
atactaggaa actagcggta taattgtcct acaaatgaac aaatgaagaa atttgttcag  73680
tctcgtttaa atcctgtatt agaaaaagaa tattttaggg atattgttga ttgggataaa  73740
```

```
gactctttag gttttaaaaa gataagaaat tctagtttat tctttagaac aagttctaaa  73800
gcaagtactg tagagggtgt ggatattgac tatttatctt tagatgagta tgacagggta  73860
aacttattag cagaatcgtc tgcactagaa tcaatgtctt catcaccttt taagattgtg  73920
agaagatgga gcacaccttc tgtaccgggg atgggtatac acaaattata ccaacaatca  73980
gaccaatggt attacggtca tagatgtcaa cattgtgatt acttaaatga aatgagttat  74040
aatgattaca accctgataa tcttgaagaa agtggaaata tgttatgtgt taatcctgaa  74100
ggggtagatg agcaagctaa aacagtacaa aatggtagtt accaatttgt ttgccaaaaa  74160
tgtggtaaac cactagatag atggtataat ggtgagtggc attgtaagta ccctgagcgt  74220
acaaaaggta ataaaggggt acgaggatac ctaataacac aaatgaacgc tgtatggatt  74280
tctgctgatg aattaaaaga gaaagaaatg aatacagaat ctaaacaagc attctacaac  74340
tatattttag gttatccttt tgaagatgtt aaacttagag ttaatgaaga agatgtttat  74400
ggtaacaaat cacctattgc agaaacacaa ttaatgaaac gagatagata ttctcatata  74460
gctattggta tagattgggg aaatactcac tggataactg ttcatggtat gttacctaat  74520
ggcaaggtag acttaatacg attattctct gttaaaaaaa tgacaagacc tgatttagtt  74580
gaagcagatt tagaaaaaat aatttgggaa atatctaagt acgaccctga tattataatt  74640
gcagataatg gagactcagg taataacgtt ttaaaactca ttaatcattt tggaaaagat  74700
aaagtatttg gatgtactta taaatcttct cctaaatcta caggacaatt aagacctgaa  74760
tttaatgaga acaataatag ggttacagtg gataaattaa tgcagaataa aagatatgta  74820
caagcactta agacaaagga tataagtgtt tatagtacag tagatgatga tttaaaaact  74880
ttcttaaaac attggcaaaa tgttgttatt atggatgaag aagatgaaaa aactggagaa  74940
atgtaccaag ttatcaaacg taaaggtgac gaccactatg cacaagcaag tgtttacgcc  75000
tatataggat taacaagaat aaaagaactt cttaaagaag gaaacggtac aagctttggt  75060
tctacatttg tttctactga ttacaatcaa gaaggaaata aacaattcta ctttgatgaa  75120
tagaggtgaa atagacttga cagataaatt attttatggt acaattagta atgaagaaat  75180
taataaaagt gtattgaatt tgttattggg tgaggaatta tccttagatt atgtttctaa  75240
aaatagtgat actttagatg ttaaatatga acatgtctat aaatctctag gattcgataa  75300
tttctttgat tgttttttat atgctaatag agagcctgaa atagtccaca aaggtggaga  75360
taaaaatctt ggtggactaa ataaggttaa acgtactgtt attcgtaatg gtaaagaaat  75420
ggaaatgaca gtttacgaag acggtaataa agagaacgat agtaaagaaa aacaagaagg  75480
aaaagaagaa gttagtagaa gtgcagtagg agcaagagct atttctaatg gtgaagaagg  75540
aaaggtaaac cctaaaaaag tagcaaattc attatctagt ttaagtaaaa agggtgtaga  75600
tgtatcccat attaatacaa acttatcatt gtataaagag tttgttgatg ataacggtga  75660
tacattagga attacatctt ttaaacgaac tgaaaatgat ataatattag aatcttatgc  75720
aagttcacct gattcagatg gtgtaggagc aagagctatt atggaattat tacgtttaag  75780
tattaaggaa aataaaaatg cagttgtgta tgacatagaa ttacctgaag cagtagagta  75840
tttaaaaact ttaggattta aacctaataa agatgggtac atcttaagaa aaaaagatgt  75900
aaaacaattc ttaggtgatt atagtgattt tatttagcac tatagtcatc tattctattg  75960
tatttattct atatattgta ttaaaaacaa tttatataaa gtctaatatg agtagaatag  76020
ataacacaac tgaattatta aaaatattac aggaagatat tgaaggtaag ataaaaaagg  76080
aaggaagaaa taaatgactt tagaagaaaa taaattaaca ttagaagaat caataactcc  76140
```

```
acttagtaaa gaggagaaag aagatagtat taaagaattt agtagtttat tatgtgaaat  76200
ggtaaatagg ctatacaagt cttataatgt atttagacaa gaccctatgg atgaaactca  76260
acgtctagat ggctctttaa tggtctttca aagtagatta aatgaccctt taacaggaga  76320
tttacatgat aagatgtata aacttgcttt ttcaaaacgt attgatattt tcgaagctaa  76380
taagcaattt agaaaagatg tagaagcagg taaagcaatt gagttaggtg atgtagctat  76440
tatagataca gcattaagta acatcctttc aggcaatgag ttccaaggaa gtatttcatt  76500
tatgcttaga aaagactttg aagaaaaaga acgaattaga aaagaagaag aagagaaact  76560
taataactta taaaagggaa gaattatgag actatataaa atgaggtatc ataattgaaa  76620
aagaaaccac aaggcaatga ggtaatcata accataataa cggttatgat agcagtattt  76680
gtagtcatta tgaccatatt ttttaataaa tatcaagatg ctaaagaaga taaagataga  76740
tatcaaagat tagtagagat ttataaaaaa gcagatgata atgatggtga gactaaaaag  76800
aaatatgtta aaagattaaa taaggctgaa gaagaactta aaaaagtaaa aaaagaaaca  76860
aattataaag attataataa gaagtcaagt aaagaaagac aaaaagaaga taaagaaact  76920
agagagaaaa tatatgatgt aactggtgat gatgacttaa tattagtaaa aaataatatt  76980
gattttagtg ataaagtaga caagcccgaa atacttatta gtgaagatgg aattggtacg  77040
ataactgttc ctgtagatag tgggtatgaa aaacaaacag taggttctat tattactagt  77100
gtattaggtt ctcctttcct atcacctggt tcaaatagta tagatggttt aagtgttatt  77160
aacgataatg tttatccaaa tacagtagat agcatagtag aagatacaaa accttctatt  77220
aacttaccaa tggataatcc tattataaca aatccggttg aaccaactat accttcagat  77280
actatacctc ctattgataa tccttcagtt ccggtatttc ctgagaatcc agtagataat  77340
aatcaaggaa atacagataa tccaaaccca ccgcctccag gatatacaga tgaagatggt  77400
ggaaggggct ccggtggtgg aggaaattct gaaccaccat caacggaaga accttcggat  77460
aatggtaaca ctggaggagg agattgggaa gaaaaacctg acccaggaga agaaccttca  77520
gataatggta atacaggagg caatggtgga gaagttacgc ctgaacctga ccctacccct  77580
tctgaacctg aacaaccgaa tgaaaattct gatgaaggta atgaagaaaa accatctgaa  77640
ccgtctgaca atcctgatga aaatggagga tgggaaactg aaccaactga acctgagtca  77700
ccttcagagc cggacgataa agtggacgaa gaggataaaa atgaagatac tacagatgat  77760
aaacagccca ctgaacaacc ggacgataac aacatagata atgaagataa aactgaagag  77820
gagtaattac tcctcttttt tgtttgctat attaaataag agttaaatat aaaaaaaatt  77880
gaacattacg gtggtgaaaa ctttgttagg aatgaatatt ataacgtcac tatcagtagt  77940
atttacctgt ttaagtcttt taactttaat gatttttgtt catagtaagt tctctagtaa  78000
aaacgttttt gttttgtatg taatttatgc tataatagga ataggtacat acatagtttt  78060
aactatgttt caaacaacat ctgtacttat taagaatgat gtaatagatt ccatagaaaa  78120
tactgaacat tatattggat tcaatgaccc tataattata tttactataa gttttatagg  78180
tgcaatactt ggaggaattt ggtacaagat gatgaaaatt attaaaaaga gtaactttaa  78240
agataaaaaa taaaaaagac ggtgaatagg ttgatattct ctaaagataa aaaatgggat  78300
gaagcaaaag atttcatcaa aggtcaaggt atgcaagata attggataga gattgtagat  78360
tattatagac agataggtgg aaaacacgta gctgttttta ttgctttaaa caaagtaaaa  78420
tacatgattc tagaagcaac aaaagacaat aaagtaatat tagtagataa agataataat  78480
```

```
atactattag aagattatga tattgttatg gaaagtaaga agatgtttta ttacattgaa  78540
gaaccgttcg aggttaaaat aaatatccct caacatatta gagatgtaac ttataataat  78600
actgttgtat taactacagt aagagggagt agaggtgact agtaattggc agatttattt  78660
aagcaattca gattaggtaa agactatggt aataatagta ccattgctca agttcctatt  78720
gatgaaggat tacaagctaa cattaaaaaa atagaacaag acaataaaga gtatcaagat  78780
ttaactaagt ctttatacgg acagcaacag gcttatgcag agccatttat agaaatgatg  78840
gatactaatc ctgaatttag agataagaga agttacatga agaacgaaca taacttacat  78900
gatgttttga aaaagtttgg taataaccct atccttaatg ctatcatact tacacgttca  78960
aatcaagtag ctatgtattg tcaacctgca agatattcag agaaaggttt aggttttgag  79020
gtaagattaa gagacctaga tgcggaacct ggtagaaaag aaaaagaaga aatgaaacgt  79080
atagaagatt ttattgttaa tactggtaaa gataaagatg tagatagaga ttcatttcaa  79140
actttctgta agaaaattgt tagagatact tatatctatg accaagttaa ctttgaaaaa  79200
gtatttaata agaataataa gactagacta gaaaaattca tagcagtaga cccttctact  79260
atttttatg caacagataa aaaaggtaaa attattaagg gtggtaagag atttgttcaa  79320
gtagtagata aaagagtagt agctagtttt acttctagag aattagctat gggtataaga  79380
aaccctagaa ctgaattatc ttcctcagga tatggattat cagaagtaga gatagctatg  79440
aaagagttta ttgcctataa taacactgaa tctttcaatg atagattttt ctcacatggt  79500
ggtactacta gaggtatttt acagatacgt tcagaccaac aacaatcaca acatgcatta  79560
gagaacttta agcgtgaatg gaaatctagt ttatcaggta ttaatggttc atggcaaatt  79620
ccagtagtaa tggcagatga tattaaattt gtcaatatga caccgactgc taatgatatg  79680
caatttgaga aatggttaaa ttaccttatc aatattatat ctgctttata tggtattgac  79740
cctgcagaaa ttggtttccc taatagagga ggagctacag gttctaaagg tggctctact  79800
ttaaatgagg ctgacccagg taaaaaacaa caacaatctc aaaataaagg tttacaacct  79860
ttacttagat ttattgaaga tttagttaat agacatatta tatcagaata tggagataag  79920
tatacattcc aattcgtagg tggagatact aagagtgcta ctgataaact taatattctt  79980
aaactagaga ctcaaatatt taaaacagtt aatgaggcta gagaagagca aggtaagaaa  80040
cctattgaag gtggagacat tattctagat gcttcattct tacaaggaac agcccaatta  80100
caacaagata aacaatataa tgatggtaaa caaaaagaac gtttacaaat gatgatgagt  80160
ttactagaag gagacaatga tgattctgaa gaaggacaat cagcagattc tagtaatgat  80220
gataaaagta accctgaagt aggaactgac tctcaaataa aaggggattc aaacgtttat  80280
agaacagaaa cttctaacaa gggtcaaggt aaaaaaaggg aaaagtcttc tgattttaaa  80340
cactaataag gaggtaaaat taaatgtcag ttatatataa agataataat tggattgatt  80400
taactaatgt tccttattta caaaaaggtg atagtggata tcgtaaagat ataccaagga  80460
aaaattggaa aaagtgttta aatacagaag taagtttttc ttataaaggt aaaaagggtc  80520
tattttatgt aacttatcgt aaggaagata aaggaaaagt taaagttgaa tatgataagt  80580
atgttaagat aatagaccct catgatttaa agacactaaa tataaataaa atagttaatc  80640
ctcctaataa agctaagtat cgtgagcagg aagtaattaa tggtgatact gtaagaaata  80700
ttagaaaagt taagaataca ggaattgttt atactatgtt atgttcagag tatgaagaag  80760
aatatgatat aagagaaagt gatttattaa gagggagagg tagcccttat aaatcaggta  80820
gaaaagtatg ttataacaat tcattatatt ctgttgaaaa tttgagagaa tatatctgtg  80880
```

```
atttagaata tgctaaaact gtaactaagt tttcacataa agatataaaa tgcaagtgcc  80940
ctatatgtag tgaagagaaa gttatgaagg ttaataaatt agttaataac ggtttttctt  81000
gtcatagatg tagctcaact ataacatatc ctgaacgatt aatgatagga ttactagaat  81060
taaataattt aaactatgaa tatcaaaaag tatttaaaga cctacctaat agaaaatttg  81120
atttttattt acctaaatta aatatggtta ttgaaactca tggattacaa cattataggg  81180
aattaaatgg ttacatgaat catgaaaaaa caaaggaatc ggatttagag aagtataact  81240
attgcaagaa taataatata gattatattg aaatagattg tagttacagt gatttatcct  81300
ttatattaag taatgttgag aatagtaagt taaatagcat acttaaaaat aagaattacg  81360
ataatcttag caattatatt ataagaagta aaaatgatga tgttaagtat aatatatatt  81420
tggattactg caaaggatta agcaagaaag aattgaaaga taaatataat aaaacgagtt  81480
attatataaa caggtctatt gagatattta aacattaatt aataagccta gaataaatct  81540
aggctttgtt tatttttttt gtaatttaat tttgataaat gtaataacta tggtatacta  81600
tatgtaattg atattaatac ataaaaaata ttaatatttc acttacaagt tattattgtt  81660
atattattaa cgtaaaagta aataaaataa caagtggagg tgtagacacc tttggaagaa  81720
ataaaattta atgcttttgt acctatggat ttgaagaaat ctgtatcaac agcttctgat  81780
actaatgagt attctatcgt ttcaggatgg gctagtactc caagtatgga tttacagaat  81840
gatatagtta atcctaaagg aatagatata gagtatttta agtcacaagg gtacattaat  81900
tatgagcatc aaagtgataa ggttgtaggg atacctacag agaattgcta tgtggatata  81960
gaaaaaggtt tatttattga agcaaagcta tggaagaatg acgaaaatgt tgttaagatg  82020
cttgatttag ctgagaaatt agaaaaatca ggtagtggaa gacgtttagg tttttctatt  82080
gaaggtgcag ttaaaaaacg taatataaat gacaatagag ttattgatga agttatgata  82140
accggagttg cattagttaa aaaccctgct aatcctgaag caacatggga aagctttatg  82200
aaatcatttt taactggtca tggtacatca cctgacactc aagttgatgc aggagcttta  82260
agaaaagaag aaatagcatc tagcattaca aatttagctt acgtcactaa gattaaagat  82320
ttaaaagagt ttaatgatgt atggaatggc gttgttgaag atttgagtaa atctaatagt  82380
atgggatatg aggaatcagt ccttacgtta caactagcta aaggtttatc tcgtaaagat  82440
gcagaactag cagtaatgga tataaacaaa caaaaactag aataggtaag gagaatacat  82500
tctatgagta aagaaatgca aaatatttta gaagagtatg ataagttaaa tgctcaagag  82560
gcagtttcga aatctgtaga agatgatgaa aagaatacag tagaatctac cgaagagcaa  82620
gtagcagaaa caactgaaga acctgctaaa gaacctgaaa aagtatctga ggaagatgct  82680
aaagaagcac aagagcaagg tgaaaaagtt gaatctgaag aggtagcaga ggacaatgaa  82740
gatgaggaag ttgaaaaatc agctaaagaa tcaaaagacc ctgtagacca aaaagatact  82800
aagacagaaa ataaagacaa cgagaaacgt aaaaataaaa aagataaaaa agaagattct  82860
gattctgacg atgaagataa agatactgac gatgataaag ataagaaaga agataagaag  82920
gaaaaaactt ctaaatcaat ttctgatgaa gatatcacaa cagtatttaa atctatctta  82980
acatcttttg aaaacttaaa taaagagaaa gaaaactttg ctactaaaga agatttaagt  83040
gaagttagta aatctattaa tgagttatca gcaaaaattt ctgaaatcca agctgaagat  83100
gtttctaaat cagtagacac tgatgaagaa gctgtagaaa aatcagtaac atctacaaat  83160
ggagagcaag aaaaagtaga aggttatgtt tctaaatcag tagacactga agaacaagct  83220
```

```
gaaactggtg aagcaaaatc agaagaagct gaagaagtac aagaagataa cacatttaaa  83280
ggattaagtc aagaagaacg aactaagttc atggattctt acaaagcaca agctaaagac  83340
cctagagctt ctaaacatga cttacaatca gcttaccaat cttacttgaa cattaacact  83400
gaccctacta acgcatcaga gaaagatatt aaaactgtaa aagactttgc acaaatttaa  83460
ttaatgcaca aagttgtgtt atattatacg gtgtaactaa agaatataaa tagggtacat  83520
tttactgtac cctacataaa ataaaaagaa cacaaatgaa aggtgataaa tttatatgac  83580
tatcgaaaag aacctgtcag acgttcaaca aaagtacgct gaccaattcc aagaagacgt  83640
agtaaagtca ttccaaactg gttatggaat cactcctgat acacaaattg acgcaggagc  83700
tttacgtaga gaaattttag atgaccaaat cacaatgtta acatggacta atgaagattt  83760
aatcttctat cgtgatatct cacgccgtcc tgctcaatct acagtagtaa aatacgacca  83820
atatttacgt catggtaacg taggtcactc tcgtttcgtt aaagaaatcg gagtagcacc  83880
agtatctgac ccaaatatcc gtcaaaaaac tgtatcaatg aaatacgttt ctgatactaa  83940
aaacatgtca attgcatcag gtttagtaaa taacattgct gacccatcac aaatccttac  84000
agaagatgct atcgcagttg ttgcaaaaac aattgagtgg gcttcattct acggtgacgc  84060
ttcattaact tctgaagttg aaggtgaagg tttagagttt gatggtttag ctaaattgat  84120
tgacaaaaat aacgtaatta acgctaaagg taaccaatta actgagaaac acttaaatga  84180
ggcggcggta cgtatcggta aaggtttcgg tacagctaca gatgcttaca tgcctatcgg  84240
tgtacacgca gacttcgtta actcaatctt aggtcgtcaa atgcaattaa tgcaagacaa  84300
cagcggtaac gttaacactg gttacagcgt aaatggtttc tactcatctc gtggattcat  84360
taaattacat ggttctacag taatggaaaa tgaattaatc ttagatgaat cattacaacc  84420
attaccaaat gctccacaac ctgctaaagt tacagctact gttgaaacta agcaaaaagg  84480
tgcttttgaa aatgaagaag accgtgcagg attatcatat aaagtagtag ttaactcaga  84540
tgacgctcaa tcagctcctt ctgaagaagt aacagctaca gtatctaacg tagacgatgg  84600
tgttaaactt tcaattagtg ttaacgctat gtaccaacaa caaccacaat tcgtttctat  84660
ctaccgtcaa ggtaaagaaa caggtatgta cttcctaata aaacgtgtac cagttaaaga  84720
tgcacaagaa gatggaacaa tcgtattcgt agataagaac gaaacattgc ctgaaacagc  84780
agacgtattt gttggtgaaa tgtcaccaca agtagttcac ttattcgaat tacttccaat  84840
gatgaaatta ccattagctc aaattaatgc ttctattaca tttgcagtat tatggtatgg  84900
tgcattagca ttacgtgctc ctaaaaaatg ggctcgtatt aaaaacgttc gttatatcgc  84960
agtttaatag aataagaaaa actgaataca agagaatagg gataaactta gggtttatcc  85020
ctttttattt aaaataaact tgaagggatt taataaatat gttatactat aagaaactat  85080
tagataaaaa aatggctact gtttatggta cagtggagat tgacaaagat ggagtagtta  85140
aaggattaac taaagagcaa gaaaaagaat ttgcaaatgt tccaggtttt gaatttgaag  85200
aagaaaagaa aactactaga aaacaatcag cttctactag taaagaagaa gagcctaagg  85260
aagaggaaaa gaaagcctct actagaaaaa ctacaagtac tactagaaaa tctacagcac  85320
gtaaaacaac agccaaaaaa gatgaaaata agtaaagggt gaattaaatg gttaactcaa  85380
tgtttggagg ggacttagac ccttatgaaa aatcattaaa ctatgaatat ccttatcatc  85440
ctagtggtaa tcctaaacat atagacgtaa gtgagataga taatttaaca ttagctgatt  85500
atggatggtc accggatgca gttaaagcat atatgttcgg tatcatagtt caaaatcctg  85560
atacaggaca acctatgggt gatgagtttt ataaccatat attagaaaga gcggtaggta  85620
```

```
aagctgaaag agcattagat atatctatac tacctgacac tcaacatgag atgagagatt  85680
atcatgagac agagtttaat agttatatgt ttgtacatgc ttatagaaaa cctatattac  85740
aggtagagaa cttacagcta cagtttaatg gtagaccgat atataaatac cctgctaact  85800
ggtggaaagt agagcatcta gcaggacatg ttcaattatt ccctacagca cttatgcaaa  85860
caggacaatc aatgtcatat gatgcggtat tcaatggata ccctcaatta gcaggtgtat  85920
acccaccatc aggagcaaca tttgcacctc aaatgatacg attagaatat gtatcaggta  85980
tgcttccacg taaaaaagca ggaagaaata aaccttggga aatgcctcct gagttagaac  86040
aattagttat aaaatatgca ttgaaagaaa tataccaagt atggggtaac ttaatcattg  86100
gtgccggtat tgctaataaa acattagaag tagacggtat tacagagaca ataggtacca  86160
ctcaatcagc tatgtatggt ggagctagtg ctcagatact tcaaataaat gaagatataa  86220
aagaactatt agatggttta agagcttact ttggatataa tatgatagga ttataaggag  86280
ggttagaaaa tggaaaaacc gtatatgata ggagccaact ctaaccctaa tgttattaat  86340
aagtcaacaa catatactac tacaacacaa gcagatgaac aagataaacc taagtatact  86400
actagactag agtttgatac gattgacatg attaggttta ttaatgaccg aggtataaaa  86460
gtattatggg aagaagcata tttctgccct tgtcttaatc ctgatacagg acatcctaga  86520
gtcgattgtc ctagatgtca tggtaaaggg attgcatatc tacctcctaa agagactata  86580
atggcaatac agtctcaaga gaaaggaact aaccagttag atataggtat attagacaca  86640
ggtactgcaa taggtaccac tcaattagaa aagaggattt cctatagaga caggtttact  86700
gttcctgagg tattgatgcc tcaacaaatg atttattttg tgaataaaga tagaattaaa  86760
aaaggtatac ctctatacta cgatgtaaaa gaagtaactt atatagccac tcaagatggt  86820
acagtctatg aagaagatta tgaaattaag aataatagat tgtatttaaa tgaaaaatat  86880
gagaatcata cagtaacttt aaagatactt atgactttaa gatatgtagt atcagatata  86940
ctaaaagaaa gtcgttacca atatactaag tttaatcaac ctaaatcaaa atttgaaaac  87000
ttacctcaaa aattacttct taaaagggaa gatgttattg tactacaaga cccttataaa  87060
gttaatgatg gtatagaaga agacctagaa attcaagtag atgaccctaa ggcttcggca  87120
tctaatccta gtaatttagg tggattcttc ggaggtgcat ttaaataatg ccagttcacg  87180
gaaagagacc taatttattt aaaaataaaa actataagca ggtaggtaag agaacaattg  87240
atggtatgcg ttcagaagtt cttgataaat tacaagcaac agcacagcaa gtagagaata  87300
ctagtattaa acgtatgcct acttacctac aaataacaga gaaaaagctt gaaaaagaag  87360
gagtagtaga ccttaaaaaa gcttttgctc actcatctaa aaagaaaact agtaaagatg  87420
gcggatggta tttaactgta ccaatccgca tcaaaactag tagaatgaat aacagtactt  87480
accaagatat gagaacttta aaagtagata aaggtacagg ttcagtctct aagataactg  87540
attacctaga aggacgtaga aagaatgtaa gccacccttc aatgaagcct gagcctatga  87600
ctcataatat gactaaagtt aaaagaggaa agcaatcttc ttactttata tttagaactg  87660
tttctagtaa gtcacctgct agttcttgga tacttaacag agataaagtt aatgaagata  87720
acttctctaa aacaactcta aaaactgtta agcaattaat gaactggaag atgaaaaatt  87780
taaattaaga ggagggatag tattaaatgg caataacatc agttgattca tatttattat  87840
cagaaataaa gcctagactt aacactgtgc tagagaattg ttatattata gatgaagttt  87900
taaaagactt tgattatcaa actagagaga gctttaaaga agctttctgt ggtaagaatg  87960
```

```
cacaacatga agtaacggta ggatttaact tcccaaaatt taaaaataac tatgaagctc  88020
attacttgat acaattaggt caaggacaag agacaaaaaa ctctttaggg agtattcagt  88080
catcttactt tgaggcaaca ggagatacct tagtcgaatc ttctacagca ataagagaag  88140
atgataagtt agtttttact gtttctaaac caataggaga gttaataaag gtagaagata  88200
tagagtttgc taaatacgat aatcttcaag ttgaaggtaa taaggtatca tttaagtatc  88260
aaacaaatga agattatgag aactacaatg ctaacattat atttaccgaa aagaaaaatg  88320
attctaaagg tttagtaaaa ggattcacag ttgaagaaca agtaacagtt gtaggtcttt  88380
catttaatgt agacgttgca agatgtttgg atgctgtact gaaaatgatt ttaatatcta  88440
tgagagatag tatagaagag caacaaacat tccaattaca gaatttgtct tttggtgata  88500
ttgcaccaat aatagaagat ggtgactcaa tgatttttgg tagaccaaca attattaagt  88560
acacaagttc tctagatttg gattatacta ttacacaaga tattaataaa ctaactttta  88620
aagaaagaaa ggattggaag taggatggct agaaaaaaga cacctgaaaa taacactcct  88680
aaatttaatg gttatgttca tatagataca ttccttgata ctgcaaaaac ccttttttaat  88740
atgaaggatt cacaagtagc aggatttaaa gcttatatgg aaggtagtca ttatttgttt  88800
agtgagcaag aattcttacc atcattagag aagtatctag gtaggaaatt agatatataa  88860
taacattcag ataaggagaa ttaaatatgg cagtagaacc attcccaaga agacctatta  88920
cccgtcctca tgcatctatt gaagtagata cttcaggtat cggtggctca gcaggttcaa  88980
gtgaaaaagt attttgctta atcggtcagg ctgaaggcgg agaaccaaat acagtttatg  89040
aattacgtaa ctatgcacaa gctaaacgtt tattccgttc aggagaatta cttgatgcaa  89100
tagaattagc atggggttct aaccctaact atacagcagg taagatttta gctatgcgta  89160
tagaagatgc taaacctgct tcagcggaaa tcggtggatt aaaagtaaca tctaaaatct  89220
atggtaatgt tgctaacaac attcaagtag gattagaaaa gaatacatta agtgattcat  89280
tacgtttaag agtaatcttc caagatgacc gtttcaatga ggtttatgat aatatcggta  89340
atatcttcac aatcaagtac aaaggagaag aagctaacgc aactttctct gtagaacatg  89400
atgaagaaac tcaaaaagca agtcgtttag tattaaaagt tggagaccaa gaagttaagt  89460
catatgattt aactggtgga gcttatgact acactaatgc tattattaca gacattaatc  89520
aattacctga tttcgaagct aaattatcac ctttcggaga taagaactta gaatctagta  89580
aattagataa aattgaaaat gcaaatatca aagataaagc tgtatatgta aaagcagttt  89640
ttggtgactt agaaaaacaa acagcttaca acggtatcgt atctttcgag caacttaatg  89700
cagaaggaga agtaccaagt aatgtagagg ttgaagcagg agaagaatca gctacagtaa  89760
ctgctacttc acctattaaa actattgagc cgtttgagtt aactaagtta acgggcggta  89820
ctaatggaga accacctgct acatgggcag acaagttaga taaatttgca catgaaggcg  89880
gatactacat tgtcccatta tcatctaaac aatcagttca tgcagaggta gcttcttttg  89940
ttaaagaacg ttctgatgca ggggaaccaa tgagagctat tgttggtgga ggattcaatg  90000
aatctaaaga acaattgttc ggtagacaag catcattatc taatccacga gtatcattag  90060
tagctaactc aggtactttt gttatggatg atggacgtaa aaaccacgta cctgcttaca  90120
tggtagccgt agctctaggt ggtcttgcaa gtggtttaga aatcggtgaa tcaatcacat  90180
tcaaaccact acgtgtaagt tcattagacc aaatctatga gtcaatagat ttagatgaat  90240
taaatgaaaa tggtattatt agtatcgagt ttgttcgtaa ccgtactaat acattcttca  90300
gaatcgttga tgacgtaact acattcaatg ataaatcaga cccagttaag gctgaaatgg  90360
```

```
ctgttgggga agctaatgac ttcttagtaa gtgagcttaa agttcaactt gaagaccaat  90420
ttattggtac tcgtactatc aatacaagtg cttcaatcat taaagacttt atccaatctt  90480
acttgggtcg taagaaacgt gataatgaaa ttcaagactt ccctgctgaa gacgtacaag  90540
ttattgttga aggtaacgaa gcaagaattt caatgacagt ttacccaatc agaagcttca  90600
agaaaatctc tgttagcttg gtttacaagc aacagacatt acaagcctag tctaggtgac  90660
ggagtacctg gattaggtac tcctattaat ataatttgaa tactttagga gagtgaatac  90720
agatggcatc agaagctaaa caaaccgtcc atactggtaa taccgtccta cttatgatta  90780
aaggtaaacc ggtaggaaga gcacaatcag catcaggtca acgtgaatac ggtacaactg  90840
gtgtatacga aatcggttct atcatgcctc aagaacacgt atacttacgt tatgaaggta  90900
caattacagt agaacgttta cgtatgaaaa aagaaaactt tgcagattta ggatatgctt  90960
cacttggtga agaaattctt aagaaagata tcattgatat tttagtggta gataacttaa  91020
cgaaacaagt tattatctca tatcatggtt gctctgcaaa taactacaat gaaacttggc  91080
agacaaatga aattgtaaca gaagaaatcg agttcagtta cctttaacta atagaggcta  91140
tgtttggtga caagcataga aaacacttta aattgcgtga aagtcttaaa gactagataa  91200
ctacaacgta actcgaaagg gtaagcgtga atgttgagaa atcagaaaaa atatctagta  91260
tagtataagg ttaaatccta agtacagtaa aatagatgat acgcaggcaa gcctacaaat  91320
gtgggaagct tcaacgacta taataggtga gtcttagtta cacattaaga ttatggtata  91380
gtctactccc tttaaaatat atcgaaagat agggtacaaa ggacagcatc agataaagct  91440
agaacttaaa tttcttatta agaccaacaa taaaagttgg tcttatattt tatacttgct  91500
ttgtctgagg cagtgtgcta taattaaaat acaaggaggt aataatatgg gaaaaaatca  91560
atatacattt aatattaaag aaaataaaaa taaatggtat gaatggtgta aactacaaaa  91620
cgtaaaacct ttagtagaat atgaaaatgc acaacaaata ttttattttg aatttcttga  91680
aggtaaattt aaaggactaa taggaaaaac atattgggct agtataaata gaggttctaa  91740
tatgcgtatg agttgtttaa catcagaaag taaagataaa tatttaaaaa atttaggaaa  91800
aagaaaaggt atagaggtag tagaagacta taagggtggc agaaaattaa aacataaatt  91860
tatagtttta gaaggtaagt accaaggatg tgaaggatat ataactttaa atgatttaga  91920
gaatttaggt agagtagata atagaagttt atctgaaaaa ggaaggaaac aatactttga  91980
taaacaggca agacttagag attgtattat tctagagtac cctaaagact atagaataaa  92040
aactaaagat aagatagtag taaaagataa agaagggcat gttcataata ttattgttca  92100
ggactttttt gagaaatcat ctttattgga gttatcttgt gctagtgaag gagagaaaat  92160
agttaaagaa atacttacta aaaattctat aaaatttgaa aaagaaaaat catttagaaa  92220
caaagaaggt aaagtacaaa gatttgattt ttatattaat gaaaataata aagaatatgc  92280
aatagagtac aatggtgcac agcactacat agattctaca ggatatctta aagatacttt  92340
ggaaacaacc cagaaaagag ataaactaaa aaaagaatac agtaaagata aaggtataaa  92400
tttattaatt attccttaca caataacaga taagaaagaa atggaaaaaa ttattttaaa  92460
ttttttaaac aaataaccct tgacactccc tcaagggata tgttattata ataacaggtt  92520
aggagtaata agtatgaata ataggcaagc taaaataaaa ggatataacc aatttcatta  92580
ttatgatttt ccaacaacta aaggtaagtt taaagatata atgaaaagaa aatctagaac  92640
agaacttaaa aaagatttac aaaaagaaag gaagtattat cttgacaaat aagagaaaaa  92700
```

```
cgataggtaa gatgagtaac acaagagcaa catggaatat taatccggta actaaagtta  92760
aaaaagataa aacaaaatat tctagaaaaa ataaacataa aggtcttgac aattataatt  92820
aactaaggta tattattagt ataacaaaaa aggagatggg tatatgagta cattttggtc  92880
agaaagaaga acaactaata aagataggca agttaaaaaa cattatactc aaatgagtat  92940
gtatgaaaga aagaaatgtg tagagttatt acaagagaca attactgaaa atagaattat  93000
taattttaca cgacatagtg caaagaaagt taaaggtaaa ccaacaacaa atatacctaa  93060
attaataggt tttattttta aaaataagtt tgcctacgaa aatatcatag aatacaataa  93120
cacagattat aatggtaata ttgagaggag aattgttgtt aaacatccta aagttataac  93180
tgtagaagga aaacctagct atcagttttt gacaattagt cttgaagatg ctagagttat  93240
tacagtatgg tacaacagtg tagatgatac acatagaaca ctagatttaa attattatag  93300
taaagacttg acaattcaat aaggaggtat tataatgggt atcacaatag taaatagtta  93360
ttttattctg tctaacatct tcctcatcat attaaccata ttaaatggta agggtactgt  93420
tacaagggaa tcactaacta tgagtaaaat attagtagta ataacatcaa ttcaattttt  93480
agcatgttta attattaatg gtatttattg gtcactaaaa ttttagaata aaagtattga  93540
caaattaaaa ctaataaatt ataataaagg tataacaaat taaaggagaa gatataaaat  93600
gtcacaagat aaattaagag caatttacac agaaatgaaa gtagaattac acaaatttcc  93660
taaagaggta gatataacaa gtaaatcaac tgcaattgca atcaatcaga ttttagataa  93720
attcaaaaca ttaacagaac aagcaggaaa gattactaga aaatatttag aaggtcaaga  93780
aatattaact attgattatg agtattatga ttcattacaa gaatactata tttacctact  93840
tagaaatagt gaaaagattg aacaaagttt acaagaaatt actaagcgca caggtgaata  93900
tgtaaagtaa ttttgattta aaaacaaaat atgatatact atgtttaaag tagtaagcct  93960
acactagtcc gtgttatatt aatattgaat cggataagcg taggctttat taatatttaa  94020
aaaaggaagg tatatcatat tatggcagaa gaaattaaaa aggaacaaga tgtacaagaa  94080
acaactaaag aagaaaaaaa agatgttagt aaaatgacac cggaagaaat agataaatta  94140
aaatatcaag acaaacaaga aaaagaacaa gttattaaca aagttattaa aggtgttaat  94200
gatacttggg aaaaagaata taactttgaa gaattagact taagatttaa agttaaaatt  94260
aaattaccta atgcacgaga acaaggtaat atatttgcgt tacgttctgc ttacttaggt  94320
ggtatggata tgtaccaaac agaccaagta attagagcat atcaaatgtt agctacatta  94380
caggaagtag gtattgaagt tcctaaggaa ttccaagacc ctgacgatat ttataactta  94440
tatcctttaa ctgttatgta tgaagattgg ttaggattct taaactcctt tcgttactaa  94500
tagtatagaa acattagata aagatataga acgattgggc ggtatggaat caattgttaa  94560
acaaccttta tctagaaatc tatgggctat tatgaaagag tttaatgttt tacctactga  94620
gcaaagattt aaggacttag atgattatca gatagagttt attattggga atatgaacag  94680
agatgtttat gaacataaca aacaacttaa acaagctcaa aaaggtggaa aattcgatag  94740
tcaattcgaa gatgatgata gtagttggtg gaatgaatct catgaagact ttgacccagt  94800
acctgatttc ttagatgctg atgatttagc acaacaggtg gaagctaaat tatccgatag  94860
agataaggaa gaaagagcta agagaaacga tgcggagtta aatgatgaaa cagaaggact  94920
tactacacaa catctagcta tgatggaata catcagacag aaacaacaag aattagatga  94980
tgaagtagga aatggtaaga ctagtgaaga ggatgctact atatcacaag atagcgttaa  95040
taaagcacta gaagacctag atgatgactg gtatatgtaa agggtggtag gtgatactac  95100
```

```
catccttatt tttttaaaat ggatggtgaa taatgatggc aatgaatgac gattatagat  95160
tggtcttgtc cggtgatagt tcggatttag agaatagtct gaaggcaata gaactttata  95220
tggattcttt agagtctaag aatattgatg ctcctttaga taatttctta aaaaaattaa  95280
aagtaattgc taaagaagtt aaaaatgtac agaacgcaat ggataaacaa gatggtaaat  95340
ctgttatatc ttctaaagac atggatgaat ctattaaatc cactcaatct gctacaaaga  95400
atataaatga attaaagaaa gctttagatg accttcaaaa agagaatata tctaaaggta  95460
ttgcacctga ccctgaagtt gaaaaagcat atgctaagat gggtaaagtt gtagatgaaa  95520
ctcaagaaaa acttgagaaa atgtcttcac aaaaaatagg ttctgatgct agtattcaaa  95580
atagaattaa ggaaatgaaa accttaaatc aagtaactga agaatacaat aaaataagta  95640
aagattctag cgcaactaaa gattatacaa aacgattaag agctaatcgt aatatgacta  95700
gaggttacat ggagcgttca gaaggaacag gacgtttgac atatgaccaa ggtgcacgag  95760
ttagaagtga actaggtaaa ataagttctt atgagagcca aagaaaacaa aaccaacgta  95820
atttaggaca agcaagagag caatatagca actatagaaa ccaacaacaa gacttgacta  95880
aacgtagagc tagcggtcaa attaataagg cacaatatga acaagaatta gcttctatta  95940
aacaggaaat gaaagctaga gaagaactta tatctaacta cgagaaacta ggagcagaac  96000
ttgataaaac agtccagtat tataagggtt cagttcaaaa ggatttccaa tctagagatg  96060
tagaccaaca acgaggaaca tttggtagaa tggttcaaga acgtttgcca tctattggtt  96120
ctcatgctat gatgggtact acagctatgg ctacaggttt atacatgaag ggtgcctcat  96180
taagtgaaac taatagaccg atggttacat cattaggtca aaattccgat aatatggata  96240
tagattctgt aagaaatgca tatggagact tgtcaattga caacaaatta ggttataata  96300
gtactgacat gttaaaaatg gctacttcat atgaagcatc agtagggcat aaaagtgacg  96360
aggacacaat ggcaggaact aaacaacttg ctattggagg acgttcttta ggtattagag  96420
accaagaagc ttatcaagag tctatgggtc aaatcatgca tactggtgga gtaaattctg  96480
ataacatgaa ggaaatgcaa gatgcattcc taggtggtat taaacaatca ggcatggttg  96540
gtcgtcaaga tgaacaactt aaagcactag gttctatagc ggaacaatca ggagaaggaa  96600
gaactctaac taaagaccaa atgagtaatc ttactgccat gcaatctact tttgcagagt  96660
caggaagtaa aggattacaa ggtgaacaag gtgccaatgc tattaacagt atagaccaag  96720
gacttaaaaa tggtatgaat agttcttatg ctcgtatagc aatgggatgg ggaacacaat  96780
accaaggtct tgaaggtgga tatgatttac aaaaacgtat ggatgaaggt atatctaatc  96840
ctgaaaactt gacagatatg gctgatatgg ctactcaaat gggtggcagt gaaaaagaac  96900
aaaaatacct atttaataga agtatgaaag aaataggcgc taacctaact atggagcaat  96960
ctgatgaaat atttaaagat gctcaatccg gaaaactatc taaagaagag ttagctaaga  97020
aagctaagaa aatggaaaaa gaaggtaaaa aagaaggaga agataacgcc actgattata  97080
aagaatctaa atcaggaaaa aatgaccaaa ataaatctaa gactgatgat aaagcagaag  97140
atacttatga tatggctcaa ccattaagag atgctcatag tgctttagca ggtcttcctg  97200
cccctatata tttagctata ggagctatag gagcatttac agcttcacta attgcatctg  97260
caagtcaatt tggagcaggt cacttaattg gtaaaggagc caaaggactt agaaataaat  97320
ttggtagaaa taagggtggt agctccggcg gtaatcctat ggcaggtgga atgcctagtg  97380
gtggtggttc acctaagggc ggaggctcac ctaaaggtgg aggcactcgt tctactggag  97440
```

```
gaaaaatact tgatagcgct aaaggtcttg gaggattcct agtaggtggc gcaggatgga  97500
aaggtatgtt tggtggggag tctaaaggta aaggctttaa acaaacatct aaagaagcct  97560
ggtcaggtac tagaaaagta tttaatagag ataatggtag aaaagccatg gataaatcta  97620
aagacatagc taaaggtact ggtagtggtc ttaaagatat ctataatgat agtatatttg  97680
gtaaagaaag aagacaaaac ctaggagaaa aagctaaagg ttttggtggc aaagctaaag  97740
gtctttatgg taaatttgct gataagtttg gtgacggagg taaaaatggt atcctttcac  97800
aatcaccaaa agcaggtgga agtggcatag ggaaacttgg aaaacttgca ggtggacttg  97860
gaaaaggagc cggagtttta ggtgttgcta cgtctgcctt atcattaata cctgctttag  97920
cttccggaga tagtaaagct atcggcggtg gaataggctc tatgggtgga ggaatggcag  97980
gtgcatcagc aggagcttct ataggagctt tatttggtgg tgtaggtgca atacctggag  98040
ctttaatagg tggagctata ggttccttcg gaggaggagc tgttggtgaa aaagtcggag  98100
acatggctaa aaaagctaac actaaagaag gatggaacct aggatggact aatggagata  98160
aagatggtaa gaataaattc caagattctt tattaggaaa acctatatct aaagcatgga  98220
gcggtataac aggtctcttt gataatgacg ctgaagcatc cgaagaagat agtaaagata  98280
agaaaaaagg tgttaaaggc gttaaaggag atactaagaa gaaagaaaaa atgacagcag  98340
aacaacttag agaaaagaat aaccaatctg aaactaagaa tcttaaaatc tatagtgatt  98400
tacttgacag agctcagaaa attattgaga gtgctaaagg tattaatata gatggaggaa  98460
cttctgatag tggttctgat agtggaggct ctgcatctga tgtaggtgga gaaggtgcag  98520
agaagatgta caagttcctt aaaggaaaag gactatctga taatcaggta ggagctgtta  98580
tggggaactt acaacaagaa tctaatcttg accctaatgc taagaatgct tctagtggag  98640
catttggtat tgctcagtgg ttaggagcta gaaaaacagg attagaaaac tttgctaaat  98700
ctaaaggtaa aaaatctagt gacatggatg ttcaattaga ttacctatgg aaagaaatgc  98760
agtctgatta tgaaagcaat aatcttaaaa atgcaggttg gagcaaaggt ggaagcttag  98820
aacagaatac aaaagcattt gctactggat ttgaacgtat gggagcaaac gaggctatga  98880
tgggtactcg tgttaacaat gctaaggaat tcaagaagaa atatggaggc tccggtggcg  98940
gaggtggtgg aggagcttta tcctctactt atcaagaagc tatgagtaat cctgtattaa  99000
ctactggttc taattataga ggctctaatg atgcttctaa tgcttctaca actaacagaa  99060
taacagtcaa tgttaatgtt caaggtggaa ataatcctga agaaactgga gacattatcg  99120
gaggaagaat tagagaagtt ctagatagta atatggatat ctttgcaaat gaacataaga  99180
gaagttatta gtaattttgt attgacacaa gagtagtatc atagtatact actcttatac  99240
atataaaaaa taaaaggaag tatgtgtata tgcgtagaat aagaagacct aaggtaagaa  99300
tagaaatcgt tacagatgat aatacattta cattgagatt tgaagataca cgtgactata  99360
atggtgatga gtttggagct aaacttttag gattccaaac taaaaactct atggaagatg  99420
atagttcagt tttccaaata aatatggcag gagatactta ttgggataag ctagttatgg  99480
ctaatgatat cataagaata tttattacac ctaatgatga ccccaacgat aaagaaggaa  99540
gacaagaacg acttatccag gtaggtatgg tttctcaagt atcaaaagta ggtagttacg  99600
gtaatgacca aactcaattt agaataacag gtcaatcttt tgtaaaacct tttatgaaat  99660
ttggattagg cgttattcag gaagttcaag ctgtattgcc tgaagtaggt tggcttattg  99720
atggtgatgg agataatgaa gtaaaattta ctggtagctc agctcatgaa gtaatgactg  99780
gcattatacg tagatttata ccttatatga aatataacta tactgaaaaa acatataata  99840
```

caattgataa ctatcttgat tatgatgatt taagtagttg ggatgagttt gaaaaactta 99900
cagaagtttc agcctttact aattttgacg ggtcattaaa acagttaatg gatatggtaa 99960
cagctagacc ttttaatgag ttattcttca aaaattcaga aaaaacacct ggaaaggctc 100020
aacttgtatt aagaaagacc ccttttaatc ctactgagtg gagagcttta gatatgatta 100080
aagtacctac tgaggatttt atagaagagg atgtaggtaa aagtgatgta gagacatatt 100140
ctatatttac agcaacacct gcaggtatgt tgaaagagct taacggtgat gtattttcca 100200
aaccacaatt ccatcctgaa ttaactgata gatacggtta taccaaattt gaagtagaaa 100260
atatttatct tagtacaaaa tcaggttcag ccactgagga ttcagattct tcaggtgatg 100320
ataatggtac agaacgagga acttactcta aaattatgaa agatttaagt aactatggaa 100380
gagataatat atctaaaggt atagataagt atacaagtaa attatcttca aaatataaaa 100440
acttaaaaaa agcccaagct aaaaaaatta tagagaagtt tgtcaaagaa ggaaaagtaa 100500
cagaaaaaga atatgaaaaa ataacaggta ataaggtaga tgatgaatta acatcagata 100560
acagaccgaa gttgacaaaa gataaattaa agagtatact aaaagagaag tttaaaacac 100620
aagatgattt taataattct aagaaaaaga aaaaagctaa gacagatgca cttaaagaat 100680
tgacaactaa atatcgtttt ggtaataaaa cacatgctac aactttgtta gatgaatata 100740
ttaaatacaa aggagaaccg cctaatgatg aggcttttga taaatatctt aaagctattg 100800
aaggtgttag taacgtagct acagacacag gttcagatgc aagtgatagc cctctagtta 100860
tgttttctag aatgttattt aattggtatc atggtaaccc taacttctat gcaggagata 100920
ttattgtttt aggagaccct aagtatgacc taggtaaaag attatttatt gaggataagc 100980
aacgaggaga cacatgggag ttctatattg aatctgtaga acataaattc gattataaac 101040
aagggtatta tacaactgta ggagtaacta gaggtttaaa agacgctatt ctagaagatg 101100
gtaaaggtag tcctcataga tttgcaggat tatggaatca atcatcagac ttcatgggag 101160
gtcttatggg tgaagatact tctaaagaac ttaaagaaaa aggtgtagca gagaaacaaa 101220
gtagtggagg taaagatggt ggttctgata gtggcggagc tcaagatggt ggctctttag 101280
attcacttaa aaaatataac ggcaaacttc ctaaacatga cccaagtttt gttcaacctg 101340
gtaaccgaca ttataagtat cagtgtacat ggtatgctta taatagaaga ggtcaattag 101400
gcattcctgt gcctttatgg ggggacgccg ccgactggat aggcggtgct aaaggagcag 101460
gttatggtgt aggtagaaca cctaaacaag gtgcttgtgt tatatggcaa agaggagttc 101520
aaggaggtag cccacaatat ggtcacgtag cttttgtaga gaaagtatta gatggaggta 101580
aaaaaatatt tatctctgaa cataactatg ctacccctaa tggatatggt actagaacaa 101640
tagatatgag ttcagccata ggtaagaatg ctcaattcat ttacgataag aaataaagga 101700
ggatagtcta tggcaacaga taaagaagct aaagatgtta ttgataaatt tatagacaat 101760
gtatttaatt ttgatgtact tacaaaagaa agaataaaag aaaaagatga agaaattaaa 101820
aaaataacta cagatgatat gtatgaaaag gttgtgtata tacgacccta cgttggagta 101880
atacaaagtc ttaaccctca acatgtgcag tatgaatcat tttctaataa tggttatgat 101940
atagaggcag aattaagttt caggaaagta agttatttag ttgataaagg gtctatacct 102000
acagattctt tatctacttt aacagttcac ttagtagaac gaaatcaaga actattaata 102060
gattactttg atgagataca agatgtgttg tatggagaat atatggaaga agaatatgta 102120
tttgatgaag atgtaccatt aagtacgata ctagcattag acttaaatga taatcttaaa 102180

```
tccttatcaa atataaagta tatgttcaaa ggtgctccta aagagaatcc atttggaaca 102240
gataaagatg tttatataga tacttataac ttattatact ggttatattt aggtgaagat 102300
gaagagttag catacoctat gaatattaat tacttcttta cagagggaag attctttact 102360
atattcggta aaggacataa gtataaggta gatgttagta aatttatagt tggagatata 102420
ttattctttg gtagaagtga tactaatata ggtatttatg taggagatgg ggagtttata 102480
tctatgatgg gtaaattccc taaagatgaa acacctatag gaaaatataa acttgatgat 102540
tactggaatg aatttaacgg aagagttatg agattcgatg aagaggtgta tatttaatgg 102600
tagtaagatt ccaatcttcc atggggagaa gtttaaaaag agtagattca gatgatttaa 102660
atgtaaaagg attagtttta gctacagtta gtaaaattaa ttataaatat caatcagtag 102720
aagttaaagt taacaactta actctaggaa gccgtatagg tgacgatggt agcttagctg 102780
taccttatcc taaatctttc ataggaagaa cacctgaagg aagcgtattc ggtacaaaac 102840
ctcttattac tgaaggttct gtagtattaa taggatttct aaatgatgat ataaatagtc 102900
ctattatttt aagtgtttat ggtgataatg aacaaaataa aatgattaat accaatcctt 102960
tagatggggg taagtttgat acagaaagtg tctataaata tagtagttca ctatatgaaa 103020
ttttaccatc tttaaattat aaatatgatg atggagaagg aacaagtatt aggacttata 103080
atggtaaatc atttttctct atgacatcag gtgaagaaga gaaacctcag gcaacagatt 103140
tttatactgg aactgagtat caagatttat ttacttctta ttatggtaat aagacattaa 103200
ttgagcctag aatacaaaag gctcctaata tgttatttaa acatcaaggc gtttttatg 103260
atgatggcac gccggataat catataacta ctttatttat atctgaaaga ggggatataa 103320
gagcctcagt tttaaataca gaaacacaga aaagaaccac acaggaaatg tcaagtgatg 103380
ggtcttatag ggttataaaa caagatgacg atttaatgtt ggatgaagct caagtttgga 103440
ttgagtatgg tattagtgaa gataataaat tctatattaa aaatgacaag cataaatttg 103500
aatttactga tgagggaatt tatatagatg ataagcctat gttagaaaac ttagatgaga 103560
gtatagcaga ggctatgaag aatttgaatg aaatacaaaa agaactcgat gatataaatt 103620
accttctcga gggtgtaggt aaggataact tagaagaatt aatagagtct acaaaaagagt 103680
ctatagaagc ttctaaaaaa gcaacttcag atgtcaatag acttacaact cagatagcag 103740
aagttagtgg tagaactgaa ggtattataa cacagttcca aaaatttaga gatgagactt 103800
ttaaagattt ttatgaagat gcttctactg ttattaatga agtaaatcag aatttcccta 103860
ctatgaaaac agatgttaag accttaaaga ctaaagttga taacctagag aaaactgaaa 103920
taccaaatat taaaactaga ttaacagaac tagagaacaa taataacaat gctgataaaa 103980
taatatcaga tagaggagaa catataggtg ctatgataca gttagaggaa aatgtcactg 104040
tacctatgag aaaatatatg ccaataccat ggagcaaagt tacttataat aatgcagagt 104100
tttgggattc taataatcct actcgattag tagtacctaa aggaataaca aaagtaagag 104160
ttgcaggtaa tgttttgtgg gactctaacg ccacaggaca acgtatgttg agaatattga 104220
aaaatggtac ttatagtata ggattacctt atacaagaga tgtagctata tctacagcac 104280
ctcagaatgg tactagtgga gttattcctg ttaaagaagg agattacttt gagtttgaag 104340
ctttccaaga ctcagaaggt gacagacaat tcagagcaga cccttataca tggtttagta 104400
ttgaagctat agaattagaa actgaaacta tggagaaaga ctttatgctt ataggacata 104460
gaggagcaac cggatacaca gatgagcaca cgataaaagg atatcaaatg gctttagata 104520
aaggtgcaga ttatatagaa ttagatttac aattaacaaa agataataag ttattgtgta 104580
```

```
tgcatgattc tactatagac agaacaacaa caggaacagg taaggtagga gatatgacct 104640
tatcttatat acaaactaac tttacatccc tcaatggtga gccgatacca tctcttgatg 104700
atgtactaaa tcattttgga acaaaagtta aatattatat agaaactaaa cgtccgtttg 104760
atgctaatat ggataaagaa ttattaactc aattaaaagc aaaaggatta ataggaatag 104820
gttcagagag attccaagta attattcaat catttgctag agaatcgtta attaatattc 104880
ataatcaatt ctctaatata cctttagctt acttaacaag tacattctct gaaagtgaaa 104940
tggatgattg tttaagttat ggttcttatg ctattgcgcc taaatataca actataacta 105000
aagaattagt agatttagct catagtaaag gcttaaaagt ccacgcatgg acggtaaata 105060
caaaagaaga aatgcaaagc ttaatacaaa tgggtgtaga tggattcttt acaaactacc 105120
tagatgaata taaaaagatt taatattaaa gacctattaa tttaggtctt tttttagttg 105180
taatttaaac tagttcgtga tatattagta gtatgagatt tatatacata ctgaaaagga 105240
gaggataaaa tgccacaatc agatggaata agtaatcttc atagaatagc tttacgtttc 105300
cctaaagaag gcggtggtta tgatatgtat agatttaaag ttaaccctga gaactacaca 105360
atagattcac cacaacgtac gacagcaatt aaaacaaaat cagatatcgt aatagaagat 105420
tatggtaaag atatagaagt tattaacttc acaggtacaa ctggttttag acctgttaga 105480
gaagcagatg ggttaaaaac aggtaagcag aaaatggaag agttacaaag tagagttagt 105540
gaatatgcta tgcaaggtgg cagtggtaat gtaagtggtt cttacttaca attttttaac 105600
tttacagatg atagttatta taaagttcat ttagctcctc aggggttaaa gataactagg 105660
tctaaagatg aaccattact ttttagatat gaaataacat tagtagttat tggttcatta 105720
acagaagcag atagaagtgc tgtaactact gaagagtttg gtaatgttaa acctaatgct 105780
tctcaaagag tagatgaagg tataaaagaa ttagataaaa atgctcgtaa aacgagagat 105840
agaaacaatc aagaaatatc tagaagagaa aatacaatac ctaaatccac aggagataat 105900
acgaacgagg gtaatagact taagcaaagc ttccctagta gttctatata taatcctaga 105960
caatctacta atggattaaa aggtaatatt gacaatatgg ctctgataat aggttacggt 106020
gatggaggtg tatctagcta atgaataatt ttataccaca acctcaaggt ctacttagat 106080
ttttaaatgc cctagataca gatttaactt cttctcatat gaatttactg gatgaagagg 106140
tatcatttgt atctaaattt tatacaccac agttacaatt aagtgaatta gcaaaaaaag 106200
tattgacaaa tataaagaca gatgatatac ctgtattaga aagggaattt aatgataata 106260
caattatcca taaagctaac gatacattac taaaagtaca ggctccaaga atgtatatga 106320
ttctacagtc tattgtactt gaagcatatg ctattgttaa ttgctttgta gaaaatccaa 106380
gttctttaaa atacttaact gaagaagatg ttagtataac acgagaaaac ttaaattatg 106440
tagctgacta cttaggtaac tatgatgact acaatagtgt tgtattagac ttaagagatt 106500
tagacttatg ttttagtgct atagaattac aattacctct aattaaaaag gaggctaacg 106560
tataatgaga tttaagaagc acgtagttca acatgaagaa acgatgcaag caatagcaca 106620
gagatactat ggtgatgtta gttattggat agacctagta gagcataata atttaaagta 106680
tccctattta gtagaaactg atgaagaaaa aatgaaagac ccggaacgat tagcttctac 106740
cggtgataca ctgattatac ctatagaatc tgatttaaca gatgtatcag caaaagaaat 106800
taattctaga gataaagatg tactagttga attagcttta ggaagagatt taaatattac 106860
tgcagatgaa aagtatttta atgaacatgg tactagtgat aatatactag cattcagcac 106920
```

-continued

```
aaatggtaat ggagatttag atactgtaaa aggcatagat aatatgaaac agcaattaca 106980
ggcacgttta ttaactccta gaggttcctt aatgttacat cctaattacg gttcagattt 107040
gcataattta tttggtctta atatacctga acaagctacg cttatagaaa tggaagtatt 107100
gagaacatta acatcagata atagagtaaa atctgctaat ttaattgatt ggaaaataca 107160
aggtaatgtt tattcaggtc aattttcagt ggaaataaaa tctgttgaag aatcaataaa 107220
ttttgtctta ggacaagatg aggaaggaat ttttgcttta tttgaatagg aaaggattaa 107280
attatgaaaa ctagaaaatt aactaacata ctatcaaaat taatagataa gacaatggca 107340
ggtacaagca agataacaga ctttactcct ggttcagctt cccgttcatt attagaagct 107400
gtatcattag agatagagca attctatatt ctaacaaaag aaaatattga ttggggtata 107460
caagaaggta tcattgaagc ttttgatttt caaaaaagac aatctaaaag agcttatggt 107520
gatgttacta ttcaattcta ccaaccctta gatatgagaa tgtatatacc tgcaggaaca 107580
acttttactt caacacgaca agaataccct cagcaatttg aaacattagt tgattattat 107640
gcagagcctg attctactga gattgttgtt gaagtttatt gtaaagaaac aggggttgca 107700
ggtaatgttc ctgaaggaac gattaatact atagcatcag gttctagttt gattagaagt 107760
gttaataatg agtattcttt taatacagga actaaagaag aaagtcagga agactttaaa 107820
cgtagattcc actcttttgt agaatctaga ggtagagcaa ctaataaatc agtaagatat 107880
ggtgcactgc agatacctga tgtagaaggt gtttatgttt atgaagaaac agggcatatt 107940
acagtatttg ctcatgatag aaacggtaat ttatcagata ccttaaaaga agatataatt 108000
gatgctttac aagactatag accaagtggt ataatgttag atgttacagg tgtagaaaaa 108060
gaagaagtta atgtttctgc tacagtaact atatctaata aatctagaat tggtgataca 108120
ttacaaaaac atatcgaaag tgttattaga agctatttaa ataatttaaa aacttctgat 108180
gacctaataa ttacagacct tattcaagct ataatgaata ttgatgacgt attaatatat 108240
gatgtgtcat ttgataactt agatgagaac attatagtac caccacaagg gattattaga 108300
gcgggagaaa taaaagtaga attaaagtaa agagaggtga aacttaagtc gtggctaatt 108360
ttttaaagaa tcttcatcca ttattaagaa gagatagaaa taaaaaagat aatcaagacc 108420
ctaactttgc tctgatagat gcactcaatg aagagatgaa tcaagtggag aaagatgcta 108480
tagaaagtaa attacaatcc tctctaaaga catctacaag tgaatattta gataagtttg 108540
gggattggtt tggagtttat cgtaagaccg atgagaacga tgatgtttat agagcaagaa 108600
ttataaaata tttactcttg aaaagaggaa ctaataatgc tataatagat gctataaaag 108660
attatttagg tagagatgat attgatgtaa gtgtatatga gccctttaca aatatttttt 108720
atacgaacaa atcacattta aatggtgaag accatttaat gggatactat tatagatttg 108780
ctgttattaa tgtatctata ggtgattatt ttcctgtaga gattatagat gtaattaatg 108840
aattcaaacc tgcaggtgta actctatatg tcacttatga tggagcttct actattagag 108900
gtggagcaat tattaagtgg ttagatgggt tacctaaaat agaaacatac caagagtttg 108960
atagatttac aggttatgat gatacattct atggtcatat taatatgaat caaagtaaag 109020
atactgataa cagttcatca gatattttta aaacaaatca tagcttaatt aatagtttag 109080
atgttttaac aggttcatct agtgtaggta gacagtatat taactatgga tatgtaacat 109140
catatgttta taatccaggt atgacatcct ctgtaaacca aataagtgct agtacagaag 109200
gtagaggtca agaagtacct actgattact atatgtatac tagtactaag aataacaata 109260
cagtagaact tagtatgcaa actacttccg gtgtgtctta tttatataat aactttaatt 109320
```

ttagagatta tatgagtaaa tatagacctc aagtagattt acaatctgat gaggctagaa 109380
gaattgtatc tgattatata aaagaattaa gtattgatta ctatcttagt gctgtgatac 109440
ctcctgatga aagtatagaa attaaactac aagtttatga tttttctatt aatagatggc 109500
ttacagtatc aattaataac ttatctttct atgaaaaaaa tattgggagt aatatagggt 109560
atataaaaga ctatctaaac agtgaattaa atatgtttac taggttagag ataaatgcag 109620
gtaaaagaga ttcagtagat attaaagtta attacttaga tttaatgttt tattactatg 109680
aacgaggtat ttatacaata aaaccttata aagcattaat agaaaattat ttagatatat 109740
ctagagagac ttatgtagaa gcatttaaaa tagcatcatt atctaatgga gatattataa 109800
ctaaaacagg ttttcagcct atagggtatt taaaactagt tggtaattat gaaaatacaa 109860
gacctagcac aataaatata gtagctaaag atacagataa taaccctata gaatctaatg 109920
aattagatgt atataataca gtagagaata gaaatctatt acaatcttat aaaggtgcaa 109980
atacgatagc tagagaaata acttctacaa aagagtttac tgtatcagga tgggctaaag 110040
agatatactc aactaattat ctttctaaag tattaaaacc aggtaaagtg tatacgttat 110100
cttttgatat agaaataaca ggtaatgacc taactcttaa atcttattct gataatcatg 110160
gtatatattt atacagtaat actaagggaa ttgttgttaa tggtgttaaa tctatggaac 110220
gtactatagg taacaaagta tccgtaactc aaacttttac agcccctact attactgacc 110280
atagattatt aatatatact ggaagatata catctgatgg taaagcatca actcctccag 110340
tgttctttaa tacagttaaa attacggaat taaaattgtc tgagggtacc tctaatctag 110400
agtactcacc tgctccggaa gataaaccta acgtaataga aaaaggaatt aaatttaata 110460
atatcctaac taatatacag actttaagta ttaattcgga tactatctta aaaaatgtaa 110520
ctttatatta ttcttactat ggtgataatt gggtagaact aaagactcta ggaaatatta 110580
gtactggaga aacaacagaa accaataact taatagattt atatggatta cagacagtag 110640
attattctaa tataaatcca atgtctaaag tatcattacg ttccatttgg aatgttaaac 110700
taggtgaatt gaacaatcaa gaaggttctt tatctaatat gcctaatgat tactttaatg 110760
ctgtatggca ggatatagat aaattatcag atattgagat aggttctatg agaatggtta 110820
aagacactga gggtggagta ttcgatggag ctacaggtga aattattaag gctactctat 110880
ttaatgtcgg ttcttatact gatttagaca tgttagctta tactttgact aactatactg 110940
aaccgttaac tttaggctct agtcgattaa taagtgagtt aaaagaagaa cttctaacat 111000
cagaatcatt taatgttgat aatagaatta aagtaattga ctcaatatat gaggagttac 111060
caaatacaag cattattaaa aatggatttg ttgaaagaga ggttacaggc tctaaatatt 111120
tagattatgg tttatatgag cctatagaag atggtactag atataaactt attgtcgaag 111180
gagaatttaa agataatata gaatttatat atttatacaa ttctaaccct aactttaatg 111240
aaacatttat atatccatca gagataatta atggagttgc tgaaaaagaa tttattgcaa 111300
aaccatccac cgaagacaaa ccaaggttaa atacagatgt tagaatatat atacgacctt 111360
atgattcaac tatctctaaa gtaagaagag tagaattaag gaaagtttaa taaataagtt 111420
gacagaaagt taataatatg gtatacttat aaagtaatat ttagtgggta taccatgtta 111480
tattaataaa gaaaacaaca gatgaaagga attaaaaaat atggcaattg caacgtataa 111540
ttctcatgtt gagttagcaa aatatctagt tagtaaagct gattcagttt acttaacaat 111600
tggaaagagc acaccgtggt ctaatgaaac aaacccaccg caacctgatg aaaatgcaac 111660
agtattacag gaggttattg gatacaaaaa agctactaaa gttactttag ttagaccttc 111720
taaatcacct gaagatgata ataagaattt aatttcttat ggtaataaat catgggtaga 111780
agtaacacct gaaaatgcta aagctgaagg agctaaatgg gtttacttag aaagtagtat 111840
tgttggtgac gaactgcctc ttggaacata tagacaggta ggatttgtta tggacttagt 111900
agcaaaaagt ggtattagta aatttaactt agtacctagt gaagtagaat caactggaac 111960
attattattc tttgataata aacaattcca aaatagaagt gagcagacaa ctgctaaaga 112020
aagatttatt gtagaagttt aaagaaaggg agataattct aaatggcaat taattttaaa 112080
ggttcacctt atttagatag atttgacccg tctaaagata gaacaaaagt attatttaat 112140
cctgatagac ctctacaaca ggcagaatta aatgaaatgc agtctataga ccaatattat 112200
ttaaaaaatc taggagacgc tatttttaaa gacggagata aacagtcagg acttggattc 112260
acattgtctg aagataatgt attgacagta aatcctggtt atgtatatat caacggtaaa 112320
ataagatatt acgataatga cgattcagtt aaaataactg gcgtaggtaa agaaactatc 112380
ggtattaagt taacagaacg tattgttaca cctgatgaag atgctagtct attagaccaa 112440
actagtggag taccaagtta cttctctaaa ggtgcagata gattagaaga aaagatgtca 112500
ttaacagtta atgaccctac atcagcaact atttatactt tcatggatgg agatttatat 112560
attcaatcaa ctaatgctga aatggataaa atcaataaag tattagctga acgtacttat 112620
gatgagtcag gttcatataa agtaaatggt tttgagttat tctcagaagg taatgctgaa 112680
gatgatgacc acgtttctgt agttgtagat gcaggtaaag cttatgtaaa aggttttaaa 112740
gtagataaac ctgtatcaac aagaattagt gtacctaaat cttatgactt aggaacagca 112800
gaaaatgaaa gtactatctt taataagtct aataattcta ttagtttagc taatagccct 112860
gtaaaagaaa ttagacgtgt tacaggtcaa gtacttattg aaaaagaacg agttacaaga 112920
ggagcccaag gtgatgggca agattttctt tcaaataata cagcatttga aattgtaaaa 112980
gtttggactg aaacaagccc tggtgttact acaaaagagt ataaacaagg agaagacttc 113040
agattaacag acggtcaaac gattgattgg tcacctcaag gtcaagaacc ttcaggaggt 113100
acttcatact acgtttctta taaatataac aaacgtatgg aagccggtaa agattatgaa 113160
gtaacaactc aaggtgaagg tttgagtaag aaatggtaca ttaacttcac accttcaaat 113220
ggtgctaaac ctattgacca aacagtagta ttagtagact atacttacta cttggctcgt 113280
aaagattcag tgtttattaa taaatatggt gatattgcaa tattacctgg tgaacctaat 113340
attatgagat tagttacacc accattaaac acagaccctg agaatttaca attaggtaca 113400
gttacagtat tacctgattc agatgaagca gtatgtattt catttgcaat cactagattg 113460
tctatggaag acttacagaa agttaaaaca agagtagata acttagagta taaccaagca 113520
gtaaatgctc tagatgatgg tgctatggaa ggacagaacc cactaacatt acgttcagta 113580
tttagtgaag ggttcattag tcttgacaaa gcagatatta cacatcctga cttcggaatt 113640
gtatttagtt ttgaagatgc agaagctact ttggcttata cagaagcagt taaccaacct 113700
aagattattc caggagatac aacagctcat atttggggta gattaatttc agcaccattt 113760
actgaggaac gtacaatcta tcaaggtcaa gcatcagaaa cattaaatgt taacccttat 113820
aatattccta acaaacaagg tgtgttaaag ttaacaccta gtgaggataa ctggattgat 113880
actgaaaatg ttacaatcac tgaacaaaaa actaaaaaag taactatgaa acgattttgg 113940
agacataatg agagttacta tggtgagact gagcattact tgtattctaa cttacagtta 114000
gatgcaggac aaaagtggaa aggtgaaact tacgcttatg atagagagca tggacgtact 114060
ggtactttat tagaatcagg aggacaacgt actctagaag aaatgattga attcattaga 114120
atcagagatg tatccttcga agttaaagga ctaaacccta atgataataa cttatattta 114180
ttatttgatg gggtaagatg cgctataaca cctgcaactg gttatagaaa aggctctgaa 114240
gatggtacga taatgacaga tgctaaagga acagctaaag gtaaatttac tattcctgca 114300
ggtattcgtt gtggtaaccg agaagttaca cttaagaatg ctaactctac aagtgctaca 114360
acttacacag cccaaggacg taaaaaaacc gttcaagata ttattatcag aactcgtgta 114420
acagtaaact tagtagaccc attagcacaa tcattccaat atgatgagaa cagaactata 114480
tcatcattag gattatactt tgcttctaaa ggtgataaac aatctaatgt tgttatccaa 114540
attagaggta tgggtgacca aggttatcct aataaaacaa tctatgcaga aacagttatg 114600
aatgctgatg atattaaagt atctaataat gctagtgctg aaactagagt atactttgat 114660
gaccctatga tggctgaagg cggtaaggaa tacgctattg ttattattac tgagaacagt 114720
gattatacaa tgtgggtagg tactagaact aagcctaaga ttgataaacc taatgaggtt 114780
atctcaggta acccatacct tcaaggtgta ttattcagtt catcaaatgc atcaacatgg 114840
actcctcatc aaaactctga ccttaaattt ggtatttata cttctaaatt taatgagaca 114900
gcaacaattg aattcgaacc aattaaagat gtatcggcag atagaatagt tcttatgtct 114960
acgtacttaa ctcctgagag aacaggatgt acatgggaaa tgaaattaat tctagatgat 115020
atggcatctt ctacaacatt cgaccaatta aaatgggagc ctatcggtaa ctaccaagat 115080
ttagatgttt taggtctagc aagacaagtt aagttaagag caactttcga atctaataga 115140
tatatctcac cattaatgag ctctagtgat ttaacattca ctacattctt aacagagtta 115200
acaggttcat atgttggtag agctattgat atgacagagg ctccttacaa tacagtaaga 115260
tttagttatg aagctttctt acctaaaggt actaaagttg ttcctaagta ttctgcggat 115320
gatggaaaaa cttggaaaac atttactaaa tcccctacaa ctactagagc caataatgag 115380
tttacacgct atgtcattga cgagaaagta aaatcatcag gaacaaatac taaactacaa 115440
gttagattag atttatcaac tgaaaatagc tttttacgtc ctcgtgttcg tagacttatg 115500
gttactacta gggatgaata aactagaggg gttgattgac ccctctttat ttaataagga 115560
gagatttata tgcctagaga agttagagac ccttattctc aagctaaatt atttatacct 115620
acagttgaag aaaaatcaat taaggaatta gaaaaaacat acaaagaaaa aattgatgaa 115680
gctactaagt taatcaatga attaaagaaa gagagaggag aaaaatagat ggcatttaac 115740
tacacgcctc ttactgaaac acagaagtta aaagatatgt atcctaaagt taatgatata 115800
ggtaactttt taaaaacaga agttaacctt agtgatgtaa aacaaatatc acaacccgac 115860
tttaataata ttttagcatc tatacctgat agtggtaact actatgtaac taattcaaaa 115920
ggtgctccta gtggagaagc tacggcagga tttgtaagat tggataaacg aaatgtaaat 115980
tattataaaa tttactattc accatatagt agtaataaaa tgtatatcaa gacttatgct 116040
aatggtactg tatatgattg gattagtttt aaattagatg aaggtaactt atacaatgaa 116100
ggtaatactt taaatgtaaa ggaacttact gaatctacaa ctcaatatgc aacactagtt 116160
aatcctccaa aagagaactt aaatacaggt tgggttaatt acaaagaaag taaaaatggt 116220
gtttcttctt tagtagaatt taacccggtt aactccactt caacttttaa gatgataaga 116280
aagttaccag tacaagaaca aaagcctaac ttattgaaag atagtttatt tgtttatcct 116340
gaaactagct attctaatat taaaacagat aactgggata cgcctccatt ttggggatat 116400

```
tcttctaata gtggtcgttc aggagttaga tttagaggag agaatacagt acagatagat 116460
gatgggtcta atacgtaccc tttagtagtt tctaataggt ttaaaatggg taaagaactt 116520
tctgtaggtg atactgtaac ggtatcagta tatgctaaaa ttaatgaccc tgctttactt 116580
aaagataact tagtttactt tgaattagca ggatacgata ctgtagatga tactagtaaa 116640
aatccttata caggaggacg tagagaaata acagcaagtg agataacaac tgagtggaaa 116700
aaatactctt tcacatttac gatacctgaa aatacaatcg gagcatcagg cgttaaagtt 116760
aattacgtat ctttactact aagaatgaat tgttcatcta gtaaaggtaa tggtgctgta 116820
gtatactatg ccttacctaa attagaaaaa tcacctaaag ttacaccatt tattacacat 116880
gaaaatgatg ttcgtaaata tgatgagatt tggtctaatt ggcaagaagt tattagtaaa 116940
gatgaattaa aaggtcactc tcctgtagat attgaatata atgattattt taaatatcag 117000
tggtggaaat ctgaagttaa tgaaaagagt ttaaaagatt tagctatgac agtacctcaa 117060
ggatatcata cattttattg tcaaggctct attgccggga cgcctaaggg acgttctatt 117120
agaggaacca ttcaggtaga ttatgacaaa ggtgacccct acagagctaa taagtttgtt 117180
aaattattgt ttactgacac agaaggtata ccttatacat tatactacgg agggtataat 117240
caaggttgga aactcttaaa gcaatcagaa acttctactt tactatggga aggtacttta 117300
gattttgggt ctacggaagc tgttaactta aatgactcat tagataatta tgatttaatt 117360
gaggtaactt attggactcg ttcagcagga catttttcta caaaaagatt agatataaaa 117420
aatacatcaa atttactgta tattagagac tttaatattt caaatgatag tacaggttct 117480
agtgtagact tttttgaagg gtattgcact ttccctacta gagcatcagt acaacctggt 117540
atggtaaaat ctataacttt agacgggtct acaaatacaa caaaagtagc atcatggaat 117600
gaaaaggaac gtataaaggt atacaatatt atgggaatta atagaggata aagaaaggtg 117660
gaataaaaaa ctatggctgt taaatatgat ataggtaata atgagatagt attacactta 117720
agagaaggta aatatataac agggtttaca acagtaggag ggtatgacaa ggagttaggg 117780
caagtaaaag ttaatagaga aatcttacct gcttacttct ttgataattt tgcctatgaa 117840
agatatttgt attatagtaa acctgaagag gttatagaaa ataaaaacta tgtaccacca 117900
caaatcaatg atgatgagga atcccaacaa attactgtac ctaaagaaca atatgatagt 117960
ttaaaagaag agctagagct tatgagaaaa caacaagaag ctatgatgga aatgcttcaa 118020
aagctcttag gtcaaaaggg gtaattataa atggcattaa attttactac aataacggaa 118080
aacaatgtta ttagagacct gactactcag gtcaataaca ttggagaaga attaacaaaa 118140
gaaagaaata tatttgacat taccgatgat ttagtttata attttaataa atcacagaaa 118200
attaaactaa ctgatgataa aggattaact aaatcttatg gaaacataac agcccttaga 118260
gatataaaag aacctggtta ttactatata ggtgctagaa cattagcaac attattagat 118320
agacctgata tggaatctct tgatgttgtt ttacatgtag tacctcttga tacttctagt 118380
aaggtagttc aacatttata tacactatct actaacaata accaaattaa aatgttatat 118440
agatttgtct cagggaactc tagttcagaa tggcaattta ttcaaggatt acctagtaat 118500
aaaaatgctg ttatatcggg cactaatatt ctagatatag cttcaccagg tgtttacttt 118560
gttatgggaa tgacaggagg aatgcctagt ggagtaagct ccggattttt agacttaagt 118620
gtagatgcta atgataatag attagctaga ctaactgatg ctgaaactgg taaagaatat 118680
actagcatta agaaacctac aggaacatac acatcttgga aaaaagaatt tgagccaaaa 118740
gatatggaga aatatttact aagtagtatc agagacgatg gtagtgcatc attcccactc 118800
```

ctagtttata ctagtgataa taaaacgttt caacaagcta ttatagacca tatagataga 118860
acaggtcaaa caacctttac tttctacgtt caaggtggtg tatcaggttc ccctatgtct 118920
aatagttgtc gaggtctatt catgtcagat acacctaaca cttctagttt acatggtgtc 118980
tataatgcta taggtacaga tggtagaaat gtaacaggtt cagtggtagg aggtaattgg 119040
acttcaccaa agacatcacc ttcccataaa gaattatgga cgggagcaca atcattccta 119100
tctgtaggta ctactaagaa tctagcagat gatattagta attactctta tgtagaggtt 119160
tatactaaac ataagacagt agagaagact aaaggtaatg atgactcggg tacaatttgc 119220
cacaagttct acttagatgg tagcggtact tacgtttgct caggaacttt tgtttcagga 119280
gatagaacag atacaaaacc acctgttaca gagttctata gagtaggtgt atctttcaaa 119340
ggttcaacat ggacgcttgt agatagtgca gtacaaaata gtaaaactca atacgttaca 119400
agaattatag gtattaatat gccatagact aggataagtt tcctagtctt tttttcttga 119460
cttgaaaagg attctatggt atactataac tcgtgtaagg atataaggag attaaaatga 119520
gattaagaat taagaactta tatacctatg tagaatttga ggaggatgat aaatacttaa 119580
aagatatatt tttaaagaga gtccatacta ctataggagc aaggcaagaa ggttttcaat 119640
atagccctgc gtacaaaaga ggtagttggg atggttatgt agacttttat gtttatgagg 119700
aagataaatt ccctactgga cttttattta aaattgagtt attattaggt gagttacaat 119760
caaggtataa cttccagttt gaaacaattg atgagcgtga tgaaagtttc ttatctgaag 119820
aagatattga tgatgagata acattgcttg ataataatgt cggtcaaatt accttaagag 119880
attaccaata tgaagcagtg tacaatagct taacatttta caatggtatt gctcacttag 119940
ctactaatgg tggtaaaact gaggttgcta gtggtattat agaccaacta ttacctcaat 120000
tagaaaaagg tgaaagagta gcgttcttca caggctctac ggagatattt catcagtctg 120060
cggatagact acaagaacgt ttaaatattc ctattggtaa agtaggtgca ggtaaatttg 120120
atgttaaaca ggttacagtt gtaatgatac ctactttaaa tgcaaacctt aaagacccaa 120180
cacaaggggt aaaggttaca cctaaacaaa atattagtaa aaagattgct caagagatat 120240
tacctaaatt tgaaggtgga acaaatcaaa agaaattact aaaagtatta cttgataaca 120300
caacacctaa aacaaaagta gaacaaaacg tattaagtgc cttagagata atttaccaaa 120360
atagtaagac agatgcagaa gttttattaa acttaagaaa tcataatgca cattttcaaa 120420
aaattgttag agaaaagaac gaaaagaaat atgataaata tcaagatatg agagattttt 120480
tagactcagt tacagttatg atagttgatg aggcacacca ttctaaatct gattcttggt 120540
acaataatct aatgacatgt gaaaaagctt tatatcgaat tgcattaaca gggtctatag 120600
ataaaaaaga tgaattactt tggatgagat tacaggctct atttggtaat gttattgcac 120660
gaactactaa taagttttta attgatgaag gtcattctgc tagaccaaca ataaatatta 120720
tacctatagc taatcctaat gacatagata gaattgatga ttatagggaa gcttacgata 120780
gaggtataac aaataatgat tttagaaata aacttattgc aaaactaaca gaaaagtggt 120840
ataatcaaga taaaggtaca ttgattattg taaacttcat tgaacatgga gacacgatat 120900
cagaaatgtt aaatgattta gatgtagagc actacttctt acatggagaa atagactctg 120960
aaactaggag agaaaaatta aatgatatga gaagtggtaa gcttaaagta atgatagcta 121020
catcacttat tgatgagggt gtagatatat ccggtattaa tgcactaata ttaggtgcag 121080
gaggtaagtc attaagacaa acattacaac gtattggtcg tgctttacgt aagaaaaaag 121140
acgataatac aacacaaata tttgatttta atgatatgac aaatagattt ttatatactc 121200
atgctaatga gcgtaggaaa atttatgaag aggaagattt tgaaataaaa gacttaggaa 121260
aataggaggg taagagatgg caacaaaaac acaaagaaag ctataccaat atctagagga 121320
aaatgctaca gaaaataaat ttcatatttc tactaagaaa gagctagcag attctctagg 121380
tgtttccatc tctgctttat ccaataacct taaaaagtta gaagaagaaa ataaagtcgt 121440
tactgtttct aaaagaggaa aaaacggcgg agtaataata actttagtta gagagtatga 121500
tacagaagaa ttgaaagaat ttaataattc tacagataat attattactt ccgatttaca 121560
gtatgctaag gcattaagag aaaagcactt cccttcttat agatatgaga gaaaagaaca 121620
acgtagacgt actaaaatag aaatggcaca atacaatgcc attaaggatg agaagagaag 121680
aattatagca gatatgaact tctattcaga aggtcttcct tatccttcta aagatatttt 121740
taatatgtct tatgacccgg aagggtttta taaagcatac atcttatgta agttatacga 121800
ccaatatgct atttctcata tggatgctaa acatacaagt catcttaaag caatgagtaa 121860
ggcaacaact aaagatgaat atgactatca tcaacatatg tctgaatact atagaaataa 121920
aatgattcaa aatttaccta gaaatagcgt tagtgataat ttctttggta gtaaaatgtt 121980 taatacettt tataattttt atttaaaaat aaaagataaa aatattaatg tatttaaata 122040
tatgcaaaac gtatttaaaa atgtaacatt ttattatgag aatggtatgc aacctaatcc 122100
aataccttct cctaacttct ttagttcaga taagtatttt aaaaactata ataattatat 122160
taaaggaata aaaaaaggtg ttaacagtac gaatagacac ctaggtgata cagacagcat 122220
cattaattca tcagactacg tgaaaaaccc tgctgtatta catctacacc aactatatac 122280
tacaggatta aattctactt tacatgatat tgatactatg tttgaacaag ccttagacct 122340
tgaaaatgcc tcctatggac tatttggaga tatgaaacat attattttac tacagtataa 122400
ttctatgatt gaagaagaaa ttaagaattt acctagagaa gaaaaggata ttattaataa 122460
atatgtaaaa caatgcataa ttaatgatta ttcaccaaca agtatttcac catctgcaag 122520
gttatcaatg tttactatgc agaaagagca tatagtttac aataagcagt taaataaggg 122580
aatcaagaga gaggatttat taccattaag tctaggaggt atagtgaata aagattcatt 122640
gagtggtatg gatatacaaa acttagaaca gaatggtaat gaatacctgt atatgagaca 122700
acatacttca acttattata tattaagaat gtttggtgac tatttaggat atgaggtaaa 122760
cttaagagaa gtaaaatata ttgtagagaa atataattta attgataaaa taccattgac 122820
aaaagagggt atgttggatt ataataaact tatacattta gtagaggaag aggttaataa 122880
ctatgagtaa gaagataaag gagcttatcc ttcataaatc aatgaaggat atacattttg 122940
caagagaagt attagataac ttacctaaga atctattttc agcagagtct gaggacatgg 123000
gttacttatt tacagctata aagagaacag cacatatttc cgataagatg tcaaatgaag 123060
cattagcaat taaagtagaa cagcttatgg gtaataataa ggaagatgaa gagaaagtaa 123120
ccaagacatt aacttactta gaagatttat ataaagtaga cgttaatgaa aaagatgaat 123180
ctgttaatta tgaaatagag aagtatatta aaacagaaat gtcaaaagaa gttttagtta 123240
aatttattgc agaaaataaa caagaagact ctgataatct acatgaactt gtagacaaac 123300
taaagcaaat agaagtaagt gacatctcag gaggtaatgg agagtttatt gacttctttg 123360
aagatacaga aaagaaacaa gaactattga gtaatttagc tacaaataaa ttctctactg 123420
gatttacttc tattgacaac catattgaag gtggtatagc aagaggagaa gttggattaa 123480
ttatagctcc tactggtaga ggtaaatcat taatggcttc aaacttagct aagaattatg 123540

```
ttaaaagtgg attaagtgtt ttatatattg ccttagagga aaaaatggat agaatggttt 123600
tgcgtgctga gcaacaaatg gcaggagcag aaaagagtca aattgtaaat caggatatgt 123660
ctttaaataa taaagtttat gatgcaatac aaaatcatta tcagaagaat agaaagttat 123720
taggtgactt ttatatttct aaacatatgc caggtgaagt tacaccaaac caattagagc 123780
aaattattgt taatacaaca attaagaagg ataaaaatat tgatgttgtt attattgact 123840
atcctcactt aatgagaaat ccttatgcta aatatcattc agaatcagat gcaggaggaa 123900
aattgtttga agatattcgt agattatcac agcaatatgg atttgtttgt tggacgttag 123960
ctcaaactaa ccgtggtgct tatggttcag atgttattac aagtgagcat gtagaaggtt 124020
ctcgtaagat tgtcaatgct gttgaggtgt ctttagcagt aaaccaaaaa gatgaagaat 124080
tcaagagtgg tttcttaaga ttatatttag ataaaattcg taatagctcc aacacaggag 124140
aacgatttgt taatcttaaa gtagaaccaa ctaagatgat tgtaagagat gaaacacctg 124200
aagaaaaaca agagcatata caattgctat cagataatgg aaaagaagac acaagtaaat 124260
ttcaaaataa agataataaa atagaagcta taaataacac attcggagga ttaccgggag 124320
tttaattttt taaaatatac cacttgacat tttatatgtt aggtggtata attattttat 124380
aaagaataaa ggagagatta ataatgaaat ttgtattctt tacagatagt cattttcacc 124440
tatttactaa ctacgctaaa cctgataatg aatttgtgaa tgatagattt aaagaacaga 124500
tagaagcatt acagaaagtt tttgatattg ctaaaaaaga agaagcaaca gttatatttg 124560
gtggagattt atttcataaa cgtaactcgg tagatactag agtatacaac aaagtattta 124620
gtacatttgc caaaaatgat gaggttcctg tattattact tagaggtaat catgatgcta 124680
caactaattc attatatact gattcaagta tagatacatt tgagtatcta cctaatgtaa 124740
gtgtaataaa atcattaaat acaattttaa aagataatgt taatattgtg tttactgctt 124800
atggggatga gacgaaggaa ataaagacat acattaatag taattacgat aaagatatgg 124860
tcaatatact agtaggtcac ttaggtgtag aaggttcatt aactggaaaa ggctctcata 124920
gattagaagg ggcatttgga taccaggatt tattacctga taaatatgat ttcattttac 124980
taggtcatta tcaccgtaga cagtatttcc aaaatccgaa tcatttttat ggtggctcat 125040
taatgcaaca atcattttct gatgaacaag aagctaatgg tgttcattta atagatacag 125100
aaaaaatgac tacagaattc atcccaattc atacacgtag atttattact attcaaggag 125160
aagatattcc tgagaacttt gaacagttaa tcgaggaagg taattttatt agggttatcg 125220
gtacagcaaa tcatgctaag gttttagaaa tggatgacag tatgaaagat aagaatgttg 125280
aagttcaaat taaaaaagaa tatactgtag agaaacgtat tgatagtgat gtatctgatg 125340
accctttaac aattgctagt acctatgcta aacaatactc acctgaatca gaacaagaaa 125400
tacttgagtg tttgaaggag gttttataat gaaaaaatat agagaatacc taaataagac 125460
agatgcagaa aatttagcag aggattggga gaaagtaacc gaagatttat ggaaagtgtt 125520
taaagatatg aaacctaaaa ttaatacatt agatattagt aatgtagaaa gtaaaaactt 125580
agataaaagt aaacctatac tacaattcca agattcagat ggagtaatag agaatatttg 125640
taatgttgag ggtttagaag atggtttaag taaaatgaaa aaggtttttg atgatagtaa 125700
ctttgaaaag cattattata gtagagtcgt agaccatgat gagtattact ggattgatta 125760
tggttctcat cattgtttct ttagagttac gaaaggggat aagtaatggt tgtatttaaa 125820
caagtagaag ttaataattt tttagcaatt aaagaagcta cgctagagtt agacaataga 125880
```

ggattaattc taattgaagg tgagaataaa tccaatgagt catttcattc aaacggttca 125940
ggaaaatcaa ctttaatatc tgccattact tacgctttat atggtaaaac tgaaaaagga 126000
ctaaaagcag acgatgtagt aaataatatt gagaagaaaa atacatctgt taaacttaag 126060
tttgatattg gggaagatag ctatttaatt gaacgttatc gtaaggacaa agagaataag 126120
aataaagtaa aattatttgt taatgaaaaa gagattacag gttcaacaaa tgacgttact 126180
gataaacaaa tacaagactt atttggtatt gagtttaata cttacgttaa tgctatcatg 126240
tatggtcaag gagatatccc tatgttctcc caagcaacag ataaaggtaa gaaagaaatt 126300
cttgaatcta ttactaagac agatgtatat aaacaagcgc aagatgtagc aaaagagaaa 126360
gttaaagaag tagaagaaca acaaaataac ataagacagg aaatctataa actaggttat 126420
cagttatcta caaaagatga gtacttccaa agagaaatag aacagtacaa ccagtataaa 126480
gaacaattgg ttcagataga aaacagtaat aaggaaaaag atagattaag agaacaagag 126540
gagaagcaaa tagaagctca aatagagcaa ttagcttcac agataccaac aatacctgaa 126600
gatgaattta agcactcaga ggagtataat aaagcttctc aaagcctaga tttactttct 126660
aataaattaa cggagctaaa tcaagtatac tcagaatata ataccaaaga acaagtacta 126720
aaatctgaaa tagctacatt aagcaatagt ctaaataagt tagatacaaa tgaccattgt 126780
cctgtttgtg gctcccctat agataattct cataaattaa aagaacagga aaatattaat 126840
aatcagattg agaataagaa acaagagatt actagtgtat tagaaatgaa agatacgtat 126900
aaagaagcta ttgataaagt aaaagataaa tcacaagaaa ttaaagataa aatgtcacag 126960
gaagaccaac aagaacggga gcacaataat aagattaaca gtataattca agaggcttct 127020
aggattaaat cagacattag ctcattagag aataataaaa cttatttaaa agtgaaatac 127080
caacatcaat ctgttcaagg attagagaga gaagaaccaa gtaaagaaaa acatgaggaa 127140
gataaaaaag aattacaaga atctattgac aaacatgaag agaatatagt acaattagaa 127200
actaagaaag gtaaatatca acaagctgta gatgctttta gtaataaagg tatacgttca 127260
gtagtgttag actttattac accattctta aatgagaaag caaatgagta ccttcaaact 127320
ttatcaggtt cagatattga aatagagttc caaactcaag tgaagaatgc taaaggagaa 127380
ctaaaagata agtttgatgt tattgttaag aatagcaagg gtggaggctc atacaaatct 127440
aattcagcag gagaacaaaa acgtattgat ttagcaatta gttttgcaat tcaggattta 127500
attatgagta aagatgagat atctacgaac attgcacttt acgatgagtg ttttgatggg 127560
ttagatacta tcggttgtga aaacgtgatt aaattattaa aagatagact taatacagta 127620
ggaacgatat ttgtaattac tcataatacc gaacttaaac cactatttga acaaacaatt 127680
aaaatagtaa aagaaaatgg agtatcaaaa ctggaggaaa aataatgaaa ttaaagattt 127740
tagataaaga taatgcaaca cttaatgtgt ttcatcgtaa taaggagcac aaaacgatag 127800
ataatgtacc aactgctaac ttagttgatt ggtaccctct aagtaatgct tatgaataca 127860
agttaagtag aaatggagaa tatttagaat taaaaagatt acgttctact ttaccttcat 127920
cttatggttt agatgataat aaccaagata ttattagaga taataaccat agatgtaaaa 127980
taggttattg gtacaaccct gcagtacgca aagataattt aaagattata gagaaagcta 128040
aacaatatgg attacctgtt ataacagaag aatatgatgc taatactgta gagcaaggat 128100
ttagagatat tggagttata ttccaaagtc ttaaaactat tgttgttact agatatctag 128160
aaggtaaaac agaggaagaa ttaagaatat ttaacatgaa atcagaggaa tcacaattga 128220
atgaagcact taaagagagt gatttttctg tagacttaac ttatagtgat ttaggacaaa 128280

```
tttataatat gttgttatta atgaaaaaaa ttagtaaata gtaaggaagg atattatgag 128340
gtttgaagac tttttaaccc aagaattagg agaaccaaaa gaaaatacta taggtgagct 128400
aagatactgt tgtccgtttt gtggagaaaa aagttataag ttctatgtta agcaagccct 128460
agactctagt aatggtcagt atcattgtaa aaaatgtgat gaatcaggta atcctattac 128520
atttatgaag acttattata acattacagg taagcaagct tttgatttat tagagtctaa 128580
gaatatagat atagagagag ccccttttact tacaaccaat aataaggatt taacagaatc 128640
agagaaactt atattaatgc ttagaggtgt gcatcaagat aagggaacta ctagtattaa 128700
acctcctcga ttacctgaag gatataaatt attaaaagat aacttaaata ataaagagat 128760
tataccttttt ttaaaatact taaaaggtag aggtataact ttagaacaaa tcattaataa 128820
caatataggt tatgttatta atgggagctt ttataaagtt gacggggaat ccaaagtatc 128880
attaaggaat agtattatat tttttactta tgataatgat ggaaactacc agtactggaa 128940
tacaagaagt atagagaaga acccttatat taaatctatt aatgctcctg ctaaacaaga 129000
tgaagtaggt agaaaagatg tcatatttaa tttgaatata gcaagaaaga aaaagttctt 129060
agttataact gagggtgtat ttgatgcttt aacctttcat gagtatggag tagcaacatt 129120
aggtaaacaa gtaactgaga atcaaataaa aaaaataatt gattatgtta gtatagatac 129180
atcaatatat attatgttag acactgatgc attagataat aatatagact tagcttataa 129240
gttaaaaaca cattttaaca aagtttactt tgtaccacat ggtgatgaag atgcaaatga 129300
tatgggaaca aggaaagctt ttgagttatt aaaacagaac cgggtgttag taacacctga 129360
aagtatacag agttacaaaa tacaacaaaa acttaaactt taggcttgac cttagagaag 129420
ttttatgtta tactagtaat taagtaatta ataaaggaga aaaaaataat gtcaaataat 129480
aaaaaagata ttttagaatt tgtagatgaa tacattacag ctttaagagt tggtaatgag 129540
caacgacaac atcaattaga agaaatgggt aaagaagaaa cagcaacatt aacagatgta 129600
gctaaagcta ttactaacct tatgttaggt gttaatgagc agatgacaga cttagaatat 129660
aataacgagt taaacttaaa tattttaatt gatgctttat ataaagcaga gcttattaat 129720
gaagatgtat tagactacat tcaagaatca attgataaat cacaagaaga acctaaaaat 129780
gaagaagaaa aaggagaaca agaataatgg aaaaaaatat tagcacacac acaaaaggta 129840
ttagtcaagc agacatggag aaatggattg aagctgtagt acaaggaact gttgatggta 129900
aacaagttga tgagaaaaca gctaaacaat tagatagaat tggttcacga agtgtttctt 129960
tagaagaagc aactcgtatt gctaaagtcc ttaatgctgt aacagctcaa gaggttacag 130020
gagactttaa tgatgcattt aatgcaattg acttaatgat gattatcatg gaagatgagt 130080
taggagtaac tcaagaaaaa gtaggtaaag ctaaagataa actaaatgaa aaacgagaag 130140
cttacctaaa agagaaacaa gaagaattac gtcaaaaaca acaagaagag gcacaaaaag 130200
aaactgaatc tgacagcaat gaaaaagtaa ttcagttgaa gaaaaatgac gaacagtaag 130260
aaaaaagggg atacattcga acgtaaaata gctaaagaat taactgcttg gtggggatac 130320
caattcaata ggtctcctca atcaggtggt gcttcatggg gtaaagataa taatgctgtc 130380
ggagatatag tagtacccca ggaagctaat tttcctttag tagtagaatg taaacataga 130440
gaagaatgga ctatagataa cgttctttta aacaacagag agccacacac atggtgggag 130500
caagtcatta atgatagtag taaggtgaat aagacacctt gcttaatatt tactagaaat 130560
agagctcaga gttatgttgc tttaccttat aatgaaaaag tatatgaaga tttaagaaat 130620
```

```
aatgaatacc ctgtcatgag aacagatttt attattgata atattagaaa agataaattt 130680
ttttatgatg tccttataac taccatgaat gggttgacct catttacacc ttcttatatt 130740
atatcttgct acgacaaaaa agatataaaa ccatacaaga aggtcgagtc taatttatct 130800
gaggtaagta agcatgaaga tgaattgatt aatgaccttc ttagtgatat ataaggaagg 130860
taagataagt atgacaagca aagaaagacc attaatcgta tatttttcag gtacaggaca 130920
aacagaaaga ttagtaaaca aaattaatat taataattca tttgaaacat ttagggttaa 130980
gagtggaaaa gaaaaagtaa ataaaccttt tatactaata acacctactt ataagaaagg 131040
tgcaatacct aaacaaatag aaagattcct agaaattaat gggagcccta aagaagttat 131100
tggcacagga aataaacaat ggggctctaa tttctgtgga gcaagtaaaa agatttcaga 131160
gatgtttaag attcctttaa ttgctaaagt agagcaatca ggacacttta acgagataca 131220
accaatatta gaacacttta gtaataaata taaagtagcg taaaggatga gagatatatg 131280
gcaacatatg gaaaatggat tgagttaaat aatgaaataa ctcaattaga tgacaatgga 131340
aaaaataaac tctataaaga ccaagaagct ttagatgagt atttaaaata tattgaagac 131400
aatacaagaa agtttaatag tgaagtagaa agaattagag tattgacaaa agaaggaaca 131460
tatgataaaa tatttgacaa ggttcctgac actattattg atgagatgac taagttagct 131520
tacagtttta attttaaatt ccctagtttc atggcaggac aaaagtttta tgaatcttac 131580
gcatcaaaac agtatgatga aaacaaaaaa cctatttttg ttgaagacta tgaacaacat 131640
aatgttcgag tagctttata tttatttcaa aatgactatg taaaggctag agaattacta 131700
gtacaactta tggagcaaac attccaacca tctacaccta cgtataataa ctcaggtcaa 131760
gctaatagag gtgaactaag ctcatgttat ctatttgtag tagatgattc aattgagtct 131820
ttaaactttg ttgaggatag cgtagctaat gctagttcta atggtggcgg agttgcaatt 131880
gatttaacta gaattagacc taaaggagct ccagtacgta atagacctaa ttcaagtaaa 131940
ggtgttattg cttttgctaa agctattgaa cataaagtta gtatttatga ccagggcggt 132000
gtaagacaag gtagtggtgc tgtttaccta aatatattcc acaatgatat cttggattta 132060
ttaagctcta agaaaatcaa tgccagtgaa tctgttagac tagataaatt atctattggt 132120
gttacaatcc ctaacaaatt tatggagtta gttaaagaag gtagaccttt ctatactttt 132180
gatacttacg acattaataa agtgtatggt aagtatttag atgagctaaa cattgatgaa 132240
tggtatgata agttactaga taatgatagt atcggtaaag taaaacatga tgctagagaa 132300
gttatgacag atattgctaa aacgcaatta gaatcaggat acccttatgt attctatatt 132360
gataatgcta atgataatca tccattgaaa aacctaggta aagttaaaat gagtaactta 132420
tgtacagaaa tttcacaatt acaagaggta tcagaaattt atccgtactc ttacagtaat 132480
aagaatgtta ttaatagaga tgttgtttgt acattaggtt ctcttaactt ggttaatgtg 132540
gttgaaaaag gtttattgaa tgaatctgta gatattggta caagagcatt aacaaaagtt 132600
actgatatta tggatttacc ttacttacct agtgttcaaa aagcaaatga tgatattaga 132660
gctatcggtt taggttcaat gaatttacat ggacttttag ctaagaatat gattagttat 132720
ggttctagag aagcattaga cctagtaaac agtttatata gtgctattaa cttccagtct 132780
attaagacat ctatgttaat ggctaaagaa acaggaaaac catttaaagg atttgagaag 132840
tccgattacg ctacaggtga atactttgta agatatatta gagaatccaa tcaacctaag 132900
acagataaag ctaagaaagt cctagataag gtttatattc caacacaaga tgattgggat 132960
gaattagcta aagcagtaaa agtacatggc ttgtataatg gttatagaaa agcagaagca 133020
```

```
cctactcaat ctatatctta tgtacagaat gctacaagtt ctattatgcc agttcctagt 133080
gctatagaga atagacaata tggagatatg gagacatatt acccaatgcc ttacctaagt 133140
cctataactc agttcttcta tgaaggagaa acagcttata agattgacaa taaacgtatt 133200
attaatacaa gcgcagttgt tcagaaacat acagaccaag cagtatctac aatcctttat 133260
gtagagtcag aaatacctac taataaacta gtatcattat actattatgc ttgggaacaa 133320
ggattaaaat cattatacta tacacgttca cgtaaacttt ctgttattga atgtgaaaca 133380
tgttcggttt agaaaggaaa tagatatgga tattacacaa aaagtaaaac aacataataa 133440
aaatgctgta ttaaaagcaa caaactggaa tattgaagat gacgggatgt ctgatattta 133500
ttgggagcaa ggaatttccc aattttggac tcctgaagag tttgatgtat caagagattt 133560
aagttcttgg aatagtttaa ctgaaagtga aaagaacact tataagaaag tccttgcagg 133620
gctcacaggg ctcgatacca agcaaggagg agaaggtatg aacttagtat cctaccacga 133680
accaagacct aaataccaag ctgtatttgc gtttatgggt ggtatggaag agatacatgc 133740
taaatcctat agtcatatct ttacaacatt actaagtaat aaagaaacaa gctatctatt 133800
agatacttgg gtcgaagaaa acgacttttt aaaagtaaaa gctcagttta tcggatatta 133860
ctatgaccaa ctattaaaac ctaaccctac tgtatttgat agatacatgg ctaaagtagc 133920
tagtgccttt ttagaaagtg cactattcta ctcaggattt tattatcctt tacttcttgc 133980
agggagagga cagatgacac aatcaggagc tattatttat aaaattactc aagatgaagc 134040
ttaccatggt tcagcagtag gattaacagc tcaatatgat tataatcttc taacagaaga 134100
agagaaaaaa caagcagata aagaaactta tgaattatta gatattcttt acactaatga 134160
agtagcgtat acacatagtc tatatgaccc attagaatta agtgaagacg taattaacta 134220
cgttcagtat aattttaata gagctcttca aaaccttgga agagaggact attttaatcc 134280
tgaaccttat aaccctattg tagaaaatca aactaatgta gacagattac gaaatgttga 134340
tttctttagt ggtaaagcag actatgaaaa atctacaaat attaaagata ttaaagatga 134400
agatttttca ttcttagata gtaaagaata cagtactgcc aaggaattcc tataaaaagg 134460
agaaaagata ttatggatag aaaagaagca atggatttac taagtaaagc agaaatatta 134520
tttaaaaaac atgatgagtt ttcatgtgta agtgatatca atgaccctat gaagttattc 134580
agtaactcta aggatgctaa agctgatgat acgtctaagt cttttcagtt agagtttatg 134640
catgatatga ccatgtatac tttatcttat ggctcaggac agttaaaact tattgattta 134700
gcagaaggtt atgaagcaca aaaagctaca gtagttaact catttcccga aattattaaa 134760
acattagaaa aggatgattc agaagatgga aaaaatgaat agtttagtag atttaaatac 134820
agcaattaga caaaagaaag atgttattgt catgattaca caagataatt gtggtaagtg 134880
tgagatttta aaaagtgtaa tccctatgtt tcaagagtca ggtgacatta aaaaacctat 134940
cttaacatta aatctagatg ctgaagatgt agatagagaa aaagctgtta agttattcga 135000
tatcatgagt acaccagtat taattggata taaagatggt cagttagtta aaaagtatga 135060
agaccaagtt acacctatgc aattacaaga attagagtca ctttaatttg gaatttccta 135120
ctatctgtgc tatactataa tagtacaagg tagtaggatt ttttaatgga aggaagatga 135180
catatcgcaa agaataaaac attaacgata tataatagtg atagatattt taatatacac 135240
acaaaagata aagataaaat taatgaggct attaaagtca cacatggtaa tgaagaagaa 135300
attgaaaaga atatggatga attaatatct aagtctagac gatatatcat gagagatgaa 135360
```

aatcattaca tgttatttaa tgaaaagtac aataatgata gacttataga aaaagtatgt 135420
aaacacggtg gcaaagttac atactatact gattcagtat taccctatta tgttttaaaa 135480
gacttatcta gtcaccctga ctcagaagtc gtttatcgta tgcgcaatgg ttttactgca 135540
aaagaagtag ataatatagc tttgtcattt atgggtacaa aagttattat tgatatttct 135600
gtagtatttc cttatgtaaa cccttatgat attattagaa gtttacatga tattaaaaca 135660
aatgtagatg aagttcattt atcatttcca cgaatattag aagtagatga aaaacaagaa 135720
aaattttatt tctttgatgg tgaagcttat gatttaaaac ctgagtataa agtagatttt 135780
gcggataaaa ttagagtatc tttatcagta tggaaaatgt atatctatat cttaacaagt 135840
agtcgtgatt ttgaggatgt agacaatgta attacgaaac taaaacaaca acgaaagatt 135900
aagatataag gtgattatat gagtacagca aatagaagag atatagcaag aaagatatca 135960
gagaatacag gttactatat ccaggatgta gaggaaatac taagtgcaga gacagatgct 136020
atttctgact tactagaaga aggatatact aaagtaaaga atcataaatt tatgcaaata 136080
gaagttattg aaagaaaagg taaaaaagcg tgggatggtc tgaataaaga atacttccat 136140
ttacctaata gaaaagctat aaaattcaaa ccactaaaag aactagaaga ggttattgat 136200
agacttaatg aagaagagaa ataattctct tcttttttta ttgacaaggt ttaaaatata 136260
tggtatagta ttattaagtt aaaaaaggag aggaattaaa tgaaagtatt aatcttattt 136320
gaccacatta gagaagagca tttttctgta agtaaagatg ggagtgtgaa atctaatgta 136380
ctaaatacac ctaatggaaa aacacttaag aaattacttg agaagtgttc taatttaaag 136440
agagataaaa caaacagaga ttatgatatt gattttctct acaatgcagt acctacacct 136500
atcagaaatg actatggtaa aattattaaa tatcaagatg ttaaacaagc agaagtaaag 136560
ccatactatg agagaatgaa taatattatt attgataatt cttatgatat gataattcct 136620
gtaggtaaac taggcgttaa atacttatta aatgttacag ctattggtaa agtaagaggt 136680
gtaccaagta aagtaactat tgaaaatgga acatcttctc atgacgtgtg ggtattacct 136740
acttacagta ttgaatatac taatgtaaat aaaaatagtg aacgtcatgt agtatcagat 136800
ttacaaacag ttggtaagtt tgtagagcaa ggagaagagg catttaaacc taaggaagta 136860
tcttacgagt tggtagataa cattgaaaga gtaagagaaa tattcaataa ggaagtaaag 136920
aatgataatt atgatggcgt agatattacc gcatgggact tagagactaa ctcattaaaa 136980
cctgataaag aaggaagtaa acctttagta ctatctctat catggagaaa tggtcaaggt 137040
gtaactatac ctttatacaa atcagacttt aactgggaaa acggtcaaga tgatattgat 137100
gaagtcttag aattacttaa gaactggtta gctagtaaag aagatattaa agtagcacat 137160
aatggtaagt acgatattaa attcttgatg agtactgaga actttaaaga ttttgagagt 137220
attcaagata ctaaagtagg ttggtaccta gctgttaccc aagaagttaa agaatcttta 137280
agattatctg atttagctta tgaggttaca gatgtcggag gttatgataa accattagaa 137340
gattttaaat tatggtttgt tactaagtta ttaagattct tctcagataa aattaaagag 137400
atacagaaag aaaataaaaa gattgctaag aaggagtatg atgttaaagc tcccgaatat 137460
aaagaatggc tagagaataa actaaatgaa acagtagtag aactagatga tactgagaag 137520
aaatttagag ttagtgaatt agagaaaaag tatattcaac taggtctttc acctgaaatt 137580
gtaaatatga atttagttat gaataacgat gagttcataa gtattgcaga acaatcacct 137640
gagtacatgg ggttatctga ctatgctaag tcttacacat taaatactgc aattaattta 137700
attaatgagt atagagatgt aaaagatgta gttaatgata ttgatggagg taactttaat 137760

```
tatgattggt tccctattga attaatgcat ccatacgcat caggagatac tgatgtatgt 137820
agaagaattc attgtgatgt agttaagaaa cttaaagaac aagatagacc taaatcaatg 137880
catttattag aagttaatta cccaagactt actaagtctt tagctagaat tgaatcaaat 137940
ggtttatatt gtgacttaga ttatatgaaa gaaaatgatg agtcatacga gtctgagatg 138000
gctaaaaatc atgctacaat gagagagcac tgggctgtta aagaatttga agaataccaa 138060
tacaatcttt accaaatggc gttagaagaa catgagaaaa agccaaaaga tagagataaa 138120
gatatccatc agtatagaga taaatttaaa gatggtaaat ggatgttttc cccaagttcc 138180
ggagaccata aaggtagagt aatttatgat attttaggaa ttcaattacc ttatgataaa 138240
gaatatgtta aggaaaaacc atttaatgct aatgttaaag aagcagacct tacttggcag 138300
gactataaaa cagacaagaa agctattggt tatgcgttag ataatttaga attaaaagat 138360
gatgttagag aacttcttga gttacttaaa tatcatgcta gtatgcagac aaaacgtaat 138420
tcatttacta agaaattacc taatatgatt aataaacaaa aacgaacatt acatggttct 138480
ttttctgaga caggtacaga gacatcaaga ctaagtagta gtaaccctaa cttgcaaaac 138540
ttaccggcac acacatcaga tgtaaacaag tttgattaca aacatccaat taaacgttca 138600
tttgtttcta gatttgaaaa tggagtacta ctgggagccg actatagcgc cctagagatg 138660
cgtattattg gattatttac taaagaccct gatatgctac aatcattctt aaatggggaa 138720
gatattcata aggctactgc aagtattgtt tataataaac cagtagaaga ggtaactaag 138780
gaagaacgac aagcaactaa agcagttaac ttcgggttag ccttcggtga atcacccttc 138840
tcatttgcag gtaaaaataa tatggaagta agtgaagcag aagaaatatt tgaaaagtac 138900
ttccaaacaa aaccaagtgt aaaaacttct attgacaatg tacatgagtt tgtgcaacaa 138960
tatggttatg ttgatacaat gcacggacat agaagattta tccgttcagc ccaatcaaca 139020
gataaaaaga taaaaaatga aggtctaaga cagtcattta acactattat ccaaggttca 139080
ggcagtttct taacaaacat gtctttaact tacttagatg attttatcca atctcgtaac 139140
ttaaaatcaa aagttattgc cacagtacat gatagtatct taattgattg tcctcctgaa 139200
gaagctaaaa ttatggctaa agtgacaatt catattatgg aaaacttacc atttgatttc 139260
ttaaaagcag aaattgatgg aaaagaagta caatatccta ttgaagctga tatggaaatt 139320
gggttaaact ataatgatat ggttgaatat gatgaggaag aaatagatac atttaattct 139380
taccaaggtt atattaagta tatgatgaat ttacagacct tagaagatta taaagagtca 139440
ggtaaactaa cagatgaaca atttgaaaag gctactaatg ttgttaaaag tgaaaaacat 139500
atttaccaag aaatttaata aaagtattga caatacattt aacttatgtt atactatata 139560
ggtaataaat ataaggagga aaacagagtg aatacaggag agattagatt taatcgttct 139620
atggatgaat ggattataac aagtatgtac caggatgagc taggtgagat gaatattgtt 139680
gttacattct ataatagaga agaaaataaa catggttcta cagttttacc aacagagtca 139740
tctactggag aagtagcaga ggaattggca agtcttgaag aagaatatcc tctagcttta 139800
cctttaagta gtatctcagt taatatttaa aaggaggaac tgataaatgg aaatacacat 139860
tgattcccta gattttacaa actttactat taaagataga aatgggaact cacaagagtt 139920
tgatattaca gatgagttaa gaattacaga gtatacaata caagaggact ttatgcaaca 139980
atcagctaaa tatgcttttt gggcttctat attagagaag gtaagagcat attctgaaat 140040
ggaacaaaga aatctagaaa caattggtag taagctaaac cttacaatta gacaagagta 140100
```

```
cgaacaacaa ggtaaaaagc ctactaaaga tatgattgaa tctagtgttt atattcatga 140160
ttcttaccaa caacaactta aagttgttga ggcttggaat tataaagtta aacaacttca 140220
atatgttgta aaagcttttg agacaagaag agatatgatg attcaattag gtgcagaatt 140280
acgacaaaca aataaaaatg gtggaattac taatccattt tcacattaaa aaataaagta 140340
aagaatataa ttgacaaata taaaaaacta tgttataata aataagtaaa ttaattaaaa 140400
ggagaaaaga taattatgga tttcaatcaa tttattaaca atgaggcaag caaattagaa 140460
agcaataaca gttcttttaa caataatgta gagagctaca aacctaaaaa ccctgtacta 140520
cgtttaggta atattaaaga tgcaaacgga aataaggttg ttaaagaaaa tgcttttgta 140580
cgagtattac ctcctgcaca aggaacaaat gttttcttta aagaatttag aacaacaggt 140640
attaactatt ctaagaaaga tggttctcaa ggattcacag gattaacatt acctgcagaa 140700
gaaggttcat ctgtccttga cccgtacatt caggactgga taacaaatgg tgttcaattt 140760
agtagattcc ctaataaacc aggagtacgc tattacattc atgtgattga atactttaat 140820
aacaatggtc aaattcaacc aaaaacggat gctcaaggaa atgtaatgat tcaacctatg 140880
gaattatcta acacaggata taaagaatta ttagctaact taaaagatac tatgttaaaa 140940
ccatcaccta atgcacctca tagctttatc tcagcaaatg aagcattctt agttaatatt 141000
gttaaagcta agaaaggtga aatgtcatgg aaagtaagtg tttatcctaa tgctccttta 141060
ggtgcgttac cgcaaggttg ggaacaacaa ttatctgacc tagaccaatt agcaaaacca 141120
acagaagaac aaaatcctaa ttttgttaac ttcttaatca ataatgttaa taacacagag 141180
ttaagtcatg ataactttaa atttaaccgt gaaacaaatg tcttaggtga agaaccttca 141240
gagcctaaac aagcacctac gcaacaagat gtagatagtc aaatgccaag taatatggga 141300
ggacaaccta atcagcctca gcaaggtcaa gtaggtcagt atgcacaaca aggtcaaagt 141360
aatggtcaag gacagcagtt acaaggtaca caacaaccta tcaataacac gcaatttggt 141420
caaggaactc cttcaggaca acaaccaagt aacacaggtt ctgttgattg ggataactta 141480
gcgcaacaac aatcacaacc tgattcaaac ccattcaatg attttgatgt tagcagtgtt 141540
gatgattcac aggtaccttt tgagacacaa cctcaaaata cacaacaagc acctgaacca 141600
caccaaacta cacaagagcc tccaaaacaa aaacaaacac aaagtattga cgatgtatta 141660
ggtggtctag acttagataa cctataagat atagagtgcc ttagagcact cttttattta 141720
agatatataa ttactaggag gatattaaat ggcaagagca aaaaaaggta aagaagtaga 141780
tttaacagat ttaaatacaa ttgatttagg taaagaatta ggattaacat tattatcgga 141840
tagcaataga gcagacatta aaaatattgt acctactatg gttcctcagt atgatagaat 141900
tctaggagga ggcatcccat taggtagatt gacagaggtt tacggattaa caggttcagg 141960
taaatcaagt tttgcagtcc atctctctag aatttcaaca cagttaggtg ttataactat 142020
ttggattgat attgaaggta ctgcggacaa taatcgtatg gaacagcttg gcgtagatgt 142080
ttcaaaacta ttctctattc aggcaggtga aggtagactt aaaaatacag tagagttatc 142140
tgtagagact gtaggtaagg aattagatta ctggatagat actttcaacg agaaagcccc 142200
tggagtacct attttattta tttgggattc attaggagca acaagaactc aagcggagat 142260
tgaagaagga gtagaccata ggaaattagg gacaaaagcc acagctactc aaaaagttat 142320
caacgcagta tctcctaaat taaatgatac aaatacagga ttaattgtta ttaatcaagc 142380
tagagataac ttgaatatgt ctaaccctta tgatgaccct attaagtcca caggagggcg 142440
tgcgttcgag catggagcca gtctaagact taaaattact aaaggtaaag agtccgacct 142500
```

taaacaatct gattcaatga caggtaaacc tacctataaa ggtcatgtga tgagagtaga 142560
gactaaaaaa tctaaactat ctagaccagg acaaaaagca gaagcagact tactatcagg 142620
atatgaggta ggttctggtt cggatattac ccaactaaat ggaattgacc cttaccatac 142680
tatctataag gaagcagttg aaagaggtct aattacgaaa gggacttgga gaaattatat 142740
cacacttaat ggggaggaaa ttaaacttta tgataaagat tgggttcctc gtttaataga 142800
tgaccatgag ttatacttgg aattatttag tagagtctat ggagaacatt tccctaatgg 142860
ttattcacca ttacttaata ctaaagtaat tgtaactcag ttagaagaat atcaagcatt 142920
agagaattac tatgaagagt gggctaaaga taataaacaa gaagaacaag aggaagaatc 142980
aaaaggagaa tctcaagaaa aggattctga ataatagatg tataatttaa tagataaaaa 143040
catgagacag gtaaaagaat ctttggggaa tgcaaattcc tcagatgttc ttcctttacc 143100
ttataaagac atagcaaaga aatttgaaga agtaaaagaa aaaggtgaat caattatcat 143160
tgaagagggt ggattccctt acacagattc tacagtgatg tatatagaac atgtaacaga 143220
tagatgggca ggaggatact ccctaattag gcatgaaggt gaagaggtta aagtacctaa 143280
aactatccat ttctctgata tatatgttaa ggataaatca cataaagtaa gaataatctt 143340
cgagggggct aatccttatg aagaaggcta aaaatggtaa tagatatgta atagatatag 143400
atggtattcc tgttgatttt gaaagagact tggatagttt acttaacagg tataaaaacc 143460
ttaggtggtc attatatcat aagtacgcag ggattttatc taatgatttt gaaagacaag 143520
aactaagaga atatattgat gagcaattta ttaaattagt taaagaatat aatattagaa 143580
gtaaagtgga ttttcctgga tatattaaag ctaaactaac tttaagagtt caaaatagtt 143640
atgttaagaa gaatgaaaaa tataaacgta ctgaaattat tggtaaaaaa gattatacag 143700
tagagtcctt aacagaagat ttaaatgaag acttcgagga taatcaaatt atgagttacg 143760
tatttgatga tatagaattt acagaagttc aaagtgagtt acttaaagaa ttacttatta 143820
atcctgaaag agaagatgat gcctttatcg tttctcaagt agcggaaaag tttgatatga 143880
aaagaaaaga agtagcaagt gagttgacag aactcagaga ctatgttaga tttaaaataa 143940
atgcatacca tgagtactat gctaagaaag aattaaataa ccatagagtt aatactgaaa 144000
atcatatttg ggaaaactag ttacagtgcc ttccttgtgt tatataagta ctactaataa 144060
tattattagt agtacttttg atatattatt tatgtagaag agaagtgaaa atagtgagaa 144120
tagaaaagca taaaataaag aataataaag taattaatga aatgtctata acagcaaata 144180
acctctataa tcatgctaat tttattttaa gacaaaattt ctttaataat aagactaata 144240
aaggatacag aaagttttta aattataata ctattcatag aatattaaaa aatatgaatg 144300
aagagaatta tattaaactc ccaagacaaa catctcaaca agtattaagg gatttaatta 144360
ataactggtc tagttttaga aaatcagaaa aagattattt taaaaaccct aataaataca 144420
gaaatagacc aaaaccacct aaatataaag ctaaaggcgg taaaggaaca attaagttta 144480
ctaatcaaca atgtagaatt cataaaaaag atggtttaat acatttacct acacctttac 144540
aagatataac tataaaacct tataaagcta agaatataag agaacttgtt tgtattccta 144600
aaagtgatta ttttgaagtt ttagtatgtt ataaagaaga aaatagtaat aaaacactaa 144660
atgataacga aaacatagca agtattgatt taggtttaga taacttgata accatggttt 144720
ctattgtaga taaaccaata attataaatg gtaaaggtct aaaatctaaa aataaatatt 144780
ttaataaaaa aataaggtat tatcaaagtc tattacaaaa caatagttac tcttcgaaaa 144840
gaatattaaa atattgggaa aaaagacaca atattatact agattacttt cataaagcaa 144900
caaacgaagt tgttaaatac tgcgtaaaaa atgatattag taaagtagtt atagggtata 144960
ataaacagca aaagtataaa tctaaattaa aaaa 144994

<210> SEQ ID NO 3
<211> LENGTH: 72177
<212> TYPE: DNA
<213> ORGANISM: Unknown
<220> FEATURE:
<223> OTHER INFORMATION: Description of Unknown: Bacteriophage F770/05

<400> SEQUENCE: 3
ggggtatact gctggtggat tcgcagcagg ctctagaatg ctgtgctctg tcatcgcaat 60
ggggttctgg aaataatggc attcatcatc aagcctgaca tgcaggtaga tgttcctggc 120
aaagagcgca tcagtgcgct ctctgtccga ggtacggtac tcattctgga tgggcaggag 180
catgactttg ctcctatctg ggatgggggc tatctgcctc ccgaggctta tatcgggaga 240
actcctttcc aggagattaa agtagtggac ggggatgtct tcgtccgcta catccatcag 300
gtaaccgtcg aaatcctcga cgctgaacct ggcgaagtga aacctttcaa ggtgaccgaa 360
gatggtcccg tggagatgcc ttttgaatac tatcgattgg gcctcggcac taactccgaa 420
agaagtggcg atggggaagt accgggaagc actgaatatg gccaagaacc ttcgggcgaa 480
agcctaccag gaggagagcg agccgattcg gatcgaattg gaagctgacg caatggacaa 540
gggcgaggta gctgacctca ctgcttggct tgaaaaggtc aaggagatcc aagaacgcta 600
ccctctcccg gaggaaccga aatgactgct gatcaggtat tcaaccaagt gctaccggaa 660
gcctacaagc tgcttccggc cagcatgaac agtccagagg ccagcgtgat gttgctggcc 720
attggcttgc aggagtcccg ctttgcttct cgcagacagc tggtgaactc catcaacagc 780
gaagggcgta aagtccttct tcccctcgga ccggccaagg gctactggca gatggagaag 840
ggtggtgccg tcaaggggct gctcaacttc tggaagccag ccaccaagga actggtccac 900
tcggtctgta aggccagggg agtccctgcc acccaagacg ctgtgtggga tgccctggag 960
catgatgatg tcttggcttg tgccttggct cgtatcctgc tctacacgga tcctcaccgg 1020
ctgccgccta tcaaggccca ggctgaagca tgggatctct acctgcgaca gtggcgtcct 1080
ggacaacccc atgaagccac atggccggaa ctgtaccgca aggcggtaag ggtggtgacc 1140
caatgactat ctcagcccgg cagatccggt ggattgcgga agtactgctc ttcgccatca 1200
tcgccctcta cgcctacaac aagggcttcg tgaaggcgga atctaaaacc aatgcggagt 1260
gggaactccg catgatgcag gccgaaaggg ctgcggaaga aaacaaaaag gccctcgaac 1320
agagtctgct cgaagccatg aacgaggtaa aaaaagatgc tgatgaacaa ctggctgatc 1380
aagcttcccg cattgctgct gctgatgctc agtctcgcag cctgcgggag caagtcgccc 1440
gtctacgtga cgacctcatc gccgacggtg ccagagcttc cactgagcgg catgcaagca 1500
acgctgcctc tgtggtgctc gccgacctgt acggaagctg tgtcagccat cgacaagaac 1560
tcgcaggagc gcttgaccga agccatgcgg caggattgac atgccagaag agctacgcta 1620
ttgtgaagtc actggggcac gctcctcccc agtagtctcc ttcgacacca tgcgtaaccc 1680
ccttagactg cggtcttcgg gggtttttta atgcctgtca gaaatcaggt tcccagacca 1740
gtgcaccttc ttcgtgtcct tcgttctcgt ggatacgctt gtgctctgcc aggatctgct 1800
ggtcgatatc ccaggaactg gggatctcta ccgtagtggt attcagcatc tccagacgct 1860
cggctacctt ggtatccaag cgagtaccca gaaggattga ctgagctcta ttgaggtcac 1920

```
gctccagaaa ggttaactgg cgttcacgac gacagatcat gctgaagaag gcagctttca   1980
cagaagtgcg tgctcgcttg gtactaccgt ctttcagggc gagaaaggca ccgtatctct   2040
ccttagcgag atcacggata tcactggcag cggtgatctt acgaatgcgt acgacatgct   2100
ccagttcctt gagatcatct tcatctacta cccagtaggc tcggtcagtt tctaggaagc   2160
caacccaggt agtcttgaag aatctgacct gccttccgtt gcgctcagca aatccacgca   2220
catggtagaa ccgggttacc ttagagctat cgaacacggg ttcgtactta gacatgcttc   2280
cacacctcct gatccttttc cgcaaccatt gcgatgtact cttctagtac aaaccgagga   2340
tcaacgttga ttgactccag gtagtgacgg taggcgtcag cttccatgat cttgtcaccg   2400
acagccgtcg caatgacggt gttgggcatt tccaaaacgg tagtgattac ctcagccatg   2460
gtttcctcca ggcaataaaa aacccgccga agcgggtttc tggttggttt agtaggagtc   2520
cgggatgccg aatttctcct tgtacttgaa ctcaacccac tggaagactc gacctcccag   2580
gtggccacca actgcaatgc agattggcat ggtcatccac tcgtagagca gatgttggat   2640
tacagggtac acgtcgtaga tcaggtaacc gacgaggatc gctgaggata gctcggagac   2700
aacccacaca aatttaggtg ggtgtccctt tgcaatcctt gaagtgaggc tgatcacccc   2760
actcaataca ctgagtgcaa tcgcactcag caccccccag atgttagggt cgcttttcca   2820
aggcattggt actctccagc aaagttcaag gccgtatagc agccagttgc catgataaag   2880
caatccttac tggaacacac gggtatccat caggtagttg acttcttgat catcctacgc   2940
cagatgtcta tcaacagtgc cagcggccag aggaacacgt agaacatgaa ggtgctgaag   3000
aaactgagtg agatgaggat gggtggggtg atgatccgtt cgactgtttg cttggagggg   3060
actcggaaga tgtgaccgat ggcgacgaag aaccaagcag cgcccaaagc caagtacaac   3120
aagtagtagt tcatggtttc tcctgtgaaa aaggaaaggg ggagttgcct cccccgatct   3180
gttacttcag cgccttggcc aacttgtcag ccgcgtcgcc aggcatacct agaacggtcc   3240
agcccttctt cttggctttc ttgaagtcca ggcaagcctg agctttcgcc ttgtcgccct   3300
tgctatctac gaaggcttgc cacagaacct gaccttgttc gaccagggtc agggcagtct   3360
tcttatcagc cggcaggggc ttacccttgg ccttgaaggt gtcccggaca ggctgagcca   3420
cgggcttggc ttccaccttg acggacttca gcttcttggc tttgcgggca ggtacacggc   3480
tcttcgactt cttcacggcc tcggcaggct tcggctcagc gaccggcaca tccttggtca   3540
acgagggagc ttccggttcc ggcttcttgg tttccgtcat gacggtatcc accacctcca   3600
gaacgtccac cttctcccca actacttcgt tgggtttagt cggcagcgag cgagcttccg   3660
gggcgttctt cggaacagcc gtctgcacct tgttcttggt gctcgccgga cccttgtgca   3720
ccacgatgct ggagccacgg tgaccggtga tctccacatg gtaggcaggt tcgctgtgct   3780
gacccgccag agcagccccc agcatgcggg aagcttcctt gatgtcggtc atgctgcggt   3840
tggatttcag ggccaccatg gcttcgtccg gcagttcgaa gaggatgtgg taggcacgga   3900
cacgcatctt gttcgcgtcg taggacggaa cggcgatcac gtcttccggt gccaccttgg   3960
ccagcacgca cacgttgccg ctgaagctgc ccaggtactg acgacgagcc acatgcaagc   4020
cattcgagca ctcgttgcgg cgatccggat ccacgaggga ctcgttcatg cacaccagag   4080
tgccgacggc ttgcggtacc ttctgcgagt ggatgtcacg gtaggagaac tccttgtgac   4140
cgtccgggcc gcccttcaac agcagcttgt agatcacgat gcaaccatca tcggcgatgg   4200
ggagatcccc acgttcgatg aagcgcataa gatcctgcac gctgtgctga cgcttggcgg   4260
```

-continued

```
ccacagaacc agcccggcga aggaagttct cgataccgac agtgctgccc ttggctttcg   4320
actgaacagc tgcggtcagt tgggtcttga gcttctgggc gtccggtacg atggttccct   4380
ggtcggtcac ggcgatgatg gtgtcacctt cgcccacgtc atcatccggg tcttccgact   4440
ctacgccgtc ttcgctgagg ttttccaagt ccacggaact gaactgcggg gcagatgccg   4500
gtacagcgtg ggccaggatt tcatccacag ccttggccag tgcgggatcc ttgatggtga   4560
ccttttcggc cacctcttcc cccacatcct gcccagcatc cgtgtccggt gcgcagtcac   4620
caggaaccgc gccagcggtg acgggagcga cgggagcagc cggctcggat gcggaagctg   4680
ccgagaagaa ctctgcgacc ttcttcttcg ccacgcggaa gaaccgcatg atgccaccgg   4740
acttcttctc ggcggcctcg tagacgttgt tgatgaccag caggtcttcg gagtagtcca   4800
cttcaccacc ctggctcagg atggggacgt acttatcgac gaatacggcg acacggggat   4860
cgccttgggg gatacggatc tgttcagcag accctttcac gtacaacgtc agataccttt   4920
cgtcgaggac agcacctacg acagttactt tgttgctcat tggtttctcc ttcagccacg   4980
aatagctgtt ttcagtagtt tgactgtcga agcgacagtc ttcttatcgc gtaaagcagc   5040
acggacttct gagatgttca gaagtgtaat caatggtgct tctgcgattt tcttcagcat   5100
gccaagcact ttcttatcgc ccggaacagc cttgatcttt tccgctatct tgcccaaggc   5160
taccttctgg tcttcagtga agaacctgag gtccatagca cacatggtat tgagcaagtt   5220
ctcagcatca gctgtttccg gctcaggcag cttgaagtca tcacgacatt ctttgaccgc   5280
catcatggta cgaaccaggt ctactcggtc cgaatccttt gtaacctgaa ccagcatgtc   5340
gtagcgcagc gagcaagcct tgatgaactc aggtttgttc gcctcttcca ggaacttttc   5400
caggaggaag tcacgagcac ttttgatgcc cttcttctcc atgttggttt cctgggtttc   5460
gttgtacacg actgcaccca agttgccata gttcttcagc aggtaggcag agcaagtctt   5520
gtccaaacca cgaacacact tacgcacgta gtagtcgctc ttggtgttga ggcgtacgta   5580
gtaagctgga ttctccaccc gagctacgtt ctcagtacgt gccatctcca gggagaatat   5640
gccgttgcta tgacaagccg agagcatcgg ataacccttc ttctttggct tggacacgac   5700
tggggcagcg ccggtcttcg agtcatactc gattacttca gcttccttgg tcaggtccaa   5760
tacttcccag cccttcagag tactcagggc tttcctggct tcctccacct ttttcacgct   5820
acgcggaacc acgtaagcga tgagtgagtc gtcagcattg taaccaccta cccactcgtc   5880
gagatcctcc acacggctat ggatgtcacg acggctgtga gtcaggacaa tacagcggcg   5940
gaacagcggc acataggaca tcggattctt cgaccagtac gaaaccaacg gatacccatt   6000
gtgggtgttg tagttccgaa cagaatcccc gttgtgcagg tgacgaccag cgccgtacca   6060
gatcagccga gtggggcaca gcccttcttc ctggattaga ggcaacagct tggaaaccag   6120
gtgcttctgg ccccacttgc gtactgccag ggcctgccag gaatccttcc ggaacttcgt   6180
gaggttctcg aagctggtac gatcgtagtg gctggggtca gatgtcatcc caaccttctt   6240
caccagccgg atgagcgaag ggtacagggt gtttccttgg tttcgcggct gctttccgat   6300
gagggaaagc tgttgcagca gagtcttgaa gttctccttt tcactccggc tattcgaatg   6360
gtacagttgg ctcaagccaa catcttccat ggtagacatg agtcccttat gggtcagacc   6420
agaccctttc atggaactta cgagcacgcg attagccgtt acttcttcag gccgcagcat   6480
actatctgcc ctggcttgca ccagttcttc acaggacttc gccaggatgt cactgcgtac   6540
cttgttgata ttccgcgttg cacggaggaa cttgttgagc agctgaagaa gagtcttgcg   6600
ggtgtggtct tccatggaca gcgcttcccg agacggtgtg atcgacaccg agttcggttt   6660
```

```
ggcttggagc accagcacgt tgacgttgcc cggtagagag ttcacgaact tgtgcacagg   6720
gtcgtatacc tcggcgatga attcatcccg ctctacggga tagatgacat cgccgtaacg   6780
gacacagatg atgtggccgt tgtattcgag cacctgttcg gtagcgatgg accagtcttc   6840
ggtcacctgg gagaagggca gggtgggcag cttcaccccg ttgaagttgg ccagcatctc   6900
ggcgttggcc actatacggc gaatcagcgt accgaatcga cgtacgtctt cgttcttgat   6960
gttgatccgt acttccagac cggtctggtc ggtagggata tcggtcacca ccggggtgat   7020
ggcaggacgg ccaccgttct ggatggaagc cttctgcatg cggtagacgt tggttttccc   7080
ttcatggtga atggtcacct ggaagttgtc cacgtaggcg aagggagact tgcaccccaa   7140
accaaagccg ccagtctggg agccgtcgtg cttcttggtg gagccgccgt agacgccgta   7200
gatcgtgcca acgtcgtcgg gatggatccc tgggccgaag tcacggatga cgaattcgtc   7260
gtccttgagg gtgatctcga ccggggtctc tttctcgatg ccgaccatct tgtgggcatc   7320
gtaggcgttg cagagagttt cacggacgac ggcaaggatc ttgtccgtgt acagggaact   7380
cgacagaact tggaagaagg ccgggtcatc actgatgccc atggaaattg cttgcttgcc   7440
gcctatcaca acgtgagtgg cgtagtcttt ctgatgagtt acctgcatgg attactcctt   7500
ggacttggcg cgtttagcgc gacgtttctg attggtgagg tgagtgacca tctccaggtg   7560
agcggggttg caacacaacc gttgtccgca gagatggtcg atctgtttct tgcctggcac   7620
gtagccgaag tagttggtga acatgacgat gtggacggcc actgtctgac cgtccaggct   7680
catccgcccg taaccaccac ccctgcccgt acctgaatcc gggccttgcc agaggtggca   7740
ggggctgggc ttgttgtcga ggacgaagcc cgtgtcttcg actttgcagc gggcttcgat   7800
tcgctcccgg atttctttcc tgcgtccttc gaacacttgg cttcccctcg gataaaggcc   7860
atgagtttct tcttcgacaa ggttccgttg aacttacgga agctgtcgta ctcttgcatg   7920
gtcacctgct cgtacccttc aggaacaggc agttgaccga tagtccaggt gtgggtcatg   7980
cgtgtctcac ggttgacgaa gaaataccgt ccgttgacag gcgcatgacc caactttcct   8040
ggagtccaat cagctttcag tttggctttc ttcgccatga ttactcctta tgcagcacgt   8100
acatgccttt gatgtcggtg cccaagatgt aacccttggg cactgttggt ttcccataga   8160
cagccttgcc ggaagcgata gcagcctcag cttcttcgat acctccgaag tgcttgatca   8220
tatggttgaa ggaagcccag taggacttcc ggtcagttag cgagcagggt tttcgagaca   8280
acgtagtgac cccgtgttc ggtgataagg gagtccaggg tgctccaact catggctttc    8340
acattgccca tggccagcac tgtcatcccc tcgggttcat catgatcatc tcggaacagc   8400
acgagatgaa ctccatgtgt agcgatcatt tcggcacaac gaacacaagg tgccctggtg   8460
atccaaagga cagagttgtc cagtggtaca ccagagcggg acgcccaagc caagatgttg   8520
tgctcggcgt ggatcacccc gtagggagtg gttttgaagc gggtctcttc ccgaaggtac   8580
tcgccgttct cgcaacagtt gtcggttcca ggcatggtgc cgttccaccc agtgaagagg   8640
gcaccggtcg tagtgaccag cacccctcca acttgatggc gttcagctac actctgcttg   8700
gccgcatttg tcgctatcga catgtacagt ctcctgtact tcatcgacct cgggtctggg   8760
gctttcagca ctgttgatac ctctcgcaaa gtcgcaggca gcccaaaggc cgccgcattc   8820
atggacgagc acaccgtcct tacgcacggc tattacgcct tgcgacacgg tgatctcgtg   8880
gtcgtttacc aagcaggtac ttgtcacgca gatttctcct tcagtgcagc agcatgctca   8940
cggcactgtt caatgagacg ttccttggtg atggggtagt ccaaagtgca ggcttcacgc   9000
```

```
cagctgggcc agaagatgtc caggttggca cccagaggaa cccgcttgtc attgatcttg   9060
gggtcttcct gccacgccat gcacttgcag agcgtgttgt tgacccacac agtgacatca   9120
ggatcgtctg gccacatcac gtagatcgca tcgtggatca gagagatgat ctctaccttc   9180
agcttgtagg ggctggccag tagcagcttg cggaattcca cagcagcacg gttggtcagt   9240
agaccccagg actggccgga caccgcatta cccgcactgc gggattcagc agcggcctcc   9300
ttgggagtcg ccttcaagcc aagaatggtg gaccccaaca gcggcgttct cagccgcagg   9360
ttgaaggcca gttccacgta gcccgtcttg gttgctttgt cgatctcacc agccacccac   9420
tcattgctta cgcgatagag cttgttgtag ttggtttcga tctcctgggc ttcttcatcc   9480
gagaaaccta cctgccgcac cagacccatc caactgcccc catactggag caggaagtgt   9540
ggagtcttgg ctttgcttcg caggtctggg tagaccttct ggatcgagtt gatggagtca   9600
accgtgtcta tgatcccatc acacttgtac ggccagaacg caaaggtacg catcgagtgg   9660
ccatcgtagc catcggtgta caccttgatt ttgttcgggt cttgagtgag cagggcgttg   9720
atccggtctt ccagtgcagc gaagtccgcc cctccgaaga ggaagccggg gggtgcacag   9780
aagagagact tcaccagctt gccataggtc gagccagccg gaaggttttg caggttggga   9840
tcggatgagg acagccgccc agagatggtt cctccaaggt tgaaggagcc atgtaggtac   9900
atcattccgt ccgccttcat tcgacccgcc ttgaaggctg gcatgaaagc agagatgacc   9960
ttctctacgg cacccaagtc catcagagcc tggatgagat ccttgtacgg ttccgccttg  10020
atgtggttca acagcttctt cagcgtacct ccactggtgg agggttgctt ggtcgccgtc  10080
acgtccagta caggaaggtc gagaacttca tgcagcagac gtgctacttg cgggccagag  10140
ttggggttga accgaatgtg cgaaaacttg ctcagcggat gctggatcgt cttcagcttg  10200
gcattggcct tctccatctc actggtttgg atcagcacct ctaccttggc gaccgctgga  10260
tggctcatca cagtattgtg gtagccgtcc cgcagattgt ttagttcagt attgacctct  10320
gtgatcttcc gaggattcat aggcatgccc acgagttcca tttggatgat caggtccaag  10380
ctgtccttga acaggccatg gtatagagcg tcctgctggt cttgcaccat gatggggtaa  10440
tacttgttct tcacccatac ggttgtcacc gcatccaccg cgttgtaatt catgaggtcg  10500
tccagcggaa tcagccggat gtccttgata tcgtcctgtg cccagttgcc cgcatgttcc  10560
tgccccaggt ctttcaggga gtagctgaca tcagcggttg agttcagtgc gaggtacgcg  10620
atgatcttgg tgtcgtccat ccgtggagtc atgatctcca agccacgatg catgccctct  10680
ttatcgaggt catgctccat gaagagggtg tagatcagaa ccttcacgtc atggtttgca  10740
cggtggtata tgattcgccc agggtactcg gtgaagaacc acttgagcac ttcccgcatc  10800
tctgcgttcg gctcgtagta accgtggtgc ttgttctcgt cctggatcat ctccctgtag  10860
tcacactgga tctgtacagc atcatgctcg ttccaggcga agccaatggt ggcaatgccg  10920
gagtcgaaca tgctgaggct gaagccctcg atgtcacagg atatctccgg cttgtccatg  10980
agcctggcca gtgcttcctt ggcttggctt acgtggcctc ggtagatgta ggtgacatcg  11040
tgcagcaggt cagacccaac gggccgatac accccatggg catggtcaac gatggctttg  11100
aagccacggc tgagcctgtg catctgccca ggatcgaaca gcagcacctg atggttcaca  11160
cccggagtca ccaggtaccc aggatcgtaa ccagcaggtg gcgacagatt gccgaagtcc  11220
gcgtctgtct tccgcttggt ccattccttg aagtacttgg agtcagccac gtaggcatac  11280
tggactccga gatcccgcag tagctggtcg cgatccttga tgcactcctt gatcgccttg  11340
gcagatacct tcttgccctc gtaatccaga gagatcacga tgacattctt gcggggtaca  11400
```

```
ccaagccctt ccagctgctt gatgtaggtg gattcagcgg ctgaccgact caccgctgcc  11460
tccttgatca ggatagccac agggtagcta tcctgttctt cccaggtgat gtacttcatc  11520
acagtcctcc tagtacaagg ttaatcccaa cacgggtgca gagcttatcc caacccgctt  11580
ggtttgaacc tatgggactt tcggtcggga attccacccc ttccaccggc aagccaaagt  11640
gctcatagac cctcttcaga ggttcccgta aaccacttgg gaacatcttg aggtactccg  11700
acggttcgtc ggacttgttg agcacctggc tgatgaacgt gagtacagag tcacgctcgt  11760
ctatcagcac cgggtcgtac tcggacagaa gactgtctac gagtactcgg ttgccgcgac  11820
tcagccgggg aaagtagcgg aaattgggct tttctccagg tatcatgaag ttacgaccac  11880
ggtggcagaa cgcacggata ccatcgccgc gagctacagc atccgcgatg atcagttcgt  11940
tcaacttggc ttgaaaagcc ttcctcactg gaacatagag gaaaccatcc aagcagtcct  12000
tcactgccct tttgaagatc aggaactccg gggttctcgc ttgcattaca tgtcccctgt  12060
catgaccacc cgtctacgtg ctcggctgaa gccaacgtaa agaaggcgtg ccagtgcatt  12120
cgggcggtgt accttgccac agatgttgtc caggtcgatg aacaccgtat cgtaggtgga  12180
accctgcgac ttgttcacgg tgcacgagaa ggcaggccgt aggtctaccc agttctggtc  12240
gatcagctgg aggatcttgt aatcctcttc tttccgagcc agcttctccc ggtccttgcg  12300
gtccttgagg gacttgggca ggaagaagct gctgttgtgg tgcatcagct tcacgaggta  12360
gccgtccacg tcaaactctc tggttggccg aatgtcttcg atcaccacct cggatccgtt  12420
ggacagctgg gcatgcttgt tgatgacggc ttcgttcacc agcatcttct gaccgatctg  12480
cggatcactg gaaccgagca gtaacttcga gaagtgcttg ttgtactcgg tcacacaggc  12540
attggtgtaa gccaatacct tggtgttacc gtgcacttcc gggtgctgga aggcgtcttc  12600
tgccatctct acgaacttgt cccgtggtac atggatcagc tggtcaccgt ccaactggat  12660
cttcggccat tcgcccgtct tcaccgtgtg gcggaaagcg ttgcagaggt ccaacagggg  12720
accactgttc tgccgcttga cctcgataag ttccaccaca atgtccttca tggcgaaggc  12780
aggcatgatg ttggtaccga ccggagtcag ctggcagtcg tcgccgacga agatgaattt  12840
acagcagtca gttctgtcga agcagaactg gagcaacgca gggtctatgt aactggcttc  12900
gtccaccacg atcaggcacc ggtacggtag ctcgaagcgg gagatgggca tcagttcgct  12960
cttgcccgtc ttgtagtcgg tgcggagacg aaggcccaat gcccggtgaa tggtcttgac  13020
ctcgtggttg aactccttca tggccaccgc cagagcctca catgcttggt ttgtggtggc  13080
tgtcagcagg ggttcgaacg gctcgaagtt gtcgtccagg gtagacaggg cgcgatccag  13140
agtctccatt tcgtcgagga ttcgtcgaat cagagtggac ttgccagttc ctgaccagcc  13200
cttgaggacc attacctggg catcggggtt ggagtagaag ttgatgaagg tctgaaaccc  13260
ggcttcctgg cctggcgtca gtacgaaggg agcaggcttg tctactcctt cggatcgaac  13320
atgatcactt gcccgtacgg ggctttccag ttcgatttcc tgctgtacgg gtgaatcaac  13380
catagaatcg gtactcctgg gttgtcgttg tagtggtgga actccccatc agagaacacc  13440
accaatgcgt gaggtttgtt ctctgcggcc cactgcatca caggggcaat gcaggtacca  13500
ccccggccct tcaactccat gttcatgagg gcattgaggt tggggaccgt atccaccgaa  13560
cggatggaag cgtcgaactg gatgatatcc agctgtgttg gtttcagcgt gacgaagatg  13620
ttggcgatct ccgacaggta gcggcggatc tcttcgttgc tgaccgatgc cgacaggtcc  13680
attgcgatgg caatccgcag gagtgcctta ccgcgacgtg agggcaggta gtacctgttg  13740
```

atcagccggc gattgggacg tgcccaagtg aatccaccac gcttgaccac ctggaagaac 13800
tgacgcagca ggtgaggcag gggcagcttc gggaacatca ggctgtcgat gaacacctgc 13860
acttcccctg ggattgagcc agggttgcca ttggcacggg cagcggtagc agcactgagg 13920
atcaggtcgt tgatggcccc ctggatctcc gtctcagaca tgggggtacc atcgtccttg 13980
gccggagcag gccgggaaat gtcatcgaat ggcaccgggt taccgctgcc actgtttccc 14040
tgagtagacg aggacaagcc accaccacct tgagtttgct gctcctggta caggtcagcg 14100
tagacatctt ccgtggacat gttggcgtac ttgggatcac acacccaatt gcacttggca 14160
ccagtcctgt agtccgtcca ggaaatagga ccgtacccac aagccaacaa gttgttgttg 14220
atcacgtggt ccccagcgat gttgtacagc atgggatcac ggtcacccat acggacctta 14280
ccgatgtgat gccgccagac gtgttcgatc tcatggagaa tcacggtctt gcggctcatc 14340
tcgtccaggg acatgaagaa cttggggtcg atgaacatgg tgatgccgtc gatagcagca 14400
gtgcccatgc cctcttccca cacgtacttc agacccatca tgatgttggc gtagaaactc 14460
accttggagt ctccgatgat gcgaatcttc gccttggaaa gggcgatgtc ttcagcagaa 14520
cgatcagtca ttactcacct ccgatgatgg ccatcgcctt agcgaatttg caccactcaa 14580
cttgattgtg ggtttcaggt attaaggaag gaacagccag agactgggcc acgaaaactt 14640
cttcttcatc aaaaatccag tgaccattta gtggattggt tattcttatt agctccacca 14700
cttcattaat tgaagctgcg gtaccaccta gtcgagagta actctggttg tattggcttt 14760
cactattacg gcagtgaccc acataaagac caggtgttac atatgagccg tctgggggct 14820
taacggtaac tacgtacgga caaaattcag atgctagttt ttctagtact gatttagtac 14880
cgaacttgat ccccttctgg atacctttttt catagatgct aactctccag ccttcgaaat 14940
ctccagtgag tagtcgattg gggagtcgc tgtttgcata ctcgtcaact attgcttgac 15000
ctgtgaggtc ttcttgacga accataaaaa gttcccatcg accactcact ggattctcct 15060
ttagaacatg ttcaggttct tcttcaccca ctccgaaata cgcgggttct gaatcagact 15120
cttgttacgc tggcaagcca tacgcagagt gatcaccatg tggtccgggt tgaaccggtc 15180
gaggaagatc aggatcttct cgatgttgtc caccttggcg ttatccgcca gcatcgaaca 15240
catggcgaac atcagacccg gctcatcctt cggcacgtag atcgtgctcg gggaagtcag 15300
gatctcttcc aggctcggca ggcgaccgaa gtaggccagg aacgccttga agtcggtggc 15360
cacggtacca atgatgccca tggcagcagc gaggttcagc atgtcgtcca gggcacgagg 15420
gtcttgctcc ggggacatct tcaggaacca cttcgagaag tcttcccagg tacgcggaca 15480
cgcatagacc cgaccgctgt tctgcggatc gaaggtgtag aacgcacggg gactgaactc 15540
caggaatgct tgtaccttgg tggcgatgtc cagcttggga gccacgactt gaagccaacg 15600
cttcaggtca ttccgaacca cgatgtggtg cagacgactg atgagggccg atgacatcgg 15660
gttgacgatg gcaccgtcgg tttcgaggtt accggcaccc attaccaggc acttcggatg 15720
gagatcctcg ttaccgatct ggcgatccaa gatcagcttg taggccgccg cttgacgatc 15780
gtcatccgca ctggtcagtt cgtcgaggaa cagaagccag ccggcgaagg gttctttggt 15840
ttcggggttg acgggcaact cgtctccgac caggggggaac tgctcgaata cctggaactt 15900
ggcacgctcg ccggagaggt tcggcagacc attgaggtca gccgggtcca tctgggtgag 15960
acgcaggtcg atgagcttca ggttgttttc cttggcgatc tgccgggcca ctgccgactt 16020
accgatgccc ggcgaaccgt ggatcattgg cttgaggcca gctcgcagga agctctcggc 16080
gatgaacttg gcgtcgaaaa tggatacttc ttgttcctgg gggaagtgca tagtgaactc 16140

```
ctaaacgatt gatttgattg gtttaagcct tggctactac gtctttcggt gttcccggaa  16200
agcgtgcagc cgaccgctga catgccagca ctcgggcttg gccgtgttgt tgaccctggt  16260
gtagctgcca cgagcgtcga aggtcagcat ggagtagcct tcgggacgct cggtgacagt  16320
gaagatcacc acgcgagaac catcacgagt gacgtagttc ccagggcggt cgatgagaac  16380
aggtaggtct tgcagcttgc tcatttcagc ctcccggtgc tgaagtcgag ggtacgggcg  16440
aactccttct tgcctgcttg cggcttggag tcttcgcctg cgttgatgta gtactggtgg  16500
atcaaggtat tgatcaaccg caccccgatg ttgctatcgg gatactggcg accgatctcc  16560
ttgatcagcc atttctcggc cttcttgtgg tcttccttcg ggaagagaga gcggtagttc  16620
gcccacagtt ccgactcctt gaggtactgg accatcgcct ccagagtcgg tttctccagg  16680
ttgtagacca agccagtgcg accgatgaac tcggtcttga cgccgcactt cagcagttcg  16740
gtggcgtcca tgttctcctg gccattgaag gcaccggcga agatgaacag ggaacgctcg  16800
acgcacaccg tgttgtactt gccgtagtcg ccgaaggtct gggtggtact gccctccagc  16860
acacgcagga actcgttctg cacaccgatg ctgatctcgt tggcatggct gtcgttggaa  16920
ttaccggaga ggaacagctt gtccatctcg tcgcagaata cgacgttggg gacattgccg  16980
agggtagcca gtggggccag tgccttgctc aggctcaggc cggagtagcc ttccttggtc  17040
agcgatgcac agttgacctc ggtcatgggc agcatgatgt ccaggcgatt gcactggtcc  17100
atgatgttga aggacttgcc cgaaccagaa gggccggtca accagaagtg aggacgaatc  17160
tcgccttcgg acgctttgaa gatgagaagg atcttgccga tccgctcgat tgtttttttca  17220
ttggcttggg acactggtta gtctccttta aacgggaata ttaataaatc tgggaatgca  17280
taaccccaaa tattactcgg aaggggtcca ctcacctaca aagagtagaa aggtattgtg  17340
ataccccatc atggctcgca tgaagtcatg atgactgccc ccaggaagca gatgtcttgc  17400
ttcttcgagg gcttctttta aggaactgtg ggttgggtag agcttctgct ccaccggact  17460
gagatcgctg aactgcatgt tttcccctac ttaataccgt acttgcaaag atctttaaaa  17520
cctttccaag ctgtcttgat aattttggtt actgtcaggc caaatactat tggcaatgca  17580
atgggccaca atatccctag ggttactgaa cgatcagcct tgtcgtcgta gtcgtcgtac  17640
agtacaaagt cgaaaagacc agctgctact atagcggttg caaagtaggc cactatcatt  17700
gctatggcat cacctgacat agtgaaactc cttggtttaa tacacacagt agaatgccga  17760
cagttactca gtgactgcat cctgtgcagt ttggaaactc ggcattctct ttatgtacta  17820
atagtctgac tagactgtct cgccttatgc gacgctatgc gcagggagtt gtttaaagga  17880
ttaacgctaa tgcatgtctc ttgctcctaa accaataaaa gaatgaacaa acaggacaag  17940
agcgtacgga gtacgctaat gaataacctg ttctcctgtg aggtacatca tcccatctgt  18000
accgaagcgg cccgccagcc aacctcggaa gaacccatga atcaaagggt tgtcagcgta  18060
gtctccgaga cggctacgct tactcgccag ttcttcaggg gtgatgactt accccggcga  18120
aggaccacac acagtggcgg tactcttctt caaattcctt tcgcagttcg tcgctgatca  18180
cttcagcata gaacgcaggt tgttcagcag tgcctcgcca cccttcaggg actggacgta  18240
caagcacgca tcgtagacgg tttcgtccaa accatgcttc tggacgtgtt ccttgccgaa  18300
gccaagtgca tccagtacct cggccagctt attgcccatc tgggtgacca cggcatcctt  18360
caggacggca gtagtctgct cgtcttgccc ctgcccctgt acgtcgggat gcacgatagt  18420
ctggttttga cgcagttcga agaactcctt atccagttct tccaaccgct tcacgtaact  18480
```

```
ctgtacgtgc ctttccgtgg tatcgatctc ttcgctgaga atagaccgtt tgttgtgaag  18540
cacggtgatt tttcggcgga ggccatccag tacatttttc aggctactga gttcatgctc  18600
gatacgttct tcgctcaaca ttatttgttc accccgtaga gttggaagtg gtcgttcagt  18660
tcggtgtagc ggtagccatg cttgtcgatc actgcaatct cgaaacaggc atggccgcac  18720
cagttgtagt gggtttcggt gccgatctct tcgatcacca ccttcttccg tacacgctca  18780
cccggctcac cgggcagcat gaccagggta tctcctggct tgatcttggt agaccacaga  18840
acatggtcac cggtaaattg ggctttcacc agttccttcg ctccagcggt aagctgtacg  18900
caaaggtgct cctgcccctt cacgtatacg gctatgggta tgttgtggct ggagcgtcct  18960
accttgatac caacacgttg gttggccacg atgaagccat gacggacata gacgaacttg  19020
cccttcagtg cggcgtacag cttgcccacg gagataccgg tcatgaaggc gatctgaagc  19080
tgaccgaggt cgttgtggta ggcgaactga accagcttgc cgtctgccag gaagtacagg  19140
cagcggtcga tgggaacatc gatggggtta ccacgctgaa accaggtgat cttctccatc  19200
acttcttctc cttcaccaga cggcgatgag ccttcgacag gttctcgcag gaacggagca  19260
ggaggtgcgg attgttgctc ttctggaagt tggagtactc ccgcatgacg gcatgaacca  19320
gggtgtccat ggtcagttca gcatcgctac ggcgctgctt gcgaaccttg tccttgagcc  19380
gctcgatttc cttcatggct tcggcgagct tcttctccag gccagtatcc accggctcga  19440
agactgtctc ttccgggatg atctcgggag ttccttccgg ctccacgggg aacggcttgg  19500
tgagtttggc gatcttcttg tcgcgtgctt cgatggccgc cttcagcttg ctgatctggg  19560
tttgcaggcg ataattatcg ctctgagcac gcgagtagat ccgacggtag ttcttggctt  19620
ccgagagtgt tgcgtctagc ttgttgttca gcacactgat gacctgatct ttgcgttgaa  19680
ctttctgatc acagtagctg gtcagatggg acatggcttc attgaaacgc ttgcgggaaa  19740
cgaatgggat catcggagtt ctccatctag atagacctga acgtacttac cgttcaaggt  19800
atatttgagt tgtaacgtgc tgccctcgta agcatcatga gagatgtaac gcaccctttc  19860
atagaggtag tacatgaggt cagcgactgc gaagttgtca gggtattttc tacgggctgc  19920
cctgtaccca acacgaaccc aatccattgc aaggacagat gcttggtgta acacactcct  19980
tgctactggt ttgttgcggt actgactgtc tctctccatg gcttcttcga caagcttgcg  20040
gagcatctca aggaactctt cctcttcgtc cccagcttg aaccgcttgc ctacgttgtc  20100
gatgagaaag tcgttctcca ttatgaaatt ggcgatgtcg tagtacatca catgctccgg  20160
tcgttcctcc gcctgacgga atctactcca ccaagaggtc tccccccgga gccaccacat  20220
tgcaccaaag gcccgtaatt ccgcttccaa gccctcggtg ctgtcgatgt gctcaaacga  20280
gtcatgaatg actgtcatgg gatctccagg ctcaaaggtg tgcatgccat ccatcagcca  20340
gccaccatcc tcgaaagtga aattacggac ctgcatggct tacgccctta cacgagcgtt  20400
cagcttctgg agttcctcgt agatgccgta gcccaggaac cagaaaccga aggtcatgcc  20460
gatacccacg gcggcgccca gcatcacgaa cagggcgacc aggccgttgt agacggtcag  20520
cgaggcgact gccacgacta cgaagaccag cacggcgacg atccaagcca tggtatccag  20580
gaacttcagg taagacttac gcatggtatt actccttctt caattgaatg aactcactgg  20640
aaatcagcga aaatgcaaaa agcgtacgga gtacgctcaa ccccgactct tcacaatgca  20700
gtctccatgt gcgtagaaga gatcacggta gaacttggga gaccctccgt acttccgtgc  20760
cctctcttcc gcactgggta ctagcactat tggcttacca cagtacttgc atgctctgtg  20820
cttactcatg gtttctaagc tcccctcaaa aaaataagcg cccgatccca tttctgggat  20880
```

```
caggcaaatt cgggttcatg gagcgtctgg aagacgcccc ataagctcaa gacagcgcat  20940
actcgctttc acggatcagt tcagacagat tgtggatcga ccggtcgtag ctgacatggc  21000
ttccagtgat ctggtgaacg atgtcgtcga ggatgttgct gtcggccagt tcggcgaaga  21060
tgttgatgta gtgctggcgc atctcgttgc agaagttcgg gtggcacttg aactcatcat  21120
gcacggtgac cagttcgaag ggctcgtgaa cccgcatggt gtcccacagg gcacacagag  21180
cctccaggtg gtcagtctcc agctgatgta cgttggtagc gttgatgtgg ttgaagatca  21240
ctgcatcgac catgttggtg cggtcgtaca ggtcttcgta gacggccagc ttggcgtcca  21300
gggtttcacc ggcttcacac tcaccagagt gacgatccat cagttcagcc caaaccaact  21360
gcattacctt ggtgatggct tcacggtcgt agttgcagcg acggtgcatg gaacgcagca  21420
cataggcgtc gatggagtgg atgacgttgg cagcattctt cacagcacgc tctacaccgc  21480
agtcctgctt gtagatgtac tcgaagcttg cccottccat ctcgtccact tccacccgag  21540
tctcgaacac gtctaccgac ttgacgatgg agtggaagtt gtccggcagc acccaggagt  21600
gcttcatggc atagggctgc caagtgttga tcaggtcatc ccgcatctcg ttggcgatgg  21660
gagctaccat ctccacgccc tggtagaaag cttccagttc aggagtgtct tcaccgaaca  21720
ggttcttcgg ctcagccttc gaaccgtaga agtgagtcat ggttgcagtc ttgatgtctg  21780
accgcttgat ctcccctacc gactcaccca ggtgggtaga ggcagcagtg gtgaccaggc  21840
tgtatgcatc ctgacggaag ccggtgttga tgaggttggt agcttgagca ccagactcac  21900
agccacccag ggcggacatg atctgcatgc cggagcagca ggcatccagc cctaccaggt  21960
gaccaacagg ctcaccacgc tggcagcac ggatggccat gacagccttg aggtactgag  22020
gacgggtctt ctcgttgcac tccagattct ccagatcgtc gaagttgtcg tagcaccatt  22080
ggatacgttg ttcgaagagc cacttgtcat ggcccatttg gtttgcagcg tcgatcagaa  22140
ggtattcgaa agcggtgtaa ggggtcatgg tttagttccc attaaacgaa ggttgattgg  22200
aatcaaagac cgtagatggt caacagtgct tgaagttctt tcggtatttc ctcggtataa  22260
gctacaggca tgtacttatt gaaagggttg tccttcctga agtgaaacca gtaagcagta  22320
tttctcctct ttgcggtcat tctgagaagc actaaatccc gcttatctgg tcctttcaga  22380
ccagcttggt aatatgcttg gtccgataca accctattca tctcatccgt gaacaggtgc  22440
cactcaccat tgtgaagcca tgcagctaca ttcattggtt agtaccctgc aagtagtgca  22500
atagcactgg gttctttaat catttcatct gatgcttcct tgccatatgc acgtccgtag  22560
gtggggtagt acttccacat aagccagtac tgaccatcat agaaggcggt cttcctcctg  22620
gtgaacacaa caggttcttt ttctttccgg tagagagtag cgagaccctc tgcaactctg  22680
tctacggtac cgtccaaagc cgggacagca tcatcagcaa acactctcca attgtcgccg  22740
tctttccaaa ccaccagttc catttacttg tcctcttcat tactgtgaat agaagtttca  22800
ctctagcagt tggtctaaac tccagatgac cagcattgct ctgaggtctg ctggcagaag  22860
attcacgtct tctatcgcat ccttatcagt catacccatc caccaccatc tgactccatt  22920
cagcttgtag caggtacacg ctgctgcttc ttttgggctg taggccatca ttgacgcagc  22980
ttgcacaagc tcaagcaatc cgccgtactt gacgaacttc catgtatcgt cttctttgta  23040
gaaggcatag tgactcactt gcttgctcct tcacttgatc ttcaagtgct ccggtacacc  23100
agtgactacc ttcttgttgg ccaagtcgag catggccttc ttgtaagggg atccctgggt  23160
gctgatgtgg tagccctgtg catacacacg gccacgcttg tcgtacttgt gcaggaggta  23220
```

```
gaaccgattg ccttgctgaa ccatgagctt atacatctca tgggactcag agacgaatct  23280
gtaccagtcg tctttcttgt cctgcgtatc caagtacttg tgggactctt cttctacggt  23340
gctcaagaac tcagtgttca ggcacagctc aacagcgttc atcttgtcca gcacatcgag  23400
acagatgtct tcgttgtgat ggttgttgtt caggatcagg gattccttct ccagtgtgag  23460
atgaagcttc gacttgttcc cagtgagctt ggatggtttg cacaccatag gaggaaggta  23520
catagctcgc tcaacagcat gttgaagctt ctccggtagt tgaatattag agatgacctt  23580
gtacgtaccg tacttgtaca cctgctcaat gtcgtacacg tcaagctctg ccagcactgc  23640
aaccatctca gcgatggtct tgatgctgtc agccttgtcg tcgaagccaa gtacaccagc  23700
tagcttggct gtgaagctga tgaacatgtc cggtacctga cagtacgcag acgctacgat  23760
gatctcgaac acaatgtgct caaggtccag gttacgaaca gtctccatac gaaggttctt  23820
ggagttgtag ctgtactcag tggtgcgata ctcctccagt agtgctattc cccgctccat  23880
cagtgcagga aggtcttcgt caccgcgaat gaactcacgg atgtacccgt caatgtgcgc  23940
ccgagcaaag cggtactcat tggcgcgttg catatcttcg ggcagcatgt gggtaatggt  24000
catggaacga ttccttaatc gaacagaagt gattgggcac ggatctctgg cggtactagt  24060
ttctctgcaa caggattgaa gtcactgctg aagacgaacc acctgccatt gtgcttggta  24120
tagagtttct tgaacggatc agtgtagctc ttgagtctac tcatcatcag accactagct  24180
acattggaaa ggtctttacg gaatacctct tctgtcaaac catcaaagat gtacagacag  24240
gactctcctt tacgcagaga gtcagatatc agcatcgtat tgaacttgcg ggccatgttt  24300
tgctccgctt cccgtatgcc caccattgta aacatgtcct tgttatgcgc attgatcctc  24360
atcgccaact acctccattg cactagagtg aagccatccc attagggacg gctccagatg  24420
gttacgttgc cggggagacg agccaagatg tccttgatca gccaccaagg ctcgttctgt  24480
cccggctgct ccaggtggta ctggtgggtt gggttctcct gtgcccgcca catcagctga  24540
gtggtgctgg tgctgacgca acccaggtca gtgggatcac ggtagtgacg cttgtcctgg  24600
aacacaccta ccttggattg gcagcggcac ccgaagatgc caccagcccc tccattctcg  24660
gcgatgtact gccccacgct ggtctgaata ccagcatcgt ggaagcgggc taccagttca  24720
gcagccatac cagcagtcat gactactgcc ccggtggagg tgagggtgct gttgctcagc  24780
acgatgaagt gatcagcctt gtcgaaggct tcccacatgt tccctactac gaactgtggc  24840
attacaggag atcccccatg cggatgattc catcacagca gtcaggggac tgcttggtca  24900
ggacgatgtg gttgttgacg tggctgtact ggaacatcca gcggtgcccg tcatcttggt  24960
cgatgacggt caactgcttg agcaggttct tcagcttcac ttcacgcagt gcgtcaatga  25020
gagtgtctcc gtccgaaacg aacatgccgt tgtcgtcacg gatcactaca cgcttcaggt  25080
aggtgcgggt catcattcat ttccccaata cttcgtggtt ggtttgagcc atggtttcca  25140
tgcctcgctg aaatagcagt tgtcgggtgc agcctgaaac agcggagcta tgtcactgtc  25200
atggaagcca gccagaccac agccaatgcg ggtcacctgg aagctcatgt agctgtgctc  25260
cttggcgaag tccatgaacc gttgtacggc cttggctacg tcactgatgt gacaggtgac  25320
cagcctccca ccgtgggccc tgtacttggt gggcagggca taggacatgc cagtcggccc  25380
ttcccctacg cccatttctg caccccttgtt gtttcgtgca tagagggcag caccagcacc  25440
atggatacca gcagtgttgc taccgaacac gaaaatcatg tgattggttt ccatcagttg  25500
aatcctccga acttgttgcg ggggcctttg cccaggtgat tggtttcatg gttacgcaca  25560
ggcatctccc acttggggcg acgcttggac ttcttcactg gcttgggaat ctggtccagc  25620
```

```
atgtgggcca tcacccgttc ttccagtgcg gtcatgtcta tgtacaccat gtcgatcttc  25680
ctgtcggaat acttgcgcac ttccagtagc ttgttcaggt agtcacggtc cacgaccaga  25740
cgcccagtta cagtaccccc ggtgggtgtt ttgaggtcgg ttggcatatc ggttctccag  25800
ccggaaactg ccgattccag acttttactt catagtcagt aaaccagctg agtttcattg  25860
gtttgatcgg aacggatggc tgggacagtc tcttcaactg acccaaacct atactctaaa  25920
aaaccagccc acaccctact caggatcgag ttagggtgtg ggcggacgct tttacaggtc  25980
cagctgaagt tcggacttgt cacgcacgac gcggaaggac aggatcaggc gcgagcgcag  26040
gttctcgatg cgcttggcca gatccttgtc gtccttggct tcggccaggt actcgtgcag  26100
ctgtgcttcg acggcttcgc tcaggcgcag cggaatgcca ttgcccaggc gaaccggatc  26160
accgccacgg gtgccgatgg agatgttgat gaagctggca gcacgggtgt cgtcggactg  26220
agcagcggtg ttggtacgag cgttggattt cttgagtgcc atgattcagg ttccttgtaa  26280
ggagaggtgg tagatacaga tcagaagtgg ttcggctcac atgagccatc acacaggcgt  26340
agcctgctct tgctcttaca cccagcgggg ttcgtcggac aggtcgttgt cccagtcagc  26400
ccagtggttc agcacgtctt cttcggtgac cgcagacata ccaatggcat gcagttcacg  26460
agcaacgctc tcagcgtcca ggcattcacg atagccacgg tcgaggatgg aggtagcttt  26520
gcgggtgatc agaacgatca tgatgaaatt cctaagtaaa cagtgagttg agatggtttg  26580
gattaccacc ccatggccgt aggccatgag tacttacagc agaccaacca agttgaagaa  26640
gatgcacact gccccgatca gggcgaacat cccggagaag gtcagtacgt gcatcacaag  26700
gatgtcgatc accagaccca tccaggtctg ttgcatggtg tagttgttgc tggaccactt  26760
catgtagccg ttcaggacgg ccacagacga agcgatgtaa aggcatagca ggttgaggat  26820
ctctacgtca gtcacagcag acctccagcg aggaagatga agaggggacc acagcctgcg  26880
aacagcaggc ccaggccaca gacagccatt acccatgcgt ggattctccg catctccagg  26940
tcatggcgtc gggagatact cagtggaaac ctgagcatct cgttgatcac ccattgcctg  27000
tgcaggccga tgaccagcat ggacagacct acagcgaaca gcaggaacat gatgaggatg  27060
atcacaggta agcccccacg acgaagaaga ggtaggcaca cacccaggta gccactccgt  27120
acaggacggt agctaccgca gcggtaccac ggttaccacg accagtctca caccgtaccc  27180
aggtctccgc agcccatacg agcatgcgga ggaaggacaa cacagtggga acgaccagca  27240
gcagtacggc gatgacggcc aacagttgaa cgatggtcat gatggactcc ttggttttac  27300
taggcgacgt ggaagaggaa gttgattgca gtgacccaga cagctgccca gaacacgttc  27360
cagacaagac ctactacggc agctaccttc tctgccccag gcagtacgaa cagtgcaccg  27420
aagcaggtca gagaggccag gcacttgacc aggaacaggt agccacagaa cacgatgagt  27480
acgatgcaag cgatagtgag catgggttag atctccaggg taaagggttt ggttttgaga  27540
cggttggtac aggcaccagg aaggtctttg ttgacctctg tccaatgcca gtgcttgagg  27600
ttgagccgac gacgctgaag gatcgcagtc ttcaggctct tggcggtgta ctcatcacca  27660
cacatgacta cgtgggtgag tacagtgttc gggcagtcca tgttgaacaa ggtcatccgt  27720
acacggaagc cagtcagctt tccattggta gggatgatct tgatgtcgaa gagacggcca  27780
gtgagattaa ggttggtgct cataggtgtt ccttttgatg aggtcgtagt aggcccaggc  27840
atagaactga acccagttct cttctgagtc gtccaagccc actcgttcca gtaagccgag  27900
tacagagtca gatccgcgga agtgcagttt ctcccacaac cagttcttga aggaccggta  27960
```

```
ctcatcccaa gtgattggag ggccaactac cactccattt gccaggtcac tcaggacgaa  28020
acacatgtag gtttcccctc tgttggcttg ttgccattcc aggccaatct tgatcagttc  28080
agcaatggtt ctcatggatc agatcctcac gtcagcaaag ccaatggggt cagcgggaca  28140
gccacgctca ttgcagaagt ctgcgaaggc ctggtccagc atgttccaga cacgctggaa  28200
ctcttccagg gattgtatgg gactgaagcc atgctggatc aacaggaaca gacactggtc  28260
atactggaaa tcccttgccc agcactggca cgcgatgtca taaacggtga tattacggac  28320
acgtttgata cgagcgtact tgtacatcat cagttgttct ccttggtttc ggtgaggtcc  28380
agacgagcaa tgaccacttc cacatcctct gccccttcat ggggaatgcg gtagaagatg  28440
cggatgtcct tgtcactggg actacagttg aaggtgatga agtgtctggc ttcaccgaaa  28500
gtacgaacac ggttggtttg atagttgaca ccatcacgag tgaagcctac gaagcagacg  28560
tgttcctgca tcttatggta gagagtgttc atactagtac cttcccgttg tgatcgaagc  28620
gagcaaggac tacctcacag ccttctgtct cagacatgta ggagagacgg atgcctgtgt  28680
cagttggctt gcagttgttg cggttgtagt cacgcatctc ttccaggttg tggatggtag  28740
gagatgtgat gagttctccg ttggtgacca tacgtacgaa acacttgttg acacggaaca  28800
cgctatgcgg attggacatc agaggaactc cagtcagaag ggatcaaagg tgattgcttc  28860
accttgagga tcagtgaggt agatgccaga ccagagtcct tcctgacctc tgcacatggc  28920
agttgccttg atacgagcaa cttcatcaga gacagcttcg aactcatgtt cgatggagtg  28980
gagacactcg ttggtgtaaa gcagggtgta gatgttctgg tccatggttg atacctatag  29040
aggactatga agtaagtaca gaatcgaata ccactccatc accgaaggtg tagaggaaca  29100
tcagacacta cccaagtgta gataggaaca cggtgtgtat cgtgtagatg gaaaagtgat  29160
gacaaggtat agggttgaga aaggtagaga gaagggtgaa agagatgaac attgagatga  29220
acagtgaatg tagagttgat gatagtgaat gcactgcacc atgccctatc tcccctatcc  29280
tcctacacac gagagatgag ttactgtcag gtgaagagtt aacaagagag agagagtatc  29340
ccttccttcc tacaacctac tgtccctgag agagaggtgt gtgatcttga tgtgtgttct  29400
tgatcttatg tgtgctttga aaaggtaacc tctactccgt acctggatag gtaaagagta  29460
gaggtagagg gttaagcctt ggccttggta cgttccttgc ggacggattc gacagcttcg  29520
gtgagacctt tctcctgaag ttcctgagcg ttctcgatgt tgagcaaagc gatggcttgt  29580
tcgcgttgca gacgagcctt gttgttgaag tgagcggact cttcttcagc ccactcggtt  29640
acgttctccg cagccttggt caggttggtg acagcacgga acatggactc cagcatagcg  29700
aagaattggt tgagagcttt gaacatggta gtactccaga gtagtgagaa tggttgtggt  29760
gacacaggat caatccacag cacagccgaa ggcttctctt gatctagaag tacagacaga  29820
tgattgggta gaagtagagt taaacaaggt ggggtaggta gcgcgggaat tccaaaactc  29880
tagaggtacc ggggggggata accggatttg gagagccgca gactgaagta ctgcatccat  29940
acttctatga tgaatttccc acaaacccaa atcacctccc ttactcccta agccaatccc  30000
tttccaccta gctcccataa cccatagctg aggttaagtc gccaagcacc gagcgcagcg  30060
aggtgagcag gatgactggt ccgaagctat gggttatgga tacctgtgga tatctatagt  30120
caagttatcc acaggatata cacaccctag tctttacctt ggatgtagca gcctatctct  30180
ctccacgcat ccttccagtc cctgtgcttg actggtgata cgtaggctaa gccagtctct  30240
gtgtgagtgg ctacaccagt gaacaagcca gtagctgcaa accaatagag ttccagtctg  30300
tggtttcttg ctcgatcact catgaccagt acaccaagac cgccgctcat tacagtaggt  30360
```

```
gtcttcaccc aatcccttgc atcacgtaag acaggatcga agtctgcatc catgaaggta  30420
ctctccattc tgagtgtcgt acctcggatg gtacctaccc agtagaacaa gccatccttc  30480
ttaacgatat cagcctgctt acgagaacca cgactggcaa ccctgcacag gaaactctcc  30540
ctgttctctt cagtagaggt agccttaagc ttgtcctcca gttcttttac cttggcttcc  30600
agttcagcta tcttcttctc tgctgggttg ttaggtacta catcaaacag ttcagcgtac  30660
tcagccagct tgacgtaaac caagccagtg ttgtcatctc ctgcattgtt gatgtactca  30720
tgccaggaga taccaaggtc gatctctacc agttcttgcc ctggtagttt gatgttcagt  30780
actgctttgt tgttcattga gtctaagcct cgcgcgcgtt gaggtggggg agtagggaag  30840
cctcgcgcct gcggcccgag tcaaccccga gcggagcgag gggttgacga gggtaattcc  30900
tcgtggtacc cttggtatta ctcacccacg gggattacc tatatattat atagggagta  30960
gaaggaggct ttagggcctc cttttttgt gcctggaata ctaccgttgg tcgggaagat  31020
gaccgatggt tacacccggt gggtaccgga aggtaggggt agcctgcttc ttcagacggg  31080
atacctccag ttccagttca tggatcttgt gtttgaggat gtccgattcc gaggaaggca  31140
tctggggacg gatgctcacc gaagccagta cccattcgtt catgtacttg gtcttctgcg  31200
cgtcggtcat ggtgtcccat tcatccctgg tgagaagggc atcaaggtag taagccttgc  31260
cttggatggt gaggacaatg cgaatcttgc ccgtgtcgtt tagttccata aaagctccag  31320
tagcatcatg gctccgtaca ggttcatcgg taccatgggt gcgaagataa agaaggcgaa  31380
gacaggcttc tccttccatt cgggtgagta cctggtcacg tctatcgccg tccacagcag  31440
gagggcgaag aggaagtgca acaggtggaa tagccagagg tgttcctcac ttgctggctt  31500
gggtacgtac aaggaccaga ccagagcgaa gatcaggttg gacacccagt ctgctttcat  31560
tggtttggcc ccgcagtgaa gagtactcgt gagtgagtga cgttcagaac agagatgcca  31620
gtccctctgc gtaccagatt gaggatctga gctacagtgg agtagaagtc atcctgcact  31680
tcactgagag agtaggggat ctctaccttg tgagaggtag tcttcccgtt cttcagcttc  31740
atctgtacat gtgcatagct gatgtccatt acagcttacc ttcctggagt tggtggatgc  31800
cgtagctgta gagaagctca gctactttct ccgactgctc gtatcccttg ttacggagca  31860
tcactgtcat ctcttctacc tgcaccagct tgagtacacg atcaaccggg cactctgcat  31920
agcagagatg gttggggtct accagggcat ggaagaggtc gccgtcttca ttgatactgt  31980
ggactgcgat cagagggatg ttccccttct cggtgtactg gatgcacaga cccatgacga  32040
tcacttggct tcctgcaccg agggccagtt ttcttccagt gtccgggttg tgagtgaggg  32100
tgtccctcaa aaggaatacc ttggtgccac actccactcg tgcgttacgg gacatgagtt  32160
ccccgttcac gatgtggcgg gcatagggtt ctagttgcat ggtttactcc ttggtttgta  32220
cgttgtgtta tcctcggcac aacctataga caaccgaggt actaagatga ctaccacccc  32280
cgccactact gctcagcctg ggatgttgac ggtagatgag ttccgctctg tgctacctga  32340
caagatgaag aagtccatct ccccggaagt actgaagaca ctcaatgaca tgctgtccga  32400
tcctgacatg gcggaagcct tcagggacaa catcattggg tacacccatg tgatgaagga  32460
aggtaagttc aagctggaca actacctcca tgcttcgaag tacgtgacct ataagctgat  32520
ggggttgaac aacaccgagg cttacacccg taccttcccc accaagatcc agcggtggac  32580
ccaacagggt gtggccaaca aggacatggc cagctacatc accagctaca acaagtcgaa  32640
gctggtgaac ctcatcctgg aacaggcact gatcccatgc catgtgctca atgctgacat  32700
```

```
caagcagaag gcgatcaacc atctgttcca cctgatgcag aacgctcagt cggagaaggt  32760
tcagcaggag tcggccaaca gtctgctcac tcacctgaag tcgccggaga agacggagct  32820
gaagatagat gtcagtgatc gtgcagcaga tgccatcgac atcatgcggc aaaacgctga  32880
agcactggca cgtctccagc aggagatgat cgcgggcaag cagctgtcgg cgaaggatgt  32940
agctgaacgc agcatggact tcggtgaagt catcgaaggg gagcttgcct aatgaacttg  33000
gacgccacac caatagcgaa agctgttgca gatgaggtgg acttcgctgg cttggatgaa  33060
gccgccaagt ctgtagagca atggcttcgt gaagtagtct atggggatga ctcttcgtac  33120
atccccagca tctttgcctt gcagttcgtt gacttcatca agatggtcaa cggtaacgaa  33180
ggggaagaga acaagacacc agtgcttcac ctacggatgc ttgaccagat tggctctggc  33240
cagactcgga tcgccaacat ggtgttccgt ggtgcagcca agactaccgt gatgggtgag  33300
tacctgttcc tgtacattgc actgtacggt gagcttcctg gtttcggtaa ggtagacctt  33360
gctctgtacg tgtcggactc catcgacaac ggtgtgaaga acatgcgtaa gaacctggag  33420
ttccgctggg agaactccga gttcctgaag aagtacatcc ctcaaaccaa cttcactgac  33480
atccgctgga agttcacgaa cctggacggg aaggtcttca tcgtcaaggg ctacggtgcc  33540
aagactggtg tccgtggtgc gaaggagatg ggtaaacgtc cccagcttgc ggtactggat  33600
gacttggttt cggacgaaga tgctcgctcg ccaaccgtca tcgcagccat cgaagacacg  33660
gtgtacaagg cagtggacta cgcactgcac ccgaagaaga acatgatcat ctggtcgggt  33720
acaccgttca acgcgaagga tccactgtac aaagcagtgg agtctggtgc ctggaaggtc  33780
aacgtctacc ctgtgtgcga gagattcccg tgctcacggg aagagttcag gggtgcatgg  33840
gctgaccgat tcacctacga cttcgtgttg cagaagtaca ccctggccaa gaaggcaggg  33900
aagatcgata cattcaacca agagcttatg ctccagatca tgtccgacga agaccgtctc  33960
atccaggatg gtgaggtggc ttggtacatg cggcgcaacg tactggacaa caagaagcgg  34020
tacaacttct acatcaccac tgacttcgct acctctgcga agaaggcgag tgacttcagt  34080
gtgatcagtg tctgggctta ctcccacaac gaagactggc tgtgggtgga tggaatctgt  34140
gaacgccaag acatgggagc gaacctggat gatctcttcc ggttgtgtgc caagtggcgt  34200
ccacttggag taggcatcga agtctccgga cagcagggcg ggtacatccc actgatacag  34260
cgggagatgg tgaacaagga tgtctacttt cacatggttt cggagaaggg tagtagcact  34320
cctggcttgc gccctacgac caacaagctg gagcggttca tggccatggt tcctcatttc  34380
aagcgaggga agatgttctt cccttacgac atgaagagca cacggtgcat ggtagagttc  34440
gaagacgaga ttcgtttggc ttcagccggt ggcttcagat ccaagcacga cgacttcctc  34500
gacaccatct ctatgctggc tttgatgaat ccaatccctc caagccaaga gatccgcatg  34560
gagtacaatg acagcgagat gatctgggaa gaagcgtctc aacgagagaa cacctaccaa  34620
gcaggggaga gctacatcgt atgacaatcc aactcaagca ggtcattgac ctgctagcag  34680
agggggaact cagcaacatc aagtacgtga acatcgacac tggtgctctc gtactggagc  34740
gagttccttc gctgattcgt gcaatcaacc ttggagtact ggacctgcac aagaggttcc  34800
tgctcaagga aggtatgctg aagatccaac tggaagaagg tcggaggttg tatcctctac  34860
gtcctgcata ccaagtggga cagaagccaa agcctggagt accccagttc atcactgatg  34920
ggaacaagct gggcagacag tccatcctga agatcgagaa gatcatcggg gacaatggag  34980
tggagtacta cctcaacgat acctggcagc cgctcaacat cactactcct gagttcgatg  35040
tactggagat cagtgaagag ttctactgtc attcgtcgag caagactctg gaagtacggt  35100
```

```
accgtcgtgc acctacaccg atgaagatct gtgtggacaa cctggacagt tggggttgca  35160
tcgatattga tttgccttat actcacctcc aagctctgct gtactttgtt gcttcacgtt  35220
gccagactcc gattggcttc atggagaaca ctgcacaaga tgggttcaac ttctcgcaga  35280
agtacgaagc agagtgtgcg aatctggacg cacagaactt gcgtatcgat ccggtaggaa  35340
accaggaccg attcacaagg ggaggttggg tgtaagggtg aggggaccag gacggtcccc  35400
tctttttta tgcctggatt tccttgaagc ggacagcgcc gacttcagcg gaccagcctt  35460
cgatggaacc ttcttcgttg acgaagatcc attcgccggc cttcacgtcc agggtggcac  35520
cctcgttgaa gttgctgagg gagtagacac gttcgccatc agcgttgtcg ccgaaggctg  35580
ccgtgatgaa ggggaacgag ccgagcatct cttgcagtgc ctggacgttc tgctcgtggt  35640
cttcacttac ctgccagccc ttgaacttga ggggctgggc gtgttcgtac tctttgatca  35700
gttgcatggg ttattcccca gtagagccga agccgccgtc accacgattg gtttcggaca  35760
gttcttcgac gagttgaagt tcgggagtag ctaccggaac cagaagcatc tgaagcacac  35820
ggttaccggc ttcccagtgg aatggttcgc ggtcggtgga gactacagct acccactccc  35880
cacgatagtc ggagtcgatc actccgcagg tgttacgcag gcgaagacct gctttacttc  35940
ccgtacccga gcgaggcagc agcagggcta catgcccttc cggtacagca gcagagaaac  36000
ccagctttac cttggttggt tggtttggat aagccacccc accctccggc atgaagatgt  36060
cataccctcc tgcggtatca ctggcacgca cgggcatggt aaagttcggg ctcagttgtt  36120
taatttccaa gattcttacc tcattggttt gaaagagagt aactatggca gacgtggacg  36180
aagattacct gacccttccc aacgaggatg gggatcccag taagcgactc cagcctgagt  36240
ggagcaatgc tccctcactg gctcagctga agcaagacta ccaggaggcg aagcaggtca  36300
ccgacgagaa gatcactcag atcaatcgtt ggctcgacta catgcacgtc cgtggtgaag  36360
gaaagcctaa gacagagaag ggtaagtccg ctgtgcaacc tccgactatt cggaagcaag  36420
cagagtggcg atactcgtct ctgtctgaac ctttcctatc cagccccaac atcttcgaag  36480
tgaacccggt cacctgggaa gatgctgagt ctgcaaggca gaacggtctg gtactgaacc  36540
agcagttcaa taccaagctg aacaagcagc ggttcatcga cgagtacgtt cgtgctggtg  36600
tggacgaagg tactatcatc gtgaaggtag gttggaacta ccagtcccga acggtgaaag  36660
agcaggtagt cacctacgag atgatgccgg acagttccga ggaactggct cagatctacc  36720
agaccgcagc acagatccgg gaagagagtc cttcggagta cccggagatc cccgaggatg  36780
ttcgtcttgg tttggaagag acggaagcca acggtatcca ggtacgggca gtgcctgttg  36840
gttcggaaga agaagagcgg gaagagacgg tggaaaacca tcccactgcc caggtgtgtg  36900
actacaacaa catagtcatc gacccttcct gtggtagcga cttcagcaag gcgaagttcc  36960
tcatcgaaac cttcgagagt tcctacgctg aactgaaggc tgatggccgg tacaagaacc  37020
tggacaagat ccaggtggaa ggtcagaacc ttctatccga accggactac accggacctt  37080
ccgaaggtgt acgcaacttc gacttccagg acaagagccg taagcgtctc gtggttcacg  37140
agtactgggg ctactacgac atccatggtg acggagtact gcatcccatc gtagctacat  37200
gggttggtgc tgtgatgatt cggatggaag agaacccctt ccccgataag aagatcccat  37260
acgtggtggt cagctacatc ccacggaagc gtgacctcta cggtgagagc gatggtgctc  37320
tgctcatcga caaccagcgg atcatcggtg ctgtcacccg agggatgatc gacactatgg  37380
ctcgttcggc caatggccaa gtcggtgtga tgaaaggtgc acttgacgta accaaccgtc  37440
```

```
gccgcttcga ccggggtgag aactacgagt tcaacccagg tgcagatcca cgggctgctg  37500
tgcacatgca caccttccca gagatcccgc agtccgctca gtacatgatc aacctgcaac  37560
aagcagaagc tgaatccatg actggcgtga aggctttcaa cgctggcatc tctggtgctg  37620
cactcggtga caccgctact gctgtacgtg gtgcattgga tgctgcatcg aagcgtgagc  37680
ttggaatcct tcgccgtctc tcggctggca tcatcgagat cgggcggaag atcatcgcca  37740
tgaacgctga gttcctggac gatgtggaag tggtacggat caccaatgag cacttcgtgg  37800
atatccgcag ggatgacctt gctggtaact tcgacctcaa gctggacatc tccactgctg  37860
aagaggacaa cgccaaggtc aatgacctga ccttcatgct gcaaaccatg ggaccgaaca  37920
tggacccgat gctggctcag cagataatgg gtcagatcat ggaactgaag aagatgccgg  37980
acttcgccaa gcgtatccgt gagttccagc ctcagcctga tcccattgca cagcagaagg  38040
cacagcttga actcatgctg ctccaggcac agatcgaagc tgaacgtgca cgcgctgcta  38100
actacatgtc tggtgctggc ttgcaggatt cgaaggttgg tactgaacaa gccaaggctc  38160
gtgctcttgc tagccaggct gacatgaccg atctgaactt cctggaacag gagtccggtg  38220
tacagcaggc acgcaagcgt gaactgcaac aggcacagtc tgaagcacag ggtaagttgg  38280
ccatgctgaa cagccaactg aagcgactcg atgaagctac ttcagcaagg acttcccaaa  38340
agtagttaac ttcactatag ttggttcacc tttacggtga accaacaccc ctttacttga  38400
caggatttgc aaagatgaac gaagaacacg ctattcagat cacccggaag aacgctgaga  38460
agttcgtccg gctgcgtgac gcaatgctgc gtttgcacaa gaaccgggac ttccaggcgc  38520
tgatcctcaa tgacttcctc aaggacaacg ctgcacgtct ggtcctgctc aaggcggaca  38580
agaacatgga atccccggag atgcaggcac gcatcatccg cgagatcgat gcggtaggtg  38640
ctctgcacac ctacttccaa ctgatcggcg tacgtggtga cgaagctgaa caggccatca  38700
aggactgtga cgctgaactc gaacgtgtac gcgaagagga ggatgaagag taatggctga  38760
cttcctcgaa atgagtgacg acgatctgcc cgagttctac gaagtagaag agcagactcg  38820
ctccgatcaa gaagaacccg aacaggaaca acagaacgac gagcagtcgg aagaagttgt  38880
tcaggaagaa gaacctgctg acgaagagca ggaagaagaa caggaggagg aacaagatcc  38940
tctcaactcg ccggacgatg aactcggcga tcttcctgta gaagagaaac cgacggaaga  39000
agagtcggag caggaagaag aagaagaaga cggcgacaag gaagagtcgg aagaaactcc  39060
gactgaagaa aaacctgaag ccaagaagtc cgaggctacc aagcaagagg tagatcctgc  39120
tgacttcatg gcgaagatca ctgcaccatt caaagcgaat ggccgtgatc tccaggtcaa  39180
gacgccggaa gaggctatcc gtctgatgca gatgggtgct aactacaacc acaagatgtc  39240
cgcgctcaag ccgaacctgc acatgatgcg tcagttggat gatgctggtt tgctgaaccc  39300
ggatactatc gccaatgtgg tcgatcttct caaacacaag aaacctgaag ccatcgctaa  39360
gttggctaaa gatgccggtg tagatccgct agacttggat gagaagagtg ttgcggatta  39420
caaaccgact gctgtaccat tcaaccaagt tcgtgaggca ctggacgaac aactcgattc  39480
catcgagcat agtccatcct acaaccgagt ggttactacg ctgggtaagt tggataaaac  39540
ttctcagaag ttggtttccg aacatcctca agtcatcggc tacttcgaac agcacatgac  39600
caatggggta ttcgaccgaa tcgactccga gatccagcgc cgtaaggcat tcggcacgat  39660
cactgatagt accccgtacc tgcacgcata taaggcggtt ggggatgagc ttcaggctca  39720
aggtgcattc gacgatttgg ctcaagcctc ggccactgaa agccaacgta aagcacccgc  39780
tgaaccggtg aagcgagtca ccacccgcac caaggcacag gaagcggctg tgaaagaaaa  39840
```

```
acgtcgggct gctgctccga ccaaaactgt agctggaaag gctaagcctg cccagttcga  39900
tcccctagcg atgtcggacg aagagttcga gaagctgggc ttcaactaag caatccctga  39960
aactggaata aggaaaacat ctcatggccg gtcctgtaga taacatcaag ccgatgaagt  40020
acaacgaccc cgcgaacggg gtagagtctt ccatcggtcc ccagatccat acccgctact  40080
ggtacaagcg cgcgctcatc gacgccgcca aggaagcgta cttcggtcag ctggccgata  40140
ccttctcgat gccgaagcac tacggcaaag agatcgtgcg actgcactac atcccgctgc  40200
tcgacgaccg caacgtgaac gaccaggcca tcgacgcttc cggcgctacc atcgccaacg  40260
gcaacctcta cggttcgagc cgtgacgtgg gcaacatcac tgcgaaaatg ccgaccctca  40320
ccgaaatcgg cggtcgtgtg aaccgtgttg gtttcaagcg tgtcgagatc aagggcaagc  40380
tggagaagta cggcttcttc cgcgagtaca cccaagagca actcgacttc gacagcgatc  40440
cggcgatgga aggtcacgtc accaccgaaa tggtgaaggg cgcgaacgag atcaccgaag  40500
acctgctaca gatcgacctg ctcaactcgg ctggcaccgt ccgttatccg ggcgctgcaa  40560
cctccgacgc tgaagtcgat gcttccaccg aggtcaccta tgactcgctg atgcgtctgc  40620
gtctggacct ggacaacgcg cgtgctccga ccaagatcaa gatgatcacc ggtacccgca  40680
tgatcgacac ccgtaccgtg ggcaacgccc gtgctctgta cgttggttcc gatctggttc  40740
cgaccatcga agccatgaag gacaaccacg gcaatccggc cttcatcccc atcgagaagt  40800
acgctgccgg tggtgccacc atgcatggtg aagtcggtca gctgggccgc ttccgtgtca  40860
tcgtcaaccc gcagatgatg cactgggccg gcgtcggcaa ggctgtcgat ccgaacgacc  40920
aggttccgat gcatgagtcc ggcggtaagt acagcgtctt cccgatgctg tgcgtggctt  40980
ccgaggcgtt caccactgtc ggtttcgcta ccgatggcaa gaacgtcaag ttcaagatca  41040
tcaccaagcg tcctggcgaa gccactgccg accgcagtga cccgtacggc gagatgggct  41100
tcatgtccat caagtggtac tacggcttca tggtgttccg ccccgagtgg atcgccctgc  41160
tgaagaccgt ggcacgcctg taactaggca tgggggaggg taacctcccc ctcttaactc  41220
ttaccctgga gaatcaccca tgtccctcga cgaactgcaa aacctgagtg aagcaccgct  41280
ggaatccccg gatacccgtt ccgagttgga agtcctgcaa gaaaaagcta ctgcccttgg  41340
catctccttc cgctccaata ccggcgtgga aaagctgcgt gaaaagatca atgccgtcct  41400
gaacgacgaa gctgtcggcg acgaggaaga agacgaagcc accgaagcta cctcgtccat  41460
cccgaagccg tccgccgaag ctggtgcagc tgccctcaag gccgccgaag caccgcgtcc  41520
gaagaccgag ggtgaactgc gtcgtgatcg ccggctggct gcgcatcgtc tgatccgctg  41580
ccgcatcacc tgccacaacc cgaacaagaa cgactgggat gccgagtact tcagcatcgg  41640
caacgacgag atcggtacga tccgccgtct ggttccgtac gaggtggact ggcatgtgcc  41700
ggaagccctg ctgaacttca tcaaatccaa gcagtaccag cacttctaca cggttaccga  41760
gcagaccccg atgggtccgc agaaggtacg ccggtcgaag tcggtacgtg aattctccgt  41820
ggagatcctg ccgcagctga gcgaggatga actcgaatcc ctccgcaagc agcaggcagt  41880
aaacggttcc tacaaggagg actaagccat ggccgtagag ccaattacca ttgccgacct  41940
cactgaggtc aagctagacg gtaagggtgc tctcgaccaa ctcctgcaag tcacccgcct  42000
gcatctggcc aaagagcacg atgcagggcg gttgaagggg caggagtacg cagctgttct  42060
cactggtggc atcacggctg ttcttcagaa cgccgtgatg tttttgcttc agaaggatga  42120
agccgccaac aaggctgcac tggtcgaagc acagatcaag ctcaccgaga agcaaggtga  42180
```

-continued

```
gttgctggac aagcagatcg cacaagctga caaagacgct gagcttatcg ctgccaaggt  42240
caaactgacc ctggaacaag cgaagctgcc ggattctcag attcgttctg ctggcttcca  42300
ggatcttctg gttcaggaac agaccaaggt acagactgca cagactcgtc ggatcgacca  42360
agagatcctg tctgctggtt tccaagacct gcttgtgaaa gagcagactg cgaagaccaa  42420
gcaagacgta ctgactgctg tccaacagac caaggtcatg gaacagcagg tactggagtc  42480
cactcagaaa gtcctgaaca tgaagcagga actcttgaac ctcgtggctc aggaatgctt  42540
gctgaaggct cagttcgatc tgaccaagga ccaaggtctg aacacccagg agcagaccat  42600
tctggtacgc cagaaggtag cttccgaacg tgcccaaacc atcggtgctg gtgtggatgc  42660
cgactctgtg atcggtcgcc agaaggagtt gtacaaggct caggctgatg gcttcaagcg  42720
tgacgctgag cagaaggctg ccaagatcct gatcgatacc tggaacgtac gccgtaccac  42780
tgataccggt actcaagcca acaccaccaa ccggctggac gatgccaacg tcgggcgggt  42840
agtgaacatg ctgatgactg gtgtcggtgc ctaaacagcg tgctgtacac taaggggaac  42900
ttcggttccc cttttttat tggaggacag catgggtctg ttcagtagca agaagaagac  42960
tgtggtgaac actacagtgc aacgagtgtt cgatgatgca cacatcccgg actctcctcg  43020
tactggtgtg atccagggga tcactcacga gactgggatc gtcgagaaca tcctagagaa  43080
gctgtccgac tccattggag tacgggcgaa tactgcctac ctgtgggcac agcggaacaa  43140
ctactactgg ggcttgccag agtccaaggt agtgaatggt gtggatgctc gtactgtagt  43200
ggttcaaacc atcgcacgaa gcgaaggtac gatcaccacc tactacaacc agttcggtcc  43260
gctgaactcc ctgcactggg gattcactga attggtgcgg ctgtaccagt acaacccact  43320
gaccaatgaa ctgcctggac tcagcaccac gaagggttcg aaggtctacc tgttcgacat  43380
gatccctgtc ttccagaccg acactgtggc atgggcagac gagacagcga acaagggcat  43440
gcttcaggat tttggtttca gtccgaagtc tgggtacacg ccaagccgtc cgtacaacac  43500
cattggggga atgggtcagt tcgccgggtg gtcaccctat cggacagaca actctttcgg  43560
tgaggactac gttctactga cctacgaatg gaaggatgcc caggggggtca tcaagcagga  43620
aaccattcgc atgatcatga acctggacct gtccctggat taccatcagg ttcggttccg  43680
taggcagaat ggaacccagg gattcttcac ctaccaggac ggcaagggaa cctatccgct  43740
aatcgatgga gtgtttaacc tcgactacac caagcagggt acctactacc cgtggatgta  43800
ctgccgcttc aacaagatga acgtgaagga catcccaggc aatgcctaca gggatgtgaa  43860
ggaagtggcc aagatctctg gcattgggat cgacgagctt atcgatgggg ttcatgctga  43920
ccctgacatc ggtgacgtgg ctcaggtagt actgttctac ggtgtgccac caggtgccac  43980
gaaccaggac cagctgacct atatcttcga gtacctgttg ctgctccact cggaggcatt  44040
ggctcagatc cagaaggcag agaacctcca gggcaagcta ggggattact ccaacacggc  44100
tgaccagatg atcaccatgc gggacaagta cttcaagatg gacttctcct tcagcggtat  44160
cacggtaaac cgtaagtccg ggaaggttgg tcctattggt ttcatcaatg tgaagtctgg  44220
tatggccgac aagtcctctg gacagatcaa gacccagcag ccggcgtata cctacacccg  44280
tcaggccatg gactccatgt acgacgaggt gatcatctac aacccggcaa tgcactacca  44340
gatcaccagc aagaaagggc acgtagccca actgggtcaa cctgaactgc tgatccctgt  44400
ggaccgagta gtactcagtc agcttggctt gagggcacag gaacaactcc tgtgccgtag  44460
cctgcacatg gcgatcaaca cccaggtaca gatcaagacc ccttggtatg ccagtggctt  44520
cttcaaggtg atcctgattg tggtgtctgt ggcagtcacc atcttcacag ctggtagtgc  44580
```

```
ctggggaacc atcgtcgcag cagcctccct cggagtggct gctctgacca tggtgatcgt  44640
acagatgatc gttactaccc tggccgtcag ctacggtgtg aagctgtttg tccgtgctgt  44700
tgggcctgag ttgggtatcc tggctgcggt agctgccctg gctgttggtg cctacgggat  44760
gtccaataac gctacctgga gcgagaacct catggcagtg agccatggta tcgccaagga  44820
atcgcagacc atggaacaag ctggtctgat ggatactttg aaggaactgg aacggaacca  44880
gacgtactac gctgaccaac tccagagtct ggaagaccaa cgtcgtgaac ttggtttggt  44940
tcagttccaa gcacttcagg gtgaagactt cgtgaaccgt ccgctgacta tcctgggtga  45000
aagtactgat gacttcttct ccagaactgt acatgcgggg aacattgggg ctgcaagctt  45060
ccaactgacg gaatacttcg tagatgctaa gctacagctt ccttccataa acgaaaccat  45120
agaggaaatc aacaatggcc tatccgtaca gtgatatgcc tttcggagtc gagctggaca  45180
cttccactct cggttccttt ggcttgggtg gtccccaaac tcaactacag atgcagatgc  45240
ctgctgtaga cgtgaacgct gctgcctctg gtagtggtgg tttcatgtct ggcttcagca  45300
acatcttcag ccgtgattcc atgttcggtg gtgtagctcc gagcggtgct caaaccggtg  45360
gctgggtgat gcctgccctg ggcattggcc aagctgtctt cggtgccatt ggtgccaacc  45420
gacagcagcg tgctgcacgg gatcagctgg cagagtctcg ccgtcagttc gacatgaact  45480
atggtgctca acgccagtcg atcaatacca acctggaaga ccggcagcgt gcccgagtgg  45540
catccaaccc cacggcctat gagtctgtgg attcctacat ggaacggaac cggattcgct  45600
aatggcccaa gagatcactt ggcgtaacat tggtgcaacg gtaagtcctg gcagtgcatc  45660
ttcgatgtct gctgggacta ccggtgtcca acaagcactt ggtgcactgg gtgacatcat  45720
ctcccgtcaa caggagatga atgtcaacaa tgccaagttg cagcgtgaag ccaacacgca  45780
aagctatctg gaccaggtgg cagcatccac cctggaacaa ctcagcaacg cagactatcg  45840
cagtggactg gaggcccaac gtgatgcgat ggggatgaac ctggatcgtg ctgctactcg  45900
tgatgcgatc accaagcaga tcagtgctca gcagaaccaa gcggctgcta ctcagaagtt  45960
cgacgacatg caggctgagg taggtcaacg aggcatcgta gatcagcttc gtaccctggc  46020
agctgaaggc cgtgctggtg aagtcaacca gatcttggct gagcaacagc tgatcaacga  46080
gggcgagatc cgcaaggaac tcactggtgt gcaagatgct atccagaatc ggcagtaccg  46140
ggcagctggt gaacagcgtg cacaggcagc ggccaaccgg gcagctgaag cacactccct  46200
ctccatggct gctggtcggg agaacctggc tttcactcgt gagcagcgtg atgaactacg  46260
ccgtgatcgg gatgaagcga agctggtttc gggaaccatc gctactacct tccaggacta  46320
cgacgagtcc cgccaggctc agagcgagat catgcggatc gtgggcaagg aagtcggtat  46380
gcctaccgat gaccagggca tgcccgacat gagccgtgct tcgcaagacc agcttgatgc  46440
cttcagcaat gcgctgaacg aagctggtgt acaagccaat acctctccta ccgagcggcg  46500
gaatgctgca ctcaagtctc tcgtggatgc aggggtaagc tcgaagggta tcgcccaggc  46560
caagcaagag atggaactcc gggaatccct ggagggtatg gctccgcaag atcgcacgaa  46620
ggttgaagca accatcggtg cggttaacgc agaactggat accctgcaac ggacggctac  46680
cgaggactac gaacgggaag ttgcacgtaa cccgtttgtc gagcctgaca aggatccgct  46740
gggttcggtc aacaagatcg tagacaaggc tgtgaagtct ggtttcggct gggaaggtga  46800
ccgccaggat ctgaacaaca tgctcgtgga cttcgccacc aatggcatca agctgccgga  46860
cggacgtact gctgtagtcc cgtcgaagct actggagcag gcgttcaaca ccacgaacac  46920
```

```
ttggctgttc aagaatgccg gtgacgtgga gaaacggatc atcgaactca tgaccactga  46980
tggcatgact aagatgcgag aagacgctcc gaccattcgg gaaaacttcc tgaaaaccgt  47040
gtcggacatc gccaaccaaa aacggtcaaa tgccgttaag gtaactcgct cgtcagaacg  47100
ggaaaagggt gttaccatgg acccaaccga tgatctaact tttgcactac gagggaggaa  47160
acgatagatg gctgatttcg acttggatca attcctgtcg gatcgtcaag aggcgaatgc  47220
cggggctacc ccggcattcg acgctctgga ctttgccagt gcgggcctgg acatgaaggg  47280
ttcgcagaag gcttacgacc tcgacggcat ccgcgagcgc aagaagcgca acgtggaaga  47340
atccctcatc ggcaagatgg gtatcacccc cggtgctgct ggcactgaga tcctcaacac  47400
tgctgcttcc ttcgtatccg gtactggccg tgctctaggc gacgtgattg ctctgccgat  47460
caacgctgct gctgacatgg gccaggctgg tgtaaccaac gaagccatcg aagcctacaa  47520
ccgctacgtc tccgcccaga tgcaggaagg tgatgaagcc atcctgagcc agactgctgc  47580
cggtgacgac ggtgttcccc agaccatgct gcaacgtatg caaggtgtgg atgaactccg  47640
caagttttct acaaacgtgg acaagttctt cgactggtcg agcatcgtag acactactcg  47700
ccgtgaccaa ctgagcgacg acatcgctga tgcgactgct ggtggcgtag aacgtctccg  47760
caatgcaggc gagtccttca gccgtggcga gattctggat ggcttggtac aaggtgcact  47820
cggtgtcggc cagaccgctg ctaccgctat cggtgcatcg gcaaccaacc cgctggcagt  47880
cggcgagtac actgtggaaa acgctccgca gattctggcc tatgccgcta accctgtgct  47940
gggtgctgct accaccgtgg gctacgcctc ggatgaatac cgtgaaggca tcaccgagta  48000
tcaggccgag aaccaaggcc aactgccgga tgctgacgat cgtctgaaga tgggtcttgc  48060
tgctgcttca ctggcggtag ctgagcaggt agccaattct ggcatcctgc gtggtatccg  48120
tggtgaaggt ggtggtttga tccgctctac tcttggttcc agtgctcgtg aaggcgtgac  48180
cgagggttac cagacctggg gtgagaacgt tgctcacctg aaagacacca gtctggaaga  48240
gatcgtcgaa gccgcaacca ttggtgctgc tgtcggcgga accatgaaca tcggtggccg  48300
tgctgctgta ggtgcccgct ctggtgctac ccgtgctgag gctgctttgg cttcgcgtga  48360
agctgtgaat gctgcccgtg aatccggcga catctctgcc ctgaccgatg tgacctcgga  48420
gtcttataac cctgctggtg cagtggtagt tctccaggaa caagtcatgg ctgatggtgt  48480
gacccaagag gtcaaggacc gtgccctgga gcaggctgac accatcgagc aggaagctgc  48540
ccagcgtgta tcccagctgg agcaggaaca agtcctgttc agtgaagaag gtctggccaa  48600
ggtagagcaa gccatcgaac aacgtgagca ggccaagcaa ggtgctgatg aagctaccgt  48660
tgcccgcctg gatgaagaac tggccaacct gagcggcgtg cgtgagcaga tccgcaacat  48720
cactcctgag cagcgtcagg ctcaagccaa ggaactgaag gatgcccagc aagtactgac  48780
cgctactcgt gacgccatca agcgtttcca ggtggaagcc gctccgaagg ctgccgaggt  48840
agagactctg gttcaggaag ctgctgtcca gccggaagcc tccgagcgtc tggtcaccct  48900
gaccatgatc aacccggatg ccctaagcct ggagcaggta gatgctctgg tggctgacac  48960
cagcaacacc cttaccgctg agcagcgtgc attcctgcgt agcttcagcg aagcacaggt  49020
tgcactcaac gaactcaagg gtctgagcgg tgtacgcact gacatcgagt ctggtggtga  49080
tggcttcaaa ggtctgcctc agtaccgcaa cgctgtgcgt atggctctga tgaacggcaa  49140
cgaagaagcg gctgctggtc aggtagacca actgcgttcc ttcgctgaca gtcgtgtggc  49200
gaagttcaat gccatcgacg ctgcgtatca gcaggtcaag ggtaccgaca actccatccg  49260
tatcgtacgt gatgaagctg gcaactggac cgaagcaccg gagtccatga ctgcccgcca  49320
```

actgaagtcg gctggtggtc tggagatctc cgctcgctcc ttcaagctgc gtgatgctgt 49380
agcactggaa gccactgcac tgtctcgctc ggctgagtcc ctgggtgaac tggtcaaggc 49440
tggtccgatt gctcgtccgg cccctgtggt gcaagaagct gcccccgcac aggaagcgcc 49500
cgtacaggta gctgaagagg tggccccggt agaggcgcct atcgctcagg tcactgaaga 49560
tgtcccagtc agtgaaaccg agtcgatcca ggcagaacct gctaccgagg ccgaaactgg 49620
tgaactcacg gctatccgtg agggtgaagc tgtgcgtggc caggaagttg ctgctgagaa 49680
ctaccagact accaatctgg tttctgcttt cttccagcaa tccccggcac gtaacgacgg 49740
tgacactcag aagcctctgg tagcagtcaa agacttcgct accaagatcc gtactggtga 49800
aggccgcatg gctgaattcg ctggtgtgaa gagcttcact ggtcagcaac agtctgccat 49860
caagcagttc atgaagttcc aacgtgctgc caagccgatc atcgagcgta cgctgaagcc 49920
atacacctcg aagaccagtg acgccagccg ttactacttc cgggactatg ctcagttcct 49980
ggtgaatgct gacggtactc tggacgagaa cctgaccacc gccattgcct acggtgcgta 50040
cgactgggct atcgatgctt ccaacaacct ggtgaacacc gatgccggta tcaatgccat 50100
cctgggcaag gactccgatg atgaagtctc tcctgctgcc tatgcagtcc ttggcaacgt 50160
aggtactcgc caggccaccg cagcttccca gctgggtgcc aagatcgttg atgtccttgg 50220
tttggaagtc ctgccgaatg ctcctgttaa cgagcgtgct cgtctggaag cttccctggg 50280
tgagcatgcc ttggctctgc tggtgaagat gggtgtggca aagatcacca ctgtcagcga 50340
cgccaagctg aagtccctga tggactccaa tgaaccggcc aacccccgcg tcaagcacta 50400
cttcctgacc ccggtcagtg agcgtgtaga cggtaagctg gttccgggtg cagttgctcg 50460
ccagatccgt gaagccaata ccggaagcca gtccatcctg gccaagctgt tcggttcgac 50520
tgaaggccag actgaaccga gcttcactcc ggttcccttc acccagaaga acgccaagcg 50580
tactcagcag ccggtaccca aggaactggc caagatcctg gacgatgcag gcaagcgtcc 50640
catgcgtctc cgtcaggaca tgttccaagt ctggggcaac ctgtccgaga acgcattggc 50700
caccatcgct ggtgctgtag atgttgaagg tggtttcgta cacaaggcca accgtgctgg 50760
cacccaagcc aagaacgatg gactggtacg ccagatcgac aacttcaacg agttcttcgg 50820
tcggatccag gaggtttctg accttggctt ggaacagccg ctgtacttcg accggagcgt 50880
gtggaagcct cagcgtgttg gcttgactgc caacatgatc aacccgcaga ccagcaaggt 50940
gcatcgccac atgctggcaa tggaaggctg ggagaacacc atcaacctgt ccaacaaggc 51000
agagatggat agcttcaagc tgcgtgtact ggagtccttc ggtgtgaaga ctgagggcaa 51060
caacacttcg aaagtgctgg ccaagtacga cagtaaggtg aacacgccgg caatccaggc 51120
cggtgtatct gccctggctg agatcctccg tggcgaggcc caagacactg tggccaacga 51180
gtctgcaatc ctggcagccg tagccgaagc tggtgagaag ttcttcagct tggatggctt 51240
ggtagcactg gctcaagaga agattgcccg tgagaacggt gctgagtcct tcactaccca 51300
gctgctcggc gaagtggacg gtgtgaccaa cggtcctatg ctgtccctgc tgatgtccgg 51360
tgccaagggc tttgacaccc tgaaccaggg tggtttcttc agcctggaag atccgtacac 51420
ccagttcaac gactacaagg cacagggcaa cctggacctg tacgagggca ccatcaaggc 51480
tgtgctggac cgtctgggca atgaaccgct gctgtcctct gtggaagtca tcactggtgt 51540
gctgaccaac gaggaaggcg gtgtatcgtc caagggccgt aacgtcatca agaagcccct 51600
gaccgcaatg atgtttggtt ccaacaccaa gactgctgtc agcggcatgg ctgatgcctt 51660

```
catcgaaacc atctactcca agatggaaga cgctgccaat gctggtgacc aagctgccct  51720
gtccaaggtg atcgctgccg tgaacagcct catcggttcg aagaacagag acaagcgtca  51780
gctgtgggct accgacatgg gcttcgagca agcactgaat actgtctact ccccggtcca  51840
gcagaccgcc atcaaggctg ccttctatga cctgctgggt agcaaggtag agagtgcact  51900
gaacgatacc tacgaggtct tcatcgctcg ccgtgacacc atcaacaaga ctgcgaacat  51960
ggctttccag atgtacgaag ctgtcttcca ggctcgccgt gatgagctac tggcttcggc  52020
caacctgcct cgtggcaatg atggccagcc ctttactgac ctcactcgtg ctcagatcga  52080
ccagatccgc aacgagttga aggacatgga accgatcctg cacaccgctt tctcgaaagc  52140
tagtggtgac ctggattcgg ggatgctgat ggcgaagact cgtcgtgaac tgaacgactc  52200
tcccctgtac cgctcggaag tccacttcgc tgaacctctg gagttcaccg atgaggaagg  52260
ccgtaagcaa tccgtgaaga gcttccgtgc cagtggcatg accaccgtca acgaaggtcc  52320
gggtgtagct ccgttcatca ctgctaccca cgcaggtgac tcgttcatct cccacaatgc  52380
actgatggga gaagatgtcc tgaacatcca cgatgctcat ggtgtaggtg tactgggcat  52440
ggacgctgct ggccaacgcc tgaacgaaca aaccttcaag ctgatgctga actactcggc  52500
agccagtgag atggtttcga ccttcgagcg tactcttgct ggcttcagca agtgggtaca  52560
ggatccgcag gttgcaaacc agttcggcaa gtacctggaa agccagaaga ctaccgtctc  52620
cactcagctg gccagcatcc gtcacgtcgc tgaacaggct gacactgaca agctgaacat  52680
gctggccaac atgcgtgcag taggtcagta cgccactgat ggcggtagct acatcgtcac  52740
cgatgctgac cgtgctgctg ctgtgaaggc tcgtgaagag atcggtagta ccttcaatcc  52800
tgaagcggag acgatggctg atgctatcga tgctcagctg aaggctactc ctcgtgaagc  52860
caagcctgct gctcgcaagc ctctgcgcaa tgactcggta cagtccctgg ctccggctac  52920
tacgctgaac accatggacc gcatcaaggc tgaaggtcag ctgcaacagg acatccagca  52980
ggtagcccag gtgatggaga aatccaacct gagcttggag tctgcaaagg aagtcctgcc  53040
ggaagagcgt gctgctgagg tggtccaagc cgttcaacag aacagccgtg acaagacctc  53100
ggtatggggt gaactgggcc agccgataac tccgtctgac caagcactgg tggatctgct  53160
gaccgaaacc aatgacctga ccactcgtgg tctggctgag gctctggtag cccgcgccaa  53220
cgatcctttc cgcaagcagg tgctgcgtgc tgctcttcgg tccatccgtg aagatgtacc  53280
ggtcaagctg atcacctcta ccactggccc tgacggtgcc atcggtgagg gtgtgagcaa  53340
ggctcgtggc tggtatgcaa cccgtggcaa cttcgaggct ctctacgtga agagtcccga  53400
gttcgttgag tccggcatca ctgaagagat gctgacccat gaactgctgc acgtgagcct  53460
gggtcgtacc atccagcgcg aactggacaa gaaacaagcc aatgccaact acgactctgc  53520
tacttggcgt atggtcaatg acctggagat gatccgtgct cgcgccagtg acatgctgag  53580
caagaacggt ggtctgtctg ccaagtacgc caacgctgtg tcgaacgtgc atgagcttgt  53640
cagctggggc atgacaaacc aaggcttcca ggaagaagtc ctgaagaagc tggagatgcc  53700
tgctggtaag cgtgatgctg gtttcactga tggcttgctg cggttcattc gtaacctgac  53760
tgccctgctg ttccgtgaca ccaagccgtc cgataccaat gccatggctt tggtgatcag  53820
caatacctct ggcttgttcg ccgaggctgc tgcacagatg gccaagcgta gcgacctgac  53880
cctgaagtac gaggacgctg tagatcaggt caatgccatg agcagtgagc agatcttcaa  53940
tgccctggaa agcgagaaga ccccgcttac cgaggctcac agcaacaagc tgaagtctgt  54000
cctgaacagc atcgtcaccg agctttacgg acccatgggt gcattccgca acgaggttgc  54060
```

```
tcgtggccaa gcactgacca ccactgatgc tgtcctgaag gctctggaca ctggccgcct  54120
gcccttcgcc tctcaggcat tggcttcggc gttcattgtc agcccgcagg aagcctacgt  54180
gctggagcag gttgaggcta ctgtggccac cactctgaac agcaacgatg gaatcttcat  54240
ccgcagcagc ctggagaacc tctggcgtga agccaaggat cgcctgactg cgaaggactt  54300
cttcgctggt gagtgggacc aagccactca agcagagaag gatgtggcac aggagaagta  54360
caacttcctg ttccgtcctg agcgtgtggg ttcccgtagt gactacctga gccgctttgc  54420
tgccctgggt gtagcgagcc aggaagtagc gaacctgctt cagttcacta cccgtagcag  54480
cgagaagtcc ttggctggta tgccactggc tactcgtctg gttgagatgt tccgccgtct  54540
gcttacccgc ctgggtcagc tgcacgacaa gactcgtccg ggtgaggtgg ctgagagccg  54600
cctgttcact ctggtggatc gtctggtgga catcgaagcc aagcgtcgtg gccgtctggc  54660
tgaccagaaa gtgggtgccc tggaccaggt ggaaactgcc ctggcgaaca ctggtgaagc  54720
catcaaagac aacctgaacc ggatcgctga atcgaccttc ttcactcagt cgagcagtcc  54780
ctttgttcgg gtagctggca agaccatcag caccatcacc aatgagcgtg ttggcttggt  54840
cctggacggt atcactcgca tccgtgacaa cgctttcaag agccagcacg gcatggccat  54900
gcaggtagtg aacgagatgc gtggggcaca cgagggtaac ctcgctgcac acactctgtt  54960
caagcaagcc aagtccaacg agatggctcg taagcaacac atcgagtaca ccgctgcgat  55020
gatcaacgaa ggcttcaagg acaacggtca gtacctgagt actgaagacc gtgctgccct  55080
gaccaaaggt ttcctacgta ccaacatggg taacctgcgt gaagccctgg gtatggatcg  55140
gttgaaggaa gtccttctgg acaatggcga attcgccaat ctccgcaaag acctcgaaga  55200
ccaactgctg gcattgccga atggtcagta tttcctgggt gctgtgaagg atctggctta  55260
ccaccgtgtg attggtggca acgtcagtcc gaacctgatg ctgaacagtg cgaacatcgc  55320
tgacatgctg ggtaccaagc gtgtgctcca gtcctccaag gcagaccgtg cgaaagccat  55380
cgaactgctg gaccagctgc aagctgtcta tgggtgggag tactctggtt cgcaggtaaa  55440
gtctcgtgct cgtgagatcc tgaagaccga atccaaccgt accgagggta atggtgtgga  55500
cctgatcctg gccatgcatc atggcttggg caagcgttcc aaggatgccc tgttccaagg  55560
caccgaacgc ctgtacaccg atggctacgt accggacatc ttcgactcca agatcgaagt  55620
gctggctgtg gaccgcagtg atctgcccta cttccagaag cgtggttacg ctgttgctgg  55680
tgatgtgcag gtagaccaac gtgctggcct ggaatccgac aaggttctgg tgacccgccg  55740
tggtagtggt caggttggtt tgctgactgg tgcaatgagc tacaccggtg tgcatgctcg  55800
tggtaccaaa gtggatcgtc aggctaccaa catgctgtcg tctggtcctg gtactgcgaa  55860
gaacactgtt actgccatca agcgcaacat tgcacaggat gtgaatgaca tgttcctgcg  55920
tgatcgttcc tatgatccgc gtcagcagaa gtctggtcgt gtgtctcctg tggtaaaccc  55980
gaacggagcc atcgtggact atcgctacac catgactgaa cacaaccgtg acagtctgct  56040
ggaccgcgat aactctatgg aacaggtgct gggtaccctt gcagggcaga tcgtggacaa  56100
ggttgactcc gcaatccaga acgcagatgt tgtgcgtgct atgtacgacc aattccgcga  56160
ggattacgcc aaccgtccta gcagctactt ggtagtaggc aaggacagca ctgatccgca  56220
actgcttgag ttgtaccaac tgctgccgga gagcactaaa cgtgagatcc gtaagacttg  56280
gggtagcgac aacatgcaga tccctgctga tcagctgaac atgatcatgg gttatcgcaa  56340
gtacagtctg actactccgt ttggtttggc agaagacgaa cgcaacatcg ctgagaaggt  56400
```

```
gcttgtacga gttgctgaag ccatcctggg tgagaaggct gcacttcgca ttggtcgtgc  56460
tgaggatgtg atgcaggaac tggtccgtga agccaaggac atcctggtaa tcaagaacat  56520
caccactctc gtaggcaata ttgtctcgaa catgactctg ttggcttggg aaggtgttgg  56580
cttggctgag ggtgtgcgtg ctcacgctac cggtatcaag gctgctctcc agtatcgtca  56640
ggacaataag aagcttatcc agcttcaacg tgccctggat gttggttacc tgccttccgg  56700
tgagcaagct gtacgcgatg agatcgctgt gctgatggat cgcctgaatc gcaacccgat  56760
caagccgctg gtagatgctg gactgatgcc caccatcgta gaagatgtgg aagctgatga  56820
ctcgcagtac agctacaagt ctttgctcca gaagaagact gagaagtaca ccagcaagct  56880
gccgaagttg gttcgggaca ttggtcgtca ggtctacatg actcacgaca ctgctgtgta  56940
caagttcctg agccaaacca ctcagctgag tgatctggtt gctcgttacg ctctgtatga  57000
gcacctgact actcgtgcga aggatccgct gagtaaagct gatgcactgc gtcaggctga  57060
agaatcgttc atcaactacg acttgccttc tggccgtggt cttcagttca tgaacgacat  57120
gggtctggtg atgttcacca agtactatct gcgtgtgcag aaggtgatcg ctcgcttgat  57180
ccgtcagaag cctgctcgtg cgctggctct ggttgctgtc aactactttg tgagtggctt  57240
gcagtcggta atggatagct cttggatcaa ccggattggg cacaacccgt tccagtctgg  57300
tccgtggtcc tggccatcca gcttgagtga actaccaggt atcaaaggtc tgatgaacct  57360
gtaatgaaga aagggggagc tattgctccc cctccttctt cctgctgaag caatacttca  57420
accattccca tcctacccag cagaggatga gtagcacgat gaacagtgct actaccacgc  57480
cgagtattct gaatatccag ctgaatacga agccaatgaa cagaatgcca atcacggctc  57540
ctgctagtgc tccagcgccg aacaatcctt tcaggactcc catacggact ccttacttct  57600
tgtcgaggaa ggccatacct ttctgcacaa cttcttgtgc cagggcagga tcttgtaccg  57660
cagccgcata ggacatgagg tactggatgt ggatgttctc acccttctcg ccgagtgctg  57720
cacgagtcat cacaccgttc ggcagactgg cagaccagta cagcgggatg ctgtgctcgt  57780
tggccagacg cagtgcttca tccaggagag ccttcaggct cggagggatg tccgactcgt  57840
agttgctgcc acgaaggctg tgctgtacgc cctggcgctt ggcttctact accgcatcta  57900
ccaagctcat tcggccgcct tcttgatctc gttgatgttc tcgttaccta ccgcacgtaa  57960
agcgcggagg aagcggtcgg tttcctgctt cagggcagcg tcgaacatct ccagggtagc  58020
cataccgtcg tcggtggcat tgtcccgtaa ggtgttcgtc agcttgttgc gcatttcgat  58080
gaggtgtagc acacgtgtga cgtgcatgtt tttcagcatg cacgctttgc tcaaatcgcc  58140
catggcgaag ttccttctgg ttgggtgtaa gggatggagt gctctggtct ggaccccatt  58200
gcggggtggt gggtgtaccc gttgcaacgg gccagagcac tcccttatgc ctactggttc  58260
aatagacata agaaagccag ctgggggtag ctggcttggt ctacagaggc atcagttaag  58320
ggaggtggta aacggcccct tggatctagg gggacaaggg ggacttggta gtggtatcca  58380
ggggccgatg aggtggtaag aggttgtctc cacttcatgg ttctcaactt acaggaggct  58440
gacatggcag tcaacactaa aaagagtccg cctacccgta accattacga gaacttcaga  58500
aaaggaatga aggtagtgac gtatcagcgg acaaaaggga atactctttt tactgtggac  58560
tgtgatcctg tggaggttgc tgaccttcac gcatgctgaa gccagagatc cgaccattac  58620
ggtagtctgc tgcttcgacc gaaccagtag ggtacgggtt gtccttctcg gagttctcca  58680
agccagcacg cacaccttcg aggtatgcaa cggtggcatc cattccagga cggaacggtg  58740
ggttgaactc agcttcggtc atggttccca ggaaggagac actgagcatg atcgagttgg  58800
```

```
caccgatacc gctacgctcc ttgatctgag cgatgagtgg tacggtgaag tcgtggctct  58860
tgccctgctc gaaagcatgg atggccgact ggaatacggt gcctacgcct gtgggtgcag  58920
cgaaggccag gaggtagtac gacttggctt tcatggttta ctccggtaga gacagccccc  58980
tgttacgggg gctatcggcc tggaagaggt gttagctgaa gaggctacca ccggtgctgg  59040
ccggggctgc ttgttcggct accggctctt cttccttggc ttccatctcg gtagccggtt  59100
ccggctcttc ggtggctact tcgaccggcg ctgcttcgct tgccttggat tcggcaacgg  59160
cagttgccag gccggcggcc gcttcggtgt tgacgacttt cttctcggcc ttcttcggct  59220
tctcgacgac ttccacggtc tgcggttcgg tagcgaccgg tgccttggtg ccgaccaggc  59280
tggctacggc cagttccggt acttcgacga aagccacgat gccgccgtcg cccttgcgag  59340
tggtttggaa ggagatcgac agctgggagg cgtcggcttt caggccgttg gcggtcaggt  59400
aggtagcgat gccagcggcg acttcggctt gttgcagttc gattttcatc ttggttcctt  59460
ttaagtgagc atggccaggg ccagcttgaa atcattgtga tggaagaccc catactcagc  59520
tgctgcacag gcatcagcca tgtgttcagc ccggctggcg atcacttccc ctttcgaggt  59580
acgcggccag ttgagatggg ggtatttctt gactgcccat tcgatcatgg cctccttcga  59640
agctgtcttc gagttacaag ccatgacctt caggtcagtg gggtgagca ggtggaatgg  59700
cttgccgctt gctctcacgg cagagaggat cccaatacac atgccgtagc ttttcatggc  59760
tgcggcagac tgggatccta cgggcacttc cacgaagatt acgttggctt ccttgatcac  59820
ctccatgact ctggtggtga tctcggtaga cctgttcaag tcatcgctgt tgacgcgaat  59880
ctgcttgtcc ttggtcttgg aagtctggat gacttcgata tgccgtaggc tgagggtgtt  59940
ggaggttgtg tcgtactgac cgcaggctag tccccagttg ctcatactgg ggtccatgcc  60000
gattacgttc agtcttgcca ttgctgcaac cgctcttcga ggatctcgat gaggttgttc  60060
tgcacatcct tctgctgaac gagcagactg cccatgtaag catggaccga ggcagcggca  60120
tcggaacgaa ggaacgagta caggctttcc tggcgagctt tcaactcgtc cagttccagc  60180
ttgagtcgct ctttcggacc catgttctgc ttgtgcagct tctgcatgag ttcgtagccg  60240
gcgaacttcc acacctcgtc ttcagcgtta cgacgagcga cttctttgcc gatctcagca  60300
tcgaattcga tggggtccac acaggatgac tgcccggtga ccgtccagcc gttgaccagg  60360
gtaagctggc atacggtggt cagtccgctg ggaagtatcg tgaaagactc ttccacgatc  60420
atgttcttca cgtcttgcgg gttgactttc attcgctacc tccgagtagc tccagctgtt  60480
tcttcagccg gttgatttct tcccgtagct tcttggtttc ctggtaggca aaccaagatg  60540
tccccttgct gtagctcgcc atgatggtct tcacttcttc aggggtcagt acggtcagct  60600
tgatgtcgga attgggttca cagaacatcg aaccgtcatc ccaatcgaag ccaggaacca  60660
cactcagcac atccacagat ggcctcgccc cgacagtacc ggggcgcagg acagggatgc  60720
gtaaggtgtg gtccagcaac cgttcgcgtt gttgcgggtt cgtgcagtag ctcaactgcc  60780
gcttcaacga atcgagcagt tcccggacct tcatggctta gctgaacagg cttgcgggct  60840
tgccgccacc tgcttggccg cctgccggtg caggacgacc ggaagctgcg ccgccaccgg  60900
cgaccttctt ggtcttgtcg cggacggtac cggccttggc ttctttccac ttgtcgaaga  60960
actcgggttc agccttggca cgggcttcgt tcagggtctt cttggtgccg aagtggaaga  61020
ccgccgccac gtcgttcagt tcgcgggttt ccgacgaatc ttcgtactgg ccggtggctt  61080
cgttcttgac gcgcttgttc tcgatgatct tctccagggc caggtagatg tccttgccgg  61140
```

```
tcaggtcagc gaggaccgga acctgcttgg gtacttcggc cttggcgtcg tagtcgtaga  61200
tcttcagggt gcgctgttcc ggcacacagg ccgccagttc tttttcggcg gtcatgaggc  61260
agatggcgtt gacgatattg aagcccggca gatagtgctt ctcgccctcg gcgttcacgt  61320
agtagttgtt ctggcctttt tccttgctgc tcgtcacgta ctgctgaatc ttcagcttgc  61380
gaccggtgcc gtgctcttcg aactcgaagt tcactgccag agcgccgccg gaggattcgg  61440
agccgtaggc ggccaggatc ttgaaggcat agatgtcggt gtcgaagata cgactgccgc  61500
cgccgatgct gtccttggct tccttgatgt cgctgttgtt gctggtgctg aggttaccga  61560
acatagtgct gtttcctttc gatgcgtgaa tcagttgtag taccagtcca gatggtcaag  61620
aaccttctgg atgtcgttgt cgatgaaggt ttgctcgtgc gtccacatac ccatgggacc  61680
acgaatgcgc tcaccgacag tttccttggt gatctgcgtc tggaagacgt gcttgtagcc  61740
aagcatttcc tcctgcggcg tgatctccaa gagcttgttg ttctccttga acggctccag  61800
cttcccgagt tctaccttct tggtggagat caccgtggag aagtaggact caatgccgtt  61860
gttcttcaag gcgcccttga ccggaacgca cacgtccatg gccatggttg ccttgttgta  61920
ctcttccttg gtgtgagcca ggaagatcac cttgcaggga ctgctggcaa ccttctgttg  61980
catcagatcc ttgaagaact gctggaaatc catccacgca gcttgcccgt tggcagcccg  62040
gtagatgtac tgggactcgt acatgtccag caggtaggtg agggtgtcga tgatgatggt  62100
gtgggcttct acctttccct ccaccactgc atcgaagaca gtggggatct ggtagggatc  62160
ggtcaccgtc cgctcgatga agcgagactt gaacggcagc cgcttaccgg cttcgcagtt  62220
caggtagatg accttctccg gctcccggag attccgcaga caagcagact tgccagtagc  62280
ggacagaccg gaaaccaaga ccagatggtc gttcacttgc gtcatgattg actccatgtt  62340
ggaagcgaaa gggtgccgaa ggcaccccta agctcagttg ccgttggccc cagctttctt  62400
ggctacagag accatgatgg tggaagcgat ctcgatctcc gacagcttgt cagccatctt  62460
cgagttgagt tcgttcacct tgccgtggat tgcattgacg ctgaagccag catccagaag  62520
gatcattgcg taacggagca acatgttgtt cctgttgccg tcgccggtgt tgttgattac  62580
ccaacgctcc agcttgtcca tcgacgcctg atccttgagg ttacgccgac gctcttcatc  62640
cttcgtggtc ttcgggatgt agggcagtgc gtcgaacaac tcaccatcca ggtattcgta  62700
gtggccggca tgagatagcc acttccgtgc acgctgaccg acgccatcgt ccacctcgaa  62760
aggcagggat tcgatgacgg cgttgtagaa ctccttgtac tccttggcgt ccatcttcag  62820
ggtgtagttc aacggcagaa tgatgcggaa gcgatcaccg ttgccgtccg tctgatggcg  62880
tttcgtggtg tacagaagag ccttgtagcc cttcaggaat tccttggccg tggacagctt  62940
gcacccatgg tcgatgtcga taaccagcag gttgaaacca acccggcagt tctcttcatt  63000
gcggtgaccc tttcgctctt ccccaccatt gaggtggtgg ttgatccagt ggataccatt  63060
ggcttgggtc atcttccata ggtcatccca agtcgctaga tcgttgaagt agccgtacgc  63120
gatgtcctgc gagtaggcca cgatcatgct cttgtcatgg atgtcggtgg cttggagtgc  63180
ttccccacgg aggaacatga tgtcctgttc gtaggtcttc ttgatgatga tgttgttctt  63240
gtagccccag gcagtagcca tgaccagcat gtcgtctttc tgctgacggg agccacggta  63300
gaacgggaga tcttcatcca gttcggccac ggtggtttcc gagttggtcg ctgccaggta  63360
cttcgccagc ttcacgtagg gacggtccct ggtcatgagc atgtcgaagc actcaccaga  63420
ttcctcggca accttgatgg ccgcgtagag gtgatccatg gtgagtaccg gcgagtcgtc  63480
cacgaaagca taggcacctg ccagcttgag agccttgaag taccggtgcg tcacttctgc  63540
```

```
tttcttggct tcctggtgct ccggcaagcc tgctgcgatc ttctcgcact tcagcttgta  63600
ctcgatggac agcagagcgg tgtccttgtc catggtgagc actcgacgca tattgcttgc  63660
gtctgccaga cgttccaggt catcgcagag atcttcgatg aaggtggagg tggagttctt  63720
cgtcatgagg tcatagacct cttccggggt catgtccacc ttcttgcctt cgccagccat  63780
gccgaagaag caacgacgag cgtagccagt ctccagcaac tccatcagct ggtcctcggt  63840
cttgccgcca tccagcagct tgcctggggt accgaaagcc atgaggttgg tgggcgtacg  63900
gccgatgatc tcttcgccgc gaaggttgtc gttggtgttc ttgaccagct tctgcttgac  63960
cgaacccacg tcgaacagtt ccaggaacgt cggcatgatc tcggtcatgg caggcaggtt  64020
caagccaatc tcatcgacga cgaggttgac cgcaccagcg ttggccatca gcagcttgtg  64080
acgcatctgc ttgacggctg ggccagtacc cgagtcgaag tcatacagca gggggccgag  64140
agacttgaac tccttacgga cagcttcctg ttcgtcgggt agttcggacc ccttacggat  64200
gtggcgcttg aacgccagat cgtcaaggtg cttctcggct gcggtgtcga aggtttccat  64260
gaaccgatgg cggaagccat aggtaatctg gtcctccatc acctttgtgg agaaaccctt  64320
acctgcaccc gaaggcatca ggttgagggc gtacatgttg accggaatct cgccgcgttc  64380
gtgagtcttg atgtggcaac gcatgtgcgc tgccatcatc gagaactgga agccaaccaa  64440
gatcctgaag aacctgtggt tcttggattg ggtcttctca cacagaattt cgacgatgcg  64500
ttccgaggtc gggtggtgtt gcatttcctc gtacttgagc atcacttact ccaggtttat  64560
acgatgaggt cgcccttggc gatgagcatg tccttctgcg tacacagtag gtatgccggg  64620
cagtagaggc aggctttcac ttggccaggg atggtcttca ctacgccaac gttcccgtcc  64680
ttggcacggt gagccatggc ttccgacagg ctgtcgaagt tcttggtgct gcgagcaccc  64740
ttctggtcag ccttggcggg gtcacgatag tacttgtaca ccggctggct acgccatagc  64800
tcttcgtcgc tgcacagggg cagatccgct tcaggggtat ccttcaggga catcagccac  64860
ttcaccctgt tggtgatcca ctcttccgtc tcggcgatgg gcatcaggtt gaataccttc  64920
gaagccacac gactctgagg gtagtccttg ttctgcttcg ccatgaactt ctgccaatcc  64980
gtgaagatga agtggattcg catggtgtcc ttggtgatca gcccaggatt gagcgcacgg  65040
tagatcgacc cttgcaggat gtagtcgctg tccttcgagt ccttgatgta gctgaaggtg  65100
gtagtggact tgaagtcctc cacctgaccg tctgccacga agtcgtactt gccggatacc  65160
attactcctg cgtactcctt cttggaccgc tgctccatgt agacggtgat agcaggctgc  65220
tcgttggctt cgttgaacgc cttgagttcc gcctcggtgg gattcaccag cacacgttta  65280
gcgacgcttg cagggatgcc cagggcatcc agtgcccggt ccttgttcac ggtccaagcc  65340
ttctcgatgg agtcgtgaat cgccgccccc atgcggttgg cgatcatgcc ctcgatatcg  65400
gccatggagt cggatggctt gatacgacga gccaggacta cctgcctgat tggtttcagc  65460
agggtggtag ccgacagccc tgcttcgctg tagtcgtagt agtccgaagc cagccacaaa  65520
gccatggcca tcgggatacc cgtctggttg gtgtagatct gacccatgtc agtcgtcctc  65580
tcctgcgttg tcttcaagcc aacgattgag ggtatccctg gcttccttca cgtcttgcca  65640
gaggctcttg ccgccgctgc gttggcctgg tgccatcagc ttcttgcgag cgtggtccag  65700
ggcaccggat ggatccagtt cacccagggg gaacagcatg ttgatccggt acacgtctac  65760
gaacttccag gcacgtggga tcggacgctg gtagcgattc aggggtgcag tatcacgctg  65820
gaccttgtgg gccggttctg ctgacttgac cggcaacctg cggtgaagct tctcgcagtc  65880
```

```
ttcacagggt tgcccctgtg gatgctgtgc cttacacacg gggtgaggcg agtatcgtgg  65940
atctctcatt ggcttgctcc aaagtatcgg ttgaggtgga acacggctag cttggctgct  66000
gccatgtagc gaagcgcttg tcgcttctcc aaagccatgc cacccatgag caggtcgtag  66060
cacagctgag gttcttgtaa caggacgaac agacgtgcag ccgacaacgg cctctgggag  66120
ccctctgtgg ctgatgcgat gcctgagagg atgtcctcta cccctcggtc tgaaaacgca  66180
tcaggcagcc cctgtaggcg ttttgcgtgg ggattggtaa accaacgagt ccgtggtcct  66240
cctatcgatc tacgatccaa gccatgaaac ctgatggtgt cagcccgagc cttgcccatc  66300
tgagccagga gatttggcat ggagtcgatg gggaagtcct tgaagggtac gtcctcaggg  66360
gtgagttttt ccatgaaaac ctcctggtta aaaaatgatc acgaaagtgt cttatatata  66420
atagggactc tcacccctct tctttcgaag ggttcgccc ctggaagggg ccgtcccagg  66480
gcgaccacta gcgctcaccc tccccccttct ccatccaggg aaggggtcag gtgaagtggt  66540
cgcccgagga gcgagcgcag cgagtcccgc aagggatgac ccgtaacctg accccctgacc  66600
gggggaaatt gaatattcaa ttattccttc cgcctatcca cgcatccact cccgtctcgc  66660
tctgcggtgc tcgctgcgct cgatcctcgg cggactgcgt tcctgcgtgg ataggctggg  66720
ggaggttagg gaggttatac tttgaccaac tctggaggaa ccaacatggt agacacttgc  66780
aacatcaatg ggtctgcgg aaccggggac tggaatggtc ctaagcccgg tgaccccaac  66840
atgaatgatc tgctgctgaa ggcaactcct gccttcggtg gtatcgacat tgagttcact  66900
tggccaacta cgaacccagg tgcagttggc actactcgac tgttccgaag cactgacgct  66960
aacttcgctg gtgcaactat ccgggccttc gtcaacggta acttctactt cgacaagaca  67020
gaccctggct ccaaggtaga tcaacgctac tactattgga ttcagttggt ttcgatcaat  67080
ggcactgatg gggacatcat tggtccagct tcggccactg ctcgtccact cattgagcag  67140
atgattgagc agcttactgg tgagattgac agtggtcttc tttcccaaga gttgaggaaa  67200
gagattgctc agatcgaact gaacaagctg gggatcaccc aggaagagat tgagcgagcc  67260
aagaacgatg atgctcttgg tgttcgtctc actcagatcg atgcaaagat ggatcagaat  67320
actgccatct tgcaggaaga ggttcgtgct cgtgtaactg ctgacagttc tctggttcag  67380
acggtcaaca ccatgtacgc cgacttcaac gggaacatcg cagcaatcca gcaggagaac  67440
actgcactgg caaccaaggt taatgccttg gcttcttcag tgaccacgat caacgccacg  67500
gtcaacggtg actcagcctc tggtaaagtt ggcttggttg ctgaggtaca gaccctggac  67560
ggtaaggtta cccagatcgg tgctcgatgg actgcgactg ttgatgtgaa tggtttggtt  67620
ggtggcttcg gtgtgtacaa cgatggccgc actgttgagg ctggcttcaa cgtagaccgc  67680
ttttggatcg gtcgtcctgg cactccgaag aacccaggca gctacccgtt catcatcgac  67740
aacaacatcg tttacatcaa ggaagctgcc atccagaagt tgaccttcga caagctcagg  67800
gcacaggatg gcagcttcat tgttcagaac ggtaagatcc aggctgacta catcgaagcc  67860
aaggatatcg tggtgaacaa catccagtcg gacaactacc aaccaggtgt ccaaggctgg  67920
gcattccgtc ccaacgggat catggaaatc aacggtacgg caggcactgg ccgtatgact  67980
atcaacaacg ccaccatcaa ggtgtttgac caagcaggca aactccgggt gcacattggg  68040
aacctacaag catgagttac ggattccgct tttacgacgc caacggtaac gtcaccgttg  68100
actcaaccaa caagtccttc aggtctgtgt acaggcaaca ggtgtttcct gtcctagggg  68160
gcactactaa tttgcccccct ggttttgatg caagtaaggg ggacatcttc ttctttactt  68220
ggtttcaact agcacctaac ccatggcctc agtttgtaga ctttggtttc gtcaataacc  68280
```

agatccagtg gtacgacact tactctacta gctatggcaa agcctatctc aacgtggtga 68340
gcttccgatg acttacggta ttaaactgac aaacgaaaac agtgacatct gcatcgacga 68400
gttgaatccc gtctatgttg ttgtgttcga aggatcctat aagtatgaca gccctgggca 68460
agactttatc tacgtgcagt tccctacccc tatcagatca cagagcttgc caattttctt 68520
cgctaagcaa gatggccctc atggtttcat ggacttcact tggttcggtt ctaacggtaa 68580
ctggaccggt tgtcgctttg tactgaccaa ctttgctggt atggctcctt cggtgtattc 68640
cggtaagtac aagatcgttg ctgtgcatat gccaaagact gctggctggg gtatgcaggt 68700
atttgacgct gatggtaatg gcgtattcga tactggctac acaccagcag tattccttgg 68760
tggtatccag aggttcttgc cctacggcta caaccctaac ttccctggtg gtcgtacact 68820
ggggagttgg tatgccgatg caaccaaaat caagcagggt gcctacttcc gagtggactt 68880
cggtaacaca accttcaggc acaatggttt caccattgga atgcttaacg gccctacggg 68940
ttggatgtac atcgctgctt tcatcagcgg caacaagccc ggttacacta ttgaccatcc 69000
tttgttggcc atcgaataaa cggtacactg cacgctccat tcgaagagga tacaaccatg 69060
actaccaagg tgatcttcac cttccataat ccggatggca gcccacaggc gaacgagaag 69120
ttcaccgtgc gactgacccg tcctggcatg agcgatgcag agcactgcgt cgtaattccc 69180
gaaacctacg agatggtgac cgacgccaag ggcgagttca ccatggactt ggaatcgtct 69240
acctctgcct accgcgtcac tgctataggc gatgacgacg agtacgagga cgatccctgc 69300
tcgcagtaca ccttcacctt ctacgtgccg gactctgttg atccggtcta cgtacaagaa 69360
ctgatcctta tgcctccgcc caacaacttg ccatgggacg aggaagccat gaacaagatc 69420
acccaagcgg tggtcgatgc tcgcaatgca cgagacgatg ctgaagagtc tgctgaccgt 69480
gcagaggctc aggttggttt ggctgctgag caagtgaccc ttgcaaaggc agaggtgacc 69540
aaggctaccg cccaggctga ccgctccaag acggaagcgg accgggctac tacccaagcc 69600
accaatgcag ccaactcggc tactgctgcg gccaactctg ccacccaagc caacacgcaa 69660
gccaaccgtg ctaagacgga agctgaccgc tccaagagcg aggctgatcg ggcacgggat 69720
ctggctgatg ccgtggctga aaaggtcgag ggcggctcgc tgcctcctct ggtgggcatg 69780
aacgaaacct tcacctacga aggtaccgac ccctaccgat ggactgtatc tggccctgct 69840
acggctgtct cggacggtag cgtcatgcgc ctgaccaaga ccgatggcag cggttcccgt 69900
gcgttcgtac ggcaggcagt gtccttcccg gacagccact ggatcgtcta catgcgtgtg 69960
aagacccaga ccggtaccgc ctcgcggaac tgttctgcac agatccgctt catcgctgct 70020
gacaacaaga actgcgtggt ctacttcaac gtcaatgcga atggcttggt ggaacccaac 70080
accatccaca tgcaaggcac cgagggtgat acccgcaacg ctgcaaccat gttcactggt 70140
ttgggaaccg aggactggct agaccttgct gtgaagtacg atgcggtaaa ccgccacatc 70200
gaactcttcc gccgcatgcc caatggcact tggcagaagg gtggtggtcg tctgatggta 70260
gatgccatca agcctgcttt catcgagatc tcgtcgatgc cggtagcccc gcagaactgg 70320
tggctggata ctgacttcat ctcggtgtgc aagcccaacc ttatctgcta cggcgacagc 70380
attgctgctg gccagaacga gtatggggta acccgtggga acaaccccta caacaacaac 70440
cgcaactggg ctggtacctg gttcggaaag gttccgctct acgccaccaa ccggaacaac 70500
ctggtgcttg tccagggcgt ggaaggccgt cgtacctggc agtacctgag ccagctgtcg 70560
gagatctcca actccggcgt gaaggtagtc ttcattcatg ccagcacgaa tgacgtgaac 70620
gatgccacca tgaccatggc caagcgtacg tcggacaccc aagccatcat cgaccagctt 70680
catgctgtcg gtgctcaggt agtgctgttc aactccatgc agggcacgaa ggcgtacaac 70740
gatgcttcgt ccactaccgt caagctacgg gactacaccg accagtggtg gaataccgaa 70800
ctgcccaagg tcaatggttt ggctcagacc ctggacatcg ctcgactcat cgccaaggac 70860
gggtacatgg accctgccct cggtgcgagt gacggtctgc acctgaccaa tgcctcggca 70920
cagaagatcg ccgacaagct tggccagttc ttctccaact ccagcgatac caatggcttc 70980
gcttcgttgg atagcccagc cttcactggt atcccgactg tacccacgca gactcctttc 71040
ctgccttacg gcaagcagat cgccaacacg gaatacgtaa gcaccttcat ccaggactgg 71100
accagtaatt acgggtacgg cgacctgacg atgcggaacc tcaccggtgc ccagatggca 71160
ggcggtgggg tgcgtagcgg ttattactat gttcctgggg attcttctaa ccccttgccg 71220
gggaatgttt atgcattcgt gcaccacatg tcctacgaca ccaacaaggg ttgggaactc 71280
tggaaccact gctacaccga ccgtgtgtac atgcgttatt cgaacaacgc aggtgtatgg 71340
aatacgccgg tagaaatggt tactgagaag tggatggagc gtaatagctt catgacccca 71400
cgggtttctg cattcaaccg tctgcccgtg gcttcttctg ttggttttga aggggttgtt 71460
cccttgcaga ccaacagtag tggggcttgg cgtaacgtga atgctggtgt agctgggttg 71520
ggccttctcg gtgcaactac ggctggtaat gcactgaact acattggtgg tatgcccaaa 71580
gccccaacca atgatcgggc caacagtaac ctcaacaatt tacctgatga gtgtggtttc 71640
tacggtttgg gaccagcacc gtattccaat atccctccgg gggttgatgc gattaaccca 71700
gtgggttcta ccgtctacca tcaggtttac gacgccaaca ccgctacgca aattttcatt 71760
ccgcgtactt cggacatctg ctatttccgc cgtaaggcag ggggaacctg gagtccatgg 71820
gttcgttacc tgactgattt gcagctggta ggcaccacta ctgacagcag tgccggtgtt 71880
ccgaatggtg ccatcatgca ggtcaatggg agtgctgctg taaacgtagg tgttgccctc 71940
cgctttgcag acggtactca aattgttcgg gcgttactcc aattggatta cggtgcagta 72000
gatatccttc agcgtcagtt cactttcccc atggcttttg tgggtaagcc ggtggtaacc 72060
gccaccctgg aacaaggtac tgttgctgac atcaacaaca tgcctttgca ggctcttggc 72120
cctgttatgg ttgccagtat ctatgcaggc aactgcaacg tgcgtgtcat gcggtct 72177

<210> SEQ ID NO 4
<211> LENGTH: 43313
<212> TYPE: DNA
<213> ORGANISM: Unknown
<220> FEATURE:
<223> OTHER INFORMATION: Description of Unknown: Bacteriophage F510/08

<400> SEQUENCE: 4
cctactcaac gaggccgtgg ctagcaaggt gctaaactcc cgcctgggct ggtccgcagt 60
cggcgagtat gtcgaactgt tcaaccgcac gcaatcccgc gtggccgggt tgattcccga 120
gtagctcaag ccgagtacct gcatagtcgg gtgctccact ggaactactg gaatttttat 180
tgagattggc tggaggttgg ctgtctgtgg ctgggggggg tagttactcc gggtctaatt 240
ttggtatcgt cgtgtgagaa ccctcccgac tctgatcagc ccacccttcc cccgtaggcc 300
ctccgcctgg tgggccatcc ctcgcattgc ctgggtgttg cttcctagcc tcctgggagc 360
ttccagctcc gctgggtggc gtgggcttcc ctgccctgtc gccgaccatt ctacgcatcc 420
tgtcgggagt gtcaaccctt gggctggccg tagtgcctgg agcgctccag cgcttccctg 480
tgcttggtca gcgctaccgc gtactcctgg gatgcctggc gcttccgcca cggtgctgcg 540

```
tagtgccggt ggtcctgcgc tgcccacgtc gctatctgcc tctgccatgc tgcgtcctgc    600
tggtgccagg ctcgctcgcc tctgtcctgt ctgctcagca tcctgtgcct cctgtggcct    660
ctgctggtcc tgtcgggtgg tggtgcggga gtggctggcc ttgcctcttg tggtattgcc    720
tcctggctgt acctggcgtt gcctgggtgg tcccggctct gcctggggcc tacctggcca    780
ctccctctag gccacgtact ctacccgcct gcctctgcct tgtctagtcc ctcctggctg    840
gtgcctgggt gctggtctgt ctcaccctgg ctcactctgt ctctacctgt gccctgcctg    900
gctctgtcct ggctaccgct ggtcctgctg tcttgcctcg ccgctccctc gcatgctcgg    960
tcgcacctgc ggcgctgatg gactcctgtt tgtccattgt gtgtgacata accgcagccc   1020
tagtgccacg cgggttccag ggcggtgggt cgggtgcctg ggtggcggct gtcgctccct   1080
ggtaacgcaa atcctggcta gctagactaa gcctcgcacg tgggtctcta tacgtgtggg   1140
aaggctccag ggagcgccct gggagggttg acacgtgggc agtaggtctg tagagttcgc   1200
cctgtcttca cgcaacaacg cctctacagg cagcctggag acggggttga cacactgcca   1260
gggcatcggt agagtacgca gccagaacga cgggagattg caaccttcca agcgcggcac   1320
aagccatagg cgcaagggac acggcaaact cttagggcag gaaccgcagt gtgtaaggcc   1380
ggcaggcatc actgagggga ttgacacggt gcaggacacg cggtacagtt cgcaccacct   1440
gatggccact cagcaaaagg gcctatgcca gagaactgga cgaactaatc cccgacagag   1500
gattgacaag acaagcgcaa gtctctaaca tgcgcagcaa gacgaaagga tggttcagcc   1560
atctggcggt agaggttcga agcttcacca gcggtacatg gactggtgcg gtaggttgac   1620
cgaagctgca actggttagg cagggtccca gggaatacct gtcgggtgct gaagactcac   1680
ccaaaagagt ctgagcggga agcctccccg tccacggtta agcaaaggca cgttagtgcc   1740
ggtgggaacg aacagagtgt cagtgggatc gagaactaga aacctcggtt aatcgcgact   1800
gacagtatgc tgggtagtat cggcgggccg attgaacaag gccaggcaga tagcgcaaag   1860
ggtacggggg atgagtgctg acgatcccga agagtatgcg caggacaagc cagaaccgct   1920
gatactacag ggactatgcc aatgccaagg tttgtccctt gaggcccttc caccgagggg   1980
attcaagaga cagacctagt gaggattgcc gatggcacac ttcaaggcta aggctcccaa   2040
gtcgcccttt gctgctcagg tagcgtactg gcgggactgg gaagccaaac gtactaagct   2100
catcgcacag gataacgtcg aagggcgtaa agagcttcgc aagatgcgtg acgtgcgcta   2160
cgccaccgac ccggagccag cgccaggacg ctaccataac cctgaacaga aggctttcgt   2220
gaagggtagc gaaggcaagg cgcggaacat cctgaaggga tggaacgcta agaagtcgca   2280
agggaagggt ttgtaatgcc acgtgtgaat gaactgacgc cgcgtcaacg caaggccgcc   2340
aaggctcgcc gcgacaaggc tcgccggatt gatctagcgc acaggatgcc gaaaggtgcc   2400
gactgcccga tcttccgcaa ggctgagcag gcgcaagcta agcagccacg agtcgatacc   2460
ctgaccactc cccgcagtgc tggctacctg gccgccgctg cttacctgaa caaatccatc   2520
tgaggtacat accatgacca acgcaatctc caaaaccgta atcgcattcc gtggcaccga   2580
agagatcaac cgcgctatcg acgccatccg tgtccgtggc aaggaactcg acgaagccat   2640
ccaactgacc ggcctgtcga tcatccacca catcgaccag tgcggcgacg tgaccgtagt   2700
caaggcgctg tatgaagcca tgccgaaggg cagccgccgc aatgcgctgg tcgagtggct   2760
ggtgctgcac ggcaaggtac aggttaacac tgacaagaaa tcgaacaagg acctgccctt   2820
cctgtacaac aagttcggca agaccgatct cgtcggcgcc accaacagcc cgtggtacag   2880
```

```
cttcaagcct gagaaagcgc tggaccagga gttcaacctg gctgctgccc tggccacgat   2940
caaaaagcag gtgctccagg ctcagaccaa gggcaaggtg atcgtcggta tggaactgct   3000
gggtgacttg gaagcgctgg ccgccaaggc tgcacccatc gccgagcaga gcaagcgcgc   3060
tgccgcccat tgactcaagt cgaacgcctg ctaagcgggc gttccgctgg aatcaatgac   3120
aactggagaa acacgatgag cttcaaacaa cgcctgcaac gtcaaatcgc cctggcacag   3180
tacagccgcc cggctcagtt cccgtatggc gagcaagccg tccaggcgaa gggggagtga   3240
ccatggactt ctggatcgcc cttcccttcc tcgaactcgg cctcaacctc ggcgaggatg   3300
aactgcgcat gttgtggttc agcggcctga cgatattctt catccacctc ctgaagcggt   3360
gactcaagtc atggccctgg cgggcgaccc tcgcctactc cggggccatc gctggactca   3420
tcacaagcga gaactaaacc atgcaagctt tgaataccct gttgattgca atccccaagg   3480
acccgaccgc aggcatgcac gccgccgaca aggtgctgtg cgcccacgga ttccgcatgg   3540
gtgacctgaa taccgcgcac gtcctgaccc caggcgggtt cgtggtagtg ggcgccggcg   3600
tgactgtgaa ccgctatgac gaagcgtatc gtatgagccg gaacctcgac tccgaaggct   3660
tcgacgtgct gctggtccag ggcagcccgc tgtccgggcg tgtcacctgc caggcgtacg   3720
gatggatcaa cgccgagtac cacaagggct gtgcgaatgg ccgtcccatc ttcgacatcg   3780
caggaacctc gtaccatgtc atcgcgtgac ccgtaccgca tcggccaccg cgttgggctg   3840
gtgaactaca gcgaccgcta cctgggtgcc gacgcggcag gcaccaaggg catcatcgag   3900
gccataaccc gaccgtcgcg ctgtatgacg gtctaccacg ttcgctgcga gcggaccctg   3960
cgcctgatcg aggcagaggc ccgcaacgtg cgattcatcc gacagcgggc ggagcggtga   4020
gctggcgcat cgtggtagtg acgccaggca acgggtgcgc cttcgtgtgg acccgtcgca   4080
agcgcgtccg gcctctgaga ttctactccc gcaaggccgc taaacgctgg ctccgtaggc   4140
accgccgccc ggcgatcctc ggtagccagt acctgatcgt gaactggagc aaacgtatat   4200
gaccctcgtg gccaccgtag tagacagcgc gcacaacctg gaagtcgacg acctcaccgc   4260
cggcaacctg tatgccgcca gctcgcccag cgggaacatg ttcatcgtgg tagtgggtaa   4320
tcacaatggg cgcaggcttc ccgtagtcct gtcatccacc gatacccgca ccatcgggga   4380
cgtgataagc aacactgggt tccggtacag tgagatcgcc gggttctccg taaacctggc   4440
acagggagat tatgactgat ggtcacccgt actgtatacg tcacgcctga agacccgacg   4500
ccgccgatct tgtccgtggg ccgactggct ccgggagaac tctacaaggt ggtggcaccc   4560
agctcggcgg aaggtatcat tgtgctggcg accaagcaga cgccggcgct agcccaagca   4620
gccgtcgtac tgcacagcat gaaccctgcg cagtatcccg caggttcggc tatcctcaac   4680
acggcctgga agtgccgccg cctgggagtg ggcgagtacg tcaagctcgt ccaaggggag   4740
gaggactgat ggccgtggca atactcatcc tggccgtgtg gttgatcggc ggcgccctgc   4800
tattcctgcc gttcgacctt gtggtctcac cgcgcttgcc gctatcagac gaggccctca   4860
accgaaccgc actgtacacc gtgctttggc cggtaaccct acctaccctg atcgccataa   4920
ccgtggttgt catgctgcat tccgcgtaca ggggcgccat cgaactctac caggagatga   4980
aatcatgatc cgtacccata cccacaacgt cgagcgcaca ccgcaccgac tgtaccggca   5040
cactgagctg gcgtctggcg agctgtaccg tgtagtgcag cccgactcca agcgcggcac   5100
gttggtggtc ggcgtagcgg cctgggacag ccagggccgg cccgcagtgc tgcccgtggt   5160
catccatgac gatggtgacg ccaaggtgac ctgcgcacgt cctaccgtac tgcgcaacga   5220
cgggtggcgc atggtcctcg ccgacaaggg gacccaggtg acactcaccg ccgagtgacc   5280
```

```
aaggcgaagg ctggtgcgcc agccttccac cgtggccatt ccctgccgcg aaccaactca   5340
actgaggagc tacaacatga ccaacgtcaa caccaccacc gaaaccacca ccgctgctgt   5400
cctgggtgcc aagctgatca agaagccggc caccgtcgag gacttccgca acaacgtggt   5460
cttccaccat agcgccctga ccaaactgac cgaggtctac aacgaagcgg tcgccgccct   5520
gcaaaccgcc gagcgcctgt ccagcctcgt cgccggtgac gtgatcacct tcgaccacgg   5580
caagggcgag aaagccgaag tgctgagcgg cgaagtcatc agcgtggtcg ccggcgtcta   5640
tcaggtgctg gtccgcttca gcgacagcgc accggccaag ctgctggacg tgaaggccag   5700
cgccatccgc gccgtccagt cgtcggcagc ccaggctgca accctcgacg aagccatcgc   5760
ccagggcgag taaggcccgc acgtaatagg cccggccctc cgggcctatt gcgagctagc   5820
cataccatag gaggaatcac catgagcaag cgcaaccccg aacacatcaa cggcaccgtt   5880
cgtagcgtca gcgtccagaa gttggcggcc acccaggaac tggaggatcg tctggaggct   5940
gccctggccg tgtgccagca gcgggcagag gacatcgacc tgctgagccg ccgtctccag   6000
gccgccgagc gcgcccgtcg ctgggagatc gacgagattc gcaaccacca ggcgaccatc   6060
cgcctgttgc aaaacgatct gaacgctgcg catgatgccc acgaggcaca agagcgccgc   6120
gctcgcaagg caaccatcat ggcctgggta tgcctgctga ccgcaggttt ggccgtcacc   6180
ctgaagctgg caggagtctg accatgcagt gcaaagacct ttacacgaac ctcgcgtcgg   6240
gcatgttcaa cgtgccgtgc tcccaggtga ccccggagat gcgacgggta gccaagagcc   6300
gggcattcgc ccacgcctat acgcccaaga aacaggcttc gggcgggact tacaccgccc   6360
gtgtgagcgg cgtcacctgt gacggtggta aggtggaggt gcgcctggat aacgtggagc   6420
gcgtcagcac cttcgactat gccgagctgg agacgcgggt agcggccagt ctgtgccagg   6480
ccgacgcgaa gcgcgccgct gaatacgaaa agctactgct gaaagcgttc ccgtcggtat   6540
ccccgaagga tggcccgctg tccgccaagg acttcgaatt gcgcctgcat gatctgtgct   6600
caaccaagct ggtagtgctt cgtgccttgc gtgatgccgg gatagagatg gacggtccgc   6660
tgcgcagccg ggtacggaag ctggcggatc ggaataacgt gatgggtgct gagttgttca   6720
gcctcaagca ggagttggca caactggtcg cggtcggcca aaaggctgga ctgaattggg   6780
acggggcgga gactcagcgc ctgctgacgg tggccccgac caaggctctc tgtcgactca   6840
tcagcgcgct gaccggcgtg cggtataccc accacaccgt cgtagccaag gccgaggctg   6900
aggcgcgcga gcgggcaaag gccgaggcca aggattcatt gcaggcggca accttcgcag   6960
ccgccatcgc tggtggcgtc gtcggcagcg ccctgatgtt cctgctcggc tagggcgacc   7020
agggcctact ccggggtcaa atccgagggc gttcctagag cgccctctcg tgtgagtctg   7080
gaggatcacg aacatgcaat accacttcac gcattacaac ggataccgct tcggcgtcga   7140
gctggaggac gaggctgtct tcccgtgcat cgacggtaag cgggcgacct gggacaaggt   7200
ggcggcatgt gccggtagcc ttgtgcatta catggcgcag gacctgatcg actttggcca   7260
gcgcaagtta agggagtttg aagatgagca agacgagcct gtatccgctg aacctgcatc   7320
ccggcctgat tcaaatcagg acgattcacg tattcagcat ccaagccccg agcaacgccg   7380
agaactggtg gcagtggttc ctctggcagc ggaagtacca cccgctccgg gaaagcctga   7440
gtccagccgg ggagctgagt gcgagtatcg ccgagtgtgt gctccacctc cgccggaatg   7500
gctggcaaga tagcgacatc tggcgcaaga agggaggcgt gctggccctc ggtgccttcg   7560
acctgtccgg cctgatggta ggttcctgcc tcgtagtagg tggtgagctg aaggccctgt   7620
```

```
gcgttgatga ccggcacagc aggcagggta tcggcgctga gctggtgcgg gccgctgagc   7680
tggctggtgc cgagtatctg acctgcttcg agttcctgga gccgttctac gccgacttgg   7740
gctggagcac cacccaccgc gaggcgaact ggacagcagg agagccggac gtgctgcaca   7800
tgagggcacc cggtcatgac gtatgaggtg atgacatggc ttatcgagaa caaaccgctg   7860
gtcatcggag tcgccttcag tctggtggcc ctgggcgtgc tgctcacaca gaacaacggc   7920
ggcccgccta cggcgcccgc atgacctggc acctccagga catgttcgag gcccgaggcg   7980
ggctgcggcc tttgtgggag gaatggtacc aatggcactg cgccgtgact cctggctaaa   8040
gcaagcgcaa tccctggcgg tcggtcaggc gggtcgattc cgccacgtcc tgggatgcca   8100
gagcatgagc cggggcggga ccaacatgac ctgcaagaac cttcctgacc gctgggtggc   8160
ttactgctac tcctgtcagg agggtggcgt ggtcgagaaa acgcatgtgc ggagggtaca   8220
atgcgcggat caagaacgct tcatgccctg gcccgaggat gcctcggact ggacgcaagc   8280
cgactgctat caatcgcttt atggtttgct gctgtccaag ggcatagact acaacgtgat   8340
gacgccaggg ctgccgctgc tgtacagcga aaggcagcat cggcttatct tccctaccga   8400
cgcgggctgg attgggcgcg ctactgccga ccaaaatccc aagtgggtgg gttacgggta   8460
tcctgccccg gattaccatg gatggcccca ggaattatca atgggcaggc catgggtgct   8520
gacggaagac tacttgtcgg cgctgaaggt gcggtgggcc tgtcccgaag tctttgctgt   8580
cggtctgaac ggtacaaggc tgcgcgacag gctggcggcg atcatgttgc agcagacctg   8640
caagcgcgcc ttcatcttct tggatggcga ccgggcaggt gtccgtggta gtgcaggcgt   8700
gatgcgccgg ctccggtccc tgcttatcga aggccaagtc ataccaacgc cggacgggtt   8760
cgaccccaag gacctgaccc gcgagcagat aaggagccta gtaattggac gtattgacgc   8820
ttcacgcact gagtgaccgg gaccgcttcc gcacattgcg gagtgtggtg cccgaaggaa   8880
tgatggggcc ggagacgtgc ttcgtcatcg actggatcga gcagtattgg aaggtctacc   8940
cggcgcatca gaaggtagac ccgcaggcac tgcgcgaact gatcaagctg cgaggtggct   9000
accagccgga gcaactggcg gtggtcctga acctcgtcaa ccaactggac aagccggtgg   9060
acccggactc gctacagggc gtcgtgtccc agctcaacga actggatttc tcagggcggg   9120
tggatgccct cctggcgcag tacaaccagg gcgaggacat cgacctggcg tatgagctgc   9180
gccggctgag cgacgaggcc ctgcgccgcg gaggggtcag cacgccgacc gactacgtga   9240
cggacgacgt gtttgatatc ctcgcggagg agcagggtga ccacggcatc aagctgccgg   9300
ggctggtgct accggcgtac atgaagggcc tccacgccgg ggcctcggtg ctggtggcag   9360
cgccgccgga tgcgggcaag acctcgttca tggcctggat cgctgtccat atcgcgccgc   9420
agctcaagcg gtacttcgac cccggacgac ccatcctgtg gctgaacaac gagggcaagg   9480
gccggcggat caagccgcgc ctgtactcgg cagccttggg catgaccgtg ggcgagattc   9540
ttgccctgga cccggaggaa gttcgcagga tgtacgccga gaaaatcggc ggcgactctg   9600
agctgatccg catcaaggac ttccacggcg ggtccctggc ccaggccgag caggtcattg   9660
acgcgatgaa gccgtcggtg gtgttttggg acatgatggc tcacgtcaag ggtggacagc   9720
gcaaggacca gaaccgcacc gacgagatgg agtacaaggt ggccgaggtc cgcgagatgg   9780
cggtgcgcca cgacttcatc agcttcatga cgtggcagat tagcaacgac ggccacgacc   9840
agttgttccc accgcagtcc tgcctcaagg attcgaagac agcagtgcag ggtgcggtag   9900
atgtgcaaat ccacctgggc cgtctcaacg gtgcggatca acaggtcatg cgtggcctgt   9960
ccctgccgaa gaacaagttc cagatggacg ggaagccttc gaacgtggag gctatgatta  10020
```

```
acttcgacgc cgcacggtgt cgattcttcg agagtgtaga ccatgcaagc taagcatagc  10080
cgggtgctcg aaggcaccaa agaaattccg ctgggtagca tcgagccgtt actgggcagc  10140
gtcgcgggcc tgctgttgtg cctgtactcc gacgcaactc acgaggaggg cgtcgccttg  10200
gccggtgggt tccctcgcga cttgatgcac ggcgccactc ccaaggacgt ggatgtggcc  10260
ctgtatagca tgacctgggg gcgggcagag cacctgatcc agaaggcact cccggtcctg  10320
aaccccatct tcgtccggga tggtgggtgg cgctcggact acgctgatgg tggtgacggt  10380
ggtatcttca agggcgtgat gtccctcgtg ggctgccgtg ggttgaatgg catggacttg  10440
gactttaact actacgacgc cgacagcctc ggtcgagtga tggagtcgtt cgacttcacc  10500
atcaaccagg taggcatcgc gtacaactgg cccgaccccg agggtgggcc gcgcctgggt  10560
gcgtacctgc acaaggacgt tacctggggc gtgaacaagg aagtcggtgc cggctcacgt  10620
ctgccggaac gatgcgagaa aatgcgagcc aaggccgcgt actacggatg ggagaacgtg  10680
tgatgagcaa gcgcgacgtg gtactggata tcgagaaagg catctggcgt ggtgttgacc  10740
agaacgacaa ggccgtcgag gccatcatca agaagaacgg gtacgtgatc gtcgagccta  10800
agatcgacgg gtgccgtgcc atcgtcggtg cgcatggcgt ggtgtcccgc agtgggcgcc  10860
gcttcccggc cctggatggc ttggaagacc gcatcatcga gcgactggcc cgaccggggc  10920
tggactccgg cctggtgctg gactgcgaga tgtacctggc cggcatgccc ttcagcgagg  10980
cgactggccg catgtcgagt aagaccccgc tgaccgagga agagctggag tgcctgcact  11040
tcgcggtatt cgacgccacc catatcgacg tgctccgaaa ggcgcgcacc tcacacctgg  11100
tatacgaaga gcgccgagcc atggccagca gcctcctggc agcctgtcgg ctcagcgaca  11160
ctccgacgtt cttccaggtg gggttcaccg tctgccggag aatgtctgac gtttaccgcc  11220
agtacaagtt caaccgggag gtgggctacg agggatcaat ggagaaagac cccagcctgg  11280
tctaccgcaa cggcaaggtc gccggctgct acaagcgcaa gccgggcatc accgtagatg  11340
gccgcatcgt cgggtacgtg atgggcaaga ctggcaagaa cgtgggccgc gtcgtgggct  11400
accgcgtgga gctggaagat ggttccggca ccgtggccgc caccggcctg agcgaggagc  11460
acatccagct cctgacctac gcccacctca acgcccacat cgacgaggcc atgccgaact  11520
acggtcgtat cgtcgaggtc tccgcgatgg agcgctcagc caacaccctc cgccatccca  11580
gcttcagtcg cttccgcgac ctggccagta atccaggagt caaggtatga agattcgaaa  11640
gtcccgtaac cgcaactacc cggaagatat ggtgtaccac gccaccaacc gggattcact  11700
gctgtatccg aagtacgtca tgggttccgt gttcatcagc caggacggaa cattccgcat  11760
ctgcgtcatg gcagggacct gggaccacgt tgggtccgaa gttctgcatc atgcacggga  11820
catccaatcc cttggcgccg gtcgccgtaa gttgcaccgg gtcatgcgac ggctgcgccg  11880
caatctgcaa caggtaggag tcaaggtatg agaatgccaa ccgaagaaga acgcacgatc  11940
cgctgcctgc tggcagatat ccacgaaccc ttgaacctgc tgttccccgg tatccgtgta  12000
aaggccgaga caatgccctt gggctgggga gatagtatct gtgccctggt actccgggtg  12060
agctacgaac atctcacgct ggggcgcctg gagtacatgc acgaggtccc catcctgcac  12120
ctgtcgcagt ggggccggga cggcctgcta cagcacctga tgaacgagat tccccgtcgg  12180
gtgctggatg gcatgctacg tcaggcacag aaatacagcc agagtaactg gtacagcaaa  12240
tgacgactat ccgaatcctc gacctcgaaa ccgagagcta cgagcacaaa gggcgcaagg  12300
cgtcgccctt tgacccccgc aactatatcg tcatggccgg ctggcgtgac gatgttgacg  12360
```

```
gcaaggtcgg ccagaaggtg gagcatcgct tccgcagccg ggccgaagcc gaagacccga  12420
acaaccgctg gttcaacctc gacggcgtgg acgtgatcgt agcgcacaac gccatgttcg  12480
aatcgaactg gttcttcacc cgctaccggg acgagtacct ggccttcctg cgacgtggtg  12540
gccgggtctg gtgtacccag caggccgagt atctgctgag tcatcagacg tggctgtacc  12600
cggcgctcga cgagctggcc ccgaagtacg gcggcaccca caaggtggac ggcatcaaga  12660
tgctgtggga ccagggtgtg ctcacctcgg agatggacca ggacctgctg agcgaatacc  12720
tgtctggccc gtgcggcgac atcgagaata ccgccctcgt attctacggt cagttgatga  12780
agctccaggc ccgtggcatg tgggctggtt acctggagcg ctgcgaggcc ctgatcggtt  12840
tctcggcgat ggagtgcgcc ggcctgaagg tggacctcga agtcgccaag gtgaaccacg  12900
ccaagcaact ggaagaggtg gccgggatcg aggccgagct gaagaagctg atgcccgact  12960
tcccggaata cttcgagttc aagtatacca gcctctacca tatgagcgca tggctatacg  13020
gtggcgaggt gcggtacaag ggccgggtgc cctacgaaga tggccggatg gagaaagccg  13080
acttcgtgcg cttcggcaca gccaagcggg ggactcctat cgagagtacc tcggtacggg  13140
tcccgatcca cgaagtgacc gaccagggtg aatggcactg gcccaccatc accgagctgg  13200
cgaccaagca cggtccggtc atcacgttct ccgccggcaa gaacaagggc agcgtcaaag  13260
tgttccgtga ggatacggac atcccggcga ccaagtggga cgatgaccag cgattccggt  13320
tccccggcct gatcaacctg accaacctgc cggaagtagt gcgtgagaaa ttcctgggca  13380
agcgcccgga gttccagtgc gccctcaccc tggcggatgg atcgcccgtg ttcagcacca  13440
gcggcgacgc cctcaaggct ctggagaaac agggcttcga ggcggccaag ctgttgatgc  13500
gcctggccga gctgcacaag gacaactcct cgttctacat cacccacacc tacaacaagg  13560
atgggacgat taaggacacg aaggggatgc ttcagtacgt ggacgatgat ggtatcatcc  13620
accactcgct gaatacgacg gcgacggcga caacgcgtct gtcgtccagc cgcccgaacc  13680
tccagcagct cccgtcgaag gacgaggacg acccggaagc cggcagccgc gtgaaggaga  13740
tgttcgtgtc tcgcttcggc gcagacggga tgatcggcga gaccgactat accgccctgg  13800
aggtggtgat gttggcggcc ctgtcgaagg accggaacct cctggcgaaa ctgatggccg  13860
gcactgacat gcacttgtac cgcctggcag ggaagcacaa caactggaac gggttcgact  13920
acgaccagct cgtggccatc aagaaggacc ccaaccaccc gtggcacggt cgcatgatgc  13980
aggctcgaaa gaacatcaag cccaaggcat tctcggcgca gtacggcgcg agtgcggctg  14040
gtatcgcatt caacaccggc tgtaccgtgg aagaggccca ggaattcctg gacaacgagg  14100
cggccctgtt cccagagtcc atcgcattcc ggcagatcgt ccgagacagt gcagaggcca  14160
ccagcctcgt catgtacaag gccgaggacc agatgccggc aggcgccttc agcgagatgg  14220
ggccggatgg caactggcgc cagtaccgcc ggggattctg gcaagcgccg ggtggcacct  14280
gctacagctt ccgccaacag gagcgctggg acaaggaaca gcgcaagacg gtcatggact  14340
tcaaggacac gcagatcgcc aactactgga accagggcga ggctgggttc atgatgaccg  14400
tgagcgtagg gcgcatcttc cgttggatgc tgcatcgccc aggattcatg gtcaccgagt  14460
tcctgatcaa caacgtacac gatgccgtgt acaccgactg ccacaaggac accgccgccg  14520
aggtcaacaa gggcgtgcgc gacatcatgg ccgacgctgc ccgctacatg agcgagcgcc  14580
tgggctacga catcgccgac gttccgttcc cagcagtggc tgagatgggg ccgaacatgt  14640
tcaatatgga ggtgatccag tgaaagaact gcacccgctg cacacgcctg agttcgtcaa  14700
gacattcctg gaccagaccg ggtgcctgcc gggagtacgc cgtacgggtc gcaccaccgg  14760
```

```
cattgctcta caggccattg gcatggcgct gtcccatccg agggaaaccc tgacgttcgt  14820
ggaccacccg gacggcagcg cggcagcact ggtggccagc attgaaacca tactggcgac  14880
cctgggctac aagaacgtcc tcgttcgacc cacaacccgt gcggatgggc gcagcgtgag  14940
catcgtcttc aagacgctgc cgaacgcctg acgacccttc cctactccgg ccttaaatct  15000
tcatccgaca cgagagagac cacgcatgac tcaacaactc aacgctctgc aagccgccct  15060
cgccctggcc aacaaggctg ccgagaccgc aaccatcgac atgtccgaaa cctccaccgg  15120
cggtggcggc ggtcgcatct tcccggcggg caccgccatg ggccgcttct gcatctacat  15180
cgagctgggt gaccacgcca aggaattcca gggcaagctc aagaacccgg cgcctcaaat  15240
ccgcctgggc ttcgcactgt ggggcgacgt gaacccgcag gccggtaacc cgcagagccg  15300
cccggacgac ctgttccaca cttacgaggc cgacggctcg atcaagcccg gcctgttccg  15360
taccttcgag atgaccctcg gcaacaacga aaagtccaag accaagctgg ccttcgacaa  15420
gatgaactgg agcgggcagc atacccactt cgctcagatg ctcggccagg cgttcatcat  15480
cccgatcaag cgcaccaaga tcaccaaggg caacaacgcc ggcaaggaac gcaacgacat  15540
cgattggggc ggcatcatga agccctacaa cccggtcgat ggcagcccgt acaacgtgcc  15600
ggaactgccg atggacctgt tgcagtattt cttcttcgac gcgccgacca aggagacctg  15660
ggacgccctg tatatcgagg gcacctcgga caacggcaag tccaagaact tcctgcaaga  15720
gaccattcgc tcggccacca acttccccgg ctcggccctg cacatcatgt tgggcggcgg  15780
cgacgatctg atcatcaagc caacgagcca ggccgcaggc agcaacctgc cggcagtgcc  15840
caacgtggcc gccgatgcag gcgtagcagc agcccctgcc gtcccggcag tcccgcaggc  15900
agtggctcag acggccccca gcgtgcccca ggtggcgaat gtggctgccc ctgtggtagg  15960
tactgccgag gcgcagaacg tgctgcctga cgtgccccag gtggctcaga cggcggctcc  16020
ggcagcggtc gaagtcccgg cggtcccggt agtgccggca gtaccgcagg tctaatgcgc  16080
ctgccatcgg aagagttcct ggcaggacta tccgcgcagt tcgaccgcag catggcaggc  16140
gggacgttgg tgtgtgacgc cgatggaccc gcctacgtgg ctgcggccac tgctaagacc  16200
ctggacactg cactccgaag attctggaag ctcattttgg agcagcagtt cctagcgcac  16260
tgcacaggga cacgggttca cctcacggca gcaggtgggg cgaaggcgta ccgcgacacg  16320
tatccgacca tgaaaccgta ccagggccag cgcaagggca aggcaaagcc cgcgctgctg  16380
gagccactgc ggcgggccgt ggcggacgtg catgagcgag gcggggcgcc ggaggggatc  16440
gatgtcatcc tgcacacgtt cttcgaggcg gacgacggca tgatgatgga cgcctacgcc  16500
atgcaggaca aggccatcat ccggtccgac gacaaagacc tgcggatgac gatctacccg  16560
tattgggaga tcgatacggc gtgtgtgagc aggatcgaag gcggcttcgg ctacctcaag  16620
gaagcgtaca cgccttccgg ccagttcaag ctcaagggcc atggacggaa gttcttcttg  16680
gcgcagtggc tcggcggcga caccgctgac aacatccgag ggatcgatcg attcaacggt  16740
aagctctgcg gtatgaagac ggccttcgac atcctccatc cgatcacgga tgaggacgag  16800
gccatcgaca tgatcctgga ggcgtacgcc aagatcaagc aaaacccgct ggcagaggcc  16860
gaggtgctgt ggatgcgccg aacgcctacc gacaacgcag cgcagtacct gttaagccgc  16920
gaccttcgtc cggccttccg ccagtggatc atcgagctgg acgcctacca cgaggcgctg  16980
ctccagaagc ggagggagag cgattatgac gagtgagccg aaggtctacc agataccgcg  17040
cagtcaacag cgcaccttca ccctgaagct atgggccgag cagaacaagc tgtgcccgct  17100
```

```
ctgcggcaag cccatcgata tcagcgtgaa gggcgaagcg gtgatggacc acgaccacga  17160
aacggggctg gtgcggggcg tcctgcaccg gtcctgtaac accgcagaag gcaagataac  17220
gaatgcggca ggttcctggg gatgcaagtc gatgaagtat tcagacatca tcccctacct  17280
tcgtgccctc ctgacgtatc tggaggggcc gaagcatccg ctgatctacc ccctgcacaa  17340
gaccgacgag gagaaacacg aagcgaagct ggccaagcgc cggcaggcag ccgccaaacg  17400
caaggcggcg atggccgtcg caaagcacaa cgcgaggaac gtatgagcaa actccgcaag  17460
caattcacca atgagtacct gcgaaacgtc tatgtcgagc tgggcctcaa gaagggtgcc  17520
gagcacctga ccgagcattc gcgcttcggt gaggtgagcc gccagtgctt ccgcaactgg  17580
tgcatcaagc tgggcttcca cgacagcagg acgcgcggca tgtacgccaa gaagggcgcg  17640
atgcactggc tgggccgcaa ggctgccgag gtagtgcgca agttccctgg cgccgtgggc  17700
aacgtggtag gccagggtcc gaaggtgctg agcctggaca tcgagacctc gcctatcgag  17760
ggctgggtct ggtcgctctg gaagcagaac gtgggcctca accagatcaa gcgggactgg  17820
accatcctgt cgttctgtgc gaagtggatg cacagcgacg aggtgatcta catggactgc  17880
cagggtgatc ccttggacga catgcacctg ctggtcgcgc tgcacaagct gttggacgag  17940
gccgacatca tcatcgtcca gaacggcaag cgcttcgacg tgcccaagat caacgcccgg  18000
ttcttcctga acaagatgcc gccgccgcga ccgttcaagg tgatcgacac cttgatcatc  18060
gccaagcagc aattcgcgtt caccagccgc aagctggagt acatgaccca caaggcatgc  18120
accatcaaga agcgactgca cggcaagttc cccggattcg acctgtgggc ggcctgcctc  18180
caggacaacc cggaggcgtg ggaagagatg cgcctgtaca acatcgacga cgtacggtcg  18240
atggaagagc tgtacatcct gatgcgtcca tggttcgtcg gccaccccaa cgtggccgtg  18300
tacttcaatg acgccgaacc gaccatccgc tgcccgaagt gcggcgacac ggatgttaag  18360
caagaaggct gggtgcatac gcagaccggc aagtacgagc actatcactg cggtggctgc  18420
ggtggctgga gccgagggcg gtacacccgc aacacctcgg aacagcgcaa agccctgctg  18480
agcaactaag gaggtagcat gagcctagca ttcccggact cttacgagtc gacgatcacg  18540
actgaaccgt accgcaaagg tgcgagtctg gaagaacgca aggtcggcaa gcttcccatg  18600
cacctggtag tcgaggggtt cccgctgctg aagcgggagc ttgctcgaat gatgcaatgg  18660
gctgccgagg tcaaggggta tctgccgcac gactggaaga agatgacggt gggcgagttc  18720
aagtccgccc aacacaggca cgagtccaag cggctgatcg acgggccgct ggatgacgag  18780
tccaacctga tgcacctggt gcatgaggca ttcaacgcaa tggccgccgc cgaggtggcc  18840
ctgatggacc gggagaaagg caatgagtaa aatctgttgg tgtacccgac cgcacgagac  18900
cgatgaaggt gttcgggtca tctgggcctt caacgagcgg ggcatcgggg tcaactacgt  18960
cacagcgtac atcacgccgg cgatggtcag ccatcgggac tggagcgatg tcatactccc  19020
ggacattctc cgggagatgg cggagcgcct ggagcgggaa gtgaagctgg tggaactgcg  19080
ctggttccgc gctgagattc tgagctgcgg ggaatggcgt gactaccgag cgatgacgct  19140
ggagggggcg gttagcctgg ccgaggccga gtggggtccc gaggatatcg ggcgcgtaat  19200
cgaaagacga taggagatgg aatggacctg atacagcagc agatcgccca cgaagaggcc  19260
ctggtcgggg cggcgcagaa tgacgcccgc attgccttgg aaaaggcgat tgcccaaggg  19320
tccatcgacc gcatcccgag ggcgcgcatc atgttgatgc ggatgctccc catcgtgacc  19380
gaagcgatct tcgcccacca ggaagcgaag gcggcggggc cggcagcgaa gcttcggcac  19440
ctgctgcgga tcatcgacgc ccaggacctc gcggtcatgg cgctgcgggc tgggctgtcg  19500
```

```
atgctcatca actacccaac gatcacagcg acgaagtatt acacccacat gggtaagata  19560
ctctgtcgag agatcgaagt gcggttggcc ttcaaggtca accaacccta ttacgaccgg  19620
acgctggact acctcaagac cagcaggact cgcagcgtcc ggcacatcca gaagacgatg  19680
gacgctcttc tggacgcggt actaccggaa gaggcacgta tcgacctgcc ggatggcgac  19740
tacctgcgcc tcggcaagtt catcggtgat ccgctgatac agtgcggcct gttcgagccg  19800
aaccgcttca caggtcgtgg aggtactagc gtccacctgg agccgtcgcc ggaagccaag  19860
gagttcctgc aagacccttc ggcggcgatg acctggggag gcccaggccg tagcgtgatg  19920
ctggcaccgc cgcgaccatg gaacgactgg tgcgatggcg gttactacag cgctaaggcg  19980
cagaaacacc atgtgctagt gcgccgtacc aagcaccaga ccaagcgggc gcgccagatg  20040
cagctacgcc acctgggccg ggacaagatg cccagggtgt atgaggcggt caacgcgctg  20100
caatcagtgg cctacgagat caaccacgac gtgtacgaga tcatcgagcg cgtcttcact  20160
tccggcggcg gtgtgctggg catccctcag cgcacctacc cggacaaacc tgagttcccg  20220
ctcggcgacg agtgggccaa ggagaacgcc agtgaacaag agctggaagc cttcaaccgc  20280
tggaagcgat ccgtccaccg atggtacacc ggcgagcggg agcataccgc caagcttcgc  20340
gagtttgctg cactctaccg agttgttcga gagcatcatg gcaaggcagt gtacttcccg  20400
atgcacgttg actcccgtgg ccgcatgtac tattggggca caccgaatcc ccaggggtcc  20460
gacatcgcca aggcatgtct gcgattccac gaaaagcgtg ccctcggtaa gcgcggactg  20520
tactggctca aggtccacgt cgccaactcc ctcggatgcg acaaggtgta cttcgacgac  20580
cgagcagcct gggtcgatga gcgctgggac gacttccagc gagcgctcga cgaagggccg  20640
gagaactatc cgaatctctt ccccgaagac gagtccccac tgtgcgccat cgcaggtctg  20700
ctggagttgc gggcggccta cgcttccggc aatcccgagg gctacgccag tggtttcatc  20760
gtccacatgg acgccacctg ctccggcctc caacactact cggctattct ccgcgacgag  20820
atcggcgggg cctacgtcaa cctgctgcca cctggacttg caaaagctga tatctactcc  20880
cgagtgctcg gactcgttaa tgagtctctg gagagagacc gagcggaagg cgcggatggc  20940
gaggcgcggg gttatgccat tctatgggat aaagctggtc tgacgcggag cctgaccaag  21000
aagccctgca tgacgctggt gtacggcacc acgttcaagg gcgtcgtgga ccactgcctg  21060
gactacctcg acgagtccgg tgtggagatt cccgagggtg tgccgtcata ccgcctagga  21120
agctacatgg cgacgctcat actggacgca atccgcgaga cagtaccatc ggcagtcttc  21180
gccatggagt ggctccagcg gcttgctagg gcccttcctg acgcatccaa ggatttgcac  21240
tggaccacgc cgctcggcat gcaggtcttc cagtcctacc cgaagaccga ggaggtgcga  21300
gtacggctgc gcgccgaggc tgtcgagtac gtcaccctgt acgaggccaa ggacgagctg  21360
gacccggtac gcaacgccaa cggcatcgct ccgaacttcg tccacgggct ggacagcagc  21420
cacctgggcc tgacggcctt ggcatgcgcg gcagagggaa tcccgatcca ggccatccac  21480
gacagcatgg gcacttatgc ggcagacgtg gaccggatgc acgttcacat cagggagcag  21540
ttcatcgcca tgtacagtgg cccctgtgtg ctcgtagagc tggcaaagca gcttggtata  21600
gaggctaccc cgcccccggag aggatcgttg aatctggagg ctgtacggga ctcctgggcg  21660
ttcttctgct gaggcggatt atgtcaccca cataggagca agtgcatccg tccaaggccc  21720
tcgtagaggg agcgggggag aggagaggtc agggaagacc tggtagagga gaggtgaaga  21780
tgagaatgga tgactacgaa ggattctaga tagaatagac taaccagcat aggagatatg  21840
```

```
atagatggct actatgaaga cccaccgccc tacggttatg tcacccacag tggaaggatc  21900
gagaacaggc aagggtacgg cccgtcctgt cacgttcacc tctcagcaga tcgagtggtt  21960
agaacagacc ttccccgaac atcagatcgg tcctggaacc acgatggaag acatccagtt  22020
ccaggccggt aggcgagacg tggtgcgagc agtacgcctg cgccgacgcg atgccatcgc  22080
agtggagctg aagtgatgaa caagtccatc tggcgagtcc acgcaaaggc cggcactccc  22140
tcggaactcc agggcctgtg ctggctggcg atacaggagt tggaggagtt caccctcttc  22200
cgctcgaaag acgacgccct gaatgcgatg ctggacagta tcgagggcaa tgatcgaacc  22260
gagctgttgg tattccgcga tggccagttg gctggcggtg cctgcattgt gttcgaggac  22320
gatccccacg tcggcccgtg cgtcacagca cagtggcagt acgtcctacc gcgctaccgc  22380
aatacaggcg tggtccggga gttcatccgc gaactccacc gtcaggccgg ctggggtcaa  22440
atccccctcg tgtgctggag ccatcgtgaa agcgatagcc ggtacacgat ccactaccgg  22500
agagccaagc cttatgggca agaaagtaaa gaaggtgctg ggcaagacca tcatcggcaa  22560
actcgctgat ggcctgctgg gcaccgacct gagcggcgca caatccgatg cccgcaagat  22620
ggaagagcag aaccgcctaa tgcagcagca ggcggaccag ctcgcacgaa accagcaggt  22680
tgacctcacc gccgagaacg tggcgcaggt tgacctagga gcgatggccg atgccactgg  22740
caccggcacg cgacggcgcc ggaatcaggc gggcacaggc gtatcgcaaa ccctcggtat  22800
caactactga cgaggtacgc catgaaaacc accgcagcta tgctgtggga gaaacttcgg  22860
gatgggagcg tggagagtcg agccatcgag ttcgccaaga ccacgcttcc ctacctgatg  22920
gtcgatccca tgtccggcag ccggggagtc gtagagcatg acttccagtc cgccggtgcc  22980
ctcctggtga acaacctcgc cgccaagctg gcgagatcgc tgttccccac ggggattccg  23040
ttcttccgat ccgaactcac tgatgcgatc cgccgcgagg ccgacagccg ggacacagac  23100
attaccgaag tgaccgctgc cttggctcgg gtggatcgca aagcaacaca gcgcctgttc  23160
cagaacgcct ccctggcggt cctgacgcag gtgatcaagc tactgatcgt gactggcaat  23220
gctctgctgt accgagacag cgccgccgct acggtggtcg catggtcgct ccgctcctat  23280
gcggtgcgtc gagatgcgac tggccgctgg atggatatcg tcctaaagca gcgctacaag  23340
tccaaggacc tggatgaaga gtacaagcag gacctgatgc gcgcaggccg caacctatcc  23400
ggttcgggca gcgtggacct gtacacccac gtacagcgca agaagggcac ggcgatggaa  23460
tacgccgagc tgtaccacga gatcgacggc gtgcgtgtgg gcaaggaggg ccgctggcct  23520
atccacctgt gcccgtacat cgtgccgacc tggaacctcg cacctggcga gcactacggt  23580
cgaggccacg tcgaggacta catcggcgac ttcgccaagc tgtccctgct gagcgagaaa  23640
ctcggcctgt acgagctgga gtcgctggag gtcctgaacc tcgtggacga ggccaagggt  23700
gcggtggtcg atgactacca agacgccgag atgggtgact acgtgccagg tggcgcggag  23760
gccgtccgtg cttacgagcg tggcgactac aacaagatgg ctgctataca gcagagcttg  23820
caagccgtag tcgtccgcct gaaccaggcg ttcatgtatg gtgccaacca gcgcgacgcc  23880
gagcgcgtta ctgccgagga agtccgcatc actgcggagg aggcagagaa cacgctgggt  23940
ggtacatact cgctcttggc tgagaacctc cagtcgcccc tggcctacgt ctgcctatcc  24000
gaggtggatg acgcgctact ccagggcttg atcaccaagc agcacaagcc ggctatcgag  24060
acgggcctcc cagctctgtc ccgctccgcc gctgtgcaga gcatgctcaa cgcttcccaa  24120
gtcatcgctg gcttggcccc gattgctcag ctcgatcccc gcatctcgct accgaagatg  24180
atggacacga tttgggcagc cttcagtgtc gatacgtcgc agttctacaa gagcgccgac  24240
```

```
gaactggaag ccgaggcaga acagcagcgc cagcaggccg cacaggccca ggcagcgcag  24300
gagaccttgc tggaaggcgc ttccgacatg accaatgcac tcgcaggagt ctgatagatg  24360
acccaaccga acgatcagca actgccaccg ggcctcgcta acctggttgc caacgtaccg  24420
cccgccgccg cgccgacccc gagtcatgtg caggtgttgc cgaacccggt gatccagccg  24480
caggctccgg tccagcccgg ccaggtaggt gcgccgcagc aactggccat cccgacccag  24540
cagccgcaac ccgttccgac cagcgccatg acgccccact accagccggt agcggtgccc  24600
gtcgccggtc aacccgttgt tccgcaagca cccgctcagc cggccccggt agctccgccg  24660
gctgcgggtg cagttcttcc cgagaacctg gaagtcccgc cgcctccggc cttcactccc  24720
aacggggaga tcgtaggcac cctggcaggg aacctcgaag gcgacccgca gttggcgccc  24780
tctatcagct atctggaagc attctctgac aagctggata ccgtccgtgc cttcggcaag  24840
gccgccgaga accgcgatcc gcgattcatc gacgagcact atctgaagga agtcctgggt  24900
ccggcccagg cacagcacgt catcaacgtg gccaagggcg tcctgaccta tgtcgatgcg  24960
cagaccaagg ccgtcctgaa tcagacctat gccgccgtcg gcggtgaggc cgtcctgaag  25020
caggctgccg gagtcttcaa ccagcacgct gacccggcca ccaaggccgc catcggtcgg  25080
ctgatggact cgggcgatgc ccaggccatg cagtacgcag cgaagcaaat tgtggccttc  25140
gcacaaggct cgggtgccgt ggtacaggct accggccaac ccctgggtgc tgcggcacct  25200
gcactggcag ctctgagcgc tgagcagtac cgcttggaag tatctaagct gccgctgaac  25260
gcatccgaag ccgagatggc tgcgctgcgc gagcgtcgta aggcaggcat ggcgcagggt  25320
atctaacgac cctgccctac tccggcctta aacccacatc caaaagagag agaatcgcat  25380
gagctttctg aacgacctga ctcgtccgaa ctacgctggc aagaacgcgg acgttgacat  25440
ccacctggaa gagcacctcg gcatcgtcga taagcacttc gcctacacct ccaagttcgc  25500
accgctgatg aacatccgcg acctgcgtgg ctcgaacgtg gtccgcctgg atcgcctggg  25560
taacgtcgag gccaagggtc gccgcgccgg tgaagagctg gagcgcagcc gagtcgtgaa  25620
cgacaagtgg aacctgaccg tcgacaccct gctgtacctc cgccaccagt tcgaccacca  25680
ggacgagtgg acccaatcct tcgacatgcg caaggaagtc gccgagctgg acggccagga  25740
actggctcgc aagttcgacc aagcctgcct gatccaggtg atcaaggctg ccgcgatgga  25800
cgcgccggtg gacctggaag atgcgttctc gccgggcgtg ctggagaaac tggacctgac  25860
cggcctgacc gccaagcagg ctgccgacaa gatcgtccgc atgcaccgcc gcgtagtcga  25920
gaccttcatc gaccgcgacc tgggcgatgc ggtttactcc gagggcctga ccccgatgtc  25980
gccgcgtgtg ttcagcctgc tgctggagca cgacaagctg atgaacgtcg agtaccaggc  26040
aaccggcgcg accaacgact acgtgaagtc ccgcgtggcc atcctcaacg gcgtcaaggt  26100
gctggagact ccgcgcttcg ccaccaaggc aatcgcagcc cacccgctgg gccgtcactt  26160
caacgtgagc gccgaggagt ccgagcgcca gatcgccctg ttcctcccga gcaagaccct  26220
gatcaccgcc caagtggcgc cggtccaggc caagctgtgg gaagacaacg agaaattctc  26280
gtgggtcctg gataccttcc agatgtacaa catcggtgcc cgtcgtccgg acaccgctgg  26340
tgccatcgaa ctgaagggta tcggcgcctt cgacatcacc gcgtgatgcc acgaaacccc  26400
gcacttcggt gtggggtttc ttcaaagcct aacgacccgc gcagattccc tgcgtgggtt  26460
tttgcgcttt aggagaaacc ctatgctact actcgacgca gtgaatgtca tcctgcgcaa  26520
gatcggcgag ctgccgattc cgagcatgga tgagacgtat cccaccatgg ccattgccct  26580
```

```
cccggagttg gaggaccagc gcatccagtt gctgacgcaa ggctggtggt tcaacacctg  26640
gtggaagcac aagctgacac ctgacccgca gggtcgcatc aacctgccca aggatacctt  26700
ggcattctac cccgactccc cggacctcca gtgggacggc ctgggagtac gggatgccaa  26760
caccggcgac gaccgtatcg gcaagtcggt cgagggtcgg ctggtgctgt cccgcgagtg  26820
ggaccgtatc ccggagattg cgcagcgcgt cattgcgcac caagccgccc ttgcggtata  26880
cacccacgag attggcccgg acgagaccgc ccaggtcatc gcccaggaat tgcaggcgta  26940
tcagaacgaa ctgtctcgca tgcacactcg atcccgtccg ctgaacaccc aggccaagcg  27000
tagcttcagc cggtggcggc gtagcttgag gacctgagca tgagctacaa gcaatccgcg  27060
tatcccaatc tgctgatggg cgtgagccaa caggtgccct tcgagcgcct gcccggccag  27120
ctcagcgagc agatcaacat ggtatccgac cccgtgtcgg gactgcggcg gcgcagtggt  27180
atcgagctga tggctcacct gctgcatacc gaccagccct ggccgaggcc gttcctctac  27240
cacacgaacc taggtggccg cagcattgcg atgctggtgg cccaacaccg tggcgagctg  27300
tacctgttcg acgagcggga tggacgcctg ctgatgggcc agccgctggc ccacgactac  27360
ctcaaggccg acgactatcg gcagctacgg gccgctacgg tggcagatga cctgttcatc  27420
gccaacctga gcgtgaagcc cgaggccgac cgcaccgatg tcaagggtgt agaccccaac  27480
aaagcgggct ggctgtacat caaggccggg cagtattcga aggcattctc tatgaccatc  27540
aaggtcaagg acaacgccac gggcaccacc tacagccata ccgccactta cgtgacgccg  27600
gacaacgcca gcacgaaccc caacctcgct gaggcgccat tccaaacgag cgtaggctac  27660
atcgcgtggc agctctacgg caagttcttt ggtgcgccgg agtacactct gcccaactcg  27720
acgaagaagt acccgaaggt ggacccggac gccaacgcgg caaccatagc cggctacctc  27780
aaccaacggg gcgtgcagga cgggtacatc gcgttccgtg gtgatgccga tatcgtggtc  27840
gaagtgtcca cggacatggg caacaactac ggcatagcct ccggcggtat gagcctcaac  27900
gccacggcag acctgccagc cttactgccg ggcgcgggtg ctcctggcgt gggtgtgcag  27960
ttcatgggcg gcgctgtcat ggccaccggc tccaccaagg ccccggtata cttcgagtgg  28020
gattccgcta accgccgctg ggcagagcgg gccgcctacg gcaccgattg ggtcctgaag  28080
aagatgccac tggccctgcg ctgggatgag gctaccgaca cctacagctt gaacgagctg  28140
gagtatgatc gacgtggctc cggcgacgag gatacgaacc ccacgttcaa cttcgtcacc  28200
cgaggcatca ccggcatgac gaccttccag ggtcgcctcg tcctcctgtc gcaggagtac  28260
gtctgcatgt cggccagtaa caatccgcac cgctggttca agaagtcggc agccgcgctg  28320
aacgacgatg atcctatcga gatcgcagcc caggggagcc tgactgaacc gtacgagcac  28380
gcggtcacct tcaacaagga cttgatcgtc ttcgccaaga agtatcaggc cgtggtcccc  28440
ggtggcggca ttgtaactcc ccgcacggcg gttatcagca tcaccacgca gtacgacctc  28500
gataccaggg cggcacctgc cgtgactggc cgcagtgtgt acttcgctgc ggagcgtgcc  28560
ctgggtttca tgggcctgca tgagatggcc ccgtctccgt ccacggacag ccactacgtc  28620
gccgaagacg ttaccagcca catcccgagc tacatgccgg ggcctgctga gtacatccag  28680
gcggcggcct ccagcggcta cctggtgttc ggcaccagca cggcggacga gatgatctgc  28740
caccagtacc tctggcaggg caacgagaaa gtgcagaacg cgtttcatcg ctggacgttg  28800
cggcatcaga tcatcggcgc ctacttcact ggcgacaacc tgatggttct gattcagaag  28860
ggccaggaga tcgccctggg acggatgcac ctgaacagcc tgccagcccg tgagggtctg  28920
caatacccta aatacgacta ctggcggcgt atcgaggcga ccgtcgatgg tgagctggaa  28980
```

ctgaccaagc agcattggga cctgatcaag gatgcctctg ccgtgtacca gctacagcct 29040
gtggccggcg cctacatgga gcgtacccat ctaggcgtga agcgcgagac gaatacgaag 29100
gtgttcctcg acgtgcccga ggccgtggtc ggggcggtgt atgtggtcgg ctgcgagttc 29160
tggtcgaagg tggagttcac tccgccggtt ctccgggacc acaatggcct gcccatgacc 29220
tcgacccgtg cagtgcttca tcggtacaac gtaaacttcg gctggaccgg cgagttcctg 29280
tggcgcatca gcgacacggc tcgacccaac cagccgtggt acgacacgac gccccttcgg 29340
ttgttcagcc ggcaactcaa tgccggggag cctctggtgg atagcgctgt ggtgccgctg 29400
ccggcacggg tcgatatggc cacgtccaag ttcgagctga gctgtcacag tccgtacgac 29460
atgaacgttc gggctgtcga gtacaacttc aagtccaacc aaacctacag gagggtgtga 29520
tggctttctg gctaccacta ttggccgctg gcggcatgtc cgcccttcaa cagggattgg 29580
ccaacaagga agagcgcaac aagatcaagg ccgagaacaa ggctcgactg aagacggacc 29640
tcgacaacct gggcgccgct gcccgcgaca tcgccaacct cggagtcatg gctgctagct 29700
accgcaagca agccgtggcc tcgcaggtgg aggccaagcg ccaggggatg ctagccggcg 29760
gaagcgccga ggctcaggcc ggggcgttcg gcgtcaaggg tgcatccgtc gatgcggtgg 29820
ccctggatat cgagcgggag gtcggcgagg ccctgatcca gattgacgac aacctggaca 29880
atcagatgtg gaacctcgcc gagcaggcgc actccatcca ggctcaggct aaggccggcc 29940
tgctgggtca gaagagtacc acggcggggc aacggtcccc gctggtggcc ggtctgatgt 30000
cggcgggttc cctgtacgca agtcaatact tcaagttcgg cgccacgcct aaaggaggca 30060
actgatggcg gaatcgcaac gtgcttccca agagcttggg atcaacgtcg gacagacgca 30120
actccagccg ggccagagtg ctcggcgcgg agtgcgcgac tccgaggtca actacagcgg 30180
tccgagcgta ggctcgcaga ttctcgacgg catcctgggt gccggtcagc agatcgctgg 30240
caaatggttc gagcacaacg tgcagcagga agttctgcgc ggtgagcgtg cccgtatggc 30300
cggcgaggcg gaggaggcag tagacagcaa cgtactggcc aaaccattcg tgaagggtgg 30360
ttggcgtaag caggactacc gtatcgccca ggcggacttc agcctgaaga tgcagcgatt 30420
catcgccaac aagggccggg agatgactcc cgaggagttc cgcaagtacc tgtcccagga 30480
ggctacgcac gtcctggact cgaccgaggg catgaacccc aacgatgcct tacaggcgct 30540
ggcgcagcag cagaaggccg aggaacagct cttcggcatg caggctaagg cgtacatgga 30600
ctggtccatc gaccaggccg cccgtggctt ccgtacccag ggtaacagta tcctggccaa 30660
ggctgtgcag gctcaggcca ccggcgacga actgtcccgg cagctcagcc tggaagaggc 30720
cggcctgttc tataccaaca tcatgacctc cgaggatatc ccgctggagg tgcgcgacaa 30780
ggtaggcatg cagttcctgg cggccagcct ggacatgaac cagcggggca tctatgaggg 30840
cctgcgcgat gccgggttcc tggacagtat gtcctttgac gaccggcgtg cgctcaacgg 30900
cctctatgaa aaatcgaagg cacagacccg tgccaaggaa tcgatggcta ccctgcgggc 30960
cgacgcggac ttccagcagc gggtggccaa cggcgccatc acagaccttg ccgaggttga 31020
agcgtactca cgaggcatgg tcgaggaggg ccgctggagc gacgctcagg ccatctcatt 31080
catgaccaag gccatgaccg gtctgggcaa tgcccaacgc atgcagggca tcatggcggc 31140
cctggaagcg ggggacatca acgccctaca cacgctgggg acgaacgtta ctgaggccct 31200
ggagcagtgg gacaagatgc aggccgccaa cggctcaagc ctgactgacc gtctcgtgca 31260
gggcacacag ctcggcctgc gcctggggac cttccccaag acctacggcg agtccgtggg 31320

```
cagcgcggtg cgcatgatcc aggccgccaa agaaggcgag gcaaacccgg agctggtcaa  31380
cacgctgaac agcatcttcg agcaggtggc ctcggcccag gagatcaacc cctccgccgg  31440
caacgtgatg ctatccggca tcccggaagc cgagcaaggt gccgtggcct gggcactcaa  31500
gcagatgaag atgggcatcg caccagctca agctctgcgc gagttcagcg ccaacgccga  31560
agtcgtgaaa cagatggacg agttcgagaa aggccagaac accaaggcat tcaaggacaa  31620
cctcggcaag caggtcaacg acaagttcgt gaacaacatc ttcggtcggg cctggaacat  31680
gctgaccggt gaaagcgacc tgagtaacaa cgaggccgtt ctcagcatgt accgtcgagc  31740
aaccatcgac gaggcgaact ggctggccag cgaccgcaag catgcgggtc tgctcaccag  31800
tgacacgggc cgcgaggccc tgctggagat cgccgccgcc aacgtgcgta accgcaccat  31860
ccaggtaggc gaaggtcgga atctgaagga aggggaccta ttcagccgcc gcgatagcgc  31920
gccgctgatc ctgccgcgtg gcaccaccgc cgagcagcta ttcgggacca acgacaccga  31980
gaccatcgga accgtcctgg ccgagcagca caagccgcat gtcgaaggac tcctcggcta  32040
caagtcggta gtcgccttcg agtacgaccg caccaggggc agcctcctcg ccgtcgagta  32100
cgacgagaac ggtgtggccc tggaccgcac gcgggttgat ccccaggcag tcggtaacga  32160
ggtgctcaag cgcaacgcgg ataagctgaa tgcgatgcgg ggcgccgagt acggtgccaa  32220
cgtcaaggtc agcggcacgg acattcgcat gaacgggggt aacagtgccg gcatgctgaa  32280
gcaggacgtg ttcaactggc ggaaggaact ggctcagttc gaggcttacc gaggggaggc  32340
gtataaggat gccgatggtt atagtgtggg cctggggcat tacctgggca gtggcaatgc  32400
tggggcaggc actacagtca cgcctgagca agccgcgcag tggttcgccg aggacaccga  32460
ccgcgcactc gaccagggtg tgaggttggc cgacgagctg ggcgttacga acaatgcctc  32520
tatcctggga ttggccggta tggccttcca gatgggcgaa ggacgtgccc ggcagttccg  32580
taacaccttc caggcgatca aggatcgcaa caaggaagcc ttcgaggctg gtgtacgaaa  32640
cagcaagtgg tacacgcaga cgcccaaccg ggccgaggca ttcatcaagc gcatggcgcc  32700
ccacttcgat acaccgagtc aaatcggtgt cgattggtac agcgccgcaa cagcggagta  32760
agacatggca aagcaattca agggccgcat gacgcccaag tatccccttg accaagtaca  32820
gctcgacgag gcccaagtac agggccaact cgacgcggtg cctaccgtgg ggttcgacgc  32880
cctgacgggt ggtgagatcg gagaacggaa cgtggcagcg ggccaacgag ccaatgcgcg  32940
ggaactggaa cgcatcgtag cggaccagga actgccggcc cttgaccgtg cttccgcact  33000
ctggaaccag tccaccctcg tcggacgctg ggtcgatgcg ctccagctcg acgcagacct  33060
tgcggcgaac agtaccggcg aggtggaccc taacttcgac gctgggacct atggggtcca  33120
ggcgctccag gcggcaggta tccagccgac tgataactac cttcagatca tggcccgtgc  33180
cggcaatgcc gaggacgcgg cctacctcct atcgaggatt caacggtatg agcaggacga  33240
acaaatcgtg cgggacaacc catactggaa cttcgcggtt ggtatgctgg acccggcagc  33300
cctggcagtt gatgcggtta ctttcggcgc tggccgtgct ctgcggctcg gtcgtgctgg  33360
catggctgct gctggcggcg ctgggcaagt cgggtatgtt gctgggctgg atgccgcagg  33420
ggccgatgtg gatgctggaa cctacatcgt ggcgggtgct cttggcgctg gcgtgggtgc  33480
tctgctgggg tctggtgcgg gacgcattgc cgcagaggcc ccaacgcaac cgcatgtgcc  33540
cgaagtatcg gcgcctactg tcgggctgcc agaagtagcc atgaccgccg aggaggccgc  33600
agcacgcggc ttcaaggcag gtgacgtggt agacctgctg gacgagggca ctgtgctatc  33660
ccgtgtcagt gcccgcgtgg agcaggctga gataccggct attccgcgac gtgacactgc  33720
```

```
cttcggcgac gagctgcata gcctgtcggg ccggaagctg tctgaggtcc tggaccacat  33780
caagacccac gcagaggtgc ccaagccgct ccagggcatc gccgccaagg tggctgacac  33840
tatcaggacc ctggagggcc tggggcagcg taccgcgttc cgtgtggtgc agggcggtga  33900
cactgccagc tctgccttcc tcaaaccggg tacggcgggg attcactcca cccagggcct  33960
cgacaccctg gtccaggtac gcggcagcac cgcacctggt cgagttggca ccaacccggt  34020
gaccgtgctc cacgaggcgg ttcacgctgc caccgtgggc gtgatgaacg ccgccctgcg  34080
caaccccggt gcgatgagtc cgaaggtggc tcaggccatg cagaccctgg agaatgtccg  34140
gggtaacgtg ctcaacgccc tgaagcagga ccgcgccgcc ggtcggcaac tgtccgagtt  34200
cgaagagaca ctgctggccg gtaactccaa caccctggcc aacgtcaagg aactggtagc  34260
ctggggcctg acggataccc gcttccagcg gaccctgaat cgcctccgct acagcgacgg  34320
cgggccgggc ctgtggtccc gcttcgtgga gggcatccgc accctgctgg gtctgcggtc  34380
cgatgctgac acggccctga gccgcgtcct ggccgcctct gagacgatta tggaggccat  34440
gcccggttac actaaggcac aggccaagtg ggccaacaag ggcgctccgg taaccgagga  34500
ggccagcctg gagaccatcg tccggtccac cagggagcgc gcccgcgagg gtgccggctt  34560
cgtgaacagg ttcttcagcg aggcagacct cctggcacag cccggagagg gcgcacggcg  34620
actcctgagc cgtcttattg acgacccggt acgtcgggat gggttcagca cgaacgacaa  34680
cgcagcgagc tatctccgcc gctatcggaa cgagttcgag ggctacgtga agtcctacga  34740
cgagatgatg gccaaggcaa tggctgagca gggtgtgggc ctgacggcac gtgcgctgaa  34800
ctcccgccgc gccatggcag tccgggacca gctcaacgag caggtcaccc gcgagctgct  34860
gcgccgggac cgggagtgga ccgcctacgg cagcgtccgc gtggacccta acctacctcc  34920
gaccatcaag gccctggccg accgctcaga cgagattcat ggtctgatgg gccagcgtgc  34980
cagggaagct ggggtgcgcg ggttcgagaa cttcgcaccg cgaccgggat acttccaccg  35040
ctcgtggaac tggtcgaaga tggcgcagat ggacgaggcc gcccctggcc tggcccgccg  35100
tgccatcagt gaggccgtgt tccgtggcat ccctgggctg gagcgcgccg acgccgatac  35160
catcgcacag gccattgtgc agcgggcgcg ggatcgggcc accggaatcc gctccgagtt  35220
catgggcgcg atgggcgtgg cggacacggc attcatccgg caggcgctgg aggaggccaa  35280
cgtgtcccag gccaagttcg acagcatcat ggccaagatc gagcagaagc agtccgacca  35340
gggcaccgtc aagtacggca agggccggct gtcgctggac atgaccgccg agatcaacca  35400
caacggcacc gtgtatcgtg tgcaagacct gatcgaccgg gacctcgacc ggctgatgga  35460
gaactacgcc ggcagtatgt cgggccgctc agcattggcc cgcgcaggca tgccggggga  35520
ctcggagatc gaagccttca tccgggagta ccagcgagag gcagcccacc tgggcaccga  35580
taaggtgcag gagctgacgg ggcaactgcg gggagtcttc ggggacttca ccggcaacgt  35640
gccgagggag catcagctcg gcccggttgc tcagcgggcc agcggcctaa ccagcgccac  35700
catgctggga ttctccggcg tgtaccagct cgccgaactg gccacgatgg cgcaccgtca  35760
aggcgtcttc aacgtcatga aggccatgct gaactcccgc ctgggagact tcgtgggcgc  35820
catgcgtcgc gacccggacc tcgctgacga gatgcagacc gtcctcggcc tgaacctcgc  35880
caacgatatc cggatgaagc cctggaagcg gcagttcgac accttcctgg tcagccaaga  35940
caccttcatg gatcgcttcc tccacgcagg taagcaggct gtcccagtgc tcaacggcat  36000
gaagttcatc cacaactggc aatcccgtat gaacgccaac ctcaccttga acaaggtggc  36060
```

```
gcgggcggcg caggggggatg aagcagccct tcgcgtgctc cagcagtacg ggaaggacgt  36120
ggactggacg ccagtcctgg cgcgggttcg cggttatgtc acatacagag gaaggaacgc  36180
ccgatccatg aattggggcg cctggagcca agcagacgtg aacactgtca tgaacaccgc  36240
actgcggatc atggacgact cactcctgta cggtagggtc ggtcagaact cgggcttcgc  36300
tcggtctccg gtcggtcaaa tcctgggcca gttccgcagc tttgtggcct tcgcacacaa  36360
caagctcctc cggggaacct atgagaactc cggcgtgctt ggcgtggcct cgctcctcgc  36420
attccagtat ccgctcaccg cgctgatgat gggtgccaag gcagcgatca acggcaagtt  36480
cgacacctct gatgaaggca tccgcaagat ggccatcgac ggcatcggtt acactgccgg  36540
cctcggcttc accgccgaca tgtggggtgt gatcaccggg cactcccgga tgtccgcacc  36600
ggtctttggc ctggcggagc actccaacga ggtgttccgc ggcgtcaagg acctagtaac  36660
cggcgacgac cccgcagccg ccaccggcga tatcgtcaac ggcgccgcag gggcactgcc  36720
tttcgtcaac gtattcccgg cgaccaagtt gctgctggaa tccatcaaag gggaataacg  36780
tggctcggtt caagaatccc gagaccatcc acgtcgcaga tggggtcgag gctgtcttca  36840
gtctcgactt cccgttcctg cggcgtgagg acgtattcgt ccaggtcgat aagatactcg  36900
tcaccgacta tacgtgggta gacgacacca acattcaatt ggccgtggtg ccgaagaagg  36960
atcaagaggt ccgcatcttc cgcgacacac ccgcccaggt cccggacact cagttcagcc  37020
agggcatccc gttcctgcct cgatacatcg acgcgaacaa caagcagctc ctgtacgctg  37080
tgcaggaagg catcaacacc gcgaacctcg ctctcgacgg cgtactcgac gcgatccgca  37140
tcgccgagga agctcgtcgc ctggcacagg aagcactcga cgccgccaat gaggcgctgc  37200
gccgtgccct aggcttcgcc gagattcgca ccgtgaccga ggactcggac atcgatccga  37260
gctggcgtgg ttactggaac cgctgcatca cctccgagca gtccctgact ctgaccatgc  37320
agatggagga cccggacgag ccttggatcg agttcagcga ggtccacttc gaacaggcgg  37380
gcattcgcga cctcaacatc gtggccggcc ctggcgtgac catcaaccgc ttgcagaaca  37440
ccaccatgca gctctatggc gagaacggtg tgtgtaccct gaagcgcctc ggccctaacc  37500
actggatcat cttcggggcg atggaggacg actaatgcgt ggcattatcg caggtgtggt  37560
ggcgtcgcag attcgccggc ccaagccggt gctgaccacc atcacctacc cgcagtcttc  37620
ctcggatcgt gggggtatga cgtttcatgc catcgccggg atcatccaag ataccgtgaa  37680
gttcgcggat agtaaggacc tgggtagtta tgagatgctt gtgcgggacg ctaccctgaa  37740
gagcatggtc attacactca ctgaggttaa ggacagtagc gtctggagta tgggtgtgct  37800
gagtgcggca atcaaatccg tagttcagtt cttgacacca gtcgaggaga aatcctcgtt  37860
ggatatgagc atcatccacg gcgagcacaa gcaatcggtc attccatact cccgctgggc  37920
tgaggctggg tccctgtcca tgggtatcac agagggtaaa gtttatgtac catagcagca  37980
ccattcgagg tgagttcgat ctggagattg tacgtcctga cggtacagtc cgccagcacc  38040
tgcacttcaa gaacctgatc accgacttgg cccttgaggc catgagttcc aagggcgtcc  38100
cgagtggcgg ctggacgaac atgttcgccg gcactggcaa ccgtaccccg gtccccgctg  38160
acgtgtccct cgtggcgcct gtggctaatg ccagtgcctc gctgaactac ggcaaccgcg  38220
cagtgtggga ttccaccact ggcgagaaag tgcatactgg cacggggacc ttccgcgcag  38280
gttccttcca aggccagtcc ctggccgagg taggaatcgg tcgggtagtc tctgagctgt  38340
actcccgatc cctgatcaag gacgccaacg gcgatcctac cacgatcacg gtgctggtgg  38400
atgaggaact gcgtgtgacc tacactctgc ggattgctcc gccggcgtcc agtgaagtca  38460
```

```
agatcacgat gaagggtatc gagtacaccc tgagcatgcg ggaccgccgt accttccggg  38520
acttatcgcc cgagcctgcg gctgagtttg gcactcgcgg cagtctgtcg tggagcgcta  38580
tcagtgcgcc ggacagtaac ggccagacca agaccgccaa cttgagcggc gacgccggga  38640
ccgggattat ccaggttcct gcacagtctg cacagatcat gcgtatccag cccgccgatg  38700
ccaactggac ggaaggtatt cagtacctcc gctgggagac tccggcagga cgtgagctgg  38760
agatcaagct ggacccgcct ctggtcaaga acagcttgga gcgcgtggac atcaccgtaa  38820
cccacatctt caatcgggta tgattcagtt caagttcggt gactaccgga cccgtgtgcc  38880
cttccagggt gcgcgggacc ggcgggatat caacgaccgc agcgactacg tggacggtgg  38940
cgtcgccatc caagacccta gtcaaggtct gttgtatcag gagtggcacg ccgagctact  39000
cgaagacggc atctacctga cacctgagaa agagcgagtg actacccgca tcggaccagg  39060
tatcaatgaa ggcgtggcta gtatggcggt cacgttcgac cagaacatga actatgtcct  39120
ggtgtatacc aagcaaggcg aaggcttcat cgacttcttc gattccgcta ccgaagagcg  39180
caatgtgatg aaccttgggc cggtggacta tatcaagaca gacctagacg atcggcggcc  39240
agagggcagc gcctgggcgc aggttctggt ctgctacaca cggcagggaa acttctacgt  39300
ccgagccagc tcaactcgct ttactgaaga ggagcttatc gtcggtacgg gcaaagtgac  39360
ccggcctatc gtcaaatgcg gaatggcagc gaactggaga ttccaggtcc tgttccgagg  39420
gagaatgtaa tgagcaagaa gcagaccgcg agtgctgagc ggctgggcct gctacatgag  39480
ctggtctgca ccgccatcga gcgtaacttc aagtggtaca tggacaacga catcccgatc  39540
cccgcatcgg atatcgctgc cgccaccaag ttcctcaagg acaacgagat cacctgcgat  39600
ccgtccgaca ccatcaacat cgaccgcctc cgcgaggaga tgcggcaggc gcaggcggag  39660
aatcgccgta tcgcgctgga gggcttcatc gccggtgaga cggacgatga gatggaacgc  39720
ctgtacaccc actaaggagg cagcatgacg ccgcaagaac gattccagat agcccacgag  39780
gtgcgggaca tgtacccgcg cttccgggac ttctgcctgg acgccatgct gttcctcggc  39840
ttcaagatga cgtggatgca gctcgacatc gccgacttca tgcaggactc gcccaacaag  39900
gcgatggtcg ctgcacagcg cggcgaagct aagtccacca tcgcctgtat ctatgtggtg  39960
tggtgcataa cgcagaaccc ggctacccgc gccatgctgg tatccggttc cggtgacaag  40020
gccgaggaga acggccagtt gatcacgaag ctgatcatgc attgggacct gctggcgtac  40080
ctgcgccccg aggcccgcat gggtgaccgt acctcggcca ccagcttcga cgtgaactgg  40140
gcgttgaagg gtgtcgagaa atcggcctct atcaactgca tcgggatcac cgctgccctc  40200
cagggctacc gggctgacat cctgatccct gacgacatcg agaccacgaa gaacggcctc  40260
accgccaccg agcgggccaa gctgacgcgg cagtcgcagg agttcacctc tatctgtacc  40320
cacggtaaga ttctctacct gggcacgccg cagtcccgtg agtcgatcta caacggtctg  40380
ccggcgcggg gcttcctgat gcgcatctgg ccgggccgct tcccgaccct ggatgagcag  40440
gaacgctacg gtgactggct cgcaccttcc atcctagcgc gcattgcccg cctggaggag  40500
aaaggccaca acccgcgtac tggcaagggc ctggatggca ctcgtggctg ggcggctgat  40560
ccgcagcgct acaacgaaga ggacctgctc gacaaggagc ttgaccaagg ccccgagggc  40620
ttccagcttc agtacatgct ggacaccagc ctcgccgacg agcagcgtat gcagctcaag  40680
ctgcgcgacc tgctgttcat cgacgccacg catgagagcg tgccggagca agtggcctgg  40740
gctgccgacg agcgcttcaa gctcaagttc gacgcccacc gattcccggt catcaagcct  40800
```

```
gagctgtacc tgccggcgct gatggctggc ggctgggcac cactccagca aatgacgatg  40860
ttcgtggacc ctgccggcga cggtggcgac gagctgtcgt atgccgtggg cgggactctt  40920
ggcccgtaca tccacgtcgt gagcatcggc ggctggaagg gtggctttgc tgaggagaac  40980
ctggagaaat gtattgccct agctgcgcgt tatggcgtca aggtgatcta tgtcgagaaa  41040
aacctcggcg ctggtgcagt tggccagctc ttccgcaacc acatgcgatc catcgacccg  41100
gacaccaaca agccccgcta tgaggggatc ggcgtagaag accgccagaa gtccggacag  41160
aaagagcgtc gtatcatcga caccctgcgg cccatcatgc agcggcaccg tctgatcttc  41220
cacgtatcgg cgatggattc cgaccacgtg gcctgccagc agtacccagc ggacaagcgc  41280
aatgagcgct ccgtgttcca ccagattcac aacatcacca ccgaccgagg ctcactgccg  41340
aaggacgacc ggatcgatgc ccttgagggc cttgtccgcg agctagcacc cacgctcgta  41400
aaggacgacg aagccgcaac ccgcgctcgt gaagaggctg ccaagaagga atggctgaac  41460
aacccgatgg gttacactaa gtctgtcctt cggtctctcg gcatgggccg ggagcgtcgc  41520
aagggccgcc caaaaggacg aagactatga tgctcgatac cgccaccgag gcgggcaaag  41580
gcaccctcgc cgtcactggc gtggggatcg ccgtttactc gccctatgag atcgccagcc  41640
tctgtgctgc ggtactcacc gcgctctatg tgggcgccca gctcatcacc ctgctcccga  41700
agatgctcga tagcatcgcg gagcttcgcc ggaggttcaa gaagtgaaca agcccctgcg  41760
cggcgcagcc cttgcggctg ccctcgccgg ccttgtcgcc ctggaaggta gtgagaccac  41820
tgcctaccgg gacatcgccg gcgtgcccac catctgttct ggcaccactg ccggggtcaa  41880
gatgggtgac aaagccacac cggagcagtg ctaccagatg acgctcaagg actaccagcg  41940
cttcgagcgc atcgtcctgg acgccatcaa ggtgccgctg aacgtcaacg agcagaccgc  42000
cctgacgttc ttctgctaca acgtgggtcc agtctgtaca accagcacag cgttcaagcg  42060
cttcaaccaa ggccgcgcca ctgagggctg ccaagccctg gccatgtgga acaaggtcac  42120
gatcaacggc cagaaggtcg tatccaaggg cctcgtgaat cgccgcaacg cggagatcaa  42180
gcaatgcctc gaaccatcgt cgcaatactc gtccttgctg tggtagccct gggagcctca  42240
tacggcttcg tccagagcta ccgggccttg ggtatcgccc aggaggagat caagcggcag  42300
acggcccgtg cggaggccct ggaggtgcgt tatgccacct tgcagcgcca cgtcaaggag  42360
gtcgctgcca ggaccaacac ccagcgccag gaggtggacc gtgccctgga ccagaaccgc  42420
ccgtgggctg accggcctgt tcctgctgct gtcgttgaca gcctgtgcaa ccgccccggc  42480
gcccgctgtg ctgtgcgaac acccactgat tgaccctacc acccaggctg gcctgatccg  42540
cgctgtagcg gcctatcagg acgccctgga cctatgcaac gccttgaatc aaggagactg  42600
acatggcgaa cacccgtgag caatacctcg ctggccgtaa caccggcctg accttctacc  42660
aggtctgcca gcccggcacc gacaaccgca tcgccctgca cgacatggac gaggccgatg  42720
tcaaggccaa ggccaccgcc gtaatcgcag cagccaccgc cctgggcggc gaaggtggcg  42780
ctactccacc ggacccgctc accgcctaca aggtgaagaa cggtgacacc ctgcccgtgg  42840
acggcggtgg ttccgtgaag gtgaccgtag ccaacggtgc tatcaccaag gtcgtgtaca  42900
ccgcaccggc gggctgagct acagcccgtc ccacctgact ccatccctaa cacaaggaac  42960
tgaaccatgg caaccttcgc cgctgcaact cagaaagacc tccgcgcctt cgccggcgct  43020
atcgagaacc tgatccgccc tctggaagaa gcggccttgg gttccggctt caccgaggtg  43080
atcaccatca ccaagggcac cgatggcaac gagactcgca cctccgagcg taaggtacgt  43140
cccgagctgg tcgctaacct cgacgccctg atggccgctg tcgagaccgc caaagccgcc  43200
```

gtctacaagt aaggggacac catgagcaaa gccaaactac gagtcatcgc cgacaccccg 43260
gagctggagt cagtgctaaa agcattgctg accgccacct acgctatcga gga 43313

<210> SEQ ID NO 5
<211> LENGTH: 43016
<212> TYPE: DNA
<213> ORGANISM: Unknown
<220> FEATURE:
<223> OTHER INFORMATION: Description of Unknown: Phage F1245/05

<400> SEQUENCE: 5
cgggttcgat gtaacaatcg agcctattgc acaagacaaa tatttcttag ttgattcaaa 60
acaaattcgt gagtaccgag gttaacatgt ttcttaaatt atttattgct atatacacag 120
aacaacatct aaatgctgcc aaaaaacgagc ttgagcgttt agggtataag tgtacaagtg 180
atttccatag cgcattagat caacctgtta cacatattac tacatatcct aacggcacat 240
acacaatatg gacgcttgat cttgatatgt gtcgtcgttt agcacgtgct aataccacag 300
tacgtgttat taatctccgt cagttacgtg gtgtacatcg tcgtttacgt acctcattta 360
gccaagacaa tcactctaag cttgagattg tacctgtacg ctctgttaat atcttccctg 420
aacttgagaa actaagcccg ttagagacgg aagcaatgca agctgcgatt aagtggtctt 480
ctcctaaagt acctacacct aatgtattct ttaagctatg gtataacaca gcgattagct 540
ggaccaaagc aattgttaac cgtttagttc gtcactttaa ataaggagct gttgtgagta 600
agatcaagat gaatgaatac cgtggtaaac ctccatactc tatggatgat cttgctgagg 660
accctcaatt agaacgtcgt tacattcaac gtgaacgtcg taaccatgtt aaggagcgcg 720
accttgatcg acgtaacaaa cgccaagcca agcgaaacgg gtattagaat acctgtacgt 780
atcaagatca agtcagtcaa gcactactgt aaggttgtac agtgtttaaa ggattatggt 840
gtgcaagtac ctgctgaact tgcggatgaa ttaaacctca gacgcaataa ggagtactgt 900
aaacgtgctt gggtatggat aggtactaat gatgtggcgt gggtgtttgg ctcttataaa 960
atagttaaat ttgctaaggt gatgacacgt aaggagtacg taacgtggcg acaatccaca 1020
gctctgaatg gttagatcaa gcaaagaaag taccagtagg tcagaagcgt cgtgtatacc 1080
atggcgctga gatgacacct gctatggatg tatggaacaa tgaggactca tggagttgtt 1140
attgtcaccg ttgtcatgca ggtggtaagg tgtataaaca gttcctacaa cgtgttaatc 1200
ctgaacaacc agtataccgt aagtacttga acactaaaga cttaataact attgacgagt 1260
tatacagtac cgataagctc aagtacaaac gtcttatgaa gctcttacat gataagggta 1320
tgagcatgat aaccattgca gcattgaagc ctatgtacaa taaggttgat gatagacttg 1380
tgtttagatt caaaggtgtt gatataggtc gtgactgtac tggtttacat ggggctaagt 1440
ggttagtgta tcattcagat aatccaagcg ggtacgtgta cttgcaaggt aaaaatccat 1500
attgcacacg agagcctgtt atcttgtgtg aggatttatt ctctgctcag aaggtacggt 1560
actatactgg atggtcttca ttgtttctta tgggtactaa ctttaaagac gagactgctc 1620
atttcttaat gagtagatta cctgtgatag caactgatgg tgatgctgct ggatgggcag 1680
ctagaaaggt tatacgtaca cggtgtgaga tgtttaatat acctgtgcaa tctgtggatg 1740
ttcctgtagg tcttgatcct aaagatatga agcctatgga acttattaat ttatttaaac 1800
acttggagaa ccctgatggg tagtaaatat aatcggatta aattccgtgt aagtcgtcgc 1860
agtgagtggt tactaggtat ccaacatgcc gagaataatg gcttccccgt tggccctgac 1920

```
catgaatgga agattgaacg ttatcgtggt ggtaaagcgc taattaatgt acgtcttgat   1980
tataatgata caggtttaaa ccctgagtct tggtatagta cacccatagg tactgcacta   2040
tgggtggata ccctaggaga ctttaaacat gcagttaact gtttctgtca cgatggttac   2100
ttagacgttg ataacttaaa ggtggtgtaa tatggctata ataagaatcc caattagaac   2160
cgaagcagag gctaatcaat tcatctctat tgtgaaatcg caagggttag cactacccga   2220
tcttgatgta gttcatcgtt taggcttggc tactgcacgt gtaggtagtg atgcctgtgt   2280
ttggacaggt attgaacagt acataggtac acgtcatgat ttcccacatt ctgatgagac   2340
tgtaacagta aaccaattat ataaacgact acaggagcga taatgtcaga tttgaaccta   2400
ctccgtgtaa tgatggagcg taagcagttc acaggttctt tcaaatcaat cccgatggat   2460
ttatacgatc ctcacacagt cactatgctt ggttggttta agttgtacta caagagttat   2520
gaagatcatg agcgtattga tgttgatacg cttggttctt taattaaact caagactaaa   2580
ccacacgaag ataaggccaa acgtgacgct cagacagctt taatgaatga gatgctacgt   2640
aacctcaagc aaccgcttcc gttggatata cgagcaacca cgctgaatgc gcttgaggaa   2700
agacggctta gtgctgaggc agctatgatc tgtcgtaagt acgatgaagg tgaagagatt   2760
gatgtaatct ttgaactgaa taagttagcg attgcaacta agcaacgggt tgaattacag   2820
actcatgcag cttggtgcga tacggatgtt tgggaactca ttcaagccga tgcagatgat   2880
gcgggttatg tgtttgactt cttaccagag gagttctaca caaacattaa aggtgtgaac   2940
gagggtaaca acatcggcgt tgctgcacct acagacaagg gcaaaacatc cttccttgta   3000
cgtgtcgctg taagcttcgc taagcaacgt tttaaacgta tgcagaatga tgactcaatg   3060
aagttccgac ctgtcttata cctcgttaat gaaggcacag cagaggttat tacaccgcgt   3120
gtatatcaga ctgcgcttga gattaatcga gagcagatgt gggcacgcgg taaatctggt   3180
acgatcaccc aagactatat taatgttatg ggtagaaaag atgctattcg cttaattaac   3240
attcatggta aatcagtggc acaagtggcc cgcatcatcg aatcacatga tccattctta   3300
gtgatctctg acatgactgg acgtattaaa gctaatggcg gtgcaaacgg tagtaatgat   3360
attgcacagc tggaagaagt ctggaatgat atgcgtatgc ttgcagcaat gatgaacttc   3420
atccatgtag gtacagcgca gattagtgca gaagggtttg ataatctgta cccaccattg   3480
agtgcattac agaatagtaa aacaggtatt cagactacgt tagacttagg tatctggatt   3540
ggggcatacg ttaaccctgc accagagaat gaagatttac gtgggattag tactcctaaa   3600
aacaaactgg tcaagagtgg taaacgaagt tacaacacag tgatgacgaa cttcttacct   3660
gagacaaata attggaacgc agtaggatga aatttaaacg cggcgatatc gtaaaggctg   3720
taatgactgg tggttgttac agcataactt ctggtcaaat gtatgaagta cttgatgtac   3780
gagcaggtgg gaacattaac attaagccga gtcgtgggcc ttgtaattgg tccaaatctc   3840
atcgttttga attggtacgt agtaaagaag atacagtagg agtgcaacca actatgaata   3900
ttaaattata tgatacagtc gttcgcacaa ccattagcca tcatttaaag attggtgaga   3960
agtacacagt tacaacacta tatccacaga gtaatcatat cgctgttgag ggttttccga   4020
atatgcgttt cagtgctgct gactttattg ttgtacctga ccttgaagat cgacctaagt   4080
cattagggtt tgataaggta tgtgctgcat tgaaagatgg tacaccccta cagtacttct   4140
tcaatgagaa gtgggtggat gtcgtacgtc ctgatagtat cagtataggt atgattaata   4200
aaagtatctg gcgttatgca attaacacga ttgactacta tggacaggaa atccctgcac   4260
ctataaagca atatcctagt actggccttg tgtatggtat ctcattgact aagcatgaag   4320
```

```
tctataaatg caatgtgaac aaacgtctcg ggcaattgca ctataagact gctgaggatg   4380
cacacgctgt actcacaact atattagcgc cgtttggtat cacaccgaag gcacttgatt   4440
tctcacttac acaagaggtt atccaatgag tttacgtgaa caagtacgta agtacctaga   4500
tgttactaaa tcacctgtac aacttgttaa gcacatggat gaggtacttg agaagaacat   4560
caagtaccct ttaatagctc aacataagta cgacggtgta tacgtcctag ttgctgtgac   4620
tgatggtatc cctacgttat atagtcgcac aggtaaagag tgttttgaag gcctctataa   4680
tactgacttt gtgatgagtt taaatggtat cactgatggt atatacattg gtgagttatg   4740
taactctaag tttagtcttg aggtgttcaa tggtcttgtg agtactaacc gtaagaaaag   4800
ttgggaagat agtgagtcac aagatactat ccagttactt gaagagcata cattcattat   4860
gttccatgat tacatattcc ataactgttt attagaaggt cattgtaaac ttccttattg   4920
ggcacgttat gatttactac gtaagagatt acgtgtcgca gaactactag attaccttgt   4980
tgtatccgac gaagtgaaaa gccgtgaaga tgcagatgcc tatgcacaac tgattattga   5040
tgtaggtggt gaaggtgctg tatttaaaca tccagcagaa gagtgggtag caggtcataa   5100
aggttatcgt acaatgaaga ttgtgcggga cttggtactt gatctgctat gcgtaggagt   5160
tgagtatggt aagggtaaac gtgaaggtca aattgctaag cttaaattct cttataaggg   5220
cagtgtgttc tccgctgact tgggtaaggg gtggacggac gagaaacgaa agcaactcac   5280
agagcattat gaaatctacc aaagctatga accagagata caaccagcaa tcgaagcata   5340
tacacctgta ggtaagattt gggaagtcaa agcccttcaa gaatcaagta caggtaaggc   5400
attacgatta cctaaagtag ttcgagtacg cgaagataag acagaacctg atgcgtaaca   5460
caatcttaca caaattgatc taagtacttg atttaatgta ctaaatcatt gttattatat   5520
gtaacataaa cctttaaaat tgtagatttc tattaatata agtctatgat tttaaaggta   5580
attattgaat gctacatgta taagatagat agattccaga ttggagatta tatgtcacag   5640
attaattggt tagtactaga ctttgaagta cagaaccatg atcactatgg atcattagca   5700
agtccacatc atccagataa ctacttagta gcaactggtt ggtcggaaga tggtaactct   5760
gttcaagctg aatatcatca tagtaaagat gaacagtact gtaaacgatt cgctgatgca   5820
ttaagtagag ctaagaatct agtagctcat aacttaacat tcgaattaca ctggttgatg   5880
aaagtatatc ctaatgattt acaagcattc attaatcgtg gaggtagatt cttctgtaca   5940
caatacgctg agtatatcct aagtaatcag attgaaatgt atccgaactt agaagacaca   6000
gcacgtaagt acggagggtc acctaaagta gatgctgtta aacttctatg ggaacagggt   6060
gtattaacag cagatattga tcaagcatta ttaatgacgt acttagctgc tgatggtaag   6120
aatgaatggt ctaatccaga agacccatct ttccaaggtg acgtagcgaa tacacgtaga   6180
gcttgctttg cacaagtagc ggagttacgt aagcgtggta tgatgggtat gtttaaagaa   6240
cgtatggatt cattgttgtt taatgcttgg gccacttata acggattgta tgttgactta   6300
cctactgcac agcgtaacca agctgaacag gagaaacaaa ttgctcaaat taaatctgat   6360
attcttggta tgttacctaa tgatttacca gatgatttgg acttctcatt cacatccgat   6420
tatcacagat cagcgttctt gtttggtggt acagtcaagt acaaagcgaa agtaagttat   6480
gatcctatta agtacgagca aatcgaggtt tatggttgga tcggacccga aggtaacacc   6540
tactacttag ccgaagatga tcccatgtta cttacaggtg aatttactca gattgttttt   6600
aaagcaggta agaacaaagg acaacctaaa gtatttaaga ttgactctga tgtggagaaa   6660
```

```
cttaaatggg gtgagaaaga gttcaagttc aaaggtctta ttgatttcaa ttcactacct   6720
aaaattgttg cagatgctta tattggtaag cgtgcagagt tcaggggtaa acgggattta   6780
gtagatggta cacctgtata tagcacaggt aaggatagct tggatgtact tgcaaatcat   6840
actgaggttg caaaaccatt aaagctcttg gctgcgttga ttaaagatac aactacgtac   6900
tacctcacag atgacggtaa ggggatgttg aagttcgttg aacctaatag catcattcac   6960
caccaactaa acaactgtgc aacgattacg ggccgtttat cgggtagtaa gcctaacatg   7020
cagaacatcc cgcgagatgg tacatcaaaa gttaaagaga tgtttagttc tcgctttggt   7080
gaacaaggtc gtatcgttga ggtggattat tctgcacttg aagtagtgac actcgctagt   7140
atttctggtg ataagaactt actacgtatg ttgattgaag gtattgacat gcactgttat   7200
cgcttagctg caaagcttgg tgaggactat gaaagtgtat tcgagaaatg tcataacaaa   7260
gatcatcccg atcataaaca gtacaaacaa tggcgtacag atattaaacc tcgtgccttt   7320
gcccaccaat acggtgcaag tgctgagggt attgcgtact caactggttg tacaccagag   7380
gaagcttatg aatttaaacg tattgaattt gaactattcc ctgaatctaa tgagttccct   7440
gctaaattcg ttagaccgat ggtcgaaaag actggtctag aaggattacc taaacgtgaa   7500
caaaatccag aaacaggtca atggtcattg taccgtcaag gttatttcca agctaaatcg   7560
ggtacatgtt attctttccg acaattcgag aaacgcgtcg aaggtcagaa gatcatggac   7620
tacaaggaca cacagattgc taactactgg tgtcaaggtg aagcatcatt cattgtgcaa   7680
gctgcttgtg gtcgtgtcat ccgtgagctt attaagcgga actttgctga tggtttggtt   7740
cttcctatta acactgtaca tgatgctatt tatttagatt gtgccacaga agaattagct   7800
aaggaatatg gtgcattagt tcgggatatt atggagcaga cacctaagta cttagcagaa   7860
gctatcccag cacttaaaga ttggaattac cacattactc ctttccctgc tgctgctgaa   7920
ttcggtatta atatgatgag taaacaggac gtataatcat tctgtactca caactcaatt   7980
attctattaa ctcattggag acatatacta tgacatttaa cgcacttgaa ctcgtacaag   8040
gtattgacac ttctacttta gctgacatga ctgacactac aacaggtggt ggttctaaac   8100
gtggattgtt acctgctggg ttcgcttttg ctgtattcag ttcttacatt gaatacggta   8160
aacagccaca aatgtttgat ggtaaaaaga aagaccctgc attagagttc cgcttaggat   8220
tccacattgt aggtggtgtt ggtactaact tagcaggtga ggatgaagat tatgtacagg   8280
acgggttctt acctacaatc agtacatggg atactgctca atcccgtaat gagaaatcta   8340
aggcagttaa gtactttaac gcaattaaca tcgtaccaaa gggtacacac ttcattcaga   8400
aattaggtac tatgtacttg gttgaggtta aagtaactaa gaacaagaag actggtaaag   8460
atcagaatga gttcgacttt acatcattac agcaagcccg tgatcaggca acacgtaaag   8520
catacacatc ctacacaaac gcagcgggta ttgaggttgc tatgggtgaa cttaaaccag   8580
aagactacaa agtattccta tggaatcgtc caacaaatgt gactatagag caatatcaag   8640
ctatgtggga tagtatcgag attaaaggtg agactgagat caaagatgct gctggtaatg   8700
ttactggtaa acgttctaag aacttcttac aagagaagtg tcaacgtgca ttagactttg   8760
aaggctcaag tttacaacaa cttattggcg gtgtagcttt accaagcatt actgcggacg   8820
atgaagccga acctgaacct gctgaggaac ttacacctcc accattagat gacgaagctg   8880
acttagttgt accacctgcg gatgaggaat aatcatggaa gatactaatc gtgcaacggg   8940
tcgtactaca cgtatgatcc ttaaagctgt agagtactta atcaaacatc caaaaaagac   9000
tgtgcgtatt gtgtgctata acaattacgg ttgtgtatgg atggctgact atatcaaatc   9060
```

```
aattgtatct gataggttat ggcaacgcat tgagttggcg acttatcagc actggcaatg   9120
tagtggtata ggtaaacggg atgattactt ctttgatcat cactgtttct accatgaggt   9180
atataactta aacaaccgac ttaaagaagt taaagctcaa ctagagcgtg ctgagaagga   9240
ctaccgcaaa tatgatgcct aatctaagtc actttgggtt agacgctcag acacttagtg   9300
atcaaagcac attcaagcca agtaaagggg atagcaatat cctcctttac gatggggatg   9360
gtggttgcta tcagtctgct gctggtgctg caaagcaaga aacagctatg cgtcgctttg   9420
aacgggatat ccttgagaac atgtttctcg ctggatgtac aaaggcccgt gtacatttaa   9480
caccaagcgg atgttttaag aacggacggc acttactact aggtgctaag aagtatcaag   9540
acaatcgcag taataagaat aaacctcaac atcttgagta tctacgtagt cctgcatctg   9600
tagagtactt caaagatcat gaagatattg agataatcct taactatcga gttgaagcag   9660
atgatgctct aatgatggat cattatagat atcataatgg tatcttagtg agtcctgata   9720
aagacttaaa catctcacca tttaaatcat ataaagccga gttaggtaag cacttagttc   9780
tacccgaagg tgatcgatat ggttggattg atcgtgagtt ctggttaaca cctagtcaga   9840
agccaagcag taagatgatt ggtaaaggta ctaagttctt cttagctcaa ttacttatgg   9900
gtgatacagc agataatgtt aagggtattc taaagctcaa tggtaagctt tgtggtgaaa   9960
gcgctgcttt tgatgcattg aatcccatta cagacgagca tgaggctgtg aacttcatta  10020
ttgaggctta caagaagatt gaccaaaaca tcattccaga agcagaggcc atgtggttat  10080
tacgtaaccc taatgatagt gccttcaaat acctgtcaga gcataactta accgatagta  10140
acttaaactt cttaaacgaa tgctaccacg aacgcaagtg gaaattagac gaaactgatt  10200
tggagtacac tgatgaatta taatgaaact cttaaacgtg ctgagtttgc tgtacagatt  10260
cttaatgctg ctggttatga tgcacatatt gtaggtggtg cattacgagt acaggctcta  10320
ggcggtacaa caaatgatat agatattgct gtaatcacca cctttaaaga gggtgaatta  10380
cttaacaagg acgtaaatat tttacttgac cgcttaggtt ttaattttaa attacagcat  10440
caaaattcag attatacaga tgactctgat ttatttatag ctgactggtg ctcaggtgat  10500
attaacctta ttgcatataa tcgtagtgtg acacctacgg tacgtgatct agttaataca  10560
tttgacctta gtattaatat gttctacaag gaaaatggtg ttttaaaaaa tgatgtgtgg  10620
ttgcagggtg tatgtgctgt agttcttaat cccaatcgtc taggtcataa tccaaaactt  10680
aatgaacgta tcgcacgttt taaacaagaa tatgatcatc tagactggtc accagtcgac  10740
aaacagcttg caatagagga gcatatgaat gccatcctct agaccattac aacgtatatc  10800
ccgacaacaa ttaaaaggta tcatgattgc actataccaa cgtcaaggta acaaatgtgc  10860
aatctgtggt aagcctattg actttagtat tacaggtcat aaagcaaatt acgccgtgga  10920
tcataatcat gagactggtg agattagagg cacactacat aaatcatgta actctgcgga  10980
aggtaaggta actaatgctg ctggtcgctg ggatgtaag agtactgact acaatgatgt  11040
tatcccttgg ttagagagtc ttattaacta tctcaagaca gctcatcgta atggtacagg  11100
tatgatgtat cctgatcata aaacaccaga acagcaaaaa gatgctgcta atcttaaacg  11160
tcgtaaacag tatgcagcta agaaggctgc ggagagaatg aatgcaagtc ggaagtaagg  11220
ttgtctgcgt ttatgcaggt gactccacac taattgaaac acatggtaca tatgaagtct  11280
taggcttctc tagctatgat ggccctaact ctcatgtaga gatagggtta gatggtcgtc  11340
tcttgggtag ttactcacct aagcgtttta tgacagttga agaagtaact aaacaaactc  11400
```

```
aggagaattt gaatgactaa gaaacaccat gctttgaaag gtattaaact cgacattatg  11460
aaattatggt gggatggtaa atcttatcag caaatcgcag aggtggtatg taaaccttat  11520
gatactgtat acggtatcgt tcaacgctat cgtgatcaac aaccgcctgt acagcatacg  11580
cgtaagccta cgatctttgt tattggtgac acacagtgta aacaaggtat agaccttgcg  11640
tacttgcatt atgttggtaa ttacatctta gagaagcgac ctgatatcat tgtacatatc  11700
ggtgatcatt atgacatggc ctcactcagc acctacgata aaggccaact aagtgcagaa  11760
ggccgtcgag ttgctgagga tatcaaagca ggtgataagg gtatcgagat cattgagaac  11820
tatattgcac gtgctaaaga ttataaccct cgtaaggtag tgacactagg taatcatgaa  11880
gaacgtatcg atcgctttgt taatcataac cctgagtttg aaggtcttat cggtacagat  11940
aaactagcct ttgctaacta tggttgggaa gtatacccat tcttaacacc agcaaatatc  12000
tgtggtatta actttgtaca ctttgtacag aatggtatga caggtaaacc tctcggtggt  12060
actgtgatga ctcgattgaa gaacgtaggt gagtcatttg taatgggcca ccagcaagta  12120
cttgaccatt gtttacgtta cttaccttta agcggtaagg ctcagatcgg tgttattatc  12180
ggtgcttgtt atgagcatga tgagggttat aaaggtgttc aagggaatca tcatttccgt  12240
ggatgtgtta tgctatacga atgcgaagat ggttatggtt tagttaaacc tgtatcgctt  12300
agtcacatga aagaagttta cgaacgtcga ggtactaaat gatcatagat ggtactaagc  12360
tgcgctgtat aaatgacaaa ggtcaacgta ttgtcaaaga aggcagccta tatacagctt  12420
gggttagaga cggtataggt atagatggca gaatctttat taaagaacat aaacgttttg  12480
cattgttaat tactagattt gaggtggttg aatgaagatt ggtttgattg gtttagctgg  12540
tgctggtaaa gatacttctg ctgtaatcct acaacgtgtt cttgcagagc agggcttaaa  12600
atttgaaatt gaccgttatg ctgcaccatt aaagaatgca gctaaagaag tgttcggtgc  12660
taactttgat gagcgtaatg tcaaggaagt ggatgtgttt gttgatcaag ataccatgat  12720
cgaagcatct ttccgatgtt tacgtcaatt aggtttcact gatgacgaag atgagaaagc  12780
ctctgagtta ttctttgagc atattggatt cttggagtac ttatcgccac gtctgtacca  12840
acaattatta ggtacggaag ttgtacgtgc tgtacgtcct tctgcttggg tagacagaat  12900
ccgcaggcta aatcgtaata tcattatccc tgatgcacgc tttgagaatg aagtaagtga  12960
ttgtaattta ttaatcactc gcttccagaa tatagataaa cctaaacatc caagtgagca  13020
tttagcttgg gatttacagt ttacaggtaa agttctacca gtggatacaa tcaatatcaa  13080
caacgaacag ggtactactt tagagcttct agaggaacgt atccgtagtg tagtatcatt  13140
aatcaatttc aatgaggtag tttaacagta tgtctttgta ccaacgtcag ttagagcttg  13200
aagaaaaata cagtacaatg agtttagtag ctggtcagca gcaaattcta gatgcattta  13260
aacagggtag ggcttctgac gttggttcag ggcgtatctt gttagctaaa gcattcgcag  13320
catctttaga agatgttaag gcgttgttag acaaaaagat tactggtatc ggtggtaagt  13380
acaagaagct acttaccctt gctagtcctg atgtattagt aatggcagtt ctacgtgagg  13440
tggtcaatgg ttgtgcttca cctgaacctg tgaccatgca acaattccta cgttctgtag  13500
gtcgtattat tgaatccgaa tcaatgttag cttgtatgga taaagtaagt ccagagtata  13560
caagtcgtac agtgcagtat ctagattcag cgggtacgaa aagtattcaa catcgttacc  13620
gtactttttt aaagggtgct gagaacatta acttacattg ggatcagtgg agttctgagg  13680
aacgtactgg tacagctaag ttaatcttag gtgttattta cgaaagtact ggtctattta  13740
aatggaaaac taatccacat agtgcaagtg atagtatgta ctaccttgta cctagtgagg  13800
```

```
aattagagaa gcatttcggt gaggtacaag ccgctgcacg agcagtagtt aagtacccgc  13860
ctatgctaat cccacctatg gattggcaag gttataatga aggtggttat atcacagatt  13920
ggttccgtat gcattctccg atgtgtggta ttcgattcat caaacctgaa cataagaaat  13980
ggatcattga gggccttgga aacgctcagg ctgctcctgt acgctctgca atgaataaag  14040
cacagaatgt accttatcgt gtgaatcatc gcgtattgac gatcctacgc actgctacgg  14100
ctatgcgtgt aggtattcta ggtttaccga gttttgtagc tgctccacaa cctgagttcc  14160
cattaggttt aaactggcag aaagaggatg ccactgctgc cgagcttgaa cagtttaact  14220
tctggaaatc acagatggct gcatggtata ctaatgaagc taaacgtaaa ggtcgtcaca  14280
tgggtatctt aggccgtatt aatgagctag ttgcttatga aaacgaagaa cgattgtact  14340
tccctacgtt cattgattgg cgtggtcgtt tgtacttccg tagtaacctt aatccccagt  14400
cttctgatgc tgttaagggt tgtttggaat ttgctgaggg taaacctctt ggtaaagaag  14460
gtcttaaatg gttaaaagtt catgttgcaa actgttgtgg ttttgataaa catgatgctg  14520
atactaagga gaaatggtgt gatgagaact ggtcacaaat tgaaaatttt atcgataacc  14580
cactcgatgt ggatgcgccc gaacctgaca cagcatttac tttattgcag gctggattgg  14640
cacttaaagc tgctctcgcc cttagtgacc caacgaccta catatgccat gtccctgtcg  14700
caatggatgc tacttgctca ggcttacaac atttatcagc gcttacccgc gatccagtcg  14760
gatcatacta cacaaaccta gttgataata acacagatca aaagtctgat atttatatgc  14820
gtgttgcaga agtagcacgt gagttactac caaattatgt tagtgacgcg gttgtggatc  14880
atttctggca attgaatgag attactcgtt ctatggctaa gaaccctgtg atgacgtatg  14940
tatatggtgc aactttatta cgttgtattg atacgattgg tttgaacttg gttgattcag  15000
gtgtggaacc tattatggaa ggacgtaagg tactctatag tatcacagca ttagcaacac  15060
cagtaggtaa ggcattacgt aaaggtgttg aggatactgt acctgagtct gctaagatga  15120
tgaaatactt acagaaagtg gttcgtgcgt atcctgaaca ctgtatgcaa tgggtaacac  15180
ctgttggagt acctgtggtc aattgggcag aaggttctgt agtgaaacgc ttattcattc  15240
gttctatggg tgtcgaagct attaccatga aagttggtga taaaacttat aatactcgtg  15300
cagcagctaa tggtattgtt ccaaactttg tacatagtct tgatggtagt catttatgta  15360
tgactatcaa tgctttcgat gggcagattc tacctatcca tgattcattc gccacacacc  15420
cgagtgacgt tacagctatg catggggcat tacgttctca atttgttagc atgtactcac  15480
aattcaaaat cgaggacttc ttaaaattca atgaagtcga tatcgaaact catgaagtac  15540
ctgatcaatg taacttcgat ttaaacaaag tgcttaatgc accattcatg ttctgctaag  15600
gagtccttat gttattactt attatcacta ttcttgttgt agtacttgct gttgttattt  15660
ataaatcaga gaaagaaaca gtacgtgaat gtttcggcat tctggttgaa ggtgtcacat  15720
tagccaaagc caaatcagac attctcaaag ttgctaaggt atggttctat acgttaaagc  15780
ttacaggtga gctaatccta gtacctttct taactatcgc attgatttta ttcattattg  15840
caggtgctac atatcgagca atcattaagt aagttacaca aagttacata cacttataca  15900
ctatatcttg aatagttatg taagtgtatg atttaattta ttaaattgaa agctacacgt  15960
ataagatagg agaggactat gtctgtcgat aaaattccaa acttcacaga ggatcagata  16020
tattggttag atagtatatt tccagagaat acacaattaa ccactaaccc taatgaagta  16080
tatgttaagt taggacagag acaagtaatc caacgtatca aacaagacac tgctcgtaag  16140
```

```
cgtaatgctt ataatagggc taacggaggg taatatgggc ttaggaagtt tcttaaagaa  16200
atccattaag aactcattcc gtggtggtag tttatacaag ttatccgata agggtgataa  16260
catgttgcgt gacgtctttg gcttaaatgc atttaaagat ttagcggctg gtcaagatgc  16320
tcagattcga gctatggctg aacagaataa actaaacact gctaatgaga ttcagaatgt  16380
ggtgcagttt gaggacgatg tgaatacggg cggtagctca gatcagcgtc gtcgtaaaaa  16440
tagtgcgggt gcttatgctc gtgcattaaa tctgaacgtc taggagatac attatggcgg  16500
gagttccaga gttgcattat tcactcagtt ccctgtttca tcagtatcgt gatgacgggt  16560
tattagatcg tattgagacg tatgcactct ggactatccc tagtgttttt cctcgtgatg  16620
aacatacgtt ctataatgca aataaaaatc gtaccattga gtatgactat cagtctatcg  16680
gtgcgttgtt agtcaatcga ctagcatcta aactagctag atcattattc ccagccaata  16740
catccttttt ccgtattgac tcggatgatc ctagactaca acaaattttt aaagcgcgca  16800
agcttgacag tgtaattgag tatgaaaacg ctgcatgcgc tcgtttattc tataatgcat  16860
cttatgcaca attagtgcaa gcattgagac tattaattat tacaggtgaa tgcctactct  16920
atcgtgttaa tgatagtatg cgtgtttact ccttaaaaga ttatgtggtt aaacgtaaca  16980
acgttggtga ggttctagac attgtaatct gtgagcataa gttcatggaa gaattagacc  17040
ctgccatgaa agttaaagta ggtgttgtac ctgcggatac tacagttaag ttatatactc  17100
gtgttcagcg tcaacttatc aatggtatta cttcttggaa agttacgcaa gaaatcaatg  17160
ggcgtgatgt tggtactaac atggtttatc gtgataagtt atgtccttat atccctgttg  17220
tatggaactt cgtaaatgga gactcatacg gtcgtgggta tgttgaggaa tacggtgctg  17280
acttttctaa gttatctgat ctgtcccgtg aacttatgtc ttatgagtta gaagcacttc  17340
gtgtgctgca tctagcgaat caggctggtg gtattgacgt ggatgaggtg gcgaatgcac  17400
caaacggtac tgttgtacat ggtagccctg agatgcttca accttatgaa gctggttctt  17460
atcagaagat cgttactatt cgtgatgacc ttgctgctgt agaggcccgt cttaatactg  17520
catttatgta cactggtaat acccgtgatg ctgaacgtgt cacagcttat gaactcaaag  17580
caaatgctga ggaagctgag caagttctag gtggtgtgta ctcacaatta gcggagtcca  17640
tgcatttacc attagcgtac ttattattaa atgaggtacg tagtgatatt atcaacgcac  17700
tgaatgcacg agagatcaca cttaacatcg taacaggtat tcaagcctta tctcgtaata  17760
ccgagaatca aggaatgatt attgcatgta acgaacttaa cgttgtaatc cctgttgtag  17820
cacagcttgg gaaacgattt aatctagacg ctatcgctga taagattttc ttgtctaatg  17880
gtgtcaatat caaagaaatt actcgtactg aggatgagtt aagagctatc cagaaagcag  17940
agcaagaagc tcaagctgcg caggaaggtc aactagcaca ggctgctatg gcccaacaag  18000
ctccacaaca actaggtacg gctgaatccg cagtcaatgc actgcaacaa gtaatgtaag  18060
aggtataata tatgtcagtt gagaatttac cagaaggtca ccctgcacgt gaagcagcac  18120
agcctactcc gtcagtaaca ccagcggtaa cacctgctcc gactacacag cctgaaccac  18180
aggttgtata tcagaacatc cctacttatg acacagactc aattactgat acggctgtta  18240
atgtgtttgc tacatctgct ggtattgagg catctcgctt tgatgcagca ttagttaatg  18300
cgcttaatta tggtgatgaa aagttaattg attacacagc actgacacaa ggtctaaaac  18360
ctgatcaagc tgctcaagct aaagcactcg ctgcatctgt atttaaagat cgtgttgcac  18420
gtgagcaggc tcatattcaa gcaagtactc aaaaggtata tgctgtagct ggttctgctg  18480
aggcatggaa agaagcatct gatgctttta acgttagcgc acctgatcac ctcaaagcaa  18540
```

```
ttgtacgtca aatgcttgac aatggtgatg tggagaatgc agctaaattc gtaattgaaa  18600
ctgcgcgagg tacaggaatg gttaataacg gaacacctcc aattcaaggt ggtacaggtg  18660
cagttcaaca aggactcact caagaacaat attatgctga attagcaaaa ctagaaagaa  18720
gcgcgggtaa ccgatcattt gaaagtggtc aagttggagc agagttccaa cgtctacgta  18780
atgcgcgtat cttaggacgt aagcagggcc tctaagcctt gctgtctgct cacttaccta  18840
actaggagaa tttatcatgg ctcaaggtac tatttatcaa ccaaacacaa cccgcgatca  18900
ttggggtggt gctaattccg atgtggatca gcatttagag gattacactg gtattgtgga  18960
ttctcgtttc cagtacactc aaatctttgg tgctttatct gcacaacgtt ctgtagctga  19020
tcgctcgaat acagtgcgtg tagaccgctt caatacatct aaagtcaaag gccgtaaggc  19080
tggtgaggct atcgagtccc aacgtgtgac ttctgataag ttgaacgtga tcgtagaatg  19140
tatgatgtac attcgtaatc ctatcgactg gatggatgac tggactgctc ctgaccgtct  19200
tgttgaaatg tcacgtaaca acggtacaga gttcgctatc gcttatgacg aagcacatat  19260
catccgttta cagaaagcac gttcttgggt agcccctgat catctaaaac ctgcgttctc  19320
tgacggtatg ttcgtacctg ctacgcttaa acttactact gctggtgttg cagacctaga  19380
ggctaatgct tctgctcttg tagtagcaca tggtaagatt gtagaggcac tgatcaaacg  19440
tcgtgtccct ttaacagata tggttacgct tgtaactcca actgtattca ctgagcttgt  19500
gaatcaccct aaactaatca ataaagatta tgttgagtcc aatggtgatt tcgctgatcg  19560
tcgtgttgtg cgtgtaaatg gtatcaacgt tgtggagtgt actactttcc caactgcacc  19620
tatcactaac cacatcttgt ctacctctac taatgctaac gcgtttaacg cgactgctga  19680
ggatatcaag tgtgagatga tcgtgttctc taaatcacag tctttaatca ctgtaactgc  19740
acaaccattt acttctaact tctggaagga taatgctgag atgtgtaacg tacttgactg  19800
ttactcaatg ttcactcttg atgtacgtcg tccagataca gtaggttcag tattaattac  19860
tcgtgctgat acaccataat tttaactggc ccgcctatgt gcgggctttt gtcgtttagg  19920
agatttacta tgccacaatt atgtgaagca attatcagtc cagcattaac tggtcaagca  19980
ttagaagttg gtgatcgcgc atttgaacaa ggtaatacac ctgctgcaaa tgaccgtgtc  20040
gctacattag aaggtcaggt acaagctctc ttagctttat tacaaggtca gcaagctgct  20100
ggtgcccctg tagctcctgt tgaagtggtt gctgaggaag tcaaggctcc agctaagaaa  20160
gctactgcgg agaagtaaca tgcaattaga cccgatagat tataaagact tttatcgtaa  20220
cgcgggttta actgagttgg aagagactat aactgatcta ataaatacat tggatttaaa  20280
agtacactct actgaggcca ttgttcacga cactacagtt aatacagact gtaacgtctt  20340
ggtcaatggt cgtcacgtgg tgtatactga tggtactggt aatgcaccgc caaccgcagg  20400
tctgtatttg cttgagcaga catacataac tactgaggtt gatcaagagg ctatagcgca  20460
gacagctact cgatacagta caggtttatt ctatacacgt attcgacggt ctggtgtgtg  20520
gacttcttgg aacaaagtag gttaattagg taaactcgaa agggtttact ttaagatgta  20580
atccataaat cccaagcggt cgagattata tcttaaagta aatcaatcac tcattaggag  20640
gtagtatgaa attattagat gctgttaatg ctgcactctc ttacatgggt gagcataaaa  20700
ttacacgtgt ggagggttct aatcacccta ctgtagattc tattgtatct gcaattaatc  20760
gacaacgtgc tgctttatta agtacaggtt ggtggttcaa tgaacttcat ttaacaatcc  20820
ctgtagagac agatggtcgc atccagacac ctgcgcgctc tttagctatt tatggtaaga  20880
```

```
gtactcgtgt gtccatggaa ggtgagcatc tttttaattt agatacaggt agtgtttatt  20940
ttactgagcc tgtagatgta cgtattgtac gtgatattga ttttgaggac ttacctgaat  21000
atgcagcaca gtacagcctg tatgtggcta ctgcggaagt gtactctgct gagttaggtg  21060
ttgataacgt agttagtgtt ttagatggtc tggccaaaga tgctattgct aatttaagac  21120
aagagaactt acgtaatcgt cgttataacc caagacgtaa tgctgttcgg caatcacgtt  21180
acacatggtt ccgtaatcgt taggaggttt tatggcagtt cgtgagggta cttacaaatc  21240
cttaattcaa ggtgtgtccc aacaaatccc acaagaacgt agtgatgggc agttaggttc  21300
tcaatggaac atgttgtctg accctgttac tggtctacgt cgtcgtgctg gtgtcaagtt  21360
acatgcacgc ttaaccaact tatcgtctag ctcttatatc cgtatggttg atatcttagg  21420
tgtgtactac ttcatgtgca tcgatacatc tactggtact atgaagattt atacctatga  21480
tggtgtatta aaaaagacgt atacatctga gtacttgaaa gcagtatcta aggcgagtat  21540
ccgtagtact gtatcgcgta gtagctgtta tgttgttaat actgataaag tacctcagaa  21600
agttgtaggt gcaacgtcta gtacgtttaa ccctgcacat ggcggctact ttagtatccg  21660
tgctggtgca ttcagtaaac agtacactat taccgttaag tggggcactg ttacaaaaga  21720
gttctctatt atgtctgatg gcggtagtgc agatcaagta acgcctgctg cgttagcaca  21780
gagattatgg gcgctagtag gtacagaccc gcaagttact gctgtgtttg atgtggtgaa  21840
tgatggccct actgtagcgc ttaaagctaa agctggtcag aaccctgcac aattatctat  21900
tgaaactggt gactcaagta cctacattat ggtatctaat gcgtcacgtg ttgcatcacg  21960
gaatgactta ctaggtaatt taccctcatt actagatggt tacatcatgg ccgttggtac  22020
agagaagaac tcatcatact acagatttaa tgatcaaact aacgtctggc gtgaagtagg  22080
tgcttgggaa aaggattaca ctatcagtaa tgaacctatc tactggactg tagatgatac  22140
acaaaccgat ccctatgtag ttaaagagtt agacattaaa atgcgtagtg ctggtgatga  22200
tgagaataac ccactaccta aattcattgg gtatggtatt acaggtatcg gtacgtatca  22260
atctcgtctt atcttattat ctggttcgta tgttaacatg tctaagacta ctgatttctc  22320
ggagtactca cgcactactg tcacagaagt gcttgacgat gacccgattg agattgctag  22380
tgcttctttg agcagtacac agtttgaata ctgtattccg tataataagg atttattact  22440
tattgcacag aaccaacaag ctgttatccc tgctaacaat acagtcttga ctcctaaaac  22500
tgcggttatt tatccaagta ctaaagttga attgagtctt gctaatgaac ctcaaattgt  22560
atcacgtagt gtgtactaca cgtatcaacg tggtgatgat tactatcaag taggtgagtt  22620
tattcctaac tcatacacag atgcacaata ctataatcag aacttaacag atcatatttc  22680
attgtatgct aagggtgtct gtacatgtat tgcatctagt actactaaca acatggcctt  22740
aatgtcatca gatgatgcag aggtgttagt taatcaattt atgtggggtg gcgatgaacg  22800
tcttctaatg gcattccata aatggagatt catgctacct gttgtgtaca tgcagttcct  22860
acaagaaaac actatcttct ttatggacga tggggatgat gttgtagttg ctacattgaa  22920
cacacagtta aaccagttaa ctgagaagcc tgtgccatac ttggatttat actctatgat  22980
ccctgttact aacggtgtag gtactatccc tgattattac ttaggtaaag acttcacagt  23040
agtactatat gacaaccgta acttacgtca ctacgagatt caaccagagg ttgatggtaa  23100
cattatcaaa gttcctcaag atggtaatgt agttattggt ttcaagtatg aatctgagtt  23160
cacactgaca cctccattct taaaggatga gaacggtaag gtgattgcag ggtcacgtag  23220
cacgttacat aagcttgata tggaatttgt taacactgga agttttaagg ttcatgtgac  23280
```

```
ggatgcacgt ggtgaggctt atgatggaca acacgttact gctctaactt ggtcggagac  23340
tgagctaggt tatacgtggg taggtcggat tggtaatgtt agtgtaccgt gtaaaactcg  23400
gttgtctagt acagagtgtt ccttgtatac caatggaaca actgatatga acttgactac  23460
atgtaactac tggattcgat taaatcaacg ttatcggaga gtataatggc aggtaacttt  23520
actgctggtg ttaatacagg tatgcaaggc gcacagcttg ggctaactt tggcccacaa  23580
ggtgcggtga tcggtggtat tgctggcttc gcgttagggt ttcaaacacc tgactatgag  23640
aagattgctc gtgagaagta caactcggag gtattaaaga actttgctaa aagtctattt  23700
gacacacgta aggttcaaaa tatcgagaat atgcgtacag cacaggcact tgcagcttac  23760
caagataatc tacgggtaca aggaagttcc tacaacgcac agtatggtgc agccgatatg  23820
attggtagtt ctactacagc tttaaaacaa gctatggact ttcaaacaca agaggctaag  23880
cgtggtgtgt tgatcaattg ggaaacacag gtagataata tgaataccag tattgatgct  23940
atggcaaatc aatctatggc aggcctacgt aggacaaagg gcgatactcg tcaaatggac  24000
tatgctggac tagttaaaac aggtttagac ttgtatggtc agtaccgtaa cacattcaat  24060
aacccgaata catctaccac tcaactaggt atcaataaga ttcctgataa tatgtctgac  24120
tttggtagct atggtaaatc aggttctatg ggtggtttcg gaggtagcgg atcattattt  24180
ggataatata ggagaacatc atgccgacta tggtacagtc accagactta atcacaccga  24240
caatcagtcg tgaacaagct attgatcgtc ctgttgaaca agacgggtta agtacatttc  24300
tacaggatgt tctacctaaa gttaaagagg gttacgatca atatcaaaaa gagaatcaag  24360
atcattatat cgcattaggt atgaatgatg aactcaacca gatcacacgt gatgtatctt  24420
ggttagactc tcgtaactat gagcaaggta aggaatttca gaaggtatct agtactcagg  24480
aagcacaaaa gaaagccttc actgatacag ttacccgtat ggcgcgtgaa ggtaagaatg  24540
cagatgaaat tttcgatgca ggtcgtgaat acctcacagc ttatacaaac tcagtttata  24600
atagtcaatt gagtcctgat ttaaaaaacg ccttatatga ggctggtatt aaagagaata  24660
ccatctatca gaaattgatt accaaaacaa tgtctgctgt tgcagaggaa cgtgaacaat  24720
tcgatgctca gactcgtgta gcgggtttat atcaaactgt tagtactggt ctagacgatc  24780
aagaaattaa tgatgcatta gaggctcacg tgcgtaaggc gtatgctgct aagattgcag  24840
taggtgttga tcctaaagaa gctatgaatg cagcacagaa tgaaatctcg gctacattta  24900
aattctggaa tggtcagatt gatccaagtt cgcctaatgc ctcagagcag gttaataacc  24960
tacgtcgtgt tatggatgtt gcagctaaag aaggtatctt gagttttaat acccttggtg  25020
acattcagaa tgatatgaat aaaatgcgag atggtatttt agagtacaat ggtgttcagg  25080
ctggtaatac cctagatgaa atgatgtggg gtattgagtc tggtcagaaa cagtactcac  25140
atgctgaggt tgaacgtcag ttgacatacg ttaaccagct agagacagac ggtagtatta  25200
cacctgcacg cgctgcacag ctacgccgtg acttacagaa ctttggtagc actcaatatc  25260
aaaaactact tacaggtgaa atggatcctg ctcagcttgt agctaataat gtatccctac  25320
aagagtttac attcttaggt aaaggcggtg aggaagctta tagtaatcaa ctagtacgtt  25380
attatgaagg tgctaacaat ggtaatcctg tagcatcagg tcaacaaatg attcaacacg  25440
gtttgaaagg tgatccacat ggtgagcgtt tagatcatct tgttcaatat ggtactcaga  25500
agttagcttc acagttcaca tcattcttga gtatgacacc tgaaatggca gctaagcaag  25560
agaactttca aaatgctcaa gttgcattta acagcttacg tgacacgtat aataaactac  25620
```

```
gtgcccaagg tagtccttta agtactcaaa ttcttgctgg tattccagag gaacaacgtg  25680
gtattgtaca gcaattattt actaatggtg gtagtatgtt cagtgctaac caagcattag  25740
ctaaccctgt gcaaactaac cgtaaagtgg ctaatgtagt tgagggtact aagaacatta  25800
aatgggatac ggaaggtgtg ggtaacaaac tatttaaccg tggttctggt ggtggctcta  25860
gactgtttaa aggtatctct aaagatgttc aaagcactta tgtagataca atgcaaatga  25920
tctatgagga ttctaagtac gagttagcgg gtgctagtac aagtgctgac cctgcgttac  25980
ttgtggcttc tgctactagt ttaggtatgc atgttaaatc acctgcgggt tataatgatg  26040
ctttacttac agcgcgagca gctaaggctt atcgtaatgt tacctataag ggtgttactc  26100
tatcaggtga ctacatcggt gctgctgcgg atagtatccg tgaacagatt gctaagaacg  26160
ctaatacaga cgctagtaac gttatgatct atagtaatgc tagtggtagt caaatttatg  26220
tgcagccatt gaagaaagat ggctccgtgc aaaaggacac tgctggtcgt actatgactg  26280
tagctttttc acaggctcaa ttcacacaac gtatgaaaga agcttatgat aaggatgcat  26340
cacgttacaa gaagaacacc agtgtattta ctactattgg tactgctgca cgtgagacgt  26400
tcagtggtca gctaggttct gatactcgta attacagaca gaacgttcaa gagtggaata  26460
agacattcac agttaataag aatggtacat taggtaatac tgttatcaat ggtaatatcc  26520
gtgcccaaat ccctgctatg acagctgtgc cgtttaacgg taacgtaacg ttagctaatc  26580
attggcagaa ctaccttaat aactatgaag ggtttaagac tactgcgggc gttgtgaaag  26640
gtactggtac tgataaagat ggtttcatca ttggcaatgg tatcaactta tatgcacatc  26700
caaaatggaa acaacgtgct atcgctgcac aaggtaatcc tcaagcgatt ctgaatctac  26760
aagcagagtt catggcagag aacatgcgtg accaacaatc ggtagctaag aaattaggta  26820
tccctgttgc aactgcatct ccgtacaact cacgctttgt atccgctcag attctacttg  26880
ctgattataa atggcacaat ggtaactata gtgttatcag tgatattatg tcacaaccta  26940
actactcatc cgcattagct aagatgcgta agtctgctgc atacactcat gcaggggatg  27000
atcatcgtcg taatgtggca cgtagaaaca tgttacgtga ttactatatg gcaattggta  27060
aactttaata atggagggct gttatggcta gtaaatatgg tgttggtaaa gatatccgta  27120
ctctagaggc tgtgcagcct gatattccag aaaatattgg aacaggtaaa ggtaaaaaat  27180
taattggtac gcttgcagcg gattcttata aaccgctggg gcgtgctaat actgctgatt  27240
tgttagtccc tgagcaacaa ctacaggatg ctaaagcacg tgaagaggct agtctgttag  27300
agacggttac tgctgctgtt gcacctactg cacgcgattg gggtaatgct atctatgaat  27360
cttataagtt cacacctgat gtattctacc gccccgatgc agatgcacaa gagttcttca  27420
atgaatatca aatcactaat caagatgaag tagcttatat taatgctgct aactcttacg  27480
aggatatgga gtttcgtaaa cgtcgcattc tagatcgtcg tgatgatcag caaaagattg  27540
cagacaatcc tattacaggt attgtagcta gtatgttcga tattgatgct gctgctatgt  27600
tagtacctgc tgtaggtgaa gtagctggtg ctgctaaatt tggacgtatt gctcaacgta  27660
ctgctaatgc ctctatcggt gctggtggtg cttacgctat taactctgct ttagaggata  27720
agagtacccg tacacaaaca gagcgtgact tagacagctt aacctttggt ctagttggtt  27780
tcatgtcgcc tatcaaatac aaacctaaag agctagacgc tgctatcact aaagagatgg  27840
cagatgtagc tgctcagaat actgctaagg cagatgaggt cggttccgtt ggtacaacta  27900
acttatttaa tcatcaaatg aaagtaccta tctctcaacc aattgacaca tctaagttga  27960
tggtgcctga ttgggctaag tcaaataaga ctgtagctgc tctgcaatct agcgctgact  28020
```

```
atatgtacca catcactcat ggtgacatgg ataacgtagt aaacaagatt ctagcagcgc  28080
cacgtacaca aggtgataac gtaccttatg ctactgcacc tgtacaagct ttacttgagg  28140
ctaagttaac atctgttgag caagctattg agaaggctgc tattgctctt aaagatacta  28200
gacctaatcg cgggtttggt cgtaaagagc atacacaggc tcagtatgaa gtaggtgaac  28260
aattcgggca agcaatgcaa cgtcttgatc aaactgtggt ggatcgtcta gatgctggtc  28320
ttaaagtaac taaagaggac attgccgctc ttattgatga acaagccatc ccaaatgaaa  28380
ttaaggatat tcaacgtgct tatgttaatt cgggttttgc cgaagaagca ttatcacgtg  28440
ctaaacaagt aggtttatta gagaacttgg acgacgctgc tgcactgcac tcccgtagta  28500
cgtatatgcc tgtaaaacac tcatgggaac gtatgaataa tcttatgaag tcaggtgtaa  28560
ctcgtgatga gattgctacc tttattggta aacagatcaa gcagatgtac cctgactttg  28620
ataaggcact agctaaatcg cagaaggcta agttcgtctt gacagagaag caactaggtt  28680
tgaacttcat tgagaaccaa gagaaattag ctctcggctt atcagaggta cagactgctg  28740
gtttaactaa agatcaaatg atcacactct tacgtaagtc tggtgtggat gatgagaacc  28800
ttaaccgtat cgcggatgtt atctataaag gtacacaaga tgcaggtaca ggtgttgcta  28860
aaccattccg taaacgtatg cgttgggatt ttaatgctgt cggtgaatcg gcaagcggta  28920
gacaattcac aatgggtgat ttagtcgatg gtaatgcgta tatgaattta actgattata  28980
cacgtactat gtctaagcgt attggtcttg cccagtatgg tttaaaaacc actaatgact  29040
tagaccaagc tttagcagag actatgaaga atttacctaa gaatgtatct gtagaagagg  29100
ctagacgttt cctacagaat gtacgcgctc aagctttagg tcatcctatg ggtgaggctg  29160
ttcctgaaac agttcgttca ttgaatacta ttgcaggtgc tacattccta tctaactcag  29220
gtttatataa tacagtagac ttggtgactc aggttgctaa gatgggccta ttgcgtacac  29280
tacctgagat taagaaaggt ttaggtaata tcattaaccc tatgaagaag atgaccaaga  29340
gtgaagctac tgacctttat gacgtattaa caggtatgtt aagtactgac ggtcgttgga  29400
gaaacatcac tacacgctat gctgatgact ttgaggttac aagtggtatc catgaaggta  29460
ttcagtatta tggtcaaagt actcgcttct taaacctatc ggaatatgtt aagcgttttc  29520
agatcggcct tattggtggt acattcatta gtgcatttaa gaatgcagct aaaggtagtg  29580
ctaaagatat cgcatggtta cgtaatgata tgaagttctc tgatgaatta gtgcgtggtg  29640
tccaagagca atacaagcta catggtggtg ctattgatct atgggataat aacattcgta  29700
tggctatgga acagaaagtc ttttatgagg ctgacaacct agcacatact atccgtgctg  29760
gtgaaatccc cgcatttatg gagcatagct ctgtaggtaa gatcatcttc ccgtttatgt  29820
cttttgcatt cgctatgcag caaaaggtac tacgtaacac ttatcaacgt gatggtggtg  29880
ctggtattgc tatgttagct gctgtgcagt tacctactgc tgttttagtg ggtatggcta  29940
aaaatgtgaa aaatggtaag gaacctgatg aggatttagc taagaactct gttaatgctt  30000
taagtatgtt aggttcattt agttatcctt tagagatcat cattaatggt ggtttaaata  30060
gttccagtgc gactttagca cctattgcca atgttgctac attaggtaag aaagctgctg  30120
agggtaatct agatatgcgt gctattaaag gtgcgacacc tctaggtagc tttactggac  30180
tagatttatt tattacagct atcgaggaat aatatggcaa ttaatcagaa acaatcatac  30240
tcggagtacg atgtaagtac tccacaagga gacttcgcta ttggttttga agactataac  30300
gaaggtgaga aggatcgtat caatgtgact gttgatggtg atgatgctgc tagtaaaggt  30360
```

```
tatacagttc tacgtaagaa cgctttaact attgcaatga caccatttgt gccgtctggt  30420
attgtacgcc tcactcgtga aacaaacatt gatactacat tctacaaatt tacagcaggt  30480
gctatctttg atgctgctaa cgtagatgct aactttacac aagttctaca ctctcaacag  30540
gaagtacgtg atcgtcaatc ctacgtagag ggtagagtac tacctttagt aactggatta  30600
gaagatgcac ttgctaaggc agatgaggct agtaaggctg ctcaggaagc tgctgaggct  30660
gcggcagagg ctgcacaaca aactcgtagc gctgacaagg ttatcgatgc tagtgggtta  30720
actcagcaag atattaacaa ccgcctagca attacatatc caactgcggt aggtttagtt  30780
ggtaagccta acttaaagga tgcagatgta gtttatgttc agagttacag taacatcttt  30840
gatggtggtg atggttatta tcgcgtgtct gcggatacta ctactgtagc cgatggagcc  30900
tatgtaattc gtattaaccc taacttaatt gcaacaatgc ttaatactac aggtagtgta  30960
gacgtagctc gttttggtgc tgtgatgaat gcggacgtag gaccgttcat tgagaaagca  31020
tttaagtact tccgtgatgt atgtttaact aaaccctata aactgaacac tgtagttggt  31080
atccctgatc agaacaacta tgctaagaac gtttattatt tacgtggttt tggtgatcca  31140
gagattacag tggattgtcc tagtgctgta ttcacatcgg ctgctgcaaa gttagaccca  31200
aatagtgtag ctaataagtt tacagctaag cttgatgtgt ctaatattag tttcattggt  31260
acaactgtag ctaattctgt agtatttaat ggtgatcgac tttacaatat taacgtacac  31320
cacaataact ttaagggtaa tattactatc ttcaaggcgt atgttaaacg tgaagccgaa  31380
cgtcagtata ctcaaagtat ctctattaat cataaccacc tagcaaatgt atatcgcgtc  31440
attgagacag acaaggctta taatctagac ttctcttaca atatgtgtga agcttgtatc  31500
ggtggtattt atgtaggtgt aaatgcgccg tgggacccta ataaatatct attaactatc  31560
caccgtaatt tgtgggaagg tagtggtatg ttattgaaaa ccaatggcgg cattattggc  31620
ggtactatct cagctaacta ctttgagaat aacacatttc atgatgcagg tattgagaaa  31680
tgccttatca gtattaatcg tactggtgca ggttcaggtt acgctagtgg tttagttgta  31740
ttgggtaata cgttctcagg taataattcc atccctgatt tcgtagatgt acgttataac  31800
aaccagagta ccgagtcttc tgctaccagt aagacagcga atgttaaacc catagtattc  31860
attagtaact ggtcaaatag ttcacttatg actaactttg caggtgccct gcttatcaac  31920
aaccgttgta ataaccgtaa tactatgttt aatgcttaca gcccgcaaga gggccgtgta  31980
acatttgcat cagggtactt agataaaaacg ttagctagta tgttagcagg taatcaattg  32040
aacttattaa cgttcgatac acgaccatgc ttcactgctg gttatatcaa cacgaacttt  32100
aagactcggt ttgatgtgac agtattgttt aagactgctg gtggtattaa tacagctagt  32160
tgcagttttg gcttagatgt atttgtgtat acaccgctag gtgcaggtgc gccgcctaag  32220
tctaatctta aagcagttat gtcaggcttt atgcagtcag acactaatga tattattagt  32280
gtagctgcta acgagactat gaaaactgtt attgcaacac ctgctatcac agtagtaaat  32340
aacggcgacg gtacttatgg tattcgctta ggtaacttta ctaatgcatc ctcacctaat  32400
tggggtgcta tcactactgc gcgtattgag tatacttacc aaggtacact cattgcatcg  32460
catacttcaa catactcgac tgctaactta ttgacagtcg cataaggagg ttacatgaac  32520
atcgtagatc aaatctactt tggtttggtc tatgtgtggt caagcctaga taaattaatc  32580
atgggtgctg ctgctacggc ttttgtagtg gcactcctac gtacacgtaa acgtgacggt  32640
aaagcttcat ggattgaggc tactttatgt ggtatctttg ctactattgc tttagtaggg  32700
tttagcttta ttgctccaat cctagtaggt attctagcag gtatggggat tacaattaat  32760
```

```
cttcctgtag accctagtgc aggtatcgct ggtattgtcg ctgggtttat cggttggtat  32820
ggtacagaac gtactatcga atttgtggaa gataacttag gaggtgataa gaatgggtaa  32880
gttcatcacc cttgatgaga ttacgtccaa ggctaaggag tacggtatag aaacagccgc  32940
actccgtgct gttatggatg ttgagtgtaa aggtcatggc tttaattccg atggtgcacc  33000
tgttatactg tttgaacgtc ataaattcta ttatggccta caggctatca attggataac  33060
taaatcgaag gaatggtata aactgtaccc tgacatttgt aaccctagtt ggggcggtta  33120
tggtaaagag tcacaacaac acgaacgtct acgtagagcc tctgctctaa atcgtgatgt  33180
ggcccttgaa tccgcatcat ggggtttagg gcaggtgcta ggtgagaact ggaaagacct  33240
tggctacaag agcttacagg acttcattaa cgctatgtac aaagacgaag tatctcagct  33300
tgatgctatg tgtcggttca ttaaacataa tggtctaatc aagcacatcc agtctaagtc  33360
gtgggcaaag ttcgcgcgtg cttataatgg gcctaagtat gcggataata agtatgatac  33420
taagcttgct gctgcttata agaagttcgg aggtatctaa tggcaaaacg taatagtgca  33480
agtgtaagtc taatgaacga attacatgca gctattgcaa gttacatgtt agctcgtcta  33540
aaagcgagta ttcctgatcc taatgcacca gtggagtatg atgaagagac aggtgaagaa  33600
atccctgctt tcttcatccc actagctgca tctgaattac aggttatggt aacgttcttg  33660
aataacaaca agattactgc tacacctgat gtggaacaca tggctgcttt agcaaatgag  33720
ttcaagggtg atttagaagc tgctcgtaaa gagcgtgctg aaagtattac taaagtaaat  33780
gagaatgatg cattcatggc atcgttatta tcataggagt tattatgggc cgagtatcca  33840
gaattaccga gcaaactaaa cgccgtttag ctatgttgct tgaacgctgt aatcgctata  33900
aggataatcc tgtagctatt ccagccgaag aacgcgaaga actatctatg atgttcgctg  33960
cgacatttaa aggctttgct gagtttgctg aattaggtat gaagtatctc ggctttgacc  34020
tctctgaaat ccaagatgat atcgcagagt acatgcagta cggcccagct aagaagatgg  34080
tacaggctca acgtggtcaa gctaagtcta ccttagctgc actgtattgt atctggcgat  34140
tgattcagaa tccaactgca cgtattttaa ttgtatctgg tggtgaacgt caagcatcgg  34200
atgtagcttt acttattatc cgtattatta tgcaatgggg tatactatgt tggatgcgtc  34260
ctgatacttc taagggtgat agaacaagtg ctagcgcatt tgatattcat tactctctta  34320
aaggtattga taaatctgct agtgtatctt gtgttggtat tacagctaac ttacaaggta  34380
tgcgtgctga cttcatcctt gctgatgata ttgagacaca acgtaactct atgactcaaa  34440
cagagcgtga gaagttacta ttattaacta aagaatttgc tgctatctgt attacaggtg  34500
agatcatgta cttaggtacg ccgcagacta aagactctgt gtatcgctct ctacctgctc  34560
gtggttacga cgttcgtgtc tggtgtggtc gttaccctac cgatgaagaa cttgagcgct  34620
acggggctgg tgtacaggtt gcaccgctta ttatgaaccg attacttgct gacccttcat  34680
tacaaactgg tggtggtgtc gatggtactc gtggtcaagc aaccgaccct gcacatatta  34740
atgagcttat cttgcaagag aaagagcttg agtacggccc cgaagggttc tcactacagt  34800
acatgcttga tacaacgctc tcagatgctc ttagaacgaa gattaagatt tctgatatga  34860
ttgtgctgga ttgtggttat gatcgcgtac cagagcaatt agagtggtta ggtgcgatga  34920
ataacacctt taaagaacac acggagtata gcaaagactt cactatgtat aatgctgtag  34980
gtgtatcgga tatcctaatc ccatttgaac ataaactaat gactcttgac cctgctggtt  35040
caggggggcga tgaagtgtct ttcgctatcg gtggtgctac taactcttat atctatttat  35100
```

```
taggtatggg tggtttcgct ggtggtatga ctgaacataa catcgataag attctattga  35160
agatgattca cacgggtacg aaggttctag atgttgaaca gaacatgggc catggtactg  35220
tgactatgtt gattcaatct caattaacaa acctgattaa cctgcttaaa tacaatgacc  35280
ctaaagctga tgagttcatt cagaaatctg gtatgtcccg taatgaatta ctacctttac  35340
ttactggtat cggtattact cagtactatg tgactacaca gaaagagaag cgtattatta  35400
atactattag tccagtgact cgccgtcata agctagttat atctaagaac tgtatcattg  35460
aagatcatga gtactgtcaa ccacatccag tggataaacg taaacagttc gcagggttgt  35520
accaattagg taacatcact tatgatcgta atagtttagt ccatgatgac cgagctgact  35580
gtgtacaacg tattgtagag gtgttgaagg gacacttaac taaagacgct gataaggctg  35640
ctcagaagcg cgtagagaac gatatcgctg agtggagacg taaccctatg ggttattcag  35700
aagacgtctt aaaacgcatg ggcaaggtt ctagaggccg tccacgtgtt ataactaatc  35760
gtagaggtcg tagatgagtc cagaagaaat ccgcagacgc ttggatacaa tcaccgagcg  35820
tattgctaat gctgtaatga ttgttaactt aattaaggag aaatctaaat gagtactaaa  35880
cgagaagtag ttgtacaagc tgtagataac gctgtaagcg tcgctaaggc tgttaatgct  35940
aatgctgagt acaaacataa ggacaaggtc actaaaggcc ttgaattagc tggtaacgtc  36000
ctacagctat tgaaattgtt taagtaagga ggttgctatg gatggctttg aaagtacagt  36060
taaggttggt gttaagcata ctcagtatga ggagttacgt gaccttaaac aacgtggtga  36120
gacattcgac gatgtgattc gccgtttact agatgctcac aagagtctca agagtattgg  36180
cttattagac taggagatta gtatggttaa tagtgcagtg gtagcattag acgagtgtat  36240
ttagtatcat gttgccttag attatttaga tggtaagtac gttagctttt tatctacgta  36300
tgtggtatgg ctgtgaggat tactggacac agagtggaag ttacctgtac gattaactag  36360
attaccttct cagatgtgag tactaacttg aatttatatt ttgggttaga tttctgagag  36420
ggtgtctccc actccaccgc agccgacttc cccgtatacc ttgggtttgt atgaatctct  36480
agggaactag ctagggtatg cttatcagtt ccttatcaga tacacagaga tacgatgcaa  36540
tgcatcagta catcggagaa catcttatca gtacgggtag agtacagctt atcagatagt  36600
atgtcaatac tcttagagaa ttatttcagt atttatttat agttctgttt gagatacttc  36660
tatacttgag tgtgcttgcc ttttattgtc ttcatatcta tatctatgtg tatacctatc  36720
tagatactct tatcattcta tcttatctat atctcttagt acttcttatc gatatctctt  36780
atcttatcta tatagttctc ttagtagtat ctatagtatt actcttatag ttatatctat  36840
ttatatctat atagttatct cttattgttc tctctttatg ttctttattc tttattctta  36900
tacgtgtagc attcaatatt attcattaat atcaataact taaaataata gaatcgtaag  36960
ttttcccgta gttatgtaaa cggttgatac aaaagtattc tcttatatat taataactta  37020
gcttaattta ggtaacattg tgtaactaga tagaactttc ttcaattatt tatcaaataa  37080
gtattgacac gttatttaaa ccattatact atgcactcat accaagcaac gacgagttac  37140
taggttactc cttaaagtac ttattcagat agttctaata agtgtatcaa tcgacaaggt  37200
aatacactat gaaaacttta acacatcata tagcagttca atgtacttgt ggtgctactg  37260
gtcagactgg cgatttcttg gtagatattg agcacttcaa gttaacgggt gaattaatag  37320
ctttagatgg tatggtcttt cgatctttaa ccgctttata tgcttatgct aatacatatg  37380
gtttaccaac taagcggtta aatactccga tagtatatca gtcataaggc tgatacactt  37440
attagaatta aatgaataaa taatttaaat aaagtattga cagattaaat cgaaagaatt  37500
```

```
aagatgcaca acataacgag agattagcta gatcactagc aagcttgatg ctctaacagg  37560
ttgatagctc taaggtgtta aggttatgat cttcctagta gatgatacta gggtattatt  37620
taaagccatt aatttaaatc cgagtgtgtg acgatgtaca tcttgtatgt ataagcacat  37680
gtacggttga agtgtagtga taggctcgtg ggatgtactc gcaagttaat ttcatatact  37740
gcacgtaaag ctatgatgaa tctcttagag tttatattta gctaggttgg tttggatgct  37800
atgcacatcg acctagcgct aatgtaatct cggtgattac ttccatcaag tccataagga  37860
tactagtatg aaattacttc ttaatgttca agagatcaac aaagcaatcg agtctatcgc  37920
taaccgtggt aagaaacttg atcatgatat tcatgtagct ggtgtgtcag tgttaaagca  37980
tgtcgctgaa catggtgata caactttgct tgataagctc gttaatgcaa tgcctaaagg  38040
cgcacgtaaa ggtgcattct gtgagtgggc actagcgttc ggtaatgtac gtatgcttga  38100
ccgttctaat gaagctgata agttagctat cgaacaaggt cgcttattcg ctaaggataa  38160
gactaaggaa tacaatgaag ttgaagctat ggctaaagct tggtatgact ttaaacctga  38220
acctgattta ctgactacgt ttgatgctgc tcaagctgtt aagtctttgt tgaagaagta  38280
caagacagca ctcgataatg gtgcagagat caagggcggt gatgttgcta tgcagcagct  38340
taaatcgttt atgcaaacac ttaacacaat ggatgagcaa gtatgaaggt aaaggtgcgt  38400
aataaattcg ctgcggctac tagcattaac tacaaaggtc attatgtggt acgtaatggt  38460
aatggtacat tgactttagg tgctgaacat ataaccgaag aacaggctgc tgttcttaat  38520
ttacaagagt tttctaaggt acgtgagtgg ttaggtccta gttattcggt ggagattatt  38580
gtatgattaa acgtgttgat cctatattag gcagcttagt gcgttgtccg ttctgtaaga  38640
aagtttatac gcagtgtcgc tgcttatggt agcgtacatt attcctcgct tattgctcac  38700
tgtagccatt ctgattgcag tgggtatgat tacactatct ggatttaatc ctcgcttata  38760
cgagcgtata cagccacaca tgtggtgtat tagtattgca ttaaccatga tagggatgtg  38820
gtatctatga tagatgctcc gctgtacttg caaatcatta tgttcatagc atgcctaagt  38880
gtaggtgtgc ttctctcttt cttctgttac aatggtgact gatatgacag acacaaaaga  38940
tcaaggttat gaccttggcg atgaaaactt attatctgtg gctaagctag ctatgcgtcg  39000
tggtgagtac ctactatctg cgtgggatca gtttgcagct atggatatag tggacggtct  39060
aaaccgcata cctagtgctg atggtttaat tgtgtacctt aaacatggtt tatgtactaa  39120
tataaggttt gaaattagtc ctatggctaa ccacagatta cgtggttcac aggcgttgga  39180
tagcttatta gaactagcct atcctcagtg ggatggttac tcaggtaatt caacctaccc  39240
tgtagatggc tactatgagt atgaggggta tactgaggat ggtgaacacg atgcaggtat  39300
gtatcatgag cctaatctat tccgtaaccc taaacgtaaa gaacttctta cgtggttagt  39360
aacctctttc cttcctgaat acatcaagca ttggagtgct gaataatgtt aatcgttcct  39420
aaagtaaatc ctaacgtcac tgtcacattg aacatcggct taggcgaatc aatcgcatgg  39480
ggtaaataca agaaagagaa tgcagagcat ggccctgtac aatctcttgt cgatatcctt  39540
gacacaccgc atcgtgtagc acgtatctta gaacgtattc aaggtatggc gtacaatccg  39600
aatcagcacc atcacgggcc acatgtggca cataatagct atggtattga ttatggtcat  39660
catgtacttc caaatgttaa ttggcgtact gtgcaagttg gtaatgaaat gacactggtg  39720
gtgaagtttg aagcggttgc tcgtgacatt atcggtcaag tgttctacct tgcagaagaa  39780
ctcaaacaag actgcattgc tgtatggatt cataacgata ccaatggcgg tatcggtcag  39840
```

```
ttgattggtc gctacaacta tgtgtggtct ggtgggtact tcaaccctga gtactttgtt  39900
cacttggagg tatagcatgt tcaaggaata caactactgc ggtcagtgtc gagttaatta  39960
tatcaactgt cattgtccta cgcattatcc tgaacgtaat aaggatgatc accacctatg  40020
aaaaagctag gtttaattgt tgtgtatacg gctgcttatg cagccatctc tttagtccaa  40080
tggttacagg atgataaata atgtttgtac ttaaatcaac acatcagaaa gcgcttgatg  40140
aaatcaaatc tttacgtgcc caactagatg ctgctgctaa aactaaacgt gagttgcaag  40200
aacgtataga ctcagtacgt aaagtacgtg atacggttat aaaatataat gcttgtttaa  40260
ctgcattatg tcagtaccta cccgagggtg tttaccgcat tgactatgga gcagaacgtc  40320
gtagttgcag tactctccgt aaaacatctg tggtgtcata cagcacatcc gtgacggtag  40380
atcataaagc tgctaagatg accaatcgca actatacaat ccaacatgaa cctctagcac  40440
ggacatgtaa acaggctgaa ttaacagcgc gcctagttgc ccttgaagtc caatataata  40500
ttattaatcg tgatatagtt gtattggatc aaaccattaa actggctcaa gcgctgtatg  40560
atgtacctac cgtatgtcat tcggtgacta aacgtagcgt attatctaag caacgtaaac  40620
gtattaaaca cgagttggac ttggttaaag tcgagctaaa taacttatag tctgtactcg  40680
caaatcaatt tcgcatttaa tagatgtagg tggtaacaca tgaaatacta tgataactct  40740
caccctgaat tacaagggta taaacagttt attcctgaaa atcctaatca atggttcgac  40800
ttaatgtctg ctaaccgtgc tgtgtttata cgtgaggata agcgtgtaga tgcagatgtt  40860
tgggatatga ttgtacagca tcttactggc gtgtcttata aacctcacag atatggtgaa  40920
ggtaaacgtc actacacaga gttccaatta ctccaagggc atcgtaaact tggtgagggt  40980
tattgtagtc gtgtttatac acacccaacc aaccctgaac gtgtggttaa gttcttcgag  41040
cgttaccatg aagatgtgtg ctgttacgag tacttacgta tgtgtgtaca aggtaagcta  41100
ccagtgtttg attggctacc tgaagtacat agtctagcat gtatcaaagt tcttatccgt  41160
gaagatgata aggtgcgtat cattacttat ggtgtggctg tgttccctag atatgaccca  41220
atagaatcag actatgagaa gcaaaaccga ttcgttcaag atggtattaa tgctgagttc  41280
aagaaatatg tgcatccata tctaccgcat gcgcgtattg acctacattg gggtaatatc  41340
atgtgggatc gtagacttaa tcaatatgta gctactgatc ctgtaatcaa ttcagcacct  41400
gtagaaacac atgtacaaac tattgattgg ttccctaaag aaattagtgc taagtactca  41460
ggtgcgaccg catgttcacg tcctaatgta agtactcgaa tgactacgca ggattatgca  41520
ggtaatacaa cgcacccact agcaccacat tgggctaaaa tacgtgaaca cgtgatgcag  41580
gtacaacatt cagaagcagc gcgattagag cgtgcttgga gagtgcatag acctgtacta  41640
gttgaccatg ctatgtttgt gcgtgagttg atgcggtgtc ctaaaagccg tatgttcctt  41700
agtttaaaga cacctaaacc aaggctacct caatccgcta agtacaaagt acagcgtaag  41760
gtggttaatg aacgcttacc acaaggtaag ttcttgaata atttaagaca ggagttacga  41820
catggtcgtg tatggtaatg taatctttga gcgcgattta gcgcagacca tgtataaacg  41880
tatgagttca cgactagcag atggtgtacg ccgttgctgt atggttgatg aacatacatt  41940
gtactttgaa tcagaagtat ctgacagact aagtcgtaag aagttcaata acatcctcac  42000
aggtcaacgt attgcgccgt acagcgagat taagtacccg aaggtaggtg agcatacact  42060
tatgtctgat caagccatag cagaagctaa ggcgattcta agcagtgaaa cacgtacacg  42120
tagttgaggt tattatgtgg attttaataa tgagtattgt ggtgggttct tatagaggtg  42180
tgtctgcaac cacacaggag ttcactagta aagaacgttg tatggtagct gctcaaatgg  42240
```

```
cactggataa gaaaatggga ggtggggata actccaatag actcaccgct atatgtgtac  42300

ctaaataagc ttatagatag cagcattcaa acggatgctg ttagtgtata agtttccttt  42360

cgctactcaa tggagtatat tatgtcatta gctaaacaat tcaacgctgc tggtatccgt  42420

ggttctaaac ctaagtctga taaaggttgg accttcaagg ctcagaaagc ttatgtacgt  42480

aaccgctttg aaaatgtaga gcgtgttatt gcacctgtgt ataaccacaa ggttgagcag  42540

gtagcccgtg ccatcatcgt tgaaacacct ttagcatctt tgaatgttgt ggcgcagggt  42600

tcatcacttc attatgatta ctcacctgac acattagtcc gtatcggtaa gctaactcgt  42660

aaaggtgcaa cgttctctgc ggattctaac tcagcattag ctattcttgg cttgaatggt  42720

gctgctgtgc tgtactggtt aggtggttta cgtattaaca ttgatgaaca acaatacgaa  42780

gtcatcacta atgatggtga atacatctat gctactgtag gtattatctt acaattggcc  42840

cgtgattgtg tgttcaaccg tgatgctgta cttgcaaact tccaaggagc taaacgtgtc  42900

cgcgccaaat aatatctttc ataagggtat gcgtgtcata gtaactaaag cagatcgtga  42960

cgatgtacgt ctaggtctgc atggtgatac cattgccact gttgtaggtg tacatc      43016
```